US012723052B2

(12) United States Patent
Carzaniga et al.

(10) Patent No.: US 12,723,052 B2
(45) **Date of Patent: *Sep. 1, 2026**

(54) TETRAHYDROTHIENO PYRIDINE DERIVATIVES AS DDRs INHIBITORS

(71) Applicant: CHIESI FARMACEUTICI S.P.A., Parma (IT)

(72) Inventors: Laura Carzaniga, Parma (IT); Andrea Rizzi, Parma (IT); Nicolò Iotti, Parma (IT); Fabio Rancati, Parma (IT); Anna Karawajczyk, Parma (IT); Barbara Karolina Wołek, Parma (IT); David Edward Clark, Parma (IT); Toby Matthew Grover Mullins, Parma (IT); Keith Christopher Knight, Parma (IT); Ben Paul Whittaker, Parma (IT); Stefano Levanto, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 387 days.

This patent is subject to a terminal disclaimer.

(21) Appl. No.: 18/283,861

(22) PCT Filed: Mar. 25, 2022

(86) PCT No.: PCT/EP2022/057942

§ 371 (c)(1),
(2) Date: Sep. 25, 2023

(87) PCT Pub. No.: WO2022/200580

PCT Pub. Date: Sep. 29, 2022

(65) Prior Publication Data

US 2024/0391936 A1 Nov. 28, 2024

(30) Foreign Application Priority Data

Mar. 26, 2021 (EP) .................................... 21165288
Nov. 22, 2021 (EP) .................................... 21209682

(51) Int. Cl.

| | |
|---|---|
| ***C07D 495/04*** | (2006.01) |
| ***A61K 31/437*** | (2006.01) |
| ***A61K 31/4436*** | (2006.01) |
| ***A61K 31/444*** | (2006.01) |
| ***A61K 31/4545*** | (2006.01) |
| ***A61K 31/496*** | (2006.01) |
| ***A61K 31/4985*** | (2006.01) |
| ***A61K 31/501*** | (2006.01) |
| ***A61K 31/5025*** | (2006.01) |
| ***A61K 31/506*** | (2006.01) |
| ***A61K 31/519*** | (2006.01) |
| ***A61K 31/5377*** | (2006.01) |
| ***A61K 31/5383*** | (2006.01) |
| ***C07D 519/00*** | (2006.01) |

(52) U.S. Cl.
CPC .......... *C07D 519/00* (2013.01); *A61K 31/437* (2013.01); *A61K 31/4436* (2013.01); *A61K 31/444* (2013.01); *A61K 31/4545* (2013.01); *A61K 31/496* (2013.01); *A61K 31/4985* (2013.01); *A61K 31/501* (2013.01); *A61K 31/5025* (2013.01); *A61K 31/506* (2013.01); *A61K 31/519* (2013.01); *A61K 31/5377* (2013.01); *A61K 31/5383* (2013.01)

(58) Field of Classification Search
CPC .................................................... C07D 495/04
USPC ...................................................... 514/227.8
See application file for complete search history.

(56) References Cited

U.S. PATENT DOCUMENTS

2024/0199635 A1* 6/2024 Carzaniga ............ A61K 31/496

FOREIGN PATENT DOCUMENTS

| | | |
|---|---|---|
| CL | 201201270 | 10/2012 |
| CN | 104490889 A | 4/2015 |
| CN | 108191885 A | 6/2018 |
| CN | 108558848 A | 9/2018 |
| CN | 111138449 A | 5/2020 |
| CN | 108191885 B | 8/2020 |
| JP | 2003073357 A | 3/2003 |
| JP | 2018502900 A | 2/2018 |

(Continued)

OTHER PUBLICATIONS

CL 201201270, WO 2011/062927 A1.
Search Report issued Mar. 26, 2025, received on Apr. 4, 2025, in corresponding European Patent Application No. 24221423, 3 pages.
European Search Report issued Sep. 8, 2021 in Patent Application No. EP21165288, 2 pages.
International Search Report issued Jul. 19, 2022 in PCT/EP2022/057942, 2 pages.

(Continued)

*Primary Examiner* — Niloofar Rahmani
(74) *Attorney, Agent, or Firm* — Element IP, PLC

(57) ABSTRACT

The present invention relates to compounds of general formula (I) inhibiting Discoidin Domain Receptors (DDR inhibitors), methods of preparing such compounds, pharmaceutical compositions containing them and therapeutic use thereof. The compounds of the invention may be useful for instance in the treatment of many disorders associated with DDR mechanisms.

(I)

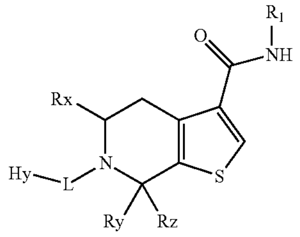

13 Claims, No Drawings

(56) References Cited

FOREIGN PATENT DOCUMENTS

| | | | |
|---|---|---|---|
| JP | 2018519317 | A | 7/2018 |
| WO | WO-0014090 | A1 | 3/2000 |
| WO | WO-2016064970 | A1 | 4/2016 |
| WO | WO-2017005583 | A1 | 1/2017 |
| WO | WO-2017068089 | A2 | 4/2017 |
| WO | WO-2022200578 | A1 | 9/2022 |

OTHER PUBLICATIONS

English translation of the Combined Brazilian Office action and Search Report issued Sep. 9, 2025, received on Sep. 26, 2025, in corresponding Brazilian Patent Application No. 112023019437-7, 8 pages.

Office Action issued Nov. 14, 2024, received Dec. 24, 2024, in corresponding Chilean Patent Application No. 202302821 (with English translation), 24 pages.

Search Report issued Nov. 14, 2024, received Dec. 24, 2024, in corresponding Chilean Patent Application No. 202302821 (with English translation), 6 pages.

* cited by examiner

TETRAHYDROTHIENO PYRIDINE DERIVATIVES AS DDRs INHIBITORS

FIELD OF THE INVENTION

The present invention relates to compounds inhibiting Discoidin Domain Receptors (DDR inhibitors), methods of preparing such compounds, pharmaceutical compositions containing them and therapeutic use thereof.

The compounds of the invention may be useful for instance in the treatment of many disorders associated with DDR mechanisms.

BACKGROUND OF THE INVENTION

Discoidin Domain Receptors (DDRs) are type I transmembrane receptor tyrosine kinase (RTKs). The DDR family comprises two distinct members, DDR1 and DDR2.

DDRs are unique receptors among the other members of the RTK superfamily, in that DDRs are activated by collagen whereas other members of the RTK superfamily are typically activated by soluble peptide-like growth factors (see Vogel, W. (1997) Mol. Cell 1, 13-23; Shrivastava A. Mol Cell. 1997; 1:25-34.). Moreover, DDRs are unusual RTKs also because they form ligand-independent stable dimers that are non-covalently linked (see Noordeen, N. A. (2006) J. Biol. Chem. 281, 22744-22751; Mihai C. J Mol Biol. 2009; 385:432-445).

The DDR1 subfamily is composed of five membrane-anchored isoforms, and the DDR2 subfamily is represented by a single protein. The five DDR1 isoforms all have in common the extracellular and transmembrane domains but differ in the cytoplasmic region (see Valiathan, R. R. (2012) Cancer Metastasis Rev. 31, 295-321; Alves, F. (2001) FASEB J. 15, 1321-1323).

DDR receptor family has been found involved in a series of fibrotic diseases, such as pulmonary fibrosis, and in particular idiopathic pulmonary fibrosis (IPF). The first evidence for a protective role of DDR1 deletion in lung fibrosis was generated in 2006 by the research group of Dr. Vogel (see Avivi-Green C, Am J Respir Crit Care Med 2006; 174:420-427). The authors demonstrated that DDR1-null mice were largely protected against bleomycin (BLM)-induced injury. Furthermore, myofibroblast expansion and apoptosis were much lower in these animals compared with their wild-type counterparts. Absence of inflammation in knockout mice was confirmed by lavage cell count and cytokines ELISA. These results indicated that DDR1 expression is a prerequisite for the development of lung inflammation and fibrosis.

DDR2 deficiency or downregulation reduces bleomycin-induced lung fibrosis (see Zhao H, Bian H, Bu X, Zhang S, Zhang P, Yu J, et al Mol Ther 2016; 24:1734-1744). Zhao et al, demonstrated that DDR2 plays a critical role in the induction of fibrosis and angiogenesis in the lung, in particular that DDR2 synergizes with transforming growth factor (TGF)-β to induce myofibroblast differentiation. Furthermore, they showed that treatment of injured mice with specific siRNA against DDR2 exhibited therapeutic efficacy against lung fibrosis. In a second publication, Jia et al showed that mice lacking DDR2 are protected from bleomycin-induced lung fibrosis (see Jia S, Am J Respir Cell Mol Biol 2018; 59:295-305). In addition, DDR2-null fibroblasts are significantly more prone to apoptosis than wild-type fibroblasts, supporting a paradigm in which fibroblast resistance to apoptosis is critical for progression of fibrosis.

Some compounds have been described in the literature as DDR1 or DD2 antagonists.

WO2016064970 (Guangzhou) discloses tetrahydroisoquinoline-7-carboxamides as selective DDR1 inhibitors useful as therapeutic agents for preventing and treating inflammation, liver fibrosis, kidney fibrosis, lung fibrosis, skin scar, atherosclerosis and cancer.

Of note, antagonizing the DDR receptors may be useful for the treatment of fibrosis and of disease, disorder and conditions that result from fibrosis, and even more antagonizing both receptors DDR1 and DDR2 may be particularly efficacious in the treatment of the above-mentioned disease, disorder and conditions.

Several efforts have been done in the past years to develop novel DDR1 and DDR2 receptor antagonists useful for the treatment of several diseases and some of those compounds have shown efficacy also in humans.

Despite the above cited prior art, there remains a potential for developing selective inhibitors of both receptors DDR1 and DDR2 useful for the treatment of diseases or conditions associated with a dysregulation of DDR receptors, in the respiratory field, in particular idiopathic pulmonary fibrosis (IPF), to be administered by the inhalation route and characterized by a good inhalatory profile, that corresponds to a good activity in the lung, a good lung retention and to a low metabolic stability in order to minimize the systemic exposure and correlated safety issues.

In this direction, we have surprisingly found a new series of compounds of general formula (I), as herein below reported, that solves the problem of providing inhibitors for receptors DDR1 and DDR2 for administration by inhalation, that are active as selective inhibitors of DDR1 and DDR2 receptors with respect to other human protein kinases. Such compounds show high potency, good inhalatory profile, low metabolic stability, low systemic exposure, improved safety and tolerability.

SUMMARY OF THE INVENTION

In a first aspect the present invention relates to a compound of formula (I)

(I)

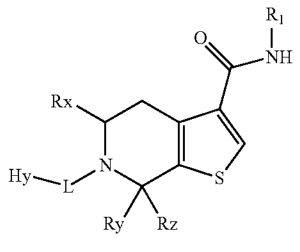

wherein

Rx, Ry and Rz are independently H or —$(C_1$-$C_4)$alkyl;

L is selected from the group consisting of —C(O)— and —$CH_2$—;

Hy is a bicyclic heteroaryl optionally substituted with at least one substituent selected from the group consisting of —$(C_1$-$C_4)$alkyl, halogen atoms, cyano, —O—$(C_1$-$C_4)$alkyl, —O—$(C_1$-$C_4)$alkylene-OH, —O—$(C_1$-$C_4)$alkylene-O—$(C_1$-$C_4)$alkyl, —O—$(C_1$-$C_4)$alkylene-heterocycloalkyl, —$(C_1$-$C_4)$alkylene-$NR_4R_5$, —$(C_1$-$C_6)$haloalkyl and heterocycloalkyl optionally substituted by one or more —$(C_1$-$C_4)$alkyl, or Hy is a bicyclic semisaturated heteroaryl;

$R_1$ is selected from the group consisting of:

Het is an heteroaryl optionally substituted with one or more substituents selected from the group consisting of —($C_1$-$C_4$)alkyl, —($C_1$-$C_4$)haloalkyl, cycloalkyl optionally substituted by one or more —($C_1$-$C_6$) haloalkyl, —O—($C_1$-$C_4$)haloalkyl, —O—($C_1$-$C_4$) alkyl, —($C_1$-$C_4$)alkylene-OH, —($C_1$-$C_4$)alkylene-$NR_4R_5$, heterocycloalkyl, —($C_1$-$C_4$)alkylene-aryl and aryl, wherein said aryl is optionally substituted with one or more groups selected from —($C_1$-$C_4$) alkyl and halogen atoms, and

X (X)

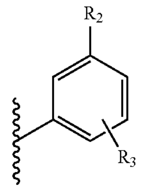

wherein $R^2$ is H or is selected from the group consisting of —O($C_1$-$C_4$)haloalkyl, halogen atoms, —O-cycloalkyl and —($C_1$-$C_4$)haloalkyl;

$R^3$ is H or is selected from the group consisting of halogen atoms, cyano, heterocycloalkyl optionally substituted by one or more —($C_1$-$C_4$)alkyl, —($C_1$-$C_4$)alkylene-heterocycloalkyl, —($C_1$-$C_4$)alkylene-heterocycloalkyl-$(CH_2)_n$—$NR_4R_5$, —($C_1$-$C_4$)alkylene-$NR_4R^5$, —($C_1$-$C_4$)alkylene-$NR_4R_6$, —O($C_1$-$C_4$)alkyl, —O($C_1$-$C_4$) haloalkyl, —O—($C_1$-$C_4$)alkylene-OH, heteroaryl optionally substituted with —($C_1$-$C_4$)alkyl, —O—($C_1$-$C_4$)alkylene-$NR_4R^5$, —O—($C_1$-$C_4$)alkylene-O—($C_1$-$C_4$)alkyl, —O—($C_1$-$C_4$)alkylene-heterocycloalkyl and —O— heterocycloalkyl, wherein each of said heterocycloalkyl is optionally substituted with one or more groups selected from —($C_1$-$C_4$)alkyl, oxo, halogen atoms, —C(O)—($C_1$-$C_4$)alkyl and heterocycloalkyl;

n is 0, 1 or 2;

$R^4$ is H or —($C_1$-$C_4$)alkyl;

R is H or —($C_1$-$C_4$)alkyl;

$R^6$ is selected from the group consisting of -heterocycloalkyl, —($C_1$-$C_4$)alkylene-O—($C_1$-$C_4$)alkyl and —($C_1$-$C_4$)alkylene-OH;

and pharmaceutically acceptable salts thereof.

In a second aspect, the invention refers to a pharmaceutical composition comprising a compound of formula (I) and pharmaceutically acceptable salts thereof in a mixture with one or more pharmaceutically acceptable carrier or excipient.

In a third aspect, the invention refers to a compound of formula (I) and pharmaceutically acceptable salts or to a pharmaceutical composition comprising a compound of formula (I) and pharmaceutically acceptable salts thereof for use as a medicament.

In a further aspect, the invention refers to a compound of formula (I) and pharmaceutically acceptable salts thereof or to a pharmaceutical composition comprising a compound of formula (I) and pharmaceutically acceptable salts thereof for use in preventing and/or treating a disease, disorder or condition associated with dysregulation of DDR.

In a further aspect, the invention refers to a compound of formula (I) and pharmaceutically acceptable salts thereof or to a pharmaceutical composition comprising a compound of formula (I) and pharmaceutically acceptable salts thereof for use in the prevention and/or treatment of fibrosis and/or diseases, disorders, or conditions that involve fibrosis.

In a further aspect, the invention refers to a compound of formula (I) and pharmaceutically acceptable salts thereof or to a pharmaceutical composition comprising a compound of formula (I) and pharmaceutically acceptable salts thereof for use in the prevention and/or treatment of idiopathic pulmonary fibrosis (IPF).

DETAILED DESCRIPTION OF THE INVENTION

Definitions

Unless otherwise specified, the compound of formula (I) of the present invention is intended to include also its stereoisomers, tautomers or pharmaceutically acceptable salts or solvates thereof.

Unless otherwise specified, the compound of formula (I) of the present invention is intended to include also the compounds of formula (Ia), (Iaa), (Iab), (Iaa') (Iab'), (Ib), (Iba), (Ibb).

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "solvate" means a physical association of a compound of this invention with one or more solvent molecules, whether organic or inorganic. This physical association includes hydrogen bonding. In certain instances, the solvate will be capable of isolation, for example, when one or more solvent molecules are incorporated in the crystal lattice of the crystalline solid. The solvate may comprise either a stoichiometric or nonstoichiometric amount of the solvent molecules.

The term "stereoisomer" refers to isomers of identical constitution that differ in the arrangement of their atoms in space. Enantiomers and diastereomers are examples of stereoisomers.

The term "enantiomer" refers to one of a pair of molecular species that are mirror images of each other and are not superimposable.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, Pure and Applied Chemistry, 68:2193-2222 (1996)).

The term "diastereomer" refers to stereoisomers that are not mirror images.

The term "racemate" or "racemic mixture" refers to a composition composed of equimolar quantities of two enantiomeric species, wherein the composition is devoid of optical activity.

The term "tautomer" refers to each of two or more isomers of a compound that exist together in equilibrium and are readily interchanged by migration of an atom or group within the molecule.

The term "halogen" or "halogen atoms" or "halo" as used herein includes fluorine, chlorine, bromine, and iodine atom.

The term "($C_x$-$C_y$)alkyl" wherein x and y are integers, refers to a straight or branched chain alkyl group having from x to y carbon atoms. Thus, when x is 1 and y is 4, for example, the term comprises methyl, ethyl, n-propyl, isopropyl, n-butyl, isobutyl, sec-butyl, and t-butyl.

The term "($C_x$-$C_y$)alkylene" wherein x and y are integers, refers to a $C_x$-$C_y$alkyl radical having in total two unsatisfied valencies, such as a divalent methylene radical.

The term "($C_x$-$C_y$)alkylene-OH" refers to an alkylene linked to OH group.

The term "($C_x$-$C_y$)alkylene-aryl" refers to an alkylene linked to an aryl group.

The term "O($C_x$-$C_y$)alkyl" wherein x and y are integers, refers to the above defined "($C_x$-$C_y$)alkyl" groups wherein a carbon atom is linked to an oxygen atom.

The term "($C_x$-$C_y$)haloalkyl" wherein x and y are integers, refers to the above defined "($C_x$-$C_y$)alkyl" groups wherein one or more hydrogen atoms are replaced by one or more halogen atoms, which can be the same or different. Examples of said "($C_x$-$C_y$)haloalkyl" groups may thus include halogenated, poly-halogenated and fully halogenated alkyl groups wherein all hydrogen atoms are replaced by halogen atoms, e.g. trifluoromethyl.

The term "O($C_x$-$C_y$)haloalkyl" wherein x and y are integers, refers to the above defined "($C_x$-$C_y$)haloalkyl" groups wherein the carbon atom is linked to an oxygen atom.

Examples of said "O($C_x$-$C_y$)haloalkyl" groups may thus include halogenated, poly-halogenated and fully halogenated Oalkyl groups wherein all hydrogen atoms are replaced by halogen atoms, e.g. trifluoromethoxy.

The term "aryl" refers to monocyclic carbon ring systems which have 6 ring atoms wherein the ring is aromatic. Examples of suitable aryl monocyclic ring systems include, for instance, phenyl.

The term "heteroaryl" refers to a mono- or bi-cyclic aromatic group containing one or more heteroatoms selected from S, N and O, and includes groups having two such monocyclic rings, or one such monocyclic ring and one monocyclic aryl ring, which are fused through a common bond.

The term "semisaturated heteroaryl" refers to a bicyclic group containing one or more heteroatoms selected from S, N and O, and includes monocyclic heteroaryl condensed to monocyclic heterocycloalkyl ring. Examples of suitable semisaturated heteroaryl include, for instance, 5,6-dihydro-8H-imidazo[2,1-c][1,4]oxazine-3-yl, 5,6,7,8-tetrahydroimidazo[1,2-a]pyridine-3-yl and 5,6,7,8-tetrahydroimidazo[1,2-a]pyrimidine-3-yl.

The term "heterocycloalkyl" refers to saturated mono- or bi-cyclic ring system of 3 to 12 ring atoms comprising one or more heteroatoms selected from N, S or O. Examples of heterocycloalkyl include piperazinyl, pyrrolidinyl, morpholinyl and piperidinyl. Said heterocycloalkyl may be further optionally substituted on the available positions in the ring, namely on a carbon atom, or on a heteroatom available for substitution. Substitution may be on a carbon atom including spiro disubstitution, forming a bicyclic system where two heterocycloalkyl rings, or one heterocycloalkyl and one cycloalkyl ring, are connected through a single carbon atom. Substitution may be as well as on two adjacent carbon atoms forming an additional condensed 4- to 6-membered heterocycloalkyl ring.

Examples of spiro rings comprise and are not limited to, for example, 6-methyl-2,6-diazaspiro[3.3]heptanyl, 6-oxa-1-azaspiro[3.3]heptanyl; and 2-methyl-2,8-diazaspiro[4.5]decanyl. Moreover, said heterocycloalkyl may be a diazabicyclo ring, an azabicyclo ring or a cyclic carbonate. Examples of diazabicyclo ring include and are not limited to, for instance, 5-methyl-2,5-diazabicyclo[2.2.1]heptanyl and 6-methyl-3,6-diazabicyclo[3.2.2]nonanyl; examples of azabicyclo ring include and are not limited to, for instance, 2-oxa-5-azabicyclo[2.2.1]heptan-5-yl; examples of suitable cyclic carbonates include, for instance, 1,3-dioxalan-2-one and 4-methyl-1,3-dioxol-2-one.

The term "heterocycloalkyl($C_x$-$C_y$)alkyl" refers to an heterocycloalkyl linked to a "($C_x$-$C_y$)alkyl" group as defined above.

The term "O-heterocycloalkyl" refers to heterocycloalkyl linked to an oxygen atom.

The term "($C_x$-$C_y$)alkylene-heterocycloalkyl" refers to an heterocycloalkyl ring linked to a alkylene group, both as defined above.

The term "O—($C_x$-$C_y$)alkylene-OH" refers to a "($C_x$-$C_y$)alkylene-OH" group as defined above where the alkylene is linked to an oxygen atom.

The term "O—($C_x$-$C_y$)alkylene-O—($C_x$-$C_y$)alkyl" refers to a "($C_x$-$C_y$)alkyl" as defined above where the alkyl is linked to "—O—($C_x$-$C_y$)alkyl", defined as described above, through an oxygen atom.

The term "O—($C_x$-$C_y$)alkylene-heterocycloalkyl" refers to a ($C_x$-$C_y$)alkylene-heterocycloalkyl as defined above linked to an oxygen atom.

The term "—C(O)—($C_x$-$C_y$)alkyl" refers to a "($C_x$-$C_y$)alkyl" group as defined above wherein the alkyl is linked to a —C(O)— group.

The term "($C_x$-$C_y$)alkylene-heterocycloalkyl-$(CH_2)_n$—$NR_xR_y$" refers to a heterocycloalkyl as defined above directly linked to a "($C_x$-$C_y$)alkylene", defined as described above. The heterocycloalkyl is further linked to a nitrogen $NR_xR_y$, wherein x and y are integers, through a —$(CH_2)_n$— wherein n is an integer. The term "($C_x$-$C_y$)alkylene-$NR_xR_y$" refers to a "($C_x$-$C_y$)alkylene" defined as described above linked to a nitrogen $NR_xR_y$, wherein x and y are integers.

The term "O—($C_x$-$C_y$)alkylene-$NR_xR_y$" refers to a "O—($C_x$-$C_y$)alkylene" defined as described above linked to a $NR_xR_y$, wherein x and y are integers.

The term "O—($C_x$-$C_y$)alkylene-O—($C_x$-$C_y$)alkyl" refers to a "($C_x$-$C_y$)alkyl" described as above linked to an "O—($C_x$-$C_y$)alkylene", described as above, through an oxygen atom.

A bond pointing to a wavy or squiggly line, such as

as used in structural formulas herein, depicts the bond that is the point of attachment of the moiety or substituent to the core or backbone structure.

When referring to substituents, a dash ("-") that is not between two letters, words, or symbols is meant to represent the point of attachment for such substituents.

The carbonyl group is herein preferably represented as —C(O)— as an alternative to the other common representations such as —CO—, —(CO)— or —C(═O)—.

Whenever basic amino groups are present in the compounds of formula (I), physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups, corresponding physiological cation salts may be present as well, for instance including alkaline or alkaline earth metal ions.

The term "half maximal inhibitory concentration" (IC50) indicates the concentration of a particular compound or molecule required for obtaining 50% inhibition of a biological process in vitro.

The term "Ki" indicates the dissociation constant for the enzyme-inhibitor complex, expressed in molar units. It is an indicator of the binding affinity between inhibitor and DDR1 or DDR2 receptors.

As above indicated, the present invention refers to a series of compounds represented by the general formula (I) as herein below described in details, which are endowed with an inhibitory activity on receptors DDR1 and DDR2. Antagonizing receptors DDR1 and DDR2 can be particularly effective in the treatment of those diseases where the DDR receptors play a role, such as fibrosis and disease, disorder and condition related to fibrosis.

Indeed, as detailed in the experimental part below, the compounds of formula (I) of the present invention are able to act as antagonists of both DDR1 and DDR2 receptors in a substantive and effective way. In particular, Table 6 below shows that for the compounds of the present invention, both the affinity for either DDR1 and DDR2 receptors and the inhibitory activity against either DDR1 and DDR2 receptors are below about 80 nM respectively in the binding (expressed as Ki) and the cell based assays (expressed as IC50). This confirms that the compounds of formula (I) are able to antagonize the two isoforms of DDR receptor mainly involved in fibrosis and diseases resulting from fibrosis. Accordingly, the compounds of formula (I) can be used in the treatment of fibrosis, in particular pulmonary fibrosis, when DDR1 and DDR2 are involved.

As indicated in the same experimental part, Table 7, the data demonstrate that, conversely to the compound $C_1$, characterized by the —C(O)NH— group substitution at the α position with respect to the sulphur, instead of the R position as in Example 1 of the present invention, the presence of the above mentioned substitution at the R position in the present invention compounds unexpectedly and remarkably determines a relevant increase in the inhibitory activity on the DDR1 and DDR2 receptors.

As a further evidence, conversely to the compound $C_2$, characterized by simultaneously the —C(O)NH— group substituting the thienyl ring linked at the a position with respect to the sulphur and the Hy group substituting the tetrahydropyridyl ring linked through a spacer to the nitrogen at the 5 position, in Example 1 of the present invention, the presence of —C(O)NH— group substituting the thienyl ring linked at the R position with respect to the sulphur and the Hy group substituting the tetrahydropyridyl ring linked through a spacer to the nitrogen at the 6 position, in the present invention compounds unexpectedly and noteworthy determines a relevant increase in the inhibitory activity against the DDR1 and DDR2 receptors.

Advantageously, the compounds of the present invention are endowed with a very high potency and could be administered in human at a lower dosage respect to the compounds of the prior art, thus reducing the adverse events that typically occur when administering higher dosages of drug.

In addition to being notably potent with respect to their inhibitory activity on both receptors DDR1 and DDR2, the compounds of the present invention are also characterized by a good inhalatory profile, that permits to act effectively on the lung compartment and have, at the same time, a low metabolic stability, that allows to minimize the drawbacks associated with the systemic exposure, such as safety and tolerability issues.

Therefore, the compounds of the present invention are particularly appreciated by the skilled person when looking at a suitable and efficacious compounds useful for the treatment of fibrosis, in particular idiopathic pulmonary fibrosis, administered by the inhalation route and characterized by a good inhalatory profile, that corresponds to a good activity on the lung, a good lung retention and to a low metabolic stability, that minimizes the systemic exposure and correlated safety issues.

Thus, in one aspect the present invention relates to a compound of general formula (I)

(I)

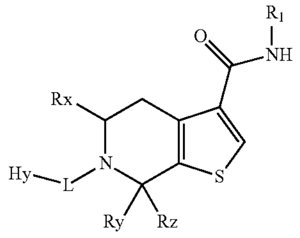

wherein

Rx, Ry and Rz are independently H or —($C_1$-$C_4$)alkyl;

L is selected from the group consisting of —C(O)— and —$CH_2$—;

Hy is a bicyclic heteroaryl optionally substituted with at least one substituent selected from the group consisting of —($C_1$-$C_4$)alkyl, halogen atoms, cyano, —O—($C_1$-$C_4$)alkyl, —O—($C_1$-$C_4$)alkylene-OH, —O—($C_1$-$C_4$)alkylene-O—($C_1$-$C_4$)alkyl, —O—($C_1$-$C_4$)alkylene-heterocycloalkyl, —($C_1$-$C_4$)alkylene-$NR_4R_5$, —($C_1$-$C_6$)haloalkyl and heterocycloalkyl optionally substituted by one or more —($C_1$-$C_4$)alkyl, or Hy is a bicyclic semisaturated heteroaryl;

$R_1$ is selected from the group consisting of:

Het is an heteroaryl optionally substituted with one or more substituents selected from the group consisting of —($C_1$-$C_4$)alkyl, —($C_1$-$C_4$)haloalkyl, cycloalkyl optionally substituted by one or more —($C_1$-$C_6$)haloalkyl, —O—($C_1$-$C_4$)haloalkyl, —O—($C_1$-$C_4$)alkyl, —($C_1$-$C_4$)alkylene-OH, —($C_1$-$C_4$)alkylene-$NR_4R_5$, heterocycloalkyl, —($C_1$-$C_4$)alkylene-aryl and aryl, wherein said aryl is optionally substituted with one or more groups selected from —($C_1$-$C_4$)alkyl and halogen atoms, and

X (X)

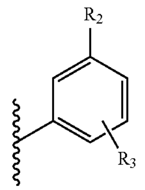

wherein $R_2$ is H or is selected from the group consisting of —$O(C_1-C_4)$haloalkyl, halogen atoms, —O-cycloalkyl and —$(C_1-C_4)$haloalkyl;

$R_3$ is H or is selected from the group consisting of halogen atoms, cyano, heterocycloalkyl optionally substituted by one or more —$(C_1-C_4)$alkyl, —$(C_1-C_4)$alkylene-heterocycloalkyl, —$(C_1-C_4)$alkylene-heterocycloalkyl-$(CH_2)_n$—$NR_4R_5$, —$(C_1-C_4)$alkylene-$NR_4R_5$, —$(C_1-C_4)$alkylene-$NR_4R_6$, —$O(C_1-C_4)$alkyl, —$O(C_1-C_4)$haloalkyl, —O—$(C_1-C_4)$alkylene-OH, heteroaryl optionally substituted with —$(C_1-C_4)$alkyl, —O—$(C_1-C_4)$alkylene-$NR_4R_5$, —O—$(C_1-C_4)$alkylene-O—$(C_1-C_4)$alkyl, —O—$(C_1-C_4)$alkylene-heterocycloalkyl and —O— heterocycloalkyl, wherein each of said heterocycloalkyl is optionally substituted with one or more groups selected from —$(C_1-C_4)$alkyl, oxo, halogen atoms, —C(O)—$(C_1-C_4)$alkyl and heterocycloalkyl;

n is 0, 1 or 2;

$R_4$ is H or —$(C_1-C_4)$alkyl;

$R_5$ is H or —$(C_1-C_4)$alkyl;

$R_6$ is selected from the group consisting of -heterocycloalkyl, —$(C_1-C_4)$alkylene-O—$(C_1-C_4)$alkyl and —$(C_1-C_4)$alkylene-OH;

and pharmaceutically acceptable salts thereof.

In a particularly preferred embodiment, the present invention relates to a compound of general formula (I) wherein $R_1$ is X'

(X')

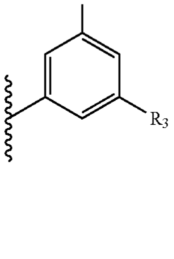

represented by formula (Ia)

(Ia)

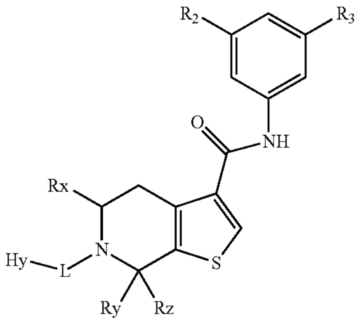

wherein Rx, Ry, Rz, L, Hy, $R_2$ and $R_3$ are as defined above.

In a particularly preferred embodiment the present invention refers to a compound of formula (Ia) wherein L is —$CH_2$—, represented by formula (Iaa)

(Iaa)

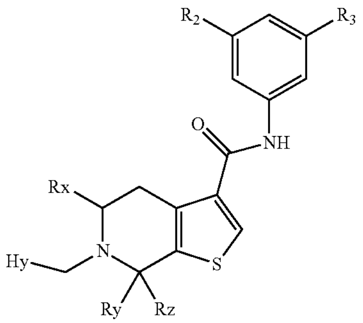

wherein Rx, Ry, Rz, Hy, $R_2$ and $R_3$ are as defined above.

In a preferred embodiment the present invention refers to a compound of formula (Iaa) wherein Hy is selected from the group consisting of imidazo[1,2-a]pyridine-3-yl, 1H-pyrrolo[2,3-b]pyridin-5-yl, imidazo[1,2-a]pyrazin-3-yl, 1H-pyrazolo[3,4-b]pyridin-5-yl, 1H-pyrrolo[2,3-b]pyridin-4-yl, pyrazolo[1,5-a]pyrimidin-6-yl, 3-methyl-1H-pyrazolo[3,4-b]pyridin-5-yl and imidazo[1,2-b]pyridazin-3-yl.

In another preferred embodiment the present invention refers to a compound of formula (Iaa) wherein $R_2$ is trifluoromethyl and trifluoromethoxy.

In another particularly preferred embodiment the present invention refers to a compound of formula (Iaa) wherein $R_3$ is H or is selected from the group consisting of 4-methyl-1H-imidazol-1-yl, 3-(dimethylamino)pyrrolidin-1-yl, 2-(pyrrolidin-1-yl)ethoxy and fluorine.

In a further preferred embodiment the present invention refers to a compound of formula (Iaa) wherein Hy is selected from the group consisting of 1H-pyrazolo[3,4-b]pyridin-5-yl and 3-methyl-1H-pyrazolo[3,4-b]pyridin-5-yl, $R_2$ is selected from the group consisting of trifluoromethoxy and trifluoromethyl, $R_3$ is H or is selected from the group consisting of fluorine, (R)—N-(3-((3-(dimethylamino)pyrrolidin-1-yl)methyl and 2-(pyrrolidin-1-yl)ethoxy.

According to a preferred embodiment, the invention refers to at least one of the compounds of Formula (Iaa) listed in the Table 1 below and pharmaceutically acceptable salts thereof. These compounds are particularly active on receptors DDR1 and DDR2, as shown in Table 6.

TABLE 1

List of compounds of Formula (Iaa)

| Example No. | Structure | Chemical Name |
|---|---|---|
| 65 | 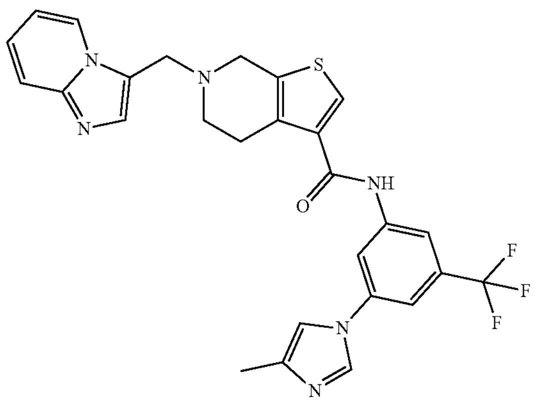 [SMILES: Cc1cn(-c2cc(NC(=O)c3csc4c3CCN(Cc3cnc5ccccn35)C4)cc(C(F)(F)F)c2)cn1] | 6-(imidazo[1,2-a]pyridin-3-ylmethyl)-N-(3-(4-methyl-1H-imidazol-1-yl)-5-(trifluoromethyl)phenyl)-4,5,6,7-tetrahydrothieno[2,3-c]pyridine-3-carboxamide |
| 66 | 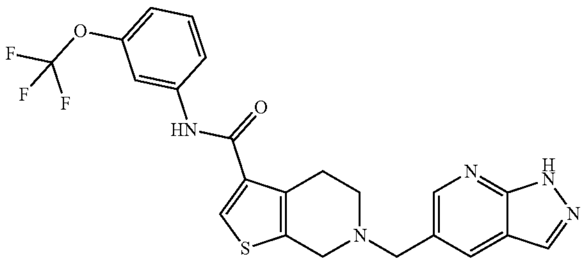 [SMILES: O=C(Nc1cccc(OC(F)(F)F)c1)c1csc2c1CCN(Cc1cnc3[nH]ncc3c1)C2] | 6-((1H-pyrazolo[3,4-b]pyridin-5-yl)methyl)-N-(3-(trifluoromethoxy)phenyl)-4,5,6,7-tetrahydrothieno[2,3-c]pyridine-3-carboxamide |
| 67 | 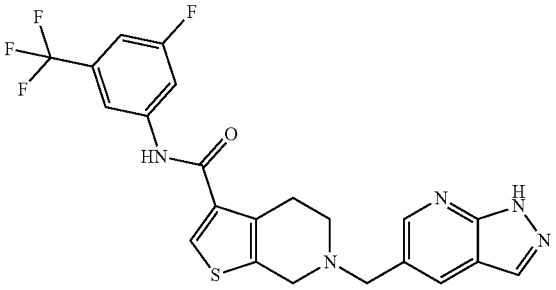 [SMILES: O=C(Nc1cc(F)cc(C(F)(F)F)c1)c1csc2c1CCN(Cc1cnc3[nH]ncc3c1)C2] | 6-((1H-pyrazolo[3,4-b]pyridin-5-yl)methyl)-N-(3-fluoro-5-(trifluoromethyl)phenyl)-4,5,6,7-tetrahydrothieno[2,3-c]pyridine-3-carboxamide |
| 69 | 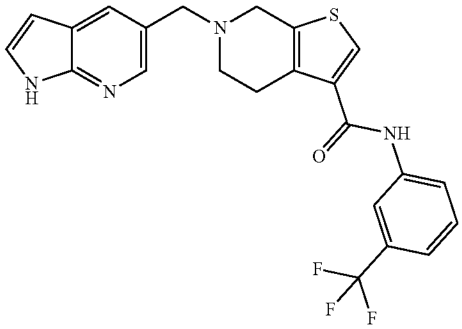 [SMILES: O=C(Nc1cccc(C(F)(F)F)c1)c1csc2c1CCN(Cc1cnc3[nH]ccc3c1)C2] | 6-((1H-pyrrolo[2,3-b]pyridin-5-yl)methyl)-N-(3-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 72 | 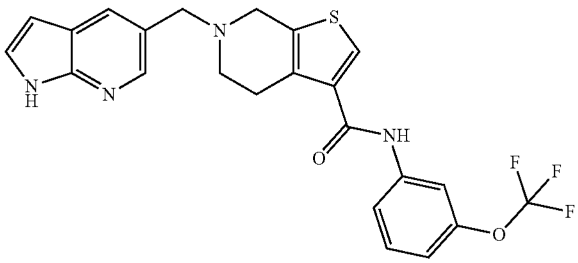 [SMILES: O=C(Nc1cccc(OC(F)(F)F)c1)c1csc2c1CCN(Cc1cnc3[nH]ccc3c1)C2] | 6-((1H-pyrrolo[2,3-b]pyridin-5-yl)methyl)-N-(3-(trifluoromethoxy)phenyl)-4,5,6,7-tetrahydrothieno[2,3-c]pyridine-3-carboxamide |
| 73 | 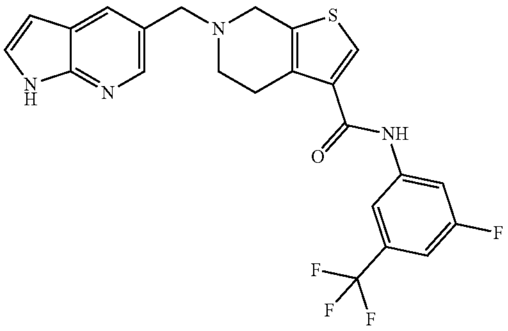 [SMILES: O=C(Nc1cc(F)cc(C(F)(F)F)c1)c1csc2c1CCN(Cc1cnc3[nH]ccc3c1)C2] | 6-((1H-pyrrolo[2,3-b]pyridin-5-yl)methyl)-N-(3-fluoro-5-(trifluoromethyl)phenyl)-4,5,6,7-tetrahydrothieno[2,3-c]pyridine-3-carboxamide |
| 84 | 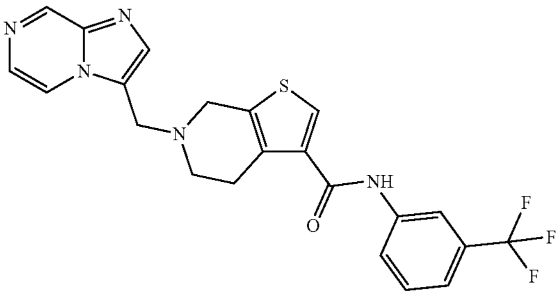 [SMILES: O=C(Nc1cccc(C(F)(F)F)c1)c1csc2c1CCN(Cc1cnc3cnccn13)C2] | 6-(imidazo[1,2-a]pyrazin-3-ylmethyl)-N-(3-(trifluoromethyl)phenyl)-4,5,6,7-tetrahydrothieno[2,3-c]pyridine-3-carboxamide |
| 85 | 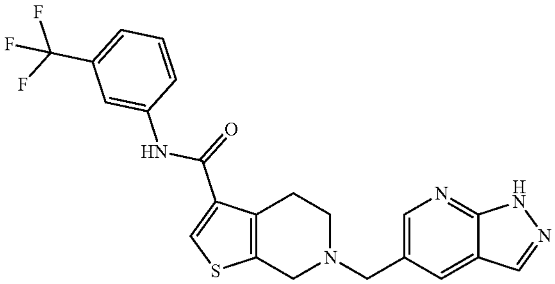 [SMILES: O=C(Nc1cccc(C(F)(F)F)c1)c1csc2c1CCN(Cc1cnc3[nH]ncc3c1)C2] | 6-((1H-pyrazolo[3,4-b]pyridin-5-yl)methyl)-N-(3-(trifluoromethyl)phenyl)-4,5,6,7-tetrahydrothieno[2,3-c]pyridine-3-carboxamide |
| 86 | 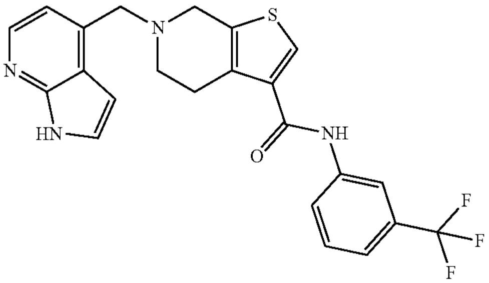 [SMILES: O=C(Nc1cccc(C(F)(F)F)c1)c1csc2c1CCN(Cc1ccnc3[nH]ccc13)C2] | 6-((1H-pyrrolo[2,3-b]pyridin-4-yl)methyl)-N-(3-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 87 | 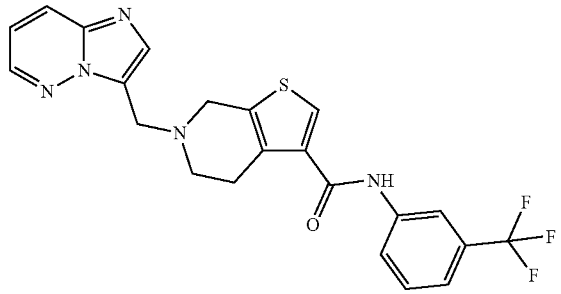 [SMILES: O=C(Nc1cccc(C(F)(F)F)c1)c1csc2c1CCN(Cc1cnc3cccnn13)C2] | 6-(imidazo[1,2-b]pyridazin-3-ylmethyl)-N-(3-(trifluoromethyl)phenyl)-4,5,6,7-tetrahydrothieno[2,3-c]pyridine-3-carboxamide |
| 88 | 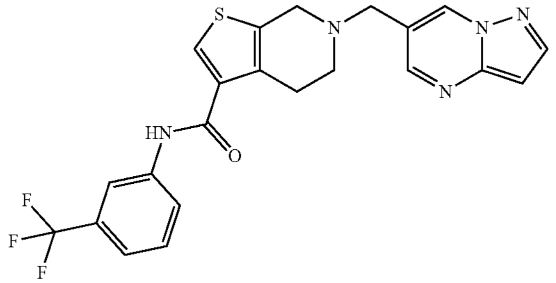 [SMILES: O=C(Nc1cccc(C(F)(F)F)c1)c1csc2c1CCN(Cc1cnc3ccnn3c1)C2] | 6-(pyrazolo[1,5-a]pyrimidin-6-ylmethyl)-N-(3-(trifluoromethyl)phenyl)-4,5,6,7-tetrahydrothieno[2,3-c]pyridine-3-carboxamide |
| 89 | 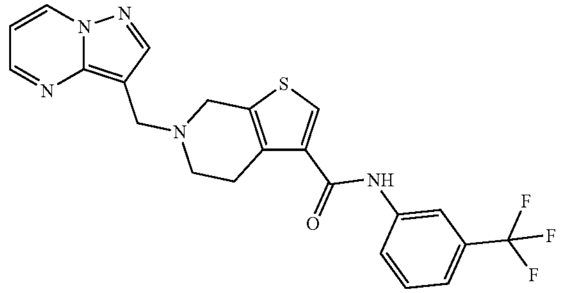 [SMILES: O=C(Nc1cccc(C(F)(F)F)c1)c1csc2c1CCN(Cc1cnn3cccnc13)C2] | 6-(pyrazolo[1,5-a]pyrimidin-3-ylmethyl)-N-(3-(trifluoromethyl)phenyl)-4,5,6,7-tetrahydrothieno[2,3-c]pyridine-3-carboxamide |
| 103 | 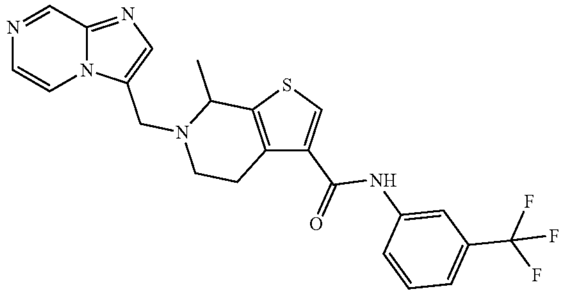 [SMILES: CC1c2scc(C(=O)Nc3cccc(C(F)(F)F)c3)c2CCN1Cc1cnc2cnccn12] | 6-(imidazo[1,2-a]pyrazin-3-ylmethyl)-7-methyl-N-(3-(trifluoromethyl)phenyl)-4,5,6,7-tetrahydrothieno[2,3-c]pyridine-3-carboxamide |
| 104 | 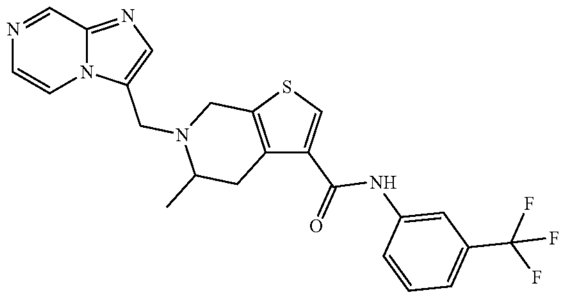 [SMILES: CC1Cc2c(C(=O)Nc3cccc(C(F)(F)F)c3)csc2CN1Cc1cnc2cnccn12] | 6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 105 | 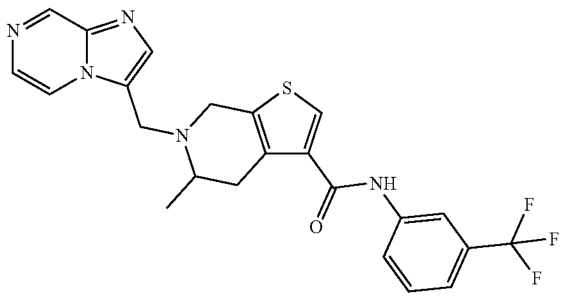 [SMILES: CC1Cc2c(C(=O)Nc3cccc(C(F)(F)F)c3)csc2CN1Cc1cnc2cnccn12] | 6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide |
| 106 | 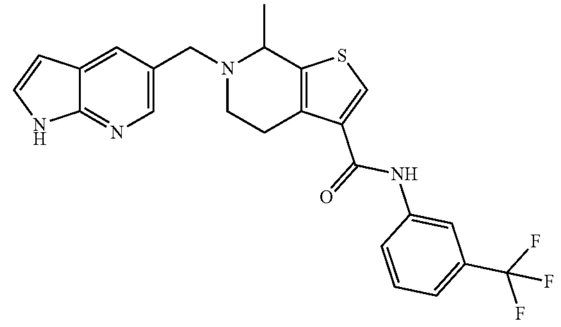 [SMILES: CC1c2scc(C(=O)Nc3cccc(C(F)(F)F)c3)c2CCN1Cc1cnc2[nH]ccc2c1] | 6-((1H-pyrrolo[2,3-b]pyridin-5-yl)methyl)-7-methyl-N-(3-(trifluoromethyl)phenyl)-4,5,6,7-tetrahydrothieno[2,3-c]pyridine-3-carboxamide |
| 107 | 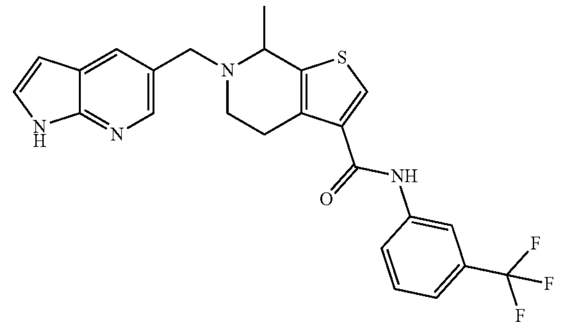 [SMILES: CC1c2scc(C(=O)Nc3cccc(C(F)(F)F)c3)c2CCN1Cc1cnc2[nH]ccc2c1] | 6-((1H-pyrrolo[2,3-b]pyridin-5-yl)methyl)-7-methyl-N-(3-(trifluoromethyl)phenyl)-4,5,6,7-tetrahydrothieno[2,3-c]pyridine-3-carboxamide |
| 157 | 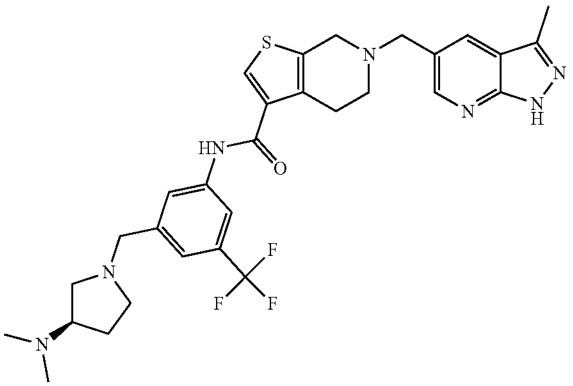 [SMILES: Cc1n[nH]c2ncc(CN3CCc4c(C(=O)Nc5cc(CN6CC[C@@H](N(C)C)C6)cc(C(F)(F)F)c5)csc4C3)cc12] | (R)-N-(3-((3-(dimethylamino)pyrrolidin-1-yl)methyl)-5-(trifluoromethyl)phenyl)-6-((3-methyl-1H-pyrazolo[3,4-b]pyridin-5-yl)methyl)-4,5,6,7-tetrahydrothieno[2,3-c]pyridine-3-carboxamide |

TABLE 1-continued

List of compounds of Formula (Iaa)

| Example No. | Structure | Chemical Name |
|---|---|---|
| 158 | 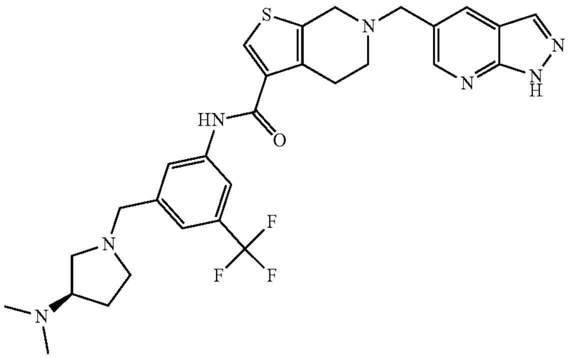 [SMILES: CN(C)[C@@H]1CCN(Cc2cc(NC(=O)c3csc4c3CCN(Cc3cnc5[nH]ncc5c3)C4)cc(C(F)(F)F)c2)C1] | (R)-6-((1H-pyrazolo[3,4-b]pyridin-5-yl)methyl)-N-(3-((3-(dimethylamino)pyrrolidin-1-yl)methyl)-5-(trifluoromethyl)phenyl)-4,5,6,7-tetrahydrothieno[2,3-c]pyridine-3-carboxamide |
| 159 | 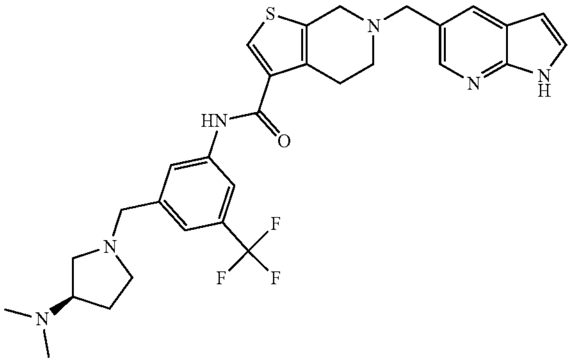 [SMILES: CN(C)[C@@H]1CCN(Cc2cc(NC(=O)c3csc4c3CCN(Cc3cnc5[nH]ccc5c3)C4)cc(C(F)(F)F)c2)C1] | (R)-6-((1H-pyrrolo[2,3-b]pyridin-5-yl)methyl)-N-(3-((3-(dimethylamino)pyrrolidin-1-yl)methyl)-5-(trifluoromethyl)phenyl)-4,5,6,7-tetrahydrothieno[2,3-c]pyridine-3-carboxamide |
| 160 | 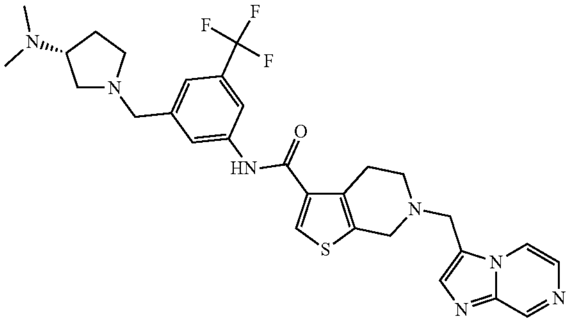 [SMILES: CN(C)[C@@H]1CCN(Cc2cc(NC(=O)c3csc4c3CCN(Cc3cnc5cnccn35)C4)cc(C(F)(F)F)c2)C1] | (R)-N-(3-((3-(dimethylamino)pyrrolidin-1-yl)methyl)-5-(trifluoromethyl)phenyl)-6-(imidazo[1,2-a]pyrazin-3-ylmethyl)-4,5,6,7-tetrahydrothieno[2,3-c]pyridine-3-carboxamide |
| 161 | 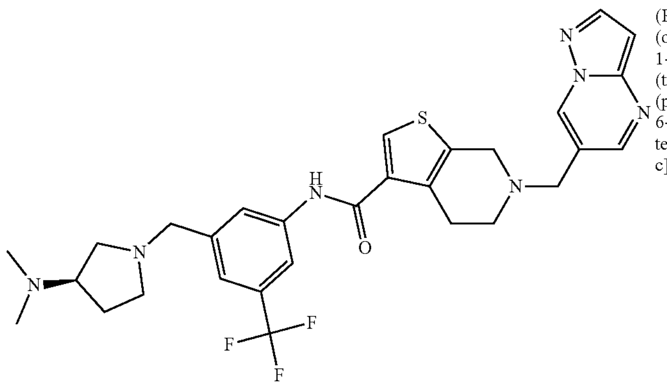 | (R)-N-(3-((3-(dimethylamino)pyrrolidin-1-yl)methyl)-5-(trifluoromethyl)phenyl)-6-(pyrazolo[1,5-a]pyrimidin-6-ylmethyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 163 | 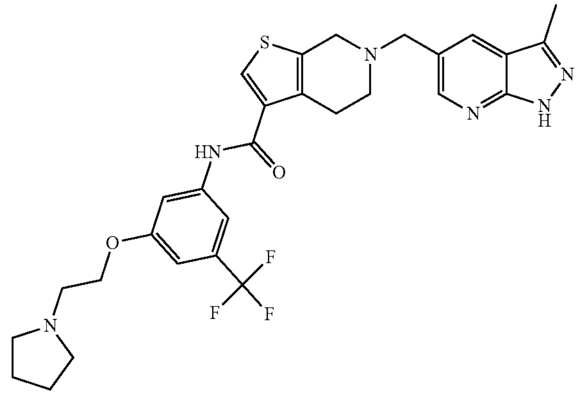 [SMILES: Cc1n[nH]c2ncc(CN3CCc4c(C(=O)Nc5cc(OCCN6CCCC6)cc(C(F)(F)F)c5)csc4C3)cc12] | 6-((3-methyl-1H-pyrazolo[3,4-b]pyridin-5-yl)methyl)-N-(3-(2-(pyrrolidin-1-yl)ethoxy)-5-(trifluoromethyl)phenyl)-4,5,6,7-tetrahydrothieno[2,3-c]pyridine-3-carboxamide |
| 164 | 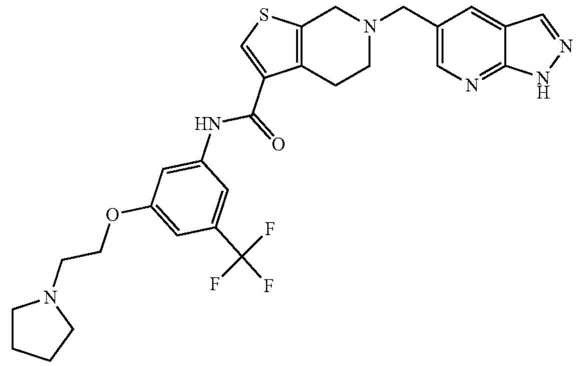 [SMILES: O=C(Nc1cc(OCCN2CCCC2)cc(C(F)(F)F)c1)c1csc2c1CCN(Cc1cnc3[nH]ncc3c1)C2] | 6-((1H-pyrazolo[3,4-b]pyridin-5-yl)methyl)-N-(3-(2-(pyrrolidin-1-yl)ethoxy)-5-(trifluoromethyl)phenyl)-4,5,6,7-tetrahydrothieno[2,3-c]pyridine-3-carboxamide |
| 174 | 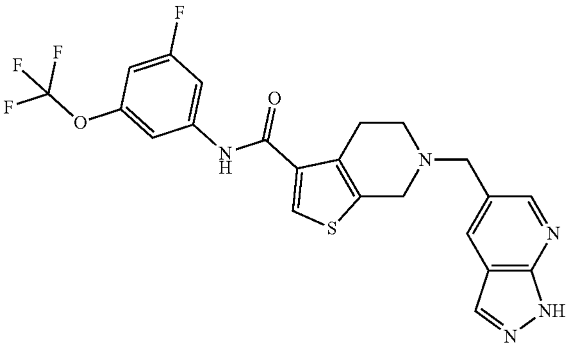 [SMILES: O=C(Nc1cc(F)cc(OC(F)(F)F)c1)c1csc2c1CCN(Cc1cnc3[nH]ncc3c1)C2] | 6-((1H-pyrazolo[3,4-b]pyridin-5-yl)methyl)-N-(3-fluoro-5-(trifluoromethoxy)phenyl)-4,5,6,7-tetrahydrothieno[2,3-c]pyridine-3-carboxamide |

In another preferred embodiment the present invention refers to a compound of formula (Ia) wherein L is —C(O)—, represented by formula (Iab)

(Iab)

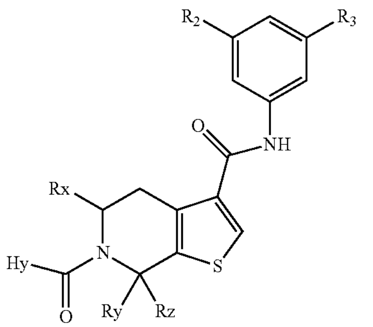

wherein Rx, Ry, Rz, Hy, $R_2$ and $R_3$ are as defined above.

In a preferred embodiment the present invention refers to a compound of formula (Iab) wherein Hy is selected from the group consisting of imidazo[1,2-a]pyridine-3-yl, 1H-pyrrolo[2,3-b]pyridine-5-yl, imidazo[1,2-a]pyrazine-3-yl, 1H-pyrazolo[3,4-b]pyridine-yl, pyrazolo[1,5-a]pyrimidine-3-yl, 5,6,7,8-tetrahydroimidazo[1,2-a]pyridine-3-yl, 5,6-dihydro-8H-imidazo[2,1-c][1,4]oxazine-3-yl, imidazo[1,2-b]pyridazine-3,6-((dimethylamino)methyl)imidazo[1,2-a]pyridin-3-yl, 4-methylpiperazin-1-yl)imidazo[1,2-a]pyridin-3-yl, 5-methylimidazo[1,2-a]pyridin-3-yl, 6-methyl-2,6-diazaspiro[3.3]heptan-2-yl)imidazo[1,2-a]pyridin-3-yl, 6-(2-hydroxyethoxy)imidazo[1,2-a]pyridin-3-yl, 2-methoxyethoxy)imidazo[1,2-a]pyridin-3-yl, 1-methyl-1,2,3,6-tetrahydropyridin-4-yl)imidazo[1,2-a]pyridin-3-yl, 6-(2-morpholinoethoxy)imidazo[1,2-a]pyridin-3-yl, 2-morpholinoethoxy)imidazo[1,2-a]pyridin-3-yl and pyrazolo[1,5-a]pyrazine-3-yl.

In another preferred embodiment the present invention refers to a compound of formula (Iab) wherein $R_2$ is selected from the group consisting of trifluoromethyl and trifluoromethoxy.

In another particularly preferred embodiment the present invention refers to a compound of formula (Iab) wherein $R_3$ is H or is selected from the group consisting of 4-methyl-1H-imidazol-1-yl, fluorine, pyrrolidin-1-ylmethyl, (dimethylamino)methyl, 3-(morpholinomethyl), 2-morpholinoethoxy, 4-(dimethylamino)piperidin-1-yl)methyl, 3-(dimethylamino)pyrrolidin-1-yl)methyl, 6-oxa-1-azaspiro[3.3]heptan-1-yl)methyl, 2-(dimethylamino)ethoxy, 2-(pyrrolidin-1-yl)ethoxy, (2-hydroxyethyl)(methyl)amino)methyl, 2-oxa-5-azabicyclo[2.2.1]heptan-5-yl, (2-methoxyethyl)(methyl)amino)methyl, (4-acetylpiperazin-1-yl)methyl, (4-methyl-3-oxopiperazin-1-yl)methyl, (piperidin-1-yl)methyl, (3-fluoropyrrolidin-1-yl)methyl, azetidin-1-ylmethyl, methyl(oxetan-3-yl)amino)methyl, (4-(oxetan-3-yl)piperazin-1-yl)methyl, (3-((dimethylamino)methyl)pyrrolidin-1-yl)methyl, 2-(4-methylpiperazin-1-yl)ethoxy, 3-(dimethylamino)pyrrolidine-1-carbonyl, cyano, 4-methylpiperazin-1-yl, N-morpholinyl, hydroxymethyl, (4-methylpiperazin-1-yl)methyl and (1-methylpyrrolidin-3-yl)oxy.

In another particularly preferred embodiment the present invention refers to a compound of formula (Iab) wherein Hy is selected from the group consisting of 6-((dimethylamino)methyl)imidazo[1,2-a]pyridine-3-yl, 6-(2-hydroxyethoxy)imidazo[1,2-a]pyridine-3-yl, 6-(6-methyl-2,6-diazaspiro[3.3]heptan-2-yl)imidazo[1,2-a]pyridine-3-yl, 6-(1-methyl-1,2,3,6-tetrahydropyridin-4-yl)imidazo[1,2-a]pyridine-3-yl, 6-(4-methylpiperazin-1-yl)imidazo[1,2-a]pyridine-3-yl and 6-(2-morpholinoethoxy)imidazo[1,2-a]pyridine-3-yl, $R_2$ is trifluoromethyl, and $R_3$ H.

According to a preferred embodiment, the invention refers to at least one of the compounds of Formula (Iab) listed in the Table 2 below and pharmaceutically acceptable salts thereof.

TABLE 2

List of compounds of Formula (Iab)

| Example No. | Structure | Chemical Name |
|---|---|---|
| 1 | 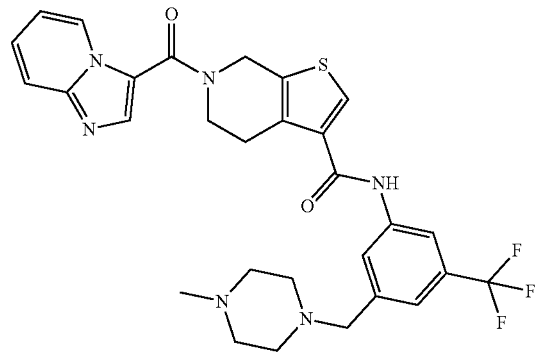 [SMILES: CN1CCN(Cc2cc(NC(=O)c3csc4c3CCN(C(=O)c3cnc5ccccn35)C4)cc(C(F)(F)F)c2)CC1] | 6-(imidazo[1,2-a]pyridine-3-carbonyl)-N-(3-((4-methylpiperazin-1-yl)methyl)-5-(trifluoromethyl)phenyl)-4,5,6,7-tetrahydrothieno-[2,3-c]pyridine-3-carboxamide |

TABLE 2-continued

| List of compounds of Formula (Iab) | | |
|---|---|---|
| Example No. | Structure | Chemical Name |
| 7 | 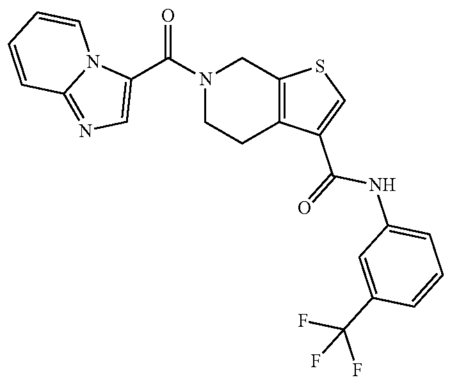 [SMILES: O=C(Nc1cccc(C(F)(F)F)c1)c1csc2c1CCN(C(=O)c1cnc3ccccn13)C2] | 6-(imidazo[1,2-a]pyridine-3-carbonyl)-N-(3-(trifluoromethyl)phenyl)-4,5,6,7-tetrahydrothieno[2,3-c]pyridine-3-carboxamide |
| 8 | 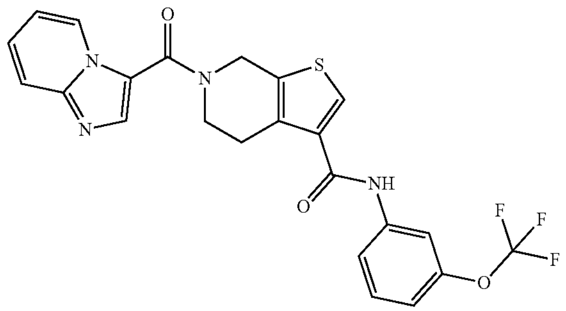 [SMILES: O=C(Nc1cccc(OC(F)(F)F)c1)c1csc2c1CCN(C(=O)c1cnc3ccccn13)C2] | 6-(imidazo[1,2-a]pyridine-3-carbonyl)-N-(3-(trifluoromethoxy)phenyl)-4,5,6,7-tetrahydrothieno[2,3-c]pyridine-3-carboxamide |
| 10 | 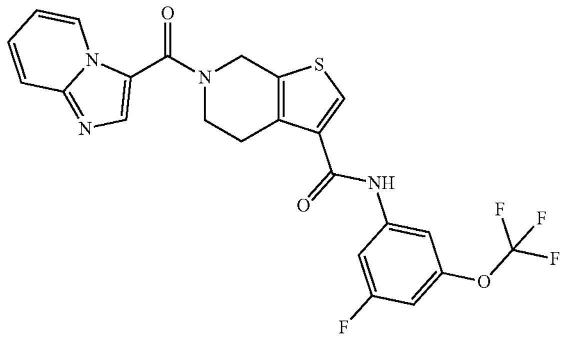 [SMILES: O=C(Nc1cc(F)cc(OC(F)(F)F)c1)c1csc2c1CCN(C(=O)c1cnc3ccccn13)C2] | N-(3-fluoro-5-(trifluoromethoxy)phenyl)-6-(imidazo[1,2-a]pyridine-3-carbonyl)-4,5,6,7-tetrahydrothieno[2,3-c]pyridine-3-carboxamide |
| 11 | 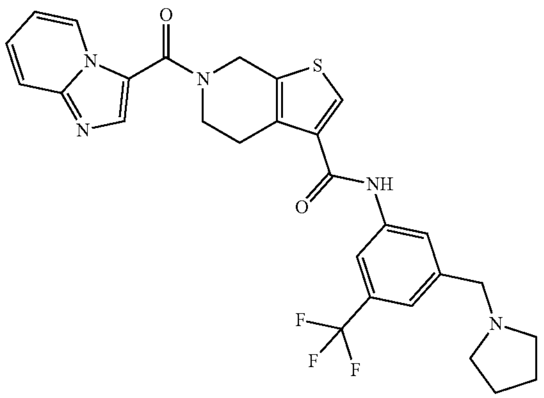 [SMILES: O=C(Nc1cc(CN2CCCC2)cc(C(F)(F)F)c1)c1csc2c1CCN(C(=O)c1cnc3ccccn13)C2] | 6-(imidazo[1,2-a]pyridine-3-carbonyl)-N-(3-pyrrolidin-1-ylmethyl)-5-(trifluoromethyl)phenyl)-4,5,6,7-tetrahydrothieno-[2,3-c]pyridine-3-carboxamide |

TABLE 2-continued

List of compounds of Formula (Iab)

| Example No. | Structure | Chemical Name |
|---|---|---|
| 19 | 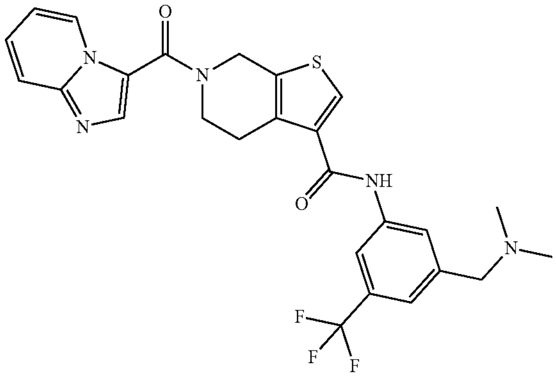 [SMILES: CN(C)Cc1cc(NC(=O)c2csc3c2CCN(C(=O)c2cnc4ccccn24)C3)cc(C(F)(F)F)c1] | N-(3-((dimethylamino)-methyl)-5-(trifluoromethyl)phenyl)-6-(imidazo[1,2-a]pyridine-3-carbonyl)-4,5,6,7-tetrahydrothieno-[2,3-c]pyridine-3-carboxamide |
| 20 | 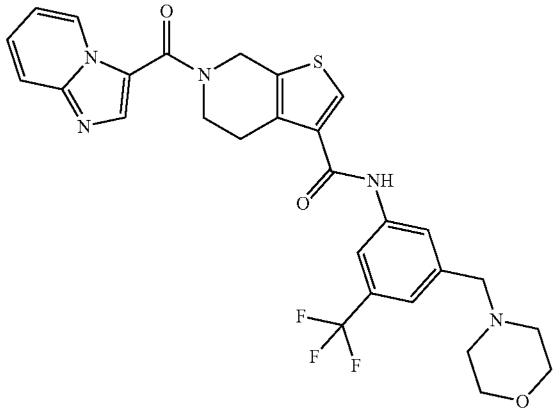 [SMILES: O=C(Nc1cc(CN2CCOCC2)cc(C(F)(F)F)c1)c1csc2c1CCN(C(=O)c1cnc3ccccn13)C2] | 6-(imidazo[1,2-a]pyridine-3-carbonyl)-N-(3-(morpholinomethyl)-5-(trifluoromethyl)phenyl)-4,5,6,7-tetrahydrothieno[2,3-c]-pyridine-3-carboxamide |
| 24 | 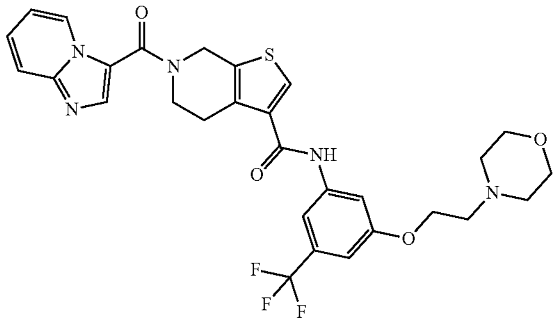 [SMILES: O=C(Nc1cc(OCCN2CCOCC2)cc(C(F)(F)F)c1)c1csc2c1CCN(C(=O)c1cnc3ccccn13)C2] | 6-(imidazo[1,2-a]pyridine-3-carbonyl)-N-(3-(2-morpholinoethoxy)-5-(trifluoromethyl)phenyl)-4,5,6,7-tetrahydrothieno[2,3-c]pyridine-3-carboxamide |
| 25 | 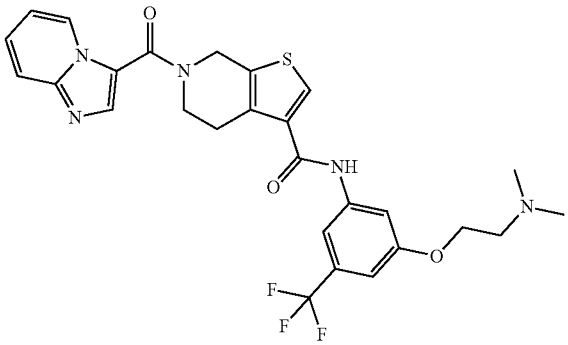 [SMILES: CN(C)CCOc1cc(NC(=O)c2csc3c2CCN(C(=O)c2cnc4ccccn24)C3)cc(C(F)(F)F)c1] | N-(3-(2-(dimethylamino)-ethoxy)-5-(trifluoromethyl)phenyl)-6-(imidazo[1,2-a]pyridine-3-carbonyl)-4,5,6,7-tetrahydrothieno-[2,3-c]pyridine-3-carboxamide |

TABLE 2-continued

| List of compounds of Formula (Iab) | | |
|---|---|---|
| Example No. | Structure | Chemical Name |
| 26 | 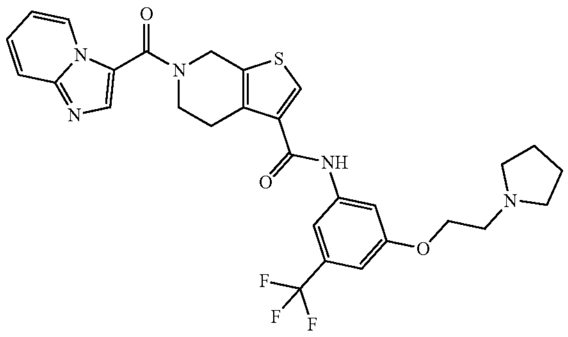 [SMILES: O=C(Nc1cc(OCCN2CCCC2)cc(C(F)(F)F)c1)c1csc2c1CCN(C(=O)c1cnc3ccccn13)C2] | 6-(imidazo[1,2-a]pyridine-3-carbonyl)-N-(3-(2-(pyrrolidin-1-yl)ethoxy)-5-(trifluoromethyl)phenyl)-4,5,6,7-tetrahydrothieno-[2,3-c]pyridine-3-carboxamide |
| 44 | 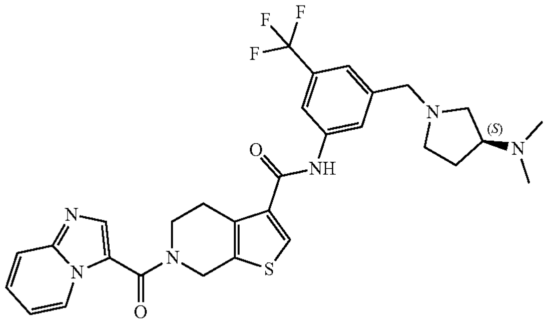 | (S)-N-(3-((3-(dimethylamino)pyrrolidin-1-yl)-methyl)-5-(trifluoromethyl)phenyl)-6-(imidazo[1,2-a]pyridine-3-carbonyl)-4,5,6,7-tetrahydrothieno-[2,3-c]pyridine-3-carboxamide |
| 45 | 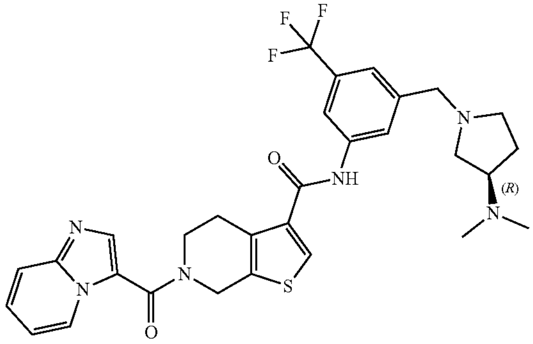 | (R)-N-(3-((3-(dimethylamino)pyrrolidin-1-yl)-methyl)-5-(trifluoromethyl)-phenyl)-6-(imidazo[1,2-a]pyridine-3-carbonyl)-4,5,6,7-tetrahydrothieno-[2,3-c]pyridine-3-carboxamide |
| 46 | 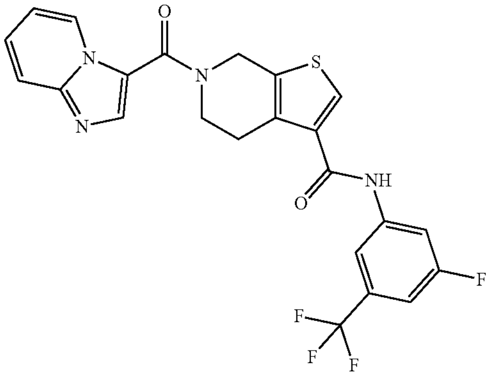 [SMILES: O=C(Nc1cc(F)cc(C(F)(F)F)c1)c1csc2c1CCN(C(=O)c1cnc3ccccn13)C2] | N-(3-fluoro-5-(trifluoromethyl)phenyl)-6-(imidazo-[1,2-a]pyridine-3-carbonyl)-4,5,6,7-tetrahydrothieno-[2,3-c]pyridine-3-carboxamide |

TABLE 2-continued

| List of compounds of Formula (Iab) | | |
|---|---|---|
| Example No. | Structure | Chemical Name |
| 48 | 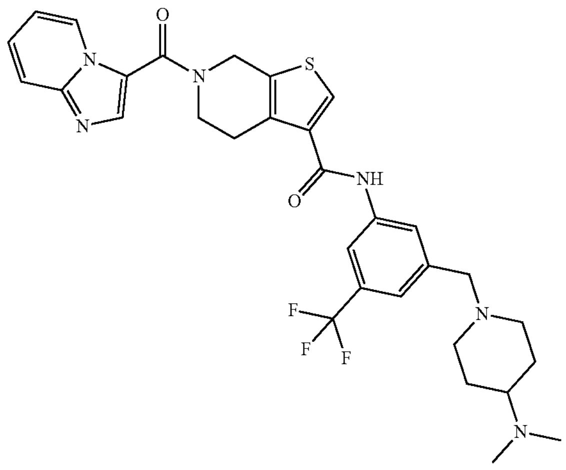 [SMILES: CN(C)C1CCN(Cc2cc(NC(=O)c3csc4c3CCN(C(=O)c3cnc5ccccn35)C4)cc(C(F)(F)F)c2)CC1] | N-(3-((4-(dimethylamino)-piperidin-1-yl)methyl)-5-(trifluoromethyl)phenyl)-6-(imidazo[1,2-a]pyridine-3-carbonyl)-4,5,6,7-tetra-hydrothieno[2,3-c]pyridine-3-carboxamide |
| 49 | 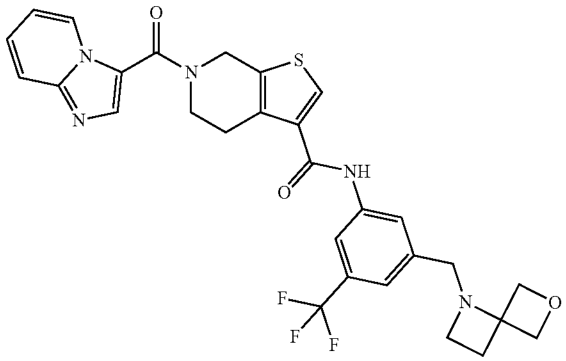 [SMILES: O=C(Nc1cc(CN2CCC23COC3)cc(C(F)(F)F)c1)c1csc2c1CCN(C(=O)c1cnc3ccccn13)C2] | N-(3-((6-oxa-1-azaspiro-[3.3]heptan-1-yl)methyl)-5-(trifluoromethyl)phenyl)-6-(imidazo[1,2-a]pyridine-3-carbonyl)-4,5,6,7-tetra-hydrothieno[2,3-c]pyridine-3-carboxamide |
| 50 | 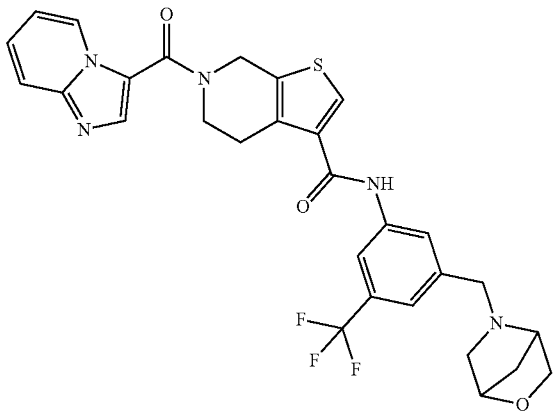 [SMILES: O=C(Nc1cc(CN2CC3CC2CO3)cc(C(F)(F)F)c1)c1csc2c1CCN(C(=O)c1cnc3ccccn13)C2] | N-(3-((2-oxa-5-azabicyclo-[2.2.1]heptan-5-yl)methyl)-5-(trifluoromethyl)phenyl)-6-(imidazo[1,2-a]pyridine-3-carbonyl)-4,5,6,7-tetra-hydrothieno[2,3-c]pyridine-3-carboxamide |

TABLE 2-continued

| List of compounds of Formula (Iab) | | |
|---|---|---|
| Example No. | Structure | Chemical Name |
| 51 | 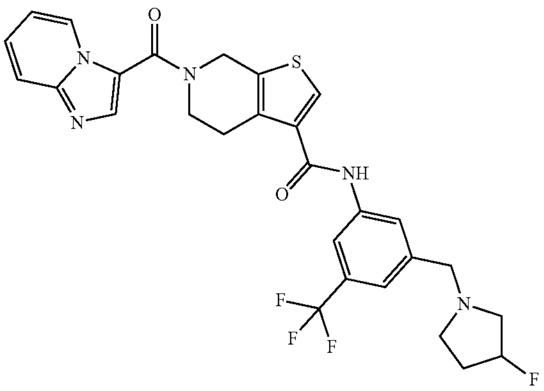 [SMILES: O=C(Nc1cc(CN2CCC(F)C2)cc(C(F)(F)F)c1)c1csc2c1CCN(C(=O)c1cnc3ccccn13)C2] | N-(3-((3-fluoropyrrolidin-1-yl)methyl)-5-(trifluoro-methyl)phenyl)-6-(imidazo-[1,2-a]pyridine-3-carbonyl)-4,5,6,7-tetrahydrothieno-[2,3-c]pyridine-3-carbox-amide |
| 52 | 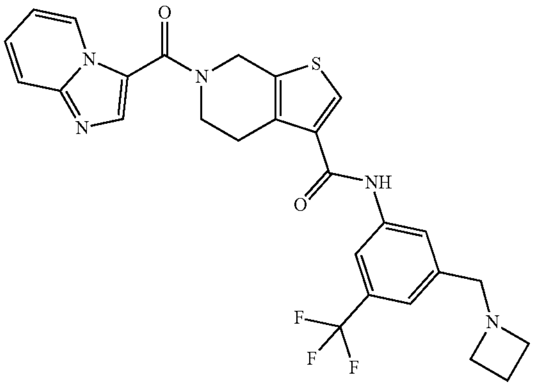 [SMILES: O=C(Nc1cc(CN2CCC2)cc(C(F)(F)F)c1)c1csc2c1CCN(C(=O)c1cnc3ccccn13)C2] | N-(3-(azetidin-1-ylmeth-yl)-5-(trifluoromethyl)-phenyl)-6-(imidazo[1,2-a]-pyridine-3-carbonyl)-4,5,6,7-tetrahydrothieno-[2,3-c]pyridine-3-carbox-amide |
| 53 | 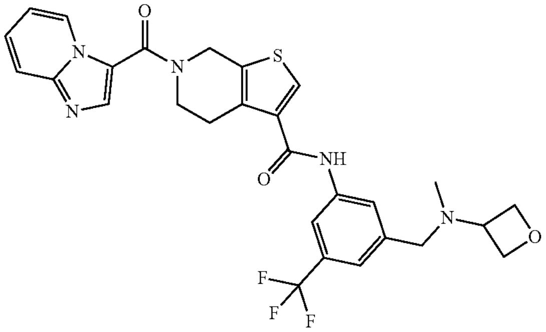 [SMILES: CN(Cc1cc(NC(=O)c2csc3c2CCN(C(=O)c2cnc4ccccn24)C3)cc(C(F)(F)F)c1)C1COC1] | 6-(imidazo[1,2-a]pyridine-3-carbonyl)-N-(3-((methyl-(oxetan-3-yl)amino)meth-yl)-5-(trifluoromethyl)-phenyl)-4,5,6,7-tetrahydro-thieno[2,3-c]pyridine-3-carboxamide |

TABLE 2-continued

List of compounds of Formula (Iab)

| Example No. | Structure | Chemical Name |
|---|---|---|
| 54 | 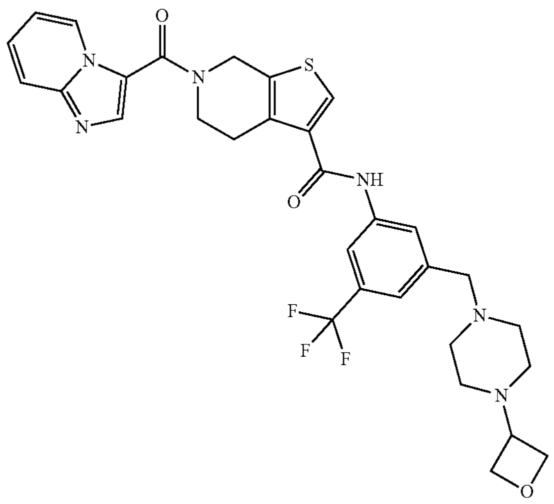 [SMILES: O=C(Nc1cc(CN2CCN(C3COC3)CC2)cc(C(F)(F)F)c1)c1csc2c1CCN(C(=O)c1cnc3ccccn13)C2] | 6-(imidazo[1,2-a]pyridine-3-carbonyl)-N-(3-((4-(oxetan-3-yl)piperazin-1-yl)methyl)-5-(trifluoro-methyl)phenyl)-4,5,6,7-tetrahydrothieno[2,3-c]-pyridine-3-carboxamide |
| 55 | 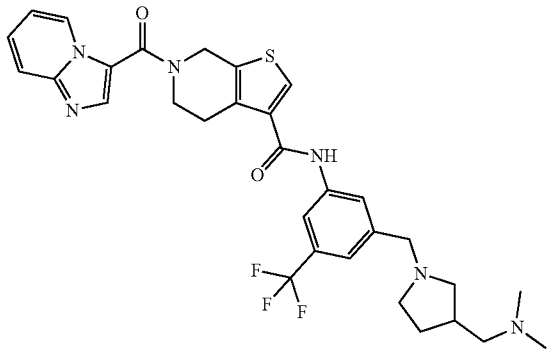 [SMILES: CN(C)CC1CCN(Cc2cc(NC(=O)c3csc4c3CCN(C(=O)c3cnc5ccccn35)C4)cc(C(F)(F)F)c2)C1] | N-(3-((3-((dimethylamino)-methyl)pyrrolidin-1-yl)-methyl)-5-(trifluorometh-yl)phenyl)-6-(imidazo[1,2-a]pyridine-3-carbonyl)-4,5,6,7-tetrahydrothieno-[2,3-c]pyridine-3-carbox-amide |
| 56 | 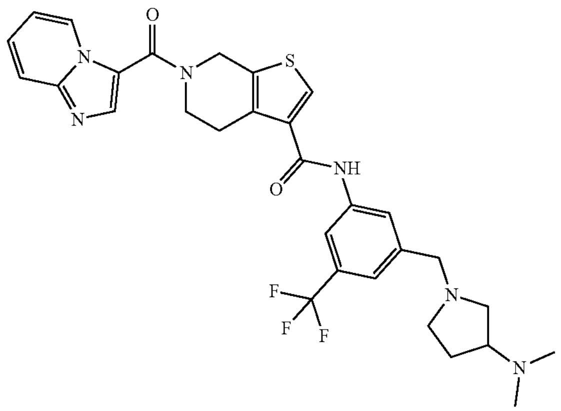 [SMILES: CN(C)C1CCN(Cc2cc(NC(=O)c3csc4c3CCN(C(=O)c3cnc5ccccn35)C4)cc(C(F)(F)F)c2)C1] | N-(3-((3-(dimethylamino)-pyrrolidin-1-yl)methyl)-5-(trifluoromethyl)phenyl)-6-(imidazo[1,2-a]pyridine-3-carbonyl)-4,5,6,7-tetra-hydrothieno[2,3-c]pyridine-3-carboxamide |

TABLE 2-continued

| List of compounds of Formula (Iab) | | |
|---|---|---|
| Example No. | Structure | Chemical Name |
| 57 | 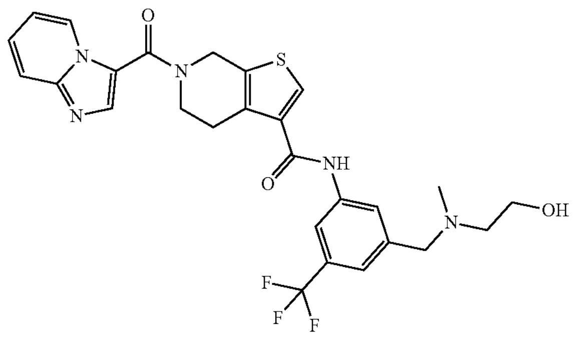 [SMILES: CN(CCO)Cc1cc(NC(=O)c2csc3c2CCN(C(=O)c2cnc4ccccn24)C3)cc(C(F)(F)F)c1] | N-(3-(((2-hydroxyethyl)-(methyl)amino)methyl)-5-(trifluoromethyl)phenyl)-6-(imidazo[1,2-a]pyridine-3-carbonyl)-4,5,6,7-tetra-hydrothieno[2,3-c]pyridine-3-carboxamide |
| 58 | 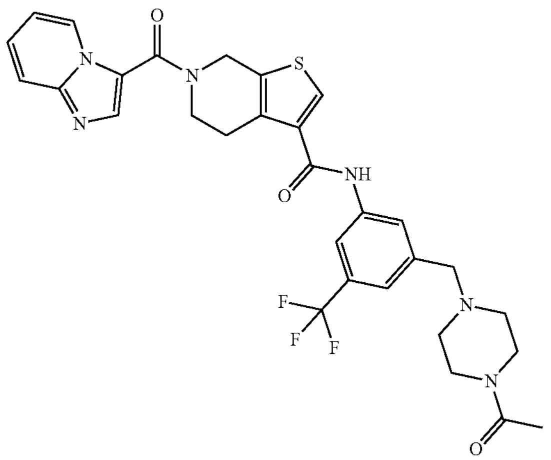 [SMILES: CC(=O)N1CCN(Cc2cc(NC(=O)c3csc4c3CCN(C(=O)c3cnc5ccccn35)C4)cc(C(F)(F)F)c2)CC1] | N-(3-((4-acetylpiperazin-1-yl)methyl)-5-(trifluoro-methyl)phenyl)-6-(imid-azo[1,2-a]pyridine-3-carbonyl)-4,5,6,7-tetra-hydrothieno[2,3-c]pyridine-3-carboxamide |
| 59 | 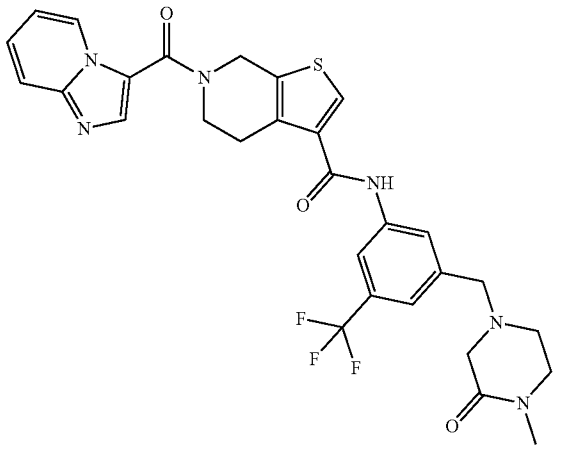 [SMILES: CN1CCN(Cc2cc(NC(=O)c3csc4c3CCN(C(=O)c3cnc5ccccn35)C4)cc(C(F)(F)F)c2)CC1=O] | 6-(imidazo[1,2-a]pyridine-3-carbonyl)-N-(3-((4-methyl-3-oxopiperazin-1-yl)methyl)-5-(trifluoro-methyl)phenyl)-4,5,6,7-tetrahydrothieno[2,3-c]-pyridine-3-carboxamide |

TABLE 2-continued

| List of compounds of Formula (Iab) | | |
|---|---|---|
| Example No. | Structure | Chemical Name |
| 60 | 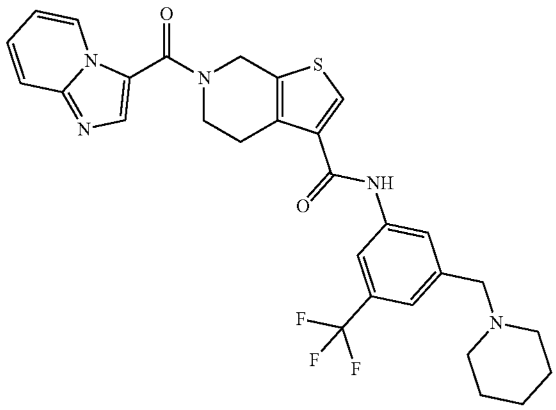 [SMILES: O=C(Nc1cc(CN2CCCCC2)cc(C(F)(F)F)c1)c1csc2c1CCN(C(=O)c1cnc3ccccn13)C2] | 6-(imidazo[1,2-a]pyridine-3-carbonyl)-N-(3-(piperidin-1-ylmethyl)-5-(trifluoromethyl)phenyl)-4,5,6,7-tetrahydrothieno-[2,3-c]pyridine-3-carboxamide |
| 61 | 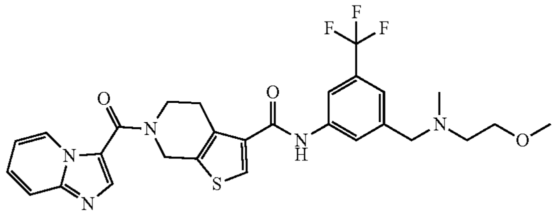 [SMILES: COCCN(C)Cc1cc(NC(=O)c2csc3c2CCN(C(=O)c2cnc4ccccn24)C3)cc(C(F)(F)F)c1] | 6-(imidazo[1,2-a]pyridine-3-carbonyl)-N-(3-(((2-methoxyethyl)(methyl)-amino)methyl)-5-(trifluoromethyl)phenyl)-4,5,6,7-tetrahydrothieno[2,3-c]-pyridine-3-carboxamide |
| 62 | 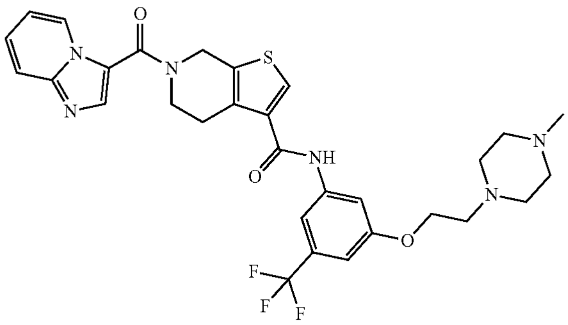 [SMILES: CN1CCN(CCOc2cc(NC(=O)c3csc4c3CCN(C(=O)c3cnc5ccccn35)C4)cc(C(F)(F)F)c2)CC1] | 6-(imidazo[1,2-a]pyridine-3-carbonyl)-N-(3-(2-(4-methylpiperazin-1-yl)-ethoxy)-5-(trifluoromethyl)phenyl)-4,5,6,7-tetrahydrothieno[2,3-c]pyridine-3-carboxamide |
| 63 | 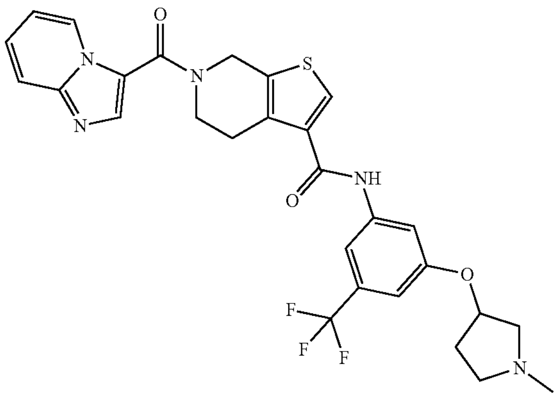 [SMILES: CN1CCC(Oc2cc(NC(=O)c3csc4c3CCN(C(=O)c3cnc5ccccn35)C4)cc(C(F)(F)F)c2)C1] | 6-(imidazo[1,2-a]pyridine-3-carbonyl)-N-(3-((1-methylpyrrolidin-3-yl)oxy)-5-(trifluoromethyl)phenyl)-4,5,6,7-tetrahydrothieno-[2,3-c]pyridine-3-carboxamide |

TABLE 2-continued

List of compounds of Formula (Iab)

| Example No. | Structure | Chemical Name |
|---|---|---|
| 68 | 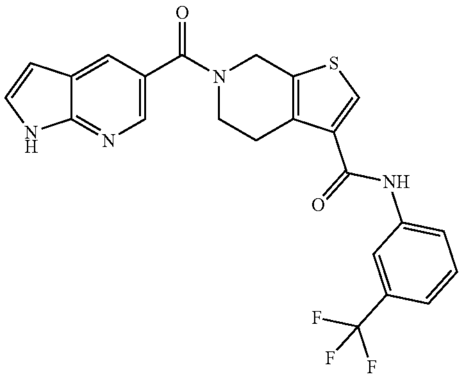 [SMILES: O=C(Nc1cccc(C(F)(F)F)c1)c1csc2c1CCN(C(=O)c1cnc3[nH]ccc3c1)C2] | 6-(1H-pyrrolo[2,3-b]pyridine-5-carbonyl)-N-(3-(trifluoromethyl)phenyl)-4,5,6,7-tetrahydrothieno-[2,3-c]pyridine-3-carboxamide |
| 74 | 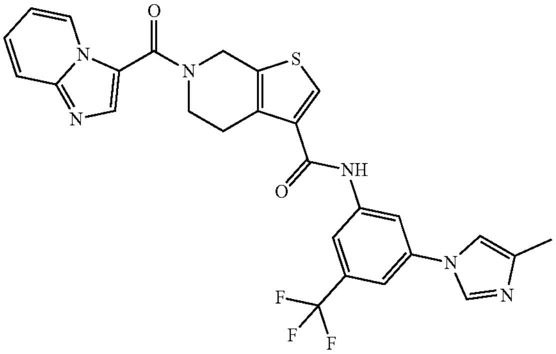 [SMILES: Cc1cn(-c2cc(NC(=O)c3csc4c3CCN(C(=O)c3cnc5ccccn35)C4)cc(C(F)(F)F)c2)cn1] | 6-(imidazo[1,2-a]pyridine-3-carbonyl)-N-(3-(4-methyl-1H-imidazol-1-yl)-5-(trifluoromethyl)phenyl)-4,5,6,7-tetrahydrothieno-[2,3-c]pyridine-3-carboxamide |
| 90 | 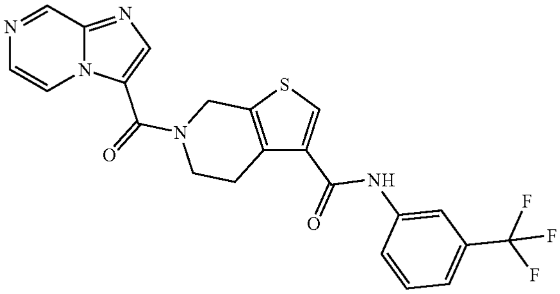 [SMILES: O=C(Nc1cccc(C(F)(F)F)c1)c1csc2c1CCN(C(=O)c1cnc3cnccn13)C2] | 6-(imidazo[1,2-a]pyrazine-3-carbonyl)-N-(3-(trifluoromethyl)phenyl)-4,5,6,7-tetrahydrothieno-[2,3-c]pyridine-3-carboxamide |
| 91 | 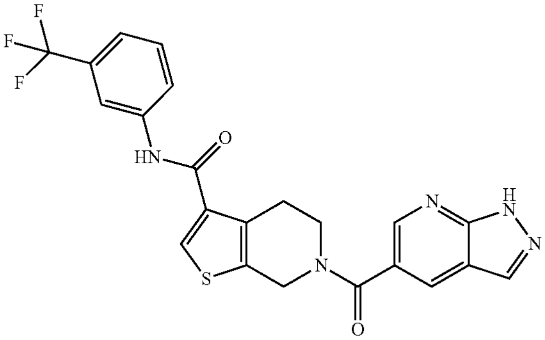 [SMILES: O=C(Nc1cccc(C(F)(F)F)c1)c1csc2c1CCN(C(=O)c1cnc3[nH]ncc3c1)C2] | 6-(1H-pyrazolo[3,4-b]pyridine-5-carbonyl)-N-(3-(trifluoromethyl)phenyl)-4,5,6,7-tetrahydrothieno-[2,3-c]pyridine-3-carboxamide |

TABLE 2-continued

| List of compounds of Formula (Iab) | | |
|---|---|---|
| Example No. | Structure | Chemical Name |
| 92 | 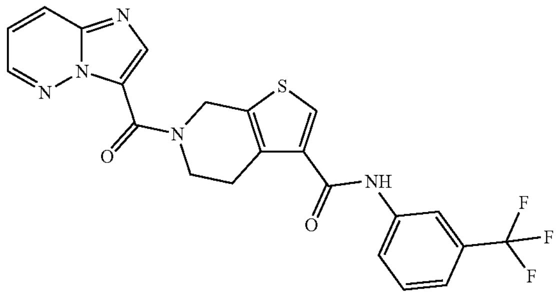 [SMILES: O=C(Nc1cccc(C(F)(F)F)c1)c1csc2c1CCN(C(=O)c1cnc3cccnn13)C2] | 6-(imidazo[1,2-b]pyridazine-3-carbonyl)-N-(3-(trifluoromethyl)phenyl)-4,5,6,7-tetrahydrothieno-[2,3-c]pyridine-3-carboxamide |
| 93 | 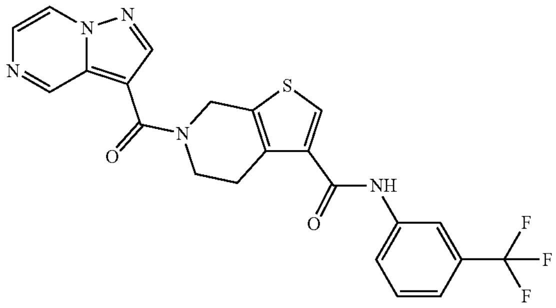 [SMILES: O=C(Nc1cccc(C(F)(F)F)c1)c1csc2c1CCN(C(=O)c1cnn3ccncc13)C2] | 6-(pyrazolo[1,5-a]pyrazine-3-carbonyl)-N-(3-(trifluoromethyl)phenyl)-4,5,6,7-tetrahydrothieno[2,3-c]pyridine-3-carboxamide |
| 94 | 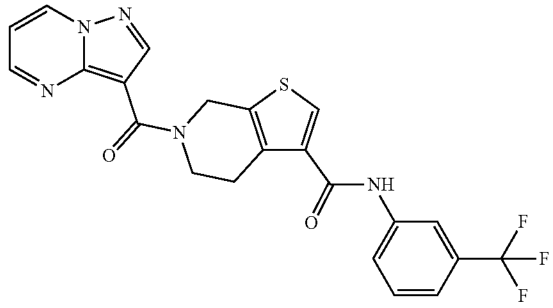 [SMILES: O=C(Nc1cccc(C(F)(F)F)c1)c1csc2c1CCN(C(=O)c1cnn3cccnc13)C2] | 6-(pyrazolo[1,5-a]pyrimidine-3-carbonyl)-N-(3-(trifluoromethyl)phenyl)-4,5,6,7-tetrahydrothieno-[2,3-c]pyridine-3-carboxamide |
| 95 | 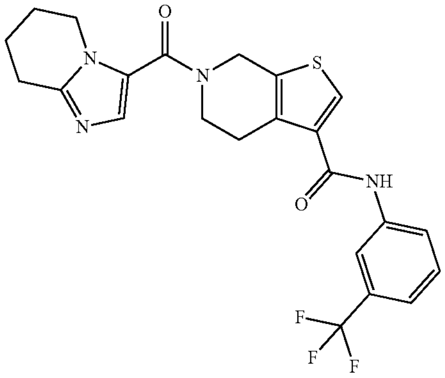 [SMILES: O=C(Nc1cccc(C(F)(F)F)c1)c1csc2c1CCN(C(=O)c1cnc3n1CCCC3)C2] | 6-(5,6,7,8-tetrahydroimidazo[1,2-a]pyridine-3-carbonyl)-N-(3-(trifluoromethyl)phenyl)-4,5,6,7-tetrahydrothieno[2,3-c]pyridine-3-carboxamide |

TABLE 2-continued

| List of compounds of Formula (Iab) | | |
|---|---|---|
| Example No. | Structure | Chemical Name |
| 96 | 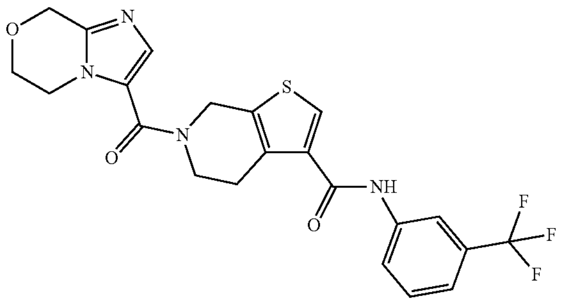 [SMILES: O=C(Nc1cccc(C(F)(F)F)c1)c1csc2c1CCN(C(=O)c1cnc3n1CCOC3)C2] | 6-(5,6-dihydro-8H-imidazo[2,1-c][1,4]oxazine-3-carbonyl)-N-(3-(trifluoromethyl)phenyl)-4,5,6,7-tetrahydrothieno[2,3-c]pyridine-3-carboxamide |
| 97 | 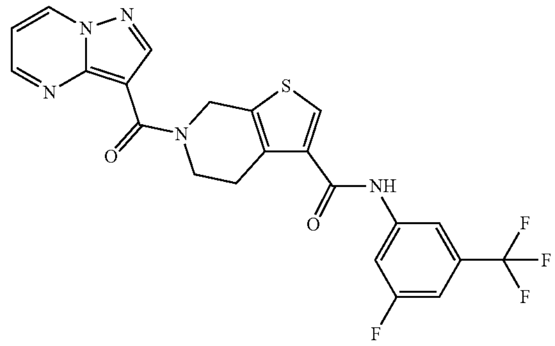 [SMILES: O=C(Nc1cc(F)cc(C(F)(F)F)c1)c1csc2c1CCN(C(=O)c1cnn3cccnc13)C2] | N-(3-fluoro-5-(trifluoromethyl)phenyl)-6-(pyrazolo[1,5-a]pyrimidine-3-carbonyl)-4,5,6,7-tetrahydrothieno[2,3-c]pyridine-3-carboxamide |
| 98 | 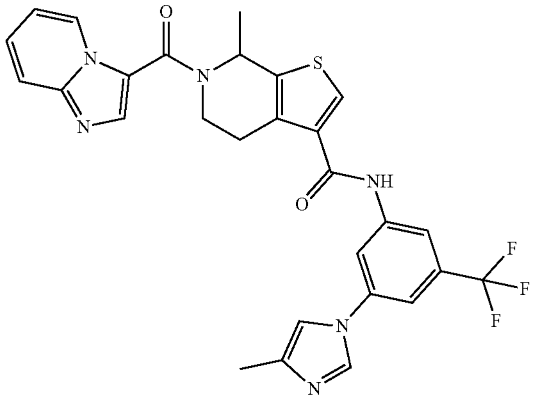 [SMILES: Cc1cn(-c2cc(NC(=O)c3csc4c3CCN(C(=O)c3cnc5ccccn35)C4C)cc(C(F)(F)F)c2)cn1] | 6-(imidazo[1,2-a]pyridine-3-carbonyl)-7-methyl-N-(3-(4-methyl-1H-imidazol-1-yl)-5-(trifluoromethyl)phenyl)-4,5,6,7-tetrahydrothieno[2,3-c]pyridine-3-carboxamide |
| 100 | 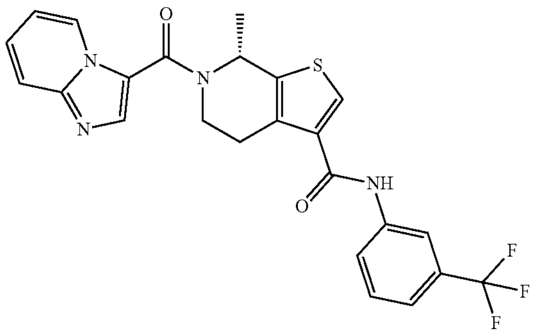 [SMILES: C[C@@H]1c2scc(C(=O)Nc3cccc(C(F)(F)F)c3)c2CCN1C(=O)c1cnc2ccccn12] | (R)-6-(imidazo[1,2-a]pyridine-3-carbonyl)-7-methyl-N-(3-(trifluoromethyl)phenyl)-4,5,6,7-tetrahydrothieno[2,3-c]pyridine-3-carboxamide |

TABLE 2-continued

| List of compounds of Formula (Iab) | | |
|---|---|---|
| Example No. | Structure | Chemical Name |
| 101 | 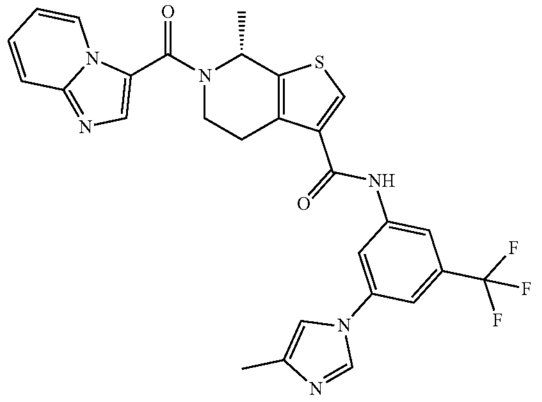 | (R)-6-(imidazo[1,2-a]pyridine-3-carbonyl)-7-methyl-N-(3-(4-methyl-1H-imidazol-1-yl)-5-(trifluoromethyl)phenyl)-4,5,6,7-tetrahydrothieno[2,3-c]pyridine-3-carboxamide |
| 102 | 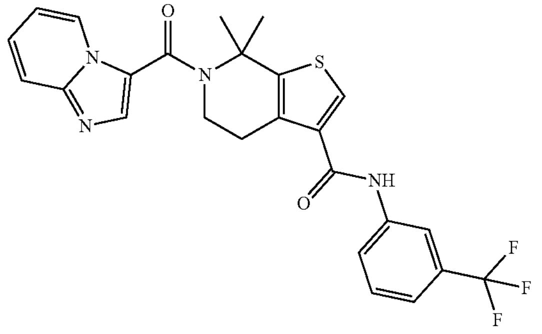 [SMILES: CC1(C)c2scc(C(=O)Nc3cccc(C(F)(F)F)c3)c2CCN1C(=O)c1cnc2ccccn12] | 6-(imidazo[1,2-a]pyridine-3-carbonyl)-7,7-dimethyl-N-(3-(trifluoromethyl)-phenyl)-4,5,6,7-tetrahydro-thieno[2,3-c]pyridine-3-carboxamide |
| 130 | 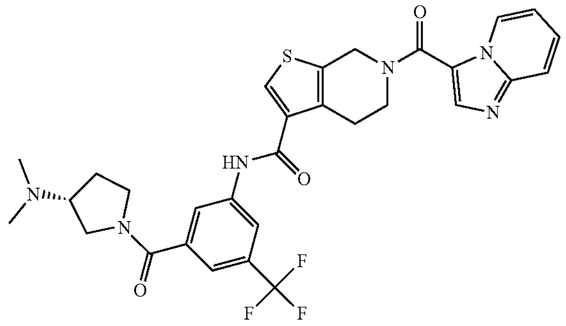 [SMILES: CN(C)[C@@H]1CCN(C(=O)c2cc(NC(=O)c3csc4c3CCN(C(=O)c3cnc5ccccn35)C4)cc(C(F)(F)F)c2)C1] | (R)-N-(3-(3-(dimethylamino)pyrrolidine-1-carbonyl)-5-(trifluoromethyl)phenyl)-6-(imidazo[1,2-a]pyridine-3-carbonyl)-4,5,6,7-tetrahydrothieno-[2,3-c]pyridine-3-carboxamide |
| 131 | 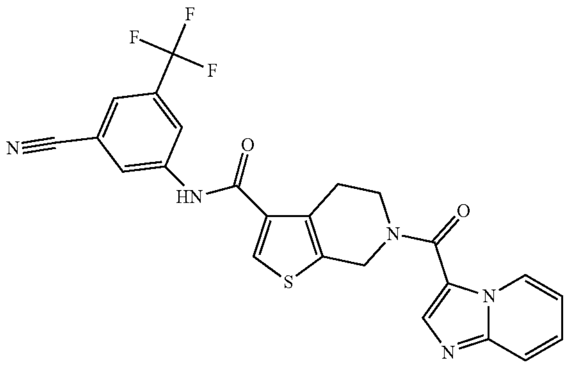 [SMILES: N#Cc1cc(NC(=O)c2csc3c2CCN(C(=O)c2cnc4ccccn24)C3)cc(C(F)(F)F)c1] | N-(3-cyano-5-(trifluoromethyl)phenyl)-6-(imidazo[1,2-a]pyridine-3-carbonyl)-4,5,6,7-tetrahydrothieno[2,3-c]pyridine-3-carboxamide |

TABLE 2-continued

| List of compounds of Formula (Iab) | | |
|---|---|---|
| Example No. | Structure | Chemical Name |
| 135 | 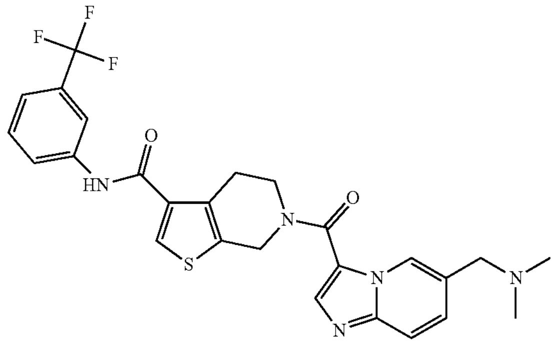 [SMILES: CN(C)Cc1ccc2ncc(C(=O)N3CCc4c(C(=O)Nc5cccc(C(F)(F)F)c5)csc4C3)n2c1] | 6-(6-((dimethylamino)-methyl)imidazo[1,2-a]pyridine-3-carbonyl)-N-(3-(trifluoromethyl)phenyl)-4,5,6,7-tetrahydrothieno-[2,3-c]pyridine-3-carboxamide |
| 136 | 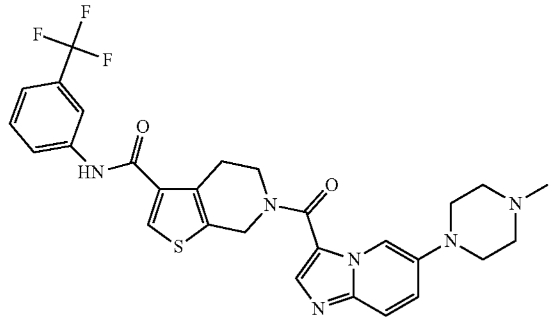 [SMILES: CN1CCN(c2ccc3ncc(C(=O)N4CCc5c(C(=O)Nc6cccc(C(F)(F)F)c6)csc5C4)n3c2)CC1] | 6-(6-(4-methylpiperazin-1-yl)imidazo[1,2-a]pyridine-3-carbonyl)-N-(3-(trifluoromethyl)phenyl)-4,5,6,7-tetrahydrothieno-[2,3-c]pyridine-3-carboxamide |
| 137 | 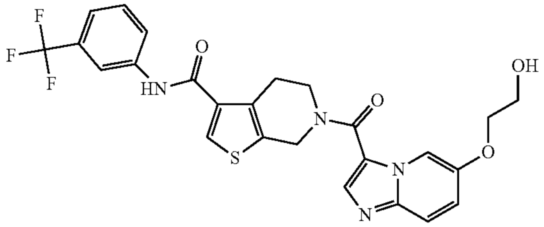 [SMILES: O=C(Nc1cccc(C(F)(F)F)c1)c1csc2c1CCN(C(=O)c1cnc3ccc(OCCO)cn13)C2] | 6-(6-(2-hydroxyethoxy)-imidazo[1,2-a]pyridine-3-carbonyl)-N-(3-(trifluoro-methyl)phenyl)-4,5,6,7-tetrahydrothieno[2,3-c]pyridine-3-carboxamide |
| 138 | 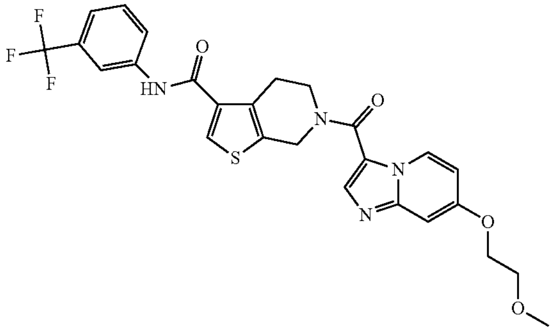 [SMILES: COCCOc1ccn2c(C(=O)N3CCc4c(C(=O)Nc5cccc(C(F)(F)F)c5)csc4C3)cnc2c1] | 6-(7-(2-methoxyethoxy)-imidazo[1,2-a]pyridine-3-carbonyl)-N-(3-(trifluoro-methyl)phenyl)-4,5,6,7-tetrahydrothieno[2,3-c]pyridine-3-carboxamide |

TABLE 2-continued

List of compounds of Formula (Iab)

| Example No. | Structure | Chemical Name |
| --- | --- | --- |
| 139 | 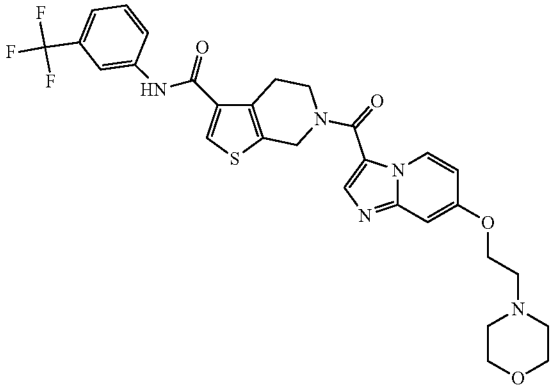 [SMILES: O=C(Nc1cccc(C(F)(F)F)c1)c1csc2c1CCN(C(=O)c1cnc3cc(OCCN4CCOCC4)ccn13)C2] | 6-(7-(2-morpholinoethoxy)-imidazo[1,2-a]pyridine-3-carbonyl)-N-(3-(trifluoro-methyl)phenyl)-4,5,6,7-tetrahydrothieno[2,3-c]pyr-idine-3-carboxamide |
| 162 | 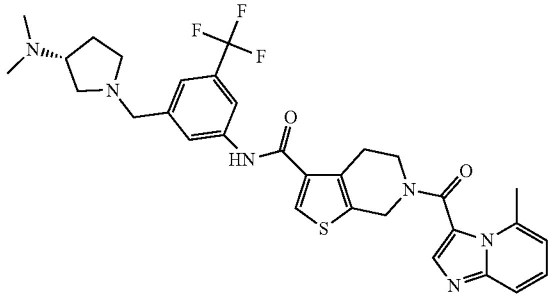 [SMILES: Cc1cccc2ncc(C(=O)N3CCc4c(C(=O)Nc5cc(CN6CC[C@@H](N(C)C)C6)cc(C(F)(F)F)c5)csc4C3)n12] | (R)-N-(3-((3-(dimethyl-amino)pyrrolidin-1-yl)-methyl)-5-(trifluorometh-yl)phenyl)-6-(5-methyl-imidazo[1,2-a]pyridine-3-carbonyl)-4,5,6,7-tetra-hydrothieno[2,3-c]pyridine-3-carboxamide |
| 166 | 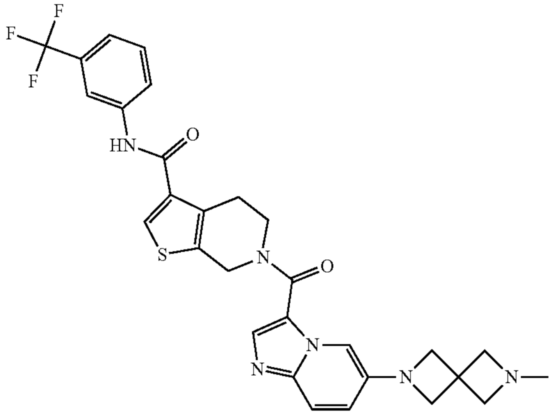 [SMILES: CN1CC2(C1)CN(c1ccc3ncc(C(=O)N4CCc5c(C(=O)Nc6cccc(C(F)(F)F)c6)csc5C4)n3c1)C2] | 6-(6-(6-methyl-2,6-diaza-spiro[3.3]heptan-2-yl)-imidazo[1,2-a]pyridine-3-carbon-yl)-N-(3-(trifluoro-methyl)phenyl)-4,5,6,7-tetrahydrothieno[2,3-c]-pyridine-3-carboxamide |

TABLE 2-continued

| List of compounds of Formula (Iab) | | |
|---|---|---|
| Example No. | Structure | Chemical Name |
| 167 | 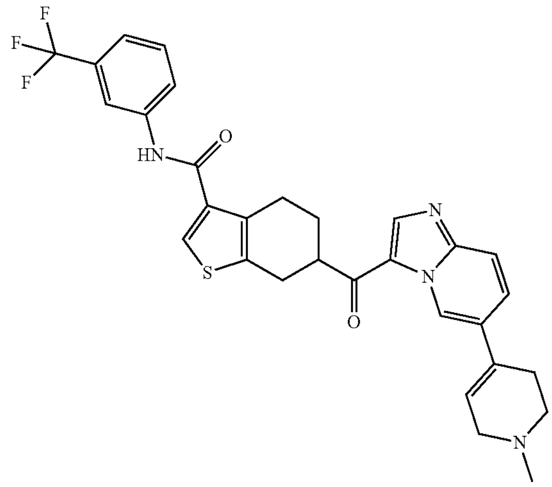 [SMILES: CN1CC=C(c2ccc3ncc(C(=O)C4CCc5c(C(=O)Nc6cccc(C(F)(F)F)c6)csc5C4)n3c2)CC1] | 6-(6-(1-methyl-1,2,3,6-tetrahydropyridin-4-yl)-imidazo[1,2-a]pyridine-3-carbonyl)-N-(3-(trifluoro-methyl)phenyl)-4,5,6,7-tetrahydrothieno[2,3-c]-pyridine-3-carboxamide |
| 170 | 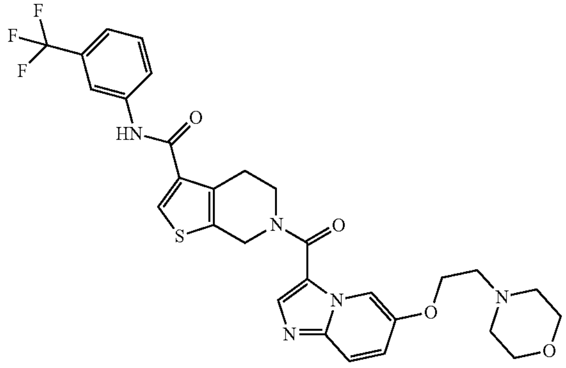 [SMILES: O=C(Nc1cccc(C(F)(F)F)c1)c1csc2c1CCN(C(=O)c1cnc3ccc(OCCN4CCOCC4)cn13)C2] | 6-(6-(2-morpholinoethoxy)-imidazo[1,2-a]pyridine-3-carbonyl)-N-(3-(trifluoro-methyl)phenyl)-4,5,6,7-tetrahydrothieno[2,3-c]-pyridine-3-carboxamide |
| 172 | 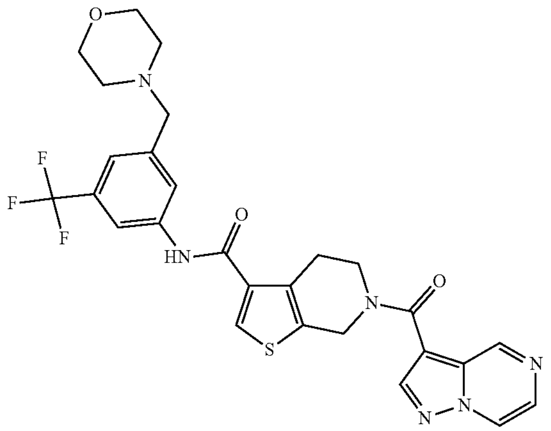 [SMILES: O=C(Nc1cc(CN2CCOCC2)cc(C(F)(F)F)c1)c1csc2c1CCN(C(=O)c1cnn3ccncc13)C2] | N-(3-(morpholinomethyl)-5-(trifluoromethyl)phenyl)-6-(pyrazolo[1,5-a]pyrazine-3-carbonyl)-4,5,6,7-tetra-hydrothieno[2,3-c]pyridine-3-carboxamide |

TABLE 2-continued

| List of compounds of Formula (Iab) | | |
|---|---|---|
| Example No. | Structure | Chemical Name |
| 177 | 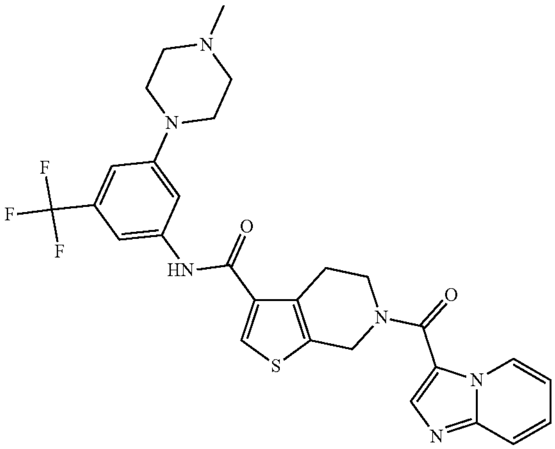 [SMILES: CN1CCN(c2cc(NC(=O)c3csc4c3CCN(C(=O)c3cnc5ccccn35)C4)cc(C(F)(F)F)c2)CC1] | 6-(imidazo[1,2-a]pyridine-3-carbonyl)-N-(3-(4-methylpiperazin-1-yl)-5-(trifluoromethyl)phenyl)-4,5,6,7-tetrahydrothieno-[2,3-c]pyridine-3-carboxamide |
| 178 | 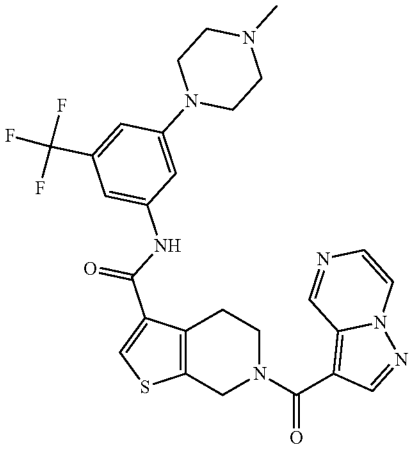 [SMILES: CN1CCN(c2cc(NC(=O)c3csc4c3CCN(C(=O)c3cnn5ccncc35)C4)cc(C(F)(F)F)c2)CC1] | N-(3-(4-methylpiperazin-1-yl)-5-(trifluoromethyl)-phenyl)-6-(pyrazolo[1,5-a]pyrazine-3-carbonyl)-4,5,6,7-tetrahydrothieno-[2,3-c]pyridine-3-carboxamide |
| 181 | 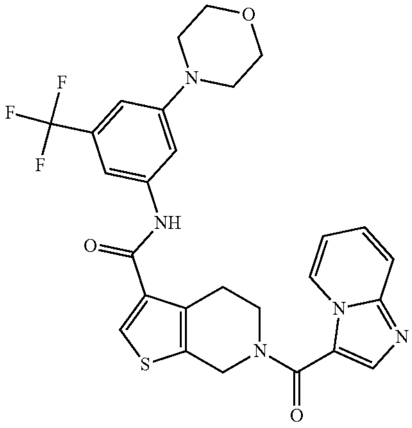 [SMILES: O=C(Nc1cc(N2CCOCC2)cc(C(F)(F)F)c1)c1csc2c1CCN(C(=O)c1cnc3ccccn13)C2] | 6-(imidazo[1,2-a]pyridine-3-carbonyl)-N-(3-morpholino-5-(trifluoromethyl)-phenyl)-4,5,6,7-tetrahydro-thieno[2,3-c]pyridine-3-carboxamide |

TABLE 2-continued

| List of compounds of Formula (Iab) | | |
|---|---|---|
| Example No. | Structure | Chemical Name |
| 182 | 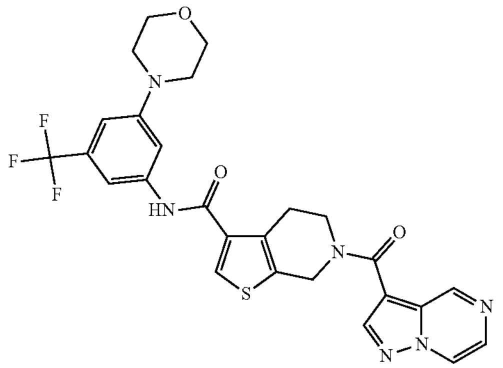 [SMILES: O=C(Nc1cc(N2CCOCC2)cc(C(F)(F)F)c1)c1csc2c1CCN(C(=O)c1cnn3ccncc13)C2] | N-(3-morpholino-5-(trifluoromethyl)phenyl)-6-(pyrazolo[1,5-a]pyrazine-3-carbonyl)-4,5,6,7-tetrahydrothieno[2,3-c]pyridine-3-carboxamide |
| 184 | 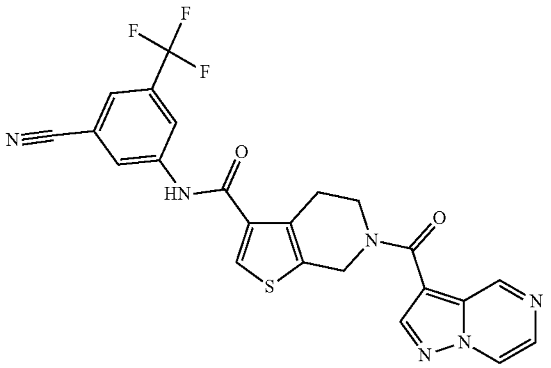 [SMILES: N#Cc1cc(NC(=O)c2csc3c2CCN(C(=O)c2cnn4ccncc24)C3)cc(C(F)(F)F)c1] | N-(3-cyano-5-(trifluoromethyl)phenyl)-6-(pyrazolo[1,5-a]pyrazine-3-carbonyl)-4,5,6,7-tetrahydrothieno[2,3-c]pyridine-3-carboxamide |
| 185 | 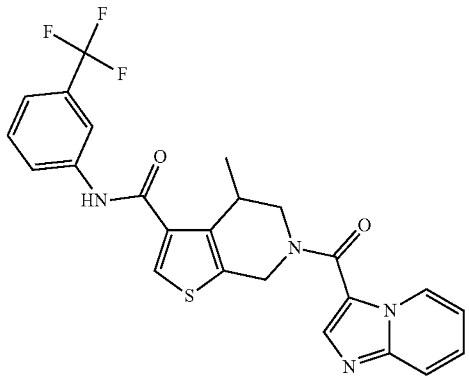 [SMILES: CC1CN(C(=O)c2cnc3ccccn23)Cc2scc(C(=O)Nc3cccc(C(F)(F)F)c3)c21] | 6-(imidazo[1,2-a]pyridine-3-carbonyl)-4-methyl-N-(3-(trifluoromethyl)phenyl)-4,5,6,7-tetrahydrothieno-[2,3-c]pyridine-3-carboxamide |
| 187 | 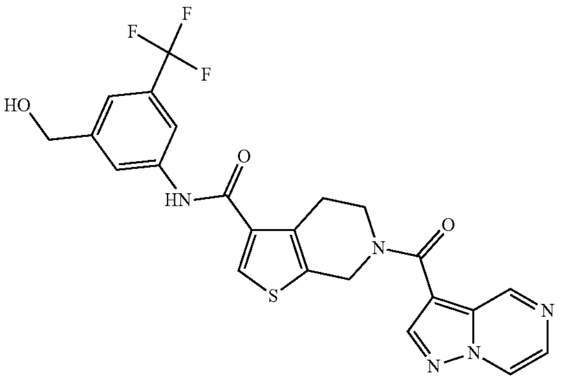 [SMILES: O=C(Nc1cc(CO)cc(C(F)(F)F)c1)c1csc2c1CCN(C(=O)c1cnn3ccncc13)C2] | N-(3-(hydroxymethyl)-5-(trifluoromethyl)phenyl)-6-(pyrazolo[1,5-a]pyrazine-3-carbonyl)-4,5,6,7-tetrahydrothieno[2,3-c]pyridine-3-carboxamide |

In a further preferred embodiment the present invention refers to a compound of formula (I) wherein $R_1$ is X"

(X")

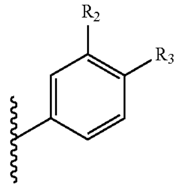

represented by formula (Ia')

(Ia')

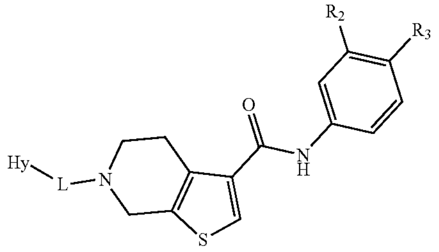

wherein Hy, $R_2$ and $R_3$ are as defined above.

In a further preferred embodiment the present invention refers to a compound of formula (Ia') wherein L is-$CH_2$—, represented by formula (Iaa')

(Iaa')

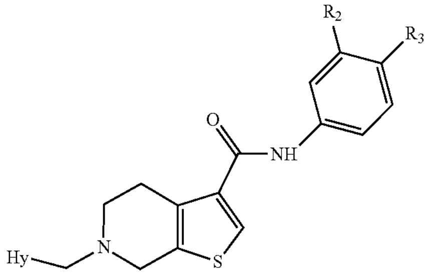

wherein Hy, $R_2$ and $R_3$ are as defined above.

In a particularly preferred embodiment, the present invention relates to a compound of general formula (Iaa') wherein $R_2$ is trifluoromethyl.

In another particularly preferred embodiment, the present invention relates to a compound of general formula (Iaa") wherein $R_3$ is methoxy.

In a further preferred embodiment, the present invention relates to a compound of general formula (Iaa') wherein Hy is 1H-pyrrolo[2,3-b]pyridin-5-yl.

According to a preferred embodiment, the invention refers to the compound of Formula (Iaa') listed in the Table 3a below and pharmaceutically acceptable salts thereof. This compound is particularly active on receptors DDR1 and DDR2, as shown in Table 6.

TABLE 3a

List of compounds of Formula (Iaa')

| Example No. | Structure | Chemical Name |
|---|---|---|
| 71 | 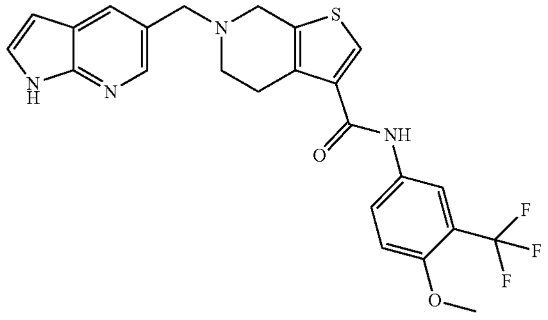 [SMILES: COc1ccc(NC(=O)c2csc3c2CCN(Cc2cnc4[nH]ccc4c2)C3)cc1C(F)(F)F] | 6-((1H-pyrrolo[2,3-b]-pyridin-5-yl)methyl)-N-(4-methoxy-3-(trifluoro-methyl)phenyl)-4,5,6,7-tetrahydrothieno[2,3-c]-pyridine-3-carboxamide |

In a further preferred embodiment the present invention refers to a compound of formula (Ia') wherein L is —CO, represented by formula (Iab')

(Iab')

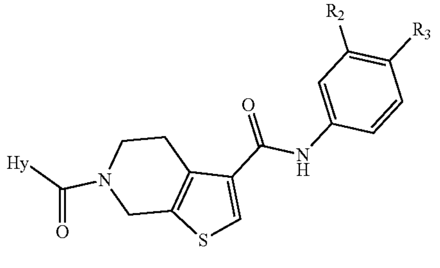

wherein Hy, $R_2$ and $R_3$ are as defined above.

In a particularly preferred embodiment, the present invention relates to a compound of general formula (Iab') wherein $R_2$ is trifluoromethyl.

In another particularly preferred embodiment, the present invention relates to a compound of general formula (Iab') wherein $R_3$ is selected from the group consisting of methoxy, (tetrahydrofuran-3-yl)oxy, (4-methylpiperazin-1-yl)methyl, oxetan-3-yloxy, pyrrolidin-1-ylmethyl, morpholinomethyl, oxetan-3-ylmethoxy, 2-methoxyethoxy, (dimethylamino)methyl, 2-hydroxyethoxy, (1-methylpiperidin-4-yl)oxy, hydroxymethyl, chlorine and (1-methylpyrrolidin-3-yl)oxy.

In another preferred embodiment, the present invention relates to a compound of general formula (Iab') wherein Hy is pyrazolo[1,5-a]pyrazine-3-yl, $R_3$ is selected from the group consisting of hydroxymethyl, (dimethylamino)methyl and chlorine, and $R_2$ is trifluoromethyl.

According to a further preferred embodiment, the invention refers to at least one of the compounds of Formula (Iab') listed in the Table 3b below and pharmaceutically acceptable salts thereof. These compounds are particularly active on receptors DDR1 and DDR2, as shown in Table 6.

TABLE 3b

List of compounds of Formula (Iab')

| Example No. | Structure | Chemical Name |
| --- | --- | --- |
| 4 | 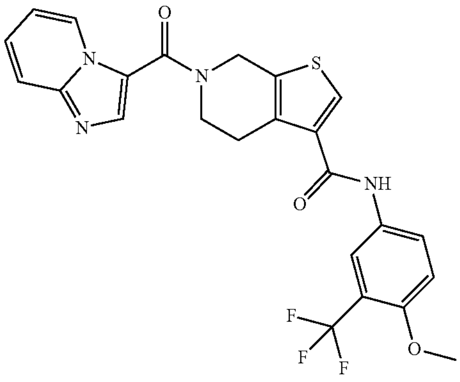 [SMILES: COc1ccc(NC(=O)c2csc3c2CCN(C(=O)c2cnc4ccccn24)C3)cc1C(F)(F)F] | 6-(imidazo[1,2-a]pyridine-3-carbonyl)-N-(4-methoxy-3-(trifluoromethyl)phenyl)-4,5,6,7-tetrahydrothieno[2,3-c]pyridine-3-carboxamide |
| 12 | 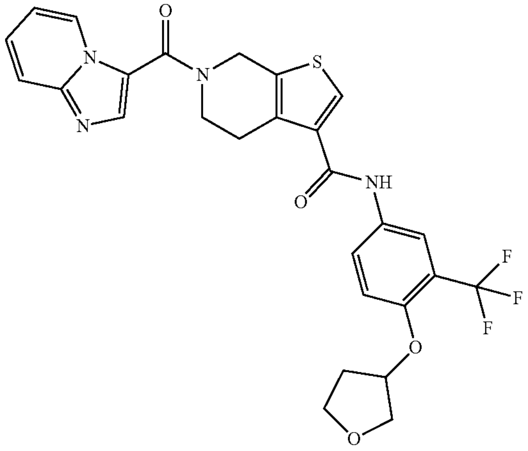 [SMILES: O=C(Nc1ccc(OC2CCOC2)c(C(F)(F)F)c1)c1csc2c1CCN(C(=O)c1cnc3ccccn13)C2] | 6-(imidazo[1,2-a]pyridine-3-carbonyl)-N-(4-((tetra-hydrofuran-3-yl)oxy)-3-(trifluoromethyl)phenyl)-4,5,6,7-tetrahydrothieno-[2,3-c]pyridine-3-carbox-amide |
| 13 | 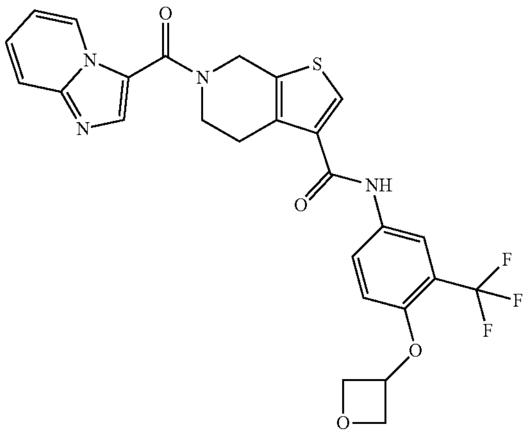 [SMILES: O=C(Nc1ccc(OC2COC2)c(C(F)(F)F)c1)c1csc2c1CCN(C(=O)c1cnc3ccccn13)C2] | 6-(imidazo[1,2-a]pyridine-3-carbonyl)-N-(4-(oxetan-3-yloxy)-3-(trifluoromethyl)-phenyl)-4,5,6,7-tetrahydro-thieno[2,3-c]pyridine-3-carboxamide |

TABLE 3b-continued

List of compounds of Formula (Iab')

| Example No. | Structure | Chemical Name |
|---|---|---|
| 14 | 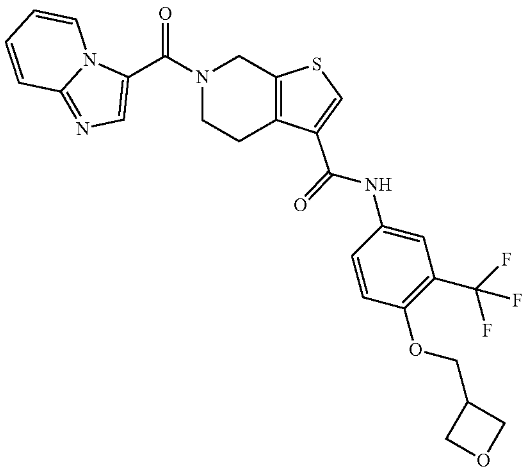 [SMILES: O=C(Nc1ccc(OCC2COC2)c(C(F)(F)F)c1)c1csc2c1CCN(C(=O)c1cnc3ccccn13)C2] | 6-(imidazo[1,2-a]pyridine-3-carbonyl)-N-(4-(oxetan-3-ylmethoxy)-3-(trifluoromethyl)phenyl)-4,5,6,7-tetrahydrothieno[2,3-c]pyridine-3-carboxamide |
| 15 | 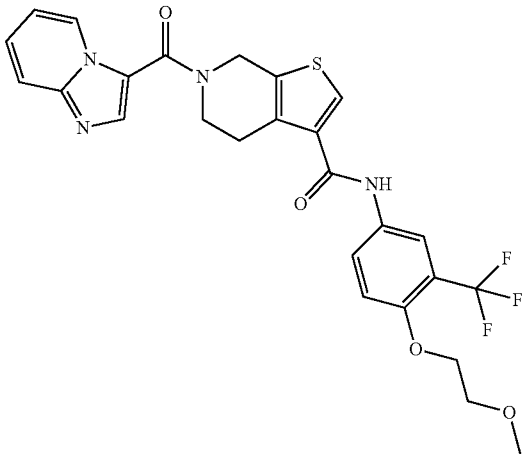 [SMILES: COCCOc1ccc(NC(=O)c2csc3c2CCN(C(=O)c2cnc4ccccn24)C3)cc1C(F)(F)F] | 6-(imidazo[1,2-a]pyridine-3-carbonyl)-N-(4-(2-methoxyethoxy)-3-(trifluoromethyl)phenyl)-4,5,6,7-tetrahydrothieno[2,3-c]pyridine-3-carboxamide |
| 16 | 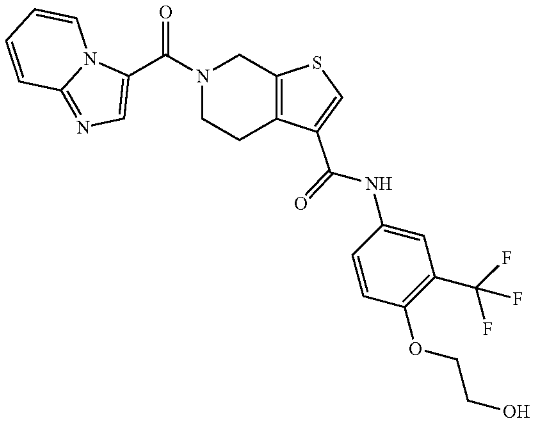 [SMILES: O=C(Nc1ccc(OCCO)c(C(F)(F)F)c1)c1csc2c1CCN(C(=O)c1cnc3ccccn13)C2] | N-(4-(2-hydroxyethoxy)-3-(trifluoromethyl)phenyl)-6-(imidazo[1,2-a]pyridine-3-carbonyl)-4,5,6,7-tetrahydrothieno[2,3-c]pyridine-3-carboxamide |

TABLE 3b-continued

| List of compounds of Formula (Iab') | | |
|---|---|---|
| Example No. | Structure | Chemical Name |
| 18 | 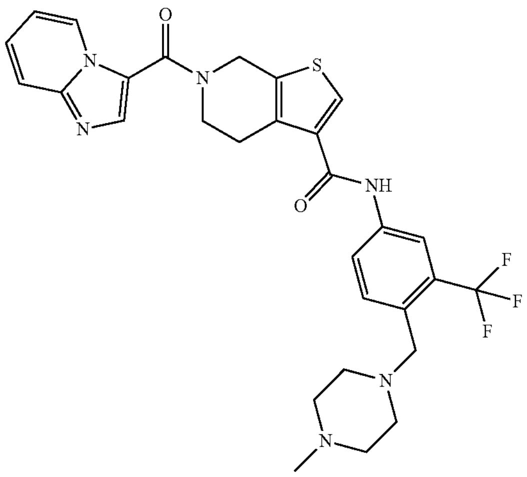 [SMILES: CN1CCN(Cc2ccc(NC(=O)c3csc4c3CCN(C(=O)c3cnc5ccccn35)C4)cc2C(F)(F)F)CC1] | 6-(imidazo[1,2-a]pyridine-3-carbonyl)-N-(4-((4-methylpiperazin-1-yl)methyl)-3-(trifluoromethyl)phenyl)-4,5,6,7-tetrahydrothieno[2,3-c]pyridine-3-carboxamide |
| 22 | 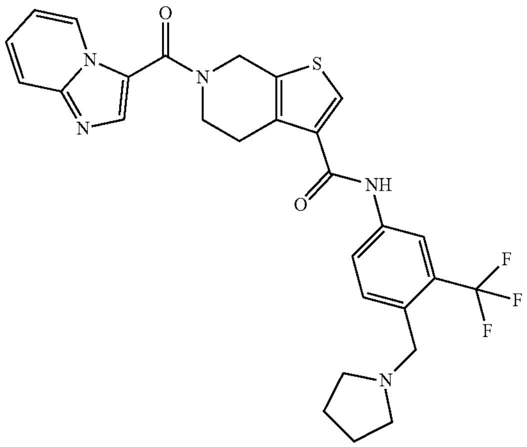 [SMILES: O=C(Nc1ccc(CN2CCCC2)c(C(F)(F)F)c1)c1csc2c1CCN(C(=O)c1cnc3ccccn13)C2] | 6-(imidazo[1,2-a]pyridine-3-carbonyl)-N-(4-(pyrrolidin-1-ylmethyl)-3-(trifluoromethyl)phenyl)-4,5,6,7-tetrahydrothieno[2,3-c]pyridine-3-carboxamide |
| 23 | 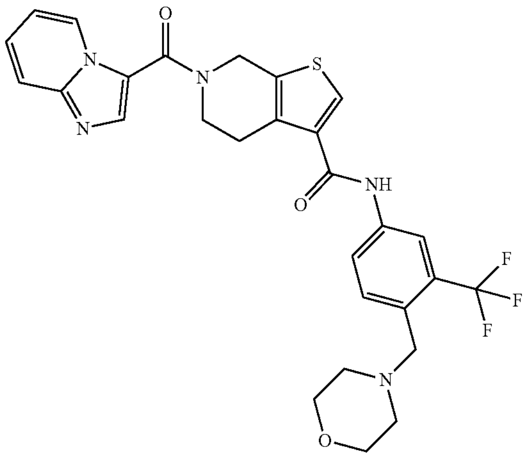 [SMILES: O=C(Nc1ccc(CN2CCOCC2)c(C(F)(F)F)c1)c1csc2c1CCN(C(=O)c1cnc3ccccn13)C2] | 6-(imidazo[1,2-a]pyridine-3-carbonyl)-N-(4-(morpholinomethyl)-3-(trifluoromethyl)phenyl)-4,5,6,7-tetrahydrothieno[2,3-c]pyridine-3-carboxamide |

TABLE 3b-continued

| List of compounds of Formula (Iab') | | |
|---|---|---|
| Example No. | Structure | Chemical Name |
| 27 | 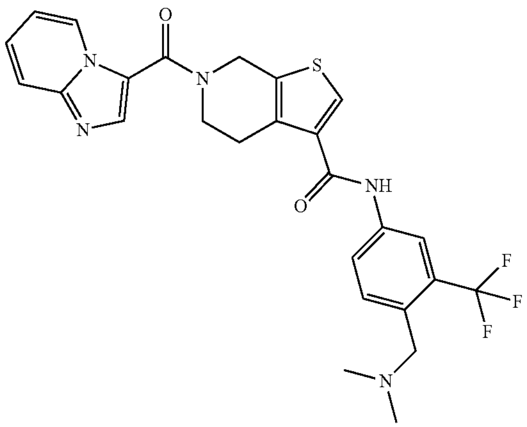 [SMILES: CN(C)Cc1ccc(NC(=O)c2csc3c2CCN(C(=O)c2cnc4ccccn24)C3)cc1C(F)(F)F] | N-(4-((dimethylamino)methyl)-3-trifluoromethyl)phenyl)-6-(imidazo[1,2-a]pyridine-3-carbonyl)-4,5,6,7-tetrahydrothieno[2,3-c]-pyridine-3-carboxamide |
| 31 | 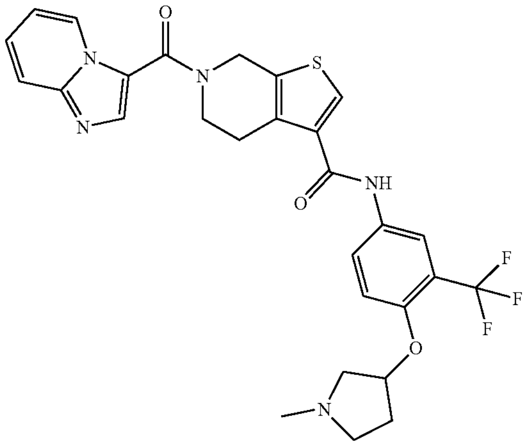 [SMILES: CN1CCC(Oc2ccc(NC(=O)c3csc4c3CCN(C(=O)c3cnc5ccccn35)C4)cc2C(F)(F)F)C1] | 6-(imidazo[1,2-a]pyridine-3-carbonyl)-N-(4-((1-methylpyrrolidin-3-yl)oxy)-3-(trifluoromethyl)phenyl)-4,5,6,7-tetrahydrothieno-[2,3-c]pyridine-3-carboxamide |
| 32 | 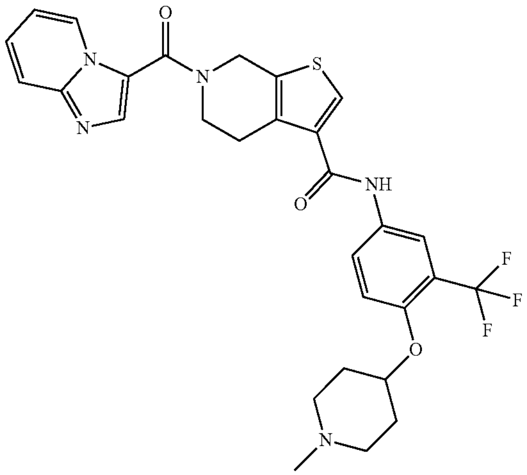 [SMILES: CN1CCC(Oc2ccc(NC(=O)c3csc4c3CCN(C(=O)c3cnc5ccccn35)C4)cc2C(F)(F)F)CC1] | 6-(imidazo[1,2-a]pyridine-3-carbonyl)-N-(4-((1-methylpiperidin-4-yl)oxy)-3-(trifluoromethyl)phenyl)-4,5,6,7-tetrahydrothieno[2,3-c]pyridine-3-carboxamide |

TABLE 3b-continued

| Example No. | Structure | Chemical Name |
|---|---|---|
| | List of compounds of Formula (Iab') | |
| 132 | 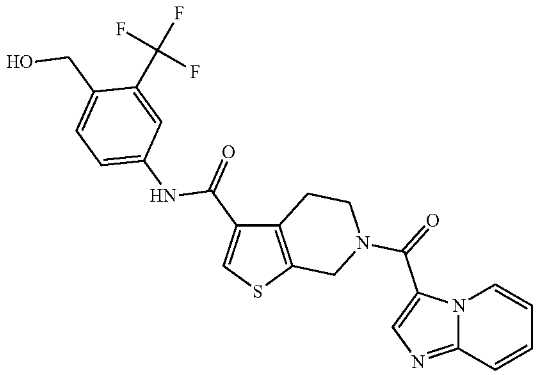 [SMILES: O=C(Nc1ccc(CO)c(C(F)(F)F)c1)c1csc2c1CCN(C(=O)c1cnc3ccccn13)C2] | N-(4-(hydroxymethyl)-3-(trifluoromethyl)phenyl)-6-(imidazo[1,2-a]pyridine-3-carbonyl)-4,5,6,7-tetrahydro-thieno[2,3-c]pyridine-3-carboxamide |
| 171 | 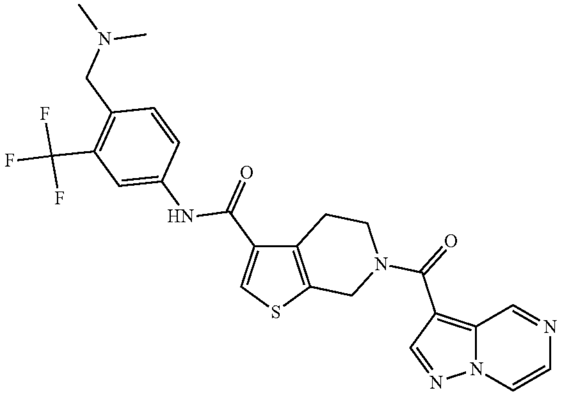 [SMILES: CN(C)Cc1ccc(NC(=O)c2csc3c2CCN(C(=O)c2cnn4ccncc24)C3)cc1C(F)(F)F] | N-(4-((dimethylamino)-methyl)-3-(trifluoromethyl)-phenyl)-6-(pyrazolo[1,5-a]-pyrazine-3-carbonyl)-4,5,6,7-tetrahydrothieno[2,3-c]pyr-idine-3-carboxamide |
| 176 | 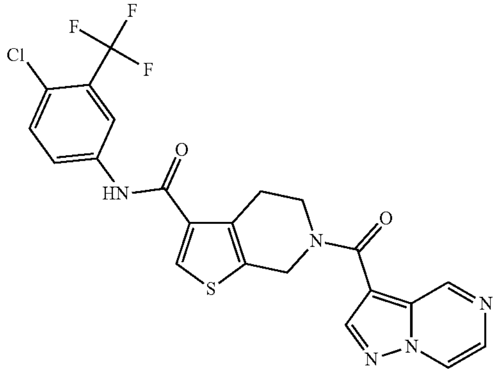 [SMILES: O=C(Nc1ccc(Cl)c(C(F)(F)F)c1)c1csc2c1CCN(C(=O)c1cnn3ccncc13)C2] | N-(4-chloro-3-(trifluoro-methyl)phenyl)-6-(pyrazolo-[1,5-a]pyrazine-3-carbonyl)-4,5,6,7-tetrahydrothieno[2,3-c]pyridine-3-carboxamide |
| 180 | 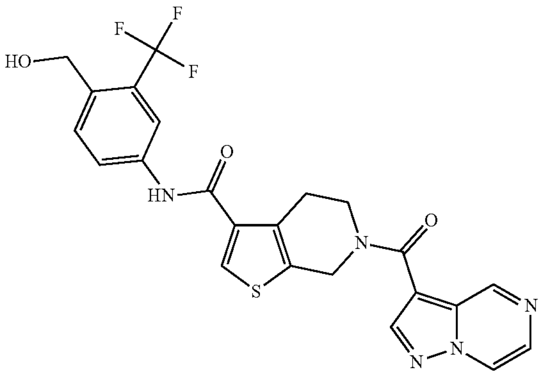 [SMILES: O=C(Nc1ccc(CO)c(C(F)(F)F)c1)c1csc2c1CCN(C(=O)c1cnn3ccncc13)C2] | N-(4-(hydroxymethyl)-3-(trifluoromethyl)phenyl)-6-(pyrazolo[1,5-a]pyrazine-3-carbonyl)-4,5,6,7-tetra-hydrothieno[2,3-c]pyridine-3-carboxamide |

In a particularly preferred embodiment the present invention refers to a compound of formula (I) wherein $R_1$ is Het, represented by formula (Ib)

(Ib)

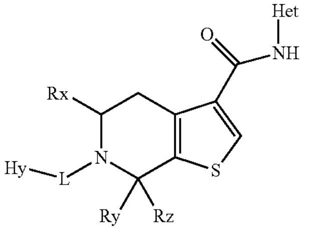

wherein

L is selected from the group consisting of —C(O)— and —$CH_2$—;

Hy is a bicyclic heteroaryl optionally substituted with at least one substituent selected from the group consisting of —($C_1$-$C_4$)alkyl, halogen atoms and —($C_1$-$C_6$)haloalkyl;

Het is an heteroaryl optionally substituted with one or more substituents selected from the group consisting of —($C_1$-$C_4$)alkyl, —($C_1$-$C_4$)haloalkyl, cycloalkyl, —O—($C_1$-$C_4$)haloalkyl, —($C_1$-$C_4$)alkylene-OH, —($C_1$-$C_4$)alkylene-aryl, aryl optionally substituted with one or more groups selected from —($C_1$-$C_4$)alkyl and halogen atoms;

and pharmaceutically acceptable salts thereof.

In a particularly preferred embodiment the present invention refers to a compound of formula (Ib) wherein L is —$CH_2$—, represented by formula (Iba)

(Iba)

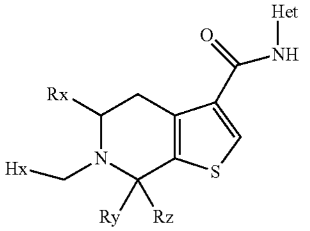

wherein Rx, Ry, Rz, Hy and Het are as defined above.

In a preferred embodiment the present invention refers to a compound of formula (Iba) wherein Hy is selected from the group consisting of 1H-pyrrolo[2,3-b]pyridin-5-yl, 1H-pyrazolo[3,4-b]pyridin-5-yl, pyrazolo[1,5-a]pyrimidin-6-yl, imidazo[1,2-a]pyrazin-3-yl, (4-methylpiperazin-1-yl)-1H-pyrazolo[3,4-b]pyridin-5-yl, pyrazolo[1,5-a]pyrazin-3-yl, 7H-pyrrolo[2,3-d]pyrimidin-4-yl and 3-methyl-1H-pyrazolo[3,4-b]pyridin-5-yl.

In another preferred embodiment the present invention refers to a compound of formula (Iba) wherein Het is selected from the group consisting of 3-(tert-butyl)-1-methyl-1H-pyrazol-5-yl, 3-cyclopropyl-1-methyl-1H-pyrazol-5-yl, 3-(tert-butyl)isoxazol-5-yl, 5-cyclopropylisoxazol-3-yl, 5-(trifluoromethyl)pyridin-3-yl, 5-(tert-butyl)isoxazol-3-yl, 1-methyl-5-(trifluoromethyl)-1H-pyrazol-3-yl and 3-(tert-butyl)-1-(p-tolyl)-1H-pyrazol-5-yl.

In another preferred embodiment the present invention refers to a compound of formula (Iba) wherein Hy is selected from the group consisting of 3-(4-methylpiperazin-1-yl)-1H-pyrazolo[3,4-b]pyridin-5-yl, 3-methyl-1H-pyrazolo[3,4-b]pyridin-5-yl, 1H-pyrazolo[3,4-b]pyridin-5-ylmethyl, pyrazolo[1,5-a]pyrimidin-6-yl, imidazo[1,2-a]pyrazin-3-yl, pyrazolo[1,5-a]pyrazin-3-yl and 7H-pyrrolo[2,3-d]pyrimidin-4-yl, and Het is 5-(trifluoromethyl)pyridin-3-yl.

According to a preferred embodiment, the invention refers to at least one of the compounds of Formula (Iba) listed in the Table 4 below and pharmaceutically acceptable salts thereof.

TABLE 4

List of compounds of Formula (Iba)

| Example No. | Structure | Chemical Name |
|---|---|---|
| 70 | 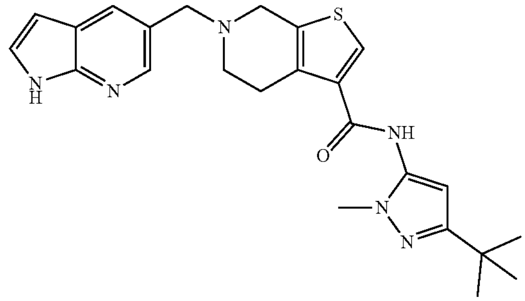 [SMILES: Cn1nc(C(C)(C)C)cc1NC(=O)c1csc2c1CCN(Cc1cnc3[nH]ccc3c1)C2] | 6-((1H-pyrrolo[2,3-b]pyridin-5-yl)methyl)-N-(3-(tert-butyl)-1-methyl-1H-pyrazol-5-yl)-4,5,6,7-tetrahydrothieno[2,3-c]pyridine-3-carboxamide |

TABLE 4-continued

| List of compounds of Formula (Iba) | | |
|---|---|---|
| Example No. | Structure | Chemical Name |
| 75 | 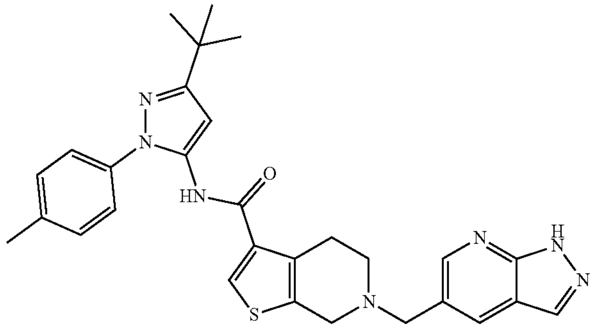 [SMILES: Cc1ccc(-n2nc(C(C)(C)C)cc2NC(=O)c2csc3c2CCN(Cc2cnc4[nH]ncc4c2)C3)cc1] | 6-((1H-pyrazolo[3,4-b]pyridin-5-yl)methyl)-N-(3-(tert-butyl)-1-(p-tolyl)-1H-pyrazol-5-yl)-4,5,6,7-tetrahydrothieno[2,3-c]pyridine-3-carboxamide |
| 76 | 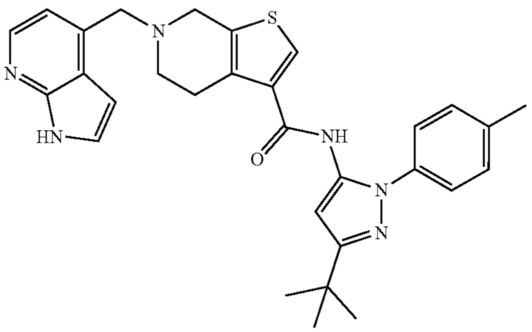 [SMILES: Cc1ccc(-n2nc(C(C)(C)C)cc2NC(=O)c2csc3c2CCN(Cc2ccnc4[nH]ccc24)C3)cc1] | 6-((1H-pyrrolo[2,3-b ]pyridin-4-yl)methyl)-N-(3-(tert-butyl)-1-(p-tolyl)-1H-pyrazol-5-yl)-4,5,6,7-tetrahydrothieno[2,3-c]pyridine-3-carboxamide |
| 77 | 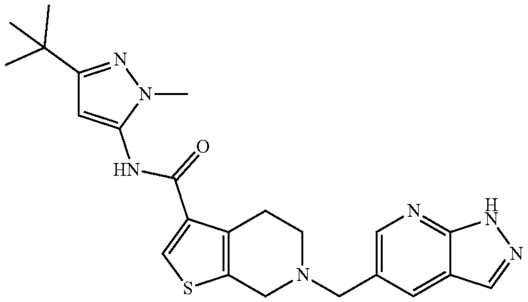 [SMILES: Cn1nc(C(C)(C)C)cc1NC(=O)c1csc2c1CCN(Cc1cnc3[nH]ncc3c1)C2] | 6-((1H-pyrazolo[3,4-b]pyridin-5-yl)methyl)-N-(3-(tert-butyl)-1-methyl-1H-pyrazol-5-yl)-4,5,6,7-tetrahydrothieno[2,3-c]pyridine-3-carboxamide |
| 78 | 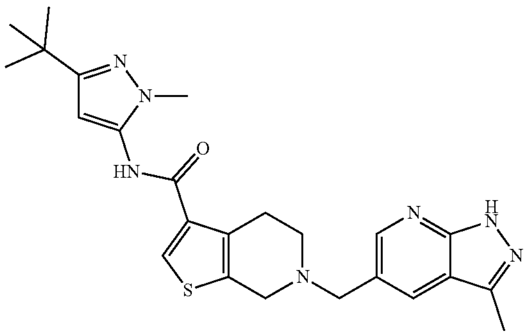 [SMILES: Cc1n[nH]c2ncc(CN3CCc4c(C(=O)Nc5cc(C(C)(C)C)nn5C)csc4C3)cc12] | N-(3-(tert-butyl)-1-methyl-1H-pyrazol-5-yl)-6-((3-methyl-1H-pyrazolo[3,4-b]pyridin-5-yl)methyl)-4,5,6,7-tetrahydrothieno[2,3-c]pyridine-3-carboxamide |

TABLE 4-continued

List of compounds of Formula (Iba)

| Example No. | Structure | Chemical Name |
|---|---|---|
| 133 | 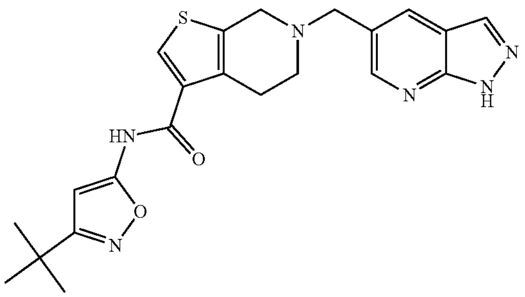 [SMILES: CC(C)(C)c1cc(NC(=O)c2csc3c2CCN(Cc2cnc4[nH]ncc4c2)C3)on1] | 6-((1H-pyrazolo[3,4-b]pyridin-5-yl)methyl)-N-(3-(tert-butyl)isoxazol-5-yl)-4,5,6,7-tetrahydrothieno[2,3-c]pyridine-3-carboxamide |
| 134 | 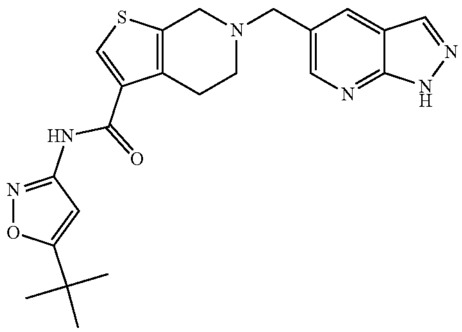 [SMILES: CC(C)(C)c1cc(NC(=O)c2csc3c2CCN(Cc2cnc4[nH]ncc4c2)C3)no1] | 6-((1H-pyrazolo[3,4-b]pyridin-5-yl)methyl)-N-(5-(tert-butyl)isoxazol-3-yl)-4,5,6,7-tetrahydrothieno[2,3-c]pyridine-3-carboxamide |
| 146 | 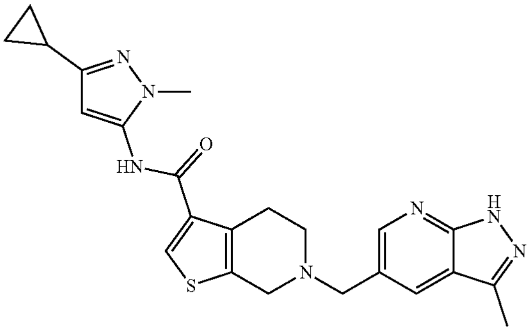 [SMILES: Cc1n[nH]c2ncc(CN3CCc4c(C(=O)Nc5cc(C6CC6)nn5C)csc4C3)cc12] | N-(3-cyclopropyl-1-methyl-1H-pyrazol-5-yl)-6-((3-methyl-1H-pyrazolo[3,4-b]pyridin-5-yl)methyl)-4,5,6,7-tetrahydrothieno[2,3-c]pyridine-3-carboxamide |
| 147 | 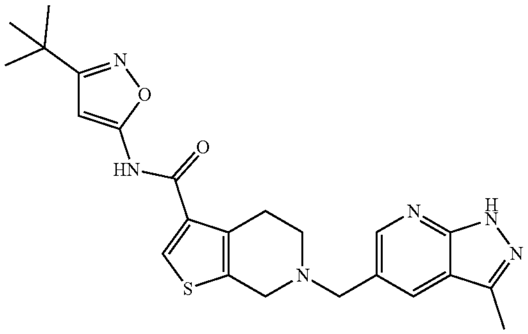 [SMILES: Cc1n[nH]c2ncc(CN3CCc4c(C(=O)Nc5cc(C(C)(C)C)no5)csc4C3)cc12] | N-(3-(tert-butyl)isoxazol-5-yl)-6-((3-methyl-1H-pyrazolo[3,4-b]pyridin-5-yl)methyl)-4,5,6,7-tetrahydrothieno[2,3-c]pyridine-3-carboxamide |

TABLE 4-continued

List of compounds of Formula (Iba)

| Example No. | Structure | Chemical Name |
|---|---|---|
| 148 | 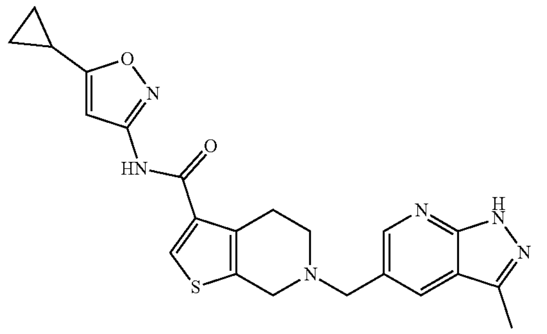 [SMILES: Cc1n[nH]c2ncc(CN3CCc4c(C(=O)Nc5cc(C6CC6)on5)csc4C3)cc12] | N-(5-cyclopropylisoxazol-3-yl)-6-((3-methyl-1H-pyrazolo[3,4-b]pyridin-5-yl)methyl)-4,5,6,7-tetrahydrothieno[2,3-c]pyridine-3-carboxamide |
| 149 | 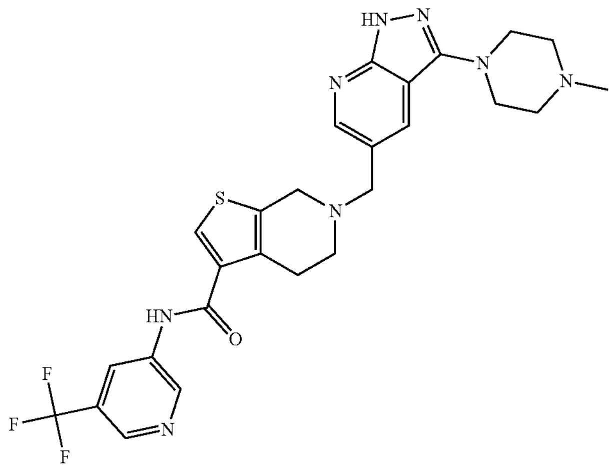 [SMILES: CN1CCN(c2n[nH]c3ncc(CN4CCc5c(C(=O)Nc6cncc(C(F)(F)F)c6)csc5C4)cc23)CC1] | 6-((3-(4-methylpiperazin-1-yl)-1H-pyrazolo[3,4-b]pyridin-5-yl)methyl)-N-(5-(trifluoromethyl)pyridin-3-yl)-4,5,6,7-tetrahydrothieno[2,3-c]pyridine-3-carboxamide |
| 150 | 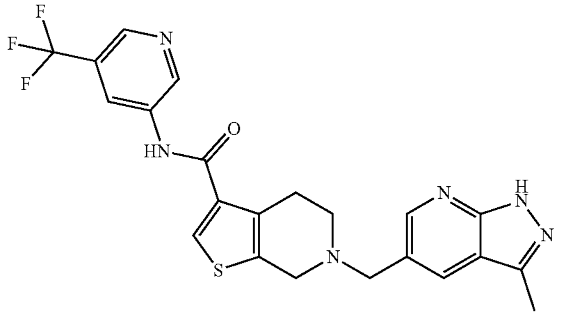 [SMILES: Cc1n[nH]c2ncc(CN3CCc4c(C(=O)Nc5cncc(C(F)(F)F)c5)csc4C3)cc12] | 6-((3-methyl-1H-pyrazolo[3,4-b]pyridin-5-yl)methyl)-N-(5-(trifluoromethyl)pyridin-3-yl)-4,5,6,7-tetrahydrothieno[2,3-c]pyridine-3-carboxamide |
| 151 | 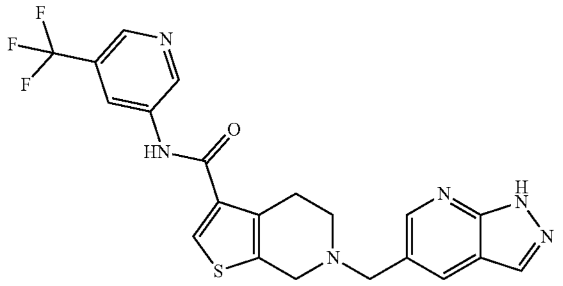 [SMILES: O=C(Nc1cncc(C(F)(F)F)c1)c1csc2c1CCN(Cc1cnc3[nH]ncc3c1)C2] | 6-(1H-pyrazolo[3,4-b]pyridin-5-ylmethyl)-N-[5-(trifluoromethyl)-3-pyridyl]-5,7-dihydro-4H-thieno[2,3-c]pyridine-3-carboxamide |

TABLE 4-continued

List of compounds of Formula (Iba)

| Example No. | Structure | Chemical Name |
| --- | --- | --- |
| 152 | 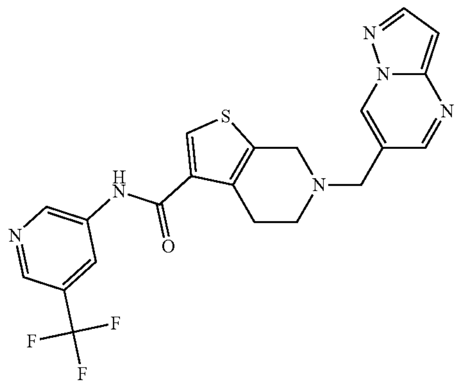 [SMILES: O=C(Nc1cncc(C(F)(F)F)c1)c1csc2c1CCN(Cc1cnc3ccnn3c1)C2] | 6-(pyrazolo[1,5-a]pyrimidin-6-ylmethyl)-N-(5-(trifluoromethyl)pyridin-3-yl)-4,5,6,7-tetrahydrothieno[2,3-c]pyridine-3-carboxamide |
| 153 | 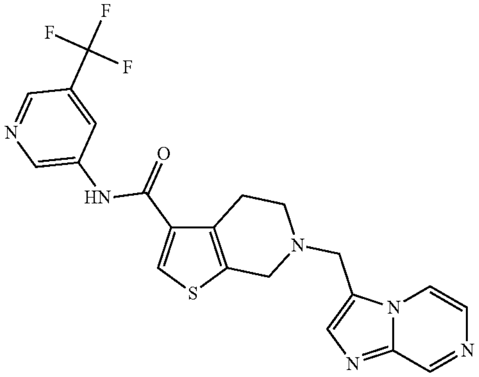 [SMILES: O=C(Nc1cncc(C(F)(F)F)c1)c1csc2c1CCN(Cc1cnc3cnccn13)C2] | 6-(imidazo[1,2-a]pyrazin-3-ylmethyl)-N-(5-(trifluoromethyl)pyridin-3-yl)-4,5,6,7-tetrahydrothieno[2,3-c]pyridine-3-carboxamide |
| 154 | 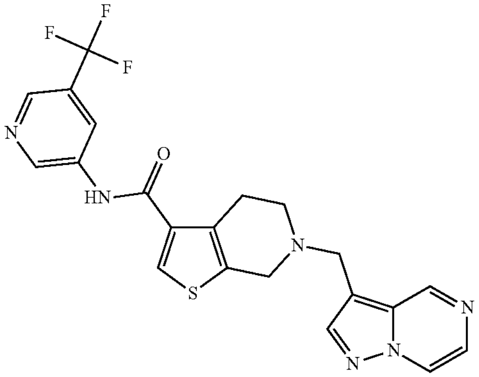 [SMILES: O=C(Nc1cncc(C(F)(F)F)c1)c1csc2c1CCN(Cc1cnn3ccncc13)C2] | 6-(pyrazolo[1,5-a]pyrazin-3-ylmethyl)-N-(5-(trifluoromethyl)pyridin-3-yl)-4,5,6,7-tetrahydrothieno[2,3-c]pyridine-3-carboxamide |
| 155 | 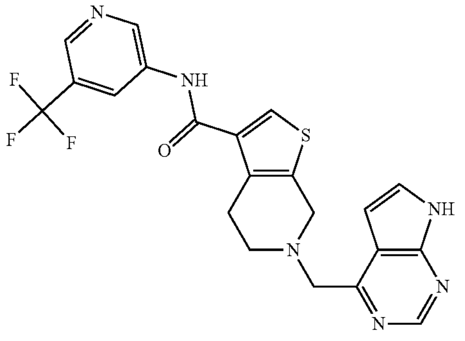 [SMILES: O=C(Nc1cncc(C(F)(F)F)c1)c1csc2c1CCN(Cc1ncnc3[nH]ccc13)C2] | 6-((7H-pyrrolo[2,3-d]pyrimidin-4-yl)methyl)-N-(5-(trifluoromethyl)pyridin-3-yl)-4,5,6,7-tetrahydrothieno[2,3-c]pyridine-3-carboxamide |

TABLE 4-continued

| List of compounds of Formula (Iba) | | |
|---|---|---|
| Example No. | Structure | Chemical Name |
| 156 | 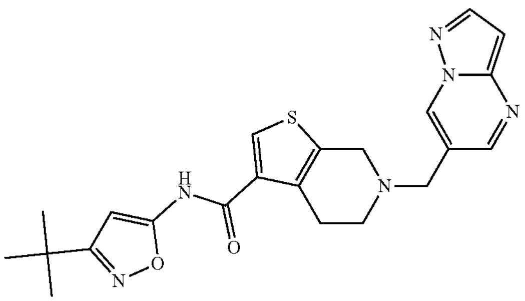 [SMILES: CC(C)(C)c1cc(NC(=O)c2csc3c2CCN(Cc2cnc4ccnn4c2)C3)on1] | N-(3-(tert-butyl)isoxazol-5-yl)-6-(pyrazolo[1,5-a]pyrimidin-6-ylmethyl)-4,5,6,7-tetrahydrothieno[2,3-c]pyridine-3-carboxamide |
| 169 | 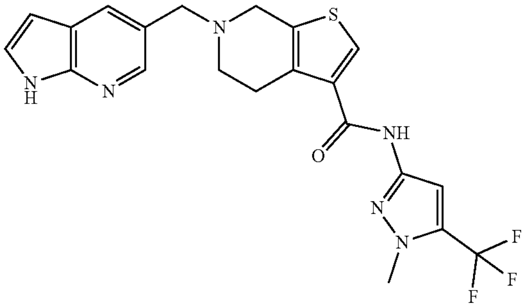 [SMILES: Cn1nc(NC(=O)c2csc3c2CCN(Cc2cnc4[nH]ccc4c2)C3)cc1C(F)(F)F] | 6-((1H-pyrrolo[2,3-b]pyridin-5-yl)methyl)-N-(1-methyl-5-(trifluoromethyl)-1H-pyrazol-3-yl)-4,5,6,7-tetrahydrothieno[2,3-c]pyridine-3-carboxamide |

In a particularly preferred embodiment, the present invention refers to a compound of formula (Ib) wherein L is-C(O)—, represented by formula (Ibb)

(Ibb)

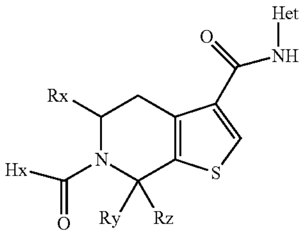

wherein Rx, Ry, Rz, Hy and Het are as defined above.

In a preferred embodiment, the present invention refers to a compound of formula (Ibb) wherein Hy is selected from the group consisting of imidazo[1,2-a]pyridine-3-yl, 6-methylimidazo[1,2-a]pyridine-3-yl, 6-methylimidazo[1,2-a]pyridine-3-yl, 6-fluoroimidazo[1,2-a]pyridine-3-yl, 6-(trifluoromethyl)imidazo[1,2-a]pyridine-3-yl, 6-chloroimidazo[1,2-a]pyridine-3-yl, pyrazolo[1,5-a]pyrazine-3-yl, pyrazolo[1,5-a]pyrimidine-3-yl, 5,6-dihydro-8H-imidazo[2,1-c][1,4]oxazine-3-yl, 5,6,7,8-tetrahydroimidazo[1,2-a]pyridine-3-yl, 5,6,7,8-tetrahydroimidazo[1,2-a]pyrimidine-3-yl, pyrazolo[1,5-a]pyridine-3-yl, (4-methylpiperazin-1-yl)imidazo[1,2-a]pyridine-3-yl, 5-methoxypyrazolo[1,5-a]pyridine-3-yl, pyrazolo[5,1-b]thiazole-7-yl, 7-methoxyimidazo[1,2-a]pyridine-3-yl, 1-methyl-1H-imidazo[1,2-b]pyrazole-7-yl and imidazo[1,2-a]pyrazine-3-yl.

In another preferred embodiment the present invention refers to a compound of formula (Ibb) wherein Het is selected from the group consisting of 3-(tert-butyl)-1-(p-tolyl)-1H-pyrazol-5-yl, 3-(tert-butyl)-1-methyl-1H-pyrazol-5-yl, 3-(tert-butyl)-1-(4-fluorophenyl)-1H-pyrazol-5-yl, 3-(tert-butyl)-1-phenyl-1H-pyrazol-5-yl, 5-(1,1,1-trifluoro-2-methylpropan-2-yl)isoxazol-3-yl, 2-(trifluoromethyl)pyridin-4-yl, 6-(trifluoromethyl)pyrimidin-4-yl, 6-(trifluoromethyl)pyrimidin-4-yl, 4-(trifluoromethyl)pyridin-2-yl, 5-(trifluoromethyl)pyridin-3-yl, 5-(tert-butyl)isoxazol-3-yl, 3-(tert-butyl)isoxazol-5-yl, 4-(tert-butyl)oxazol-2-yl, 3-cyclobutyl-1-methyl-1H-pyrazol-5-yl, 6-fluoroimidazo[1,2-a]pyridine-3-yl, 6-(trifluoromethyl)imidazo[1,2-a]pyridine-3-yl, 6-chloroimidazo[1,2-a]pyridine-3-yl, 3-isopropyl-1-methyl-1H-pyrazol-5-yl, 4-(trifluoromethyl)pyrimidin-2-yl, 2-(tert-butyl)pyridin-4-yl, 3-(tert-butyl)-1-isopropyl-1H-pyrazol-5-yl, 1-methyl-3-propyl-1H-pyrazol-5-yl, 3-(tert-butyl)-1-(2-hydroxyethyl)-1H-pyrazol-5-yl, 3-(tert-butyl)-1-(2,2,2-trifluoroethyl)-1H-pyrazol-5-yl, 1-benzyl-3-(tert-butyl)-1H-pyrazol-5-yl, 3-(tert-butyl)-1-ethyl-1H-pyrazol-5-yl, 3-isobutyl-1-methyl-1H-pyrazol-5-yl, 1-methyl-3-(1-(trifluoromethyl)cyclopropyl)-1H-pyrazol-5-yl, 5-(1,1-difluoroethyl)pyridin-3-yl, 5-(tert-butyl)-1-methyl-1H-pyrazol-3-yl, 5-(difluoromethoxy) pyridin-3-yl, 3-(tert-pentyl)isoxazol-5-yl, 6-methoxy-5-(trifluoromethyl)pyridin-3-yl, 5-(tert-butyl)pyridin-3-yl, 2-((dimethylamino)methyl)-6-(trifluoromethyl)pyridin-4-yl, (trifluoromethyl)pyridazin-3-yl, 3-isobutylisoxazol-5-yl, trifluoromethoxy)pyridin-3-yl and 5-(trifluoromethoxy)pyridin-3-yl.

In another preferred embodiment, the present invention refers to a compound of formula (Ibb) wherein Hy is selected from the group consisting of pyrazolo[1,5-a]pyrazine-3-yl and 6-(4-methylpiperazin-1-yl)imidazo[1,2-a]pyridine-3-yl, Het is selected from the group consisting of 5-(trifluoromethyl)pyridin-3-yl, 3-(tert-butyl)isoxazol-5-yl, 5-(tert-butyl)-1-methyl-1H-pyrazol-3-yl, 6-methoxy-5-(trifluoromethyl)pyridin-3-yl, 5-(1,1-difluoroethyl)pyridin-3-yl, 5-(tert-butyl)pyridin-3-yl, 5-(difluoromethoxy)pyridin-3-yl, 5-(1,1,1-trifluoro-2-methylpropan-2-yl)isoxazol-3-yl, 5-(trifluoromethoxy)pyridin-3-yl, 5-(tert-butyl)isoxazol-3-yl, 3-(tert-pentyl)isoxazol-5-yl and 3-isobutylisoxazol-5-yl.

According to a preferred embodiment, the present invention refers to at least one of the compounds of Formula (Ibb) listed in the Table 5 below and pharmaceutically acceptable salts thereof. These compounds are particularly active on receptors DDR1 and DDR2, as shown in Table 6.

TABLE 5

List of compounds of Formula (Ibb)

| Example No. | Structure | Chemical Name |
|---|---|---|
| 2 | 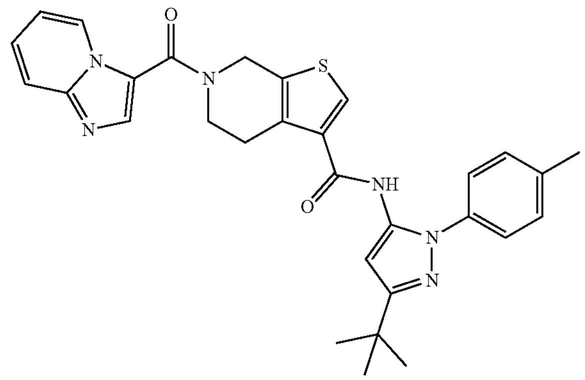 [SMILES: Cc1ccc(-n2nc(C(C)(C)C)cc2NC(=O)c2csc3c2CCN(C(=O)c2cnc4ccccn24)C3)cc1] | N-(3-(tert-butyl)-1-(p-tolyl)-1H-pyrazol-5-yl)-6-(imidazo[1,2-a]pyridine-3-carbonyl)-4,5,6,7-tetrahydrothieno[2,3-c]pyridine-3-carboxamide |
| 3 | 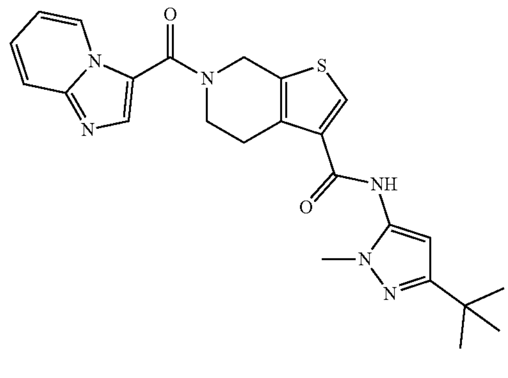 [SMILES: Cn1nc(C(C)(C)C)cc1NC(=O)c1csc2c1CCN(C(=O)c1cnc3ccccn13)C2] | N-(3-(tert-butyl)-1-methyl-1H-pyrazol-5-yl)-6-(imidazo[1,2-a]pyridine-3-carbonyl)-4,5,6,7-tetrahydrothieno[2,3-c]pyridine-3-carboxamide |
| 5 | 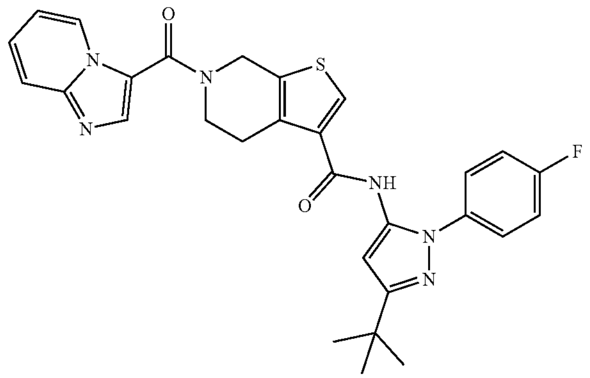 [SMILES: CC(C)(C)c1cc(NC(=O)c2csc3c2CCN(C(=O)c2cnc4ccccn24)C3)n(-c2ccc(F)cc2)n1] | N-(3-(tert-butyl)-1-(4-fluorophenyl)-1H-pyrazol-5-yl)-6-(imidazo[1,2-a]pyridine-3-carbonyl)-4,5,6,7-tetrahydrothieno[2,3-c]pyridine-3-carboxamide |

TABLE 5-continued

List of compounds of Formula (Ibb)

| Example No. | Structure | Chemical Name |
|---|---|---|
| 6 | 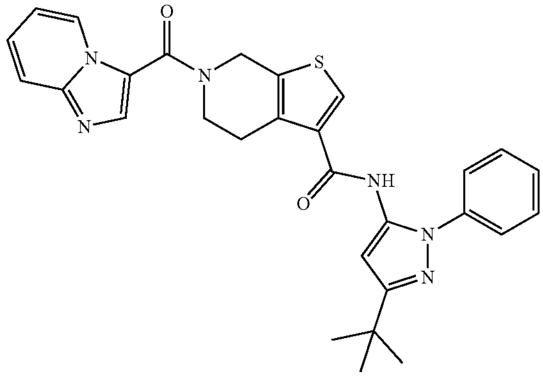 [SMILES: CC(C)(C)c1cc(NC(=O)c2csc3c2CCN(C(=O)c2cnc4ccccn24)C3)n(-c2ccccc2)n1] | N-(3-(tert-butyl)-1-phenyl-1H-pyrazol-5-yl)-6-(imidazo[1,2-a]pyridine-3-carbonyl)-4,5,6,7-tetrahydrothieno[2,3-c]pyridine-3-carboxamide |
| 9 | 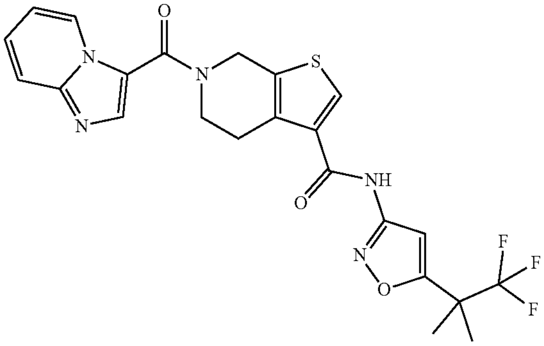 [SMILES: CC(C)(c1cc(NC(=O)c2csc3c2CCN(C(=O)c2cnc4ccccn24)C3)no1)C(F)(F)F] | 6-(imidazo[1,2-a]pyridine-3-carbonyl)-N-(5-(1,1,1-trifluoro-2-methylpropan-2-yl)isoxazol-3-yl)-4,5,6,7-tetrahydrothieno[2,3-c]pyridine-3-carboxamide |
| 17 | 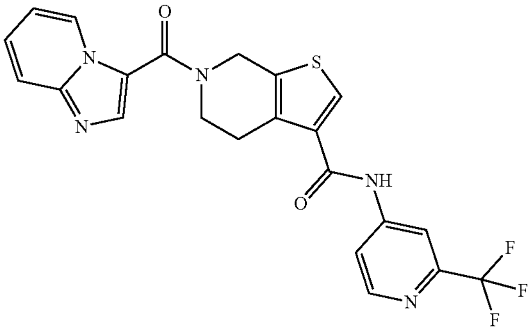 [SMILES: O=C(Nc1ccnc(C(F)(F)F)c1)c1csc2c1CCN(C(=O)c1cnc3ccccn13)C2] | 6-(imidazo[1,2-a]pyridine-3-carbonyl)-N-(2-(trifluoromethyl)pyridin-4-yl)-4,5,6,7-tetrahydrothieno[2,3-c]pyridine-3-carboxamide |
| 21 | 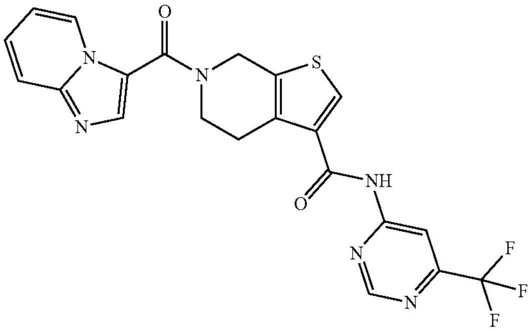 [SMILES: O=C(Nc1cc(C(F)(F)F)ncn1)c1csc2c1CCN(C(=O)c1cnc3ccccn13)C2] | 6-(imidazo[1,2-a]pyridine-3-carbonyl)-N-(6-(trifluoromethyl)pyrimidin-4-yl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 28 | 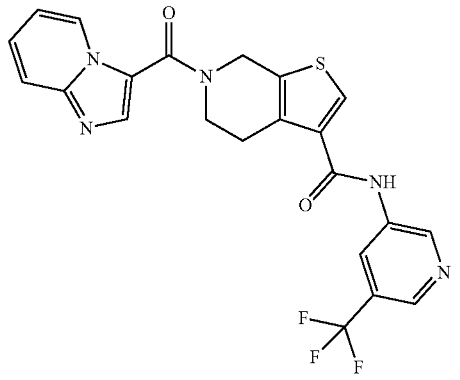 [SMILES: O=C(Nc1cncc(C(F)(F)F)c1)c1csc2c1CCN(C(=O)c1cnc3ccccn13)C2] | 6-(imidazo[1,2-a]pyridine-3-carbonyl)-N-(5-(trifluoromethyl)pyridin-3-yl)-4,5,6,7-tetrahydrothieno[2,3-c]pyridine-3-carboxamide |
| 29 | 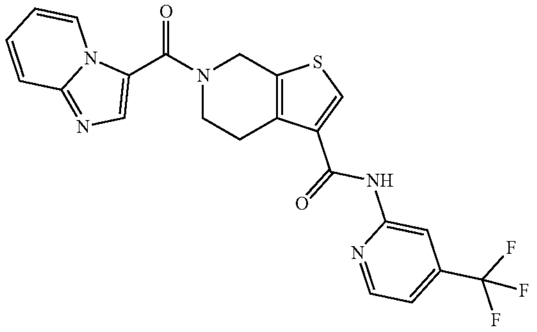 [SMILES: O=C(Nc1cc(C(F)(F)F)ccn1)c1csc2c1CCN(C(=O)c1cnc3ccccn13)C2] | 6-(imidazo[1,2-a]pyridine-3-carbonyl)-N-(4-(trifluoromethyl)pyridin-2-yl)-4,5,6,7-tetrahydrothieno[2,3-c]pyridine-3-carboxamide |
| 30 | 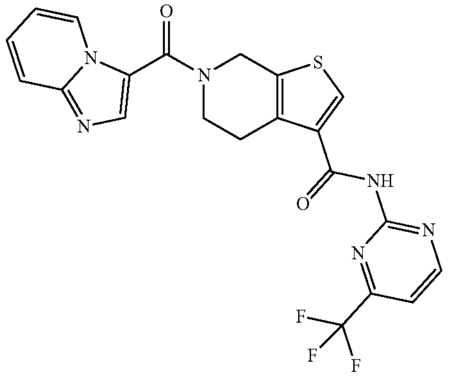 [SMILES: O=C(Nc1nccc(C(F)(F)F)n1)c1csc2c1CCN(C(=O)c1cnc3ccccn13)C2] | 6-(imidazo[1,2-a]pyridine-3-carbonyl)-N-(4-(trifluoromethyl)pyrimidin-2-yl)-4,5,6,7-tetrahydrothieno[2,3-c]pyridine-3-carboxamide |
| 33 | 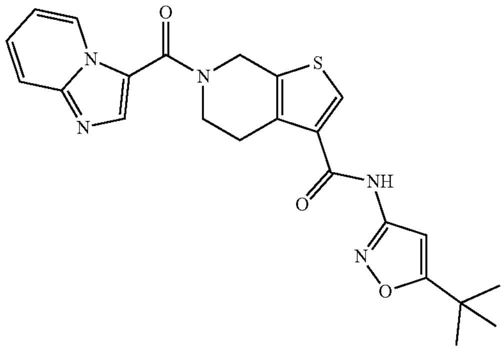 [SMILES: CC(C)(C)c1cc(NC(=O)c2csc3c2CCN(C(=O)c2cnc4ccccn24)C3)no1] | N-(5-(tert-butyl)isoxazol-3-yl)-6-(imidazo[1,2-a]pyridine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 34 | 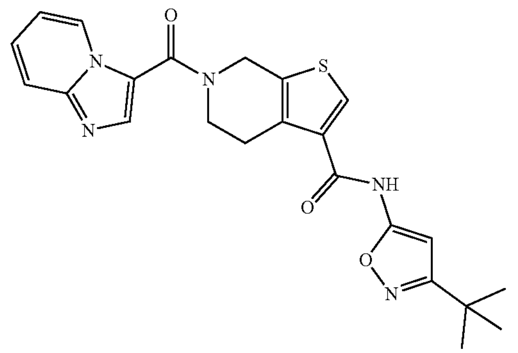 [SMILES: CC(C)(C)c1cc(NC(=O)c2csc3c2CCN(C(=O)c2cnc4ccccn24)C3)on1] | N-(3-(tert-butyl)isoxazol-5-yl)-6-(imidazo[1,2-a]pyridine-3-carbonyl)-4,5,6,7-tetrahydrothieno[2,3-c]pyridine-3-carboxamide |
| 35 | 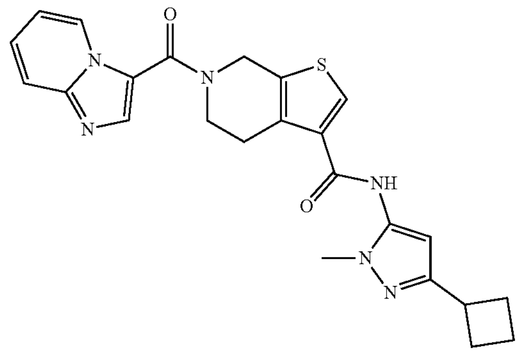 [SMILES: Cn1nc(C2CCC2)cc1NC(=O)c1csc2c1CCN(C(=O)c1cnc3ccccn13)C2] | N-(3-cyclobutyl-1-methyl-1H-pyrazol-5-yl)-6-(imidazo[1,2-a]pyridine-3-carbonyl)-4,5,6,7-tetrahydrothieno[2,3-c]pyridine-3-carboxamide |
| 36 | 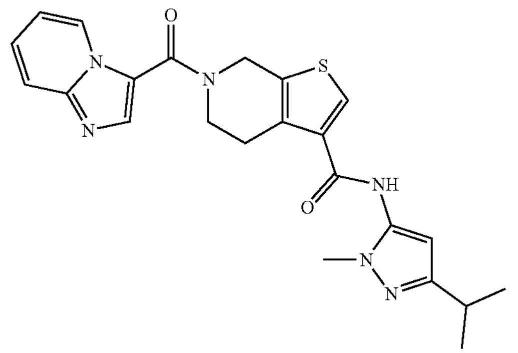 [SMILES: CC(C)c1cc(NC(=O)c2csc3c2CCN(C(=O)c2cnc4ccccn24)C3)n(C)n1] | 6-(imidazo[1,2-a]pyridine-3-carbonyl)-N-(3-isopropyl-1-methyl-1H-pyrazol-5-yl)-4,5,6,7-tetrahydrothieno[2,3-c]pyridine-3-carboxamide |
| 37 | 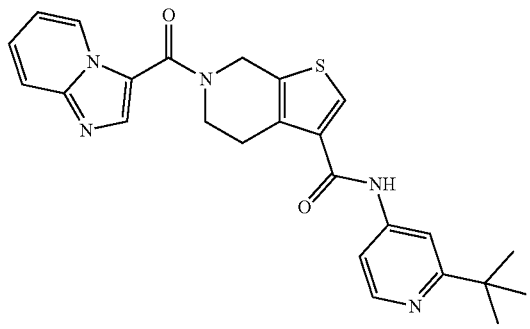 [SMILES: CC(C)(C)c1cc(NC(=O)c2csc3c2CCN(C(=O)c2cnc4ccccn24)C3)ccn1] | N-(2-(tert-butyl)pyridin-4-yl)-6-(imidazo[1,2-a]pyridine-3-carbonyl)-4,5,6,7-tetrahydrothieno[2,3-c]pyridine-3-carboxamide |

TABLE 5-continued

List of compounds of Formula (Ibb)

| Example No. | Structure | Chemical Name |
| --- | --- | --- |
| 38 | 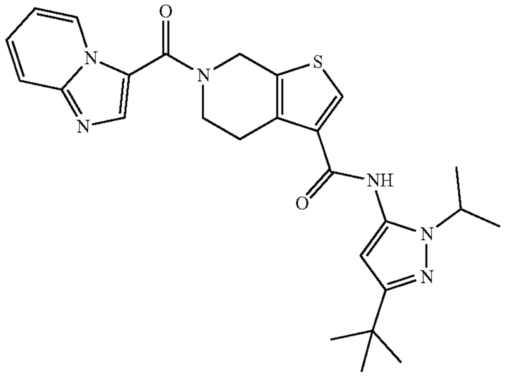 [SMILES: CC(C)n1nc(C(C)(C)C)cc1NC(=O)c1csc2c1CCN(C(=O)c1cnc3ccccn13)C2] | N-(3-(tert-butyl)-1-isopropyl-1H-pyrazol-5-yl)-6-(imidazo[1,2-a]pyridine-3-carbonyl)-4,5,6,7-tetrahydrothieno[2,3-c]pyridine-3-carboxamide |
| 39 | 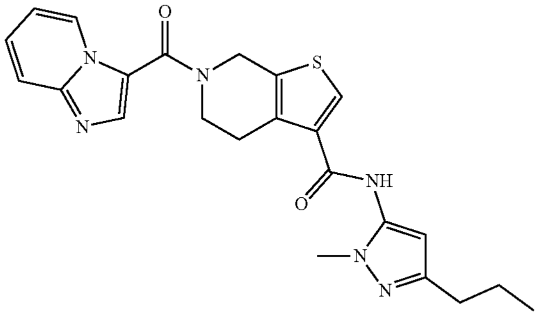 [SMILES: CCCc1cc(NC(=O)c2csc3c2CCN(C(=O)c2cnc4ccccn24)C3)n(C)n1] | 6-(imidazo[1,2-a]pyridine-3-carbonyl)-N-(1-methyl-3-propyl-1H-pyrazol-5-yl)-4,5,6,7-tetrahydrothieno[2,3-c]pyridine-3-carboxamide |
| 40 | 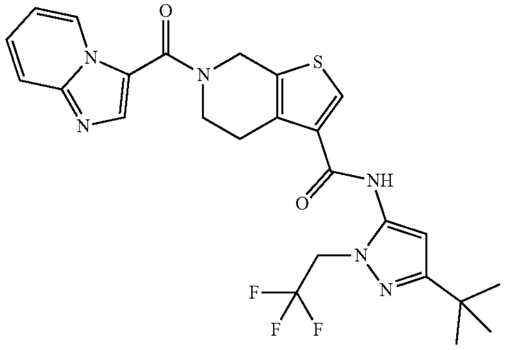 [SMILES: CC(C)(C)c1cc(NC(=O)c2csc3c2CCN(C(=O)c2cnc4ccccn24)C3)n(CC(F)(F)F)n1] | N-(3-(tert-butyl)-1-(2,2,2-trifluoroethyl)-1H-pyrazol-5-yl)-6-(imidazo[1,2-a]pyridine-3-carbonyl)-4,5,6,7-tetrahydrothieno[2,3-c]pyridine-3-carboxamide |
| 41 | 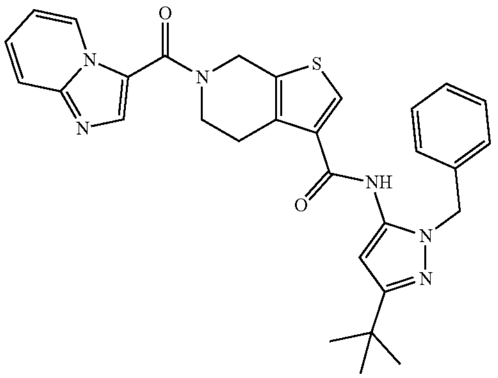 [SMILES: CC(C)(C)c1cc(NC(=O)c2csc3c2CCN(C(=O)c2cnc4ccccn24)C3)n(Cc2ccccc2)n1] | N-(1-benzyl-3-(tert-butyl)-1H-pyrazol-5-yl)-6-(imidazo[1,2-a]pyridine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 42 | 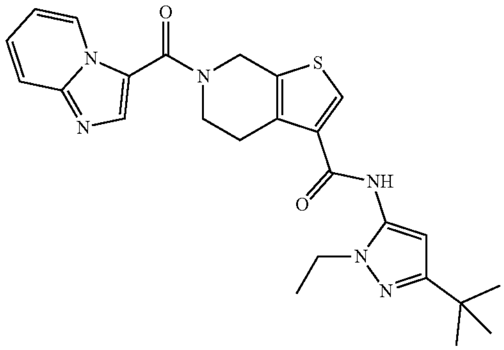 [SMILES: CCn1nc(C(C)(C)C)cc1NC(=O)c1csc2c1CCN(C(=O)c1cnc3ccccn13)C2] | N-(3-(tert-butyl)-1-ethyl-1H-pyrazol-5-yl)-6-(imidazo[1,2-a]pyridine-3-carbonyl)-4,5,6,7-tetrahydrothieno[2,3-c]pyridine-3-carboxamide |
| 43 | 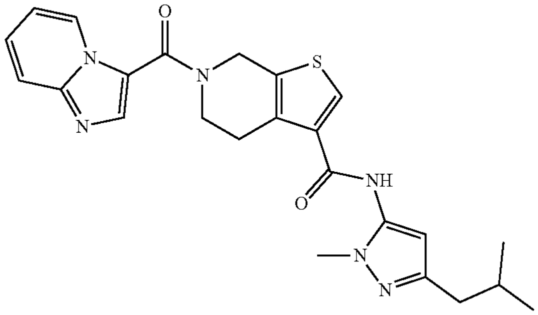 [SMILES: CC(C)Cc1cc(NC(=O)c2csc3c2CCN(C(=O)c2cnc4ccccn24)C3)n(C)n1] | 6-(imidazo[1,2-a]pyridine-3-carbonyl)-N-(3-isobutyl-1-methyl-1H-pyrazol-5-yl)-4,5,6,7-tetrahydrothieno[2,3-c]pyridine-3-carboxamide |
| 47 | 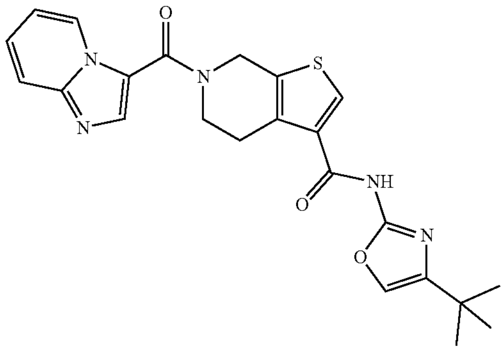 [SMILES: CC(C)(C)c1coc(NC(=O)c2csc3c2CCN(C(=O)c2cnc4ccccn24)C3)n1] | N-(4-(tert-butyl)oxazol-2-yl)-6-(imidazo[1,2-a]pyridine-3-carbonyl)-4,5,6,7-tetrahydrothieno[2,3-c]pyridine-3-carboxamide |
| 64 | 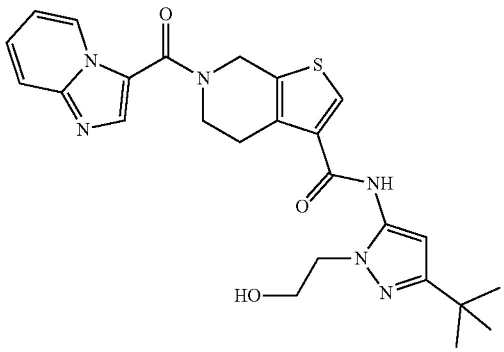 [SMILES: CC(C)(C)c1cc(NC(=O)c2csc3c2CCN(C(=O)c2cnc4ccccn24)C3)n(CCO)n1] | N-(3-(tert-butyl)-1-(2-hydroxyethyl)-1H-pyrazol-5-yl)-6-(imidazo[1,2-a]pyridine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 79 | 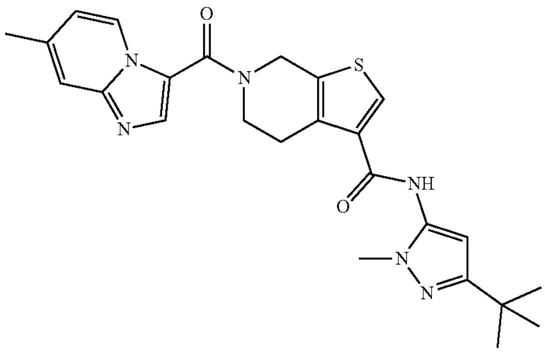 [SMILES: Cc1ccn2c(C(=O)N3CCc4c(C(=O)Nc5cc(C(C)(C)C)nn5C)csc4C3)cnc2c1] | N-(3-(tert-butyl)-1-methyl-1H-pyrazol-5-yl)-6-(7-methylimidazo[1,2-a]pyridine-3-carbonyl)-4,5,6,7-tetrahydrothieno[2,3-c]pyridine-3-carboxamide |
| 80 | 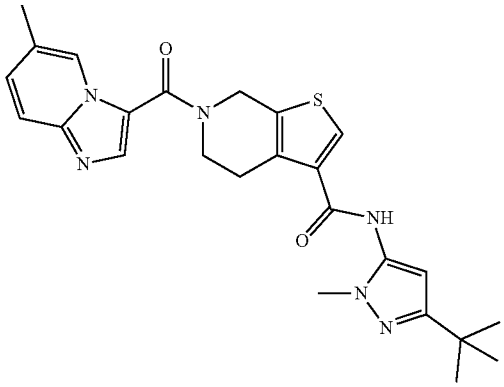 [SMILES: Cc1ccc2ncc(C(=O)N3CCc4c(C(=O)Nc5cc(C(C)(C)C)nn5C)csc4C3)n2c1] | N-(3-(tert-butyl)-1-methyl-1H-pyrazol-5-yl)-6-(6-methylimidazo[1,2-a]pyridine-3-carbonyl)-4,5,6,7-tetrahydrothieno[2,3-c]pyridine-3-carboxamide |
| 81 | 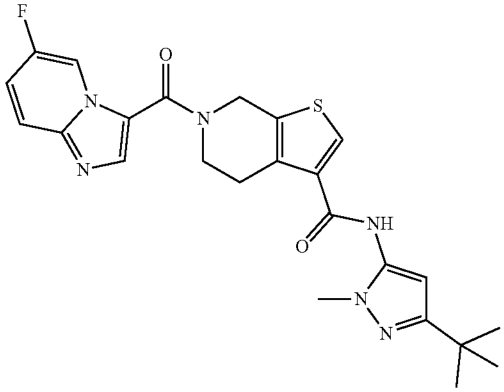 [SMILES: Cn1nc(C(C)(C)C)cc1NC(=O)c1csc2c1CCN(C(=O)c1cnc3ccc(F)cn13)C2] | N-(3-(tert-butyl)-1-methyl-1H-pyrazol-5-yl)-6-(6-fluoroimidazo[1,2-a]pyridine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 82 | 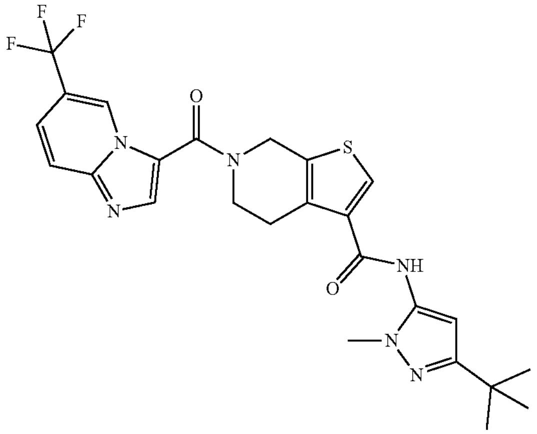 [SMILES: Cn1nc(C(C)(C)C)cc1NC(=O)c1csc2c1CCN(C(=O)c1cnc3ccc(C(F)(F)F)cn13)C2] | N-(3-(tert-butyl)-1-methyl-1H-pyrazol-5-yl)-6-(6-(trifluoromethyl)imidazo[1,2-a]pyridine-3-carbonyl)-4,5,6,7-tetrahydrothieno[2,3-c]pyridine-3-carboxamide |
| 83 | 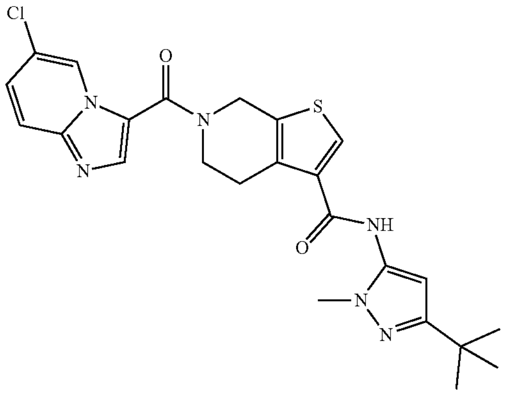 [SMILES: Cn1nc(C(C)(C)C)cc1NC(=O)c1csc2c1CCN(C(=O)c1cnc3ccc(Cl)cn13)C2] | N-(3-(tert-butyl)-1-methyl-1H-pyrazol-5-yl)-6-(6-chloroimidazo[1,2-a]pyridine-3-carbonyl)-4,5,6,7-tetrahydrothieno[2,3-c]pyridine-3-carboxamide |
| 99 | 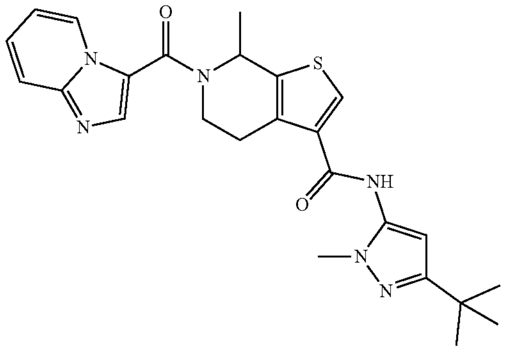 [SMILES: CC1c2scc(C(=O)Nc3cc(C(C)(C)C)nn3C)c2CCN1C(=O)c1cnc2ccccn12] | N-(3-(tert-butyl)-1-methyl-1H-pyrazol-5-yl)-6-(imidazo[1,2-a]pyridine-3-carbonyl)-7-methyl-4,5,6,7-tetrahydrothieno[2,3-c]pyridine-3-carboxamide |

TABLE 5-continued

List of compounds of Formula (Ibb)

| Example No. | Structure | Chemical Name |
| --- | --- | --- |
| 108 | 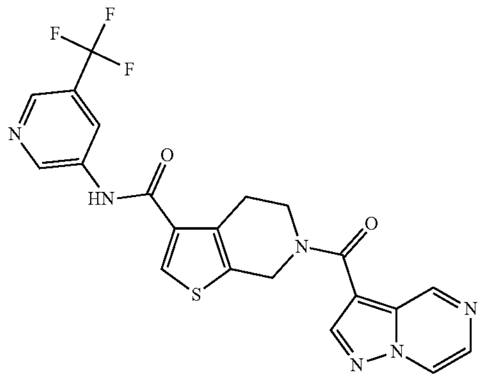 [SMILES: O=C(Nc1cncc(C(F)(F)F)c1)c1csc2c1CCN(C(=O)c1cnn3ccncc13)C2] | 6-(pyrazolo[1,5-a]pyrazine-3-carbonyl)-N-(5-(trifluoromethyl)pyridin-3-yl)-4,5,6,7-tetrahydrothieno[2,3-c]pyridine-3-carboxamide |
| 109 | 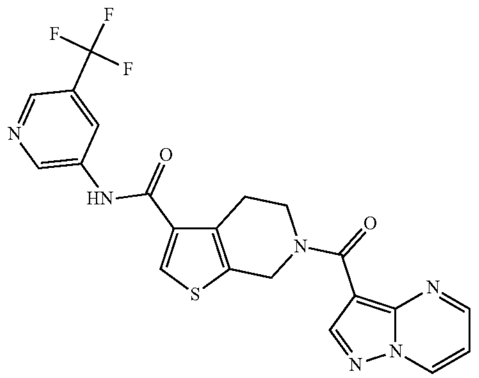 [SMILES: O=C(Nc1cncc(C(F)(F)F)c1)c1csc2c1CCN(C(=O)c1cnn3cccnc13)C2] | 6-(pyrazolo[1,5-a]pyrimidine-3-carbonyl)-N-(5-(trifluoromethyl)pyridin-3-yl)-4,5,6,7-tetrahydrothieno[2,3-c]pyridine-3-carboxamide |
| 110 | 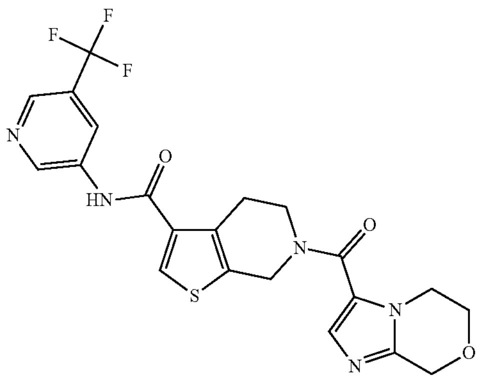 [SMILES: O=C(Nc1cncc(C(F)(F)F)c1)c1csc2c1CCN(C(=O)c1cnc3n1CCOC3)C2] | 6-(5,6-dihydro-8H-imidazo[2,1-c][1,4]oxazine-3-carbonyl)-N-(5-(trifluoromethyl)pyridin-3-yl)-4,5,6,7-tetrahydrothieno[2,3-c]pyridine-3-carboxamide |
| 111 | 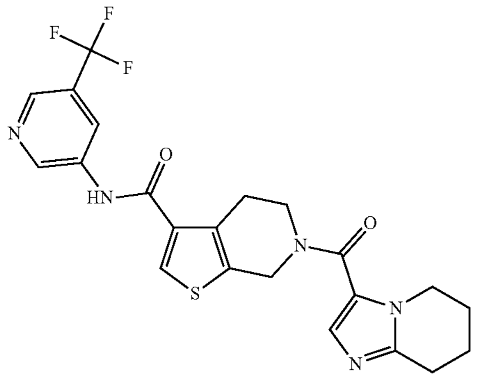 [SMILES: O=C(Nc1cncc(C(F)(F)F)c1)c1csc2c1CCN(C(=O)c1cnc3n1CCCC3)C2] | 6-(5,6,7,8-tetrahydro imidazo[1,2-a]pyridine-3-carbonyl)-N-(5-(trifluoromethyl)pyridin-3-yl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 112 | 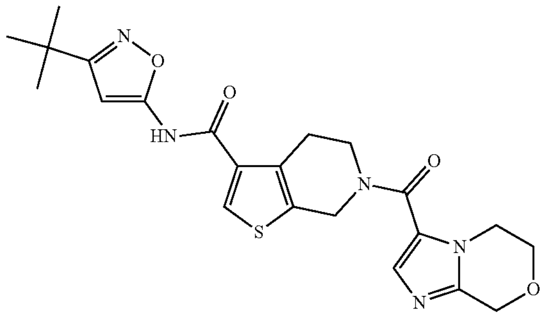 [SMILES: CC(C)(C)c1cc(NC(=O)c2csc3c2CCN(C(=O)c2cnc4n2CCOC4)C3)on1] | N-(3-(tert-butyl)isoxazol-5-yl)-6-(5,6-dihydro-8H-imidazo[2,1-c][1,4]oxazine-3-carbonyl)-4,5,6,7-tetrahydrothieno[2,3-c]pyridine-3-carboxamide |
| 113 | 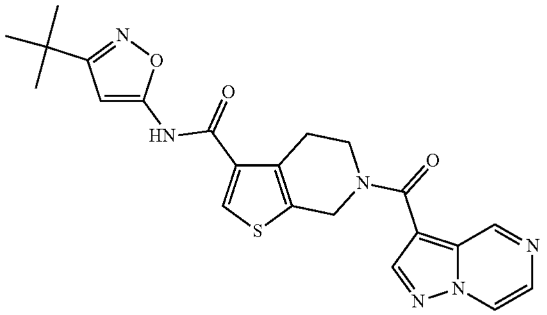 [SMILES: CC(C)(C)c1cc(NC(=O)c2csc3c2CCN(C(=O)c2cnn4ccncc24)C3)on1] | N-(3-(tert-butyl)isoxazol-5-yl)-6-(pyrazolo[1,5-a]pyrazine-3-carbonyl)-4,5,6,7-tetrahydrothieno[2,3-c]pyridine-3-carboxamide |
| 114 | 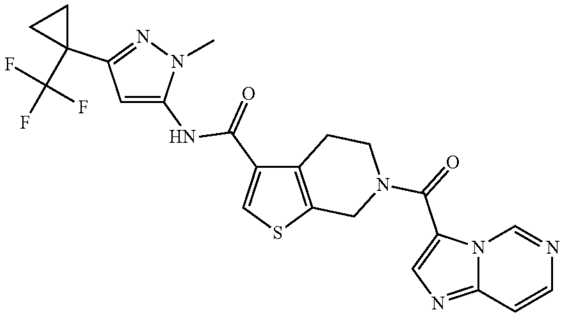 [SMILES: Cn1nc(C2(C(F)(F)F)CC2)cc1NC(=O)c1csc2c1CCN(C(=O)c1cnc3ccncn13)C2] | 6-(imidazo[1,2-a]pyridine-3-carbonyl)-N-(1-methyl-3-(1-(trifluoromethyl)cyclopropyl)-1H-pyrazol-5-yl)-4,5,6,7-tetrahydrothieno[2,3-c]pyridine-3-carboxamide |
| 115 | 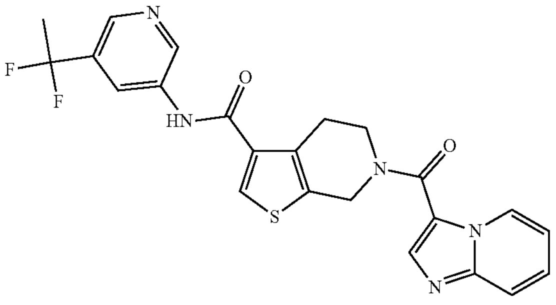 [SMILES: CC(F)(F)c1cncc(NC(=O)c2csc3c2CCN(C(=O)c2cnc4ccccn24)C3)c1] | N-(5-(1,1-difluoroethyl)pyridin-3-yl)-6-(imidazo[1,2-a]pyridine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 116 | 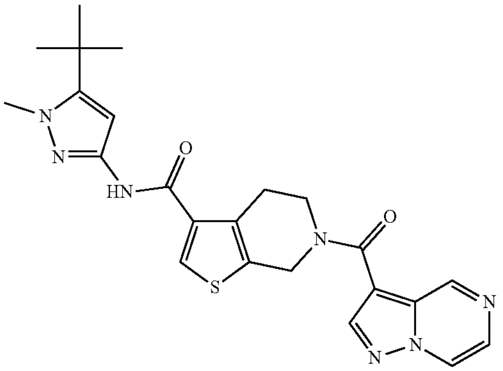 [SMILES: Cn1nc(NC(=O)c2csc3c2CCN(C(=O)c2cnn4ccncc24)C3)cc1C(C)(C)C] | N-(5-(tert-butyl)-1-methyl-1H-pyrazol-3-yl)-6-(pyrazolo[1,5-a]pyrazine-3-carbonyl)-4,5,6,7-tetrahydrothieno[2,3-c]pyridine-3-carboxamide |
| 117 | 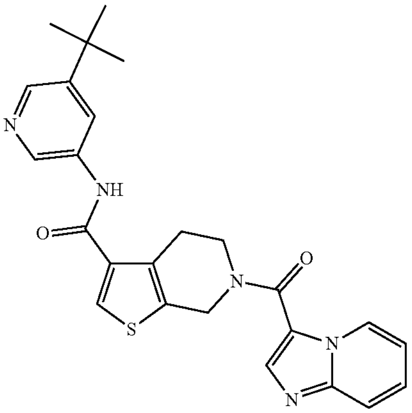 [SMILES: CC(C)(C)c1cncc(NC(=O)c2csc3c2CCN(C(=O)c2cnc4ccccn24)C3)c1] | N-(5-(tert-butyl)pyridin-3-yl)-6-(imidazo[1,2-a]pyridine-3-carbonyl)-4,5,6,7-tetrahydrothieno[2,3-c]pyridine-3-carboxamide |
| 118 | 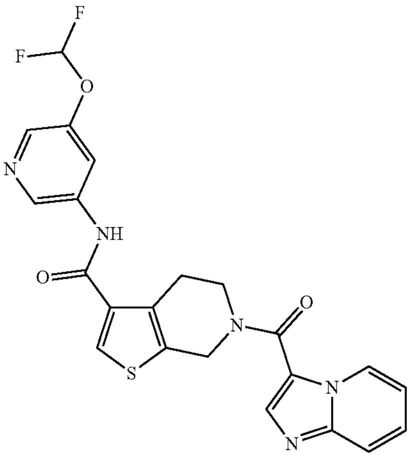 [SMILES: O=C(Nc1cncc(OC(F)F)c1)c1csc2c1CCN(C(=O)c1cnc3ccccn13)C2] | N-(5-(difluoromethoxy)pyridin-3-yl)-6-(imidazo[1,2-a]pyridine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 119 | 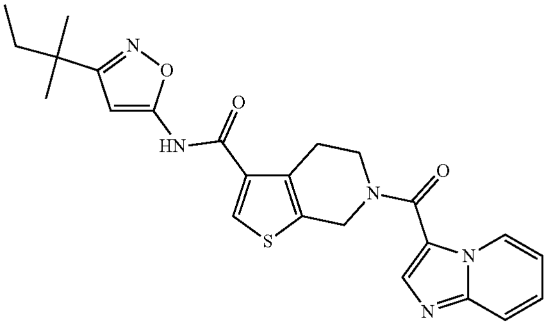 [SMILES: CCC(C)(C)c1cc(NC(=O)c2csc3c2CCN(C(=O)c2cnc4ccccn24)C3)on1] | 6-(imidazo[1,2-a]pyridine-3-carbonyl)-N-(3-(tert-pentyl)isoxazol-5-yl)-4,5,6,7-tetrahydrothieno[2,3-c]pyridine-3-carboxamide |
| 120 | 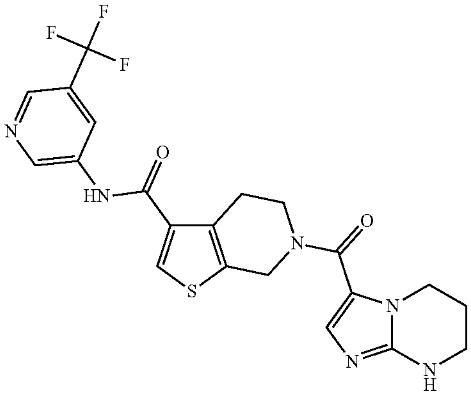 [SMILES: O=C(Nc1cncc(C(F)(F)F)c1)c1csc2c1CCN(C(=O)c1cnc3n1CCCN3)C2] | 6-(5,6,7,8-tetrahydroimidazo[1,2-a]pyrimidine-3-carbonyl)-N-(5-(trifluoromethyl)pyridin-3-yl)-4,5,6,7-tetrahydrothieno[2,3-c]pyridine-3-carboxamide |
| 121 | 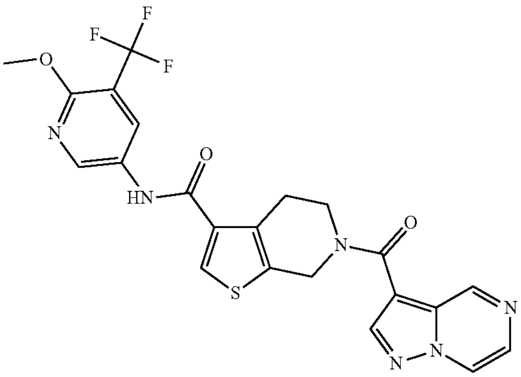 [SMILES: COc1ncc(NC(=O)c2csc3c2CCN(C(=O)c2cnn4ccncc24)C3)cc1C(F)(F)F] | N-(6-methoxy-5-(trifluoromethyl)pyridin-3-yl)-6-(pyrazolo[1,5-a]pyrazine-3-carbonyl)-4,5,6,7-tetrahydrothieno[2,3-c]pyridine-3-carboxamide |
| 122 | 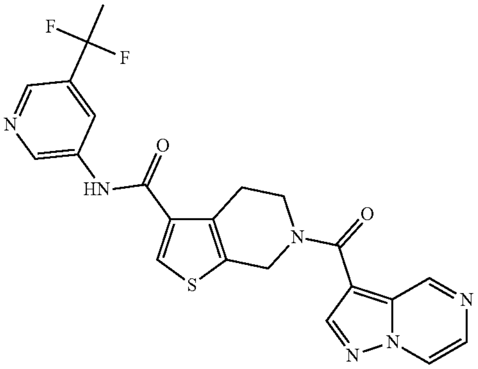 [SMILES: CC(F)(F)c1cncc(NC(=O)c2csc3c2CCN(C(=O)c2cnn4ccncc24)C3)c1] | N-(5-(1,1-difluoroethyl)pyridin-3-yl)-6-(pyrazolo[1,5-a]pyrazine-3-carbonyl)-4,5,6,7-tetrahydrothieno[2,3-c]pyridine-3-carboxamide |

TABLE 5-continued

List of compounds of Formula (Ibb)

| Example No. | Structure | Chemical Name |
| --- | --- | --- |
| 123 | 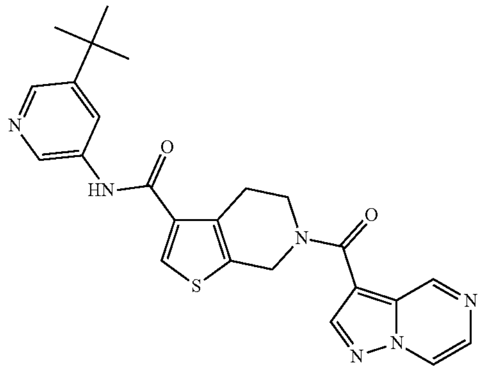 [SMILES: CC(C)(C)c1cncc(NC(=O)c2csc3c2CCN(C(=O)c2cnn4ccncc24)C3)c1] | N-(5-(tert-butyl)pyridin-3-yl)-6-(pyrazolo[1,5-a]pyrazine-3-carbonyl)-4,5,6,7-tetrahydrothieno[2,3-c]pyridine-3-carboxamide |
| 124 | 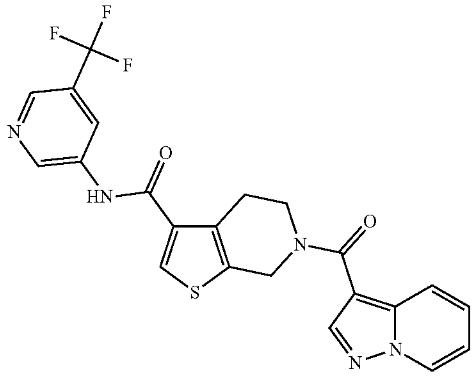 [SMILES: O=C(Nc1cncc(C(F)(F)F)c1)c1csc2c1CCN(C(=O)c1cnn3ccccc13)C2] | 6-(pyrazolo[1,5-a]pyridine-3-carbonyl)-N-(5-(trifluoromethyl)pyridin-3-yl)-4,5,6,7-tetrahydrothieno[2,3-c]pyridine-3-carboxamide |
| 125 | 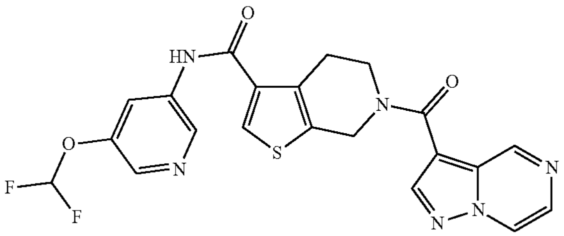 [SMILES: O=C(Nc1cncc(OC(F)F)c1)c1csc2c1CCN(C(=O)c1cnn3ccncc13)C2] | N-(5-(difluoromethoxy)pyridin-3-yl)-6-(pyrazolo[1,5-a]pyrazine-3-carbonyl)-4,5,6,7-tetrahydrothieno[2,3-c]pyridine-3-carboxamide |
| 126 | 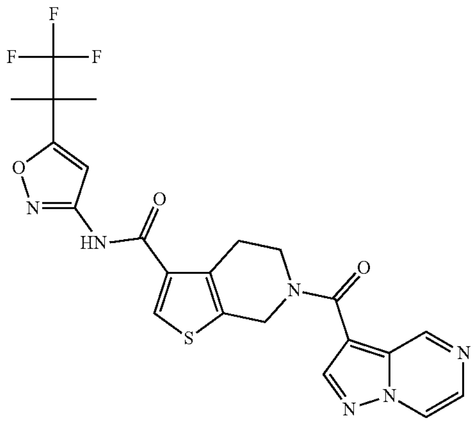 [SMILES: CC(C)(c1cc(NC(=O)c2csc3c2CCN(C(=O)c2cnn4ccncc24)C3)no1)C(F)(F)F] | 6-(pyrazolo[1,5-a]pyrazine-3-carbonyl)-N-(5-(1,1,1-trifluoro-2-methylpropan-2-yl)isoxazol-3-yl)-4,5,6,7-tetrahydrothieno[2,3-c]pyridine-3-carboxamide |

TABLE 5-continued

| Example No. | Structure | Chemical Name |
| --- | --- | --- |
| | List of compounds of Formula (Ibb) | |
| 127 | 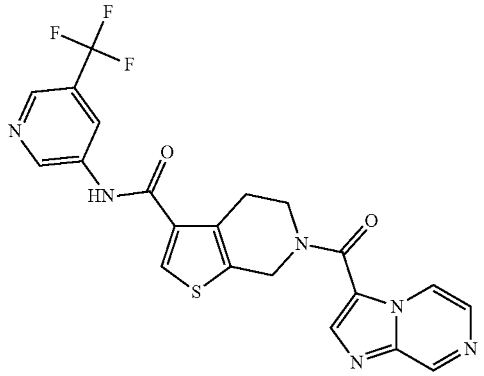 [SMILES: O=C(Nc1cncc(C(F)(F)F)c1)c1csc2c1CCN(C(=O)c1cnc3cnccn13)C2] | 6-(imidazo[1,2-a]pyrazine-3-carbonyl)-N-(5-(trifluoromethyl)pyridin-3-yl)-4,5,6,7-tetrahydrothieno[2,3-c]pyridine-3-carboxamide |
| 128 | 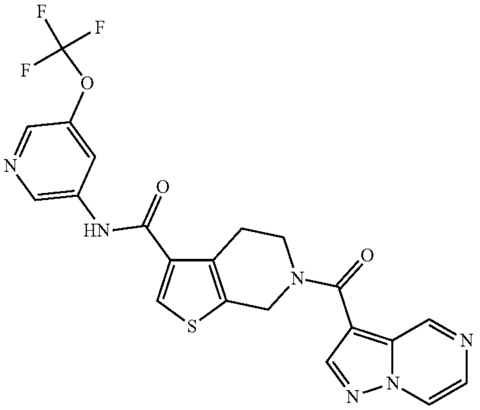 [SMILES: O=C(Nc1cncc(OC(F)(F)F)c1)c1csc2c1CCN(C(=O)c1cnn3ccncc13)C2] | 6-(pyrazolo[1,5-a]pyrazine-3-carbonyl)-N-(5-(trifluoromethoxy)pyridin-3-yl)-4,5,6,7-tetrahydrothieno[2,3-c]pyridine-3-carboxamide |
| 129 | 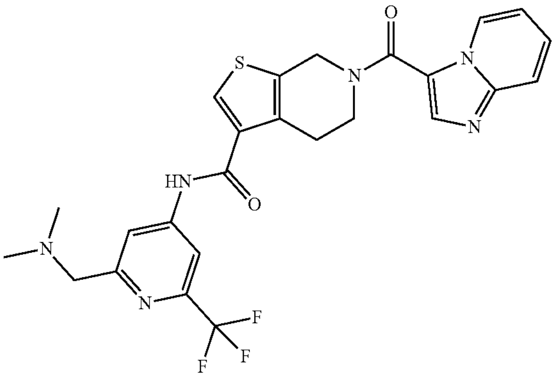 [SMILES: CN(C)Cc1cc(NC(=O)c2csc3c2CCN(C(=O)c2cnc4ccccn24)C3)cc(C(F)(F)F)n1] | N-(2-((dimethylamino)methyl)-6-(trifluoromethyl)pyridin-4-yl)-6-(imidazo[1,2-a]pyridine-3-carbonyl)-4,5,6,7-tetrahydrothieno[2,3-c]pyridine-3-carboxamide |
| 140 | 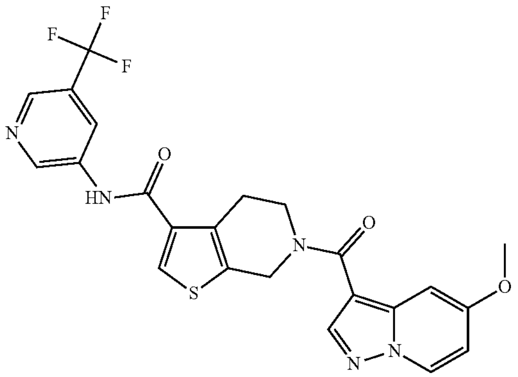 [SMILES: COc1ccn2ncc(C(=O)N3CCc4c(C(=O)Nc5cncc(C(F)(F)F)c5)csc4C3)c2c1] | 6-(5-methoxypyrazolo[1,5-a]pyridine-3-carbonyl)-N-(5-(trifluoromethyl)pyridin-3-yl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 141 | 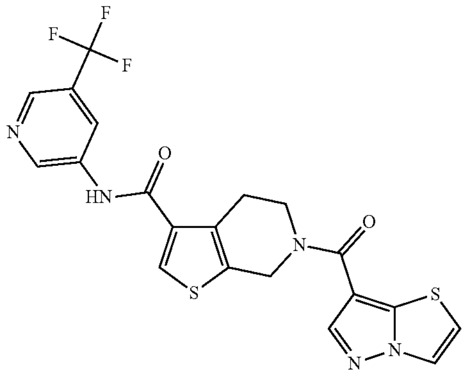 [SMILES: O=C(Nc1cncc(C(F)(F)F)c1)c1csc2c1CCN(C(=O)c1cnn3ccsc13)C2] | 6-(pyrazolo[5,1-b]thiazole-7-carbonyl)-N-(5-(trifluoromethyl)pyridin-3-yl)-4,5,6,7-tetrahydrothieno[2,3-c]pyridine-3-carboxamide |
| 142 | 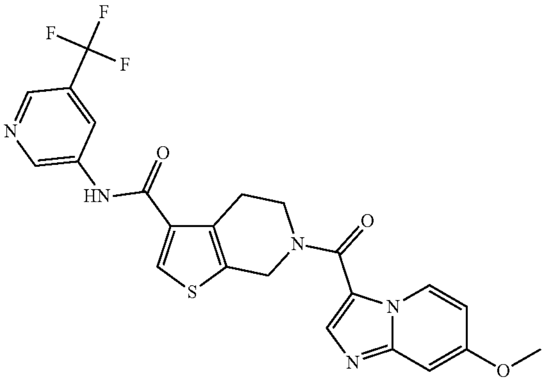 [SMILES: COc1ccn2c(C(=O)N3CCc4c(C(=O)Nc5cncc(C(F)(F)F)c5)csc4C3)cnc2c1] | 6-(7-methoxyimidazo[1,2-a]pyridine-3-carbonyl)-N-(5-(trifluoromethyl)pyridin-3-yl)-4,5,6,7-tetrahydrothieno[2,3-c]pyridine-3-carboxamide |
| 143 | 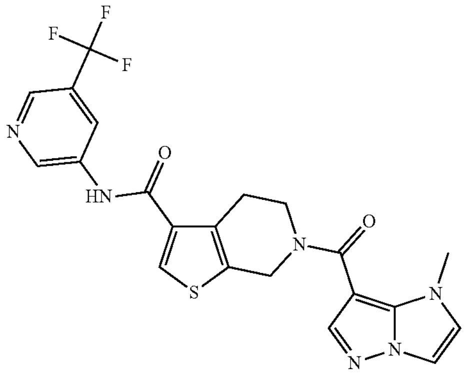 [SMILES: Cn1ccn2ncc(C(=O)N3CCc4c(C(=O)Nc5cncc(C(F)(F)F)c5)csc4C3)c12] | 6-(1-methyl-1H-imidazo[1,2-b]pyrazole-7-carbonyl)-N-(5-(trifluoromethyl)pyridin-3-yl)-4,5,6,7-tetrahydrothieno[2,3-c]pyridine-3-carboxamide |
| 144 | 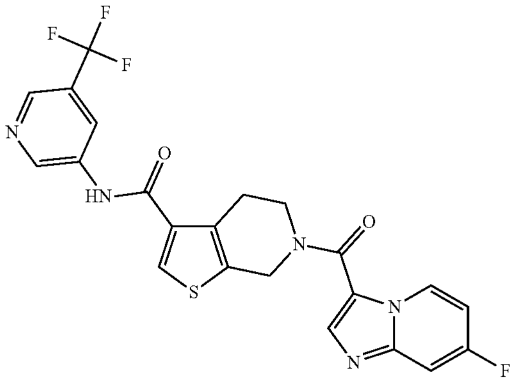 [SMILES: O=C(Nc1cncc(C(F)(F)F)c1)c1csc2c1CCN(C(=O)c1cnc3cc(F)ccn13)C2] | 6-(7-fluoroimidazo[1,2-a]pyridine-3-carbonyl)-N-(5-(trifluoromethyl)pyridin-3-yl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 145 | 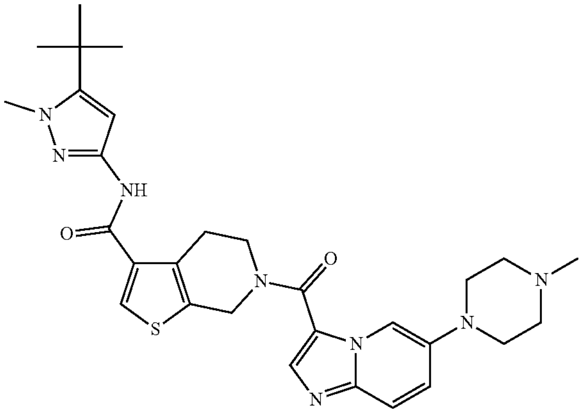 | N-(5-(tert-butyl)-1-methyl-1H-pyrazol-3-yl)-6-(6-(4-methylpiperazin-1-yl)imidazo[1,2-a]pyridine-3-carbonyl)-4,5,6,7-tetrahydrothieno[2,3-c]pyridine-3-carboxamide |
| 165 | 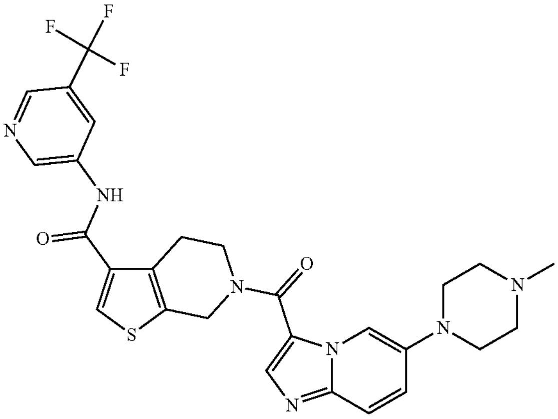 [SMILES: CN1CCN(c2ccc3ncc(C(=O)N4CCc5c(C(=O)Nc6cncc(C(F)(F)F)c6)csc5C4)n3c2)CC1] | 6-(6-(4-methylpiperazin-1-yl)imidazo[1,2-a]pyridine-3-carbonyl)-N-(5-(trifluoromethyl)pyridin-3-yl)-4,5,6,7-tetrahydrothieno[2,3-c]pyridine-3-carboxamide |
| 168 | 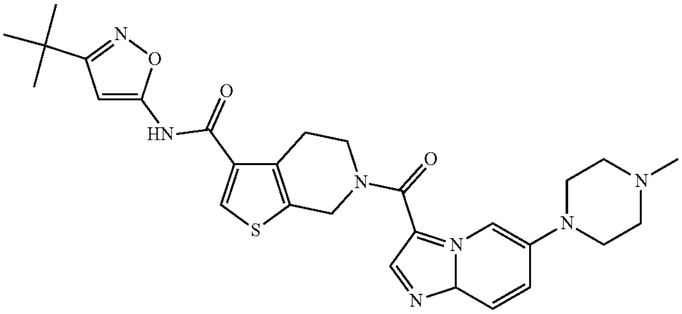 | N-(3-(tert-butyl)isoxazol-5-yl)-6-(6-(4-methylpiperazin-1-yl)imidazo[1,2-a]pyridine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 173 | 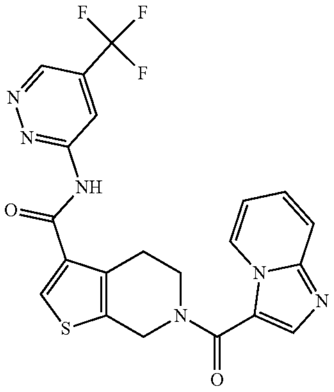 [SMILES: O=C(Nc1cc(C(F)(F)F)cnn1)c1csc2c1CCN(C(=O)c1cnc3ccccn13)C2] | 6-(imidazo[1,2-a]pyridine-3-carbonyl)-N-(5-(trifluoromethyl)pyridazin-3-yl)-4,5,6,7-tetrahydrothieno[2,3-c]pyridine-3-carboxamide |
| 175 | 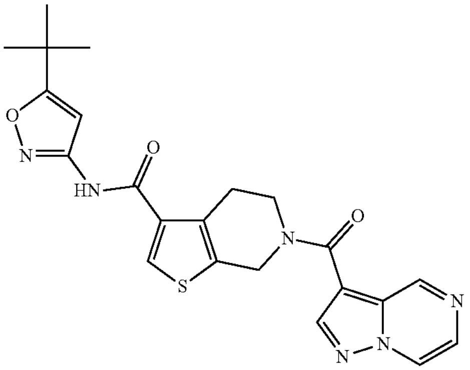 [SMILES: CC(C)(C)c1cc(NC(=O)c2csc3c2CCN(C(=O)c2cnn4ccncc24)C3)no1] | N-(5-(tert-butyl)isoxazol-3-yl)-6-(pyrazolo[1,5-a]pyrazine-3-carbonyl)-4,5,6,7-tetrahydrothieno[2,3-c]pyridine-3-carboxamide |
| 179 | 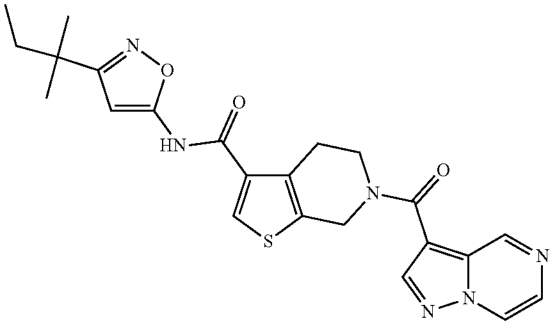 [SMILES: CCC(C)(C)c1cc(NC(=O)c2csc3c2CCN(C(=O)c2cnn4ccncc24)C3)on1] | N-(3-(tert-pentyl)isoxazol-5-yl)-6-(pyrazolo[1,5-a]pyrazine-3-carbonyl)-4,5,6,7-tetrahydrothieno[2,3-c]pyridine-3-carboxamide |
| 183 | 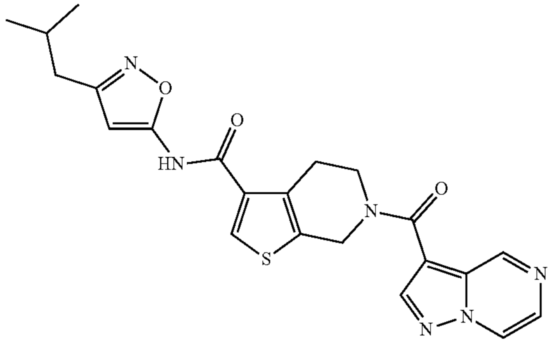 [SMILES: CC(C)Cc1cc(NC(=O)c2csc3c2CCN(C(=O)c2cnn4ccncc24)C3)on1] | N-(3-isobutylisoxazol-5-yl)-6-(pyrazolo[1,5-a]pyrazine-3-carbonyl)-4,5,6,7-tetrahydrothieno[2,3-c]pyridine-3-carboxamide |

TABLE 5-continued

| List of compounds of Formula (Ibb) | | |
|---|---|---|
| Example No. | Structure | Chemical Name |
| 186 | 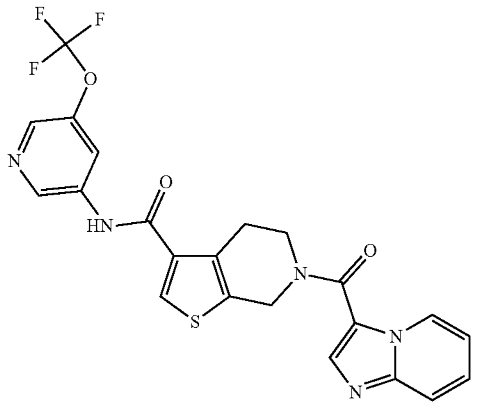 [SMILES: O=C(Nc1cncc(OC(F)(F)F)c1)c1csc2c1CCN(C(=O)c1cnc3ccccn13)C2] | 6-(imidazo[1,2-a]pyridine-3-carbonyl)-N-(5-(trifluoromethoxy)pyridin-3-yl)-4,5,6,7-tetrahydrothieno[2,3-c]pyridine-3-carboxamide |

In another preferred embodiment the present invention refers to a compound of formula (I) wherein Rx, Ry and Rz are H.

In another preferred embodiment the present invention refers to a compound of formula (I) wherein Rx is H, Ry is methyl, Rz is H.

In another preferred embodiment the present invention refers to a compound of formula (I) wherein Rx is methyl, Ry is H, Rz is H.

In another preferred embodiment the present invention refers to a compound of formula (I) wherein Rx is H, Ry is methyl, Rz is methyl.

It is clearly understood that any compound of the present invention may be encompassed by more than one general formula. For instance, and not limited to that, a compound having $R_1$ being X' may be encompassed by both formula (Ia) and formula (Iab).

The compounds of the invention, including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be obtained using the methods described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

In some cases, generally known protective groups (PG) could be employed when needed to mask or protect sensitive or reactive moieties, in accordance to general principles of chemistry (Protective group in organic syntheses, 3rd ed. T. W. Greene, P. G. M. Wuts).

The compounds of formula (I) of the present invention have surprisingly been found to effectively inhibit both receptor DDR1 and DDR2. Advantageously, the inhibition of receptors DDR1 and DDR2 may result in efficacious treatment of the diseases or condition wherein the DDR receptors are involved.

In this respect, it has now been found that the compounds of formula (I) of the present invention have an antagonist drug potency expressed as inhibition constant Ki on DDR1 and DDR2 lower than 80 nM, as shown in the present experimental part. Preferably, the compounds of the present invention have a Ki on DDR1 and DDR2 lower than 50 nM. Even more preferably, the compounds of the present invention have a Ki on DDR1 and DDR2 lower than 25 nM.

In addition, it has been found that the compounds of formula (I) of the present invention have both the affinity for either DDR1 and DD2 receptors and the inhibitory activity against either DDR1 and DDR2 receptors below about 80 nM respectively in the binding (expressed as Ki) and the cell based assays (expressed as IC50), as shown in the present experimental part. Preferably, the compounds of the present invention have a Ki and/or an IC50 on DDR1 and DDR2 receptors lower than 50 nM. Even more preferably, the compounds of the present invention have a Ki and/or an IC50 on DDR1 and DDR2 receptors lower than 25 nM.

In one aspect, the present invention refers to a compound of formula (I) according to any of the embodiments disclosed above for use as a medicament.

In a preferred embodiment, the invention refers to a compound of formula (I) and pharmaceutically acceptable salts thereof, for use in treating a disease, disorder, or condition associated with dysregulation of DDR.

In another aspect, the invention refers to the use of a compound of formula (I) as above described in the preparation of a medicament for the treatment of disorders associated with dysregulation of DDR.

In a preferred embodiment, the invention refers to a compound of formula (I) or a pharmaceutically acceptable salt thereof, for use in the prevention and/or treatment of a disease, disorder or condition associated with DDR receptor mechanism. In one embodiment, the present invention refers to a compound of formula (I) useful for the prevention and/or treatment of fibrosis and/or diseases, disorders, or conditions that involve fibrosis.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Preferably, the compounds of formula (I) as above described are useful for the treatment and/or prevention of fibrosis such as pulmonary fibrosis, idiopathic pulmonary fibrosis (IPF), hepatic fibrosis, renal fibrosis, ocular fibrosis, cardiac fibrosis, arterial fibrosis and systemic sclerosis.

More preferably, the compounds of formula (I) as above described are for the treatment of idiopathic pulmonary fibrosis (IPF).

In one aspect, the invention also refers to a method for the prevention and/or treatment of disorders associated with DDR receptors mechanisms, said method comprises administering to a patient in need of such treatment a therapeutically effective amount of a compound of formula (I) as above described.

In a further aspect, the invention refers to the use of a compound of formula (I) as above described for the treatment of disorders associated with DDR receptors mechanism.

In another aspect, the invention refers to the use of a compound of formula (I) as above described in the preparation of a medicament for the treatment of disorders associated with DDR receptors mechanism.

In a further aspect, the invention refers to a method for the prevention and/or treatment of a disorder or condition associated with dysregulation of DDR receptors 1 and 2, said method comprising administering a patient in need of such treatment a therapeutically effective amount of a compound of formula (I) as above described.

In a further aspect, the present invention refers to the use of a compound of formula (I) as above described for the treatment of a disease, disorder or condition associated with dysregulation of DDR receptors 1 and 2.

As used herein, “safe and effective amount” in reference to a compound of formula (I) or a pharmaceutically acceptable salt thereof or other pharmaceutically-active agent means an amount of the compound sufficient to treat the patient’s condition but low enough to avoid serious side effects and it can nevertheless be routinely determined by the skilled artisan.

The compounds of formula (I) may be administered once or according to a dosing regimen wherein a number of doses are administered at varying intervals of time for a given period of time. Typical daily dosages may vary depending upon the route of administration chosen.

The present invention also refers to a pharmaceutical composition comprising a compound of formula (I) according to any of its embodiment in admixture with at least one or more pharmaceutically acceptable carrier or excipient.

In one embodiment, the invention refers to a pharmaceutical composition of compounds of formula (I) in admixture with one or more pharmaceutically acceptable carrier or excipient, for example those described in Remington’s Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably, the compounds of the present invention are administered orally or by inhalation.

In one preferred embodiment, the pharmaceutical composition comprising the compound of formula (I) is a solid oral dosage form such as tablets, gelcaps, capsules, caplets, granules, lozenges and bulk powders.

In one embodiment, the pharmaceutical composition comprising the compound of formula (I) is a tablet.

The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like.

In a further embodiment, the pharmaceutical composition comprising a compound of formula (I) is a liquid oral dosage forms such as aqueous and non-aqueous solutions, emulsions, suspensions, syrups, and elixirs. Such liquid dosage forms can also contain suitable known inert diluents such as water and suitable known excipients such as preservatives, wetting agents, sweeteners, flavorants, as well as agents for emulsifying and/or suspending the compounds of the invention.

In a further embodiment, the pharmaceutical composition comprising the compound of formula (I) is an inhalable preparation such as inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

The compounds of the invention can be administered as the sole active agent or in combination with other pharmaceutical active ingredients.

The dosages of the compounds of the invention depend upon a variety of factors including among others the particular disease to be treated, the severity of the symptoms, the route of administration and the like.

The invention is also directed to a device comprising a pharmaceutical composition comprising a compound of Formula (I) according to the invention, in form of a single- or multi-dose dry powder inhaler or a metered dose inhaler.

All preferred groups or embodiments described above for compounds of formula (I) may be combined among each other and apply as well mutatis mutandis.

The compounds of the invention, including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be obtained using the methods described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes described below and reported in the following schemes should not be viewed as limiting the scope of the synthetic methods available for the preparation of the compounds of the invention.

The compounds of formula (I) including all the compounds or at least one of the here above listed can be generally prepared according to the procedure outlined in detail in the Schemes shown below, using generally known methods.

In a first embodiment of the present invention, compounds of formula (I) wherein $R_1$, Rx, Ry, Rz, L and Hy are as defined above, can be prepared as described in Scheme 1.

Compounds of formula (I) may be prepared according to Scheme 1 as described hereinafter providing at least one non-limiting synthetic route for the preparation of all examples.

Scheme 1

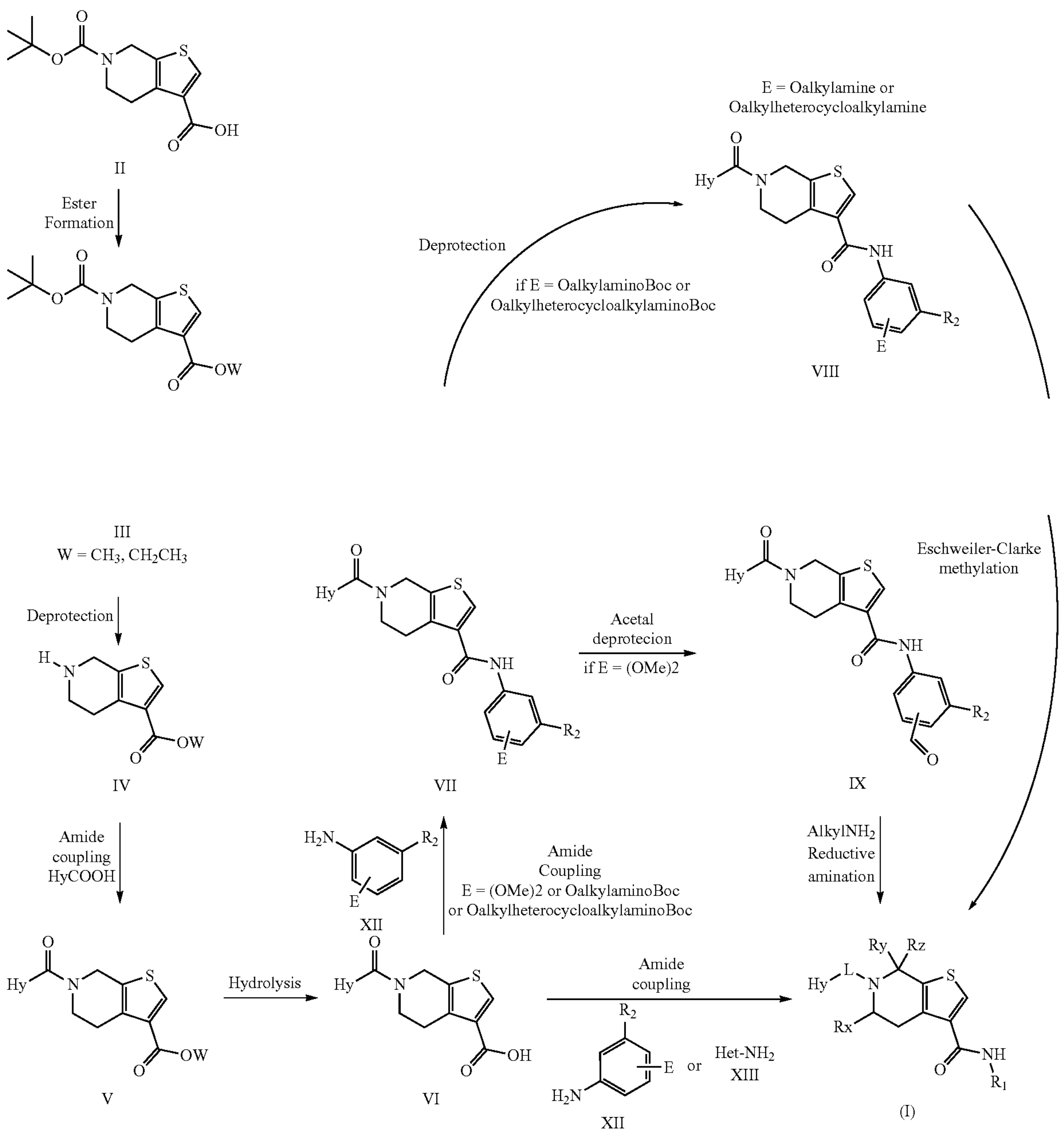

-continued

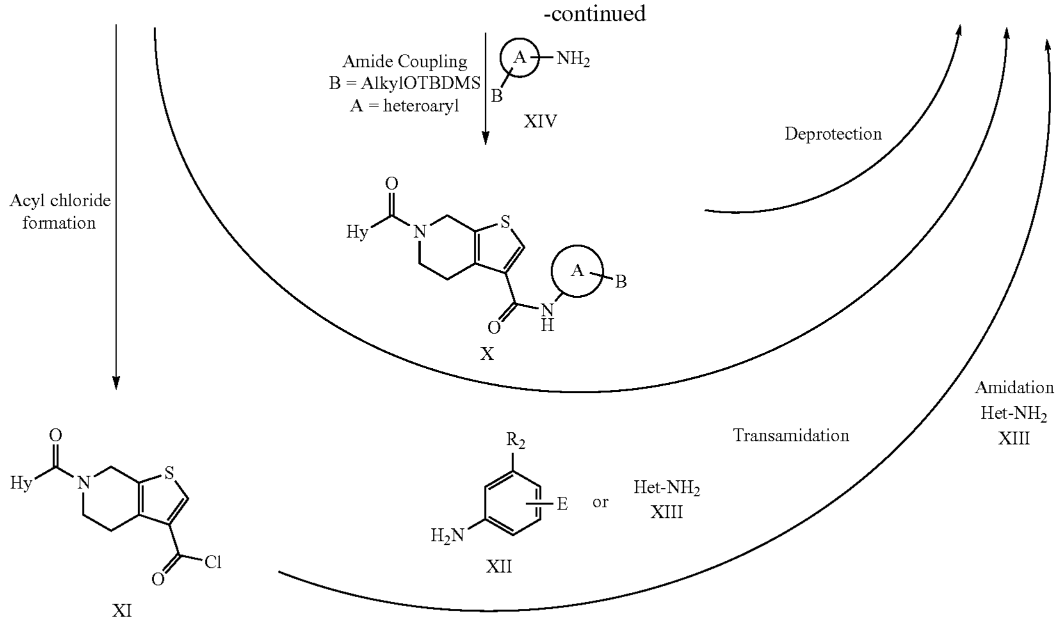

XI

According to Scheme 1, Intermediate III may be prepared following a one-step synthesis starting from intermediate II, under suitable ester formation conditions in the presence of an alkylating agent, such as methyl iodide, with an inorganic base such as cesium carbonate, in a suitable organic solvent such as DMF, and at a temperature generally around room temperature for a time ranging from a few hours to overnight. The intermediate III can be converted into intermediate IV by deprotection of a BOC-protected amine under acidic conditions such as concentrated aqueous hydrogen chloride or hydrogen chloride in dioxane, in a suitable solvent, for example ethanol or diethyl ether, at room temperature.

Intermediate V may be prepared following a one-step synthesis starting from intermediate IV and the proper carboxylic acid, under suitable amide coupling conditions, in the presence of an agent that activates the carboxylic acid partner, such as TBTU or HATU or T3P, in the presence of organic base such as DIPEA or TEA, in a suitable organic solvent such as DCM or DMF, and at a temperature generally around room temperature. Direct amidation of esters (transamidation) may be carried on between Intermediate V and Intermediate XII or XIII to obtain compounds of formula (I), using for example butyllithium as a promoter in a suitable organic solvent as THE or Dioxane, at a temperature ranging from −78° C. to room temperature for few hours. In a different approach, intermediate V may be converted into intermediate VI by hydrolysis in basic conditions using for example aqueous sodium hydroxide in a suitable solvent, for example methanol, at room temperature for few hours. Successively, intermediate VI is reacted with intermediate XII or XIII, under suitable amide coupling conditions, in the presence of an agent that activates the carboxylic acid partner, such as TBTU or HATU or T3P, for subsequent reaction with amines in the presence of an organic base such as DIPEA or TEA, in a suitable organic solvent such as DCM or DMF, and at temperature generally around room temperature for a time ranging from a few hours to overnight.

Alternatively, compounds of formula (I) may be prepared via amidation starting from intermediate VI in the presence of TCFH and 1-methylimidazole to give the transient activated acylimidazolinium intermediate that reacted with the appropriate amine XII or XIII in a solvent such as DMF, at RT. In a different approach, compounds of formula (I) can be obtained starting from intermediate VI in the presence of an appropriate chlorinating reagent, such as $POCl_3$ or thionyl chloride in a solvent such as pyridine, at 5° C., to get the corresponding acyl chloride that is treated directly with the appropriate amine XII or XIII in Py at RT.

Compounds of formula (I) may also be prepared via acyl chloride formation starting from intermediate VI in the presence of thionyl chloride at 50° C. followed by reaction with XXIII in presence of a suitable base such as LiHMDS, in a suitable solvent such as DCM, at a temperature of −78° C.

Intermediate VI may be converted into Intermediate X performing an amide coupling with Intermediate XIV following conditions described above, and subsequently can be converted into the compounds of formula (I) performing the deprotection of the silyl group under suitable deprotection conditions, such as HCl or TFA in a suitable solvent, such as MeOH or THF, at RT.

In a different approach, the intermediate VII can be prepared form Intermediate VI performing an amide coupling with Intermediate XII, following conditions described above, and successively undergo the deprotection of the BOC-protected amine, following conditions reported above, and performing a final methylated applying Eschweiler-Clarke reaction conditions to give the compounds of formula (I). In a different approach, intermediate VII can be converted into intermediate IX performing the deprotection of the acetal group using a suitable acid such as TFA in a suitable solvent such as DCM at room temperature. Intermediate IX can be transformed into the compounds of formula (I) with the appropriate alkylamine by applying reductive amination conditions with a suitable reductant agent, such as $Na(OAc)_3BH$ or $NaCNBH_3$, in a suitable solvent, such as DCM or EtOH, in presence of an acid, such as acetic acid, and a coordinating agent, such as Titanium tetrahydroisopropoxide, at room temperature.

In another embodiment, compounds of formula (I) may be prepared according to Scheme 2a and 2b.

Scheme 2a
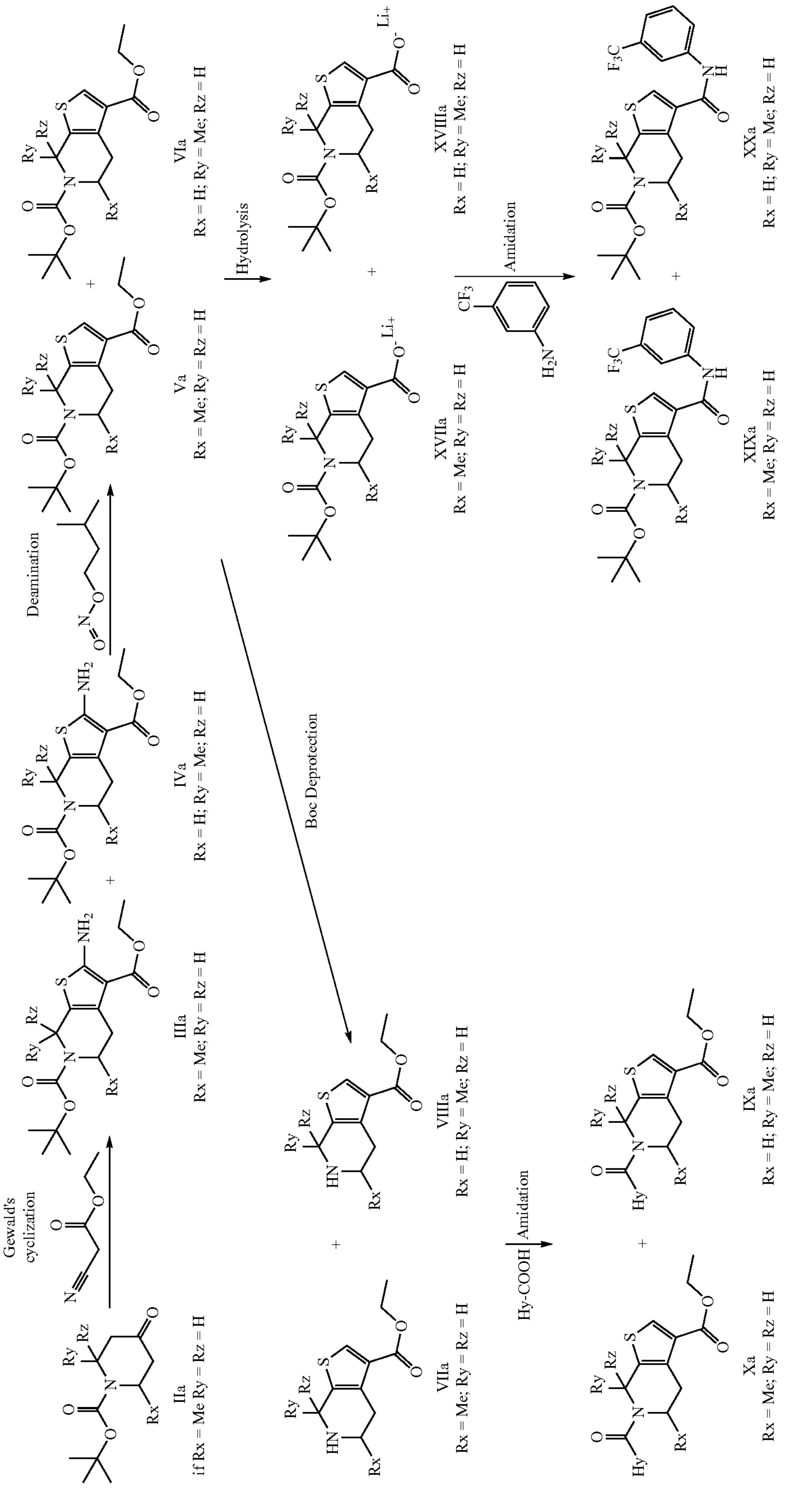

Scheme 2b
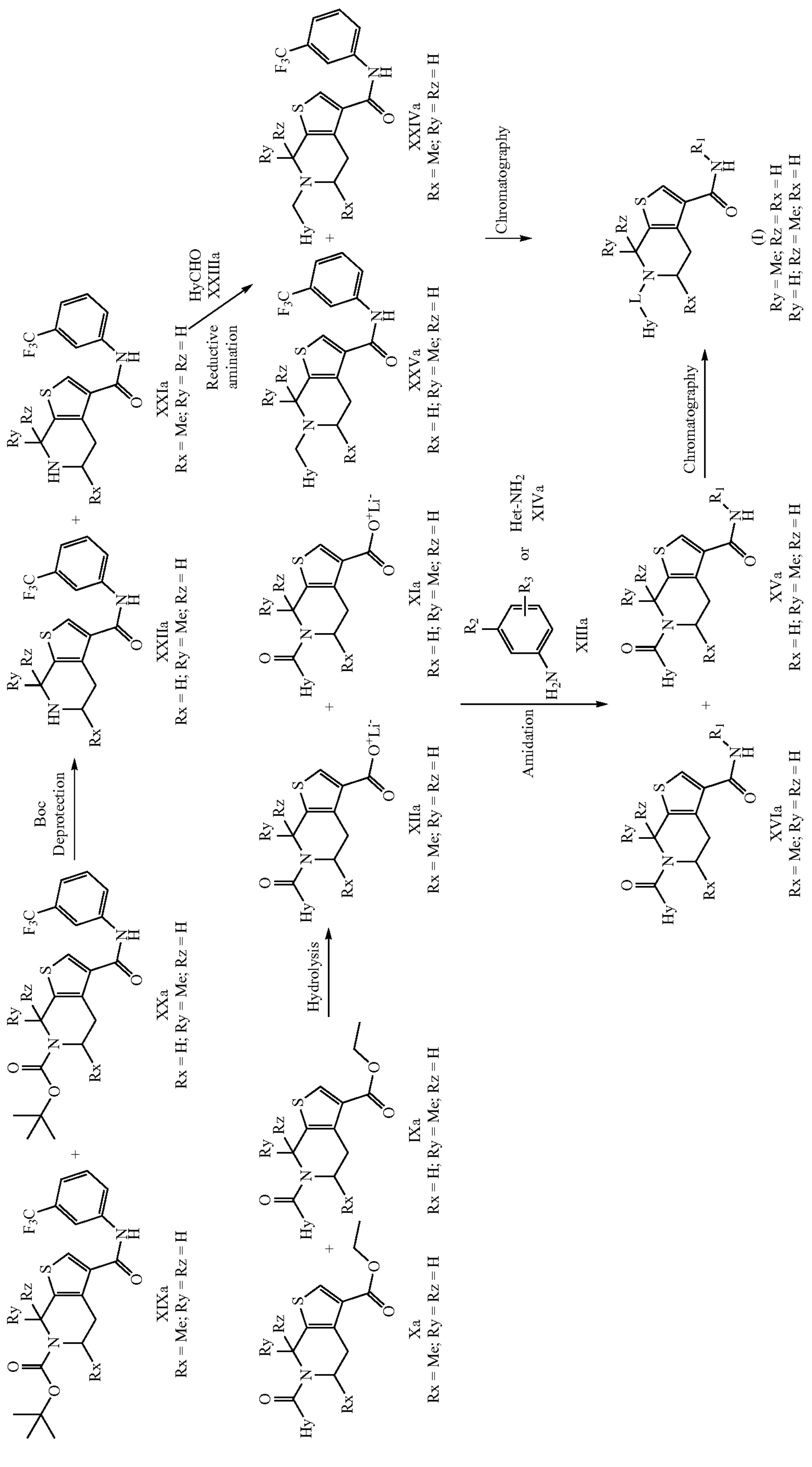

According to Scheme 2a, a mixture of intermediates IIIa and IVa may be prepared from intermediate IIa following Gewald's multicomponent cyclization conditions with ethyl 2-cyanoacetate using a suitable sulphur source, such as sulphur, in a suitable solvent, such as EtOH, at reflux. A mixture of intermediates VIIa and VIIIa can be obtained applying deamination conditions to a mixture of intermediates IIIa and IVa using the proper diazotisation agent, such as isoamylnitrite or isopropylnitrite, in a suitable solvent, such as THF or acetonitrile, at a temperature ranging from 0° C. to reflux followed by the deprotection of the BOC group under acidic conditions, such as concentrated hydrogen chloride or hydrogen chloride in dioxane, in a suitable solvent, for example ethanol or diethyl ether, at room temperature. A mixture of intermediate IXa and Xa can be prepared from a mixture of intermediate VIIa and VIIIa with the appropriate carboxylic acid applying amide coupling conditions in the presence of an agent that activates the carboxylic acid partner, such as TBTU or HATU or T3P, with an organic base, such as DIPEA or TEA, in a suitable organic solvent, such as DCM or DMF, and at a temperature generally around RT. The mixture of intermediates Xa and IXa can undergo hydrolysis using a suitable inorganic base, such as aqueous NaOH or LiOH, in a suitable solvent, such as MeOH or EtOH, at room temperature, followed by amide coupling conditions described above on the mixture of intermediate XIIa and XIa with a proper amine XIIIa or XIVa. Compounds of formula (I) can be isolated from the mixture of intermediates XVIa and XVa performing a column chromatography using the proper stationary phase, such as silica gel, with the suitable mobile phase, such as water/acetonitrile or DCM/MeOH or Hex/AcOEt. In a different approach the mixture of intermediates Va and VIa can be converted into the mixture of intermediates XVIIa and XVIIIa by applying hydrolysis conditions using an appropriate inorganic base, such as NaOH, in a suitable solvent, such as EtOH, at room temperature. The mixture of intermediates XVIIa and XVIIIa can be converted into the mixture of intermediates XIXa and XXa performing an amide coupling following the conditions described above, followed by deprotection of the BOC group using the conditions described above. The mixture of intermediates XXIVa and XXVa can be obtained performing a reductive amination using the appropriate aldehyde XXIIIa with a suitable reductant agent, such as $Na(OAc)_3BH$ or $NaCNBH_3$, in a suitable solvent, such as DCM or EtOH, in presence of an acid, such as acetic acid, and a coordinating agent, such as titanium tetrahydroisopropoxide, at room temperature.

In another embodiment, compounds of formula (I) may be prepared according to Scheme 3.

Scheme 3
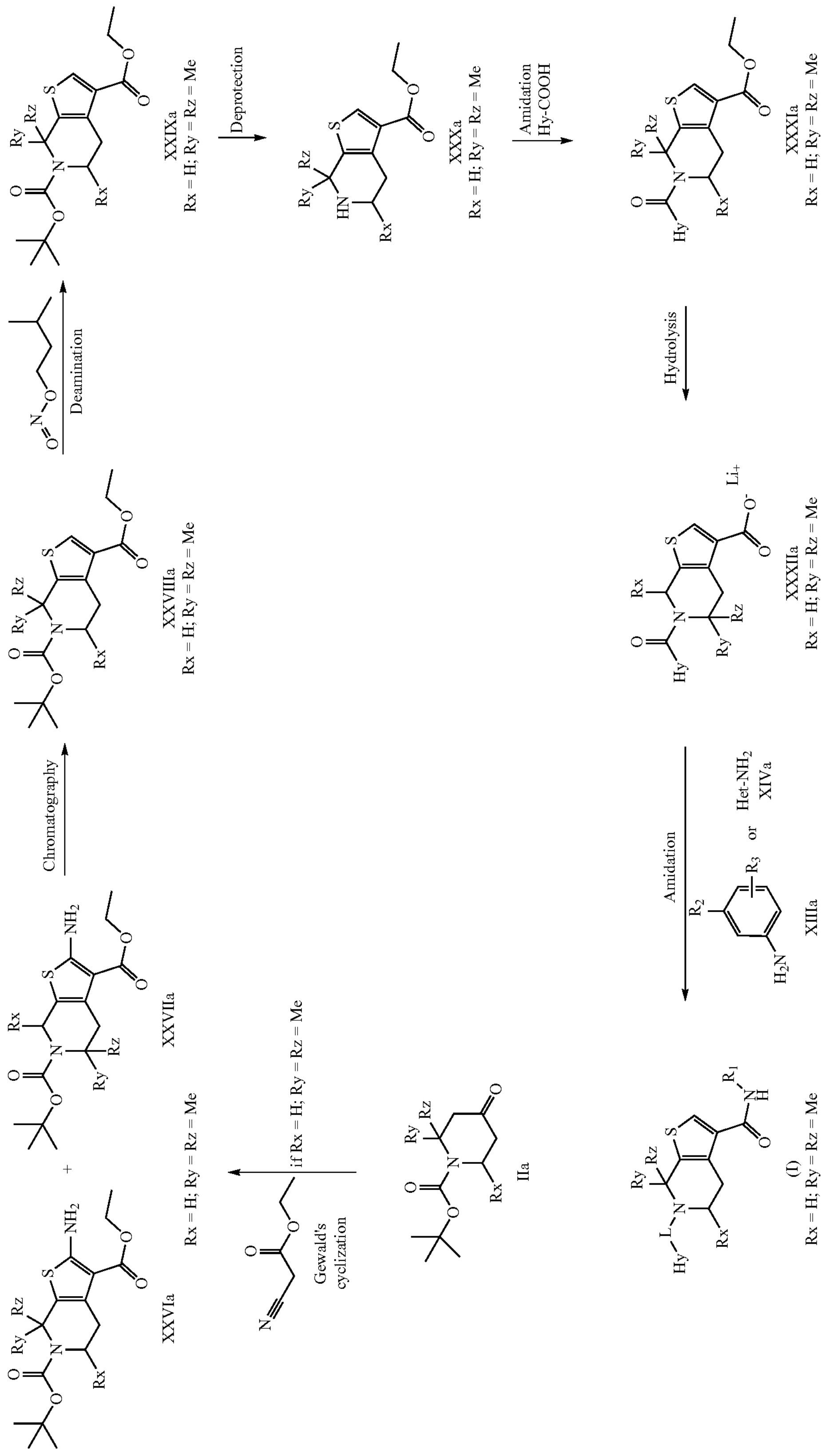

According to Scheme 3, Intermediate XXVIIIa can be obtained from compound IIa performing the Gewald's multicomponent cyclization conditions with ethyl 2-cyanoacetate using a suitable sulphur source, such as sulphur, in a suitable solvent, such as EtOH, at reflux followed by the appropriate column chromatography using the proper stationary phase, such as silica gel, with the suitable mobile phase, such as water/acetonitrile or DCM/MeOH or Hex/AcOEt. Intermediate XXVIIIa can be converted into compound of formula (I) performing deamination, followed by BOC deprotection, amidation with the proper acid, hydrolysis of the ethyl ester and final amidation with the appropriate amine XIIIa or XIVa following conditions described in Scheme 2b.

In a further preferred embodiment, compounds of formula (I) may be prepared according to Scheme 4.

Scheme 4
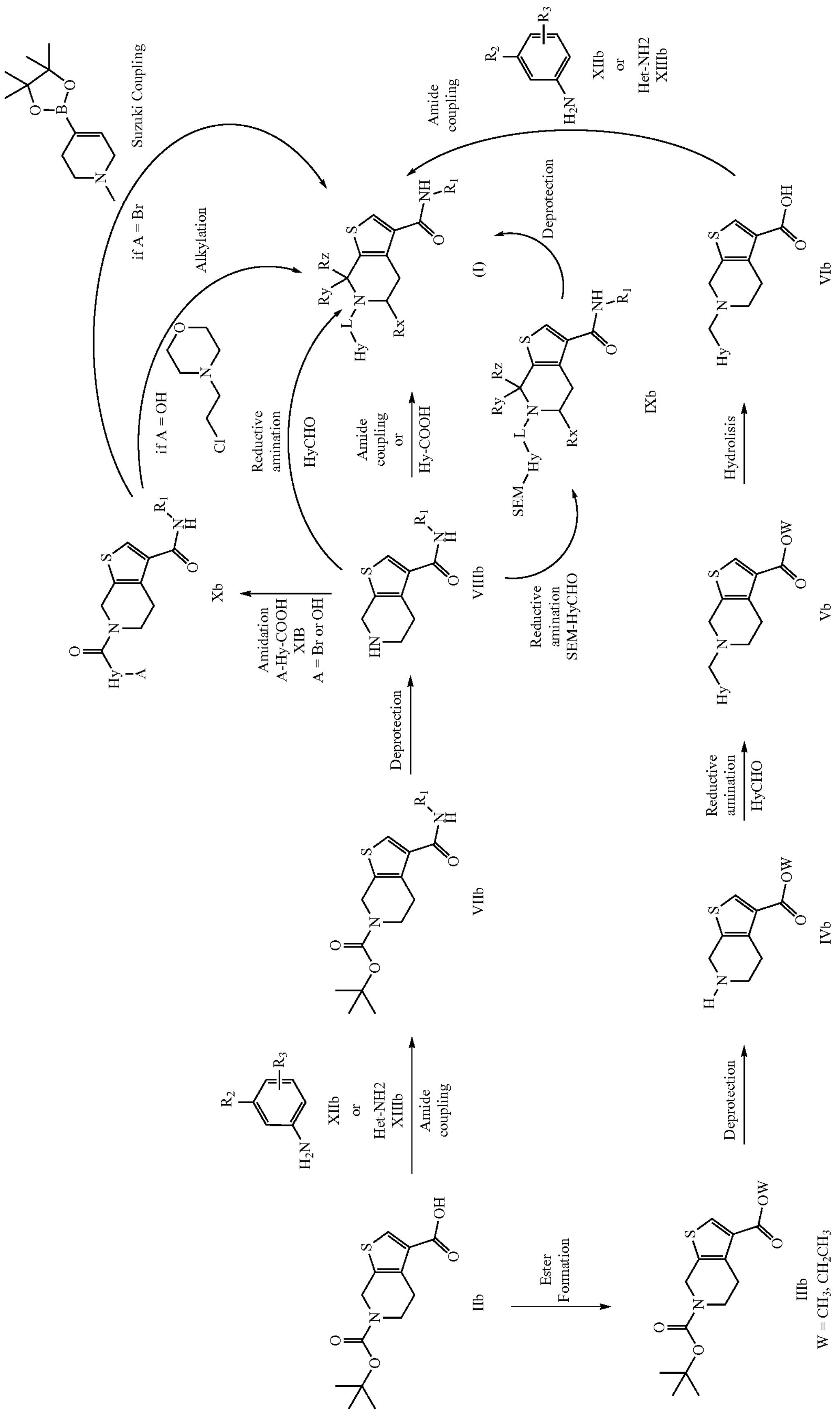

According to Scheme 4, Intermediate IIIb may be prepared following a one-step synthesis starting from intermediate IIb, under suitable ester formation conditions in the presence of an alkylating agent, such as methyl iodide, with an inorganic base, such as cesium carbonate, in a suitable organic solvent, such as DMF, and at a temperature generally around RT for a time ranging from a few hours to overnight. The intermediate IIIb can be converted into intermediate IVb by deprotection of a BOC-protected amine under acidic conditions, such as concentrated hydrogen chloride or hydrogen chloride in dioxane, in a suitable solvent, for example ethanol or diethyl ether, at room temperature and subsequently converted into intermediate Vb by applying reductive amination condition in presence of a suitable aldehyde, with a suitable reductant agent, such as $Na(OAc)_3BH$ or $NaCNBH_3$, in a suitable solvent, such as DCM or EtOH, in presence of an acid, such as acetic acid, at room temperature. Compounds of formula (I) may be obtained performing an hydrolysis on intermediate Vb using a suitable base, such as NaOH or LiOH, in a suitable solvent, such as MeOH or EtOH, followed by an an amide coupling with the proper intermediate XIIb or XIIIb, under suitable amide coupling conditions, in the presence of an agent that activates the carboxylic acid partner such as TBTU or HATU or T3P, with an organic base such as DIPEA or TEA, in a suitable organic solvent such as DCM or DMF, and at a temperature generally around RT. Alternatively, compounds of formula (I) can be obtained starting from intermediate VIb in the presence of an appropriate chlorinating reagent, such as oxalyl chloride or thionyl chloride in a solvent such as pyridine, at 5° C., to get the corresponding acyl chloride that can be treated directly with the appropriate amine XIIb or XIIIb in Py at room temperature.

In a different approach, intermediate VIIb may be prepared form intermediate IIb performing an amide coupling following the conditions described above, or by reacting intermediate IIb in the presence of TCFH and 1-methylimidazole to give the transient activated acylimidazolinium intermediate that may be reacted with the appropriate amine XIIb or XIIIb in a suitable solvent such as DMF, at RT. Compounds of formula (I) can be prepared from intermediate VIIb after deprotection of the BOC group, followed by amide coupling, applying suitable conditions described above with the appropriate carboxylic acid.

Differently, intermediate VIIIb can be converted into intermediate IXb by performing reductive amination following proper conditions described above, with the appropriate SEM-protected aldehyde. For the skilled in the art, it will be clear that in the case the aldehyde contains a moiety that could interfere with the reaction, such a moiety would need to be protected. Applying SEM deprotection conditions, using a proper acid, such as acetic acid, in a proper solvent, such as DMF, at room temperature, to intermediate IXb, compounds of formula (I) can be obtained.

In a different approach intermediate VIIIb may be converted into intermediate Xb performing an amide coupling following the conditions described above, with intermediate XIb, that can be transformed into compounds of formula (I) by alkylation using a suitable inorganic base, such as potassium carbonate, in a suitable solvent such as DMF, with the appropriate haloalkyl, such as chloroethylmorpholine. Alternatively, compounds of formula (I) can be obtained from intermediate Xb applying Suzuki coupling conditions using a suitable inorganic base, such potassium carbonate or sodium carbonate, a suitable catalyst, such as $Pd(dppf)Cl_2$, in a suitable organic solvent, such as DMF or DMA, at 100° C., with the proper boron reagent, such as 1-methyl-4-(4,4,5,5-tetramethyl-1,3,2-dioxaborolan-2-yl)-1,2,3,6-tetrahydropyridine.

Differently, the compounds of formula (I) can be obtained from intermediate VIIIb applying amide coupling conditions described above, with the appropriate acid. Alternatively, the compounds of formula (I) can be prepared from intermediate VIIIb performing a reductive amination using the appropriate aldehyde with a suitable reductant agent, such as $Na(OAc)_3BH$ or $NaCNBH_3$, in a suitable solvent, such as DCM or EtOH, in presence of an acid, such as acetic acid, and a coordinating agent, such as Titanium tetrahydroisopropoxide, at room temperature.

The various aspects of the invention described in this application are illustrated by the following examples which are not meant to limit the invention in any way.

Preparations of Intermediates and Examples

Chemical Names of the compounds were generated with Structure To Name Place IUPAC Name by PerkinElmer ChemDraw Professional 19.1.1.21. All reagents, for which the synthesis is not described in the experimental part, are either commercially available, or are known compounds or may be formed from known compounds by known methods by a person skilled in the art.

In the procedures that follow, some of the starting materials are identified through an "Intermediate" or "Example" number with indications on step number. This is provided merely for assistance to the skilled person.

A "similar" or "analogous" procedure means that such a procedure may involve minor variations, for example reaction temperature, reagent/solvent amount, reaction time, work-up conditions or chromatographic purification conditions.

Abbreviation—Meaning

ACN=acetonitrile; $Et_2O$=diethyl ether; DCM=dichloromethane; DMF=N,N-dimethylformamide; CPME=Cyclopentyl methyl ether; AcOEt=ethyl acetate; EtOH=ethanol; MeOH=Methanol; THF=tetrahydrofuran; HCOOH=formic acid; FA=formic acid; AcOH=acetic acid; TFA=trifluoroacetic acid; DIPEA=N,N-diisopropylethylamine; TEA=triethylamine; Py=pyridine; $Boc_2O$=di-tert-butyl dicarbonate; HATU=(Dimethylamino)-N,N-dimethyl(3H-[1,2,3]triazolo[4,5-b]pyridin-3-yloxy)methaniminium hexafluorophosphate; TBTU=2-(1H-Benzotriazole-1-yl)-1,1,3,3-tetramethylaminium tetrafluoroborate; T3P=Propanephosphonic acid anhydride; HOBt=1-Hydroxybenzotriazole hydrate; TCFH=Chloro-N,N,N',N'-tetramethylformamidinium hexafluorophosphate; n-BuLi=n-butyllithium; XPhos Pd G3=(2-Dicyclohexylphosphino-2',4',6'-triisopropyl-1,1'-biphenyl)[2-(2'-amino-1,1'-biphenyl)]palladium(II) methanesulfonate; Xphos Pd G2=Chloro(2-dicyclohexylphosphino-2',4',6'-triisopropyl-1,1'-biphenyl)[2-(2'-amino-1,1'-biphenyl)]palladium(II); Xphos=2-Dicyclohexylphosphino-2',4',6'-triisopropylbiphenyl; RT=room temperature; FCC=flash column chromatography; MeOH-$d_4$=deuterated methanol; DMSO-$d_6$=deuterated dimethyl sulfoxide; $CDCl_3$=deuterated chloroform; ACN-$d_3$=deuterated acetonitrile; NMR=nuclear magnetic resonance; LC-MS=Liquid Chromatography/Mass Spectrometry; ESI=electrospray ionization; Prep HPLC=preparative high performance liquid chromatography; SCX=solid cation exchange; SM=starting material; DP=desire product; wt=weight; e.e.=enantiomeric excess; SEM-Cl=2-(trimethylsilyl)ethoxymethyl chloride; PyBOP=Benzotriazole-1-yl-oxy-tris-pyrrolidino-phosphonium hexafluorophosphate; $Pd_2(dba)_3$-tris(dibenzylideneacetone)dipalladium(0); $NaBH_3CN$=sodium cyanoborohydride; Pd-PEPPSI(TM)-IPent=[1,3-Bis(2,6-Di-3-pentylphenyl)imidazol-2-ylidene](3-chloropyridyl)dichloropalladium(II); Pd(dppf)$Cl_2$·DCM=[1,1'-Bis(diphenylphosphino)ferrocene]dichloropalladium(II), complex with dichloromethane; BINAP=2,2'-Bis(diphenylphosphino)-1,1'-binaphthalene; XantPhos=4,5-Bis(diphenylphosphino)-9,9-dimethylxanthene.

General Experimental Details

NMR Characterization:

$^1$H NMR spectra were recorded on Varian MR-400 spectrometer operating at 400 MHZ (proton frequency), equipped with: a self-shielded Z-gradient coil 5 mm 1H/nX broadband probe head for reverse detection, deuterium digital lock channel unit, quadrature digital detection unit with transmitter offset frequency shift or on Bruker Avance III HD 400 MHz or on Bruker Fourier 300 MHz. Chemical shifts are reported as 6 values in ppm relative to tetramethyl silane (TMS) as an internal standard. Coupling constants (J values) are given in hertz (Hz) and multiplicities are reported using the following abbreviations (s=singlet, d=doublet, t=triplet, q=quartet, dd=doublet of doublets, dt=doublet of triplets, m=multiplet, br=broad, nd=not determined).

In some cases, signals NH from amide bond or amine bond (exchangeable protons) are not visible.

In a few cases, some signals could be hidden under the signal of water or under the signal of DMSO or other residual solvents.

LC/UV/MS Analytical Methods

LC/MS retention times are estimated to be affected by an experimental error of ±0.5 min.

Method 1: Acquity CSH C18 column 50 mm×2.1 mm 1.7 μm, maintained at 40° C.; Mobile Phase: Eluent B (ACN/water 95:5+0.05% HCOOH) in Eluent A (water/ACN 95:5+0.05% HCOOH) from 1% to 99.9% within 3.5 min. Flow rate: 1 mL/min. Wavelength: 210-400 nm DAD. UPLC+Waters PDA+Waters QDA.

Method 2: Kinetex® XB-C18 column, 4.6×50 mm, 2.6 μm maintained at 25° C. Mobile phase: water (0.1% formic acid) in ACN (0.1% formic acid), from 70% to 5% within 3.90 min; Flow rate: 1.0 mL/min; wavelength: 190-340 nm DAD. Dionex UHPLC Ultimate 3000 with DAD detector/Thermo Scientific MSQ Plus.

Method 3: Kinetex® XB-C18 column, 4.6×50 mm, 2.6 μm maintained at 25° C. Mobile phase: water (0.1% formic acid) in ACN (0.1% formic acid), from 80% to 5% within 3.90 min; Flow rate: 1.0 mL/min; wavelength: 190-340 nm DAD. Dionex UHPLC Ultimate 3000 with DAD detector/Thermo Scientific MSQ Plus.

Method 4: Kinetex® XB-C18 column, 4.6×50 mm, 2.6 μm maintained at 25° C. Mobile phase: water (0.1% formic acid) in ACN (0.1% formic acid), from 70% to 5% within 3.90 min; Flow rate: 1.0 mL/min; wavelength: 190-350 nm DAD. Dionex UHPLC Ultimate 3000 with DAD detector/Thermo Scientific ISQ EC mass spectrometer Method 5: Acquity UPLC BEH C18 column, 100×2.1 mm, 1.7 μM, maintained at 40° C. Mobile phase: ACN (0.03% ammonia) in water (0.03% ammonia), from 5% to 95% within 5.6 min; Flow rate: 0.4 mL/min; Wavelength: 100-800 nm DAD. Acquity UPLC with PDA detector and ZQ Mass Spectrometer.

Method 6: Acquity UPLC BEH Shield RP18 column, 100×2.1 mm, 1.72 μm (Plus guard cartridge), maintained at 40° C. Mobile phase: ACN in water+10 nM ammonium bicarbonate from 5% to 95% within 5.6 min. Flow rate: 0.4 mL/min. Wavelength: 210-400 nm DAD. UPLC+Waters DAD+Waters SQD2, single quadrapole UPLC-MS Method 7: Acquity UPLC HSS C18 column, 100×2.1 mm, 1.8 μm (Plus guard cartridge), maintained at 40° C. Mobile phase: ACN (0.1% formic acid) in water (0.1% formic acid) from 5% to 95% within 5.6 min. Flow rate: 0.4 mL/min. Wavelength: 210-400 nm DAD. UPLC+Waters DAD+Waters SQD2, single quadrapole UPLC-MS Method 8: Kinetex© XB-C18 column, 4.6×50 mm, 2.6 μm maintained at 25° C. Mobile phase: water (0.1% formic acid) in ACN (0.1% formic acid), from 90% to 5% within 3.90 min; Flow rate: 1.0 mL/min; wavelength: 190-340 nm DAD. Dionex UHPLC Ultimate 3000 with DAD detector/Thermo Scientific MSQ Plus.

Method 9: Kinetex© XB-C18 column, 4.6×50 mm, 2.6 μm maintained at 25° C. Mobile phase: water (0.1% formic acid) in ACN (0.1% formic acid), from 90% to 5% within 3.90 min; Flow rate: 1.0 mL/min; wavelength: 190-340 nm DAD. Dionex UHPLC Ultimate 3000 with DAD detector/Thermo Scientific MSQ Plus.

Method 10: Gemini-NX C18 column, 4.6×150 mm, 3 μm maintained at 35° C. Mobile phase: water (0.1% formic acid) in ACN (0.1% formic acid), from 80% to 5% within 8.50 min; Flow rate: 1.0 mL/min; wavelength: 190-340 nm DAD. Dionex UHPLC Ultimate 3000 with DAD detector/Thermo Scientific MSQ Plus.

Method 11: Gemini-NX C18 column, 4.6×150 mm, 3 μm maintained at 35° C. Mobile phase: water (0.1% formic acid) in ACN (0.1% formic acid), from 65% to 5% within 8.50 min; Flow rate: 1.0 mL/min; wavelength: 190-340 nm DAD. Dionex UHPLC Ultimate 3000 with DAD detector/Thermo Scientific MSQ Plus.

Method 12: Lux C1 column, 4.6×150 mm, 5 μm maintained at rt. Mobile phase: 90:10 ACN:IPA in isocratic conditions; Flow rate: 1.0 mL/min, 1 wavelength: 254 nm. Waters/Thar SFC systems with Waters SQD.

Method 13: Amy-C column, 4.6×250 mm, 5 μm maintained at 40° C. Mobile phase: 25:75 MeOH:$CO_2$ (0.2% v/v $NH_3$) in isocratic conditions; Flow rate: 4.0 mL/min, 125 Bar backpressure; wavelength: 210-400 nm. Waters/Thar SFC systems with Waters SQD.

Method 14: Agilent Zorbax column 4.6×50 mm, 3.5 μm, maintained at 40° C. Mobile phase: MeCN (0.1% formic acid) in water (0.1% formic acid), from 40% to 100% within 2 min. Flow rate: 3.0 mL/min. Wavelength: 210-400 nm DAD. Waters 2795/2695 separations module+Waters DAD+Micromass ZQ, single quadrapole LC-MS.

Method 15: Acquity BEH UPLC column, 2.1×50 mm, 1.7 μm, maintained at 40° C. Mobile phase: MeCN (0.03% ammonia) in water (0.03% ammonia), from 8% to 97% within 1.5 min; Flow rate: 0.8 mL/min; Wavelength: 210-400 nm DAD. Acquity H-Class UPLC with PDA detector and QDa.

Method 16: Waters Sunfire C18 column, 4.6×50 mm, 3.5 μm, maintained at 40° C. Mobile phase MeCN in water+10 mM ammonium bicarbonate, from 5 to 95% within 2.5 mins. Flow rate: 2.0 ml/min. Wavelength: 210-400 nm DAD. Waters 2795 separations module+Waters DAD+Micromass ZQ, single quadrapole LC-MS Method 17: Agilent Zorbax column 4.6×50 mm, 3.5 μm, maintained at 40° C. Mobile phase: MeCN (0.1% formic acid) in water (0.1% formic acid), from 5% to 95% within 2 min. Flow rate: 3.0 ml/min. Wavelength: 210-400 nm DAD. Waters 2795/2695 separations module+Waters DAD+ Micromass ZQ, single quadrapole LC-MS.

LC/SFC Chiral Preparative Methods

Method prep1: separation run was performed on a Gilson Preparative LC system (Gilson Pump 333; Gilson 151; Gilson Valvemate 6 position) using a Lux C1 (21.2 mm×250 mm, 5 um) column with a isocratic run (90/10 ACN:i-PrOH, 0.2% v/v $NH_3$) at 21 mL/min, column maintained room temperature; wavelength: 210 nm Method prep2: SFC-MS separation run was performed on a Gilson Preparative LC system (Gilson Pump—333; Gilson 151; Gilson Valvemate 6 position) using a AmyC (20 mm×250 mm, 5 um) column with a isocratic run (70/30 MeOH:$CO_2$, 0.2% v/v $NH_3$, 125 Bar backpressure) at 50 mL/min, column maintained 40° C. wavelength: 210 nm.

Method prep3: SFC-MS separation run was performed on a Gilson Preparative LC system (Gilson Pump—333; Gilson 151; Gilson Valvemate 6 position) using a Lux A1 (21.2 mm×250 mm, Sum) column with a isocratic run (40/60 MeOH:$CO_2$, 0.2% v/v $NH_3$, 100 Bar backpressure) at 50 mL/min, column maintained 40° C. wavelength: 210 nm.

Where the preparation of starting materials is not described, these are commercially available, known in the literature, or readily obtainable by those skilled in the art using standard procedures. All solvents were purchased from commercial sources and were used without additional purification.

Compounds were purified by reverse phase HPLC using a Waters Fractionlynx preparative HPLC system (2525 pump, 2996/2998 UV/VIS detector, 2767 liquid handler) or Gilson preparative HPLC system (322 pump, 155 UV/VIS detector, GX-281 liquid handler) or equivalent system, both in basic conditions (ACN+0.1% $NH_3$, $H_2O$+0.1% $NH_3$) and in acidic conditions (ACN+0.1% HCOOH, $H_2O$+0.1% HCOOH), in the last case, the residue Fractions containing the required product (identified by TLC and/or LCMS analysis) were pooled and the solvent either removed under reduced pressure or lyophilised; or alternatively extracted by SCX (NH).

The specific details of the conditions used, including the column, solvents, gradient and modifier (acidic or basic), are provided for some examples and merely provided for assistance. When specific conditions are not provided, they can be readily optimized by those skilled in the art.

Thin layer chromatography was performed on Merck silica gel 60 F254 TLC plates. Preparative thin-layer chromatography (pTLC) was performed with Uniplate 1000 micron or 500 micron silica gel plates. Flash chromatography was performed on Interchim PuriFlash 450 and 520Plus or using the Biotage SPl purification system or equivalent MPLC using pre-packed silica gel cartridges.

General Synthetic Procedure

General Procedure A

Sodium hydride (60% in mineral oil, 1.10 eq) was added to a stirred solution of the required alcohol (1.20 eq) in ACN (0.5M concentration) under an inert atmosphere. The reaction mixture was stirred for 1 h then the required aryl-fluoride (1.00 eq) was added in one portion. The reaction mixture was stirred at room temperature until LCMS indicated consumption of starting material. The reaction mixture was partitioned between water and DCM, and the aqueous phase was re-extracted with DCM (×2). The combined organic phases were filtered through a hydrophobic frit and the concentrated under vacuum.

General Procedure B

The required aryl-nitro (1.00 eq) and iron powder (5.00 eq) were combined in acetic acid (0.3M concentration) and methyl alcohol (0.3M concentration). The reaction mixture was stirred at 50° C. until LCMS indicated consumption of starting material. The reaction mixture was allowed to cool to room temperature and concentrated under vacuum. The residue was partitioned between DCM and saturated Na2CO3 (aq). The combined organic phases were filtered through a hydrophobic frit and concentrated under vacuum.

General Procedure C

To a solution of the required aldehyde (1.00 eq) in DCM (0.1 M concentration) was added the required amine (1.10 eq), titanium(IV) isopropoxide (2.00 eq) and acetic acid (3.00 eq). The reaction mixture was stirred at room temperature for 1 h. Sodium triacetoxyborohydride (2.00 eq) was added and the reaction mixture was stirred at room temperature until LCMS indicated consumption of starting material. The reaction mixture was partitioned between DCM and saturated $NaHCO_{3\ (aq)}$ and the mixture filtered through a bed of Celite. The aqueous phase was extracted with 2×DCM and the combined organic phases were washed with saturated aqueous NaCl (aq), passed through a hydrophobic frit and concentrated under vacuum.

General Procedure D

To palladium (10% on carbon) (10 wt %) was added a solution of the required nitro-aryl (1.00 eq) in EtOH (0.1M concentration). The flask was evacuated and purged with argon (×3) then evacuated and purged with hydrogen (×3). The reaction mixture was stirred at room temperature until LCMS indicated consumption of starting material. The reaction mixture was diluted with DCM and filtered through Celite. The filter cake was washed with DCM and the combined filtrates were concentrated under vacuum.

General Procedure E

To a solution of the required phenol (1.00 eq) in DMF (0.2M concentration) was added the required alkyl halide (1.20 eq) followed by cesium carbonate (2.00 eq). The mixture was stirred at 80° C. until LCMS indicated consumption of starting material. The reaction mixture was diluted with water and extracted with DCM (×2). The organic phases were combined and concentrated.

General Procedure F

To a solution the required nitro-aryl (1.00 eq) in ethanol (0.1M concentration) under one atmosphere of nitrogen was sequentially added 1-methyl-1,4-cyclohexadiene (30.0 eq) and palladium on carbon (10%) (1.00 eq) and the reaction mixture was stirred at 80° C. until LCMS indicated consumption of starting material. The reaction mixture was allowed to cool to room temperature and filtered through a pad of Celite, which was washed with EtOH and AcOEt. The filtrate was concentrated under reduced pressure.

General Procedure G

To a mixture of the required carboxylate sodium salt or acid (1.00 eq) and HATU (1.20 to 2.00 eq) in DMF/DCM (0.1M concentration) was added DIPEA (3.00 to 8.00 eq). The reaction mixture was stirred at room temperature for 15 mins then the required amine (1.00 to 2.00 eq) was added. The reaction mixture was stirred at room temperature until LCMS indicated consumption of starting material and then concentrated.

General Procedure H 6-(imidazo[1,2-a]pyridine-3-carbonyl)-5,7-dihydro-4H-thieno[2,3-c]pyridine-3-carboxylic acid (1.00 eq) was suspended in thionyl chloride (10.0 eq) and the reaction mixture was stirred at 50° C. for 20 min. A further portion of thionyl chloride (10.0 eq) was added and the reaction mixture was stirred at 50° C. for 30 min. The reaction mixture was concentrated under vacuum to give 6-(imidazo[1,2-a]pyridine-3-carbonyl)-5,7-dihydro-4H-thieno[2,3-c]pyridine-3- carbonyl chloride as a white solid. To a solution of the required aniline (1.00 eq) and TEA (3.00 eq) in DCM (0.1M concentration), was added 6-(imidazo[1,2-a]pyridine-3-carbonyl)-5,7-dihydro-4H-thieno[2,3-c]pyridine-3-carbonyl chloride (1.30 eq). The reaction mixture was stirred at room temperature until LCMS indicated consumption of starting material and then concentrated under vacuum.

General Procedure I

The required carboxylic acid (1.00 eq) was suspended in thionyl chloride (0.21 mL, 2.93 mmol, 30.0 eq) and the reaction mixture was stirred at 50° C. for 2 h. The reaction mixture was allowed to cool to room temperature and concentrated under vacuum. The residue was suspended in toluene and re-concentrated to give the intermediate acyl chloride. To a solution of the required aniline (1.00 eq) and DMAP (0.20 eq) in pyridine (0.1M concentration), was added the acyl chloride followed by DIPEA (3.00 eq). The reaction mixture was stirred at 40° C. until LCMS indicated consumption of starting material and then concentrated under vacuum.

General Procedure J

To a solution of the required aldehyde (1.00 eq) in DCM (0.1 M concentration) was added the required amine (1.10 eq), titanium(IV) isopropoxide (2.00 eq) and acetic acid (3.00 eq). The reaction mixture was stirred at room temperature for 1 h. Sodium triacetoxyborohydride (2.00 eq) was added and the reaction mixture was stirred at room temperature until LCMS indicated consumption of starting material. The residue was loaded onto an Isolute SCX-II cartridge, washed with MeOH, then released with 2M $NH_3$/MeOH. The eluate was concentrated under vacuum.

General Procedure K

To a solution of the required amine (1.00 eq) and the required aldehyde (1.00 eq) in MeOH (0.03M concentration) was added titanium(IV) isopropoxide (3.00 eq) and refluxed for 2 h. The reaction cooled to room temperature and $NaBH_3CN$ (2.50 eq) was added and stirring continued at room temperature overnight. The reaction was quenched with water, filtered through celite and concentrated under vacuum.

General Procedure L

To a mixture of the required aldehyde (1.00 eq) and the hydrochloride salt of N-[3-(trifluoromethyl)phenyl]-4,5,6,7-tetrahydrothieno[2,3-c]pyridin-6-ium-3-carboxamide (1.00 eq) in MeOH (0.075 M concentration) was added acetic acid (9.86 eq) and the reaction mixture was stirred at 65° C. for 90 mins. The reaction mixture was cooled to room temperature and concentrated under vacuum. The residue was suspended in DCM (0.025 M concentration) and sodium triacetoxyborohydride (3.50 eq) was added. The reaction mixture was stirred at room temperature for 18 hours. The reaction mixture was diluted with DCM and treated with a 10% sol of $KHSO_{4\,(aq)}$. After stirring for 15 minutes, the mixture was basified with saturated aqueous $Na_2CO_{3(aq)}$ and the layers separated. The aqueous layer was extracted with DCM and the combined organic extracts filtered through a hydrophobic frit and concentrated under vacuum.

General Procedure M

To a solution of the required carboxylic acid (1.10 eq) in DMF (0.1M concentration) was added DIPEA (3.00 eq) and HATU (1.20 eq). The reaction mixture was stirred at room temperature for 30 minutes. Then, N-[3-(trifluoromethyl)phenyl]-4,5,6,7-tetrahydrothieno[2,3-c]pyridine-3-carboxamide hydrochloride (1.00 eq) was added and the reaction mixture was stirred at 40° C. overnight. The reaction mixture was allowed to cool to room temperature and concentrated.

General Procedure N

To a solution of the required acid (1.00 eq), the required amine (1.00 to 1.30 eq) and 1-methylimidazole (3.50 eq) in ACN (0.2M concentration) TCFH (1.20 to 1.50 eq) was added. The reaction mixture was stirred at room temperature until LCMS indicated consumption of starting material and partitioned between saturated $NaHCO_{3(aq)}$ and EtOAc. The phases were separated, the aqueous phase was extracted with 2×EtOAc and the combined organic phases were passed through a hydrophobic frit and concentrated under vacuum.

Preparation of 4-((tetrahydrofuran-3-yl)oxy)-3-(trifluoromethyl)aniline—Intermediate 1

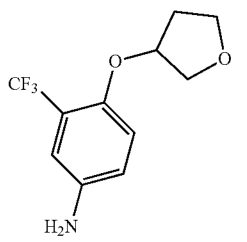

Step 1: 3-(4-nitro-2-(trifluoromethyl)phenoxy (Intermediate 2)

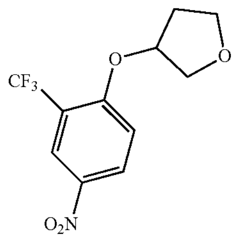 [SMILES: O=[N+]([O-])c1ccc(OC2CCOC2)c(C(F)(F)F)c1]

Prepared from 3-hydroxytetrahydrofuran (0.53 g, 6.00 mmol) and 2-fluoro-5-nitrobenzotrifluoride (0.69 mL, 5.00 mmol) according to general procedure A to give title compound (1.52 g, 99%).

$^1$H NMR (400 MHz, $CDCl_3$) δ 8.52 (d, J=3.0 Hz, 1H), 8.42 (dd, J=3.0, 9.0 Hz, 1H), 7.03 (d, J=9.0 Hz, 1H), 5.16-5.12 (m, 1H), 4.15-4.11 (m, 1H), 4.03-3.97 (m, 3H), 2.35-2.19 (m, 2H)

Step 2: 4-((tetrahydrofuran-3-yl)oxy)-3-(trifluoromethyl)aniline (Intermediate 1)

Prepared from Intermediate 2 (1.52 g, 5.48 mmol,) according to general procedure B. The residue was loaded onto an Isolute SCX-II cartridge, washed with DCM/MeOH, then released with 2M $NH_3$/MeOH. The eluate was concentrated to give the title compound (1.10 g, 75%).

$^1$H NMR (400 MHz, $CDCl_3$) δ 6.91 (d, J=2.0 Hz, 1H), 6.79-6.79 (m, 2H), 4.92-4.87 (m, 1H), 4.04-3.90 (m, 4H), 3.56 (s, 2H), 2.18-2.10 (m, 2H).

The intermediates reported in the following table were prepared via aromatic nucleophilic substitution as described for Intermediate 1, step 1-2, applying the corresponding, commercially available alcohols in step 1.

| Intermediate No | Structure | Step 1 Amount SM (yield) | Step 2 Amount final product (yield) | Data |
|---|---|---|---|---|
| 3 | 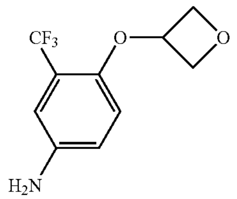 [SMILES: Nc1ccc(OC2COC2)c(C(F)(F)F)c1] | 0.69 mL, 5.00 mmol (1.37 g, 99%) | 940 mg (73%) | $^1$H NMR (400 MHz, $CDCl_3$) δ 6.91 (m, 1H), 6.76-6.70 (m, 1H), 6.40 (d, J = 8.6 Hz, 1H), 5.20-5.11 (m, 1H), 4.92 (t, 2H), 4.78 (t, 9H), 3.60 (s, 2H) |
| 4 | 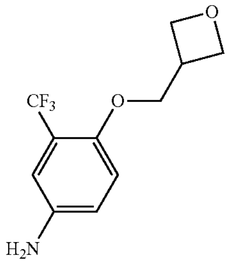 [SMILES: Nc1ccc(OCC2COC2)c(C(F)(F)F)c1] | 0.69 mL, 5.00 mmol (1.5 g, 99%) | 1.27 g (78%) | $^1$H NMR (400 MHz, $CDCl_3$) δ 6.91-6.84 (m, 2H), 6.81-6.77 (m, 1H), 4.85 (t, J = 6.9 Hz, 2H), 4.57 (t, J = 6.1 Hz, 2H), 4.19 (d, J = 6.8 Hz, 2H), 3.59 (bs, 2H), 3.50-3.39 (m, 1H) |
| 5 | 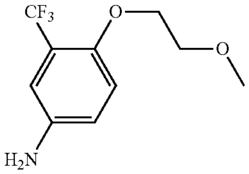 [SMILES: COCCOc1ccc(N)cc1C(F)(F)F] | 0.69 mL, 5.00 mmol (quantitative yield) | 940 mg (66%) | LC-MS (ESI): method 13 $t_R$ = 0.88 min; m/z (M + 1) = 236 |
| 6 | 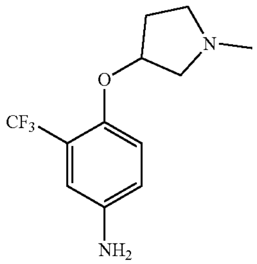 [SMILES: CN1CCC(Oc2ccc(N)cc2C(F)(F)F)C1] | 0.69 mL, 5.00 mmol (1.45 g, quantitative) | 1.45 g (84%) | LC-MS (ESI): method 13 $t_R$ = 0.63 min; m/z (M + 1) = 261 |
| 7 | 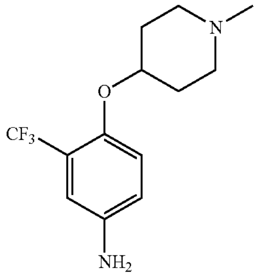 [SMILES: CN1CCC(Oc2ccc(N)cc2C(F)(F)F)CC1] | 0.69 mL, 5.00 mmol (1.49 g, 88%) | 1.34 g (quantitative) | $^1$H NMR (400 MHz, $CDCl_3$) δ 6.92-6.74 (m, 3H), 4.33 (s, 1H), 2.67 (br s, 2H), 2.35 (br s, 2H), 2.30 (s, 3H), 2.03-1.83 (m, 4H) |

Preparation of 2-(4-amino-2-(trifluoromethyl)phenoxy)ethan-1-ol—Intermediate 8

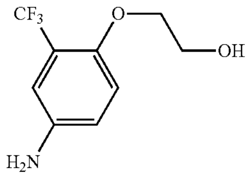 [SMILES: O=[N+]([O-])c1ccc(OCCO)c(C(F)(F)F)c1]

Step 1—2-(4-nitro-2-(trifluoromethyl)phenoxy) ethan-1-ol (Intermediate 9)

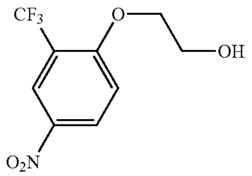

2-fluoro-5-nitrobenzotrifluoride (0.69 mL, 5.00 mmol, 1.00 eq), potassium tert-butoxide (1.23 g, 11.0 mmol, 2.20 eq) and ethylene glycol (11 mL, 0.200 mol, 40.0 eq) were combined in THF (10.00 mL) under an inert atmosphere. The reaction mixture was heated at 70° C. for 1 h then cooled to room temperature and poured onto ice/$HCl_{(aq)}$. The mixture was left to stand for 1 h and filtered. The resulting solid was washed with water and dried under vacuum to give the title compound (1.16 g, 92%).

$^1$H NMR (400 MHz, $CDCl_3$) δ 8.52 (d, J=2.5 Hz, 1H), 8.43 (dd, J=2.8, 9.1 Hz, 1H), 7.13 (d, J=9.1 Hz, 1H), 4.30 (t, J=4.3 Hz, 2H), 4.08-4.02 (m, 2H), 2.02 (t, J=6.5 Hz, 1H).

Step 2—2-(4-amino-2-(trifluoromethyl)phenoxy) ethan-1-ol (Intermediate 8)

Prepared from Intermediate 9 (1.16 g, 4.62 mmol) according to general procedure B to give the title compound (0.98 g, 89%)

$^1$H NMR (400 MHz, $CDCl_3$) δ 6.89 (m, 1H), 6.85 (m, 1H), 6.81-6.76 (m, 1H), 4.07 (t, J=4.5 Hz, 2H), 3.92 (t, J=4.5 Hz, 2H), 3.55 (s, 2H).

Preparation of 3-((dimethylamino)methyl)-5-(trifluoromethyl)aniline (Intermediate 10)

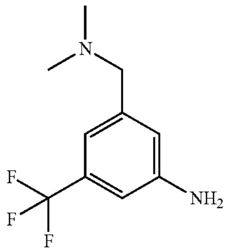

Step 1—N,N-dimethyl-1-(3-nitro-5-(trifluoromethyl)phenyl)methanamine (Intermediate 11)

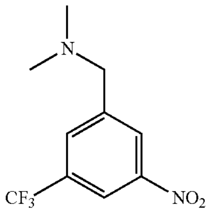 [SMILES: CN(C)Cc1cc([N+](=O)[O-])cc(C(F)(F)F)c1]

Prepared from 3-nitro-5-(trifluoromethyl)benzaldehyde (200 mg, 0.913 mmol) and dimethylamine (2M solution in THF, 0.50 mL, 1.00 mmol) according to general procedure C. Purification by column chromatography on silica gel (12 g cartridge, 0-2.5% 2 M $NH_3$ in MeOH, in DCM) gave the title compound (84 mg, 37%).

$^1$H NMR (400 MHz, $CDCl_3$) δ 8.41-8.37 (m, 2H), 7.95 (s, 1H), 3.58 (s, 2H), 2.29 (s, 6H)

Step 2—3-((dimethylamino)methyl)-5-(trifluoromethyl)aniline (Intermediate 10)

Prepared from Intermediate 11 (84 mg, 0.338 mmol) according to general procedure D to give the tile compound (67 mg, 91%).

$^1$H NMR (400 MHz, $CDCl_3$) δ 6.93 (s, 1H), 6.82 (s, 1H), 6.80 (s, 1H), 3.82 (s, 2H), 3.36 (s, 2H), 2.24-2.24 (m, 6H)

The intermediates reported in the following table were prepared via aromatic nucleophilic substitution as described for Intermediate 10, step 1-2, applying the corresponding, commercially available amines in step 1.

| Intermediate No | Structure | Step 1 Amount SM (yield) | Step 2 Amount product (yield) | Data |
|---|---|---|---|---|
| 12 | 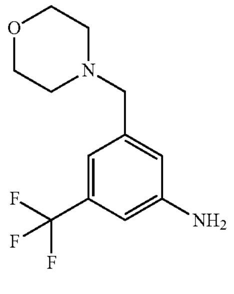 [SMILES: Nc1cc(CN2CCOCC2)cc(C(F)(F)F)c1] | 150 mg, 0.685 mmol (197 mg, 99%) | 134 mg (98%) | $^1$H NMR (400 MHz, $CDCl_3$) δ 6.95 (s, 1H), 6.84 (s, 2H), 6.79 (s, 1H), 3.82 (s, 2H), 3.74-3.69 (m, 4H), 3.44-3.43 (m, 2H), 2.46-2.43 (m, 4H) |
| 13 | 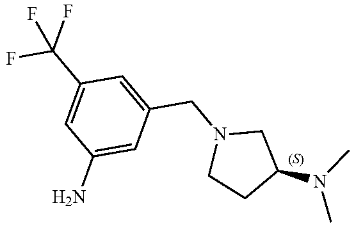 | 750 mg, 3.42 mmol (707 mg, 65%) | 638 mg (99%) | $^1$H NMR (400 MHz, $CDCl_3$) δ 6.94 (s, 1H), 6.84 (s, 1H), 6.78 (s, 1H), 3.82 (s, 2H), 3.57 (d, J = 13.2 Hz, 1H), 3.50 (d, J = 13.2 Hz, 1H), 2.83-2.68 (m, 3H), 2.53-2.45 (m, 1H), 2.31 (dd, J = 6.7, 8.3 Hz, 1H), 2.20 (s, 6H), 2.04-1.94 (m, 1H), 1.77-1.68 (m, 1H) |
| 14 | 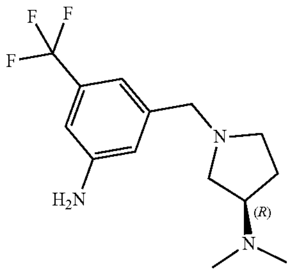 | 750 mg, 3.42 mmol (786 mg, 72%) | 710 mg (99%) | $^1$H NMR (400 MHz, $CDCl_3$) δ 6.94 (s, 1H), 6.84 (s, 1H), 6.77 (s, 1H), 3.81 (s, 2H), 3.58 (d, J = 13.2 Hz, 1H), 3.50 (d, J = 13.3 Hz, 1H), 2.83-2.69 (m, 3H), 2.53-2.45 (m, 1H), 2.31 (dd, J = 6.8, 8.3 Hz, 1H), 2.20 (s, 6H), 2.05-1.95 (m, 1H), 1.77-1.68 (m, 1H) |

Preparation of 3-(2-morpholinoethoxy)-5-(trifluoromethyl)aniline (Intermediate 15)

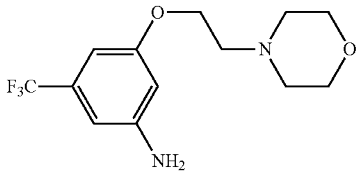 [SMILES: Nc1cc(OCCN2CCOCC2)cc(C(F)(F)F)c1]

Step 1—4-(2-(3-nitro-5-(trifluoromethyl)phenoxy)ethyl)morpholine (Intermediate 16)

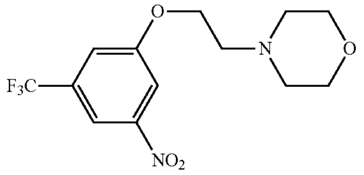

Prepared from 4-(2-chloroethyl)morpholine hydrochloride (431 mg, 2.32 mmol) according to general procedure E. The residue was purified by column chromatography on silica gel (40 g cartridge, 0-100% AcOEt in cyclohexane) to give the title compound (0.6 g, 97%).

$^1$H NMR (400 MHz, DMSO-$d_6$) δ 8.05 (d, J=2.5 Hz, 2H), 7.81 (s, 1H), 4.34 (dd, J=5.6, 5.6 Hz, 2H), 3.58 (dd, J=4.6, 4.6 Hz, 4H), 2.74 (dd, J=5.6, 5.6 Hz, 2H), 2.52 (s, 4H), 2.51 (ddd, J=5.5, 5.5, 4.3 Hz, 4H).

Step 2—3-(2-morpholinoethoxy)-5-(trifluoromethyl) aniline (Intermediate 15)

Prepared from Intermediate 16 (100 mg, 0.312 mmol) according to general procedure F to give the title compound (84 mg, 930%) that was used without further purification.

$^1$H NMR (400 MHz, $CDCl_3$) δ 6.52 (d, J=9.5 Hz, 2H), 6.36 (t, J=2.0 Hz, 1H), 4.09 (t, J=5.6 Hz, 2H), 3.83 (s, 2H), 3.75-3.72 (m, 4H), 2.79 (t, J=5.7 Hz, 2H), 2.59-2.55 (m, 4H).

The intermediates reported in the following table were prepared via nucleophilic substitution as described for Intermediate 15, step 1-2, applying the corresponding, commercially available alkyl chloride in step 1.

| Intermediate No | Structure | Step 1 Amount SM (yield) | Step 2 Amount product (yield) | Data |
|---|---|---|---|---|
| 17 | 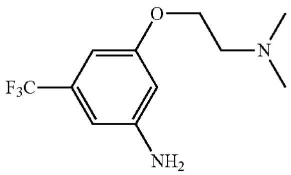 [SMILES: CN(C)CCOc1cc(N)cc(C(F)(F)F)c1] | 250 mg, 1.74 mmol (346 mg, 82%) | 305 mg (93%) | $^1$H NMR (400 MHz, $CDCl_3$) δ 6.54 (s, 1H), 6.51 (s, 1H), 6.37 (t, J = 2.0 Hz, 1H), 4.06-4.03 (m, 2H), 3.81 (s, 2H), 2.72 (t, J = 5.6 Hz, 2H), 2.33 (s, 6H). |
| 18 | 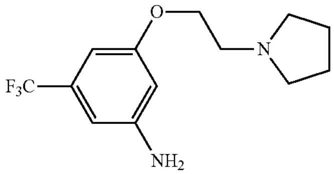 [SMILES: Nc1cc(OCCN2CCCC2)cc(C(F)(F)F)c1] | 296 mg, 1.74 mmol (305 mg, 93%) | 313 mg (90%) | $^1$H NMR (400 MHz, $CDCl_3$) δ 6.55 (s, 1H), 6.50 (s, 1H), 6.37 (d, J = 2.0 Hz, 1H), 4.10-4.06 (m, 2H), 3.81 (s, 2H), 2.91-2.86 (m, 2H), 2.64-2.58 (m, 4H), 1.83-1.79 (m, 4H). |
| 19 | 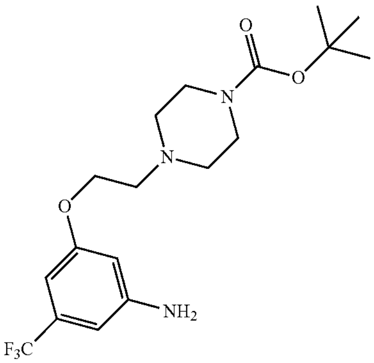 [SMILES: CC(C)(C)OC(=O)N1CCN(CCOc2cc(N)cc(C(F)(F)F)c2)CC1] | 378 mg, 1.52 mmol (544 mg, 89%) | 410 mg (80%) | $^1$H NMR (400 MHz, $CDCl_3$) δ 6.53 (s, 1H), 6.51 (s, 1H), 6.36-6.34 (m, 1H), 4.10-4.06 (m, 2H), 3.86 (s, 2H), 3.47-3.42 (m, 4H), 2.80 (t, J = 5.6 Hz, 2H), 2.54-2.49 (m, 4H), 1.47 (s, 9H). |

Preparation of 4-(pyrrolidin-1-ylmethyl)-3-(trifluoromethyl)aniline (Intermediate 20)

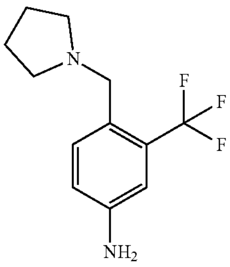 [SMILES: Nc1ccc(CN2CCCC2)c(C(F)(F)F)c1]

Step 1—3-(trifluoromethyl)-4-vinylaniline (Intermediate 21)

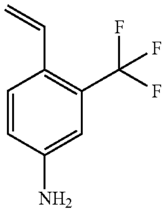

A mixture of 4-bromo-3-(trifluoromethyl)aniline (2.50 g, 10.4 mmol, 1.00 eq), XPhos (497 mg, 1.04 mmol, 0.100 eq), XPhos Pd G2 (410 mg, 0.521 mmol, 0.05 eq) and $K_3PO_4$ (5.53 g, 26.0 mmol, 2.50 eq) was suspended in 1,4-dioxane (45.00 mL) and water (5.00 mL) and sparged with argon under sonication for 10 min. Vinylboronic acid pinacol ester (2.1 mL, 12.5 mmol, 1.20 eq) was added and the reaction mixture was stirred at 80° C., under an atmosphere of argon, for 7 h. The reaction mixture was cooled to room temperature, partitioned between AcOEt and water and the aqueous layer was re-extracted with AcOEt. The combined organic phases were washed with brine, dried ($Na_2SO_4$) and concentrated under vacuum. The residue was purified by column chromatography on silica gel (80 g cartridge, 0-30% AcOEt in cyclohexane) to give the title compound (1.12 g, 57%) $^1$H NMR (400 MHz, $CDCl_3$) δ 7.48 (d, J=8.5 Hz, 1H), 7.04-6.93 (m, 1H), 6.91 (d, J=2.5 Hz, 1H), 6.78 (dd, J=2.5, 8.5 Hz, 1H) 5.58 (d, J=17.5 Hz, 1H), 5.22 (dd, J=1.0, 11.0 Hz, 1H), 3.87 (s, 2H)

Step 2—tert-butyl (3-(trifluoromethyl)-4-vinylphenyl)carbamate (Intermediate 22)

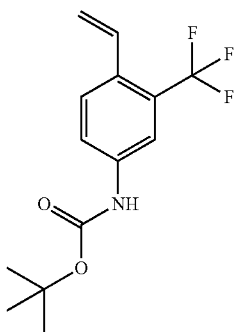 [SMILES: C=Cc1ccc(NC(=O)OC(C)(C)C)cc1C(F)(F)F]

To a solution of Intermediate 21 (1.12 g, 5.98 mmol, 1.00 eq) in toluene (12.00 mL) at room temperature was added $Boc_2O$ (1.7 mL, 7.48 mmol, 1.25 eq). The reaction mixture was stirred at 100° C. for 6 h and then concentrated under vacuum. The residue was purified by column chromatography on silica gel (80 g cartridge, 0-20% AcOEt in cyclohexane) to give the title compound.

$^1$H NMR (400 MHz, $CDCl_3$) δ 7.66 (d, J=2.0 Hz, 1H), 7.59 (d, J=8.5 Hz, 1H), 7.51 (d, J=8.5 Hz, 1H), 7.08-6.97 (m, 1H), 6.59 (s, 1H), 5.67 (d, J=17.5 Hz, 1H), 5.35-5.29 (m, 1H), 1.53 (s, 9H).

Step 3—tert-butyl (4-formyl-3-(trifluoromethyl)phenyl)carbamate (Intermediate 23)

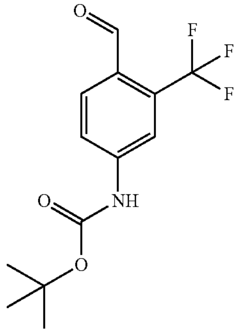 [SMILES: CC(C)(C)OC(=O)Nc1ccc(C=O)c(C(F)(F)F)c1]

To a solution of Intermediate 22 (1.72 g, 5.99 mmol, 1.00 eq) in DCM (60.00 mL) at −78° C. was passed through $O_3/O_2$ for 45 min, resulting in a green reaction mixture. DMSO (440 uL, 5.99 mmol, 1.00 eq) was added and the reaction mixture was allowed to warm to room temperature whilst sparging with argon. The reaction mixture was concentrated under vacuum and the residue was purified by FCC on silica gel (80 g cartridge, 0-20% AcOEt in cyclohexane) to give crude title compound (1.19 g, 39%).

$^1$H NMR (400 MHz, $CDCl_3$) δ 10.27 (d, J=1.94 Hz, 1H), 8.09 (d, J=8.5 Hz, 1H), 7.90 (d, J=1.94 Hz, 1H), 7.61 (d, J=8.5 Hz, 1H), 6.87 (s, 1H).

Step 4—tert-butyl (4-(pyrrolidin-1-ylmethyl)-3-(trifluoromethyl)phenyl)carbamate (Intermediate 24)

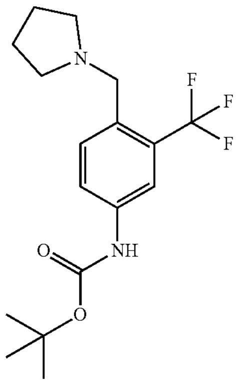 [SMILES: CC(C)(C)OC(=O)Nc1ccc(CN2CCCC2)c(C(F)(F)F)c1]

Intermediate 23 (298 mg, 1.03 mmol) and pyrrolidine (0.095 mL, 1.13 mmol) according to general procedure C to give the title compound (317 mg, 89%).

$^1$H NMR (400 MHz, $CDCl_3$) δ 7.69 (d, J=8.5 Hz, 1H), 7.65 (d, J=2.0 Hz, 1H), 7.49 (m, 1H), 6.54-6.52 (m, 1H), 3.74 (s, 2H), 2.58-2.51 (m, 4H), 1.82-1.77 (m, 4H), 1.52 (s, 9H)

Step 5—4-(pyrrolidin-1-ylmethyl)-3-(trifluoromethyl)aniline (Intermediate 20)

To a solution of Intermediate 24 (315 mg, 0.915 mmol, 1.00 eqin MeOH (6.10 mL) was added 4M HCl in dioxane (1.5 mL, 6.00 mmol, 6.56 eq). The reaction mixture was stirred at room temperature for 66 h. The reaction mixture was evaporated under vacuum to give the hydrochloride salt of the title compound in quantitative yield.

$^1$H NMR (400 MHz, DMSO-$d_6$) δ 10.34 (s, 1H), 7.66 (d, J=9.0 Hz, 1H), 6.98 (d, J=2.5 Hz, 1H), 6.87 (dd, J=2.0, 8.5 Hz, 1H), 4.28 (d, 2H), 3.43-3.36 (m, 2H), 3.11-3.02 (m, 2H), 2.03-1.88 (m, 4H)

The intermediate reported in the following table was prepared via reductive amination as described for Intermediate 20, step 1-5, applying the corresponding, commercially available amine in step 4.

| Intermediate No | Structure | Step 4 Amount SM (yield) | Step 5 Amount product (yield) | Data |
|---|---|---|---|---|
| 25 | 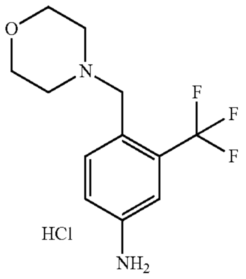 [SMILES: Nc1ccc(CN2CCOCC2)c(C(F)(F)F)c1 ; Cl] | 298 mg, 1.03 mmol (323 mg, 87%) | Quantitative yield | $^1$H NMR (400 MHz, DMSO-$d_6$) δ 10.83 (s, 1H), 7.84 (d, J = 8.3 Hz, 1H), 7.01 (d, J = 2.0 Hz, 1H), 6.90 (dd, J = 1.4, 8.3 Hz, 1H), 3.92-3.85 (m, 4H), 3.25-3.20 (m, 2H), 3.12-3.06 (m, 2H). |

The intermediate reported in the following table was prepared via Suzuky coupling as described for Intermediate 24, step 1-5, applying the corresponding, commercially available aryl bromide in step 1. Modifications of the catalyst were reported in the table below.

| Intermediate No | Structure | Step 1 Amount SM (yield) | Step 5 Amount product (yield) | Data |
|---|---|---|---|---|
| 26 | 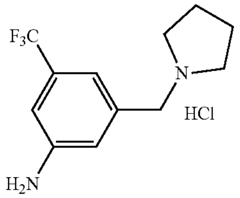 [SMILES: Nc1cc(CN2CCCC2)cc(C(F)(F)F)c1 ; Cl] | 2.50 g, 10.4 mmol (1.54 g, 79%) XPhos Pd G3 replaced XPhos Pd G2 | 140 mg (90%) | $^1$H NMR (400 MHz, DMSO-$d_6$) δ 10.64 (s, 1H), 7.12 (s, 1H), 6.98 (s, 1H), 6.96 (s, 1H), 4.27 (d, J = 6.0 Hz, 2H), 3.37-3.31 (m, 2H), 3.07-2.98 (m, 2H), 2.03-1.96 (m, 2H), 1.91-1.86 (m, 2H) |

Preparation of 4-((dimethylamino)methyl)-3-(trifluoromethyl)aniline (Intermediate 27)

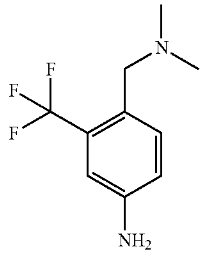

Step 1—N,N-dimethyl-1-(4-nitro-2-(trifluoromethyl)phenyl)methanamine (Intermediate 28)

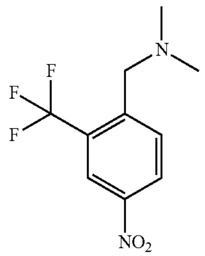 [SMILES: CN(C)Cc1ccc([N+](=O)[O-])cc1C(F)(F)F]

Prepared from 4-nitro-2-(trifluoromethyl)benzaldehyde (125 mg, 0.570 mmol) and dimethylamine (2M solution in THF, 0.31 mL, 0.628 mmol) according to general procedure C to give the title compound (132 mg, 93%).

$^1$H NMR (400 MHz, $CDCl_3$) δ 8.50 (d, J=2.2 Hz, 1H), 8.38 (dd, J=2.3, 8.6 Hz, 1H), 8.10 (d, J=8.6 Hz, 1H), 3.68 (s, 2H), 2.30 (s, 6H)

Step 2—4-((dimethylamino)methyl)-3-(trifluoromethyl)aniline (Intermediate 27)

Prepared from Intermediate 28 (132 mg, 0.532 mmol) according to general procedure D to give the title compound (104 mg, 90%)

$^1$H NMR (400 MHz, $CDCl_3$) δ 7.45 (d, J=8.5 Hz, 1H), 6.92 (d, J=2.5 Hz, 1H), 6.81 (dd, J=2.4, 8.3 Hz, 1H), 3.78 (s, 2H), 3.45 (s, 2H), 2.24 (s, 6H).

Preparation of tert-butyl 3-(3-amino-5-(trifluoromethyl)phenoxy)pyrrolidine-1-carboxylate (Intermediate 29)

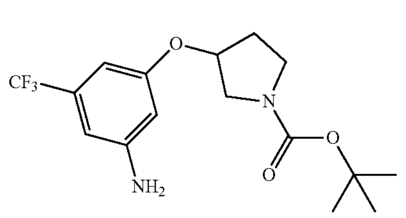

tert-butyl 3-(3-nitro-5-(trifluoromethyl)phenoxy) pyrrolidine-1-carboxylate (Intermediate 30)

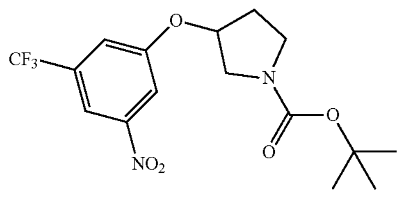 [SMILES: CC(C)(C)OC(=O)N1CCC(Oc2cc([N+](=O)[O-])cc(C(F)(F)F)c2)C1]

A mixture of tributylphosphine (0.90 mL, 3.62 mmol, 1.50 eq) and diisopropyl azodicarboxylate (0.71 mL, 3.62 mmol, 1.50 eq) in THF (10 mL) was stirred at 0° C. for 20 minutes, then a mixture of 3-nitro-5-(trifluoromethyl)phenol (500 mg, 2.41 mmol, 1.00 eq) and N-Boc-3-pyrrolidinol (678 mg, 3.62 mmol, 1.50 eq) in THF (10 mL) was added dropwise. The reaction mixture was stirred at room temperature for 3 days and then concentrated under vacuum. The crude material was purified by column chromatography on silica gel (25 g cartridge, 0-100% AcOEt in cyclohexane) to give the title compound (367 mg, 67% yield).

$^1$H NMR (400 MHz, $CDCl_3$) δ 8.10 (s, 1H), 7.89-7.86 (m, 1H), 7.44 (d, J=4.8 Hz, 1H), 5.05-4.94 (m, 2H), 3.74-3.49 (m, 5H), 2.22-2.21 (m, 2H), 1.48 (s, 9H)

Tert-butyl 3-(3-amino-5-(trifluoromethyl)phenoxy) pyrrolidine-1-carboxylate (Intermediate 29)

Prepared from Intermediate 30 (300 mg, 0.805 mmol) according to general procedure F. Purified by reverse phase preparative HPLC (Sunfire® C18 19×150 mm, 10 um 40-100% ACN/$H_2O$ (0.1% FA), 20 mL/min, RT) gave the title compound (170 mg, 61%).

$^1$H NMR (400 MHz, $CDCl_3$) δ 6.52 (s, 1H), 6.48 (s, 1H), 6.33-6.30 (m, 1H), 4.89-4.83 (m, 1H), 3.65-3.43 (m, 4H), 2.22-2.11 (m, 2H), 1.46 (s, 9H).

Preparation of 3-(tert-butyl)-1-(2-((tert-butyldimethylsilyl)oxy)ethyl)-1H-pyrazol-5-amine (Intermediate 31)

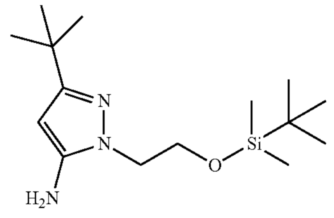 [SMILES: CC(C)(C)c1cc(N)n(CCO[Si](C)(C)C(C)(C)C)n1]

Step 1—2-(5-amino-3-(tert-butyl)-1H-pyrazol-1-yl) ethan-1-ol (Intermediate 32)

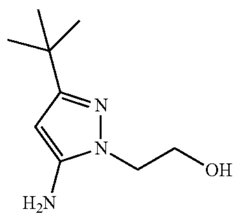

A solution of 4,4-Dimethyl-3-oxopentanenitrile (5.00 g, 39.9 mmol), 2-hydroxyethylhydrazine (3.0 mL, 43.9 mmol) and concentrated HCl (37%) (0.10 mL, 1.21 mmol) was stirred at 90° C., under an atmosphere of nitrogen, for 23 h. The reaction mixture was allowed to cool to room temperature and concentrated under vacuum. The residual oily solid was triturated under cyclohexane (30 mL), the solvent decanted and the residue was dried under vacuum to give the title compound (7.082 g, 97%).

$^1$H NMR (400 MHz, $CDCl_3$) δ 5.43 (s, 1H), 4.02-3.95 (m, 4H), 3.64 (brs, 2H), 1.25 (s, 9H).

Step 2—3-(tert-butyl)-1-(2-((tert-butyldimethylsilyl) oxy)ethyl)-1H-pyrazol-5-amine (Intermediate 31)

To a solution of Intermediate 32 (7.08 g, 38.6 mmol) in DMF (63.00 mL), stirred under an atmosphere of nitrogen at room temperature, was added imidazole (7.89 g, 0.116 mol). Tert-butyl-chloro-dimethyl-silane (8.74 g, 58.0 mmol) was added, in 3 portions, and the reaction mixture was stirred at room temperature for 2 h. The mixture was cooled over an ice/water bath and saturated $NH_4Cl_{(aq)}$ (60 mL) was added slowly. DCM (70 mL) was added and the aqueous phase was diluted with water (100 mL). The aqueous phase was extracted with 3×DCM, and the combined organic phases were washed with 3x5% $LiCl_{(aq)}$, dried over $Na_2SO_4$ and filtered. The filtrate was concentrated under vacuum and purification by column chromatography on silica gel (AcOEt/cyclohexane from 0% to 50%) gave the title compound (8.905 g, 77%).

$^1$H NMR (400 MHz, $CDCl_3$) δ 5.36 (s, 1H), 4.07 (t, J=4.7 Hz, 2H), 3.90 (t, J=4.7 Hz, 2H), 3.85 (s, 2H), 1.25 (s, 9H), 0.83 (s, 9H), −0.04 (s, 6H).

Preparation of 3-(dimethoxymethyl)-5-(trifluoromethyl)aniline (Intermediate 33)

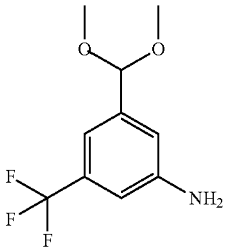

Step 1—1-(dimethoxymethyl)-3-nitro-5-(trifluoromethyl)benzene (Intermediate 34)

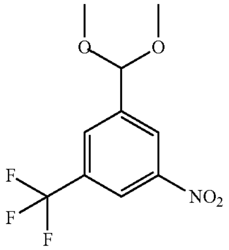

To a solution of 3-nitro-5-(trifluoromethyl)benzaldehyde (2.00 g, 9.13 mmol, 1.00 eq) in MeOH (25.00 mL) was added p-toluenesulfonic acid monohydrate (864 mg, 4.54 mmol, 0.498 eq) and trimethyl orthoformate (2.9 mL, 26.5 mmol, 2.90 eq). The reaction mixture was stirred at 65° C. for 66 h. The reaction mixture was allowed to cool to room temperature and concentrated under vacuum. The residue was partitioned between AcOEt and saturated aqueous $Na_2CO_{3(aq)}$, and the aqueous phase extracted with 2×AcOEt. The combined organic extracts were dried ($Na_2SO_4$) and the solvent evaporated under vacuum to afford the title compound in quantitative yield (2.42 g).

$^1$H NMR (400 MHz, $CDCl_3$) δ 8.53 (1H, s), 8.47 (1H, s), 8.08 (1H, s), 5.53 (1H, s), 3.37 (6H, s)

Step 2—3-(dimethoxymethyl)-5-(trifluoromethyl) aniline (Intermediate 33)

To a solution of Intermediate 34 (3.18 g, 12.0 mmol, 1.00 eq) in MeOH (15.00 mL) and acetic acid (15.00 mL) was added iron powder (3.35 g, 60.0 mmol, 5.00 eq). The reaction mixture was stirred vigorously at room temperature for 4 h. The reaction mixture was pipetted from the iron powder and concentrated under vacuum. The filtrate was dissolved in $Et_2O$ (30 mL), washed with saturated $NaHCO_3$ (aq) and the aqueous phase extracted with 2×$Et_2O$. The combined organic phases were washed with brine, dried ($Na_2SO_4$) and evaporated under vacuum to give the title compound (1.80 g, 64%).

$^1$H NMR (400 MHz, $CDCl_3$) δ 7.10 (1H, s), 6.92 (1H, s), 6.84 (1H, s), 5.32 (1H, s), 4.83 2H, br s), 3.32 (6H, s).

Preparation of 5-(trifluoromethoxy)pyridin-3-amine hydrochloride salt (Intermediate 86)

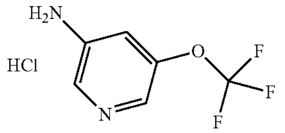 [SMILES: Cl ; Nc1cncc(OC(F)(F)F)c1]

Step 1; tert-butyl N-[5-(trifluoromethoxy)-3-pyridyl]carbamate (Intermediate 87)

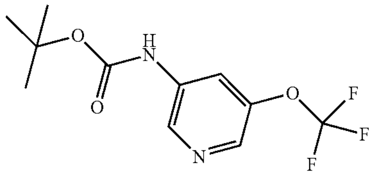 [SMILES: CC(C)(C)OC(=O)Nc1cncc(OC(F)(F)F)c1]

A mixture of tert-Butyl carbamate (102 mg, 0.868 mmol), XantPhos (63 mg, 0.108 mmol), Tris(dibenzylideneacetone) dipalladium(0)-chloroform adduct (37 mg, 0.0362 mmol) and Cesium carbonate (283 mg, 0.868 mmol) in 1,4-dioxane (5 ml) was degassed with nitrogen and treated with 3-bromo-5-(trifluoromethoxy)pyridine (175 mg, 0.723 mmol). The reaction was stirred at 100° C. for 1 hour. The reaction mixture was allowed to cool to room temperature, filtered through a pad of Celite, which was then washed with dioxane, and the combined organic phases concentrated in vacuo. The residue was purified by column chromatography on silica gel, (0-100%, EtOAc in cyclohexane), then dried in vacuo overnight to afford title compound (115 mg, 0.413 mmol, 57%).

$^1$H NMR (400 MHz, $CDCl_3$) δ 8.33 (d, J=2.3 Hz, 1H), 8.23-8.21 (m, 1H), 8.07 (s, 1H), 7.04 (s, 1H), 1.54 (s, 9H).

Step 2; 5-(trifluoromethoxy)pyridin-3-amine hydrochloride salt (Intermediate 86)

To a solution of Intermediate 87 (115 mg, 0.413 mmol) in 1,4-dioxane (3 ml) was added Hydrogen chloride 4N in Dioxane (3.0 ml, 0.413 mmol). The reaction mixture was stirred at room temperature overnight. The reaction mixture was diluted with diethyl ether (20 ml) and filtered to yield a white solid, washed with ether and dried in vacuo to afford title compound (60 mg, 0.280 mmol, 68%).

$^1$H NMR (400 MHz, DMSO-$d_6$) δ 8.07 (d, J=2.0 Hz, 1H), 8.03 (d, J=1.5 Hz, 1H), 7.30 (d, J=1.0 Hz, 1H).

Preparation of 5,6,7,8-tetrahydroimidazo[1,2-a]pyrimidine-3-carboxylic acid (Intermediate 88)

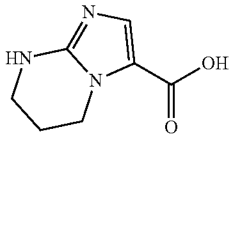 [SMILES: O=C(O)c1cnc2n1CCCN2]

Imidazo[1,2-a]pyrimidine-3-carboxylic acid (100 mg, 0.613 mmol) was dissolved/suspended in EtOH (6.00 ml) and 12 M Hydrogen chloride (0.60 m, 7.20 mmol) was added before degassing and addition of Platinum(IV) oxide (22 mg, 0.0969 mmol) followed by hydrogenation. After 2 hours under hydrogen atmosphere, water (1.00 ml) was added and the reaction left to stir overnight. The reaction mixture was filtered through celite to remove catalyst and concentrated under reduced pressure to afford desired product (100 mg, 97.58%).

$^1H$ NMR (400 MHz, DMSO-$d_6$) δ 13.09 (s, 1H), 8.78 (s, 1H), 7.71 (s, 1H), 4.18 (t, J=6.0 Hz, 2H), 3.39-3.31 (m, 2H), 2.05-1.99 (m, 2H).

Preparation of (R)-(3-amino-5-(trifluoromethyl) phenyl)(3-(dimethylamino) pyrrolidin-1-yl)methanone (Intermediate 111)

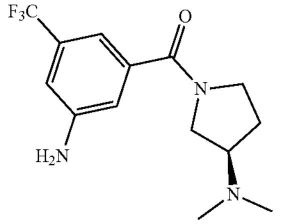 [SMILES: CN(C)[C@@H]1CCN(C(=O)c2cc(N)cc(C(F)(F)F)c2)C1]

To a solution of 3-amino-5-(trifluoromethyl)benzoic acid (205 mg, 1.00 mmol), (R)-(+)-3-(dimethylamino)pyrrolidine (0.38 mL, 3.00 mmol) and TEA (0.42 mL, 3.00 mmol) in DCM (5.00 mL) and DMF (5.00 mL), PyBOP (781 mg, 1.50 mmol) was added. The reaction mixture was stirred for 2 hrs, partially concentrated in vacuo and the residue partitioned between saturated $NaCl_{(aq)}$ and EtOAc. The aqueous phase was extracted with EtOAc and the organic extracts were washed with saturated $NaCl_{(aq)}$, dried ($Na_2SO_4$) and concentrated in vacuo. Purification by FCC (0-10% 2M $NH_3$/MeOH in DCM) gave the desired product (290 mg, 87%)

$^1H$ NMR (400 MHz, DMSO-d6) δ 6.90 (s, 2H), 6.84 (s, 1H), 5.76 (s, 2H), 3.73-3.48 (m, 2H), 3.44-3.39 (m, 1H), 3.27-3.22 (m, 1H), 2.83-2.67 (m, 1H), 2.28-2.21 (m, 3H), 2.14 (s, 3H), 2.09-2.00 (m, 1H), 1.80-1.71 (m, 1H)

Preparation of [4-amino-2-(trifluoromethyl)phenyl] methanol (Intermediate 112)

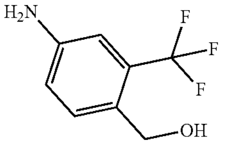 [SMILES: Nc1ccc(CO)c(C(F)(F)F)c1]

To a solution of [4-nitro-2-(trifluoromethyl)phenyl] methanol (1000 mg, 4.52 mmol) and $NH_4Cl$ (121 mg, 2.26 mmol) in EtOH (50 mL) and water (50 mL) at 75° C. iron powder (2526 mg, 45.2 mmol) was added and the reaction mixture was stirred for 30 min. The reaction mixture was filtered through a pad of celite. Combined filtrates were concentrated in vacuo, redissolved in 2:1 DCM/cyclohexane and filtered, combined filtrates were evaporated to yield the title compound (800 mg, 4.19 mmol, 93%).

$^1H$ NMR (400 MHz, $CDCl_3$) δ 7.40 (d, J=8.1 Hz, 1H), 6.93 (d, J=2.3 Hz, 1H), 6.82 (dd, J=2.4, 8.2 Hz, 1H), 4.72 (s, 2H), 3.90-3.84 (s, 2H), 1.70 (s, 1H).

Preparation of 6-(4-methylpiperazin-1-yl)imidazo[1, 2-a]pyridine-3-carboxylic acid (Intermediate 113)

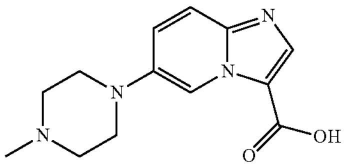 [SMILES: CN1CCN(c2ccc3ncc(C(=O)O)n3c2)CC1]

Step 1; Methyl 6-(4-methylpiperazin-1-yl)imidazo [1,2-a]pyridine-3-carboxylate (Intermediate 114)

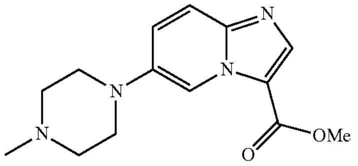 [SMILES: COC(=O)c1cnc2ccc(N3CCN(C)CC3)cn12]

To a solution of ethyl 6-bromoimidazo[1,2-a]pyridine-3-carboxylate (807 mg, 3.00 mmol) in toluene (10 mL) $Pd_2(dba)_3$ (275 mg, 0.300 mmol), BINAP (560 mg, 0.900 mmol) and sodium tert-butoxide (403 mg, 4.20 mmol) were added. The reaction mixture was sparged with nitrogen then 1-methylpiperazine (0.37 mL, 3.30 mmol) was added and the reaction mixture was stirred at 100° C. for 3 hrs. The reaction mixture was allowed to cool to room temperature and filtered through a pad of Celite, which was then washed with MeOH. The combined organic phases were concentrated in vacuo, the residue was purified by FCC (0-100% EtOAc in Cyclohexane followed by 0-100% MeOH in EtOAc). The material was taken on to the next step without further purification.

Step 2; 6-(4-methylpiperazin-1-yl)imidazo[1,2-a] pyridine-3-carboxylic acid (Intermediate 113)

LiOH (314 mg, 13.1 mmol) in water (1 mL) was added to Intermediate 114 (1200 mg, 4.37 mmol) in THF (1 mL) at 0° C. The reaction mixture was allowed to warm to RT and stirred for 18 h. The reaction mixture was concentrated in vacuo. The residue was washed with water and the aqueous phase was adjusted to pH 7 with 1M $HCl_{(aq)}$ and washed with DCM. The aqueous fractions were concentrated in vacuo to yield a mixture of product and inorganic salts. The material was taken on to the next step without further purification.

Preparation of 7-(2-methoxyethoxy)imidazo[1,2-a]pyridine-3-carboxylic acid (Intermediate 115)

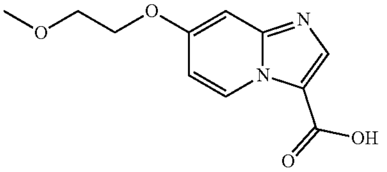 [SMILES: COCCOc1ccn2c(C(=O)O)cnc2c1]

Step 1—ethyl 7-hydroxyimidazo[1,2-a]pyridine-3-carboxylate (Intermediate 116)

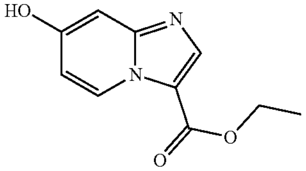

To a solution of 2-Aminopyridin-4-ol (400 mg, 3.63 mmol) in EtOH (12 mL) ethyl 2-chloro-3-oxo-propanoate (547 mg, 3.63 mmol) was added and the mixture was heated to 80° C. and stirred overnight. Mixture was concentrated and the residue was triturated in EtOAc, the solid was collected and purified by silica FCC (25 g, 0-10% MeOH in DCM, 10 CV) then concentrated to afford the title compound (367 mg, 1.78 mmol, 49%)

$^1$H NMR (400 MHz, DMSO-d6) δ 12.32 (s, 1H), 9.19 (d, J=8.0 Hz, 1H), 8.67 (s, 1H), 7.25-7.18 (m, 2H), 4.44-4.38 (m, 2H), 1.39-1.35 (m, 3H).

Step 2—ethyl 7-(2-methoxyethoxy)imidazo[1,2-a]pyridine-3-carboxylate (Intermediate 117)

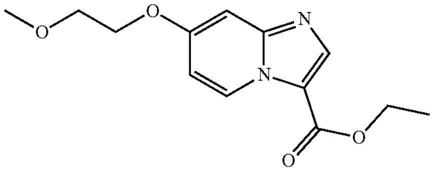 [SMILES: CCOC(=O)c1cnc2cc(OCCOC)ccn12]

To a solution of Intermediate 116 (365 mg, 1.77 mmol, 1.00 eq) in DMF (6.00 mL) $K_2CO_3$ (367 mg, 2.66 mmol, 1.50 eq) and 2-Bromoethyl methyl ether (0.18 mL, 1.95 mmol, 1.10 eq) were added and the mixture was heated to 85° C. and stirred overnight. The reaction mixture was diluted in EtOAc and washed with water, water/brine 1:1, brine, dried over $MgSO_4$, filtered and concentrated to afford the title compound (202 mg, 0.764 mmol, 43%).

$^1$H NMR (400 MHz, DMSO-d6) δ 9.05 (d, J=7.7 Hz, 1H), 8.17 (s, 1H), 7.24 (d, J=2.3 Hz, 1H), 6.97 (dd, J=2.6, 7.7 Hz, 1H), 4.38-4.25 (m, 4H), 3.74-3.71 (m, 2H), 1.35 (t, J=7.1 Hz, 3H).

Step 3—7-(2-methoxyethoxy)imidazo[1,2-a]pyridine-3-carboxylic acid (Intermediate 115)

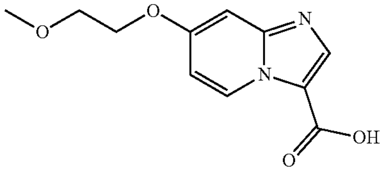 [SMILES: COCCOc1ccn2c(C(=O)O)cnc2c1]

To a solution of Intermediate 117 (200 mg, 0.757 mmol, 1.00 eq) in THF (4 mL) a solution of LiOH monohydrate (79 mg, 1.89 mmol, 2.50 eq) in water (1 mL) was added, and the mixture was allowed to stir at room temperature overnight. Reaction was then heated to 50° C. for 1 hour. The reaction mixture was acidified to pH 2 with aqueous 2M HCl and extracted with EtOAc, the organic layer was washed with brine, dried and concentrated. 18 mg of solid were recovered. The aqueous layer was concentrated then triturated with MeOH and concentrated to afford the title compound (178 mg, quantitative yield).

$^1$H NMR (400 MHz, DMSO-d6) δ 9.23-9.21 (m, 1H), 8.52 (s, 1H), 7.34 (d, J=2.4 Hz, 1H), 7.20 (dd, J=2.5, 7.7 Hz, 1H), 4.37-4.33 (m, 2H), 3.76-3.72 (m, 2H), 3.35-3.34 (m, 3H).

The intermediate reported in the following table was prepared via nucleophilic substitution as described for Intermediate 115, step 1-3, applying the corresponding, commercially available alkyl chloride in step 2. Such procedures may involve minor variations.

| Intermediate No | Structure | Step 2 Amount SM (yield) | Step 3 Amount product (yield) | Data |
|---|---|---|---|---|
| 118 | 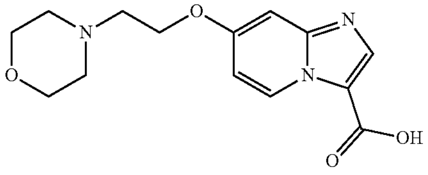 [SMILES: O=C(O)c1cnc2cc(OCCN3CCOCC3)ccn12] | 4-(2-chloroethyl) morpholine: 180 mg, 1.2 mmol Intermediate 116: 225 mg, 1.1 mmol (182 g, 52%) | 163 mg (quantitative) | $^1$H NMR (400 MHz, DMSO-$d_6$) δ 11.96-11.81 (s, 1H), 9.25-9.21 (d, 1H), 8.45-8.41 (s 1H), 7.40-7.37 (d, 1H), 7.18-7.13 (dd 1H), 4.70-4.65 (t, 2H), 4.01-3.96 (m, 4H), 3.66-3.60 (t, 4H) |

The intermediate reported in the following table was prepared as described for Intermediate 115, step 1-3, applying the corresponding, commercially available aminopyridin-ol in step 1 and applying the corresponding electrophile in the step 2. Such procedures may involve minor variations.

| Intermediate No | Structure | Step 1 Amount SMs (yield) | Step 2 Amount SMs (yield) | Step 3 Amount product (yield) | Data |
|---|---|---|---|---|---|
| 119 | 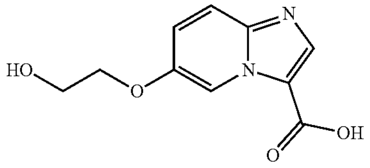 [SMILES: O=C(O)c1cnc2ccc(OCCO)cn12] | 6-aminopyridin-3-ol: 1.00 g, 9.1 mmol ethyl 2-chloro-3-oxo-propanoate: 1.37 g, 9.08 mmol (0.90 g, 48%) | Product Step 1: 100 mg, 0.485 mmol ethylene carbonate: 47 mg, 0.533 mmol (92 mg 76%) | 80 mg (quantitative) | $^1$H NMR (400 MHz, DMSO-$d_6$) δ 8.88 (d, J = 2.1 Hz, 1H), 8.23 (s, 1H), 7.76 (d, J = 9.7 Hz, 1H), 7.41 (dd, J = 2.5, 9.7 Hz, 1H), 4.99 (t, J = 5.5 Hz, 1H), 4.38 (q, J = 7.1 Hz, 2H), 4.08 (t, J = 4.8 Hz, 2H), 3.81-3.76 (m, 2H), 1.36 (t, J = 7.2 Hz, 3H) |

Preparation of 6-((dimethylamino)methyl)imidazo[1,2-a]pyridine-3-carboxylic acid (Intermediate 120)

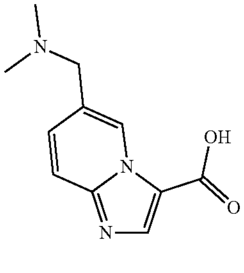 [SMILES: CN(C)Cc1ccc2ncc(C(=O)O)n2c1]

Step 1; ethyl 6-(hydroxymethyl)imidazo[1,2-a]pyridine-3-carboxylate (Intermediate 121)

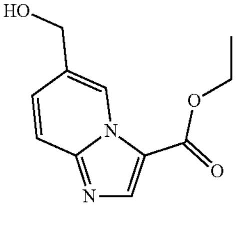 [SMILES: CCOC(=O)c1cnc2ccc(CO)cn12]

To a suspension of 2-amino-5-pyridinemethanol (0.50 g, 4.03 mmol) and potassium (Z)-2-chloro-3-ethoxy-3-oxo-prop-1-en-1-olate (1.52 g, 8.06 mmol) in EtOH (5.0 mL) at 20° C. sulfuric acid (0.21 mL, 4.03 mmol) was added dropwise. The reaction mixture was stirred at 20° C. for 15 minutes and pyridine (0.39 mL, 4.83 mmol) was added. The resulting mixture was stirred at 80° C. overnight. The solvent was concentrated under reduced pressure. The residue was partitioned between EtOAc and saturated $NaHCO_3$ $_{(aq)}$. The organic phase was washed with brine, dried over $MgSO_4$, filtered and concentrated. The residue was purified by column chromatography on silica gel (0-100% EtOAc in cyclohexane, followed by 3/1 EtOAc/EtOH) to give title product (645 mg, 73%).

$^1$H NMR (400 MHz, $CDCl_3$) δ 9.26 (s, 1H), 8.27-8.26 (m, 1H), 7.68 (d, J=9.3 Hz, 1H), 7.45 (dd, J=1.6, 9.2 Hz, 1H), 4.77 (s, 2H), 4.41 (q, J=7.2 Hz, 2H), 2.63 (s, 1H), 1.43 (t, J=7.2 Hz, 3H).

Step 2; ethyl 6-formylimidazo[1,2-a]pyridine-3-carboxylate (Intermediate 122)

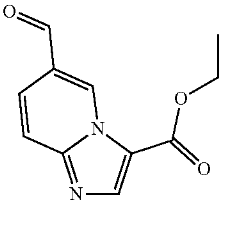 [SMILES: CCOC(=O)c1cnc2ccc(C=O)cn12]

To a mixture of Intermediate 121 (460 mg, 2.09 mmol) in DCM (25 mL) manganese(IV) oxide (1816 mg, 20.9 mmol) was added and the reaction stirred at RT for 3 days. The reaction mixture was filtered through celite and washed with DCM. The filtrate was concentrated under reduced pressure to give the title compound (414 mg, 91%).

$^1$H NMR (400 MHz, $CDCl_3$) δ 10.05 (s, 1H), 9.85 (s, 1H), 8.38 (s, 1H), 7.92 (d, J=9.7 Hz, 1H), 7.81 (d, J=9.3 Hz, 1H), 4.47 (q, J=7.2 Hz, 2H), 1.46 (t, J=7.1 Hz, 3H)

Step 3; ethyl 6-((dimethylamino)methyl)imidazo[1,2-a]pyridine-3-carboxylate (Intermediate 123)

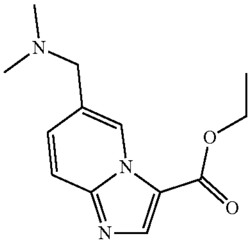 [SMILES: CCOC(=O)c1cnc2ccc(CN(C)C)cn12]

To a solution of Intermediate 122 (210 mg, 0.962 mmol) in THF (2.5 mL) 2M Dimethylamine (2.2 mL, 4.33 mmol) was added. The reaction mixture was stirred for 16 hrs at RT. A solution of $NaBH_3CN$ (67 mg, 1.06 mmol) in MeOH (0.25 mL) and AcOH (0.31 mL, 5.38 mmol) are added, and the solution is stirred for 2 hour at 60° C. The reaction mixture is diluted with water (10 mL) and adjusted to pH 8-9 by the addition of saturated $NaHCO_{3(aq)}$. Aqueous layer was extracted with EtOAc, the organic extract was washed with brine (15 mL), dried over $MgSO_4$ and concentrated under reduced pressure. The residue was purified by column chromatography on silica gel (0-100% 3:1 EtOAc:EtOH in EtOAc) to give title compound (114 mg, 61%).

$^1$H NMR (400 MHz, $CDCl_3$) δ 9.23 (s, 1H), 8.29-8.28 (m, 1H), 7.72-7.69 (m, 1H), 7.52-7.48 (m, 1H), 4.42 (q, J=7.2 Hz, 2H), 3.56 (s, 2H), 2.33 (s, 6H), 1.43 (t, J=7.2 Hz, 3H)

Step 4: 6-((dimethylamino)methyl)imidazo[1,2-a]pyridine-3-carboxylic acid (Intermediate 120)

To a solution of 2 M NaOH (1.2 mL, 2.36 mmol) in MeOH (4.50 mL), Intermediate 123 (144 mg, 0.582 mmol) was added and the resulting mixture was stirred at RT for three days. The reaction mixture was concentrated. The pH was acidified to pH 2 with 2M aqueous HCl and concentrated under reduced pressure to yield title compound without purification in the next step (quantitative yield).

$^1$H NMR (400 MHz, DMSO-d6) δ 11.20 (s, 1H), 9.58 (s, 1H), 8.56 (s, 1H), 8.08 (dd, J=1.5, 9.3 Hz, 1H), 8.03 (dd, J=0.7, 9.3 Hz, 1H), 4.57-4.53 (m, 2H), 2.79 (s, 3H), 2.78 (s, 3H)

Preparation of pyrazolo[1,5-a]pyrazine-3-carbaldehyde (Intermediate 124)

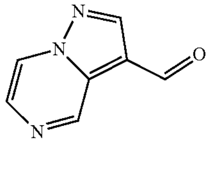 [SMILES: O=Cc1cnn2ccncc12]

Step 1; pyrazolo[1,5-a]pyrazin-3-ylmethanol (Intermediate 125)

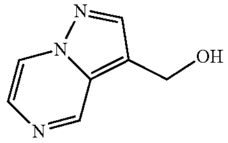 [SMILES: OCc1cnn2ccncc12]

To a solution of pyrazolo[1,5-a]pyrazine-3-carboxylic acid (130 mg, 0.797 mmol) in THF (20 mL) cooled to 0° C. isobutyl chloroformate (0.12 mL, 0.956 mmol) and 4-methylmorpholine (0.11 mL, 0.956 mmol) were added. The reaction mixture was allowed to stir for 2 hours before filtering to remove the solid residue and adding to a solution of $NaBH_4$ (45 mg, 1.20 mmol) in EtOH (5.0 mL) at 0° C. and allowing to stir overnight. The reaction mixture was acidified with 2N HCl and organics extracted with EtOAc before concentrating under reduced pressure to afford desired product (50 mg, 42%), which was used directly in the next step without purification.

Step 2; pyrazolo[1,5-a]pyrazine-3-carbaldehyde (Intermediate 124)

Intermediate 125 (60 mg, 0.402 mmol) was dissolved in THF (5.0 mL) and manganese(IV) oxide (350 mg, 4.02 mmol) was added before stirring at reflux for 2 hours. The reaction mixture was filtered through celite and concentrated under reduced pressure to afford title compound (30 mg, 51%).

$^1$H NMR (400 MHz, $CDCl_3$) δ 10.15 (s, 1H), 9.72 (d, J=1.2 Hz, 1H), 8.51 (dd, J=1.5, 4.7 Hz, 1H), 8.49 (s, 1H), 8.22 (d, J=4.4 Hz, 1H).

Preparation of 3-(4-methylpiperazin-1-yl)-1-(2-trimethylsilylethoxy methyl)pyrazolo[3,4-b]pyridine-5-carbaldehyde (Intermediate 126)

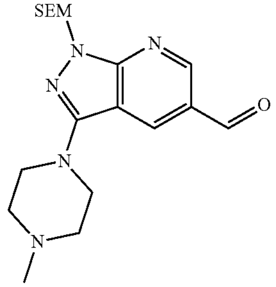 [SMILES: CN1CCN(c2nn(COCC[Si](C)(C)C)c3ncc(C=O)cc23)CC1]

Step 1; methyl 3-bromo-1-(2-trimethylsilylethoxymethyl)pyrazolo[3,4-b]pyridine-5-carboxylate (Intermediate 127)

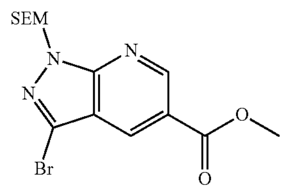 [SMILES: COC(=O)c1cnc2c(c1)c(Br)nn2COCC[Si](C)(C)C]

Methyl 3-bromo-1H-pyrazolo[3,4-b]pyridine-5-carboxylate (512 mg, 2.00 mmol) was dissolved in DMF (6.0 mL) and cooled to 0° C. followed by NaH (60%, 96 mg, 2.40 mmol) before addition of SEM-Cl (0.71 mL, 4.00 mmol, 2.00 eq) and stirring at RT for 3 hours. The reaction mixture was diluted with water before extracting with EtOAc. The organic phase was washed with water, dried ($MgSO_4$) and concentrated. The solid was purified by FCC (25 g column, 0-100% EtOAc in cyclohexane) to afford title compound (513 mg, 66%).

$^1H$ NMR (400 MHz, $CDCl_3$) δ 9.21 (d, J=2.0 Hz, 1H), 8.63 (d, J=2.0 Hz, 1H), 5.82 (s, 2H), 3.98 (s, 3H), 3.68-3.57 (m, 2H), 0.95-0.89 (m, 2H), 0.00 (s, 9H)

Step 2; methyl 3-(4-methylpiperazin-1-yl)-1-(2-trimethylsilylethoxymethyl) pyrazolo[3,4-b]pyridine-5-carboxylate (Intermediate 128)

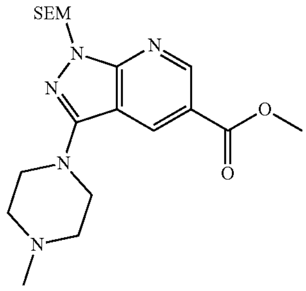 [SMILES: COC(=O)c1cnc2c(c1)c(N1CCN(C)CC1)nn2COCC[Si](C)(C)C]

A mixture of Intermediate 127 (200 mg, 0.518 mmol), $Cs_2CO_3$ (253 mg, 0.777 mmol), 1-methylpiperazine (0.29 mL, 2.59 mmol) and XantPhos (45 mg, 0.0777 mmol) in 1,4-dioxane (4 mL) was degassed under $N_2$, then $Pd_2(dba)_3$ (24 mg, 0.0259 mmol) was added, the tube capped and the mixture stirred at 100° C. overnight. Mixture concentrated to dryness. The residue was purified by FCC (0-50% [75:15:10 EtOAc:EtOH:7M $NH_3$/MeOH] in cyclohexane) to give title compound (133 mg, 63%).

$^1H$ NMR (400 MHz, $CDCl_3$) δ 9.08 (d, J=2.0 Hz, 1H), 8.72 (d, J=2.0 Hz, 1H), 5.71 (s, 2H), 3.98 (s, 3H), 3.69-3.53 (m, 6H), 2.67-2.59 (m, 4H), 2.39 (s, 3H), 0.98-0.89 (m, 2H), −0.05 (s, 9H)

Step 3; [3-(4-methylpiperazin-1-yl)-1-(2-trimethylsilylethoxymethyl) pyrazolo[3,4-b]pyridin-5-yl] methanol (Intermediate 129)

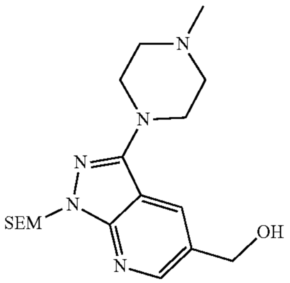 [SMILES: CN1CCN(c2nn(COCC[Si](C)(C)C)c3ncc(CO)cc23)CC1]

A mixture of Intermediate 128 (40 mg, 0.0986 mmol) in DCM (2.0 mL) was cooled to 0° C. and 1 M diisobutylaluminum hydride (0.20 mL, 0.197 mmol) was added. The mixture was stirred at RT overnight. The reaction mixture was quenched with water then 0.5 mL NaOH 2N. Mixture stirred for 10 min then $MgSO_4$ was added. The mixture was filtered and concentrated to dryness to give (45 mg, 100%) which was used in the next step without purification.

Step 4; 3-(4-methylpiperazin-1-yl)-1-(2-trimethylsilylethoxymethyl) pyrazolo[3,4-b]pyridine-5-carbaldehyde (Intermediate 126)

Following the procedure as per Intermediate 125 starting from Intermediate 129 (45 mg, 0.119 mmol) in 2-methyl-THF (1.0 mL) at 50° C. for 2 h the title compound was obtained (35 mg, 78%) and used directly in the next step without purification.

Preparation of: 2-((dimethylamino)methyl)-6-(trifluoromethyl)pyridin-4-amine (Intermediate 130)

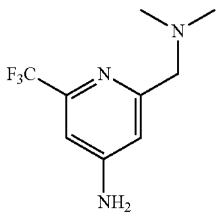

Step 1: 4-amino-N-methoxy-N-methyl-6-(trifluoromethyl)picolinamide (Intermediate 131)

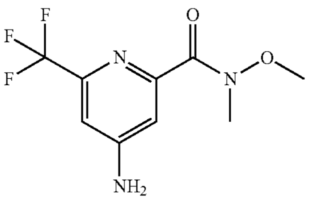 [SMILES: CON(C)C(=O)c1cc(N)cc(C(F)(F)F)n1]

Prepared from 4-amino-6-(trifluoromethyl)picolinic acid (445 mg, 2.16 mmol) and N,O-dimethylhydroxylamine hydrochloride (232 mg, 2.37 mmol) according to general procedure A. Purification was performed by silica FCC (80 g cartridge, 0-50% EtOAc in cyclohexane (+0.1% $NEt_3$)) to afford the title compound (369 mg, 68%).

$^1H$ NMR (400 MHz, DMSO-d6) δ 6.96 (d, J=2.1 Hz, 1H), 6.84-6.78 (m, 3H), 3.67 (s, 3H), 3.24 (s, 3H)

Step 2: 4-amino-6-(trifluoromethyl)picolinaldehyde (Intermediate 132)

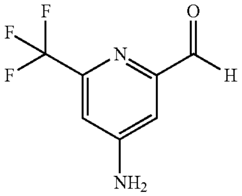 [SMILES: Nc1cc(C=O)nc(C(F)(F)F)c1]

To a stirred solution of Intermediate 131 (308 mg, 1.24 mmol) in THE (4.82 mL) cooled in an ice/water bath was added $LiAlH_4$ (2M in THF, 0.62 mL, 1.24 mmol) dropwise maintaining the internal temperature below 6° C. The reaction mixture was stirred for 1 h and diluted with anhydrous $Et_2O$ (5 mL). Water (47 μL), 15% $NaOH_{(aq)}$ (47 μL) and water (141 μL) were added, the reaction mixture was allowed to warm to room temperature and stirred for 15 min. Anhydrous $MgSO_4$ was added, the reaction mixture was stirred for 15 min, filtered and the filtrate was concentrated under vacuum to give the title compound (252 mg, >100%), which was used in the next step without purification LC-MS (ESI) Method 12: $t_R$=0.95 min; m/z (M+1)=191

Step 3: 2-((dimethylamino)methyl)-6-(trifluoromethyl)pyridin-4-amine (Intermediate 130)

Prepared from Intermediate 132 (126 mg, 0.663 mmol) and dimethylamine (2M solution in THF) (0.33 mL, 0.663 mmol) according to general procedure D. Purification was performed by silica FCC (12 g cartridge, 0-8% 2M $NH_3$/MeOH in DCM) to afford the title compound (65 mg, 44%).

$^1H$ NMR (400 MHz, DMSO-d6) δ 6.78-6.77 (m, 2H), 6.49 (s, 2H), 3.34 (s, 2H), 2.18 (s, 6H).

Example 1; Preparation of 6-(imidazo[1,2-a]pyridine-3-carbonyl)-N-(3-((4-methylpiperazin-1-yl)methyl)-5-(trifluoromethyl)phenyl)-4,5,6,7-tetrahydrothieno[2,3-c]pyridine-3-carboxamide Example 1

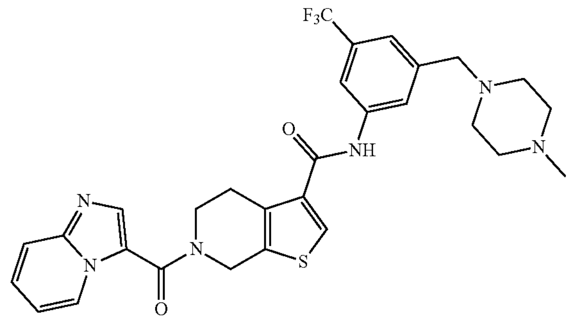

Step 1; 6-(tert-butyl) 3-methyl 4,7-dihydrothieno[2,3-c]pyridine-3,6(5H)-dicarboxylate (Intermediate 35)

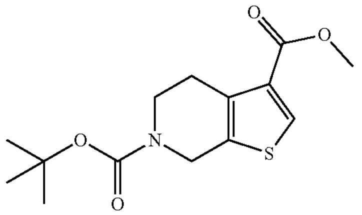 [SMILES: COC(=O)c1csc2c1CCN(C(=O)OC(C)(C)C)C2]

6-(tert-butoxycarbonyl)-4,5,6,7-tetrahydrothieno[2,3-c]pyridine-3-carboxylic acid (1.249 g, 4.41 mmol) and cesium carbonate (2.154 g, 6.61 mmol) were dissolved in anhydrous DMF (Volume: 15 ml) then $CH_3I$ (0.413 ml, 6.61 mmol) was added in one portion. The solution was stirred at RT overnight. The reaction mixture was diluted with $Et_2O$ (20 mL) then washes with sat $NH_4Cl$ (10 mL) and brine (10 mL). The organic phase was separated, dried over $Na_2SO_4$, filtered and concentrated to dryness. the crude was purified by direct phase FCC (silica, gradient n-Heptane:AcOEt from 100:0 to 80:20) to provide the title compound (1.21 g, 4.07 mmol, 92% yield).

$^1H$ NMR (400 MHz, $CDCl_3$) δ ppm 7.98 (s, 1H) 4.62 (br s, 2H) 3.84 (s, 1H) 3.67 (t, J=5.70 Hz, 1H) 2.99 (br t, J=5.48 Hz, 1H) 1.49 (s, 1H)

Step 2; methyl 4,5,6,7-tetrahydrothieno[2,3-c]pyridine-3-carboxylate hydrochloride (Intermediate 36)

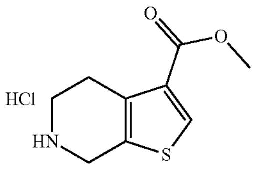

Intermediate 35 (1.21 g, 4.07 mmol) was dissolved in conc HCl (7 ml, 230 mmol) and the reaction was stirred at RT for 10 min. Then ethanol was added at the reaction and the solvent was evaporated by reduced pressure until obtaining the title compound (0.921 g, 3.94 mmol, 97% yield). The compound will be used in the next step without further purification.

Step 3; methyl 6-(imidazo[1,2-a]pyridine-3-carbonyl)-4,5,6,7-tetrahydrothieno[2,3-c]pyridine-3-carboxylate (Intermediate 37)

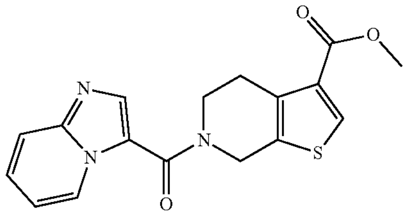 [SMILES: COC(=O)c1csc2c1CCN(C(=O)c1cnc3ccccn13)C2]

Imidazo[1,2-a]pyridine-3-carboxylic acid (208 mg, 1.284 mmol), Intermediate 36 (200 mg, 0.856 mmol) and TBTU (412 mg, 1.284 mmol) were dissolved in 6 mL DCM/DMF 1:1, then DIPEA (0.598 ml, 3.42 mmol) was added in one portion. The solution was stirred at rt for 1 hr. the crude was diluted with DCM (10 mL) then was washed with $NH_4Cl$ saturated solution (2×15 mL) and saturated solution $NaHCO_3$ (2×15 mL). The organic phase was dried over $Na_2SO_4$, filtered and concentrated to dryness. The crude was purified by reverse phase FCC (C18 column, gradient A:B from 100:0 to 0:100 eluent A: $H_2O$:ACN:HCOOH 95:5:0.1 Eluent B:$H_2O$:ACN:HCOOH 5:95:0.1) to provide the title compound (155.2 mg, 0.455 mmol, 53.1% yield).

$^1H$ NMR (400 MHz, $CDCl_3$) δ ppm 9.05-9.10 (m, 1H) 8.04 (s, 1H) 7.99-8.03 (m, 1H) 7.81 (d, J=8.99 Hz, 1H) 7.42-7.50 (m, 1H) 7.04 (t, J=6.91 Hz, 1H) 5.03 (s, 2H) 4.09 (t, J=5.81 Hz, 2H) 3.87 (s, 3H) 3.22 (br t, J=5.59 Hz, 2H)

Step 4: 6-(imidazo[1,2-a]pyridine-3-carbonyl)-N-(3-((4-methylpiperazin-1-yl)methyl)-5-(trifluoromethyl)phenyl)-4,5,6,7-tetrahydrothieno[2,3-c]pyridine-3-carboxamide (Example 1)

3-((4-methylpiperazin-1-yl)methyl)-5-(trifluoromethyl)aniline (84 mg, 0.308 mmol) was dissolved in dry THF (Volume: 6 ml, Ratio: 1.500) under Nitrogen, the mixture was stirred at −78° C. for 15 min, then n-BuLi 2.5M in hexane (0.098 ml, 0.246 mmol) was added dropwise in 5 min and the solution was stirred for 1 hr at −78° C. A solution of Intermediate 37 (42 mg, 0.123 mmol) in THF (Volume: 6 ml) was added dropwise for 10 min, then the temperature was increased at rt and the reaction was stirred for another 1 hr. 10 mL of water was added on the solution and the solvent was evaporated. the crude was purified by reverse phase FCC (C18 column, gradient A:B from 100:0 to 0:100 where eluent A=$H_2O$:ACN:HCOOH 95:5:0.1 and eluent B=$H_2O$:ACN:HCOOH 5:95:0.1) to afford the title compound (32 mg, 0.055 mmol, 45% yield).

$^1H$ NMR (400 MHz, DMSO-$d_6$) δ ppm 10.34 (s, 1H), 8.93 (d, J=6.80 Hz, 1H), 8.18 (s, 1H), 8.10 (s, 2H), 7.90 (s, 1H), 7.70 (d, J=8.99 Hz, 1H), 7.44 (br t, J=7.80 Hz, 1H), 7.30 (s, 1H), 7.07 (t, J=6.72 Hz, 1H), 4.99 (br s, 2H), 3.95 (br t, J=5.59 Hz, 2H), 3.28 (s, 2H), 3.01-3.10 (m, 2H), 2.27-2.43 (m, 8H), 2.15 (br s, 3H)

LC-MS (ESI) method 1: $t_R$=0.92 min; m/z (M+1)=583.2.

Example 2; Preparation of N-(3-(tert-butyl)-1-(p-tolyl)-1H-pyrazol-5-yl)-6-(imidazo[1,2-a]pyridine-3-carbonyl)-4,5,6,7-tetrahydrothieno[2,3-c]pyridine-3-carboxamide Example 2

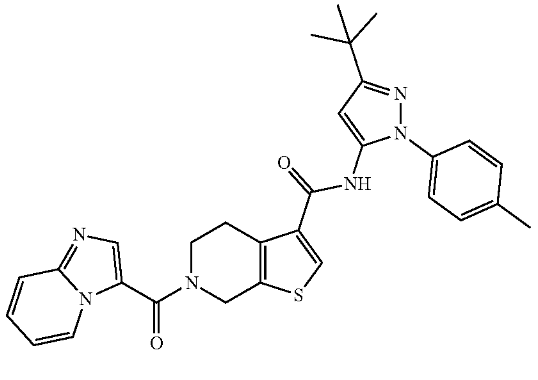

Step 1; ethyl 4,5,6,7-tetrahydrothieno[2,3-c]pyridine-3-carboxylate hydrochloride (Intermediate 38)

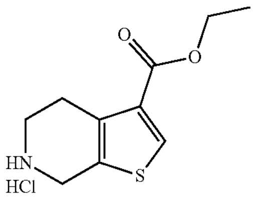

To a solution of 6-(tert-butyl) 3-ethyl 4,7-dihydrothieno[2,3-c]pyridine-3,6(5H)-dicarboxylate (4.88 g, 15.67 mmol) in $Et_2O$ (Volume: 78 ml), 4N HCl in dioxane (19.59 ml, 78 mmol) was added and the reaction mixture was stirred at RT overnight. The solid was separated and dryed under reduced pressure to afford a title compound (3.58 g, 14.45 mmol, 92% yield).

$^1H$ NMR (300 MHz, DMSO-$d_6$) δ 9.58 (s, 2H), 8.31 (s, 1H), 4.35 (s, 2H), 4.25 (q, J=7.1 Hz, 2H), 3.39-3.34 (m, 2H), 3.07 (t, J=6.1 Hz, 2H), 1.29 (t, J=7.1 Hz, 3H).

Step 2; ethyl 6-(imidazo[1,2-a]pyridine-3-carbonyl)-4,5,6,7-tetrahydrothieno[2,3-c]pyridine-3-carboxylate (Intermediate 39)

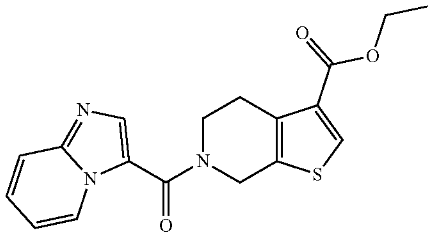 [SMILES: CCOC(=O)c1csc2c1CCN(C(=O)c1cnc3ccccn13)C2]

To a solution Intermediate 38 (1.40 g, 5.65 mmol) and imidazo[1,2-a]pyridine-3-carboxylic acid (0.916 g, 5.65 mmol) in DCM (28.3 ml), DIPEA (5.92 ml, 33.9 mmol) was added followed by T3P (6.73 ml, 11.30 mmol) and the reaction mixture was stirred at RT overweekend. The crude was diluted with DCM, water was added and this mixture was stirred for 10 min. Then the phases were separated, aqueous layer was extracted with DCM (3×50 mL), combined organic phases were washed with brine, dried over $MgSO_4$, filtrated and concentrated under reduced pressure. The crude was purified by direct phase FCC (silica, gradient DCM:MeOH from 100:0 to 90:10) to provide the title compound (1.75 g, 4.92 mmol, 87% yield).

$^1H$ NMR (300 MHz, $CDCl_3$) δ 9.03 (dt, J=7.0, 1.2 Hz, 1H), 8.03 (d, J=0.8 Hz, 1H), 7.98 (s, 1H), 7.72 (dt, J=9.0, 1.2 Hz, 1H), 7.38 (ddd, J=9.0, 6.8, 1.3 Hz, 1H), 6.97 (td, J=6.9, 1.3 Hz, 1H), 5.01 (d, J=1.8 Hz, 2H), 4.32 (q, J=7.1 Hz, 2H), 4.08 (t, J=5.8 Hz, 2H), 3.20 (tt, J=5.9, 1.7 Hz, 2H), 1.37 (t, J=7.1 Hz, 3H).

Step 3; sodium 6-(imidazo[1,2-a]pyridine-3-carbonyl)-4,5,6,7-tetrahydrothieno[2,3-c]pyridine-3-carboxylate (Intermediate 40)

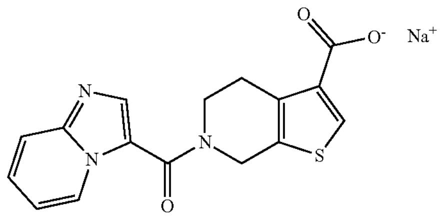 [SMILES: O=C([O-])c1csc2c1CCN(C(=O)c1cnc3ccccn13)C2 ; [Na+]]

To a solution of Intermediate 39 (1.75 g, 4.92 mmol,) in MeOH (49.2 ml), 1M NaOH (4.92 ml, 4.92 mmol) was added, reaction mixture was stirred at RT overweekend. Solvent was evaporated under reduce pressure to afford the title compound in quantitative yield.

$^1$H NMR (300 MHz, DMSO-$d_6$) δ 8.98-8.89 (m, 1H), 8.09 (s, 1H), 7.75-7.68 (m, 1H), 7.55 (s, 1H), 7.49-7.40 (m, 1H), 7.08 (td, J=6.9, 1.3 Hz, 1H), 4.93 (s, 2H), 3.92 (t, J=5.8 Hz, 2H), 3.12 (t, 5.8 Hz, 2H).

Step 4; N-(3-(tert-butyl)-1-(p-tolyl)-1H-pyrazol-5-yl)-6-(imidazo[1,2-a]pyridine-3-carbonyl)-4,5,6,7-tetrahydrothieno[2,3-c]pyridine-3-carboxamide Example 2

Prepared from sodium Intermediate 40 (100 mg, 0.286 mmol,) and 3-(tert-butyl)-1-(p-tolyl)-1H-pyrazol-5-amine (65.6 mg, 0.286 mmol) according to general procedure G. The crude was cooled down diluted with DCM and water was added. The mixture was stirred 15 min and the phases were separated. Organic phases was washed with 5% citric acid, water, brine, dryed over $Na_2SO_4$, filtered and concentrated under reduced pressure. Crude material was purified by preparative HPLC to afford the title compound (23.1 mg, 0.043 mmol, 15% yield)

$^1$H NMR (300 MHz, DMSO-$d_6$) δ 10.04 (s, 1H), 8.94 (dt, J=7.0, 1.2 Hz, 1H), 8.10 (s, 1H), 8.04 (s, 1H), 7.73 (dt, J=9.0, 1.2 Hz, 1H), 7.46 (ddd, J=9.0, 6.8, 1.3 Hz, 1H), 7.43-7.36 (m, 2H), 7.25 (d, J=8.2 Hz, 2H), 7.09 (td, J=6.9, 1.3 Hz, 1H), 6.34 (s, 1H), 4.98 (s, 2H), 3.93 (t, J=5.6 Hz, 2H), 2.92 (s, 2H), 2.31 (s, 3H), 1.30 (s, 9H).

LC-MS (ESI) method 2: $t_R$=2.18 min; m/z (M+1)=539.0.

The compounds reported in the following table were prepared via amido coupling as described for Example 2, step 1-4, applying the corresponding, commercially available or previously synthesized amine in step 4. Modifications of coupling agents (e.g. HATU instead of T3P), salt free-basing or chromatographic purification conditions (e.g. Prep HPLC or flash chromatography) were reported in the table. For Example 44 and Example 45, absolute configuration was assigned by inference, performing non-racemizing chemical reactions on reagents whose absolute configuration is known.

| Example No | Structure | General procedure - Amount reagents | Amount product (yield) | Purification method | Data |
|---|---|---|---|---|---|
| 3 | 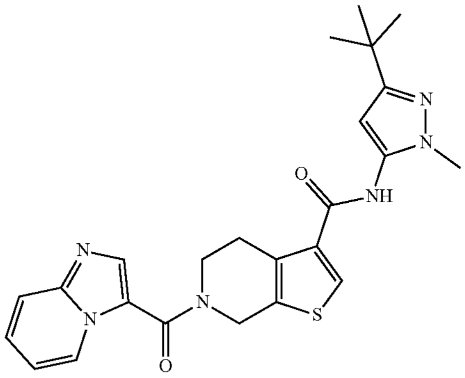 [SMILES: Cn1nc(C(C)(C)C)cc1NC(=O)c1csc2c1CCN(C(=O)c1cnc3ccccn13)C2] | General procedure G<br>Amine: 43.9 mg (1.0 eq)<br>Intermediate 40: 100 mg (1.0 eq) | 21.7 mg (16%) | Prep HPLC | $^{1}H$ NMR (300 MHz, DMSO-$d_6$) δ 10.03 (s, 1H), 8.95 (dt, J = 7.0, 1.2 Hz, 1H), 8.17 (s, 1H), 8.13 (s, 1H), 7.73 (dt, J = 9.1, 1.2 Hz, 1H), 7.46 (ddd, J = 9.1, 6.8, 1.3 Hz, 1H), 7.09 (td, J = 6.9, 1.3 Hz, 1H), 6.09 (s, 1H), 5.02 (s, 2H), 3.97 (t, J = 5.7 Hz, 2H), 3.62 (s, 3H), 3.05 (s, 2H), 1.23 (s, 9H).<br>LC-MS (ESI): method 3<br>$t_R$ = 2.80 min; m/z (M + 1) = 463. |
| 4 | 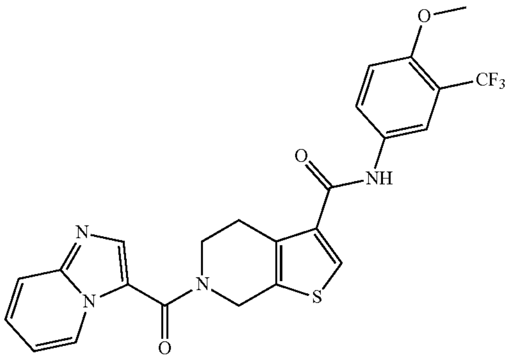 | General procedure G<br>Amine: 54.7 mg, 0.286 mmol)<br>Intermediate 40: 100 mg (1.0 eq) | 18.8 mg (13%) | Prep HPLC | $^{1}H$ NMR (300 MHz, DMSO-$d_6$) δ 10.21 (s, 1H), 8.96 (dt, J = 7.0, 1.3 Hz, 1H), 8.14 (d, J = 5.3 Hz, 2H), 8.07 (d, J = 2.6 Hz, 1H), 7.94 (dd, J = 9.1, 2.7 Hz, 1H), 7.73 (dt, J = 9.0, 1.2 Hz, 1H), 7.46 (ddd, J = 8.8, 6.8, 1.3 Hz, 1H), 7.27 (d, J = 9.2 Hz, 1H), 7.10 (td, J = 6.9, 1.4 Hz, 1H), 5.02 (s, 2H), 3.98 (t, J = 5.7 Hz, 2H), 3.87 (s, 3H), 3.07 (s, 2H).<br>LC-MS (ESI): method 3<br>$t_R$ = 2.80 min; m/z (M + 1) = 463. |

-continued

| Example No | Structure | General procedure - Amount reagents | Amount product (yield) | Purification method | Data |
|---|---|---|---|---|---|
| 5 | 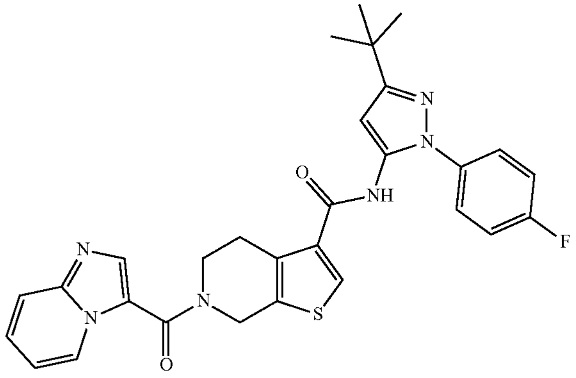 [SMILES: CC(C)(C)c1cc(NC(=O)c2csc3c2CCN(C(=O)c2cnc4ccccn24)C3)n(-c2ccc(F)cc2)n1] | General procedure G Amine: 0.067 g, 0.286 mmol) Intermediate 40: 100 mg (1.0 eq) | 4 mg (3%) | Prep HPLC | $^1$H NMR (400 MHz, MeOH-$d_4$) δ 8.96 (d, J = 6.9 Hz, 1H), 8.06 (s, 1H), 7.89 (s, 1H), 7.69 (d, J = 9.1 Hz, 1H), 7.53 (t, J = 6.5 Hz, 2H), 7.22 (t, J = 8.7 Hz, 2H), 7.11 (t, J = 7.1 Hz, 1H), 6.39 (s, 1H), 5.04 (s, 2H), 4.04 (t, J = 5.8 Hz, 2H), 3.02 (s, 2H), 1.36 (s, 9H). LC-MS (ESI): method 2 $t_R$ = 2.05 min; m/z (M + 1) = 543.2 |
| 6 | 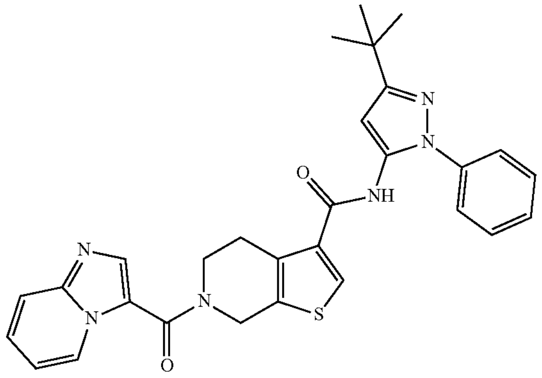 [SMILES: CC(C)(C)c1cc(NC(=O)c2csc3c2CCN(C(=O)c2cnc4ccccn24)C3)n(-c2ccccc2)n1] | General procedure G Amine: 61.6 mg, 0.286 mmol) Intermediate 40: 100 mg (1.0 eq) | 9.8 mg (7%) | Prep HPLC + washing with $NaHCO_3$ sol | $^1$H NMR (300 MHz, DMSO-$d_6$) δ 10.11 (s, 1H), 8.95 (dt, J = 7.0, 1.2 Hz, 1H), 8.11 (s, 1H), 8.06 (s, 1H), 7.77-7.69 (m, 1H), 7.57-7.43 (m, 5H), 7.36-7.29 (m, 1H), 7.10 (td, J = 6.9, 1.3 Hz, 1H), 6.37 (s, 1H), 5.00 (s, 2H), 3.94 (t, J = 5.6 Hz, 2H), 2.93 (s, 2H), 1.32 (s, 9H). LC-MS (ESI): method 3 $t_R$ = 2.44 min; m/z (M + 1) = 525.2 |

-continued

| Example No | Structure | General procedure - Amount reagents | Amount product (yield) | Purification method | Data |
|---|---|---|---|---|---|
| 7 | 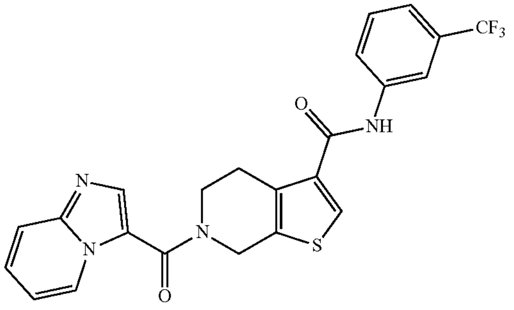 [SMILES: O=C(Nc1cccc(C(F)(F)F)c1)c1csc2c1CCN(C(=O)c1cnc3ccccn13)C2] | General procedure G<br>Amine: 0.036 ml, 0.286 mmol)<br>Intermediate 40: 100 mg (1.0 eq) | 23 mg (17%) | Prep HPLC | $^1$H NMR (300 MHz, MeOH-$d_4$) δ 8.98 (dt, J = 7.1, 1.2 Hz, 1H), 8.13 (s, 1H), 8.09 (s, 1H), 8.06 (s, 1H), 7.89 (d, J = 8.4 Hz, 1H), 7.69 (dt, J = 9.1, 1.2 Hz, 1H), 7.53 (ddt, J = 10.4, 4.1, 2.1 Hz, 2H), 7.41 (d, J = 7.8 Hz, 1H), 7.11 (td, J = 6.9, 1.2 Hz, 1H), 5.08 (s, 2H), 4.10 (t, J = 5.8 Hz, 2H), 3.18 (t, J = 6.0 Hz, 2H).<br>LC-MS (ESI): method 2<br>$t_R$ = 1.96 min; m/z (M + 1) = 471. |
| 8 | 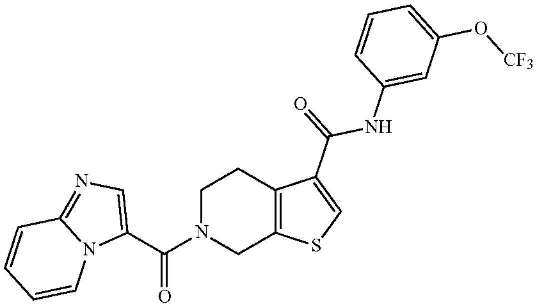 [SMILES: O=C(Nc1cccc(OC(F)(F)F)c1)c1csc2c1CCN(C(=O)c1cnc3ccccn13)C2] | General procedure G<br>Amine: (0.046 ml, 0.344 mmol)<br>Intermediate 40: 100 mg (1.0 eq) | 35 mg (25%) | Prep HPLC | $^1$H NMR (300 MHz, DMSO-$d_6$) δ 10.36 (s, 1H), 8.96 (dt, J = 7.0, 1.2 Hz, 1H), 8.18 (s, 1H), 8.13 (s, 1H), 7.89 (s, 1H), 7.78-7.65 (m, 2H), 7.53-7.40 (m, 2H), 7.15-7.02 (m, 2H), 5.02 (s, 2H), 3.98 (t, J = 5.8 Hz, 2H), 3.06 (s, 2H).<br>LC-MS (ESI): method 4<br>$t_R$ = 2.46 min; m/z (M + 1) = 487.0 |
| 9 | 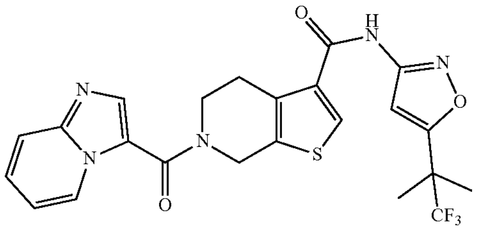 [SMILES: CC(C)(c1cc(NC(=O)c2csc3c2CCN(C(=O)c2cnc4ccccn24)C3)no1)C(F)(F)F] | General procedure G<br>Amine: (0.083 g, 0.429 mmol)<br>Intermediate 40: 100 mg (1.0 eq)<br>T3P: 2.0 eq. | 36 mg (25%) | Prep HPLC | $^1$H NMR (300 MHz, DMSO-$d_6$) δ 11.35 (s, 1H), 8.95 (dt, J = 7.0, 1.2 Hz, 1H), 8.36 (s, 1H), 8.13 (s, 1H), 7.73 (dt, J = 9.0, 1.2 Hz, 1H), 7.46 (ddd, J = 8.8, 6.8, 1.3 Hz, 1H), 7.14-7.05 (m, 2H), 5.02 (s, 2H), 3.97 (t, J = 5.7 Hz, 2H), 3.07 (s, 2H), 1.58 (s, 6H).<br>LC-MS (ESI): method 3<br>$t_R$ = 2.35 min; m/z (M + 1) = 504.1 |

-continued

| Example No | Structure | General procedure - Amount reagents | Amount product (yield) | Purification method | Data |
|---|---|---|---|---|---|
| 10 | 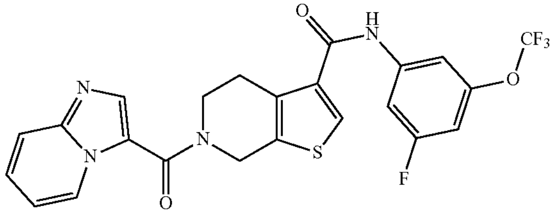 [SMILES: O=C(Nc1cc(F)cc(OC(F)(F)F)c1)c1csc2c1CCN(C(=O)c1cnc3ccccn13)C2] | General procedure G Amine (0.059 ml, 0.429 mmol) Intermediate 40:: 75 mg | 12.7 mg (12%) | Prep HPLC | $^{1}$H NMR (300 MHz, DMSO-$d_6$) δ 10.55 (s, 1H), 8.96 (d, J = 7.1 Hz, 1H), 8.20 (s, 1H), 8.13 (s, 1H), 7.78-7.64 (m, 3H), 7.46 (ddd, J = 8.8, 6.8, 1.3 Hz, 1H), 7.15-7.01 (m, 2H), 5.02 (s, 2H), 3.98 (t, J = 5.8 Hz, 2H), 3.07 (s, 2H) LC-MS (ESI): method 2 $t_R$ = 2.13 min; m/z (M + 1) = 505.0 |
| 11 | 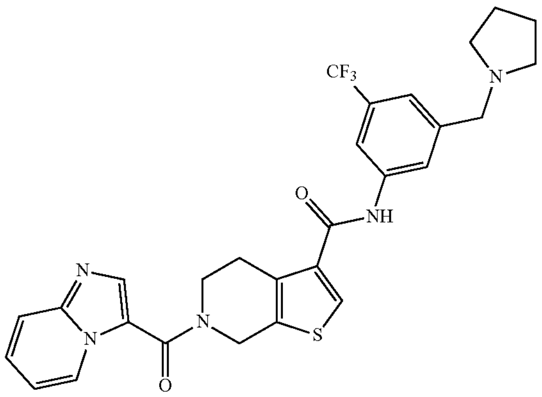 [SMILES: O=C(Nc1cc(CN2CCCC2)cc(C(F)(F)F)c1)c1csc2c1CCN(C(=O)c1cnc3ccccn13)C2] | General procedure G Amine (Intermediate 26) (118 mg, 0.420 mmol,) Intermediate 40: 140 mg, 0.420 mmol | 8 mg 4% | Reverse phase FCC | $^{1}$H NMR (400 MHz, DMSO-$d_6$) δ 10.36 (s, 1H), 8.96 (td, J = 1.0, 7.0 Hz, 1H), 8.22 (s, 1H), 8.14-8.11 (m, 2H), 7.95 (s, 1H), 7.73 (td, J = 1.0, 9.0 Hz, 1H), 7.47 (ddd, J = 1.5, 7.0, 9.0 Hz, 1H), 7.34 (s, 1H), 7.10 (dt, J = 1.0, 7.0 Hz, 1H), 5.03 (s, 2H), 3.99 (t, J = 6.0 Hz, 2H), 3.65 (s, 2H), 3.11-3.05 (m, 2H), 2.48-2.43 (m, 4H), 1.75-1.67 (m, 4H). LC-MS (ESI): method 5 $t_R$ = 2.85 min; m/z (M + 1) = 554.2 |

-continued

| Example No | Structure | General procedure - Amount reagents | Amount product (yield) | Purification method | Data |
|---|---|---|---|---|---|
| 12 | 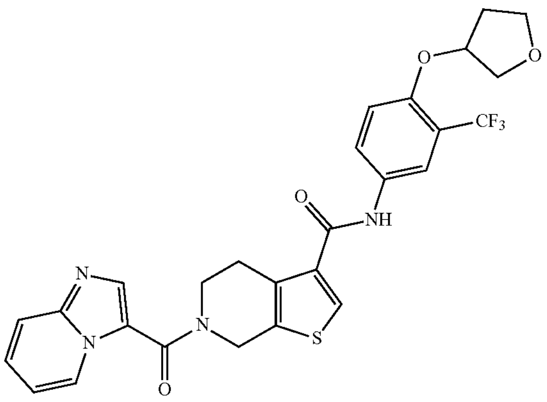 [SMILES: O=C(Nc1ccc(OC2CCOC2)c(C(F)(F)F)c1)c1csc2c1CCN(C(=O)c1cnc3ccccn13)C2] | General procedure G Amine (Intermediate 2) (38 mg, 0.153 mmol,) Intermediate 40: 51 mg (1.0 eq) | 31 mg 36% | Filtration after water quench | $^1$H NMR (400 MHz, $CDC1_3$) δ 9.04 (d, J = 7.0 Hz, 1H), 7.98 (s, 1H), 7.86 (dd, J = 2.6, 8.9 Hz, 1H), 7.75 (s, 1H), 7.72-7.68 (m, 2H), 7.66 (s, 1H), 7.40-7.35 (m, 1H), 6.99-6.92 (m, 2H), 5.02 (s, 3H), 4.12-4.06 (m, 3H), 4.00-3.93 (m, 3H), 3.23 (t,, J = 5.7 Hz, 2H), 2.23-2.17 (m, 2H). LC-MS (ESI): method 6 $t_R$ = 4.39 min; m/z (M + 1) = 557.3 |
| 13 | 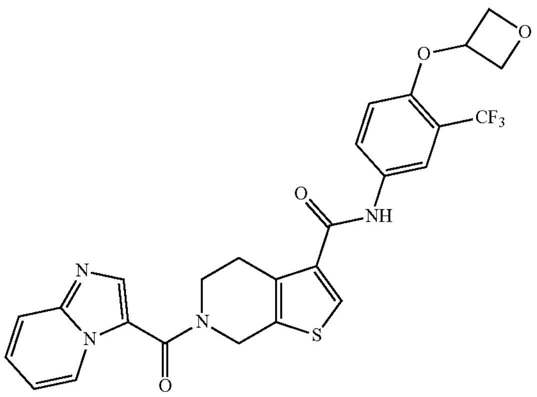 [SMILES: O=C(Nc1ccc(OC2COC2)c(C(F)(F)F)c1)c1csc2c1CCN(C(=O)c1cnc3ccccn13)C2] | General procedure G Amine (36 mg, 0.153 mmol, Intermediate 3) Intermediate 40: 50 mg (1.0 eq) Intermediate 40 was used as acid deblocking the salt via acidic washing | 14 mg 16% | Prep HPLC | $^1$H NMR (400 MHz, DMSO-$d_6$) δ 10.26 (s, 1H), 8.97 (d, J = 6.9 Hz, 1H), 8.16-8.12 (m, 3H), 7.90 (dd, J = 2.6, 9.0 Hz, 1H), 7.75 (d, J = 9.0 Hz, 1H), 7.50-7.45 (m, 1H), 7.13-7.09 (m, 1H), 6.92 (d, J = 9.0 Hz, 1H), 5.43-5.39 (m, 1H), 5.03-4.94 (m, 4H), 4.56 (dd, J = 5.0, 7.7 Hz, 2H), 3.99 (t, J = 5.7 Hz, 2H), 3.08-3.07 (m, 2H) LC-MS (ESI): method 7 $t_R$ = 3.74 min; m/z (M + 1) = 543.3 |

-continued

| Example No | Structure | General procedure - Amount reagents | Amount product (yield) | Purification method | Data |
|---|---|---|---|---|---|
| 14 | 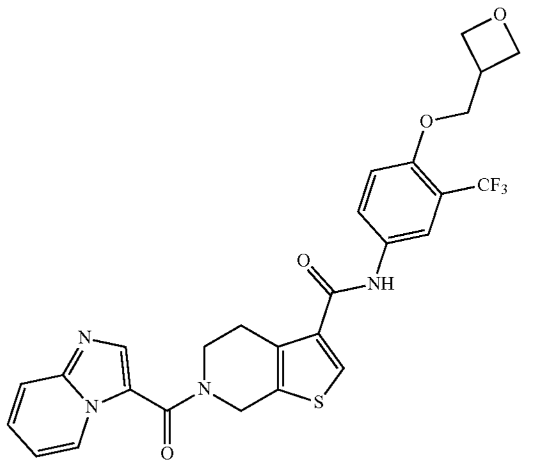 [SMILES: O=C(Nc1ccc(OCC2COC2)c(C(F)(F)F)c1)c1csc2c1CCN(C(=O)c1cnc3ccccn13)C2] | General procedure G Amine (Intermediate 4) (43 mg, 0.153 mmol,) Intermediate 40: 50 mg (1.0 eq) Intermediate 40 was used as acid deblocking the salt via acidic washing | 12 mg 13% | Prep HPLC | $^1$H NMR (400 MHz, DMSO-$d_6$) δ 10.24 (s, 1H), 8.98 (d, J = 6.9 Hz, 1H), 8.16 (d, J = 7.0 Hz, 2H), 8.08 (d, J = 2.6 Hz, 1H), 7.96 (dd, J = 2.5, 9.0 Hz, 1H), 7.75 (d, J = 9.0 Hz, 1H), 7.50-7.45 (m, 1H), 7.33 (d, J = 9.2 Hz, 1H), 7.13-7.09 (m, 1H), 5.05 (s, 2H), 4.71 (dd, J = 6.0, 8.0 Hz, 2H), 4.47 (t, J = 6.1Hz, 2H), 4.32 (d, J = 6.3 Hz, 2H), 3.99 (t, J = 5.6 Hz, 2H), 3.46-3.39 (m, 1H), 3.08 (s, 2H) LC-MS (ESI): method 6 $t_R$ = 4.27 min; m/z (M + 1) = 557.4 |
| 15 | 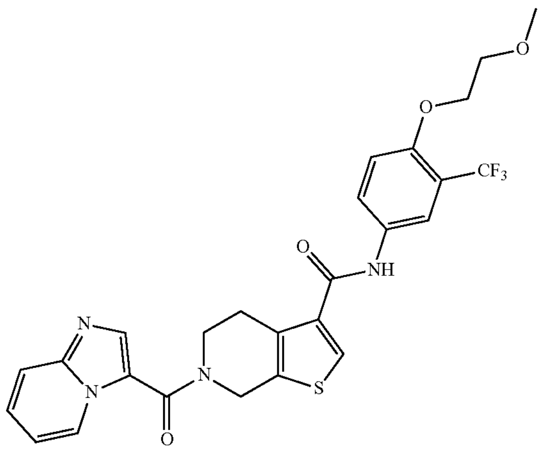 [SMILES: COCCOc1ccc(NC(=O)c2csc3c2CCN(C(=O)c2cnc4ccccn24)C3)cc1C(F)(F)F] | General procedure G Amine (Intermediate 5) (36 mg, 0.153 mmol,) Intermediate 40: 50 mg (1.0 eq) Intermediate 40 was used as acid deblocking the salt via acidic washing | 23 mg 27% | Prep HPLC | $^1$H NMR (400 MHz, $CDCl_3$) δ 9.04 (d, J = 7.0 Hz, 1H), 7.98 (s, 1H), 7.81 (dd, J = 2.6, 8.9 Hz, 1H), 7.73-7.70 (m, 2H), 7.65 (d, J = 3.1 Hz, 2H), 7.37 (t, J = 7.9, 7.9 Hz, 1H), 7.05 (d, J = 8.9 Hz, 1H), 6.97 (t, J = 6.7 Hz, 1H), 5.04 (s, 2H), 4.21 (t, J = 4.8 Hz, 2H), 4.10 (t, J = 5.8 Hz, 2H), 3.79 (t, J = 4.8 Hz, 2H), 3.47 (s, 3H), 3.23 (t, J = 5.6 Hz, 2H). LC-MS (ESI): method 6 $t_R$ = 4.51 min; m/z (M + 1) = 545. 4 |

-continued

| Example No | Structure | General procedure - Amount reagents | Amount product (yield) | Purification method | Data |
|---|---|---|---|---|---|
| 16 | 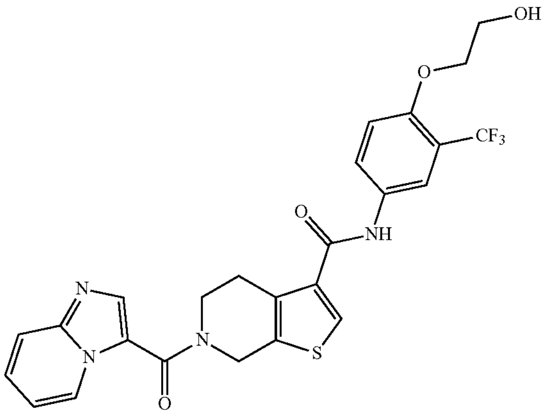 [SMILES: O=C(Nc1ccc(OCCO)c(C(F)(F)F)c1)c1csc2c1CCN(C(=O)c1cnc3ccccn13)C2] | General procedure G Amine (Intermediate 9) (34 mg, 0.153 mmol,) Intermediate 40: 50 mg (1.0 eq) Intermediate 40 was used as acid deblocking the salt via acidic washing | 27 mg 33% | Prep HPLC | $^1$H NMR (400 MHz, DMSO-$d_6$) δ 10.21 (s, 1H), 8.97 (d, J = 7.0 Hz, 1H), 8.15 (d, J = 3.0 Hz, 2H), 8.07 (d, J = 2.6 Hz, 1H), 7.93 (dd, J = 2.6, 9.0 Hz, 1H), 7.75 (d, J = 9.0 Hz, 1H), 7.50-7.45 (m, 1H), 7.30 (d, J = 9.0 Hz, 1H), 7.13-7.09 (m, 1H), 5.03 (s, 2H), 4.86 (t, , J = 5.5 Hz, 1H), 4.12 (t, J = 5.0 Hz, 2H), 3.99 (t, J = 5.0 Hz, 2H), 3.74 (q, J = 5.2 Hz, 2H), 3.08 (s, 2H). LC-MS (ESI): method 7 $t_R$ = 3.26 min; m/z (M + 1) = 531.3 |
| 17 | 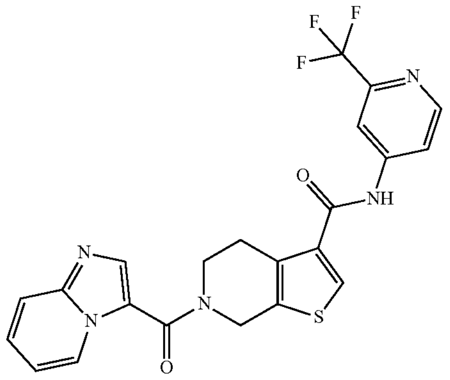 [SMILES: O=C(Nc1ccnc(C(F)(F)F)c1)c1csc2c1CCN(C(=O)c1cnc3ccccn13)C2] | General procedure H Amine (25 mg, 0.153 mmol) Intermediate 40: 50 mg (1.0 eq) Intermediate 40 was used as acid deblocking the salt via acidic washing | 10 mg 14% | Prep HPLC | $^1$H NMR (400 MHz, DMSO-$d_6$) δ 10.81 (s, 1H), 8.97 (td, J = 1.0, 7.0 Hz, 1H), 8.67 (d, J = 5.5 Hz, 1H), 8.31 (s, 1H), 8.28 (d, J = 2.0 Hz, 1H), 8.15 (s, 1H), 8.00 (dd, J = 2.0, 5.5 Hz, 1H), 7.75 (td, J = 1.0, 9.0 Hz, 1H), 7.48 (ddd, J = 1.5, 7.0, 9.0 Hz, 1H), 7.11 (dt, J = 1.5, 7.0 Hz, 1H), 5.04 (s, 2H), 4.00 (t, J = 5.5 Hz, 2H), 3.10 (t, J = 5.5 Hz, 2H) LC-MS (ESI): method 6 $t_R$ = 4.12 min; m/z (M + 1) = 472.2 |

-continued

| Example No | Structure | General procedure - Amount reagents | Amount product (yield) | Purification method | Data |
|---|---|---|---|---|---|
| 18 | 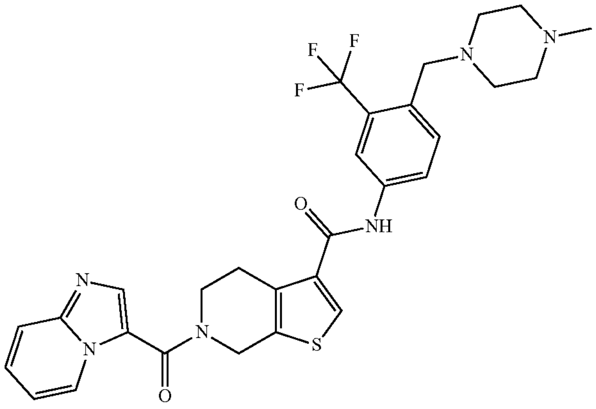 [SMILES: CN1CCN(Cc2ccc(NC(=O)c3csc4c3CCN(C(=O)c3cnc5ccccn35)C4)cc2C(F)(F)F)CC1] | General procedure H Amine (63 mg, 0.153 mmol) Intermediate 40: 50 mg (1.0 eq) Intermediate 40 was used as acid deblocking the salt via acidic washing | 35 mg 39% | Prep HPLC | $^1$H NMR (400 MHz, DMSO-$d_6$) δ 10.37 (s, 1H), 8.98 (td, J = 1.0, 7.0 Hz, 1H), 8.20 (s, 1H), 8.18 (d, J = 2.0 Hz, 1H), 8.15 (s, 1H), 7.98 (dd, J = 2.0, 8.5 Hz, 1H), 7.75 (td, J = 1.0, 9.0 Hz, 1H), 7.70 (d, J = 8.5 Hz, 1H), 7.50-7.45 (m, 1H), 7.11 (dt, J = 1.5, 7.0 Hz, 1H), 5.05 (s, 2H), 4.00 (t, J = 5.5 Hz, 2H), 3.57 (s, 2H), 3.09 (t, J = 5.5 Hz, 2H), 2.45-2.27 (m, 8H), 2.17 (s, 3H) LC-MS (ESI): method 6 $t_R$ = 4.27 min; m/z (M + 1) = 583.3 |
| 19 | 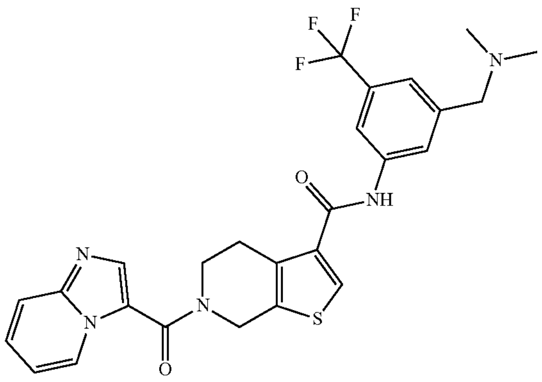 [SMILES: CN(C)Cc1cc(NC(=O)c2csc3c2CCN(C(=O)c2cnc4ccccn24)C3)cc(C(F)(F)F)c1] | General procedure H Amine (intermediate 17) (32 mg, 0.153 mmol,) Intermediate 40: 50 mg (1.0 eq) Intermediate 40 was used as acid deblocking the salt via acidic washing | 25 mg 33% | Prep HPLC | $^1$H NMR (400 MHz, DMSO-$d_6$) δ 10.38 (s, 1H), 8.98 (td, J = 1.0, 7.0 Hz, 1H), 8.24 (s, 1H), 8.15 (s, 1H), 8.14 (s, 1H), 7.99 (s, 1H), 7.75 (td, J = 1.0, 9.0 Hz, 1H), 7.50-7.46 (m, 1H), 7.35 (s, 1H), 7.11 (dt, J = 1.0, 7.0 Hz, 1H), 5.05 (s, 2H), 4.00 (t, J = 5.5 Hz, 2H), 3.48 (s, 2H), 3.13-3.07 (m, 2H), 2.20 (s, 6H) LC-MS (ESI): method 7 $t_R$ = 2.76 min; m/z (M + 1) = 528.2 |

-continued

| Example No | Structure | General procedure - Amount reagents | Amount product (yield) | Purification method | Data |
|---|---|---|---|---|---|
| 20 | 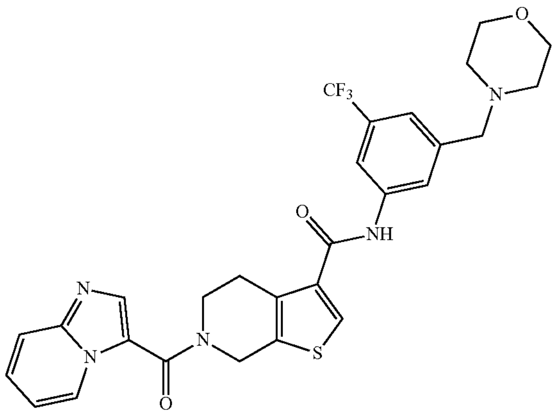 [SMILES: O=C(Nc1cc(CN2CCOCC2)cc(C(F)(F)F)c1)c1csc2c1CCN(C(=O)c1cnc3ccccn13)C2] | General procedure H Amine (Intermediate 12) (38 mg, 0.145 mmol,) Intermediate 40: 50 mg (1.0 eq) Intermediate 40 was used as acid deblocking the salt via acidic washing | 38 mg 47% | Prep HPLC | $^1$H NMR (400 MHz, DMSO-$d_6$) δ 10.40 (s, 1H), 8.98 (d, J = 7.0 Hz, 1H), 8.23 (s, 1H), 8.15 (s, 2H), 7.98 (s, 1H), 7.75 (td, J = 1.0, 9.0 Hz, 1H), 7.50-7.46 (m, 1H), 7.37 (s, 1H), 7.12 (dt, J = 1.5, 7.0 Hz, 1H), 5.04 (s, 2H), 4.00 (t, J = 6.0 Hz, 2H), 3.61 (t, J = 4.5 Hz, 4H), 3.56 (s, 2H), 3.11-3.08 (m, 2H), 2.43-2.37 (m, 4H) LC-MS (ESI): method 7 $t_R$ = 2.80 min; m/z (M + 1) = 570.3 |
| 21 | 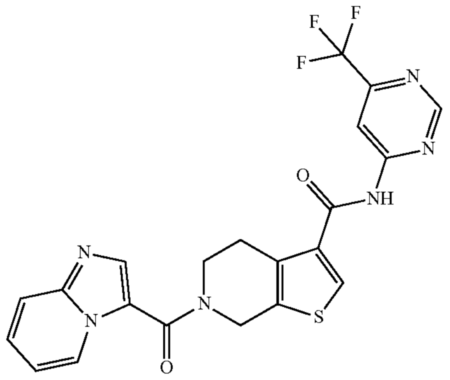 [SMILES: O=C(Nc1cc(C(F)(F)F)ncn1)c1csc2c1CCN(C(=O)c1cnc3ccccn13)C2] | General procedure H Amine (25 mg, 0.153 mmol) Intermediate 40: 50 mg (1.0 eq) Intermediate 40 was used as acid deblocking the salt via acidic washing | 2.2 mg 3% | Prep HPLC | $^1$H NMR (400 MHz, DMSO-$d_6$) δ 11.67 (s, 1H), 9.17 (s, 1H), 8.97 (td, J = 1.0, 7.0 Hz, 1H), 8.57 (d, J = 1.0 Hz, 1H), 8.54 (s, 1H), 8.15 (s, 1H), 7.75 (td, J = 1.0, 9.0 Hz, 1H), 7.48 (ddd, J = 1.5, 7.0, 9.0 Hz, 1H), 7.11 (dt, J = 1.0, 7.0 Hz, 1H), 5.05 (s, 2H), 4.00 (t, J = 6.0 Hz, 2H), 3.12 (t, J = 5.5 Hz, 2H) LC-MS (ESI): method 7 $t_R$ = 3.52 min; m/z (M + 1) = 473.4 |

-continued

| Example No | Structure | General procedure - Amount reagents | Amount product (yield) | Purification method | Data |
|---|---|---|---|---|---|
| 22 | 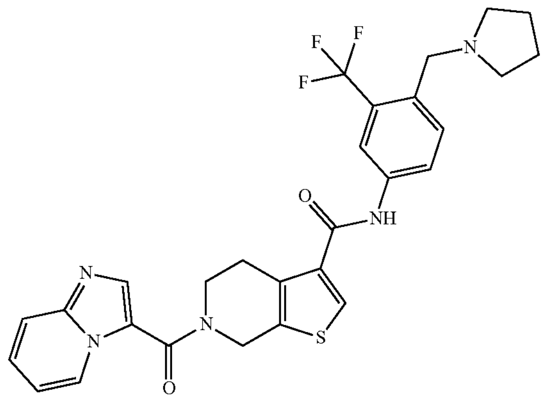 [SMILES: O=C(Nc1ccc(CN2CCCC2)c(C(F)(F)F)c1)c1csc2c1CCN(C(=O)c1cnc3ccccn13)C2] | General procedure H Amine (Intermediate 24) (61 mg, 0.217 mmol,) Intermediate 40: Intermediate 40 was used as acid deblocking the salt via acidic washing | 17 mg 14% | Prep HPLC | $^1$H NMR (400 MHz, DMSO-$d_6$) δ 10.36 (s, 1H), 8.98 (d, J = 7.0 Hz, 1H), 8.20 (s, 1H), 8.17 (d, J = 2.0 Hz, 1H), 8.15 (s, 1H), 7.98 (dd, J = 2.0, 8.5 Hz, 1H), 7.77-7.71 (m, 2H), 7.50-7.45 (m, 1H), 7.11 (dt, J = 1.0, 7.0 Hz, 1H), 5.04 (s, 2H), 4.02-3.97 (m, 2H), 3.71 (s, 2H), 3.10-3.06 (m, 2H), 2.50-2.45 (m, 4H), 1.76-1.71 (m, 4H) LC-MS (ESI): method 7 $t_R$ = 2.70 min; m/z (M + 1) = 554.3 |
| 23 | 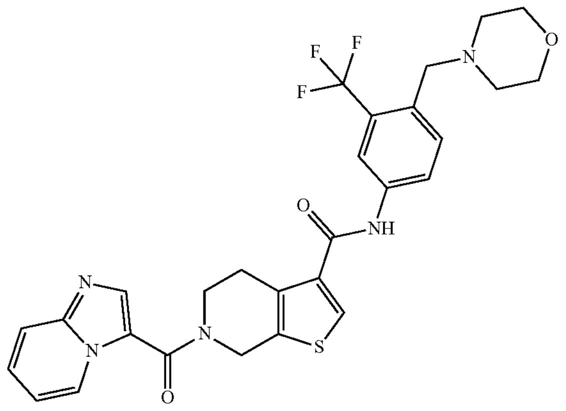 [SMILES: O=C(Nc1ccc(CN2CCOCC2)c(C(F)(F)F)c1)c1csc2c1CCN(C(=O)c1cnc3ccccn13)C2] | General procedure H Amine (Intermediate 25) (64 mg, 0.217 mmol,) Intermediate 40: 70 mg (1.0 eq) Intermediate 40 was used as acid deblocking the salt via acidic washing | 22 mg 18% | Prep HPLC | $^1$H NMR (400 MHz, DMSO-$d_6$) δ 10.38 (s, 1H), 8.98 (td, J = 1.0, 7.0 Hz, 1H), 8.20-8.18 (m, 2H), 8.15 (s, 1H), 7.99 (dd, J = 2.0, 8.5 Hz, 1H), 7.76-7.71 (m, 2H), 7.50-7.46 (m, 1H), 7.11 (dt, J = 1.0, 7.0 Hz, 1H), 5.03 (s, 2H), 4.00 (t, J = 5.5 Hz, 2H), 3.63-3.59 (m, 6H), 3.11-3.07 (m, 2H), 2.42-2.37 (m, 4H). LC-MS (ESI): method 7 $t_R$ = 2.67 min; m/z (M + 1) = 570.3 |

-continued

| Example No | Structure | General procedure - Amount reagents | Amount product (yield) | Purification method | Data |
|---|---|---|---|---|---|
| 24 | 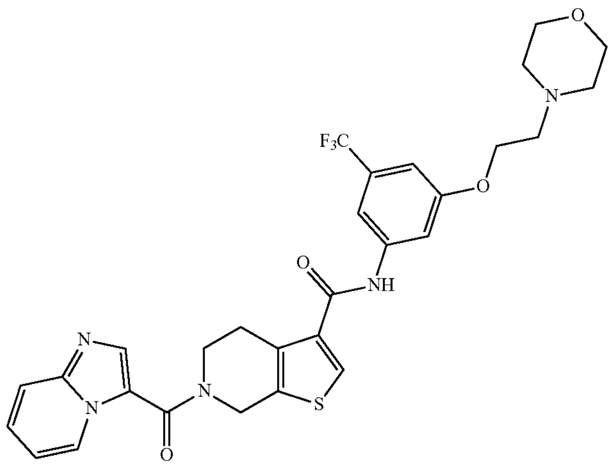 [SMILES: O=C(Nc1cc(OCCN2CCOCC2)cc(C(F)(F)F)c1)c1csc2c1CCN(C(=O)c1cnc3ccccn13)C2] | General procedure H Amine (Intermediate 16) (44 mg, 0.153 mmol,) Intermediate 40: 50 mg (1.0 eq) Intermediate 40 was used as acid deblocking the salt via acidic washing | 10 mg 10% | Prep HPLC | $^1$H NMR (400 MHz, DMSO-$d_6$) δ 10.35 (s, 1H), 8.98 (d, J = 7.0 Hz, 1H), 8.21 (s, 1H), 8.15 (s, 1H), 7.78-7.74 (m, 2H), 7.68 (s, 1H), 7.51-7.46 (m, 1H), 7.14-7.09 (m, 1H), 7.01 (s, 1H), 5.04-5.02 (m, 2H), 4.18 (t, J = 5.7 Hz, 2H), 4.00 (t, J = 5.6 Hz, 2H), 3.60 (t, J = 4.6 Hz, 4H), 3.08 (s, 2H), 2.73 (t, J = 5.6 Hz, 2H), 2.53-2.49 (m, 4H). LC-MS (ESI): method 7 $t_R$ = 2.28 min; m/z (M + 1) = 600 |
| 25 | 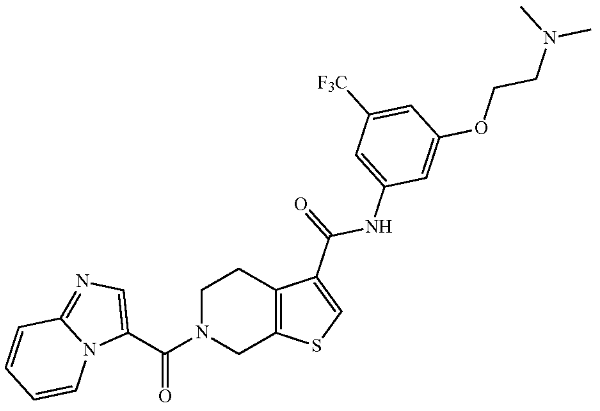 [SMILES: CN(C)CCOc1cc(NC(=O)c2csc3c2CCN(C(=O)c2cnc4ccccn24)C3)cc(C(F)(F)F)c1] | General procedure H Amine (Intermediate 17) (50 mg, 0.200 mmol,) Intermediate 40: 65 mg (1.0 eq) Intermediate 40 was used as acid deblocking the salt via acidic washing | 23 mg 20% | Prep HPLC | $^1$H NMR (400 MHz, DMSO-$d_6$) δ 10.35 (s, 1H), 8.98 (d, J = 7.0 Hz, 1H), 8.21-8.15 (m, 2H), 7.78-7.74 (m, 2H), 7.67 (s, 1H), 7.51-7.45 (m, 1H), 7.14-7.09 (m, 1H), 6.99 (s, 1H), 5.04 (s, 2H), 4.16-4.11 (m, 2H), 4.00 (t, J = 5.8 Hz, 2H), 3.09-3.07 (m, 2H), 2.69-2.64 (m, 2H), 2.24 (s, 6H). LC-MS (ESI): method 7 $t_R$ = 2.83 min; m/z (M + 1) = 558 |

-continued

| Example No | Structure | General procedure - Amount reagents | Amount product (yield) | Purification method | Data |
|---|---|---|---|---|---|
| 26 | 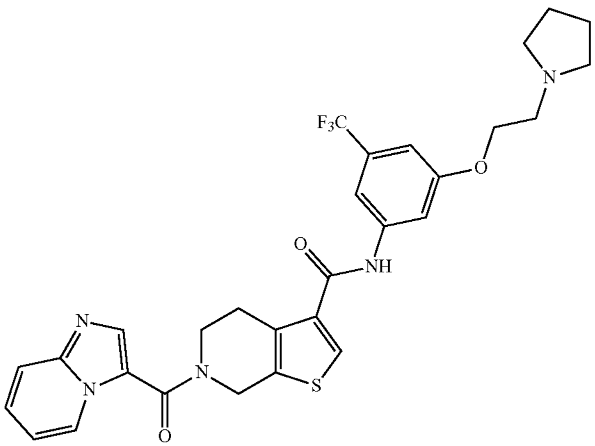 [SMILES: O=C(Nc1cc(OCCN2CCCC2)cc(C(F)(F)F)c1)c1csc2c1CCN(C(=O)c1cnc3ccccn13)C2] | General procedure H Amine (Intermediate 18) (55 mg, 0.200 mmol,) Intermediate 40: 65 mg (1.0 eq) Intermediate 40 was used as acid deblocking the salt via acidic washing | 48 mg 39% | Prep HPLC | $^1$H NMR (400 MHz, DMSO-$d_6$) δ 10.35 (s, 1H), 8.98 (d, J = 6.9 Hz, 1H), 8.21 (s, 1H), 8.15-8.15 (m, 1H), 7.78-7.74 (m, 2H), 7.67 (s, 1H), 7.50-7.46 (m, 1H), 7.14-7.09 (m, 1H), 7.00 (s, 1H), 5.04-5.02 (m, 2H), 4.16 (t, J = 5.8 Hz, 2H), 4.03-3.98 (m, 2H), 3.08 (s, 2H), 2.83 (t, J = 5.8 Hz, 2H), 2.57-2.51 (m, 4H), 1.73-1.68 (m, 4H). LC-MS (ESI): method 7 $t_R$ = 2.95 min; m/z (M + 1) = 584 |
| 27 | 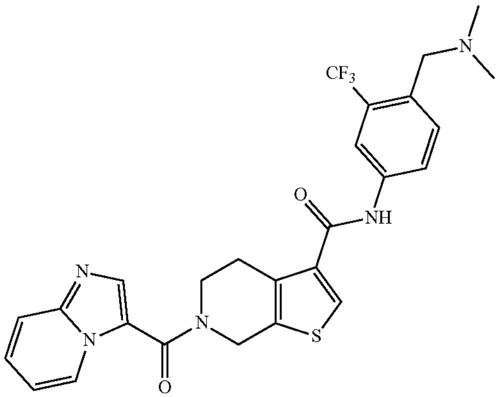 [SMILES: CN(C)Cc1ccc(NC(=O)c2csc3c2CCN(C(=O)c2cnc4ccccn24)C3)cc1C(F)(F)F] | General procedure H Amine (Intermediate 28) (55 mg, 0.200 mmol,) Intermediate 40: 65 mg (1.0 eq) Intermediate 40 was used as acid deblocking the salt via acidic washing DIPEA replaces TEA | 1.97 mg 3% | Prep HPLC | $^1$H NMR (400 MHz, DMSO-$d_6$) δ 10.37 (s, 1H), 8.99-8.96 (m, 1H), 8.21 (s, 1H), 8.17 (d, J = 2.5 Hz, 1H), 8.15 (s, 1H), 8.00 (dd, J = 2.0, 8.7 Hz, 1H), 7.75 (td, J = 1.1, 9.0 Hz, 1H), 7.71 (d, J = 8.8 Hz, 1H), 7.50-7.45 (m, 1H), 7.11 (dt, J = 1.2, 6.9 Hz, 1H), 5.04 (s, 2H), 4.02-3.98 (m, 2H), 3.50 (s, 2H), 3.11-3.08 (m, 2H), 2.19 (s, 6H) LC-MS (ESI): method 7 $t_R$ = 2.54 min; m/z (M + 1) = 528 |

-continued

| Example No | Structure | General procedure - Amount reagents | Amount product (yield) | Purification method | Data |
|---|---|---|---|---|---|
| 28 | 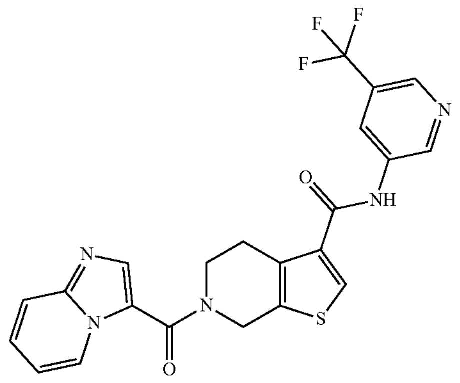 [SMILES: O=C(Nc1cncc(C(F)(F)F)c1)c1csc2c1CCN(C(=O)c1cnc3ccccn13)C2] | General procedure H Amine (16 mg, 0.096 mmol) Intermediate 40: 31 mg (1.0 eq) Intermediate 40 was used as acid deblocking the salt via acidic washing DIPEA replaces TEA | 1.8 mg 4% | Prep HPLC | $^1$H NMR (400 MHz, DMSO-$d_6$) δ 10.68 (s, 1H), 9.15 (d, J = 2.4 Hz, 1H), 8.98 (td, J = 1.1, 6.9 Hz, 1H), 8.72-8.70 (m, 1H), 8.63-8.60 (m, 1H), 8.28 (s, 1H), 8.15 (s, 1H), 7.75 (td, J = 1.1, 9.0 Hz, 1H), 7.51-7.46 (m, 1H), 7.12 (dt, J = 1.2, 6.9 Hz, 1H), 5.05 (s, 2H), 4.03-3.98 (m, 2H), 3.13-3.07 (m, 2H). LC-MS (ESI): method 7 $t_R$ = 3.42 min; m/z (M + 1) = 472 |
| 29 | 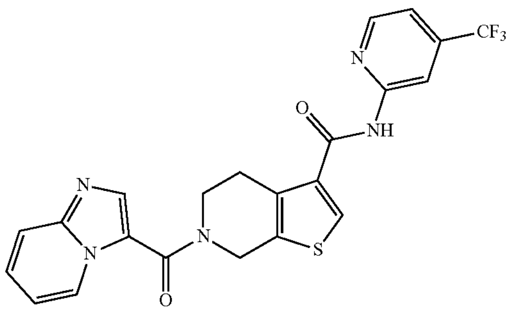 | General procedure H Amine (26 mg, 0.160 mmol) Intermediate 40: 52 mg (1.0 eq) Intermediate 40 was used as acid deblocking the salt via acidic washing Py replaces solvent and TEA | 10.6 mg 14% | Prep HPLC | $^1$H NMR (400 MHz, DMSO-$d_6$) δ 11.13 (s, 1H), 8.98 (td, J = 1.1, 7.0 Hz, 1H), 8.68 (d, J = 5.2 Hz, 1H), 8.51 (t, J = 0.8 Hz, 1H), 8.45 (s, 1H), 8.15 (s, 1H), 7.75 (td, J = 1.1, 9.1 Hz, 1H), 7.55-7.52 (m, 1H), 7.48 (ddd, J = 1.3, 6.7, 9.1 Hz, 1H), 7.11 (dt, J = 1.2, 6.9 Hz, 1H), 5.05 (s, 2H), 4.01 (t, J = 5.7 Hz, 2H), 3.15-3.09 (m, 2H). LC-MS (ESI): method 6 $t_R$ = 4.41 min; m/z (M + 1) = 472.3 |
| 30 | 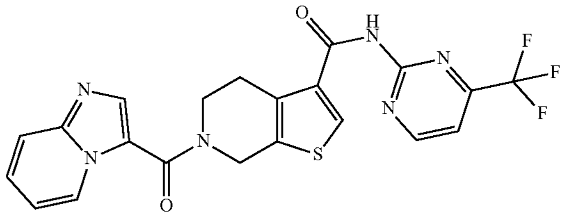 [SMILES: O=C(Nc1nccc(C(F)(F)F)n1)c1csc2c1CCN(C(=O)c1cnc3ccccn13)C2] | General procedure H Amine (26 mg, 0.160 mmol) Intermediate 40: 52 mg (1.0 eq) Intermediate 40 was used as acid deblocking the salt via acidic washing DIPEA replaces TEA | 9 mg 12% | Prep HPLC | $^1$H NMR (400 MHz, DMSO-$d_6$) δ 11.32 (s, 1H), 9.09 (d, J = 4.9 Hz, 1H), 9.00 (d, J = 6.9 Hz, 1H), 8.38 (s, 1H), 8.28-8.24 (m, 1H), 7.83-7.79 (m, 1H), 7.72 (d, J = 4.9 Hz, 1H), 7.60 (t, J = 7.9 Hz, 1H), 7.21 (t, J = 7.1 Hz, 1H), 5.04-5.04 (m, 2H), 4.02-3.97 (m, 2H), 3.10-3.08 (m, 2H) LC-MS (ESI): method 7 $t_R$ = 3.14 min; m/z (M + 1) = 473 |

-continued

| Example No | Structure | General procedure - Amount reagents | Amount product (yield) | Purification method | Data |
|---|---|---|---|---|---|
| 31 | 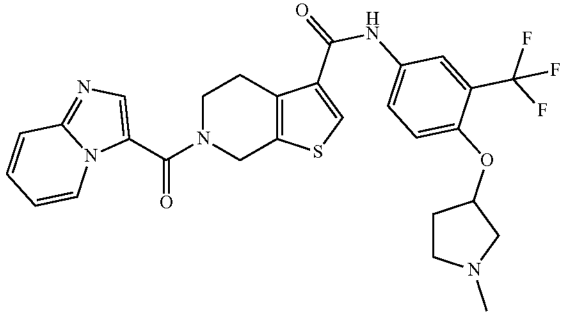 [SMILES: CN1CCC(Oc2ccc(NC(=O)c3csc4c3CCN(C(=O)c3cnc5ccccn35)C4)cc2C(F)(F)F)C1] | General procedure G Amine (Intermediate 6) (45 mg, 0.153 mmol) Intermediate 40: 50 mg (1.0 eq) Intermediate 40 was used as acid deblocking the salt via acidic washing | 7 mg 8% | Prep HPLC | $^1$H NMR (400 MHz, DMSO-$d_6$) δ 10.21 (s, 1H), 8.97 (d, J = 6.9 Hz, 1H), 8.15 (s, 2H), 8.07 (d, J = 2.5 Hz, 1H), 7.91 (dd, J = 2.6, 9.0 Hz, 1H), 7.75 (d, J = 9.0 Hz, 1H), 7.50-7.45 (m, 1H), 7.20 (d, J = 9.2 Hz, 1H), 7.13-7.09 (m, 1H), 5.05-4.96 (m, 3H), 3.99 (t, J = 5.6 Hz, 2H), 3.08 (m, 2H), 2.90 (dd, J = 6.2, 10.5 Hz, 1H), 2.70-2.54 (m, 2H), 2.46-2.29 (m, 2H), 2.28 (s, 3H), 1.83-1.75 (m, 1H) LC-MS (ESI): method 6 $t_R$ = 4.21 min; m/z (M + 1) = 570 |
| 32 | 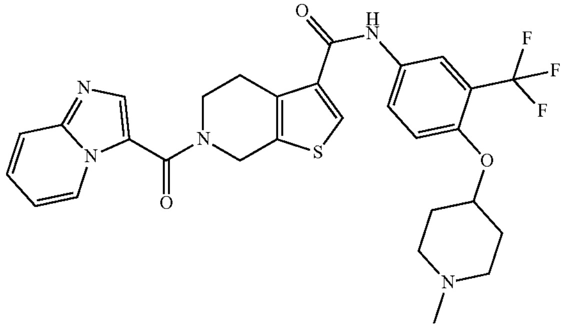 [SMILES: CN1CCC(Oc2ccc(NC(=O)c3csc4c3CCN(C(=O)c3cnc5ccccn35)C4)cc2C(F)(F)F)CC1] | General procedure G Amine (Intermediate 7) (47 mg, 0.153 mmol) Intermediate 40: 50 mg (1.0 eq) Intermediate 40 was used as acid deblocking the salt via acidic washing | 19 mg 20% | Prep HPLC | $^1$H NMR (400 MHz, DMSO-$d_6$) δ 10.20 (s, 1H), 8.97 (d, J = 7.0 Hz, 1H), 8.15 (s, 2H), 8.07 (d, J = 2.6 Hz, 1H), 7.91 (dd, J = 2.5, 9.0 Hz, 1H), 7.75 (d, J = 9.0 Hz, 1H), 7.50-7.45 (m, 1H), 7.32 (d, J = 9.3 Hz, 1H), 7.11 (dd, J = 7.0, 7.0 Hz, 1H), 5.03 (s, 2H), 4.60-4.56 (m, 1H), 3.99 (t, J = 5.6 Hz, 2H), 3.29-3.29 (m, 2H), 3.09-3.08 (m, 2H), 2.24 (m, 2H), 2.18 (s, 3H), 1.95-1.90 (m, 2H), 1.74-1.65 (m, 2H). LC-MS (ESI): method 7 $t_R$ = 2.79 min; m/z (M + 1) = 584 |
| 33 | 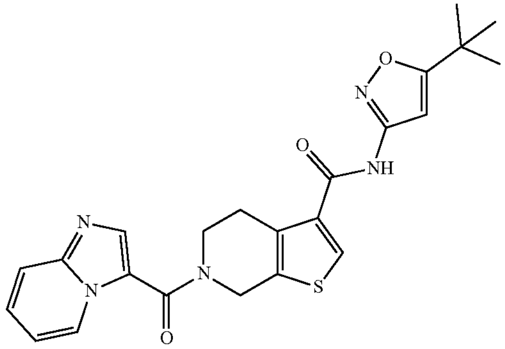 [SMILES: CC(C)(C)c1cc(NC(=O)c2csc3c2CCN(C(=O)c2cnc4ccccn24)C3)no1] | General procedure I Amine (21 mg, 0.150 mmol) Intermediate 40: 49 mg (1.0 eq) Intermediate 40 was used as acid deblocking the salt via acidic washing | 3.9 mg 7% | Prep HPLC | $^1$H NMR (400 MHz, DMSO-$d_6$) δ 11.18 (s, 1H), 8.99-8.95 (m, 1H), 8.34 (s, 1H), 8.14 (s, 1H), 7.76-7.73 (m, 1H), 7.50-7.45 (m, 1H), 7.11 (dt, J = 1.2, 6.9 Hz, 1H), 6.72 (s, 1H), 5.04 (s, 2H), 4.01-3.96 (m, 2H), 3.11-3.05 (m, 2H), 1.33 (s, 9H) LC-MS (ESI): method 7 $t_R$ = 3.75 min; m/z (M + 1) = 450.3 |

-continued

| Example No | Structure | General procedure - Amount reagents | Amount product (yield) | Purification method | Data |
|---|---|---|---|---|---|
| 34 | 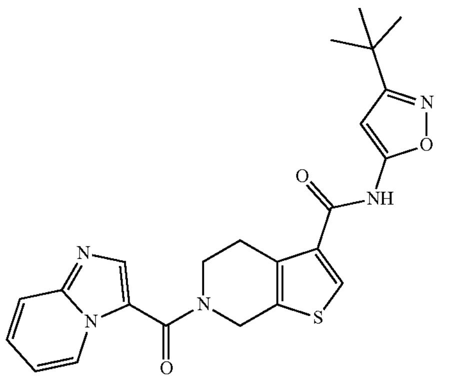 [SMILES: CC(C)(C)c1cc(NC(=O)c2csc3c2CCN(C(=O)c2cnc4ccccn24)C3)on1] | General procedure I Amine (16 mg, 0.117 mmol) Intermediate 40:38 mg (1.0 eq) Intermediate 40 was used as acid deblocking the salt via acidic washing | 4.1 mg 9% | Prep HPLC | $^1$H NMR (400 MHz, DMSO-$d_6$) δ 11.78 (s, 1H), 8.97 (td, J=1.1, 6.9 Hz, 1H), 8.34 (s, 1H), 8.14 (s, 1H), 7.76-7.73 (m, 1H), 7.50-7.45 (m, 1H), 7.11 (dt, J = 1.2, 6.9 Hz, 1H), 6.37 (s, 1H), 5.03 (s, 2H), 4.02-3.97 (m, 2H), 3.12-3.07 (m, 2H), 1.29 (s, 9H) LC-MS (ESI): method 7 $t_R$ = 3.65 min; m/z (M + 1) = 450.3 |
| 35 | 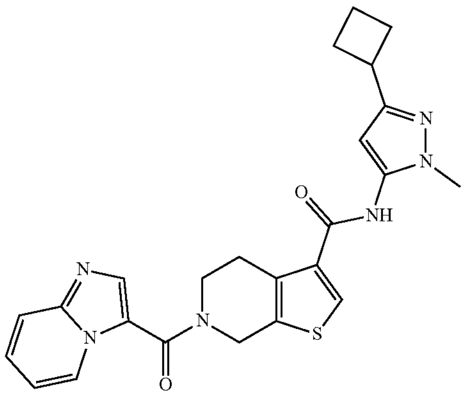 [SMILES: Cn1nc(C2CCC2)cc1NC(=O)c1csc2c1CCN(C(=O)c1cnc3ccccn13)C2] | General procedure I Amine (19 mg, 0.124 mmol) Intermediate 40: 40 mg (1.0 eq) Intermediate 40 was used as acid deblocking the salt via acidic washing | 4.1 mg 9% | Prep HPLC | $^1$H NMR (400 MHz, DMSO-$d_6$) δ 10.07 (s, 1H), 8.97 (td, J = 1.1, 7.0 Hz, 1H), 8.20 (s, 1H), 8.14 (s, 1H), 7.75 (td, J = 1.1, 9.0 Hz, 1H), 7.50-7.45 (m, 1H), 7.11 (dt, J = 1.2, 6.9 Hz, 1H), 6.11 (s, 1H), 5.04 (s, 2H), 4.02-3.97 (m, 2H), 3.63 (s, 3H), 3.45-3.38 (m, 1H), 3.09-3.04 (m, 2H), 2.28-2.20 (m, 2H), 2.16-2.09 (m, 2H), 2.01-1.81 (m, 2H) LC-MS (ESI): method 7 = 3.21 min; m/z (M + 1) = 461.3 |

-continued

| Example No | Structure | General procedure - Amount reagents | Amount product (yield) | Purification method | Data |
|---|---|---|---|---|---|
| 36 | 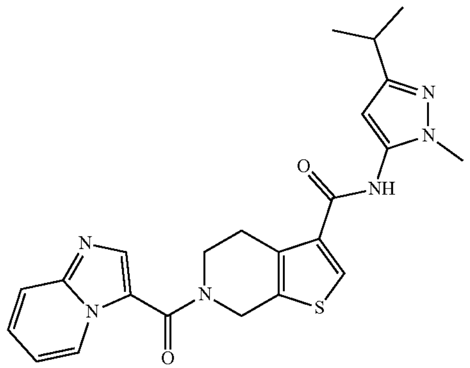 [SMILES: CC(C)c1cc(NC(=O)c2csc3c2CCN(C(=O)c2cnc4ccccn24)C3)n(C)n1] | General procedure I Amine (30 mg, 0.213 mmol) Intermediate 40: 70 mg (1.0 eq) Intermediate 40 was used as acid deblocking the salt via acidic washing | 35 mg 41% | Prep HPLC | $^1$H NMR (400 MHz, DMSO-$d_6$) δ 10.05 (s, 1H), 8.97 (td, J = 1.1, 7.0 Hz, 1H), 8.19 (s, 1H), 8.14 (s, 1H), 7.75 (td, J = 1.1, 9.0 Hz, 1H), 7.48 (ddd, J = 1.3, 6.8, 9.0 Hz, 1H), 7.11 (dt, J = 1.3, 6.9 Hz, 1H), 6.06 (s, 1H), 5.04 (s, 2H), 3.99 (t, J = 5.7 Hz, 2H), 3.63 (s, 3H), 3.07 (t, J = 5.4 Hz, 2H), 2.88-2.77 (septet, J = 7.0 Hz, 1H), 1.19 (d, J = 7.0 Hz, 6H) LC-MS (ESI): method 7 = 3.08 min; m/z (M + 1) = 449.3 |
| 37 | 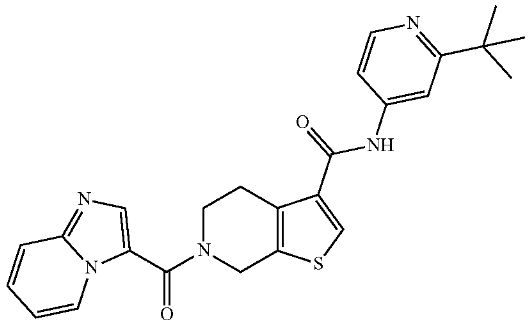 [SMILES: CC(C)(C)c1cc(NC(=O)c2csc3c2CCN(C(=O)c2cnc4ccccn24)C3)ccn1] | General procedure I Amine (36 mg, 0.211 mmol) Intermediate 40: 69 mg (1.0 eq) Intermediate 40 was used as acid deblocking the salt via acidic washing | 19 mg 28% | Prep HPLC | $^1$H NMR (400 MHz, DMSO-$d_6$) δ 10.37 (s, 1H), 8.98 (td, J = 1.2, 7.1 Hz, 1H), 8.41 (d, J = 5.5 Hz, 1H), 8.24 (s, 1H), 8.15 (s, 1H), 7.77-7.74 (m, 2H), 7.63 (dd, J = 1.9, 5.5 Hz, 1H), 7.48 (ddd, J = 1.3, 6.8, 9.0 Hz, 1H), 7.11 (dt, J = 1.2, 6.9 Hz, 1H), 5.04 (s, 2H), 4.02-3.97 (m, 2H), 3.11-3.06 (m, 2H), 1.32 (s, 9H). LC-MS (ESI): method 6 = 4.21 min; m/z (M + 1) = 460.3 |

-continued

| Example No | Structure | General procedure - Amount reagents | Amount product (yield) | Purification method | Data |
|---|---|---|---|---|---|
| 38 | 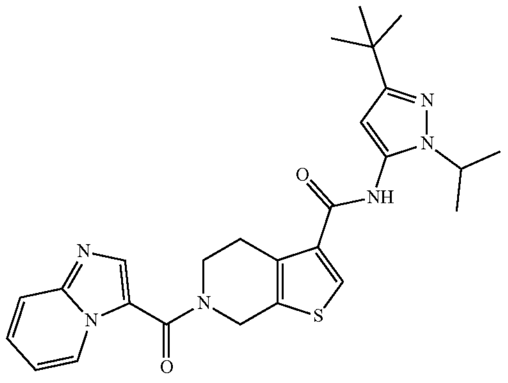 [SMILES: CC(C)n1nc(C(C)(C)C)cc1NC(=O)c1csc2c1CCN(C(=O)c1cnc3ccccn13)C2] | General procedure I Amine (38 mg, 0.210 mmol) Intermediate 40: 68 mg (1.0 eq) Intermediate 40 was used as acid deblocking the salt via acidic washing | 27.7 mg 35% | Prep HPLC | $^1$H NMR (400 MHz, DMSO-$d_6$) δ 9.92 (s, 1H), 8.97 (td, J = 1.1, 7.0 Hz, 1H), 8.18 (s, 1H), 8.14 (s, 1H), 7.75 (td, J = 1.1, 9.0 Hz, 1H), 7.48 (ddd, J = 1.3, 6.8, 9.0 Hz, 1H), 7.11 (dt, J = 1.2, 6.9 Hz, 1H), 6.05 (s, 1H), 5.03 (s, 2H), 4.46-4.35 (hept, J = 6.6 Hz, 1H), 4.02-3.96 (m, 2H), 3.09-3.03 (m, 2H), 1.34 (d, J = 6.6 Hz, 6H), 1.25 (s, 9H). LC-MS (ESI): method 7 = 3.97 min; m/z (M + 1) = 491.4 |
| 39 | 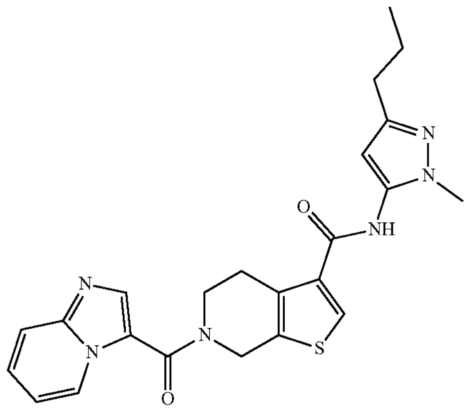 [SMILES: CCCc1cc(NC(=O)c2csc3c2CCN(C(=O)c2cnc4ccccn24)C3)n(C)n1] | General procedure I Amine (30 mg, 0.213 mmol) Intermediate 40: 70 mg (1.0 eq) Intermediate 40 was used as acid deblocking the salt via acidic washing | 40 mg 59% | Prep HPLC | $^1$H NMR (400 MHz, DMSO-$d_6$) δ 10.06 (s, 1H), 8.97 (td, J = 1.1, 7.0 Hz, 1H), 8.20 (s, 1H), 8.14 (s, 1H), 7.75 (td, J = 1.1, 9.0 Hz, 1H), 7.48 (ddd, J = 1.3, 6.8, 9.0 Hz, 1H), 7.11 (dt, J = 1.2, 6.9 Hz, 1H), 6.04 (s, 1H), 5.03 (s, 2H), 3.99 (t, J = 5.6 Hz, 2H), 3.63 (s, 3H), 3.10-3.03 (m, 2H), 2.46 (t, J = 7.6 Hz, 2H), 1.65-1.54 (m, 2H), 0.93 (t, J = 7.4 Hz, 3H) LC-MS (ESI): method 7 = 3.08 min; m/z (M + 1) = 449.3 |

-continued

| Example No | Structure | General procedure - Amount reagents | Amount product (yield) | Purification method | Data |
|---|---|---|---|---|---|
| 40 | 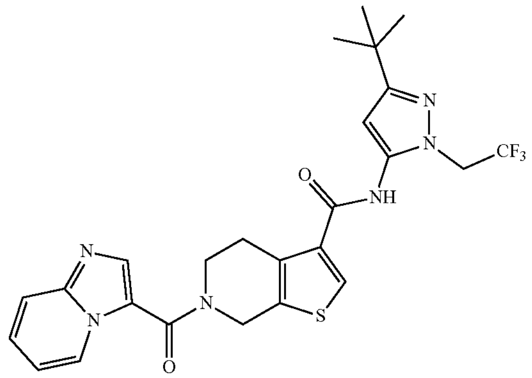 [SMILES: CC(C)(C)c1cc(NC(=O)c2csc3c2CCN(C(=O)c2cnc4ccccn24)C3)n(CC(F)(F)F)n1] | General procedure I Amine (46.6 mg, 0.211 mmol) Intermediate 40: 69 mg (1.0 eq) Intermediate 40 was used as acid deblocking the salt via acidic washing | 39 mg 44% | Prep HPLC | $^1$H NMR (400 MHz, DMSO-$d_6$) δ 10.21 (s, 1H), 8.97 (td, J = 1.1, 7.0 Hz, 1H), 8.16-8.14 (m, 2H), 7.75 (td, J = 1.1, 9.0 Hz, 1H), 7.48 (ddd, J = 1.3, 6.8, 9.0 Hz, 1H), 7.11 (dt, J = 1.2, 6.9 Hz, 1H), 6.32 (s, 1H), 5.07-4.98 (m, 4H), 4.02-3.96 (m, 2H), 3.08-3.04 (m, 2H), 1.26 (s, 9H). LC-MS (ESI): method 7 = 3.97 min; m/z (M + 1) = 531.3 |
| 41 | 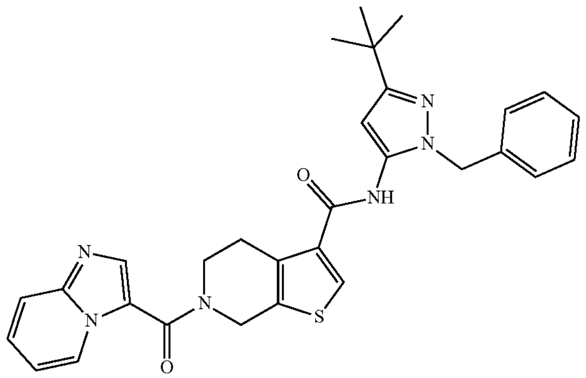 [SMILES: CC(C)(C)c1cc(NC(=O)c2csc3c2CCN(C(=O)c2cnc4ccccn24)C3)n(Cc2ccccc2)n1] | General procedure I Amine (48 mg, 0.213 mmol) Intermediate 40: 70 mg (1.0 eq) Intermediate 40 was used as acid deblocking the salt via acidic washing | 47 mg 57% | Prep HPLC | $^1$H NMR (400 MHz, DMSO-$d_6$) δ 10.07 (s, 1H), 8.96 (td, J = 1.1, 7.0 Hz, 1H), 8.12 (s, 1H), 8.01 (s, 1H), 7.75 (td, J = 1.1, 9.0 Hz, 1H), 7.48 (ddd, J = 1.3, 6.8, 9.0 Hz, 1H), 7.33-7.28 (m, 2H), 7.27-7.21 (m, 1H), 7.13-7.08 (m, 3H), 6.21 (s, 1H), 5.28 (s, 2H), 5.01 (s, 2H), 3.97-3.91 (m, 2H), 2.97-2.91 (m, 2H), 1.26 (s, 9H). LC-MS (ESI): method 7 = 4.12 min; m/z (M + 1) = 539.3 |

-continued

| Example No | Structure | General procedure - Amount reagents | Amount product (yield) | Purification method | Data |
|---|---|---|---|---|---|
| 42 | 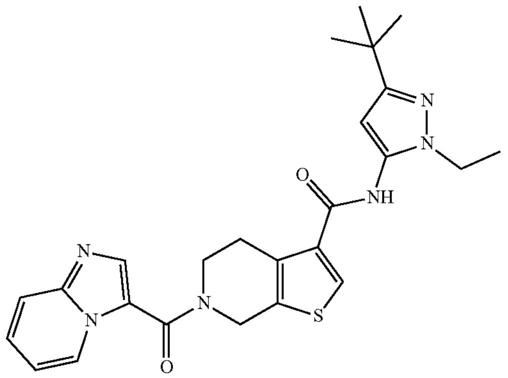 [SMILES: CCn1nc(C(C)(C)C)cc1NC(=O)c1csc2c1CCN(C(=O)c1cnc3ccccn13)C2] | General procedure I Amine (35 mg, 0.211 mmol) Intermediate 40: 69 mg (1.0 eq) Intermediate 40 was used as acid deblocking the salt via acidic washing | 30.6 mg 42% | Prep HPLC | $^1$H NMR (400 MHz, DMSO-$d_6$) δ 9.98 (s, 1H), 8.97 (td, J = 1.1, 7.0 Hz, 1H), 8.17 (s, 1H), 8.14 (s, 1H), 7.75 (td, J = 1.1, 9.0 Hz, 1H), 7.48 (ddd, J = 1.3, 6.8, 9.0 Hz, 1H), 7.11 (dt, J = 1.2, 6.9 Hz, 1H), 6.09 (s, 1H), 5.04 (s, 2H), 4.02-3.93 (m, 4H), 3.08-3.03 (m, 2H), 1.29 (t, J = 7.2 Hz, 3H), 1.25 (s, 9H). LC-MS (ESI): method 7 = 3.53 min; m/z (M + 1) = 477.3 |
| 43 | 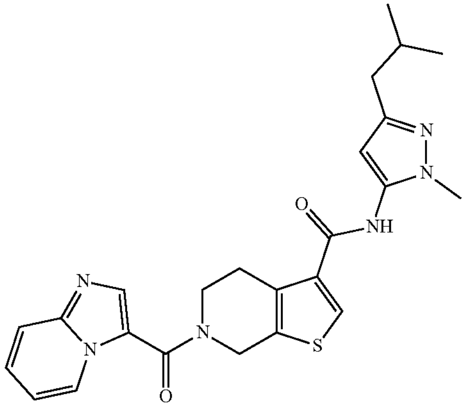 [SMILES: CC(C)Cc1cc(NC(=O)c2csc3c2CCN(C(=O)c2cnc4ccccn24)C3)n(C)n1] | General procedure I Amine (35 mg, 0.211 mmol) Intermediate 40: 69 mg (1.0 eq) Intermediate 40 was used as acid deblocking the salt via acidic washing | 30.6 mg 42% | Prep HPLC | $^1$H NMR (400 MHz, DMSO-$d_6$) δ 10.06 (s, 1H), 8.97 (td, J = 1.1, 7.0 Hz, 1H), 8.21 (s, 1H), 8.14 (s, 1H), 7.75 (td, J = 1.1, 9.1 Hz, 1H), 7.48 (ddd, J = 1.3, 6.8, 9.0 Hz, 1H), 7.11 (dt, J = 1.2, 6.9 Hz, 1H), 6.03 (s, 1H), 5.03 (s, 2H), 3.99 (t, J = 5.6 Hz, 2H), 3.63 (s, 3H), 3.10-3.04 (m, 2H), 2.35 (d, J = 7.0 Hz, 2H), 1.92-1.81 (m, 1H), 0.91 (d, J = 6.7 Hz, 6H). LC-MS (ESI): method 7 = 3.32 min; m/z (M + 1) = 463.3 |

-continued

| Example No | Structure | General procedure - Amount reagents | Amount product (yield) | Purification method | Data |
|---|---|---|---|---|---|
| 44 | 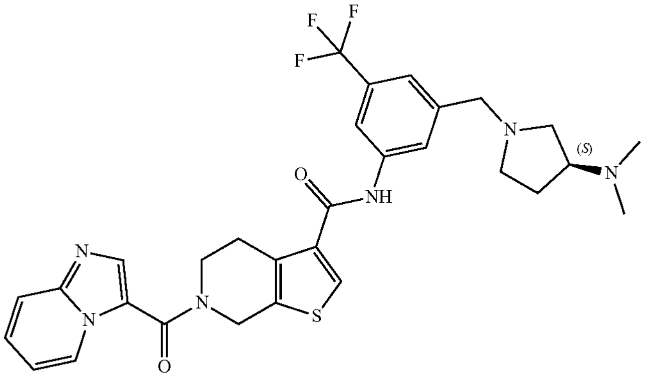 | General procedure I Amine (Intermediate 13) (147 mg, 0.513 mmol,) Intermediate 40: 168 mg (1.0 eq) Intermediate 40 was used as acid deblocking the salt via acidic washing | 187 mg 71% | Prep HPLC | $^1$H NMR (400 MHz, DMSO-$d_6$) δ 10.40-10.38 (m, 1H), 8.98 (d, J = 7.0 Hz, 1H), 8.23 (s, 1H), 8.15 (s, 1H), 8.13 (s, 1H), 7.95 (s, 1H), 7.75 (td, J = 1.1, 9.1 Hz, 1H), 7.48 (ddt, J = 1.3, 5.3, 4.5 Hz, 1H), 7.35 (s, 1H), 7.11 (ddd, J = 6.9, 6.9, 1.2 Hz, 1H), 5.06-5.02 (m, 2H), 4.03-3.97 (m, 2H), 3.71 (d, J = 13.6 Hz, 1H), 3.58 (d, J = 13.7 Hz, 1H), 3.10-3.06 (m, 2H), 2.76-2.67 (m, 2H), 2.65-2.58 (m, 1H), 2.50-2.45 (m, 1H), 2.35-2.29 (m, 1H), 2.10-2.09 (m, 6H), 1.93-1.83 (m, 1H), 1.68-1.59 (m, 1H) LC-MS (ESI): method 7 = 2.56 min; m/z (M + 1) = 597.5 |
| 45 | 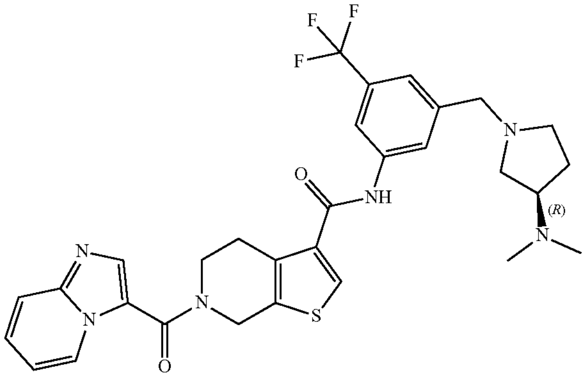 | General procedure I Amine (Intermediate 14) (160 mg, 0.555 mmol,) Intermediate 40: 181 mg (1.0 eq) Intermediate 40 was used as acid deblocking the salt via acidic washing | 87 mg 31% | Prep HPLC | $^1$H NMR (400 MHz, DMSO-$d_6$) δ 10.39 (s, 1H), 8.98 (td, J = 1.1, 7.0 Hz, 1H), 8.23 (s, 1H), 8.15-8.12 (m, 2H), 7.95 (s, 1H), 7.75 (td, J = 1.1, 9.0 Hz, 1H), 7.48 (ddd, J = 1.3, 6.8, 9.0 Hz, 1H), 7.35 (s, 1H), 7.11 (dt, J = 1.2, 6.9 Hz, 1H), 5.05 (s, 2H), 4.03-3.97 (m, 2H), 3.71 (d, J = 13.7 Hz, 1H), 3.58 (d, J = 13.7 Hz, 1H), 3.12-3.06 (m, 2H), 2.76-2.67 (m, 2H), 2.65-2.58 (m, 1H), 2.49-2.44 (m, 1H), 2.35-2.29 (m, 1H), 2.09 (s, 6H), 1.93-1.83 (m, 1H), 1.68-1.59 (m, 1H) LC-MS (ESI): method 7 $t_R$ = 2.58 min; m/z (M + 1) = 597.4 |

-continued

| Example No | Structure | General procedure - Amount reagents | Amount product (yield) | Purification method | Data |
|---|---|---|---|---|---|
| 129 | 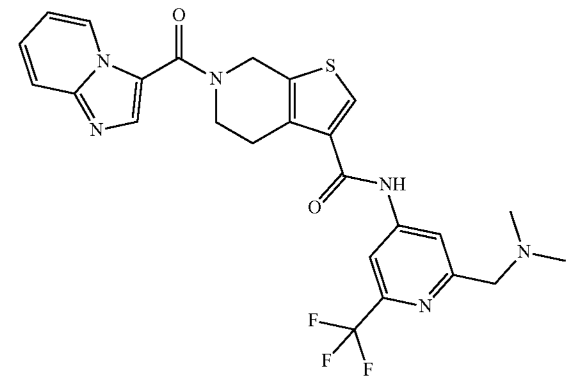 [SMILES: CN(C)Cc1cc(NC(=O)c2csc3c2CCN(C(=O)c2cnc4ccccn24)C3)cc(C(F)(F)F)n1] | General procedure I Intermediate 130 (28 mg, 1.21 mmol) Intermediate 40: 38 mg (1.15 eq) Intermediate 40 was used as acid. | 5 mg 7% | Prep HPLC | $^1$H NMR (400 MHz, DMSO-$d_6$) δ 10.77 (s, 1H), 8.98 (td, J = 1.1, 7.0 Hz, 1H), 8.32 (s, 1H), 8.19 (d, J = 1.7 Hz, 1H), 8.15 (s, 1H), 8.10 (s, 1H), 7.75 (td, J = 1.1, 9.0 Hz, 1H), 7.48 (ddd, J = 1.3, 6.8, 9.0 Hz, 1H), 7.11 (dt, J = 1.2, 6.9 Hz, 1H), 5.05 (s, 2H), 4.03-3.97 (m, 2H), 3.58 (s, 2H), 3.14-3.08 (m, 2H), 2.25 (s, 6H). LC-MS (ESI) method 7: $t_R$ = 2.58 min; m/z [M + H]+ = 529.5 |
| 130 | 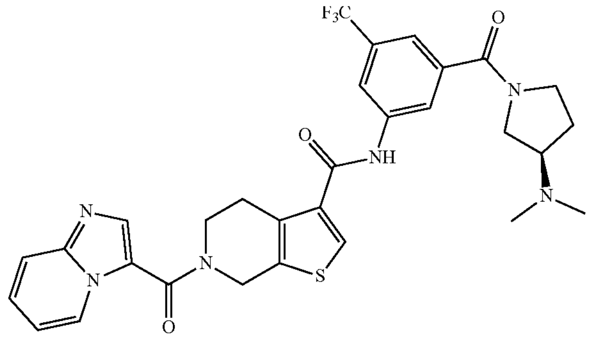 [SMILES: CN(C)[C@@H]1CCN(C(=O)c2cc(NC(=O)c3csc4c3CCN(C(=O)c3cnc5ccccn35)C4)cc(C(F)(F)F)c2)C1] | General procedure I Intermediate 111 (44 mg, 1.47 mmol) Intermediate 40: 40 mg (0.9 eq) Intermediate 40 was used as acid. | 49 mg 64% | Prep HPLC | $^1$H NMR (400 MHz, DMSO-$d_6$) δ 10.52 (s, 1H), 8.98 (d, J = 7.0 Hz, 1H), 8.28 (d, J = 7.1 Hz, 1H), 8.24 (s, 1H), 8.16 (t, J = 1.7 Hz, 1H), 8.15 (s, 1H), 7.76-7.74 (m, 1H), 7.56 (d, J = 3.4 Hz, 1H), 7.51-7.46 (m, 1H), 7.14-4.00 (t, J = 5.7 Hz, 2H), 3.78-3.46 (m, 7.09 (m, 1H), 5.06-5.03 (m, 2H), 3H), 3.30-3.23 (m, 1H), 3.12-3.07 (m, 2H), 2.77-2.67 (m, 1H), 2.21 (s, 3H), 2.13-2.11 (m, 3H), 2.06-2.01 (m, 1H), 1.83-1.72 (m, 1H) LC-MS (ESI) method 7: $t_R$ = 2.82 min; m/z (M + 1) = 611.2. |

Example 46; Preparation of N-(3-fluoro-5-(trifluoromethyl)phenyl)-6-(imidazo[1,2-a]pyridine-3-carbonyl)-4,5,6,7-tetrahydrothieno[2,3-c]pyridine-3-carboxamide Example 46

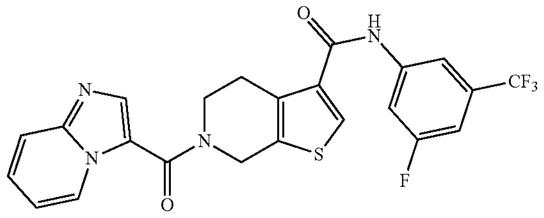

Step 1; N-(3-fluoro-5-(trifluoromethyl)phenyl)-6-(imidazo[1,2-a]pyridine-3-carbonyl)-4,5,6,7-tetrahydrothieno[2,3-c]pyridine-3-carboxamide Intermediate 40 (100 mg, 0.286 mmol) and 3-fluoro-5-(trifluoromethyl)aniline (0.056 mL, 0.429 mmol) were dissolved in anhydrous Pyridine (2.863 mL). The solution was cooled down to 5° C. and $POCl_3$ (0.059 mL, 0.630 mmol) was added. The reaction was stirred until conversion of SM was observed. The RM was diluted with AcOEt and washed with $NaHCO_{3(aq)}$, water and brine. Organic phases were then dried over $Na_2SO_4$, filtered and concentrated under reduced pressure. Crude material was purified by FCC (DCM to 10% MeOH in DCM) to afford the title compound (6 mg, 0.012 mmol, yield 4%).

$^1$H NMR (300 MHz, DMSO-$d_6$) δ 10.58 (s, 1H), 8.96 (d, J=6.9 Hz, 1H), 8.23 (s, 1H), 8.13 (s, 1H), 8.01-7.91 (m, 2H), 7.73 (d, J=9.0 Hz, 1H), 7.46 (t, J=8.0 Hz, 1H), 7.38 (d, J=8.4 Hz, 1H), 7.10 (t, J=6.8 Hz, 1H), 5.03 (s, 2H), 3.98 (t, J=5.7 Hz, 2H), 3.07 (s, 2H).

LC-MS (ESI) method 2: $t_R$=2.21 min; m/z (M+1)=489.0

Example 47; Preparation of N-(4-(tert-butyl)oxazol-2-yl)-6-(imidazo[1,2-a]pyridine-3-carbonyl)-4,5,6,7-tetrahydrothieno[2,3-c]pyridine-3-carboxamide Example 47

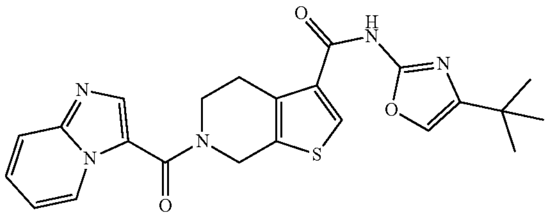

Step 1; N-(4-(tert-butyl)oxazol-2-yl)-6-(imidazo[1,2-a]pyridine-3-carbonyl)-4,5,6,7-tetrahydrothieno[2,3-c]pyridine-3-carboxamide To a suspension of Intermediate 40 acid form (40 mg, 0.122 mmol) and 4-tert-butyloxazol-2-amine (24 mg, 0.171 mmol) in DMF (0.60 mL), was added 1-methylimidazole (0.034 mL, 0.428 mmol), followed by TCFH (51 mg, 0.183 mmol). The reaction mixture was stirred at rt for 72 h, partitioned between saturated $NaHCO_{3(aq)}$ and DCM, and the aqueous phase extracted with 3×DCM. The combined organic phases were washed with saturated $NaCl_{(aq)}$, passed through a hydrophobic frit and concentrated under vacuum. Purification by reverse phase Prep HPLC (Xbridge Phenyl 19×150 mm, 10 μm 40-100% MeOH/water (10 mM $NH_4HCO_3$), 20 mL/min, RT) gave the title compound (1.55 mg, 2%).

$^1$H NMR (400 MHz, DMSO-$d_6$) δ 11.34 (s, 1H), 8.97 (td, J=1.1, 7.1 Hz, 1H), 8.28 (s, 1H), 8.14 (s, 1H), 7.74 (td, J=1.1, 9.0 Hz, 1H), 7.59 (s, 1H), 7.50-7.45 (m, 1H), 7.11 (dt, J=1.2, 6.9 Hz, 1H), 5.03 (s, 2H), 4.01-3.96 (m, 2H), 3.09-3.04 (m, 2H), 1.23 (s, 9H).

LC-MS (ESI) method 7: $t_R$=3.46 min; m/z (M+1)=450.2

The compounds reported in the following table were prepared via amido coupling as described for Example 47, step 1, applying the corresponding, commercially available or previously synthesized amine in step 1. The solvent is specified if not DMF.

| Example No | Structure | General procedure - Amount reagents | Amount product (yield) | Purification method | Data |
|---|---|---|---|---|---|
| 114 | 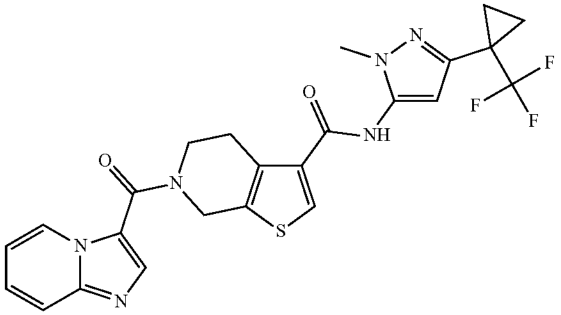 [SMILES: Cn1nc(C2(C(F)(F)F)CC2)cc1NC(=O)c1csc2c1CCN(C(=O)c1cnc3ccccn13)C2] | General procedure G 2-methyl-5-[1-(trifluoromethyl)cyclo propyl]pyrazol-3-amine (47 mg, 0.23 mmol): Intermediate 40: 75 mg, (1.0 eq) | 89 mg (73%) | No further purification | $^1$H NMR (400 MHz, $CDCl_3$) δ 9.02 (d, J = 6.8 Hz, 1H), 7.96 (s, 1H), 7.73 (s, 1H), 7.69 (d, J = 9.1 Hz, 1H), 7.62 (s, 1H), 7.37 (t, J = 7.8 Hz, 1H), 6.97 (t, J = 6.8 Hz, 1H), 6.37 (s, 1H), 5.03 (s, 2H), 4.09 (t, J = 5.7 Hz, 2H), 3.74 (s, 3H), 3.21 (t, J = 5.1 Hz, 2H), 1.34-1.22 (m, 4H). LCMS (ESI): Method 7 $t_R$ = 3.50 min; m/z [M + 1+]+ = 515.5 |
| 115 | 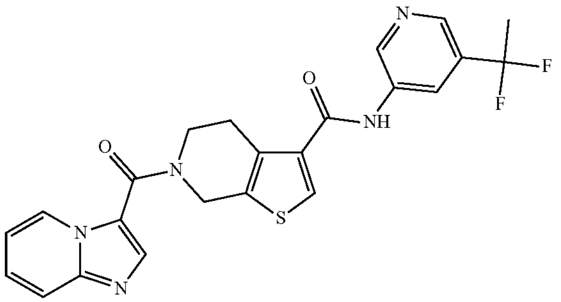 [SMILES: CC(F)(F)c1cncc(NC(=O)c2csc3c2CCN(C(=O)c2cnc4ccccn24)C3)c1] | 5-(1,1-difluoroethyl)pyridin-3-amine (36 mg, 0.23 mmol): Intermediate 40: 75 mg, (1.0 eq) | 61 mg (54%) | No further purification | $^1$H NMR (400 MHz, $CDCl_3$) δ 9.03 (d, J = 6.6 Hz, 1H), 8.78 (s, 1H), 8.54 (s, 1H), 8.41 (s, 1H), 8.29 (s, 1H), 7.98 (s, 1H), 7.73-7.66 (m, 2H), 7.42-7.34 (m, 1H), 6.99 (t, J = 6.7 Hz, 1H), 5.00 (s, 2H), 4.10 (t, J = 5.9 Hz, 2H), 3.25 (s, 2H), 1.99 (t, J = 18.3 Hz, 3H). LCMS (ESI): Method 7 $t_R$ 3.17 min; m/z [M + H+]+, = 468.4 |

-continued

| Example No | Structure | General procedure - Amount reagents | Amount product (yield) | Purification method | Data |
|---|---|---|---|---|---|
| 117 | 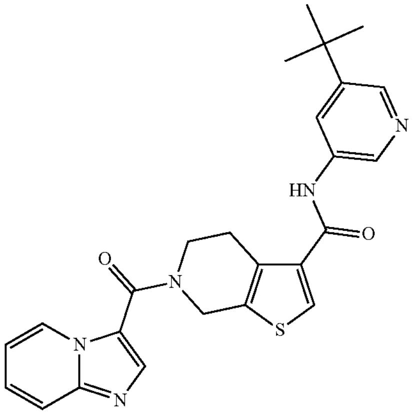 [SMILES: CC(C)(C)c1cncc(NC(=O)c2csc3c2CCN(C(=O)c2cnc4ccccn24)C3)c1] | 5-tert-butylpyridin-3-amine Amine (27 mg, 0.23 mmol): Intermediate 40: 75 mg, (1.0 eq) | 57 mg (67%) | Precipitation from water | $^1H$ NMR (400 MHz, $CDCl_3$) δ 9.03 (d, J = 6.8 Hz, 1H), 8.51 (d, J = 2.3 Hz, 1H), 8.44 (d, J = 2.0 Hz, 1H), 8.20 (t, J = 2.4 Hz, 1H), 7.98 (s, 1H), 7.92 (s, 1H), 7.71 (m, 2H), 7.37 (t, J = 8.8 Hz, 1H), 6.97 (t, J = 6.9 Hz, 1H), 5.02 (s, 2H), 4.10 (t, J = 5.7 Hz, 2H), 3.24 (t, J = 5.4 Hz, 2H), 1.38 (s, 9H). LCMS (ESI): Method 7 $t_R$ = 4.07 min, m/z [M + H+]+ = 460.5 |
| 118 | 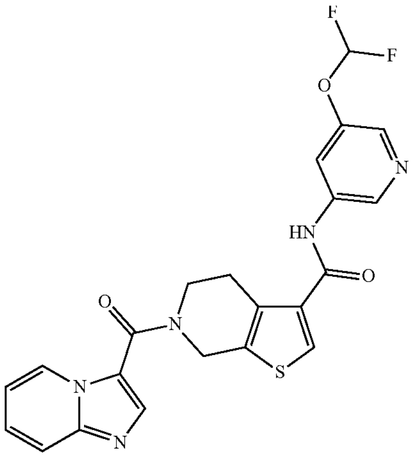 [SMILES: O=C(Nc1cncc(OC(F)F)c1)c1csc2c1CCN(C(=O)c1cnc3ccccn13)C2] | 5-(difluoromethoxy) pyridin-3-amine dihydrochloride Amine (42 mg, 0.23 mmol): Intermediate 40: 75 mg, (1.0 eq) | 44 mg (49%) | Precipitation from water | $^1H$ NMR (400 MHz, $CDCl_3$) δ 10.56 (s, 1H), 9.02 (d, J = 6.8 Hz, 1H), 8.84 (m, 1H), 8.28 (s, 2H), 8.22-8.17 (m, 2H), 7.79 (d, J = 9.1 Hz, 1H), 7.53 (m, 1H), 7.21-7.12 (m, 1H), 5.08-5.05 (s, 2H), 4.04 (t, J = 5.3 Hz, 2H), 3.17-3.09 (t, J = 5.3 Hz, 2H).(1H missing) LCMS (ESI): Method 7 $t_R$ = 3.13 min, m/z [M + H+]+ = 470.3 |

-continued

| Example No | Structure | General procedure - Amount reagents | Amount product (yield) | Purification method | Data |
|---|---|---|---|---|---|
| 131 | 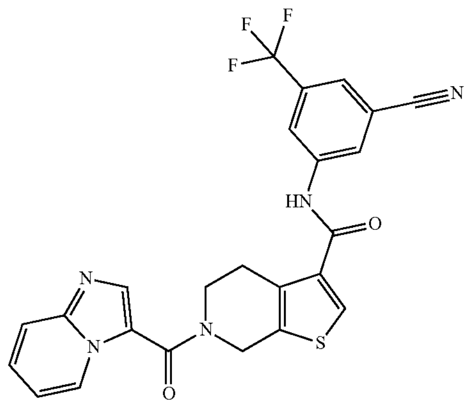 [SMILES: N#Cc1cc(NC(=O)c2csc3c2CCN(C(=O)c2cnc4ccccn24)C3)cc(C(F)(F)F)c1] | ACN 3-amino-5-(trifluoromethyl) benzonitrile (28 mg, 0.153 mmol): Intermediate 40: 50 mg, (1.0 eq) | 24 mg (30%) | Precipitation from water | $^1$H NMR (400 MHz, DMSO-$d_6$) δ 10.74-10.71 (m, 1H), 9.02 (d, J = 6.8 Hz, 1H), 8.48 (d, J = 5.8 Hz, 2H), 8.30 (s, 1H), 8.19 (s, 1H), 8.10 (s, 1H), 7.79 (d, J = 9.1 Hz, 1H), 7.52 (t, J = 7.7 Hz, 1H), 7.15 (t, J = 6.7 Hz, 1H), 5.12-5.05 (m, 2H), 4.04 (t, J = 5.7 Hz, 2H), 3.14 (t, J = 5.6 Hz, 2H). LC-MS (ESI) method 6: $t_R$ = 4.61 min; m/z $[M + H]^+$ = 496.4 |
| 132 | 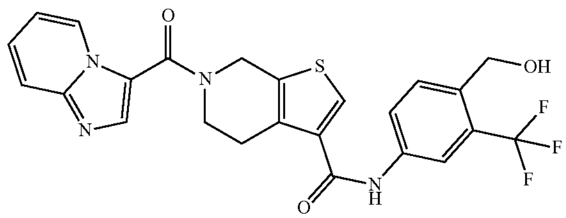 [SMILES: O=C(Nc1ccc(CO)c(C(F)(F)F)c1)c1csc2c1CCN(C(=O)c1cnc3ccccn13)C2] | ACN Intermediate 112 (29 mg, 0.153 mmol): Intermediate 40: 50 mg, (1.0 eq) | 7 mg (9%) | Prep HPLC | $^1$H NMR (400 MHz, DMSO-$d_6$) δ 10.36 (s, 1H), 8.98 (m, 1H), 8.21 (s, 1H), 8.17-8.15 (m, 2H), 8.01 (dd, J = 1.9, 8.4 Hz, 1H), 3.19 (d, J = 5.1 Hz, 1H), 3.09 (s, 2H). 1H), 5.03 (s, 2H), 4.65 (d, J = 5.5 Hz, 2H), 1H), 7.74 (m, 2H), 7.50-7.45 (m, 1H), 4.00 (t, J = 5.6 Hz, 2H), 3.30-3.28 (m, 7.13-7.09 (m, 1H), 5.44 (t, J = 5.6 Hz, LC-MS (ESI) method 7: $t_R$ = 3.27 min; m/z $[M + H]^+$ = 501.5 |

Example 48; Preparation of compound N-(3-((4-(dimethylamino)piperidin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide Example 48

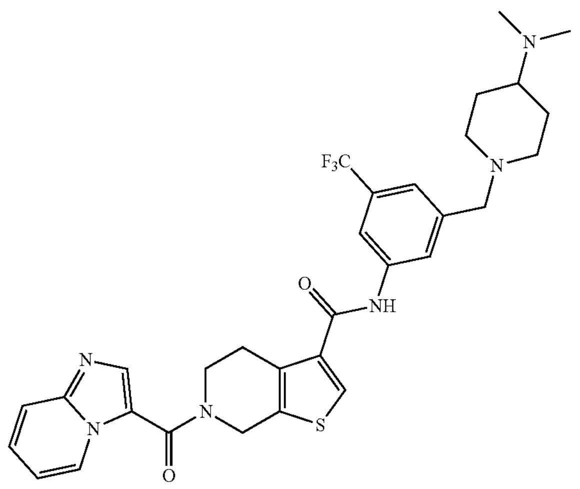

Step 1; N-(3-(dimethoxymethyl)-5-(trifluoromethyl)phenyl)-6-(imidazo[1,2-a]pyridine-3-carbonyl)-4,5,6,7-tetrahydrothieno[2,3-c]pyridine-3-carboxamide (Intermediate 41)

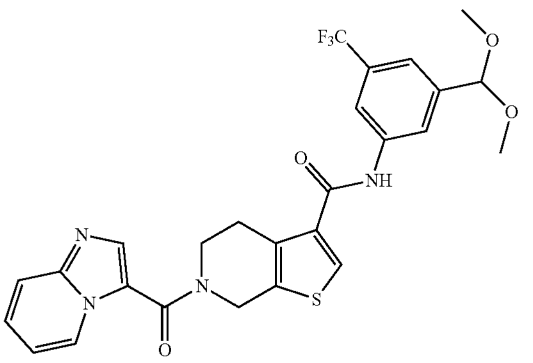 [SMILES: COC(OC)c1cc(NC(=O)c2csc3c2CCN(C(=O)c2cnc4ccccn24)C3)cc(C(F)(F)F)c1]

Prepared from 3-(dimethoxymethyl)-5-(trifluoromethyl)aniline (216 mg, 0.916 mmol, Intermediate 33) and Intermediate 40 acid form (300 mg, 0.916 mmol) according to general procedure H. The residue was triturated under $Et_2O$ and the suspension filtered to give the title compound (496 mg, 0.910 mmol, 99% of yield).

$^1$H NMR (400 MHz, DMSO-$d_6$) δ 10.46 (s, 1H), 8.98 (d, J=7.0 Hz, 1H), 8.25-8.19 (m, 3H), 8.07 (s, 1H), 7.76 (d, J=9.1 Hz, 1H), 7.55-7.49 (m, 1H), 7.39 (s, 1H), 7.15 (t, J=6.9 Hz, 1H), 5.50 (s, 1H), 5.03 (s, 2H), 4.01-3.97 (m, 2H), 3.29 (s, 6H), 3.12-3.07 (m, 2H)

Step 2; N-(3-formyl-5-(trifluoromethyl)phenyl)-6-(imidazo[1,2-a]pyridine-3-carbonyl)-4,5,6,7-tetrahydrothieno[2,3-c]pyridine-3-carboxamide (Intermediate 42)

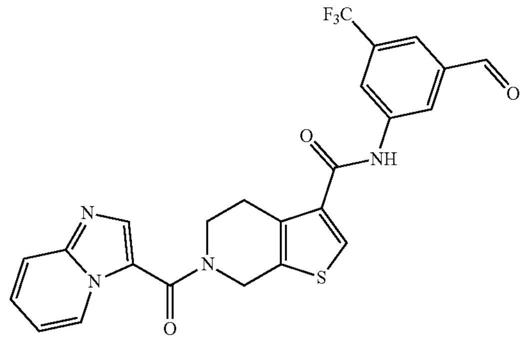 [SMILES: O=Cc1cc(NC(=O)c2csc3c2CCN(C(=O)c2cnc4ccccn24)C3)cc(C(F)(F)F)c1]

To a solution of Intermediate 41 (498 mg, 0.915 mmol, 1.00 eq) in DCM (5.00 mL) at room temperature was added TFA (0.50 mL, 6.53 mmol, 7.14 eq) and the reaction mixture was stirred at room temperature for 3 h. The mixture was concentrated under vacuum to give a pale brown mobile oil, which was triturated under $Et_2O$, and the ether decanted to the title compound (450 mg, 0.910 mmol, 99% of yield).

$^1$H NMR (400 MHz, DMSO-$d_6$) δ 10.67 (s, 1H), 10.09 (s, 1H), 9.04 (d, J=7.0 Hz, 1H), 8.57 (s, 1H), 8.46 (s, 2H), 8.29 (s, 1H), 8.01 (s, 1H), 7.93 (d, J=9.0 Hz, 1H), 7.84-7.78 (m, 1H), 7.39 (t, J=7.0 Hz, 1H), 5.03 (s, 2H), 4.01-3.96 (m, 2H), 3.14-3.09 (m, 2H)

Step 3; N-(3-((4-(dimethylamino)piperidin-1-yl)methyl)-5-(trifluoromethyl) phenyl)-6-(imidazo[1,2-a]pyridine-3-carbonyl)-4,5,6,7-tetrahydrothieno[2,3-c]pyridine-3-carboxamide Prepared from intermediate 42 (50 mg, 0.100 mmol) and N,N-dimethylpiperidin-4-amine (14 mg, 0.110 mmol) according to general procedure C. Purification by reverse phase preparative HPLC (Xbridge Phenyl 19×150 mm, 10 μm 40-100% methanol/water (10 mM $NH_4HCO_3$), 20 mL/min, RT) gave the title compound (16 mg, 26%).

$^1$H NMR (400 MHz, DMSO-$d_6$) δ 10.40 (s, 1H), 8.98 (td, J=1.0, 7.0 Hz, 1H), 8.24 (s, 1H), 8.17-8.15 (m, 2H), 7.93 (s, 1H), 7.75 (td, J=1.0, 9.0 Hz, 1H), 7.51-7.45 (m, 1H), 7.34 (s, 1H), 7.11 (dt, J=1.0, 7.0 Hz, 1H), 5.03 (s, 2H), 4.00 (t, J=5.5 Hz, 2H), 3.53 (s, 2H), 3.12-3.07 (m, 2H), 2.87-2.81 (m, 2H), 2.17 (s, 6H), 2.08-1.94 (m, 3H), 1.76-1.69 (m, 2H), 1.40 (dq, J=3.5, 11.8 Hz, 2H).

LC-MS (ESI) method 7: $t_R$=2.34 min; m/z (M+1)=611.4

The compounds reported in the following table were prepared via amido coupling as described for Example 48, step 1-3, applying the corresponding, commercially available or previously synthesized amine in step 3. The step 3 could be performed in various way as reported in the table in according with the general procedure described above. Modifications involved chromatographic purification conditions (e.g. Prep HPLC or flash chromatography) such changes were reported as a note.

| Example No | Structure | Amount SM | Purification Amount product (yield) | Purification method | Data |
|---|---|---|---|---|---|
| 49 | 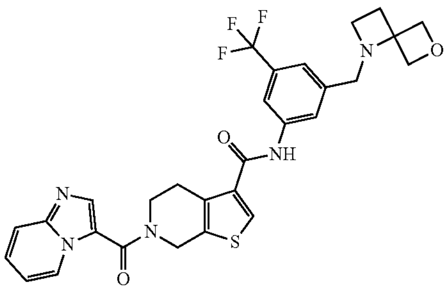 [SMILES: O=C(Nc1cc(CN2CCC23COC3)cc(C(F)(F)F)c1)c1csc2c1CCN(C(=O)c1cnc3ccccn13)C2] | General procedure C NH2: 29 mg (0.100 mmol) intermediate 42: 50 mg (0.100 mmol) | 19 mg (32%) | Preparative HPLC | $^1$H NMR (400 MHz, DMSO-$d_6$) δ 10.40 (s, 1H), 8.98 (td, J = 1.1, 7.0 Hz, 1H), 8.24 (s, 1H), 8.15 (s, 1H), 8.14 (s, 1H), 8.00 (s, 1H), 7.75 (td, J = 1.1, 9.0 Hz, 1H), 7.50-7.46 (m, 1H), 7.40 (s, 1H), 7.11 (dt, J = 1.3, 6.9 Hz, 1H), 5.04 (s, 2H), 4.87 (d, J = 7.8 Hz, 2H), 4.54 (d, J = 7.7 Hz, 2H), 4.00 (t, J = 5.6 Hz, 2H), 3.91 (s, 2H), 3.12-3.07 (m, 2H), 3.03 (t, J = 6.9 Hz, 2H), 2.35 (t, J = 6.8 Hz, 2H) LC-MS (ESI): method 7 $t_R$ = 2.77 min; m/z (M + 1) = 582.2 |
| 50 | 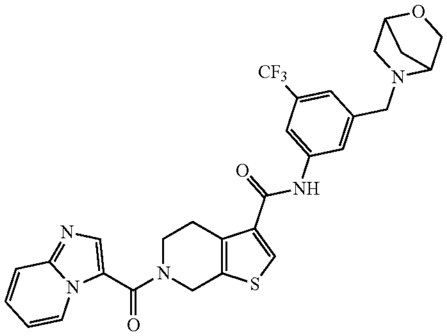 [SMILES: O=C(Nc1cc(CN2CC3CC2CO3)cc(C(F)(F)F)c1)c1csc2c1CCN(C(=O)c1cnc3ccccn13)C2] | General procedure C NH2: 15 mg (0.110 mmol) intermediate 42: 50 mg (0.100 mmol) | 10 mg (17%) | Preparative HPLC | $^1$H NMR (400 MHz, DMSO-$d_6$) δ 10.39 (s, 1H), 8.98 (td, J = 1.0, 7.0 Hz, 1H), 8.23 (s, 1H), 8.15 (s, 1H), 8.13 (s, 1H), 8.00 (s, 1H), 7.75 (td, J = 1.1, 9.1 Hz, 1H), 7.51-7.45 (m, 1H), 7.39 (s, 1H), 7.11 (dt, J = 1.2, 6.9 Hz, 1H), 5.04 (s, 2H), 4.38 (s, 1H), 4.03-3.94 (m, 3H), 3.87-3.77 (m, 2H), 3.57 (dd, J = 1.8, 7.5 Hz, 1H), 3.50 (s, 1H), 3.10-3.08 (m, 2H), 2.76 (dd, J = 1.6, 9.9 Hz, 1H), 2.46 (d, J = 9.8 Hz, 1H), 1.85 (dd, J = 2.0, 9.5 Hz, 1H), 1.65-1.62 (m, 1H) LC-MS (ESI): method 7 $t_R$ = 2.70 min; m/z (M + 1) = 582 |
| 51 | 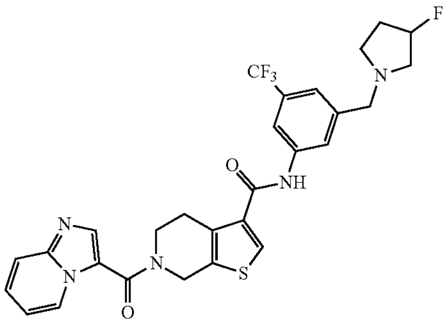 [SMILES: O=C(Nc1cc(CN2CCC(F)C2)cc(C(F)(F)F)c1)c1csc2c1CCN(C(=O)c1cnc3ccccn13)C2] | General procedure C NH2: 14 mg (0.110 mmol) intermediate 42: 50 mg (0.100 mmol) | 8.4 mg (15%) | Preparative HPLC | $^1$H NMR (400 MHz, DMSO-$d_6$) δ 10.41 (s, 1H), 8.99-8.96 (m, 1H), 8.24 (s, 1H), 8.15 (s, 2H), 7.98 (s, 1H), 7.76-7.74 (m, 1H), 7.50-7.45 (m, 1H), 7.37 (s, 1H), 7.11 (dt, J = 1.2, 6.9 Hz, 1H), 5.32-5.14 (m, 1H), 5.05 (s, 2H), 4.03-3.97 (m, 2H), 3.76-3.66 (m, 2H), 3.10 (s, 2H), 2.88-2.78 (m, 2H), 2.73-2.59 (m, 1H), 2.40-2.34 (m, 1H), 2.26-2.10 (m, 1H), 1.99-1.84 (m, 1H) LC-MS (ESI): method 7 $t_R$ = 2.80 min; m/z (M + 1) = 572.4 |
| 52 | 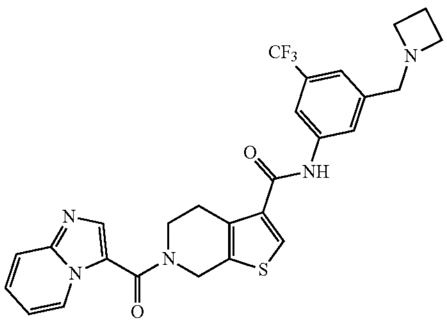 [SMILES: O=C(Nc1cc(CN2CCC2)cc(C(F)(F)F)c1)c1csc2c1CCN(C(=O)c1cnc3ccccn13)C2] | General procedure C NH2: 11 mg (0.120 mmol) intermediate 42: 40 mg (0.080 mmol) | 3.5 mg (8%) | Preparative HPLC | $^1$H NMR (400 MHz, DMSO-$d_6$) δ 10.38 (s, 1H), 8.99-8.96 (m, 1H), 8.23 (s, 1H), 8.15 (s, 1H), 8.11 (s, 1H), 7.93 (s, 1H), 7.76-7.74 (m, 1H), 7.50-7.46 (m, 1H), 7.31 (s, 1H), 7.11 (dt, J = 1.2, 6.9 Hz, 1H), 5.04 (s, 2H), 4.03-3.97 (m, 2H), 3.61 (s, 2H), 3.18 (dd, J = 7.0, 7.0 Hz, 4H), 3.12-3.07 (m, 2H), 2.06-1.98 (m, 2H) LC-MS (ESI): method 7 $t_R$ = 2.74 min; m/z (M + 1) = 540.3 |

-continued

| Example No | Structure | Amount SM | Purification Amount product (yield) | Purification method | Data |
|---|---|---|---|---|---|
| 53 | 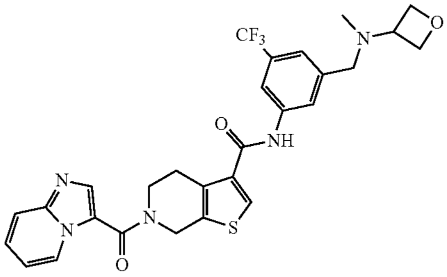 [SMILES: CN(Cc1cc(NC(=O)c2csc3c2CCN(C(=O)c2cnc4ccccn24)C3)cc(C(F)(F)F)c1)C1COC1] | General procedure C NH2: 9.8 μL (0.110 mmol) intermediate 42: 50 mg (0.100 mmol) | 1.2 mg (2%) | Preparative HPLC | $^1$H NMR (400 MHz, DMSO-$d_6$) δ 10.42 (s, 1H), 9.00-8.96 (m, 1H), 8.24 (s, 1H), 8.18-8.14 (m, 2H), 7.96 (s, 1H), 7.77-7.73 (m, 1H), 7.51-7.45 (m, 1H), 7.37 (s, 1H), 7.11 (dt, J = 1.2, 6.9 Hz, 1H), 5.06-5.02 (m, 2H), 4.57 (dd, J = 6.6, 6.6 Hz, 2H), 4.48 (dd, J = 6.2, 6.2 Hz, 2H), 4.03-3.98 (m, 2H), 3.69-3.61 (m, 1H), 3.44 (s, 2H), 3.13-3.07 (m, 2H), 2.01 (s, 3H) LC-MS (ESI): method 7 $t_R$ = 2.75 min; m/z (M + 1) = 570.3 |
| 54 | 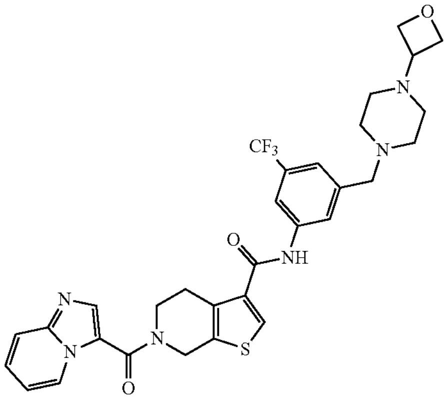 [SMILES: O=C(Nc1cc(CN2CCN(C3COC3)CC2)cc(C(F)(F)F)c1)c1csc2c1CCN(C(=O)c1cnc3ccccn13)C2] | General procedure C NH2: 13 mg (0.088 mmol) intermediate 42: 40 mg (0.080 mmol) | 14 mg (28%) | Preparative HPLC | $^1$H NMR (400 MHz, DMSO-$d_6$) δ 10.40 (s, 1H), 8.98 (td, J = 1.1, 6.8 Hz, 1H), 8.23 (s, 1H), 8.16-8.14 (m, 2H), 7.95 (s, 1H), 7.75 (td, J = 1.1, 9.0 Hz, 1H), 7.51-7.46 (m, 1H), 7.35 (s, 1H), 7.12 (dt, J = 1.2, 6.9 Hz, 1H), 5.04 (s, 2H), 4.53 (t, J = 6.5 Hz, 2H), 4.42 (t, J = 6.1 Hz, 2H), 4.02-3.97 (m, 2H), 3.57 (s, 2H), 3.45-3.38 (m, 1H), 3.12-3.08 (m, 2H), 2.49-2.39 (m, 4H), 2.37-2.24 (m, 4H) LC-MS (ESI): method 7 $t_R$ = 2.74 min; m/z (M + 1) = 625.4 |
| 55 | 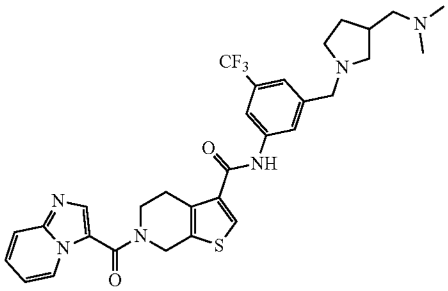 [SMILES: CN(C)CC1CCN(Cc2cc(NC(=O)c3csc4c3CCN(C(=O)c3cnc5ccccn35)C4)cc(C(F)(F)F)c2)C1] | General procedure C NH2: 14 mg (0.110 mmol) intermediate 42: 50 mg (0.100 mmol) | 11.5 mg (19%) | Preparative HPLC | $^1$H NMR (400 MHz, DMSO-$d_6$) δ 10.39 (s, 1H), 8.99-8.97 (m, 1H), 8.23 (s, 1H), 8.15-8.12 (m, 2H), 7.96 (s, 1H), 7.76-7.74 (m, 1H), 7.50-7.45 (m, 1H), 7.35 (s, 1H), 7.11 (dt, J = 1.2, 6.9 Hz, 1H), 5.05 (s, 2H), 4.03-3.97 (m, 2H), 3.69-3.58 (m, 2H), 3.10-3.08 (m, 2H), 2.63-2.57 (m, 1H), 2.35-2.25 (m, 1H), 2.24-2.10 (m, 9H), 1.95-1.84 (m, 1H), 1.45-1.35 (m, 1H). Pyrrolidine $CH_2$ obscured by DMSO. Structure confirmed by HSQC. LC-MS (ESI): method 7 $t_R$ = 2.32 min; m/z (M + 1) = 611.5 |
| 56 | 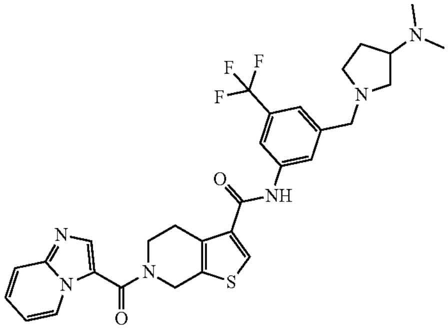 [SMILES: CN(C)C1CCN(Cc2cc(NC(=O)c3csc4c3CCN(C(=O)c3cnc5ccccn35)C4)cc(C(F)(F)F)c2)C1] | General procedure J NH2: 14 μL (0.110 mmol) intermediate 42: 50 mg (0.100 mmol) | 17 mg (29%) | Preparative HPLC | $^1$H NMR (400 MHz, DMSO-$d_6$) δ 10.39 (s, 1H), 8.98 (td, J = 1.0, 7.0 Hz, 1H), 8.23 (s, 1H), 8.15-8.12 (m, 2H), 7.95 (s, 1H), 7.75 (td, J = 1.0, 9.0 Hz, 1H), 7.50-7.46 (m, 1H), 7.35 (s, 1H), 7.11 (dt, J = 1.0, 6.9 Hz, 1H), 5.05 (s, 2H), 4.00 (t, J = 5.5 Hz, 2H), 3.71 (d, J = 13.5 Hz, 1H), 3.58 (d, J = 13.5 Hz, 1H), 3.12-3.06 (m, 2H), 2.76-2.66 (m, 2H), 2.65-2.58 (m, 1H), 2.50-2.45 (m, 1H), 2.35-2.29 (m, 1H), 2.09 (s, 6H), 1.93-1.83 (m, 1H), 1.68-1.59 (m, 1H) LC-MS (ESI): method 6 $t_R$ = 4.24 min; m/z (M + 1) = 597.5 |

-continued

| Example No | Structure | Amount SM | Purification Amount product (yield) | Purification method | Data |
|---|---|---|---|---|---|
| 57 | 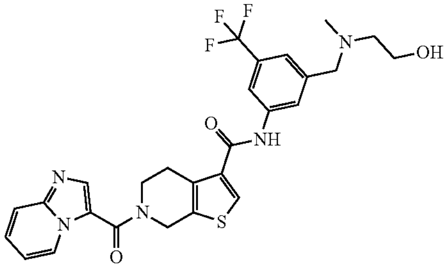 [SMILES: CN(CCO)Cc1cc(NC(=O)c2csc3c2CCN(C(=O)c2cnc4ccccn24)C3)cc(C(F)(F)F)c1] | General procedure J NH2: 9 µL (0.110 mmol) intermediate 42: 50 mg (0.100 mmol) | 17 mg (30%) | Preparative HPLC | $^1$H NMR (400 MHz, DMSO-$d_6$) δ 10.39 (s, 1H), 8.98 (td, J = 1.0, 7.0 Hz, 1H), 8.23 (s, 1H), 8.16-8.12 (m, 2H), 7.95 (s, 1H), 7.75 (td, J = 1.0, 9.0 Hz, 1H), 7.50-7.46 (m, 1H), 7.38 (s, 1H), 7.11 (dt, J = 1.0, 7.0 Hz, 1H), 5.04 (s, 2H), 4.45 (t, J = 5.5 Hz, 1H), 4.02-3.97 (m, 2H), 3.59 (s, 2H), 3.55 (q, J = 6.0 Hz, 2H), 3.11-3.07 (m, 2H), 2.48 (t, J = 6.5 Hz, 2H), 2.20 (s, 3H) LC-MS (ESI): method 7 $t_R$ = 2.68 min; m/z (M + 1) = 558.3 |
| 58 | 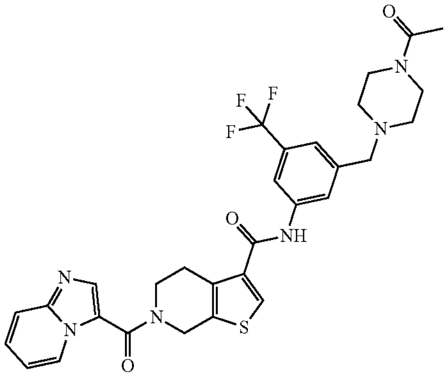 [SMILES: CC(=O)N1CCN(Cc2cc(NC(=O)c3csc4c3CCN(C(=O)c3cnc5ccccn35)C4)cc(C(F)(F)F)c2)CC1] | General procedure J NH2: 15 µL (0.110 mmol) intermediate 42: 50 mg (0.100 mmol) | 9 mg (16%) | Preparative HPLC | $^1$H NMR (400 MHz, DMSO-$d_6$) δ 10.41 (s, 1H), 8.98 (td, J = 1.0, 7.0 Hz, 1H), 8.23 (s, 1H), 8.17-8.15 (m, 2H), 7.98 (s, 1H), 7.75 (td, J = 1.0, 9.0 Hz, 1H), 7.51-7.46 (m, 1H), 7.37 (s, 1H), 7.12 (dt, J = 1.0, 7.0 Hz, 1H), 5.05 (s, 2H), 4.03-3.97 (m, 2H), 3.59 (s, 2H), 3.49-3.44 (m, 4H), 3.12-3.08 (m, 2H), 2.44-2.33 (m, 4H), 2.00 (s, 3H) LC-MS (ESI): method 7 $t_R$ = 2.70 min; m/z (M + 1) = 611.4 |
| 59 | 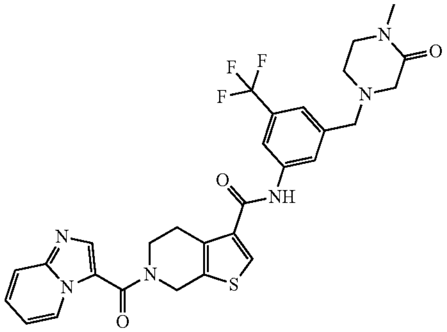 [SMILES: CN1CCN(Cc2cc(NC(=O)c3csc4c3CCN(C(=O)c3cnc5ccccn35)C4)cc(C(F)(F)F)c2)CC1=O] | General procedure J NH2: 13 mg (0.110 mmol) intermediate 42: 50 mg (0.100 mmol) | 13 mg (21%) | Preparative HPLC | $^1$H NMR (400 MHz, DMSO-$d_6$) δ 10.41 (s, 1H), 8.98 (td, J = 1.1, 7.0 Hz, 1H), 8.23 (s, 1H), 8.18-8.15 (m, 2H), 7.99 (s, 1H), 7.76-7.74 (m, 1H), 7.50-7.46 (m, 1H), 7.38 (s, 1H), 7.11 (dt, J = 1.2, 6.9 Hz, 1H), 5.04 (s, 2H), 4.03-3.97 (m, 2H), 3.64 (s, 2H), 3.32-3.27 (m, 2H), 3.12-3.07 (m, 2H), 3.01 (s, 2H), 2.84 (s, 3H), 2.72-2.67 (m, 2H) LC-MS (ESI): method 7 $t_R$ = 3.09 min; m/z (M + 1) = 597.4 |

-continued

| Example No | Structure | Amount SM | Purification Amount product (yield) | Purification method | Data |
|---|---|---|---|---|---|
| 60 | 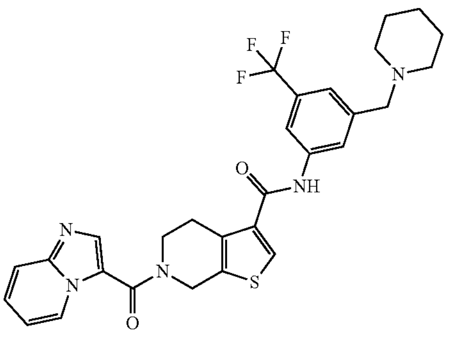 [SMILES: O=C(Nc1cc(CN2CCCCC2)cc(C(F)(F)F)c1)c1csc2c1CCN(C(=O)c1cnc3ccccn13)C2] | General procedure J NH2: 11 μL (0.110 mmol) intermediate 42: 50 mg (0.100 mmol) | 20 mg (34%) | Preparative HPLC | $^1$H NMR (400 MHz, DMSO-$d_6$) δ 10.39 (s, 1H), 8.98 (td, J = 1.1, 6.9 Hz, 1H), 8.24 (s, 1H), 8.16-8.14 (m, 2H), 7.94 (s, 1H), 7.75 (td, J = 1.1, 9.0 Hz, 1H), 7.50-7.46 (m, 1H), 7.34 (s, 1H), 7.11 (dt, J = 1.2, 6.9 Hz, 1H), 5.03 (s, 2H), 4.03-3.97 (m, 2H), 3.52 (s, 2H), 3.12-3.07 (m, 2H), 2.39-2.33 (m, 4H), 1.57-1.49 (m, 4H), 1.43-1.41 (m, 2H) LC-MS (ESI): method 7 $t_R$ = 2.89 min; m/z (M + 1) = 568.4 |
| 61 | 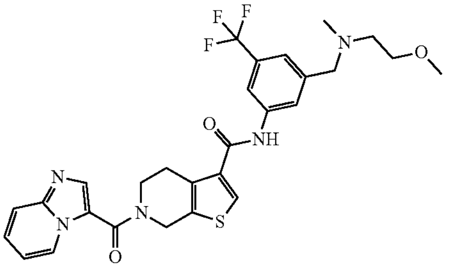 [SMILES: COCCN(C)Cc1cc(NC(=O)c2csc3c2CCN(C(=O)c2cnc4ccccn24)C3)cc(C(F)(F)F)c1] | General procedure J NH2: 12 μL (0.110 mmol) intermediate 42: 50 mg (0.100 mmol) | 22 mg (38%) | Preparative HPLC | $^1$H NMR (400 MHz, DMSO-$d_6$) δ 10.39 (s, 1H), 8.98 (td, J = 1.0, 6.9 Hz, 1H), 8.23 (s, 1H), 8.16-8.13 (m, 2H), 7.95 (s, 1H), 7.75 (td, J = 1.1, 9.1 Hz, 1H), 7.50-7.45 (m, 1H), 7.37 (s, 1H), 7.11 (dt, J = 1.2, 6.9 Hz, 1H), 5.05 (s, 2H), 4.02-3.98 (m, 2H), 3.60 (s, 2H), 3.49 (t, J = 5.9 Hz, 2H), 3.25 (s, 3H), 3.12-3.07 (m, 2H), 2.57 (t, J = 5.8 Hz, 2H), 2.20 (s, 3H) LC-MS (ESI): method 7 $t_R$ = 2.82 min; m/z (M + 1) = 572.3 |

Example 62; Preparation of 6-(imidazo[1,2-a]pyridine-3-carbonyl)-N-(3-(2-(4-methylpiperazin-1-yl)ethoxy)-5-(trifluoromethyl)phenyl)-4,5,6,7-tetrahydrothieno[2,3-c]pyridine-3-carboxamide (Example 62)

Example 62

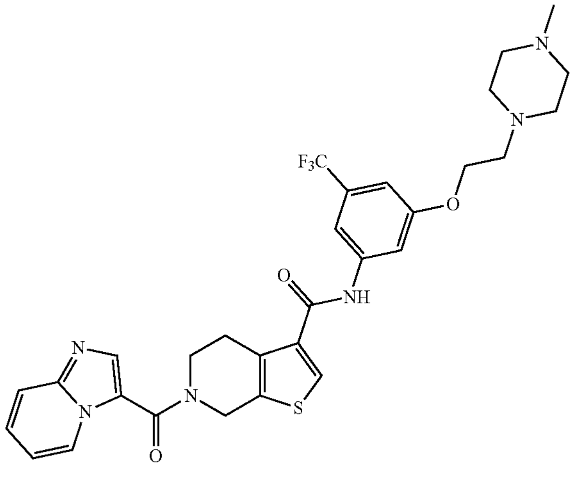

Step 1; tert-butyl 4-(2-(3-(6-(imidazo[1,2-a]pyridine-3-carbonyl)-4,5,6,7-tetrahydrothieno[2,3-c]pyridine-3-carboxamido)-5-(trifluoromethyl)phenoxy)ethyl)piperazine-1-carboxylate (Intermediate 43)

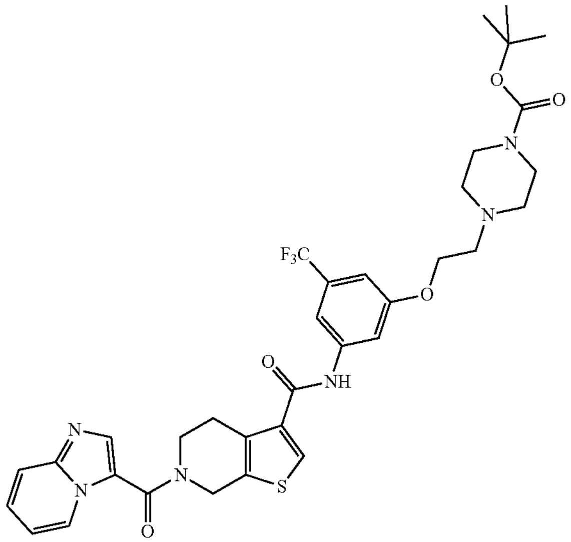 [SMILES: CC(C)(C)OC(=O)N1CCN(CCOc2cc(NC(=O)c3csc4c3CCN(C(=O)c3cnc5ccccn35)C4)cc(C(F)(F)F)c2)CC1]

Intermediate 40 was converted into its free acid form by dissolution in organic solvent followed by acidic washings, dried over sodium sulphate and evaporation under vacuum to give Intermediate 40 as free acid (150 mg, 0.458 mmol), then it was reacted with intermediate 19 (178 mg, 0.458 mmol)) according to general procedure H. Purification by FCC on silica gel (Eluent A=3:1 AcOEt/Ethanol; eluent B=Cyclohexane; gradient=from 0% eluent A to 100% eluent A) gave the title compound (210 mg, 61%).

$^1$H NMR (400 MHz, $CDCl_3$) δ 9.04 (d, J=6.8 Hz, 1H), 8.12 (s, 1H), 7.98-7.97 (m, 1H), 7.70 (d, J=9.1 Hz, 1H), 7.67 (s, 1H), 7.40-7.35 (m, 1H), 7.32 (s, 1H), 7.00-6.96 (m, 1H), 6.93 (s, 1H), 5.03-5.01 (m, 2H), 4.16 (t, J=5.6 Hz, 2H), 4.10 (q, J=4.5 Hz, 2H), 3.45 (t, J=5.1 Hz, 4H), 3.29-3.21 (m, 2H), 2.85-2.81 (m, 2H), 2.53-2.51 (m, 4H), 1.46 (s, 9H)

Step 2; 6-(imidazo[1,2-a]pyridine-3-carbonyl)-N-(3-(2-(piperazin-1-yl)ethoxy)-5-(trifluoromethyl)phenyl)-4,5,6,7-tetrahydrothieno[2,3-c]pyridine-3-carboxamide (Intermediate 44)

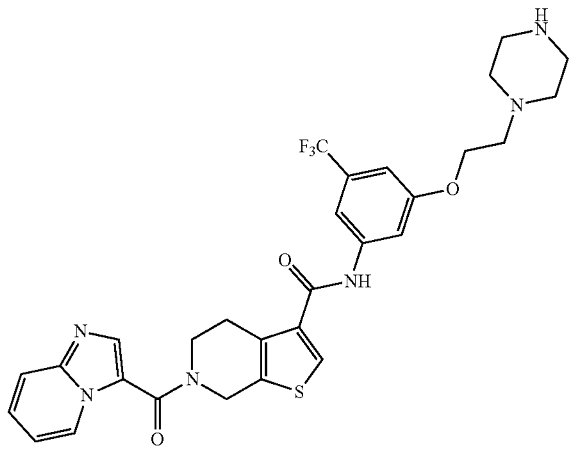 [SMILES: O=C(Nc1cc(OCCN2CCNCC2)cc(C(F)(F)F)c1)c1csc2c1CCN(C(=O)c1cnc3ccccn13)C2]

A solution Intermediate 43 (70 mg, 0.10 mmol, 1.00 eq) in MeOH (1.00 mL) was treated with 4 M HCl in dioxane (0.4 mL, 1.2 mmol, 10.0 eq) at 20° C. and the resulting reaction mixture was stirred for 1 h. The reaction mixture was concentrated under reduced pressure. The residue was purified by Prep HPLC (Sunfire C18® 19×150 mm, 10 um 5-60% ACN/H2O (0.1% TFA), 20 ml/min, RT) and the residue lyophilized to give the title compound (24.3 mg, 13.6%).

$^1$H NMR (400 MHz, MeOD-$d_3$) δ 9.16 (d, J=9.2 Hz, 1H), 8.45 (s, 1H), 8.11 (s, 1H), 7.96 (d, J=3.5 Hz, 3H), 7.76 (s, 1H), 7.61 (s, 1H), 7.50-7.46 (m, 1H), 7.02 (s, 1H), 5.14-5.12 (m, 2H), 4.28 (t, J=5.2 Hz, 2H), 4.13 (t, J=5.8 Hz, 2H), 3.32-3.30 (m, 4H), 3.25-3.16 (m, 2H), 3.04 (t, J=5.1 Hz, 2H), 2.97 (t, J=5.1 Hz, 4H)

Step 3; 6-(imidazo[1,2-a]pyridine-3-carbonyl)-N-(3-(2-(4-methylpiperazin-1-yl)ethoxy)-5-(trifluoromethyl)phenyl)-4,5,6,7-tetrahydrothieno[2,3-c]pyridine-3-carboxamide (Example 62)

A suspension of Intermediate 44 (120 mg, 0.200 mmol, 1.00 eq) in a mixture of THF (2.00 mL) and MeOH (2.00 mL) was successively treated with formaldehyde solution (37%, 0.037 mL, 0.501 mmol, 2.50 eq) and $NaBH_3CN$ (21 mg, 0.341 mmol, 1.70 eq) and the resulting mixture was stirred at 20° C. for 1 h. The reaction mixture was partitioned between DCM and saturated $NaHCO_{3(aq)}$, the organic phase was washed with saturated $NaCl_{(aq)}$, dried ($MgSO_4$) and concentrated. The residue was purified by Prep HPLC (Xbridge Phenyl® 19×150 mm, 10 um 40-100% MeOH/$H_2O$ (10 mM $NH_4CO_3$), 20 ml/min, RT) and the residue lyophilized to give the title compound (37.4 mg, 30.6%).

$^1$H NMR (400 MHz, DMSO-$d_6$) δ 10.34 (s, 1H), 8.98 (d, J=7.0 Hz, 1H), 8.20 (s, 1H), 8.15 (s, 1H), 7.78-7.74 (m, 2H), 7.67 (s, 1H), 7.50-7.46 (m, 1H), 7.14-7.09 (m, 1H), 7.01 (s, 1H), 5.06-5.02 (m, 2H), 4.18-4.13 (m, 2H), 4.00 (t, J=5.6 Hz, 2H), 3.09-3.07 (m, 2H), 2.74-2.70 (m, 2H), 2.53-2.50 (m, 4H), 2.35-2.33 (m, 4H), 2.16 (s, 3H).

LC-MS (ESI) method 7: $t_R$=2.88 min; m/z (M+1)=613

Example 63: Preparation of 6-(imidazo[1,2-a]pyridine-3-carbonyl)-N-[3-(1-methylpyrrolidin-3-yl)oxy-5-(trifluoromethyl)phenyl]-5,7-dihydro-4H-thieno[2,3-c]pyridine-3-carboxamide Example 63

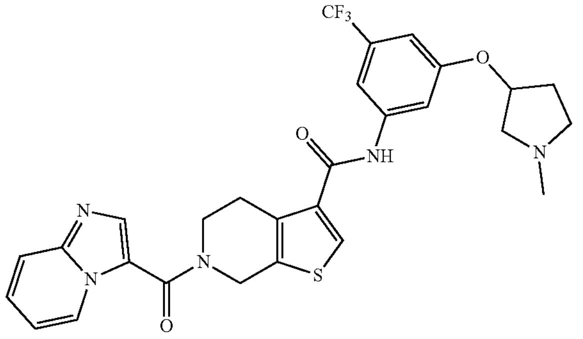

Step 1: tert-butyl 3-(3-(6-(imidazo[1,2-a]pyridine-3-carbonyl)-4,5,6,7-tetrahydrothieno[2,3-c]pyridine-3-carboxamido)-5-(trifluoromethyl)phenoxy)pyrrolidine-1-carboxylate (Intermediate 45)

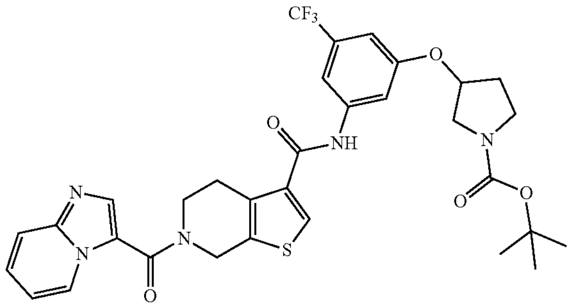 [SMILES: CC(C)(C)OC(=O)N1CCC(Oc2cc(NC(=O)c3csc4c3CCN(C(=O)c3cnc5ccccn35)C4)cc(C(F)(F)F)c2)C1]

Intermediate 40 was converted into its free acid by deblocking the salt as described in Example 62, step 1, (80 mg, 0.244 mmol) and reacted with tert-butyl 3-[3-amino-5-(trifluoromethyl)phenoxy]pyrrolidine-1-carboxylate (85 mg, 0.244 mmol, intermediate 29) according to general procedure H. The residue was purified by FCC on silica gel (AcOEt/cyclohexane from 0% to 100%, followed by AcOEt/EtOH 75%/25%) to yield the title compound.

$^1$H NMR (400 MHz, $CDCl_3$) δ 9.02 (d, J=6.8 Hz, 1H), 8.44-8.37 (m, 1H), 7.99-7.95 (m, 1H), 7.72-7.65 (m, 2H), 7.37 (t, J=9.8 Hz, 2H), 6.97 (t, J=6.7 Hz, 2H), 6.86 (s, 1H), 4.96 (s, 1H), 4.14-4.05 (m, 4H), 3.63 (s, 2H), 3.59-3.44 (m, 2H), 3.23-3.21 (m, 2H), 2.24-2.12 (m, 2H), 1.47 (s, 9H)

Step 2: 6-(imidazo[1,2-a]pyridine-3-carbonyl)-N-(3-(pyrrolidin-3-yloxy)-5-(trifluoromethyl)phenyl)-4,5,6,7-tetrahydrothieno[2,3-c]pyridine-3-carboxamide (Intermediate 46)

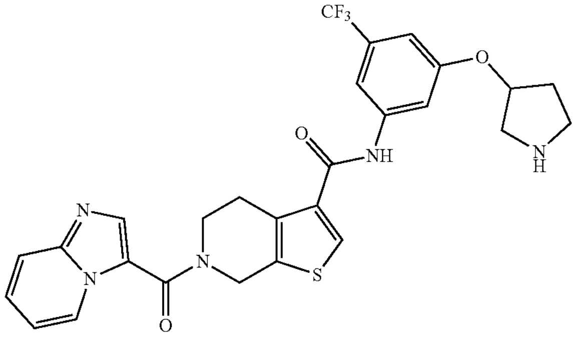 [SMILES: O=C(Nc1cc(OC2CCNC2)cc(C(F)(F)F)c1)c1csc2c1CCN(C(=O)c1cnc3ccccn13)C2]

A solution of Intermediate 45 (90 mg, 0.137 mmol, 1.00 eq,) in methyl alcohol (1.00 mL) at room temperature was treated with 4 M HCl in dioxane (0.69 mL, 2.75 mmol, 20.0 eq). The reaction mixture was stirred at room temperature for 30 mins and then concentrated under reduced pressure to give the HCl salt of the title compound in quantitative yield (81 mg, quantitative).

Step 3: 6-(imidazo[1,2-a]pyridine-3-carbonyl)-N-[3-(1-methylpyrrolidin-3-yl)oxy-5-(trifluoromethyl)phenyl]-5,7-dihydro-4H-thieno[2,3-c]pyridine-3-carboxamide (Example 63)

A suspension of Intermediate 46 (81 mg, 0.137 mmol, 1.00 eq) in THF (1 mL) and MeOH (1 mL) was successively treated with formaldehyde solution (37%, 0.025 mL, 0.342 mmol, 2.50 eq) and sodium cyanoborohydride (15 mg, 0.233 mmol, 1.70 eq) and the resulting mixture was stirred at room temperature overnight. A further portion of MeOH (1 mL) was added until all the solids dissolved and stirring continued at room temperature for one hour. The reaction mixture was partitioned between DCM and saturated $NaHCO_{3(aq)}$. The organic layer was washed with saturated $NaCl_{(aq)}$, dried ($Na_2SO_4$) and concentrated under vacuum. The crude material was purified by preparative HPLC (Luna Phenyl-Hexyl® 21.2×150 mm, 10 μm 20-80% MeOH/$H_2O$ (0.1% FA), 20 ml/min, RT) to yield the title compound (11 mg, 14%).

$^1$H NMR (400 MHz, DMSO-$d_6$) δ 10.36 (s, 1H), 8.98 (d, J=7.0 Hz, 1H), 8.19 (s, 1H), 8.15 (s, 1H), 7.78 (s, 1H), 7.75 (d, J=9.0 Hz, 1H), 7.61 (s, 1H), 7.51-7.45 (m, 1H), 7.14-7.09 (m, 1H), 6.90 (s, 1H), 5.03 (s, 2H), 4.96-4.91 (m, 1H), 4.00 (t, J=5.7 Hz, 2H), 3.08 (s, 2H), 2.80 (dd, J=6.0, 10.4 Hz, 1H), 2.73-2.62 (m, 2H), 2.42-2.30 (m, 2H), 2.28 (s, 3H), 1.85-1.77 (m, 1H). LC-MS (ESI) method 7: $t_R$=2.92 min; m/z (M+1)=570

Example 64: Preparation of N-(3-(tert-butyl)-1-(2-hydroxyethyl)-1H-pyrazol-5-yl)-6-(imidazo[1,2-a]pyridine-3-carbonyl)-4,5,6,7-tetrahydrothieno[2,3-c]pyridine-3-carboxamide Example 64

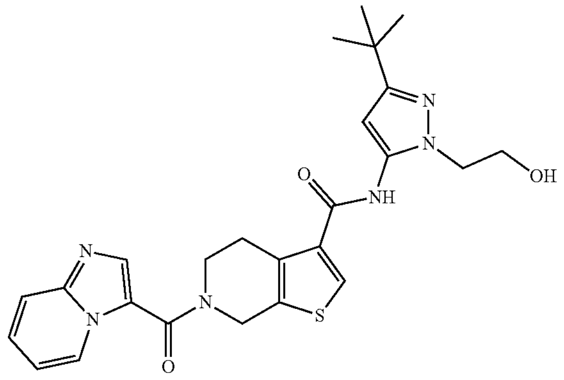

Step 1: N-(3-(tert-butyl)-1-(2-((tert-butyldimethylsilyl)oxy)ethyl)-1H-pyrazol-5-yl)-6-(imidazo[1,2-a]pyridine-3-carbonyl)-4,5,6,7-tetrahydrothieno[2,3-c]pyridine-3-carboxamide (Intermediate 47)

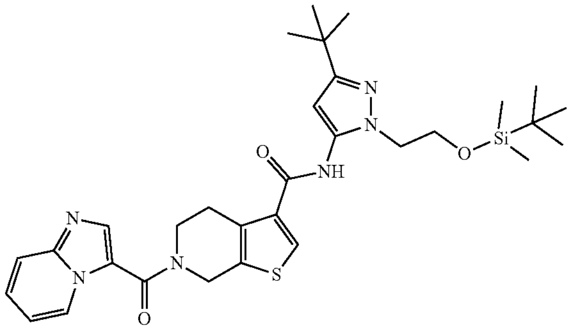 [SMILES: CC(C)(C)c1cc(NC(=O)c2csc3c2CCN(C(=O)c2cnc4ccccn24)C3)n(CCO[Si](C)(C)C(C)(C)C)n1]

Prepared from Intermediate 31 (254 mg, 0.855 mmol,) according to with general procedure I. Purification by FCC on silica gel (AcOEt/cyclohexane from 0% to 100%) gave the title compound (139 mg, 37%).

$^1$H NMR (400 MHz, $CDCl_3$) δ 9.04 (d, J=7.1 Hz, 1H), 8.90 (s, 1H), 7.97 (s, 1H), 7.72-7.67 (m, 2H), 7.40-7.35 (m, 1H), 6.97 (t, J=6.9 Hz, 1H), 6.46 (s, 1H), 5.04 (s, 2H), 4.25 (t, J=4.5 Hz, 2H), 4.12-4.09 (m, 2H), 3.99 (t, J=4.6 Hz, 2H), 3.28-3.24 (m, 2H), 1.31 (s, 9H), 0.76 (s, 9H), −0.09 (s, 6H).

Step 2: N-(3-(tert-butyl)-1-(2-hydroxyethyl)-1H-pyrazol-5-yl)-6-(imidazo[1,2-a]pyridine-3-carbonyl)-4,5,6,7-tetrahydrothieno[2,3-c]pyridine-3-carboxamide (Example 64)

To a solution of intermediate 47 (146 mg, 0.241 mmol) in MeOH (1.60 mL) and THF (0.80 mL) was added 4 M HCl solution in 1,4-dioxane (0.60 mL, 2.41 mmol). The reaction mixture was stirred at room temperature, under an atmosphere of nitrogen, for 2 h. The reaction mixture was concentrated under vacuum (165 mg). A portion (36 mg)

was removed and purification by reverse phase preparative HPLC (Sunfire C18® 19×150 mm, 10 μm 20-80% acetonitrile/water (10 mM $NH_4HCO_3$), 20 mL/min, RT) to give the title compound (18.64 mg, 15%).

$^1$H NMR (400 MHz, DMSO-$d_6$) δ 10.15 (brs, 1H), 8.97 (td, J=1.1, 7.0 Hz, 1H), 8.14 (s, 1H), 8.12 (s, 1H), 7.75 (td, J=1.1, 9.0 Hz, 1H), 7.48 (ddd, J=1.3, 6.8, 9.0 Hz, 1H), 7.11 (dt, J=1.2, 6.9 Hz, 1H), 6.21 (s, 1H), 5.32 (brs, 1H), 5.05 (s, 2H), 4.09 (t, J=5.8 Hz, 2H), 4.03-3.97 (m, 2H), 3.72 (t, J=5.8 Hz, 2H), 3.10-3.04 (m, 2H), 1.25 (s, 9H). LC-MS (ESI) method 7: $t_R$=3.23 min; m/z (M+1)=493.3

Example 65: Preparation of compound N-(3-fluoro-5-(trifluoromethyl)phenyl)-6-(imidazo[1,2-a]pyridin-3-ylmethyl)-4,5,6,7-tetrahydrothieno[2,3-c]pyridine-3-carboxamide Example 65

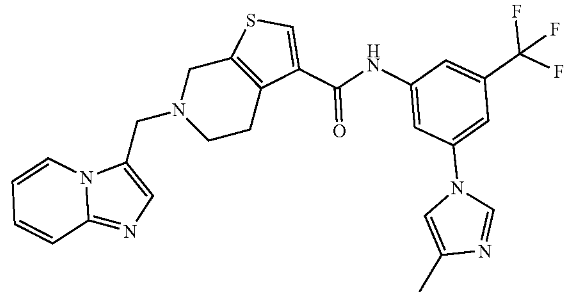

Step 1; ethyl 6-(imidazo[1,2-a]pyridin-3-ylmethyl)-4,5,6,7-tetrahydrothieno[2,3-c]pyridine-3-carboxylate (Intermediate 48)

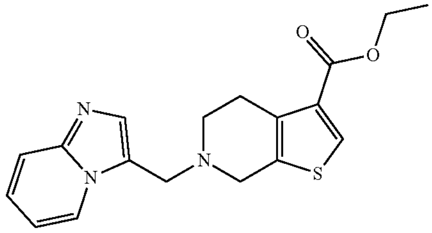 [SMILES: CCOC(=O)c1csc2c1CCN(Cc1cnc3ccccn13)C2]

Intermediate 38 (3.00 g, 12.11 mmol) and imidazo[1,2-a]pyridine-3-carbaldehyde (1.770 g, 12.11 mmol) were placed in a flask under argon. Anhydrous DCM (60.5 ml) was added followed by AcOH (0.693 ml, 12.11 mmol) and TEA (1.688 ml, 12.11 mmol). Reaction mixture was stirred 30 min at rt. Next $NaBH(OAc)_3$ (5.13 g, 24.22 mmol) was added and reaction mixture stirred at rt overweekend. Then reaction mixture was diluted with DCM and washed with a mixture of $K_2CO_3$(sat) and water 1:1. Aqueous phase was extracted with DCM twice, organic phases combined, dried over $MgSO_4$ and evaporated under reduced pressure. The crude was purified via FCC with DCM/MeOH (DCM to 10% MeOH in DCM) to afford the title compound (2.38 g, 6.97 mmol, 58% yield).

$^1$H NMR (300 MHz, $CDCl_3$) δ 8.37 (dt, J=6.9, 1.2 Hz, 1H), 7.93 (s, 1H), 7.64 (dt, J=9.1, 1.2 Hz, 1H), 7.55 (s, 1H), 7.21 (ddd, J=9.1, 6.7, 1.3 Hz, 1H), 6.80 (td, J=6.8, 1.2 Hz, 1H), 4.28 (q, J=7.1 Hz, 2H), 4.02 (s, 2H), 3.63 (s, 2H), 3.03-2.92 (m, 2H), 2.83 (t, J=5.8 Hz, 2H), 1.33 (t, J=7.1 Hz, 3H).

Step 2; sodium 6-(imidazo[1,2-a]pyridin-3-ylmethyl)-4,5,6,7-tetrahydrothieno[2,3-c]pyridine-3-carboxylate (Intermediate 49)

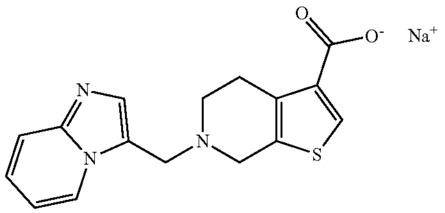 [SMILES: O=C([O-])c1csc2c1CCN(Cc1cnc3ccccn13)C2 ; [Na+]]

To a solution of Intermediate 48 (2.38 g, 6.97 mmol) in MeOH (69.7 ml), NaOH 1M (6.97 ml, 6.97 mmol) was added, reaction mixture was stirred at RT overweekend. Solvent was evaporated under vacuum to afford title compound in quantitative yield.

$^1$H NMR (300 MHz, DMSO-$d_6$) δ 8.48 (dt, J=6.9, 1.3 Hz, 1H), 7.60-7.50 (m, 2H), 7.43 (s, 1H), 7.24 (ddd, J=9.1, 6.7, 1.3 Hz, 1H), 6.91 (td, J=6.8, 1.2 Hz, 1H), 3.99 (s, 2H), 3.57 (s, 2H), 2.85 (t, J=5.8 Hz, 2H), 2.67 (t, J=5.8 Hz, 2H).

Step 3; 6-(imidazo[1,2-a]pyridin-3-ylmethyl)-N-(3-(4-methyl-11H-imidazol-1-yl)-5-(trifluoromethyl)phenyl)-4,5,6,7-tetrahydrothieno[2,3-c]pyridine-3-carboxamide (Example 65)

Intermediate 49 (0.1 g, 0.298 mmol) was dissolved in DMF (0.745 ml) and DCM (2.236 ml) then DIPEA (0.312 ml, 1.789 mmol) and HATU (0.227 g, 0.596 mmol) were added. RM was stirred for 15 minutes and then 3-fluoro-5-(trifluoromethyl)aniline (0.053 g, 0.298 mmol) was added. The reaction was stirred at RT until LCMS indicated consumption of starting material. The reaction mixture was diluted with DCM and water was added. This mixture was stirred 15 min and phases separated, organic phases were washed with water and brine, dryed over $Na_2SO_4$, filtered and concentrated under reduced pressure. Crude material was purified by FC (DCM 100% to 10% MeOH in DCM) to afford the title compound (23 mg, 0.043 mmol, 14% yield)

$^1$H NMR (300 MHz, DMSO-$d_6$) δ 10.48 (s, 1H), 8.49 (d, J=6.8 Hz, 1H), 8.18 (q, J=1.8 Hz, 2H), 8.14 (s, 1H), 8.07 (s, 1H), 7.69 (s, 1H), 7.58 (d, J=9.8 Hz, 2H), 7.46 (d, J=1.5 Hz, 1H), 7.26 (dd, J=8.6, 7.2 Hz, 1H), 6.93 (t, J=6.7 Hz, 1H), 4.05 (s, 2H), 3.67 (s, 2H), 2.86 (d, J=6.5 Hz, 2H), 2.79 (d, J=5.4 Hz, 2H), 2.17 (d, J=1.0 Hz, 3H).

LC-MS (ESI) method 8: $t_R$=1.69 min; m/z (M+1)=537.2

Example 66: Preparation of 6-((1H-pyrazolo[3,4-b]pyridin-5-yl)methyl)-N-(3-(trifluoromethoxy)phenyl)-4,5,6,7-tetrahydrothieno[2,3-c]pyridine-3-carboxamide Example 66

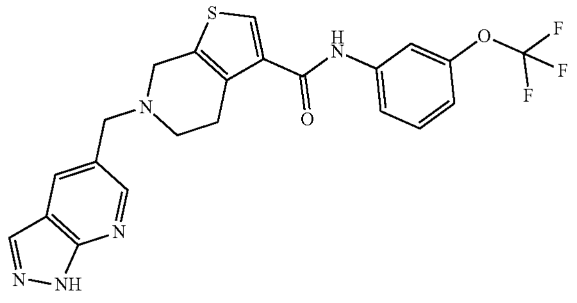

Step 1; ethyl 6-((1H-pyrazolo[3,4-b]pyridin-5-yl)methyl)-4,5,6,7-tetrahydrothieno[2,3-c]pyridine-3-carboxylate (Intermediate 50)

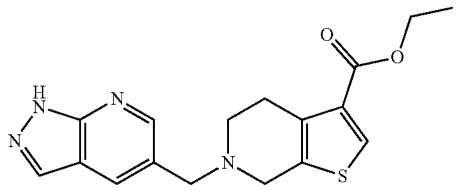 [SMILES: CCOC(=O)c1csc2c1CCN(Cc1cnc3[nH]ncc3c1)C2]

Intermediate 38 (0.73 g, 2.95 mmol) and 1H-pyrazolo[3,4-b]pyridine-5-carbaldehyde (0.650 g, 4.42 mmol) were placed in roundbottom flask under argon. Anhydrous DCM (14.73 ml) was added followed by AcOH (0.169 ml, 2.95 mmol) and TEA (0.205 ml, 1.473 mmol). Reaction mixture was stirred 30 min at rt. Then STAB (1.249 g, 5.89 mmol) was added and reaction mixture stirred at rt overnight. Then reaction mixture was diluted with DCM and washed with a mixture of $K_2CO_{3(sat)}$ and water 1:1. Aqueous phase was extracted with DCM twice, organic phases combined, dried over $MgSO_4$ and evaporated under reduced pressure. The crude was purified by FCC with DCM/MeOH (DCM to 10% MeOH in DCM) to afford the title compound (0.86 g, 2.51 mmol, 85% yield).

$^1$H NMR (300 MHz, DMSO-$d_6$) δ 13.60 (s, 1H), 8.50 (d, J=2.0 Hz, 1H), 8.16 (d, J=2.0 Hz, 1H), 8.12 (s, 1H), 8.11 (d, J=1.3 Hz, 1H), 4.22 (q, J=7.1 Hz, 2H), 3.82 (s, 2H), 3.63 (s, 2H), 2.85 (d, J=5.8 Hz, 2H), 2.75 (t, J=5.7 Hz, 2H), 1.27 (t, J=7.1 Hz, 3H).

Step 2; lithium 6-((1H-pyrazolo[3,4-b]pyridin-5-yl)methyl)-4,5,6,7-tetrahydrothieno[2,3-c]pyridine-3-carboxylate (Intermediate 51)

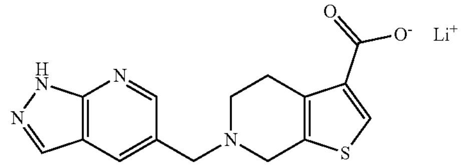 [SMILES: O=C([O-])c1csc2c1CCN(Cc1cnc3[nH]ncc3c1)C2 ; [Li+]]

To a solution of Intermediate 50 (0.86 g, 2.51 mmol,) in MeOH (24 ml), 1M LiOH (5.02 ml, 5.02 mmol) was added, reaction mixture was stirred at 45° C. overnight. The reaction mixture was concentrate under vacuum to obtain the title compound (0.98 g, 3.06 mmol) in quantitative yield.

$^1$H NMR (300 MHz, DMSO-$d_6$) δ 8.05 (d, J=2.1 Hz, 1H), 7.81 (s, 1H), 7.72 (d, J=2.1 Hz, 1H), 7.39 (s, 1H), 3.65 (s, 2H), 3.48 (s, 2H), 2.86 (d, J=5.9 Hz, 2H), 2.65 (t, J=5.8 Hz, 2H).

Step 3; 6-((1H-pyrazolo[3,4-b]pyridin-5-yl)methyl)-N-(3-(trifluoromethoxy)phenyl)-4,5,6,7-tetrahydrothieno[2,3-c]pyridine-3-carboxamide (Example 66)

Intermediate 51 (0.10 g, 0.312 mmol,) was suspended in DMF (0.781 ml) and DCM (2.342 ml) then DIPEA (0.327 ml, 1.873 mmol) and HATU (0.297 g, 0.781 mmol) were added. RM was stirred ~15 minutes and then 3-(trifluoromethoxy)aniline (0.084 ml, 0.624 mmol) was added. The RM was stirred at RT overnight. The crude was cooled down and diluted with DCM and water was added. The mixture was stirred 15 min and phases separated. Organic phases was washed with 5% citric acid, water, brine, dryed over $Na_2SO_4$, filtered and concentrated under reduced pressure.

The crude was purified FCC (DCM to 10% MeOH in DCM) to afford the title compound (7.56 mg, 0.016 mmol, 5.11% yield).

$^1$H NMR (300 MHz, MeOH-$d_4$) δ 8.59 (s, 1H), 8.27 (d, J=2.0 Hz, 1H), 8.12 (s, 1H), 7.95 (s, 1H), 7.79 (s, 1H), 7.59 (d, J=8.2 Hz, 1H), 7.41 (t, J=8.2 Hz, 1H), 7.01 (d, J=8.2 Hz, 1H), 3.92 (s, 2H), 3.75 (s, 2H), 3.04-2.98 (m, 2H), 2.93-2.85 (m, 2H).

LC-MS (ESI) method 3: $t_R$=2.17 min; m/z (M+1)=474.0

The following compounds were prepared via amido coupling as described for Example 66, steps 1-3, applying the corresponding, commercially available aniline in step 3.

| Example No | Structure | Amount Intermediate 51 | Amount product (yield) | Purification method | Data |
|---|---|---|---|---|---|
| 67 | 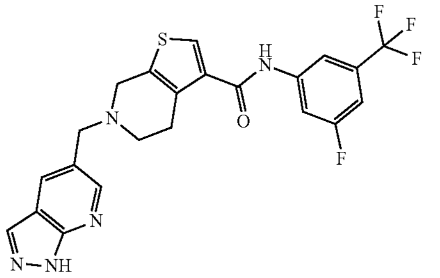 [SMILES: O=C(Nc1cc(F)cc(C(F)(F)F)c1)c1csc2c1CCN(Cc1cnc3[nH]ncc3c1)C2] | 100 mg | 11.5 mg (8%) | Prep HPLC (ACN, $H_2O$ + 0.05% $NH_3$) | $^1$H NMR (300 MHz, MeOH-$d_4$) δ 8.59 (d, J = 2.0 Hz, 1H), 8.27 (d, J = 1.9 Hz, 1H), 8.12 (s, 1H), 7.99 (s, 1H), 7.85 (d, J = 6.4 Hz, 2H), 7.16 (d, J = 8.4 Hz, 1H), 3.92 (s, 2H), 3.75 (s, 2H), 3.05-2.97 (m, 2H), 2.88 (t, J = 5.8 Hz, 2H). LC-MS (ESI): method 8 $t_R$ = 2.74 min; m/z (M + 1) = 476.0 |
| 133 | 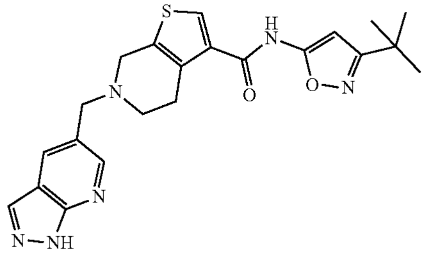 [SMILES: CC(C)(C)c1cc(NC(=O)c2csc3c2CCN(Cc2cnc4[nH]ncc4c2)C3)on1] | 30 mg (as carboxylic acid) | 5.5 mg (13%) | Prep HPLC | $^1$H NMR (400 MHz, DMSO-$d_6$) δ 13.63 (s, 1H), 11.70-11.70 (m, 1H), 8.53 (d, J = 2.0 Hz, 1H), 8.27 (s, 1H), 8.18 (d, J = 1.7 Hz, 1H), 8.13 (d, J = 0.9 Hz, 1H), 6.36 (s, 1H), 3.84 (s, 2H), 3.65 (s, 2H), 2.92-2.87 (m, 2H), 2.77 (t, J = 5.8 Hz, 2H), 1.29 (s, 9H) LC-MS (ESI): method 7 $t_R$ = 3.02 min; m/z [M + H]+ = 437.3 |
| 134 | 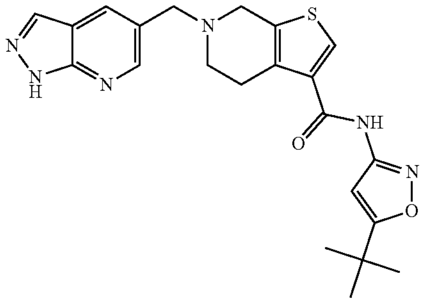 [SMILES: CC(C)(C)c1cc(NC(=O)c2csc3c2CCN(Cc2cnc4[nH]ncc4c2)C3)no1] | 30 mg (as carboxylic acid) | 7 mg (16%) | Prep HPLC | $^1$H NMR (400 MHz, DMSO-$d_6$) δ 13.62 (s, 1H), 11.11 (s, 1H), 8.53-8.52 (m, 1H), 8.26 (s, 1H), 8.18 (d, J = 1.5 Hz, 1H), 8.13 (s, 1H), 6.70 (s, 1H), 3.84 (s, 2H), 3.65 (s, 2H), 2.88 (d, J = 4.9 Hz, 2H), 2.80-2.74 (m, 2H), 1.32 (s, 9H) LC-MS (ESI): method 6 $t_R$ = 4.36 min; m/z [M + H]+ = 437.4 |

Example 68: Preparation of 6-(1H-pyrrolo[2,3-b]pyridine-5-carbonyl)-N-(3-(trifluoromethyl)phenyl)-4,5,6,7-tetrahydrothieno[2,3-c]pyridine-3-carboxamide Example 68

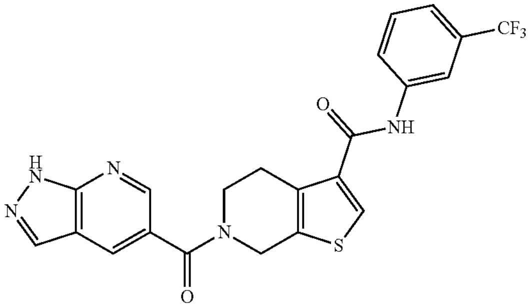

Step 1; ethyl 6-(1H-pyrrolo[2,3-b]pyridine-5-carbonyl)-4,5,6,7-tetrahydrothieno[2,3-c]pyridine-3-carboxylate (Intermediate 52)

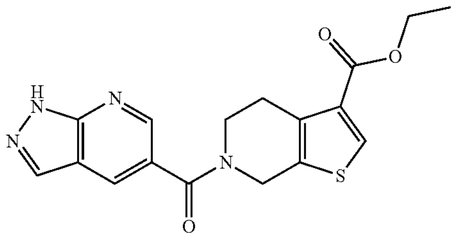 [SMILES: CCOC(=O)c1csc2c1CCN(C(=O)c1cnc3[nH]ncc3c1)C2]

To a solution Intermediate 38 (5 g, 20.18 mmol) and 1H-pyrrolo[2,3-b]pyridine-5-carboxylic acid (3.27 g, 20.18 mmol) in DCM (101 ml), DIPEA (28.2 ml, 161 mmol) was added followed by T3P (24.03 ml, 40.4 mmol) and RM was stirred at RT overnight. The reaction mixture was diluted with DCM, Water was added and this mixture was stirred for 10 min. Then the phases were separated, aqueous phases washed with DCM (3×50 mL), combined organic phases washed with brine, dryed over $Na_2SO_4$, filtrated and concentrated under reduced pressure. The crude was purified via FC with DCM:MeOH (DCM to 5% MeOH) to afford the title compound (1.57 g, 4.42 mmol, 22% yield)

$^1H$ NMR (300 MHz, CDCl3) δ 10.50 (s, 1H), 8.51 (d, J=2.0 Hz, 1H), 8.16 (d, J=2.0 Hz, 1H), 8.03 (s, 1H), 7.47 (d, J=3.6 Hz, 1H), 6.61 (d, J=3.6 Hz, 1H), 4.91 (s, 2H), 4.31 (q, J=7.1 Hz, 2H), 3.83 (s, 2H), 3.12 (d, J=6.2 Hz, 2H), 1.37 (t, J=7.1 Hz, 3H).

Step 2; sodium 6-(1H-pyrrolo[2,3-b]pyridine-5-carbonyl)-4,5,6,7-tetrahydrothieno[2,3-c]pyridine-3-carboxylate (Intermediate 53)

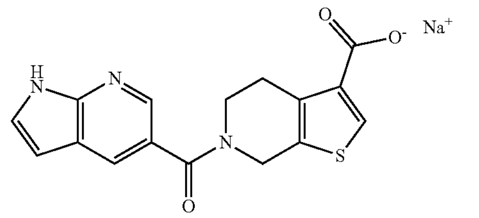 [SMILES: O=C([O-])c1csc2c1CCN(C(=O)c1cnc3[nH]ccc3c1)C2 ; [Na+]]

To a solution of Intermediate 52 (1.6 g, 4.50 mmol) in MeOH (45.0 ml), 1M NaOH (6.75 ml, 4.92 mmol) was added, reaction mixture was stirred at RT overweekend. Solvent was evaporated under reduce pressure to afford the title compound (1.52 g, 4.35 mmol, 97% yield).

$^1H$ NMR (300 MHz, DMSO-$d_6$) δ 8.22 (d, J=2.1 Hz, 1H), 7.96 (d, J=2.1 Hz, 1H), 7.60 (s, 1H), 7.56 (d, J=3.0 Hz, 1H), 6.42 (d, J=3.0 Hz, 1H), 4.76 (s, 2H), 3.71 (s, 2H), 3.04 (t, J=5.8 Hz, 2H).

Step 3; 6-(1H-pyrrolo[2,3-b]pyridine-5-carbonyl)-N-(3-(trifluoromethyl)phenyl)-4,5,6,7-tetrahydrothieno[2,3-c]pyridine-3-carboxamide (Example 68)

Intermediate 53 (0.1 g, 0.286 mmol) and HATU (0.218 g, 0.573 mmol) were weighed in a reaction tube which was backfilled with argon (×3). The reagents were suspended in DCM (2.147 ml) and DMF (0.716 ml). DIPEA (0.400 ml, 2.290 mmol) was then added to the reaction mixture. After stirring for 15 mins, 3-(Trifluoromethyl)aniline (0.036 ml, 0.286 mmol) was added. The reaction mixture was stirred over 60 h at rt. The crude was transferred to a separatory funnel and washed with water (×3). The desired compound was extracted with DCM and the organic layers combined and washed with brine (×1). The organic layer was concentrated under vacuum and the crude material purified by preparative HPLC to yield the desired compound as a formate salt. The salt was washed with 1:1 $NaHCO_{3(sat)}$:$H_2O$ solution and the desired compound extracted with DCM (×3). The combined organic layers were dried with $Na_2SO_4$, filtered and concentrated under vacuum to yield the title compound (10 mg, 0.021 mmol, 7.43% yield).

$^1H$ NMR (300 MHz, DMSO-$d_6$) δ 11.93 (s, 1H), 10.40 (s, 1H), 8.34 (d, J=2.0 Hz, 1H), 8.20 (d, J=2.4 Hz, 2H), 8.10 (d, J=2.0 Hz, 1H), 7.97 (d, J=8.5 Hz, 1H), 7.65-7.53 (m, 2H), 7.44 (d, J=8.0 Hz, 1H), 6.55 (dd, J=3.5, 1.8 Hz, 1H), 4.86 (s, 2H), 3.75 (s, 2H), 2.99 (s, 2H).

LC-MS (ESI) method 3: $t_R$=3.14 min; m/z (M+1)=471.1

Example 69: Preparation of 6-((1H-pyrrolo[2,3-b]pyridin-5-yl)methyl)-N-(3-(trifluoromethyl)phenyl)-4,5,6,7-tetrahydrothieno[2,3-c]pyridine-3-carboxamide Example 69

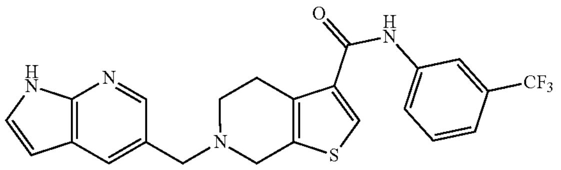

Step 1; ethyl 6-((1H-pyrrolo[2,3-b]pyridin-5-yl)methyl)-4,5,6,7-tetrahydrothieno[2,3-c]pyridine-3-carboxylate (Intermediate 54)

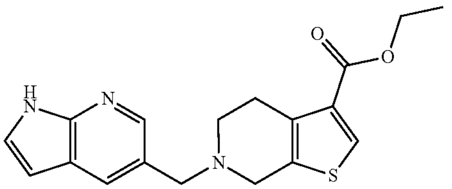 [SMILES: CCOC(=O)c1csc2c1CCN(Cc1cnc3[nH]ccc3c1)C2]

Intermediate 38 (3.00 g, 12.11 mmol,) and imidazo[1,2-a]pyridine-3-carbaldehyde (1.770 g, 12.11 mmol) were placed in a flask under argon. Anhydrous DCM (60.5 ml) was added followed by AcOH (0.693 ml, 12.11 mmol) and TEA (1.688 ml, 12.11 mmol). Reaction mixture was stirred 30 min at rt. Next STAB (5.13 g, 24.22 mmol) was added and reaction mixture stirred at rt overweekend. Then reaction mixture was diluted with DCM and washed with a mixture of $K_2CO_{3(sat)}$ and water 1:1. Aqueous phase was extracted with DCM twice, organic phases combined, dried over $MgSO_4$ and evaporated under reduced pressure. The crude was purified via FCC with DCM/MeOH (DCM to 10% MeOH in DCM) to afford the title compound (2.24 g, 6.56 mmol, 52% yield).

$^1H$ NMR (300 MHz, $CDCl_3$) δ 10.41 (s, 1H), 8.35 (d, J=2.0 Hz, 1H), 8.02 (d, J=2.0 Hz, 1H), 7.94 (s, 1H), 7.37 (dd, J=3.6, 1.9 Hz, 1H), 6.50 (dd, J=3.6, 1.5 Hz, 1H), 4.29 (q, J=7.1 Hz, 2H), 3.88 (s, 2H), 3.73 (s, 2H), 3.05 (t, J=5.9 Hz, 2H), 2.90 (t, J=5.8 Hz, 2H), 1.34 (t, J=7.1 Hz, 3H).

Step 2; sodium 6-((1H-pyrrolo[2,3-b]pyridin-5-yl)methyl)-4,5,6,7-tetrahydrothieno[2,3-c]pyridine-3-carboxylate (Intermediate 55)

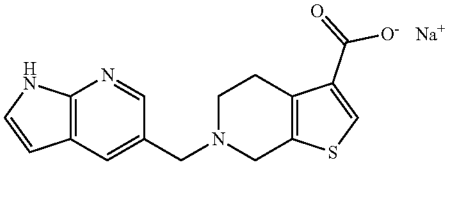 [SMILES: O=C([O-])c1csc2c1CCN(Cc1cnc3[nH]ccc3c1)C2 ; [Na+]]

To a solution of Intermediate 54 (2.24 g, 6.56 mmol,) in MeOH (65.6 ml), NaOH 1M (6.56 ml, 6.56 mmol) was added, reaction mixture was stirred at 40° C. overnight. Solvent was evaporated under vacuum to afford the title compound in quantitative yield.

$^1$H NMR (300 MHz, DMSO-$d_6$) δ 8.05 (d, J=2.0 Hz, 1H), 7.77 (d, J=2.0 Hz, 1H), 7.43 (d, J=3.3 Hz, 2H), 6.29 (d, J=3.0 Hz, 1H), 3.69 (s, 2H), 3.51 (s, 2H), 2.88 (d, J=5.8 Hz, 2H), 2.66 (t, J=5.8 Hz, 2H).

Step 3: 6-((1H-pyrrolo[2,3-b]pyridin-5-yl)methyl)-N-(3-(trifluoromethyl)phenyl)-4,5,6,7-tetrahydrothieno[2,3-c]pyridine-3-carboxamide (Example 69)

Intermediate 55 (0.1 g, 0.298 mmol) was dissolved in DMF (0.745 ml) and DCM (2.236 ml) then DIPEA (0.312 ml, 1.789 mmol) and HATU (0.227 g, 0.596 mmol) were added. RM was stirred for 15 minutes and then 3-(trifluoromethyl)aniline (0.045 ml, 0.358 mmol) was added. The reaction was stirred at RT until LCMS indicated consumption of starting material or an appreciable conversion in DP. The reaction mixture was diluted with DCM quenched with 5% citric acid. The layers were separated, the organic layer was washed again with 5% citric acid aq solution (note: semi-solid product stuck to glass). Combined organic layer was washed with sat. $NaHCO_3$ aq solution and brine. The crude product was purified via Prep HPLC to afford the title compound (18 mg, 0.039 mmol, 13% yield).

$^1$H NMR (300 MHz, DMSO-$d_6$) δ 11.59 (s, 1H), 10.33 (s, 1H), 8.19 (d, J=2.0 Hz, 2H), 8.09 (s, 1H), 7.96 (d, J=8.2 Hz, 1H), 7.91 (d, J=2.0 Hz, 1H), 7.57 (t, J=8.0 Hz, 1H), 7.49-7.38 (m, 2H), 6.42 (dd, J=3.4, 1.9 Hz, 1H), 3.78 (s, 2H), 3.62 (s, 2H), 2.86 (t, J=5.7 Hz, 2H), 2.75 (t, J=5.7 Hz, 2H).

LC-MS (ESI) method 3: $t_R$=1.93 min; m/z (M+1)=457.0

The following compounds were prepared via amido coupling as described for Example 69, steps 1-3, applying the corresponding, commercially available or previously synthesized amine in step 3.

| Example No | Structure | Amount Intermediate 55 | Amount product (yield) | Purification method | Data |
|---|---|---|---|---|---|
| 70 | 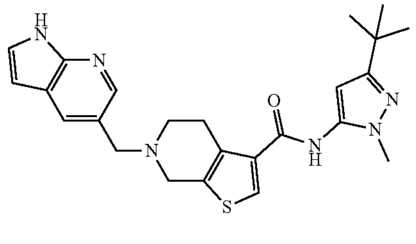 [SMILES: Cn1nc(C(C)(C)C)cc1NC(=O)c1csc2c1CCN(Cc1cnc3[nH]ccc3c1)C2] | 100 mg | 10 mg (7%) | Preparative HPLC followed by washing with $NaHCO_3$ saturated solution followed by Preparative TLC | $^1$H NMR (300 MHz, DMSO-$d_6$) δ 11.60 (s, 1H), 9.96 (s, 1H), 8.19 (d, J = 2.0 Hz, 1H), 8.04 (s, 1H), 7.91 (d, J = 2.0 Hz, 1H), 7.46 (d, J = 3.4 Hz, 1H), 6.42 (d, J = 3.4 Hz, 1H), 6.08 (s, 1H), 3.78 (s, 2H), 3.61 (d, J = 4.8 Hz, 5H), 2.86 (s, 2H), 2.76 (d, J = 5.5 Hz, 2H), 1.22 (s, 9H). LC-MS (ESI): method 3 $t_R$ = 1.46 min; m/z (M + 1) = 449.0 |
| 71 | 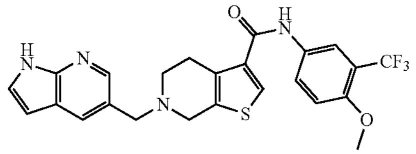 [SMILES: COc1ccc(NC(=O)c2csc3c2CCN(Cc2cnc4[nH]ccc4c2)C3)cc1C(F)(F)F] | 100 mg | 36 mg (25%) | Reverse Phase FCC + Preparative TLC | $^1$H NMR (300 MHz, DMSO-$d_6$) δ 11.59 (s, 1H), 10.13 (s, 1H), 8.19 (d, J = 2.0 Hz, 1H), 8.09-8.00 (m, 2H), 7.97-7.87 (m, 2H), 7.45 (dd, J = 3.4, 2.5 Hz, 1H), 7.25 (d, J = 9.1 Hz, 1H), 6.42 (dd, J = 3.4, 1.8 Hz, 1H), 3.87 (s, 3H), 3.78 (s, 2H), 3.62 (s, 2H), 2.86 (d, J = 5.6 Hz, 2H), 2.75 (t, J = 5.6 Hz, 2H). LC-MS (ESI): method 3 $t_R$ = 1.90 min; m/z (M + 1) = 487.1 |
| 72 | 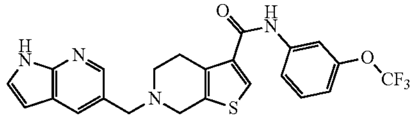 [SMILES: O=C(Nc1cccc(OC(F)(F)F)c1)c1csc2c1CCN(Cc1cnc3[nH]ccc3c1)C2] | 80 mg | 20 mg (18%) | FCC | $^1$H NMR (300 MHz, DMSO-$d_6$) δ 11.59 (s, 1H), 10.29 (s, 1H), 8.19 (d, J = 2.0 Hz, 1H), 8.06 (s, 1H), 7.91 (d, J = 2.0 Hz, 1H), 7.87 (s, 1H), 7.68 (dt, J = 8.6, 1.1 Hz, 1H), 7.51-7.39 (m, 2H), 7.10-7.00 (m, 1H), 6.42 (dd, J = 3.4, 1.8 Hz, 1H), 3.78 (s, 2H), 3.62 (s, 2H), 2.85 (d, J = 5.6 Hz, 2H), 2.76 (d, J = 5.3 Hz, 2H). LC-MS (ESI): method 3 $t_R$ = 1.99 min; m/z (M + 1) = 473.1 |
| 73 | 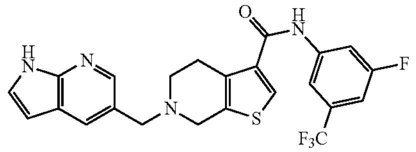 [SMILES: O=C(Nc1cc(F)cc(C(F)(F)F)c1)c1csc2c1CCN(Cc1cnc3[nH]ccc3c1)C2] | 80 mg | 3 mg (3%) | Preparative HPLC | $^1$H NMR (300 MHz, DMSO-$d_6$) δ 11.60 (s, 1H), 10.53 (s, 1H), 8.19 (d, J = 2.0 Hz, 1H), 8.12 (s, 1H), 7.99-7.88 (m, 3H), 7.45 (d, J = 3.4 Hz, 1H), 7.35 (d, J = 8.5 Hz, 1H), 6.42 (d, J = 3.4 Hz, 1H), 3.78 (s, 2H), 3.62 (s, 2H), 2.90-2.82 (m, 2H), 2.80-2.70 (m, 2H). LC-MS (ESI): method 3 $t_R$ = 2.12 min; m/z (M + 1) = 475.0 |

Example 74: Preparation of 6-(imidazo[1,2-a]pyridine-3-carbonyl)-N-(3-(4-methyl-1H-imidazol-1-yl)-5-(trifluoromethyl)phenyl)-4,5,6,7-tetrahydrothieno[2,3-c]pyridine-3-carboxamide Example 74

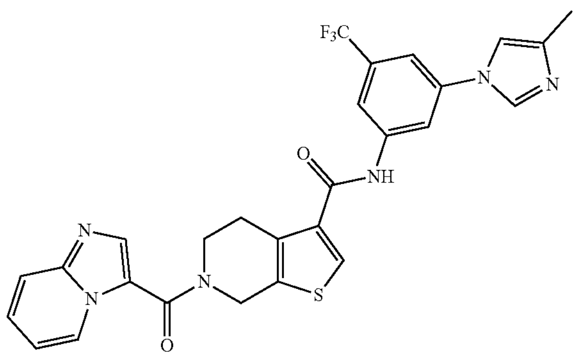

Step 1; tert-butyl 3-((3-(4-methyl-1H-imidazol-1-yl)-5-(trifluoromethyl)phenyl)carbamoyl)-4,7-dihydrothieno[2,3-c]pyridine-6(5H)-carboxylate (Intermediate 56)

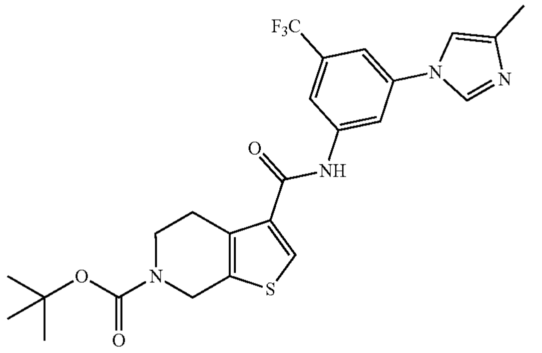 [SMILES: Cc1cn(-c2cc(NC(=O)c3csc4c3CCN(C(=O)OC(C)(C)C)C4)cc(C(F)(F)F)c2)cn1]

To a solution 6-(tert-butoxycarbonyl)-4,5,6,7-tetrahydrothieno[2,3-c]pyridine-3-carboxylic acid (1.5 g, 5.29 mmol) and 3-(4-methyl-1H-imidazol-1-yl)-5-(trifluoromethyl)aniline (1.277 g, 5.29 mmol) in DCM (26.5 ml), DIPEA (5.55 ml, 31.8 mmol) was added followed by T3P (6.30 ml, 10.59 mmol) and RM was stirred at RT overweekend. The reaction mixture was diluted with DCM, water was added and this mixture was stirred for 10 min. Then the phases were separated, aqueous phases washed with DCM (3×50 mL), combined organic phases washed with brine, dried over Na2SO4, filtrated and concentrated. The crude was purified via (DCM to 10% MeOH in DCM) to afford the title compound (362 mg, 0.715 mmol, 13.50% yield).

$^1$H NMR (300 MHz, DMSO-$d_6$) δ 10.52 (s, 1H), 8.19 (q, J=1.9, 1.4 Hz, 3H), 8.07 (d, J=1.9 Hz, 1H), 7.74-7.67 (m, 1H), 7.46 (t, J=1.3 Hz, 1H), 4.60 (s, 2H), 3.58 (t, J=5.8 Hz, 2H), 2.87 (t, J=5.8 Hz, 2H), 2.18 (d, J=1.0 Hz, 3H), 1.43 (s, 9H).

Step 2: N-(3-(4-methyl-1H-imidazol-1-yl)-5-(trifluoromethyl)phenyl)-4,5,6,7-tetrahydrothieno[2,3-c]pyridine-3-carboxamide hydrochloride

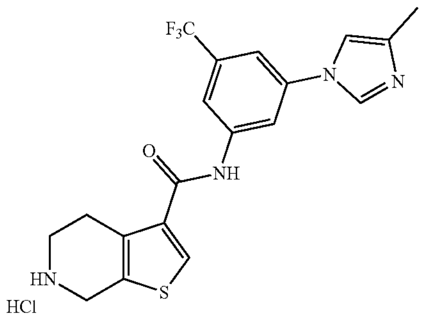 [SMILES: Cc1cn(-c2cc(NC(=O)c3csc4c3CCNC4)cc(C(F)(F)F)c2)cn1 ; Cl]

To a solution of intermediate 56 (0.362 g, 0.715 mmol) in DCM (3.57 ml), 4N HCl in Dioxane (0.893 ml, 3.57 mmol) was added and the RM was stirred at RT overnight. $Et_2O$ was added to RM till no more precipitation was observed, then the precipitate was filtered off to obtain the title compound (0.33 g, 0.745 mmol).

$^1$H NMR (300 MHz, DMSO-$d_6$) δ 11.05 (s, 1H), 9.61 (s, 1H), 9.55 (s, 1H), 8.60 (s, 1H), 8.57 (s, 1H), 8.29 (s, 1H), 7.98 (s, 1H), 7.91 (s, 1H), 4.39 (s, 2H), 3.37 (m, 2H), 3.13 (m, 2H), 2.36 (d, J=1.1 Hz, 3H).

Step 3: 6-(imidazo[1,2-a]pyridine-3-carbonyl)-N-(3-(4-methyl-1H-imidazol-1-yl)-5-(trifluoromethyl)phenyl)-4,5,6,7-tetrahydrothieno[2,3-c]pyridine-3-carboxamide (Example 74)

Imidazo[1,2-a]pyridine-3-carboxylic acid (29.3 mg, 0.181 mmol) was dissolved in anh. DMF (452 μl) and dichloromethane (1355 μl) then DIPEA (252 μl, 1.445 mmol) and HATU (137 mg, 0.361 mmol) were added. RM was stirred for 1 h then Intermediate 57 (80 mg, 0.181 mmol) was added. The RM was stirred at RT overnight. The RM was cooled down, diluted with DCM (15 ml) and quenched with 5% citric acid (10 ml). The phases were separated and organic layer was washed with sat. $NaHCO_3$ $_{(aq)}$. and brine, dried over $Na_2SO_4$ and evaporated. The crude was purified via preparative HPLC (Mobile phase: ACN+ 0.1% FA, $H_2O$+0.1% FA) to afford the title compound (40 mg, 0.073 mmol, 40.2% yield).

$^1$H NMR (300 MHz, DMSO-$d_6$) δ 10.55 (s, 1H), 8.96 (dt, J=7.0, 1.3 Hz, 1H), 8.25-8.18 (m, 3H), 8.14 (d, J=3.8 Hz, 1H), 8.10 (d, J=1.7 Hz, 1H), 7.77-7.68 (m, 2H), 7.51-7.42 (m, 2H), 7.10 (td, J=6.9, 1.2 Hz, 1H), 5.03 (s, 2H), 3.99 (t, J=5.8 Hz, 2H), 3.09 (s, 2H), 2.18 (d, J=1.0 Hz, 3H). LC-MS (ESI) method 8: $t_R$=2.19 min; m/z (M+1)=550.9

Example 75: Preparation of 6-((1H-pyrazolo[3,4-b]pyridin-5-yl)methyl)-N-(3-(tert-butyl)-1-(p-tolyl)-1H-pyrazol-5-yl)-4,5,6,7-tetrahydrothieno[2,3-c]pyridine-3-carboxamide Example 75

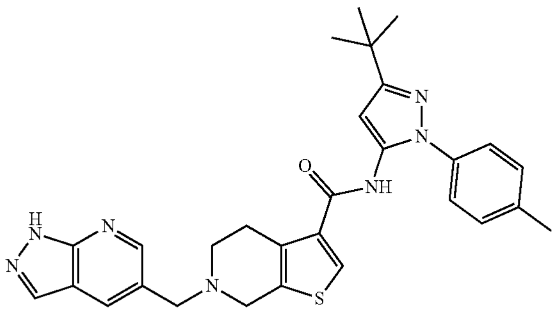

Step 1: sodium 6-(tert-butoxycarbonyl)-4,5,6,7-tetrahydrothieno[2,3-c]pyridine-3-carboxylate (Intermediate 58)

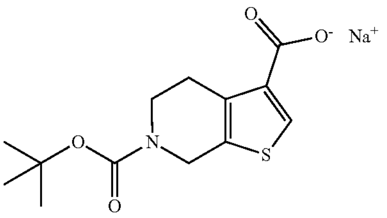 [SMILES: CC(C)(C)OC(=O)N1CCc2c(C(=O)[O-])csc2C1 ; [Na+]]

6-(tert-butyl) 3-ethyl 4,7-dihydrothieno[2,3-c]pyridine-3,6(5H)-dicarboxylate (15 g, 48.2 mmol) was dissolved in MeOH (482 ml) then 1M NaOH (72.3 ml, 72.3 mmol) was added and the RM stirred at RT overnight. The reaction mixture was dried under reduced pressure to obtain the title compound in quantitive yield.

$^{1}$H NMR (300 MHz, DMSO-$d_6$) δ 7.46 (s, 1H), 4.49 (s, 2H), 3.51 (t, J=5.8 Hz, 2H), 2.89 (t, J=5.8 Hz, 2H), 1.41 (s, 9H).

Step 2; tert-butyl 3-((3-(tert-butyl)-1-(p-tolyl)-1H-pyrazol-5-yl)carbamoyl)-4,7-dihydrothieno[2,3-c]pyridine-6(5H)-carboxylate (Intermediate 59)

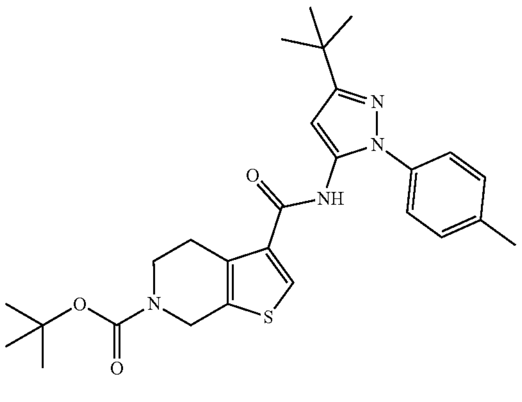 [SMILES: Cc1ccc(-n2nc(C(C)(C)C)cc2NC(=O)c2csc3c2CCN(C(=O)OC(C)(C)C)C3)cc1]

Intermediate 58 (5 g, 16.38 mmol) and HATU (12.45 g, 32.8 mmol) were weighed into a reaction tube which was backfilled with argon (×3). DCM (123 ml) and DMF (40.9 ml) were added to the reaction mixture followed by DIPEA (22.88 ml, 131 mmol). The reaction mixture was stirred for 30 mins then 3-(tert-butyl)-1-(p-tolyl)-1H-pyrazol-5-amine (3.49 g, 15.22 mmol) was added, and the reaction was stirred until LC-MS showed complete SM consumption. Further addiction of HATU and DIPEA and increase reaction temperature were necessary to obtain complete conversion. The reaction was quenched by adding water then was extracted with DCM (×3). The organic layers were combined and washed with 1:1 NaCl(sat):$H_2O$ solution followed by brine. Then the combined organic layers were concentrated under vacuum and the crude was purified via FCC (AcOEt/DCM from 0% to 100%) to afford the title compound (3.64 g, 7.36 mmol, 44.9% yield).

$^{1}$H NMR (300 MHz, DMSO-$d_6$) δ 10.01 (s, 1H), 8.01 (s, 1H), 7.48-7.35 (m, 2H), 7.29-7.20 (m, 2H), 6.33 (s, 1H), 4.55 (s, 2H), 3.53 (t, J=5.8 Hz, 2H), 2.70 (s, 2H), 2.32 (s, 3H), 1.42 (s, 9H), 1.30 (s, 9H).

Step 3: N-(3-(tert-butyl)-1-(p-tolyl)-1H-pyrazol-5-yl)-4,5,6,7-tetrahydrothieno[2,3-c]pyridine-3-carboxamide hydrochloride (Intermediate 60)

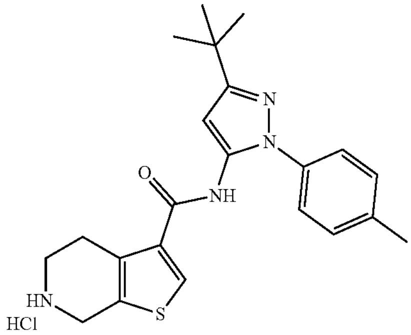 [SMILES: Cc1ccc(-n2nc(C(C)(C)C)cc2NC(=O)c2csc3c2CCNC3)cc1 ; Cl]

Intermediate 59 (2.27 g, 4.59 mmol) was dissolved in DCM (45.9 ml) and cooled to 0° C. HCl in dioxane (11.47 ml, 45.9 mmol) was added to the reaction mixture and stirred for 16 h. The crude was concentrated under vacuum and triturated with $Et_2O$ to obtain the title compound (1.834 g, 4.26 mmol, 93% yield).

$^{1}$H NMR (300 MHz, DMSO-$d_6$) δ 10.21 (s, 1H), 9.45 (s, 2H), 8.20 (s, 1H), 7.44-7.35 (m, 2H), 7.24 (d, J=8.3 Hz, 3H), 6.33 (s, 1H), 4.34 (s, 1H), 3.32 (s, 2H), 2.95 (s, 2H), 2.31 (s, 3H), 1.30 (s, 9H).

Step 4: 6-((1H-pyrazolo[3,4-b]pyridin-5-yl)methyl)-N-(3-(tert-butyl)-1-(p-tolyl)-1H-pyrazol-5-yl)-4,5,6,7-tetrahydrothieno[2,3-c]pyridine-3-carboxamide (Example 75)

Intermediate 60 (0.1 g, 0.232 mmol) and 1H-pyrazolo[3,4-b]pyridine-5-carbaldehyde (0.068 g, 0.464 mmol) was added to a small reaction tube and backfilled with argon (×3). MeOH (1.160 ml) was added to the reaction mixture followed by acetic acid (0.040 ml, 0.696 mmol) and the tube was sealed and stirred at 50° C. for 1 h. The reaction was then cooled to rt and STAB (80 mg, 1.275 mmol) was added and the reaction stirred at 50° C. until LC-MS confirming the complete consumption of SM. Further addiction of STAB was necessary to observe complete conversion. The reaction mixture was quenched with sat $NaHCO_3$, transferred to a separatory funnel and the desired product extracted with DCM (×3) and the combined organic layers washed once with brine, concentrated under vacuum and the crude mixture purified via HPLC. The pure fractions were concentrated to yield the desired product which contained formic acid. The compound was triturated with 0.1 M $NaHCO_3$ solution to afford the title compound (46 mg, 0.088 mmol, 37.7% yield).

$^1$H NMR (300 MHz, DMSO-$d_6$) δ 13.62 (s, 1H), 9.97 (s, 1H), 8.50 (d, J=2.0 Hz, 1H), 8.15 (d, J=1.9 Hz, 1H), 8.12 (d, J=1.3 Hz, 1H), 7.95 (s, 1H), 7.39 (d, J=8.3 Hz, 2H), 7.24 (d, J=8.3 Hz, 2H), 6.32 (s, 1H), 3.81 (s, 2H), 3.62 (s, 2H), 2.73 (s, 4H), 2.30 (s, 3H), 1.29 (s, 9H).

LC-MS (ESI) method 3: $t_R$=1.96 min; m/z (M+1)=526.2.

The compound reported in the following table was prepared via reductive amination as described for Example 75, steps 1-4, applying the corresponding, commercially available aldehyde in step 4.

| Example No | Structure | Amount SM | Amount product (yield) | Purification method | Data |
|---|---|---|---|---|---|
| 76 | 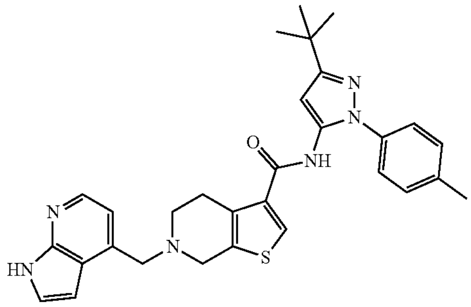 [SMILES: Cc1ccc(-n2nc(C(C)(C)C)cc2NC(=O)c2csc3c2CCN(Cc2ccnc4[nH]ccc24)C3)cc1] | 100 mg | 4.5 mg (4%) | Prep HPLC | $^1$H NMR (300 MHz, DMSO-$d_6$) δ 11.62 (s, 1H), 9.98 (s, 1H), 8.17 (d, J = 4.6 Hz, 1H), 7.95 (s, 1H), 7.40 (d, J = 9.2 Hz, 3H), 7.25 (d, J = 7.9 Hz, 2H), 7.06 (s, 1H), 6.59 (s, 1H), 6.32 (s, 1H), 3.96 (s, 2H), 3.65 (s, 2H), 2.73 (s, 4H), 2.31 (s, 3H), 1.29 (s, 9H). LC-MS (ESI): method 7 $t_R$ = 2.08 min; m/z (M + 1) = 525.3 |

Example 77: Preparation of 6-((1H-pyrazolo[3,4-b]pyridin-5-yl)methyl)-N-(3-(tert-butyl)-1-methyl-1H-pyrazol-5-yl)-4,5,6,7-tetrahydrothieno[2,3-c]pyridine-3-carboxamide Example 77

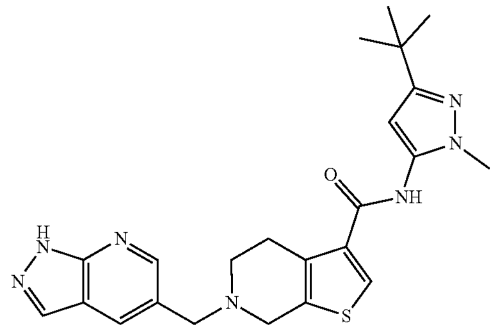

Step 1: tert-butyl 3-((3-(tert-butyl)-1-methyl-1H-pyrazol-5-yl)carbamoyl)-4,7-dihydrothieno[2,3-c]pyridine-6(5H)-carboxylate (Intermediate 61)

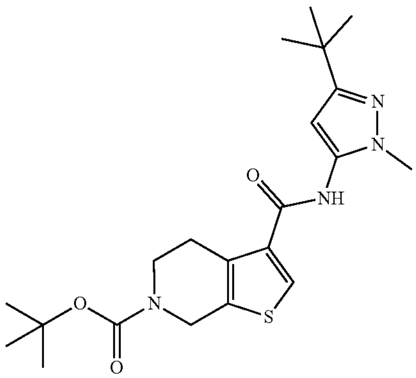 [SMILES: Cn1nc(C(C)(C)C)cc1NC(=O)c1csc2c1CCN(C(=O)OC(C)(C)C)C2]

Intermediate 58 (1 g, 3.28 mmol) and HATU (2.491 g, 6.55 mmol) were weighed into a reaction tube which was backfilled with argon (×3). DCM (24.56 ml) and DMF (8.19 ml) were added to the reaction mixture followed by DIPEA (4.58 ml, 26.2 mmol). The reaction mixture was stirred for 30 mins and 3-(tert-butyl)-1-methyl-1H-pyrazol-5-amine (0.502 g, 3.28 mmol) was added, and the reaction mixture stirred at rt until LC-MS confirming the complete consumption of SM. Further addiction of HATU was necessary to observe complete conversion.

The reaction mixture was then extracted with DCM/$H_2O$ (×3) and the combined organic layers washed with 1:1 NaCl(sat):$H_2O$ solution followed by brine. The combined organic layers were then concentrated under vacuum and the crude was purified via flash column chromatography using a Puriflash instrument (0-50% AcOEt/Hexane. Product eluted at 50% AcOEt) to give the title compound.

$^1$H NMR (300 MHz, DMSO-$d_6$) δ 10.01 (s, 1H), 8.14 (s, 1H), 6.08 (s, 1H), 4.59 (s, 2H), 3.59 (m, 5H), 2.82 (d, J=5.7 Hz, 2H), 1.43 (s, 9H), 1.23 (s, 9H).

Step 2: N-(3-(tert-butyl)-1-methyl-1H-pyrazol-5-yl)-4,5,6,7-tetrahydrothieno[2,3-c]pyridine-3-carboxamide hydrochloride (Intermediate 62)

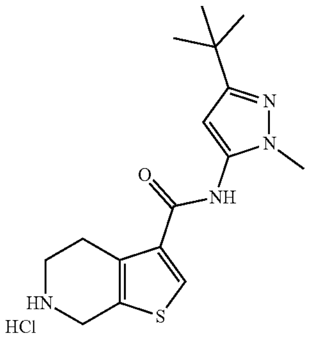 [SMILES: Cn1nc(C(C)(C)C)cc1NC(=O)c1csc2c1CCNC2 ; Cl]

Intermediate 61 (1.13 g, 2.70 mmol) was dissolved in DCM (27.0 ml) and cooled to 0° C. HCl in dioxane (3.37 ml, 13.50 mmol) was added dropwise and the reaction left to stir at rt for 16 h. Then the reaction mixture was concentrated and the residue triturated with $Et_2O$ to obtain the title compound in quantitative yield.

$^1$H NMR (300 MHz, DMSO-$d_6$) δ 10.21 (s, 1H), 9.46 (s, 2H), 8.34 (s, 1H), 6.09 (s, 1H), 4.38 (s, 2H), 3.63 (s, 3H), 3.37 (t, J=6.8 Hz, 2H), 3.07 (t, J=6.0 Hz, 2H), 1.23 (s, 9H).

Step 3: 6-((1H-pyrazolo[3,4-b]pyridin-5-yl)methyl)-N-(3-(tert-butyl)-1-methyl-1H-pyrazol-5-yl)-4,5,6,7-tetrahydrothieno[2,3-c]pyridine-3-carboxamide (Example 77)

Intermediate 62 (100 mg, 0.282 mmol) and 1H-pyrazolo[3,4-b]pyridine-5-carbaldehyde (41.5 mg, 0.282 mmol) was added to a small reaction tube and backfilled with argon (×3). MeOH (1409 μl) was added to the reaction mixture followed by glacial AcOH (48.6 μl, 0.845 mmol) and the tube was sealed and stirred at 50° C. for 1 h. The reaction was then cooled to rt and STAB (80 mg, 1.268 mmol) was added and the reaction stirred at 50° C. C until LC-MS confirming the complete consumption of SM. Further addiction of STAB was necessary to observe complete conversion. The reaction mixture was quenched with sat $NaHCO_3$, transferred to a separatory funnel and the desired product extracted with DCM (×3) and the combined organic layers washed once with brine, concentrated under vacuum and the crude mixture purified via flash column chromatography on a Puriflash instrument (0-10% MeOH/DCM) and the pure fractions concentrated to afford the title compound (39 mg, 0.087 mmol, 30.8% yield).

$^1$H NMR (300 MHz, DMSO-$d_6$) δ 13.62 (s, 1H), 9.97 (s, 1H), 8.51 (d, J=2.0 Hz, 1H), 8.21-8.05 (m, 3H), 6.07 (s, 1H), 3.83 (s, 2H), 3.64 (s, 2H), 3.60 (s, 3H), 2.85 (d, J=5.5 Hz, 2H), 2.76 (t, J=5.8 Hz, 2H), 1.22 (s, 9H).

LC-MS (ESI) method 9: $t_R$=1.90 min; m/z (M+1)=450.0

The compound reported in the following table was prepared via reductive amination as described for Example 77, steps 1-4, applying the corresponding, commercially available aldehyde in step 4.

| Example No | Structure | Amount Intermediate 62 | Amount product (yield) | Purification method | Data |
|---|---|---|---|---|---|
| 78 | 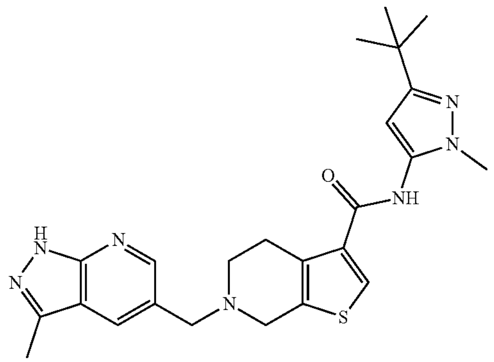 [SMILES: Cc1n[nH]c2ncc(CN3CCc4c(C(=O)Nc5cc(C(C)(C)C)nn5C)csc4C3)cc12] | 100 mg | 14 mg (11%) | Prep HPLC | $^1$H NMR (300 MHz, MeOH-$d_4$) δ 8.56 (d, J = 2.0 Hz, 1H),8.25 (d, J = 2.0 Hz, 1H), 8.02 (s, 1H), 6.13 (s, 1H), 3.96-3.90 (m, 2H), 3.79-3.73 (m, 2H), 3.70 (s, 3H), 3.00 (d, J = 5.8 Hz, 2H), 2.89 (t, J = 5.8 Hz, 2H), 2.59 (s, 3H), 1.30 (s, 9H). LC-MS (ESI): method 8 $t_R$ = 2.34 min; m/z (M + 1) = 464.2 |

Example 79: Preparation of N-(5-tert-butyl-2-methyl-pyrazol-3-yl)-6-(7-methylimidazo[1,2-a]pyridine-3-carbonyl)-5,7-dihydro-4H-thieno[2,3-c]pyridine-3-carboxamide Example 79

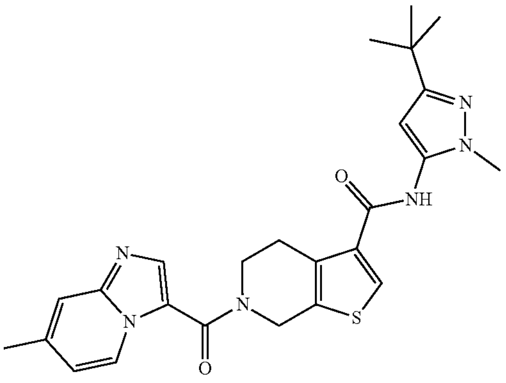

Step 1: N-(5-tert-butyl-2-methyl-pyrazol-3-yl)-6-(7-methylimidazo[1,2-a]pyridine-3-carbonyl)-5,7-dihydro-4H-thieno[2,3-c]pyridine-3-carboxamide (Example 79)

Prepared from 7-methylimidazo[1,2-a]pyridine-3-carboxylic acid (22 mg, 0.124 mmol) and Intermediate 62 according to general procedure G. Purification by reverse phase preparative HPLC (Sunfire C18 19×150 mm, 10 um 5-60% $ACN/H_2O$ (0.1% FA), 20 ml/min, RT) gave the title compound (23 mg, 43%).

$^1H$ NMR (400 MHz, DMSO-$d_6$) δ 10.04 (s, 1H), 8.88 (d, J=7.3 Hz, 1H), 8.19 (s, 1H), 8.09 (s, 1H), 7.54 (s, 1H), 6.98 (dd, J=1.7, 7.2 Hz, 1H), 6.11-6.10 (m, 1H), 5.02 (s, 2H), 3.98 (t, J=5.7 Hz, 2H), 3.63 (s, 3H), 3.05 (s, 2H), 2.42 (s, 3H), 1.24 (s, 9H).

LC-MS (ESI) method 7: $t_R$=3.33 min; m/z (M+1)=477.4

The compounds reported in the following table were prepared as described for Example 79, step 1, applying the corresponding, commercially available carboxylic acid in step 1.

| Example No | Structure | Amount SM | Amount product (yield) | Purification method | Data |
|---|---|---|---|---|---|
| 80 | 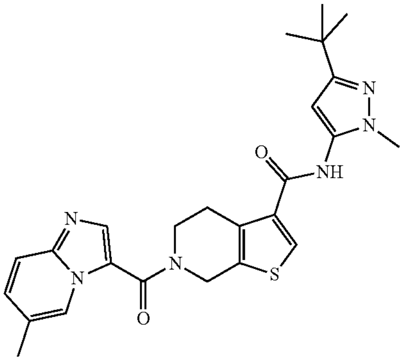 [SMILES: Cc1ccc2ncc(C(=O)N3CCc4c(C(=O)Nc5cc(C(C)(C)C)nn5C)csc4C3)n2c1] | 44 mg | 3.3 mg (6%) | Prep HPLC | $^1H$ NMR (400 MHz, DMSO-$d_6$) δ 10.04 (s, 1H), 8.77 (s, 1H), 8.19 (s, 1H), 8.07 (s, 1H), 7.65 (d, J = 9.7 Hz, 1H), 7.34 (dd, J = 1.7, 9.2 Hz, 1H), 6.10 (s, 1H), 5.04-5.00 (m, 2H), 3.98 (t, J = 5.6 Hz, 2H), 3.63 (s, 3H), 3.07-3.04 (m, 2H), 2.34 (s, 3H), 1.24 (s, 9H) LC-MS (ESI): method 7 $t_R$ = 3.44 min; m/z (M + 1) = 477.4 |
| 81 | 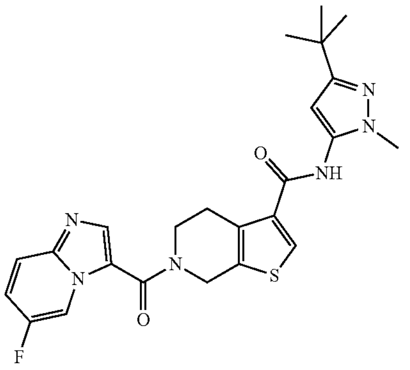 | 44 mg | 7 mg (13%) | Prep HPLC | $^1H$ NMR (400 MHz, DMSO-$d_6$) δ 10.05 (s, 1H), 9.03 (dd, J = 2.1, 5.0 Hz, 1H), 8.23 (s, 1H), 8.20 (s, 1H), 7.85 (dd, J = 5.3, 9.9 Hz, 1H), 7.62 (ddd, J = 2.3, 7.9, 10.0 Hz, 1H), 6.10 (s, 1H), 5.04 (s, 2H), 4.01-3.96 (m, 2H), 3.63 (s, 3H), 3.08-3.07 (m, 2H), 1.24 (s, 9H) LC-MS (ESI): method 7 $t_R$ = 3.94 min; m/z (M + 1) = 481.3 |

-continued

| Example No | Structure | Amount SM | Amount product (yield) | Purification method | Data |
|---|---|---|---|---|---|
| 82 | 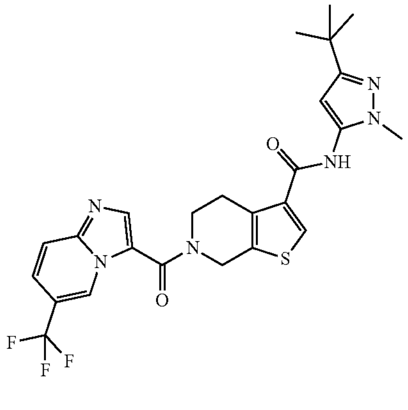 [SMILES: Cn1nc(C(C)(C)C)cc1NC(=O)c1csc2c1CCN(C(=O)c1cnc3ccc(C(F)(F)F)cn13)C2] | 44 mg | 33 mg (54%) | Prep HPLC | $^{1}H$ NMR (400 MHz, DMSO-$d_6$) δ 10.05 (s, 1H), 9.37 (s, 1H), 8.31 (s, 1H), 8.20 (s, 1H), 7.96 (d, J = 9.4 Hz, 1H), 7.73 (dd, J = 1.9, 9.4 Hz, 1H), 6.10 (s, 1H), 5.04 (s, 2H), 4.00 (t, J = 5.3 Hz, 2H), 3.63 (s, 3H), 3.12-3.04 (m, 2H), 1.24 (s, 9H) LC-MS (ESI): method 7 $t_R$ = 4.70 min; m/z (M + 1) = 531.3 |
| 83 | 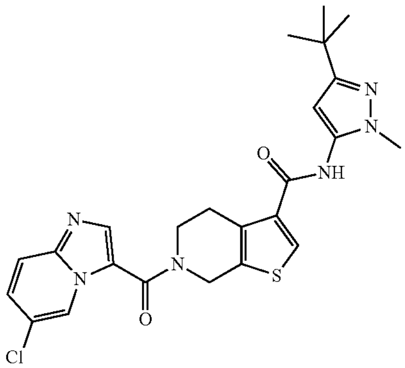 [SMILES: Cn1nc(C(C)(C)C)cc1NC(=O)c1csc2c1CCN(C(=O)c1cnc3ccc(Cl)cn13)C2] | 44 mg | 33 mg (54%) | Prep HPLC | $^{1}H$ NMR (400 MHz, DMSO-$d_6$) δ 10.05 (s, 1H), 9.05 (dd, J = 0.8, 2.1 Hz, 1H), 8.19 (s, 2H), 7.81 (dd, J = 0.8, 9.6 Hz, 1H), 7.55 (dd, J = 2.1, 9.5 Hz, 1H), 6.10 (s, 1H), 5.03-5.02 (m, 2H), 3.98 (t, J = 5.7 Hz, 2H), 3.63 (s, 3H), 3.07-3.06 (m, 2H), 1.24 (s, 9H). LC-MS (ESI): method 7 $t_R$ = 4.31 min; m/z (M + 1) = 497.2 |

Example 84: Preparation of 6-(imidazo[1,2-a]pyrazin-3-ylmethyl)-N-(3-(trifluoromethyl)phenyl)-4,5,6,7-tetrahydrothieno[2,3-c]pyridine-3-carboxamide Example 84

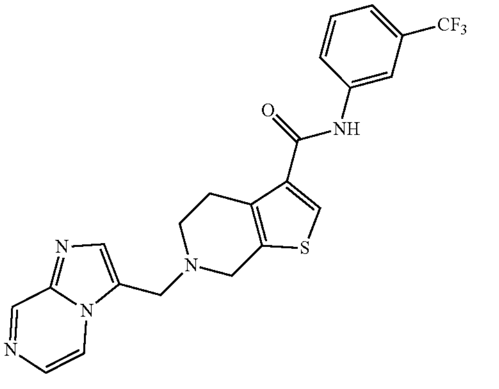

Step 1: tert-butyl 3-((3-(trifluoromethyl)phenyl)carbamoyl)-4,7-dihydrothieno[2,3-c]pyridine-6(5H)-carboxylate (Intermediate 63)

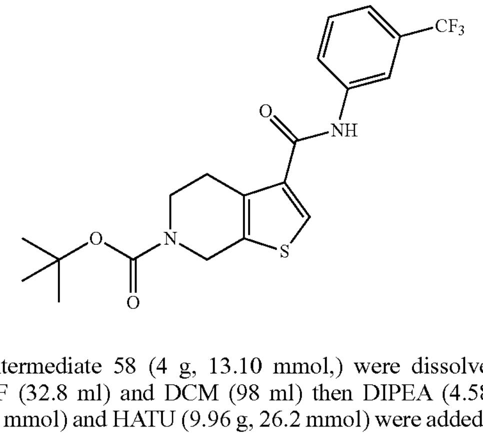

Intermediate 58 (4 g, 13.10 mmol,) were dissolved in DMF (32.8 ml) and DCM (98 ml) then DIPEA (4.58 ml, 26.2 mmol) and HATU (9.96 g, 26.2 mmol) were added. RM was stirred at RT for 15 min and 3-(trifluoromethyl)aniline (1.964 ml, 15.72 mmol) was added. The RM was stirred at RT until LC-MS showed complete SM consumption. The reaction temperature was raised to 40° C. and further addiction of HATU and 3-(trifluoromethyl)aniline was necessary to obtain complete conversion. The reaction mixture was diluted with DCM and water was added. This mixture was stirred 15 min and phases separated, organic phases was washed with water, 5% wt solution of citric acid, twice with water and brine, dried over $Na_2SO_4$, filtered and concentrated under reduced pressure. The Crude material was purified by FC (DCM to 10% MeOH in DCM) to afford the title compound (4.36 g, 10.22 mmol, 78% yield).

$^1$H NMR (300 MHz, DMSO-$d_6$) δ 10.38 (s, 1H), 8.19 (d, J=2.0 Hz, 1H), 8.16 (s, 1H), 8.00-7.92 (m, 1H), 7.58 (t, J=8.0 Hz, 1H), 7.47-7.38 (m, 1H), 4.59 (s, 2H), 3.58 (t, J=5.8 Hz, 2H), 2.85 (t, J=5.8 Hz, 2H), 1.43 (s, 9H).

Step 2: N-(3-(trifluoromethyl)phenyl)-4,5,6,7-tetrahydrothieno[2,3-c]pyridine-3-carboxamide hydrochloride (Intermediate 64)

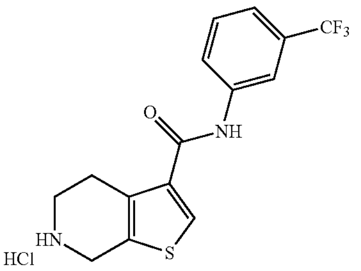 [SMILES: Cl ; O=C(Nc1cccc(C(F)(F)F)c1)c1csc2c1CCNC2]

Intermediate 63 (2.82 g, 6.61 mmol) was dissolved in minimal amound of DCM (6.01 ml) then $Et_2O$ (60.1 ml) was added, followed by 4N HCl in Dioxane (16.53 ml, 66.1 mmol) and the RM was stirred at RT overnight. $Et_2O$ was added to RM till no more precipitation was observed, then solid was filtered off and residual solvent evaporated under vacuum to obtain the title compound (2.3353 g, 6.44 mmol, 97% yield).

$^1$H NMR (300 MHz, DMSO-$d_6$) δ 10.51 (s, 1H), 8.27 (s, 1H), 8.16 (d, J=2.1 Hz, 1H), 7.95-7.86 (m, 1H), 7.58 (t, J=8.0 Hz, 1H), 7.48-7.40 (m, 1H), 4.36 (s, 2H), 3.36 (td, J=6.5, 5.1 Hz, 2H), 3.09 (t, J=6.1 Hz, 2H).

Step 3: 6-(imidazo[1,2-a]pyrazin-3-ylmethyl)-N-(3-(trifluoromethyl) phenyl)-4,5,6,7-tetrahydrothieno[2,3-c]pyridine-3-carboxamide Intermediate 64 (0.10 g, 0.276 mmol), imidazo[1,2-a]pyrazine-3-carbaldehyde (0.041 g, 0.276 mmol) and magnesium sulfate (0.033 g, 0.276 mmol) were placed in round-bottom flask under argon. Anhydrous DCM (1.378 ml) was added followed by TEA (0.038 ml, 0.276 mmol). Reaction mixture was stirred 30 min at rt. and STAB (0.117 g, 0.551 mmol) was added and reaction mixture stirred at rt overnight. The reaction mixture was diluted with DCM and washed with a mixture of $K_2CO_3$(sat) and water 1:1. Aqueous fase was extracted with DCM twice, organic phases combined, dryed over $Na_2SO_4$ and evaporated under reduced pressure. The crude was purified via FCC with DCM/MeOH (DCM to 5% MeOH in DCM) to afford the title compound (32 mg, 0.070 mmol, 25.4% yield).

$^1$H NMR (300 MHz, DMSO-$d_6$) δ 10.34 (s, 1H), 9.07 (d, J=1.5 Hz, 1H), 8.56 (dd, J=4.7, 1.5 Hz, 1H), 8.17 (s, 1H), 8.10 (s, 1H), 7.96 (d, J=8.1 Hz, 1H), 7.92 (d, J=4.6 Hz, 1H), 7.82 (s, 1H), 7.57 (t, J=8.0 Hz, 1H), 7.42 (d, J=7.7 Hz, 1H), 4.12 (s, 2H), 3.68 (s, 2H), 2.85 (d, J=5.5 Hz, 2H), 2.78 (d, J=5.2 Hz, 2H).

LC-MS (ESI) method 3: $t_R$=1.85 min; m/z (M+1)=458.0

The compound reported in the following table was prepared via reductive amination as described for Example 84, steps 1-3, applying the corresponding, commercially available aldehyde in step 3.

| Example No | Structure | Amount Intermediate 64 - procedure variations | Amount product (yield) | Purification method | Data |
|---|---|---|---|---|---|
| 85 | 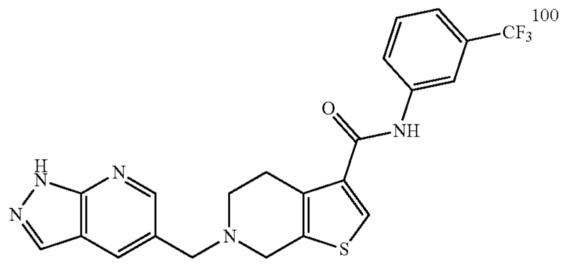 | 100 mg | 69 mg (55%) | FCC | $^1$H NMR (300 MHz, DMSO-$d_6$) δ 13.62 (s, 1H), 10.34 (s, 1H), 8.52 (d, J = 2.0 Hz, 1H), 8.19 (s, 1H), 8.17 (d, J = 1.9 Hz, 1H), 8.12 (s, 1H), 8.10 (s, 1H), 7.96 (d, J = 8.1 Hz, 1H), 7.57 (t, J = 8.0 Hz, 1H), 7.42 (d, J = 7.7 Hz, 1H), 3.83 (s, 2H), 3.65 (s, 2H), 2.92-2.83 (m, 2H), 2.80-2.71 (m, 2H). LC-MS (ESI): method 3 $t_R$= 1.78 min; m/z (M + 1) = 458.1 |

-continued

| Example No | Structure | Amount Intermediate 64 - procedure variations | Amount product (yield) | Purification method | Data |
|---|---|---|---|---|---|
| 86 | 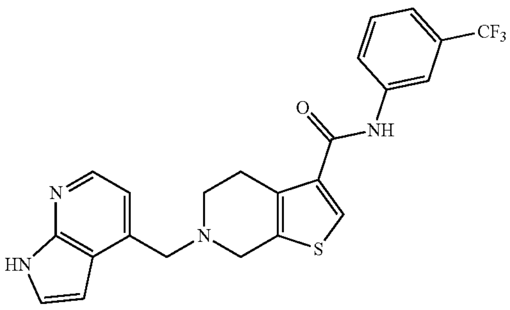 [SMILES: O=C(Nc1cccc(C(F)(F)F)c1)c1csc2c1CCN(Cc1ccnc3[nH]ccc13)C2] | 100 mg $NaBH_3CN$ replaced STAB | 44 mg (35%) | Prep HPLC | $^1H$ NMR (300 MHz, DMSO-$d_6$) δ 10.36 (s, 2H), 8.23-8.14 (m, 2H), 8.11 (s, 1H), 7.97 (d, J = 8.2 Hz, 1H), 7.58 (t, J = 8.0 Hz, 1H), 7.47-7.39 (m, 2H), 7.08 (d, J = 4.9 Hz, 1H), 6.61 (d, J = 3.5 Hz, 1H), 3.99 (s, 2H), 3.69 (s, 2H), 2.89 (d, J = 5.6 Hz, 2H), 2.79 (d, J = 5.4 Hz, 2H). LC-MS (ESI): method 3 $t_R$ = 1.89 min; m/z (M + 1) = 457.1 |
| 87 | 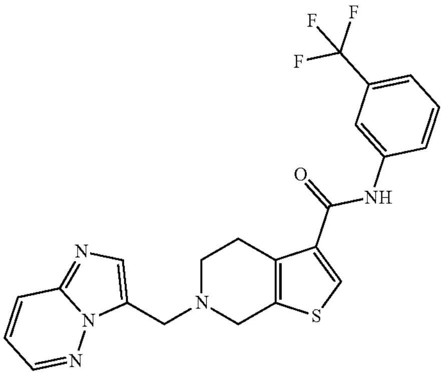 [SMILES: O=C(Nc1cccc(C(F)(F)F)c1)c1csc2c1CCN(Cc1cnc3cccnn13)C2] | General procedure K 53 mg | 26 mg (36%) | Prep HPLC | $^1H$ NMR (400 MHz, DMSO-$d_6$) δ 10.35 (s, 1H), 8.59 (dd, J = 1.6, 4.4 Hz, 1H), 8.20 (s, 1H), 8.15 (dd, J = 1.6, 9.2 Hz, 1H), 8.11 (s, 1H), 7.97 (d, J = 8.8 Hz, 1H), 7.82 (s, 1H), 7.58 (t, J = 8.0 Hz, 1H), 7.44 (d, J = 7.8 Hz, 1H), 7.25 (dd, J = 4.5, 9.2 Hz, 1H), 4.16 (s, 2H), 3.73 (s, 2H), 2.90-2.80 (m, 4H). LC-MS (ESI): method 7 $t_R$ = 3.32 min; m/z (M + 1) = 458.3 |
| 88 | 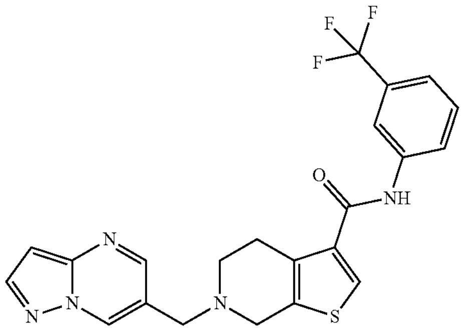 [SMILES: O=C(Nc1cccc(C(F)(F)F)c1)c1csc2c1CCN(Cc1cnc3ccnn3c1)C2] | General procedure L 50 mg | 3.7 mg (6%) | Prep HPLC | $^1H$ NMR (400 MHz, DMSO-$d_6$) δ 10.36 (s, 1H), 9.09-9.08 (m, 1H), 8.60 (d, J = 2.1 Hz, 1H), 8.22-8.20 (m, 2H), 8.12 (s, 1H), 8.00-7.97 (m, 1H), 7.59 (t, J = 8.0 Hz, 1H), 7.45-7.43 (m, 1H), 6.74 (dd, J = 0.9, 2.4 Hz, 1H), 3.81 (s, 2H), 3.73 (s, 2H), 2.91 (t, J = 5.3 Hz, 2H), 2.82 (t, J = 5.8 Hz, 2H) LC-MS (ESI): method 7 $t_R$ = 3.47 min; m/z (M + 1) = 458.3 |
| 89 | 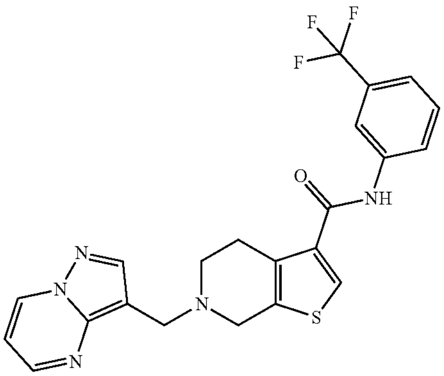 [SMILES: O=C(Nc1cccc(C(F)(F)F)c1)c1csc2c1CCN(Cc1cnn3cccnc13)C2] | General procedure L 50 mg | 6 mg (9%) | Prep HPLC | $^1H$ NMR (400 MHz, DMSO-$d_6$) δ 10.35 (s, 1H), 9.11 (dd, J = 1.8, 7.0 Hz, 1H), 8.58 (dd, J = 1.7, 4.0 Hz, 1H), 8.25 (s, 1H), 8.20 (s, 1H), 8.09 (s, 1H), 7.98 (d, J = 8.2 Hz, 1H), 7.58 (t, J = 7.9 Hz, 1H), 7.43 (d, J = 7.8 Hz, 1H), 7.05 (dd, J = 4.0, 7.0 Hz, 1H), 3.95 (s, 2H), 3.67 (s, 2H), 2.87 (t, J = 5.4 Hz, 2H), 2.77 (t, J = 5.6 Hz, 2H). LC-MS (ESI): method 6 $t_R$ = 4.51 min; m/z (M + 1) = 458.3 |

Example 90: Preparation of 6-(imidazo[1,2-a]pyrazine-3-carbonyl)-N-(3-(trifluoromethyl)phenyl)-4,5,6,7-tetrahydrothieno[2,3-c]pyridine-3-carboxamide Example 90

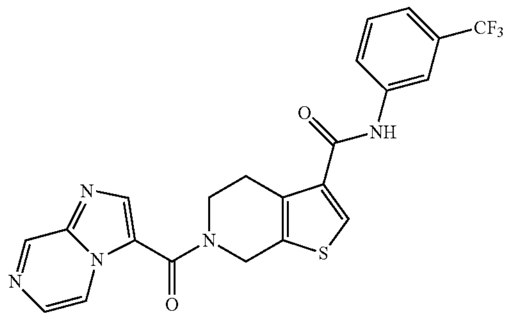

The imidazo[1,2-a]pyrazine-3-carboxylic acid g 0.303 mmol) were dissolved in DMF (0.689 ml) and DCM (2.067 ml) then DIPEA (0.289 ml, 1.654 mmol) and HATU (0.231 g, 0.606 mmol) were added. The mixture was stirred for 15 min Intermediate 64 (0.1 g, 0.276 mmol) was added. The reaction mixture was stirred at RT overnight, diluted with DCM and water was added. This mixture was stirred 15 min and phases separated, organic phases were washed with water and brine, dryed over $Na_2SO_4$, filtered and concentrated under reduced pressure. The crude material was purified by FCC (DCM to 10% MeOH in DCM) to afford the title compound (71.64 mg, 0.152 mmol, yield 55%).

$^1H$ NMR (DMSO-$d_6$, 300 MHz) δ 10.41 (s, 1H), 9.24 (d, 1H, J=1.5 Hz), 8.87 (dd, 1H, J=1.4, 4.7 Hz), 8.33 (s, 1H), 8.21 (s, 2H), 8.08 (d, 1H, J=4.8 Hz), 7.98 (d, 1H, J=8.8 Hz), 7.59 (t, 1H, J=7.9 Hz), 7.44 (d, 1H, J=7.7 Hz), 4.9-5.2 (m, 2H), 3.98 (br t, 2H, J=5.4 Hz), 3.0-3.1 (m, 2H).

LC-MS (ESI) method 4: $t_R$=2.77 min; m/z (M+1)=471.9

The compounds reported in the following table were prepared via amido coupling as described for Example 90 applying the corresponding, commercially available carboxylic acid in step 1. General procedure variations or reagents variations are reported in the table.

| Example No | Structure | Amount intermediate 64 - Procedure variations | Amount product (yield) | Purification method | Data |
|---|---|---|---|---|---|
| 91 | 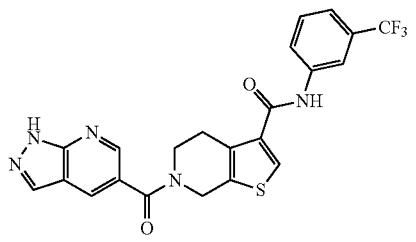 [SMILES: O=C(Nc1cccc(C(F)(F)F)c1)c1csc2c1CCN(C(=O)c1cnc3[nH]ncc3c1)C2] | 100 mg HOBt replaced HATU TEA replaced DIPEA | 10 mg (8%) | FCC | $^1H$ NMR (300 MHz, DMSO-$d_6$) δ 13.90 (s, 1H), 10.41 (s, 1H), 8.63 (d, J = 2.0 Hz, 1H), 8.41 (d, J = 2.0 Hz, 1H), 8.25 (d, J = 1.3 Hz, 1H), 8.20 (s, 2H), 7.97 (d, J = 8.2 Hz, 1H), 7.58 (t, J = 8.0 Hz, 1H), 7.43 (d, J = 7.7 Hz, 1H), 4.87 (s, 2H), 4.04-3.51 (m, 2H), 3.00 (s, 2H). LC-MS (ESI): method 3 $t_R$ = 2.53 min; m/z (M + 1) = 472.0 |
| 92 | 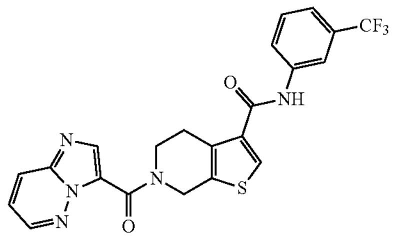 [SMILES: O=C(Nc1cccc(C(F)(F)F)c1)c1csc2c1CCN(C(=O)c1cnc3cccnn13)C2] | 50 mg General procedure M | 51 mg (78%) | Prep HPLC | $^1H$ NMR (400 MHz, DMSO-$d_6$) δ 10.42 (s, 1H), 8.65 (dd, J = 1.5, 4.4 Hz, 1H), 8.28 (dd, J = 1.5, 9.4 Hz, 1H), 8.24-8.19 (m, 2H), 8.09 (s, 1H), 8.00-7.96 (m, 1H), 7.62-7.57 (m, 1H), 7.47-7.43 (m, 1H), 7.39 (dd, J = 4.4, 9.4 Hz, 1H), 5.03-4.72 (m, 2H), 4.04-3.56 (m, 2H), 3.05-2.98 (m, 2H). LC-MS (ESI): method 7 $t_R$ = 4.41 min; m/z (M + 1) = 472 |
| 93 | 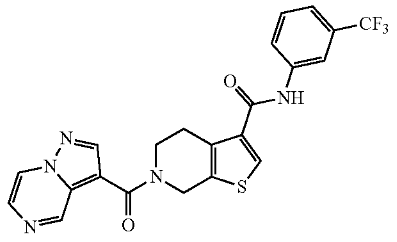 [SMILES: O=C(Nc1cccc(C(F)(F)F)c1)c1csc2c1CCN(C(=O)c1cnn3ccncc13)C2] | 50 mg General procedure M | 38 mg (58%) | Prep HPLC | $^1H$ NMR (400 MHz, DMSO-$d_6$) δ 10.42 (s, 1H), 9.37 (d, J = 1.5 Hz, 1H), 8.94 (dd, J = 1.5, 4.7 Hz, 1H), 8.57 (s, 1H), 8.23-8.20 (m, 2H), 8.11 (d, J = 4.7 Hz, 1H), 8.00-7.98 (m, 1H), 7.63-7.58 (m, 1H), 7.46-7.44 (m, 1H), 5.00-4.97 (m, 2H), 3.98-3.93 (m, 2H), 3.07 (s, 2H) LC-MS (ESI): method 7 $t_R$ = 4.6 min; m/z (M + 1) = 472 |

-continued

| Example No | Structure | Amount intermediate 64 - Procedure variations | Amount product (yield) | Purification method | Data |
|---|---|---|---|---|---|
| 94 | 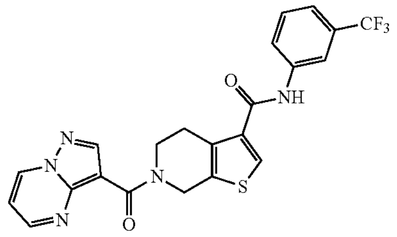 [SMILES: O=C(Nc1cccc(C(F)(F)F)c1)c1csc2c1CCN(C(=O)c1cnn3cccnc13)C2] | 50 mg General procedure M | 38 mg (58%) | Prep HPLC | $^1$H NMR (400 MHz, DMSO-$d_6$) δ 10.44-10.40 (m, 1H), 9.26 (dd, J = 1.6, 7.0 Hz, 1H), 8.75 (dd, J = 1.6, 4.0 Hz, 1H), 8.49 (s, 1H), 8.23-8.20 (m, 2H), 8.01-7.97 (m, 1H), 7.62-7.57 (m, 1H), 7.46-7.43 (m, 1H), 7.22 (dd, J = 4.0, 7.0 Hz, 1H), 4.89 (s, 2H), 3.96-3.72 (m, 2H), 3.07-3.00 (m, 2H) LC-MS (ESI): method 6 $t_R$ = 4.42 min; m/z (M + 1) = 472 |
| 95 | 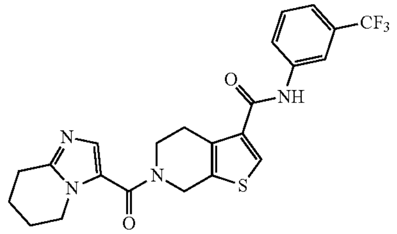 [SMILES: O=C(Nc1cccc(C(F)(F)F)c1)c1csc2c1CCN(C(=O)c1cnc3n1CCCC3)C2] | 50 mg General procedure M | 37 mg (57%) | Prep HPLC | $^1$H NMR (400 MHz, DMSO-$d_6$) δ 10.41 (s, 1H), 8.22-8.20 (m, 2H), 8.01-7.98 (m, 1H), 7.63-7.57 (m, 1H), 7.46-7.43 (m, 1H), 7.29 (s, 1H), 4.92 (s, 2H), 4.07-4.02 (m, 2H), 3.92-3.87 (m, 2H), 3.01-2.97 (m, 2H), 2.82-2.77 (m, 2H), 1.91-1.82 (m, 4H) LC-MS (ESI): method 6 $t_R$ = 4.53 min; m/z (M + 1) = 475 |
| 96 | 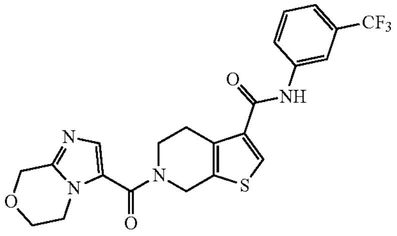 [SMILES: O=C(Nc1cccc(C(F)(F)F)c1)c1csc2c1CCN(C(=O)c1cnc3n1CCOC3)C2] | 50 mg General procedure M | 53 mg (81%) | Prep HPLC | $^1$H NMR (400 MHz, DMSO-$d_6$) δ 10.42 (s, 1H), 8.23-8.21 (m, 2H), 8.01-7.97 (m, 1H), 7.63-7.58 (m, 1H), 7.52 (s, 1H), 7.47-7.44 (m, 1H), 4.97-4.89 (m, 2H), 4.84 (s, 2H), 4.19-4.14 (m, 2H), 4.04-3.99 (m, 2H), 3.94-3.89 (m, 2H), 3.07-3.02 (m, 2H) LC-MS (ESI): method 7 $t_R$ = 3.91 min; m/z (M + 1) = 477 |
| 135 | 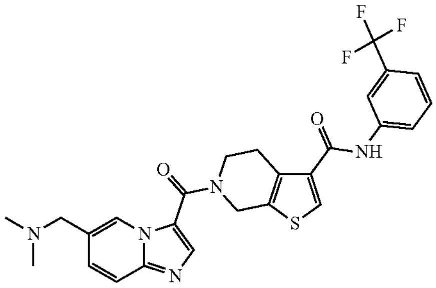 [SMILES: CN(C)Cc1ccc2ncc(C(=O)N3CCc4c(C(=O)Nc5cccc(C(F)(F)F)c5)csc4C3)n2c1] | 95 mg Intermediate 120: 64 mg, 0.292 mmol (1.0 eq) General procedure M | 0.9 mg (0.06%) | Prep HPLC | $^1$H NMR (400 MHz, DMSO-$d_6$) δ 10.41 (s, 1H), 9.69 (s, 1H), 9.11-9.08 (m, 1H), 8.21 (s, 2H), 8.17 (s, 1H), 7.98 (d, J = 8.1 Hz, 1H), 7.81-7.75 (m, 1H), 7.59 (dd, J = 8.0, 8.0 Hz, 1H), 7.50 (d, J = 9.6 Hz, 1H), 7.44 (d, J = 7.8 Hz, 1H), 5.03 (s, 3H), 4.02-3.96 (m, 4H), 3.07 (s, 3H), 2.61-2.57 (m, 4H). LC-MS (ESI): method 6 $t_R$ = 4.57 min; m/z [M + H]+ = 528.4 |
| 136 | 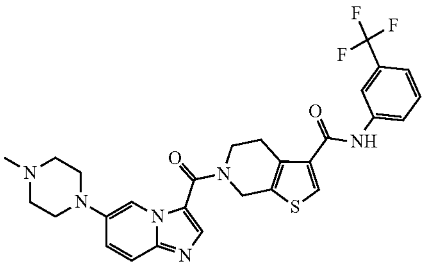 [SMILES: CN1CCN(c2ccc3ncc(C(=O)N4CCc5c(C(=O)Nc6cccc(C(F)(F)F)c6)csc5C4)n3c2)CC1] | 75 mg Intermediate 113: 120 mg, 0.230 mmol (1.0 eq, assumed 50% pure) General procedure M (at RT) | 7 mg (5%) | Prep HPLC | $^1$H NMR (400 MHz, DMSO-$d_6$) δ 10.42 (s, 1H), 8.41 (d, J = 1.9 Hz, 1H), 8.22 (s, 2H), 8.03 (s, 1H), 8.00 (m, 1H), 7.61 (m, 2H), 7.51-7.43 (m, 2H), 5.02 (s, 2H), 3.99 (t, J = 5.7 Hz, 2H), 3.08 (m, 6H), 2.50 (4H, m), 2.24 (s, 3H) LC-MS (ESI): method 6 $t_R$ = 3.21min; m/z $[M + H]^+$ = 569.4 |
| 137 | 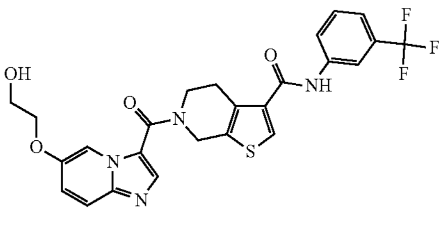 [SMILES: O=C(Nc1cccc(C(F)(F)F)c1)c1csc2c1CCN(C(=O)c1cnc3ccc(OCCO)cn13)C2] | 114 mg Intermediate 119: 78 mg, 0.35 mmol (1.0 eq) General procedure M | 59 mg (32%) | Prep HPLC | $^1$H NMR (400 MHz, DMSO-$d_6$) δ 10.42 (s, 1H), 8.63 (d, J = 2.1 Hz, 1H), 8.22 (s, 2H), 8.09 (s, 1H), 8.00 (d, J = 8.7 Hz, 1H), 7.74-7.66 (m, 1H), 7.60 (dd, J = 8.0, 8.0 Hz, 1H), 7.46 (d, J = 7.7 Hz, 1H), 7.30 (dd, J = 2.5, 9.7 Hz, 1H), 5.04 (s, 2H), 4.95 (t, J = 5.5 Hz, 1H), 4.04-3.96 (m, 4H), 3.79-3.73 (m, 2H), 3.09 (t, J = 5.9 Hz, 2H). |

-continued

| Example No | Structure | Amount intermediate 64 - Procedure variations | Amount product (yield) | Purification method | Data |
|---|---|---|---|---|---|
| | | | | | LC-MS (ESI) method 6: $t_R$ = 4.22 min; m/z [M + H]$^+$ = 531.4. |
| 138 | 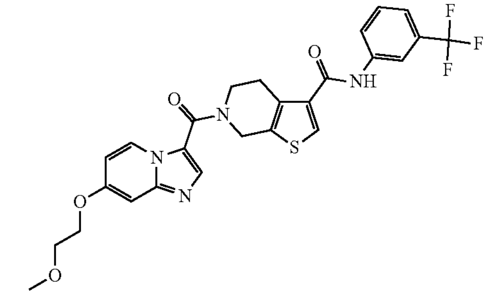 [SMILES: COCCOc1ccn2c(C(=O)N3CCc4c(C(=O)Nc5cccc(C(F)(F)F)c5)csc4C3)cnc2c1] | 246 mg Intermediate 115: 178 mg, 0.754 mmol, (1.0 eq) General procedure M | 179 mg (42%) | Prep HPLC | $^1$H NMR (400 MHz, DMSO-$d_6$) δ 10.41 (s, 1H), 8.85 (d, J = 7.7 Hz, 1H), 8.22 (d, J = 4.1 Hz, 2H), 8.03-8.02 (m, 2H), 7.60 (t, J = 8.0 Hz, 1H), 7.47-7.44 (m, 1H), 7.15 (d, J = 2.3 Hz, 1H), 6.83 (dd, J = 2.6, 7.7 Hz, 1H), 5.04-5.00 (m, 2H), 4.26-4.22 (m, 2H), 3.98 (t, J = 5.6 Hz, 2H), 3.74-3.70 (m, 2H), 3.09-3.07 (m, 2H). LC-MS (ESI) method 6: $t_R$ = 4.66 min; m/z [M + H]$^+$ = 545.2. |
| 139 | 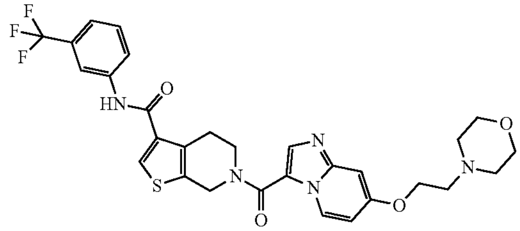 [SMILES: O=C(Nc1cccc(C(F)(F)F)c1)c1csc2c1CCN(C(=O)c1cnc3cc(OCCN4CCOCC4)ccn13)C2] | Intermediate 118: 184 mg, 0.632 mmol, (1.0 eq) General procedure M | 208 mg (55%) | Prep HPLC | $^1$H NMR (400) MHz, DMSO-$d_6$) δ 10.42 (s, 1H), 8.85 (d, J = 7.7 Hz, 1H), 8.22 (d, J = 3.4 Hz, 2H), 8.03-7.97 (m, 2H), 7.60 (t, J = 8.0 Hz, 1H), 7.47-7.44 (m, 1H), 7.16 (s, 1H), 6.82 (dd, J = 2.5, 7.7 Hz, 1H), 5.04-5.00 (m, 2H), 4.27-4.24 (m, 2H), 3.98 (t, J = 5.5 Hz, 2H), 3.61-3.57 (m, 4H), 3.08-3.06 (m, 2H), 2.80-2.75 (m, 2H). LC-MS (ESI) method 7: $t_R$ = 3.19 min; m/z [M + H]$^+$ = 600.2 |

Example 97: Preparation of N-(3-fluoro-5-(trifluoromethyl)phenyl)-6-(pyrazolo[1,5-a]pyrimidine-3-carbonyl)-4,5,6,7-tetrahydrothieno[2,3-c]pyridine-3-carboxamide Example 97

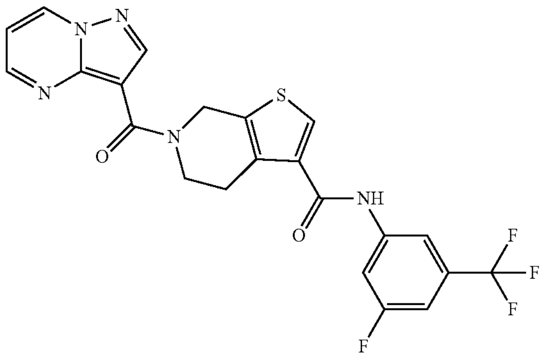

Step 1: N-(3-Fluoro-5-(trifluoromethyl)phenyl)-4,5,6,7-tetrahydrothieno[2,3-c]pyridine-3-carboxamide (Intermediate 65)

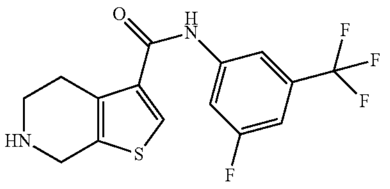 [SMILES: O=C(Nc1cc(F)cc(C(F)(F)F)c1)c1csc2c1CCNC2]

To a solution of 6-tert-butoxycarbonyl-5,7-dihydro-4H-thieno[2,3-c]pyridine-3-carboxylic acid (1590 mg, 5.61 mmol, 1.00 eq) and HATU (2560 mg, 6.73 mmol, 1.20 eq) in N,N-dimethylformamide (22.50 mL) N,N-Diisopropylethylamine (2.9 mL, 16.8 mmol, 3.00 eq) was added and the reaction mixture was stirred at room temperature for 15 minutes before addition of 3-fluoro-5-(trifluoromethyl)aniline (1055 mg, 5.89 mmol, 1.05 eq). The reaction mixture was stirred at room temperature for a further 16 hours. The reaction mixture was purified (ethyl acetate/cyclohexane from 0% to 100) to yield tert-butyl 3-((3-fluoro-5-(trifluoromethyl)phenyl)carbamoyl)-4,7-dihydrothieno[2,3-c]pyridine-6(5H)-carboxylate, (1.35 g, 3.04 mmol, 1.00 eq) that was dissolved in DCM (35 mL) and trifluoroacetic acid (5.0 mL, 65.9 mmol, 21.7 eq) was added. The reaction mixture was stirred at room temperature for 2 hours and concentrated under reduced pressure. The reaction mixture was partitioned between saturated aqueous sodium carbonate (50 mL) and ethyl acetate (40 mL) Aqueous layer were extracted with ethyl acetate (30 mL), dried with magnesium sulphate, filtered through a hydrophobic frit and concentrated under reduced pressure. The crude was purified on silica gel chromatography (ethyl acetate/cyclohexane from 0% to 100% followed 3:1 ethyl acetate:ethanol/ethyl acetate from 0% to 100%) to yield the title compound (500 mg, 2.69 mmol, yield 48%).

$^1$H NMR (400 MHz, $CDCl_3$) δ 7.80 (td, J=2.1, 10.4 Hz, 1H), 7.73 (s, 1H), 7.63 (s, 1H), 7.52 (s, 1H), 7.10 (d, J=8.3 Hz, 1H), 4.07 (s, 2H), 3.15 (t, J=5.8 Hz, 2H), 2.93 (t, J=5.7 Hz, 2H), 1.27-1.22 (m, 1H).

Step 2: N-(3-fluoro-5-(trifluoromethyl)phenyl)-6-(pyrazolo[1,5-a]pyrimidine-3-carbonyl)-4,5,6,7-tetrahydrothieno[2,3-c]pyridine-3-carboxamide (Example 97)

To a solution of Pyrazolo[1,5-a]pyrimidine-3-carboxylic acid (25 mg, 0.153 mmol, 1.16 eq) in N,N-dimethylformamide (1.50 mL) HATU (61 mg, 0.160 mmol, 1.22 eq) and N,N-Diisopropylethylamine (0.069 mL, 0.394 mmol, 3.00 eq) were added and the reaction mixture was stirred at room temperature for 30 minutes. Intermediate 65 (50 mg, 0.131 mmol, 1.00 eq,) was added and the reaction mixture was heated at 40 overnight then diluted with DMSO. Purification by reverse phase preparative HPLC (Sunfire C18 19×150 mm, 10 um 20-80% ACN/$H_2O$ (0.1% FA), 20 ml/min, RT) gave the title compound (29.2 mg, 45%).

$^1$H NMR (400 MHz, DMSO-$d_6$) δ 10.59 (s, 1H), 9.26 (dd, J=1.6, 7.0 Hz, 1H), 8.75 (d, J=2.5 Hz, 1H), 8.49 (s, 1H), 8.22-8.22 (m, 1H), 8.00-7.94 (m, 2H), 7.40 (d, J=8.5 Hz, 1H), 7.23 (dd, J=4.1, 7.0 Hz, 1H), 4.89 (s, 2H), 3.95-3.75 (m, 2H), 3.12-2.97 (m, 2H).

LC-MS (ESI) method 7: $t_R$=4.75 min; m/z (M+1)=490.3

Example 98: 6-(imidazo[1,2-a]pyridine-3-carbonyl)-7-methyl-N-(3-(4-methyl-1H-imidazol-1-yl)-5-(trifluoromethyl)phenyl)-4,5,6,7-tetrahydrothieno[2,3-c]pyridine-3-carboxamide Example 98

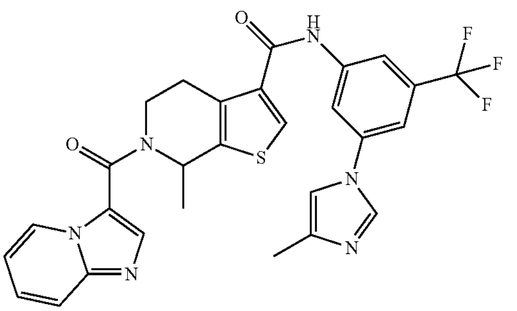

Step 1: 6-(tert-butyl) 3-ethyl 2-amino-7-methyl-4,7-dihydrothieno[2,3-c]pyridine-3,6(5H)-dicarboxylate (Intermediate 66a), 6-(tert-butyl) 3-ethyl 2-amino-5-methyl-4,7-dihydrothieno[2,3-c]pyridine-3,6(5H)-dicarboxylate (Intermediate 66b)

66a

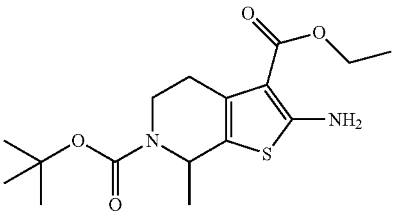

66b

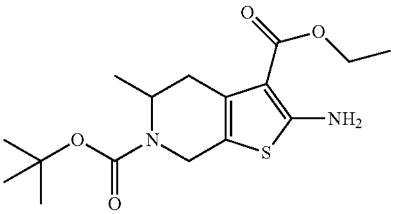

To a mixture of tert-butyl 2-methyl-4-oxopiperidine-1-carboxylate (10 g, 46.9 mmol) and sulfur (1.5 g, 46.9 mmol) in Ethanol (94 ml), ethyl 2-cyanoacetate (5.3 g, 46.9 mmol) and TEA (6.78 ml, 67 mmol) were added and refluxed for 4 hr. The reaction mixture was cooled down and the solvent evaporated. The crude products were purified by FCC (Hexane:AcOEt from 5% to 15%) to yield 13.4 g as mixture of 2 regioisomers (1:1 by LCMS and NMR).

Step 2: 6-(tert-butyl) 3-ethyl 7-methyl-4,7-dihydrothieno[2,3-c]pyridine-3,6(5H)-dicarboxylate (Intermediate 67a), 6-(tert-butyl) 3-ethyl 5-methyl-4,7-dihydrothieno[2,3-c]pyridine-3,6(5H)-dicarboxylate (Intermediate 67b)

67a

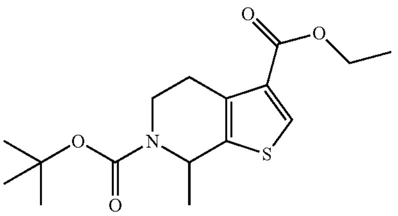

67b

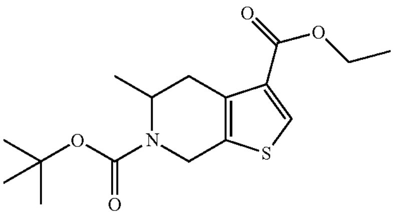

To a solution of the regioisomeric mixture obtained after step 1 Intermediate 66a and Intermediate 66b (13.9 g, 40.8 mmol) in THF (204 ml) at 0° C., isoamyl nitrite (8.25 ml, 61.2 mmol) was added dropwise and the reaction mixture was heated to RT and stirred for 30 minutes. Then the reaction mixture was heated to reflux for 6 hours. The reaction was concentrated under vacuum, and the crude products were purified via FCC (Hexane/AcOEt from 95:5 to 90:10) to afford of title compounds as 1:1 mixture of regioisomers Intermediate 67a and Intermediate 67b (2.98 g).

Step 3: ethyl 7-methyl-4,5,6,7-tetrahydrothieno[2,3-c]pyridine-3-carboxylate hydrochloride (Intermediate 68a) & ethyl 5-methyl-4,5,6,7-tetrahydrothieno[2,3-c]pyridine-3-carboxylate hydrochloride (Intermediate 68b)

68a

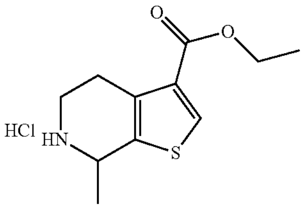

68b

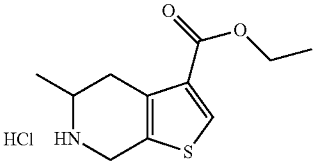

The mixture of two regioisomers Intermediate 67a and Intermediate 67b (2.05 g, 6.30 mmol) was dissolved in $Et_2O$ (31.5 ml), then 4N HCl in Dioxane (15.75 ml, 63.0 mmol) was added and the reaction mixture was stirred at RT overnight. The solid was filtered off and residual solvent evaporated under vacuum to obtained the title compounds as a mixture of regioisomers 68a and 68b (1.4 g)

Step 4: ethyl 6-(imidazo[1,2-a]pyridine-3-carbonyl)-7-methyl-4,5,6,7-tetrahydrothieno[2,3-c]pyridine-3-carboxylate (Intermediate 69a), ethyl 6-(imidazo[1,2-a]pyridine-3-carbonyl)-5-methyl-4,5,6,7-tetrahydrothieno[2,3-c]pyridine-3-carboxylate (Intermediate 69b)

69a

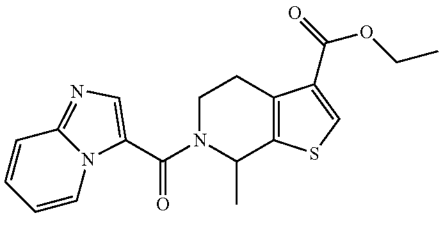

69b

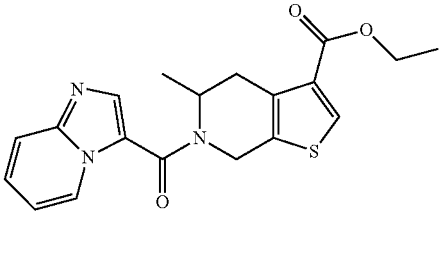

A mixture of Intermediate 68a and Intermediate 68b (1 g, 3.82 mmol) were dissolved in DCM (19.10 ml), DIPEA (4.00 ml, 22.92 mmol) was added followed by T3P (4.55 ml, 7.64 mmol) and the reaction mixture was stirred at RT overnight. The reaction mixture was diluted with DCM, water was added and this mixture was stirred for 10 min. Then the phases were separated, aqueous phases washed with DCM (3×50 mL), combined organic phases washed with brine, dried over $MgSO_4$, filtrated and concentrated under reduced pressure. The crude products were purified via FCC (DCM:MeOH from 0% to 10%) to afford 0.77 g of a mixture of title compounds.

Step 5: lithium 6-(imidazo[1,2-a]pyridine-3-carbonyl)-7-methyl-4,5,6,7-tetrahydrothieno[2,3-c]pyridine-3-carboxylate (Intermediate 70a) & lithium 6-(imidazo[1,2-a]pyridine-3-carbonyl)-5-methyl-4,5,6,7-tetrahydrothieno[2,3-c]pyridine-3-carboxylate (Intermediate 70b)

70a

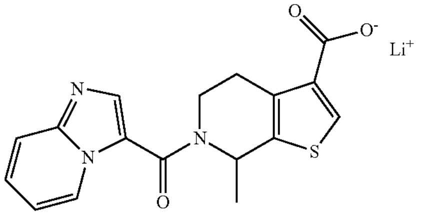

70b

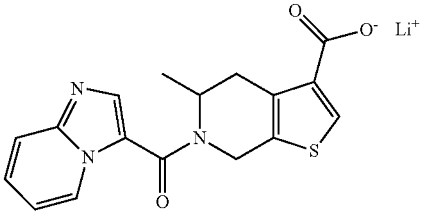

The mixture of intermediate 69a (550 mg, 1.489 mmol) and intermediate 69b (550 mg, 1.489 mmol) were dissolved in methanol (14.887 mL), then 1M LiOH (1.489 mL, 1.489 mmol) was added and the reaction was stirred at RT overnight. The reaction mixture was concentrated under vacuum to obtain the mixture of title compounds 70a and 70b.

Step 6: 6-(imidazo[1,2-a]pyridine-3-carbonyl)-7-methyl-N-(3-(4-methyl-1H-imidazol-1-yl)-5-(trifluoromethyl)phenyl)-4,5,6,7-tetrahydrothieno[2,3-c]pyridine-3-carboxamide (Example 98)

The mixture of 3-(4-methyl-1H-imidazol-1-yl)-5-(trifluoromethyl)aniline (0.250 g, 1.037 mmol), intermediate 70a and 70b (0.3 g, 0.864 mmol) were dissolved in DMF (2.159 ml) and DCM (6.48 ml) then DIPEA (0.905 ml, 5.18 mmol) and HATU (0.657 g, 1.728 mmol) were added. The reaction mixture was stirred at 45° C. until complete conversion of the starting material. The reaction mixture was diluted with DCM and water was added. This mixture was stirred 15 min and phases separated, organic phases were washed with 5% citric acid, water and brine, dryed over $Na_2SO_4$, filtered and concentrated under reduced pressure. The mixture of regioisomers was purified by Preparative HPLC to afford the title compound (35 mg, 0.062 mmol, 7.18% yield) as pure compound. The exact regioisomerism of the example 97 was assigned by $^1H$-NMR spectra.

$^1H$ NMR (300 MHz, DMSO-$d_6$) δ 10.56 (s, 1H), 8.93 (dt, J=7.0, 1.2 Hz, 1H), 8.25 (s, 1H), 8.23-8.16 (m, 2H), 8.09 (d, J=2.7 Hz, 2H), 7.77-7.67 (m, 2H), 7.50-7.41 (m, 2H), 7.10 (td, J=6.9, 1.3 Hz, 1H), 5.72 (q, J=7.7, 6.5 Hz, 1H), 4.52 (d, J=9.8 Hz, 1H), 3.46 (s, 1H), 3.19-2.96 (m, 2H), 2.18 (d, J=1.0 Hz, 3H), 1.65 (d, J=6.6 Hz, 3H).

LC-MS (ESI) method 10: $t_R$=3.94 min; m/z (M+1)=565.1

The compound reported in the following table was prepared via amido coupling as described for Example 98, steps 1-6, applying the corresponding, commercially available aryl amine in step 6. The regioisomeric structure was assigned by $^1H$-NMR spectra.

| Example No | Structure | Amount Intermediate 70a + 70b | Amount product (yield) | Purification method | Data |
|---|---|---|---|---|---|
| 99 | 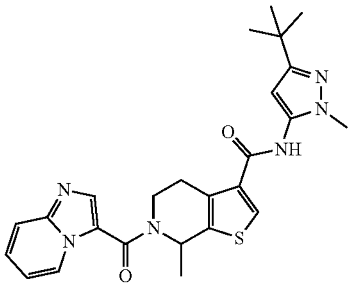 [SMILES: CC1c2scc(C(=O)Nc3cc(C(C)(C)C)nn3C)c2CCN1C(=O)c1cnc2ccccn12] | 150 mg | 15 mg (7%) | Prep HPLC | $^1H$ NMR (300 MHz, DMSO-$d_6$) δ 10.04 (s, 1H), 8.91 (d, J = 6.9 Hz, 1H), 8.20 (s, 1H), 8.11 (s, 1H), 7.73 (d, J = 9.0 Hz, 1H), 7.46 (dd, J = 8.8, 7.2 Hz, 1H), 7.08 (t, J = 6.8 Hz, 1H), 6.09 (s, 1H), 5.38 (d, J = 17.1 Hz, 1H), 5.11 (s, 1H), 4.63 (s, 1H), 3.62 (s, 3H), 3.19-3.05 (m, 1H), 2.97 (d, J = 17.0 Hz, 1H), 1.27-1.20 (m, 12H). LC-MS (ESI): method 10 $t_R$ = 6.02 min; m/z (M + 1) = 477. 2 |

Example 100: (R)-6-(imidazo[1,2-a]pyridine-3-carbonyl)-7-methyl-N-(3-(trifluoromethyl)phenyl)-4,5,6,7-tetrahydrothieno[2,3-c]pyridine-3-carboxamide Example 100

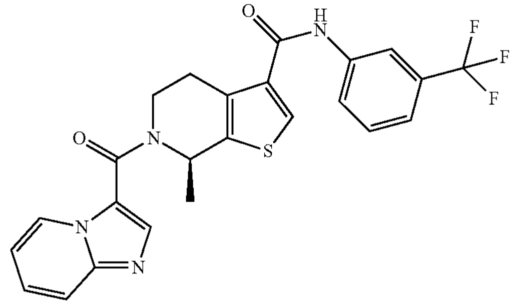

Step 1: 6-(tert-butyl) 3-ethyl (R)-2-amino-7-methyl-4,7-dihydrothieno[2,3-c]pyridine-3,6(5H)-dicarboxylate (Intermediate 71a) & 6-(tert-butyl) 3-ethyl (R)-2-amino-5-methyl-4,7-dihydrothieno[2,3-c]pyridine-3,6(5H)-dicarboxylate (Intermediate 71b)

71a

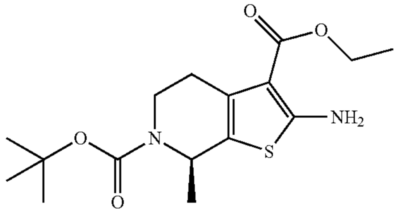

71b

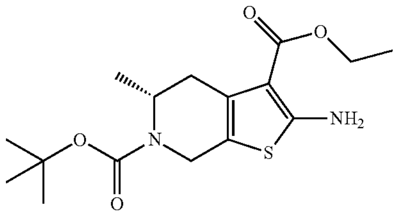

To a mixture of tert-butyl (R)-2-methyl-4-oxopiperidine-1-carboxylate (4 g, 18.75 mmol) and sulfur (0.6 g, 18.75 mmol) in ethanol (37.5 ml), ethyl 2-cyanoacetate (2.12 g, 18.75 mmol) and TEA (2.71 g, 26.8 mmol) were added and refluxed for 4 hr. The reaction mixture was cooled down and solvent evaporated. The crude products were purified by FCC (Hexane:AcOEt; from 5% to 15%) to yield 4.90 g as mixture of the two isomers 71a and 71 b in 77% of combinated yield (1:1 by LCMS and NMR).

Step 2: 6-(tert-butyl) 3-ethyl (R)-7-methyl-4,7-dihydrothieno[2,3-c]pyridine-3,6(5H)-dicarboxylate (Intermediate 72a) & 6-(tert-butyl) 3-ethyl (R)-5-methyl-4,7-dihydrothieno[2,3-c]pyridine-3,6(5H)-dicarboxylate (Intermediate 72b)

72a

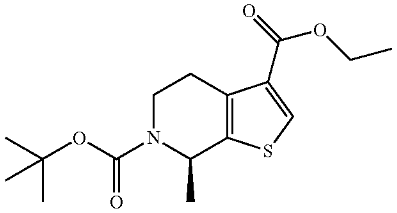

72b

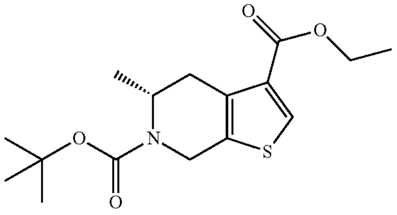

To a solution of regioisomeric mixture of Intermediate 71a Intermediate 71b (4.90 g, 28.8 mmol) in THF (72 ml) at 0° C., isoamyl nitrite (2.53 g, 21.6 mmol) was added dropwise and the reaction mixture was heated to RT and stirred for 30 minutes. Then reaction mixture was heated to reflux for 6 hours. The reaction was concentrated under vacuum, and the crude products were purified via FCC (Hexane:AcOEt from 95:5 to 90:10) to afford the title compounds as 1:1 mixture of regioisomer (1.06 g).

Step 3: ethyl (R)-7-methyl-4,5,6,7-tetrahydrothieno[2,3-c]pyridine-3-carboxylate hydrochloride (Intermediate 73a) & ethyl (R)-5-methyl-4,5,6,7-tetrahydrothieno[2,3-c]pyridine-3-carboxylate hydrochloride (Intermediate 73b)

73a

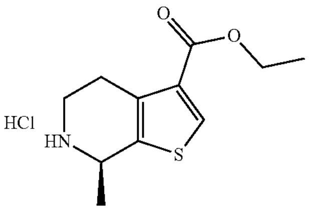

-continued

73b

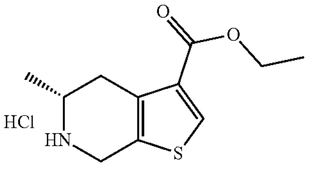

The mixture of two regioisomers Intermediate 72a Intermediate 72b (1.06 g, 3.26 mmol) was dissolved in $Et_2O$ (16 ml), then 4N HCl in Dioxane (12.2 ml, 49.0 mmol) was added and the reaction mixture was stirred at RT overnight. then it was diluted with DCM, 1:1 mixture of $H_2O$ and $NaHCO_{3\ (sat)}$ was added and this mixture stirred for 10 min. Then phases were separated, organic fase washed with water and brine, then dryed over $Na_2SO_4$, filtered and concentrated under reduced pressure. The crude mixture of regioisomers was separed via FCC (DCM: 5M $NH_3$/MEOH 98/2) to afford the pure regioisomers as follows:

Intermediate 73a (quantitative yield) $^1$H NMR (300 MHz, $CDCl_3$) δ 7.98 (d, J=0.8 Hz, 1H), 4.32 (q, J=7.1 Hz, 2H), 4.13 (q, J=6.7 Hz, 1H), 3.37 (ddd, J=12.5, 5.6, 2.2 Hz, 1H), 3.06-2.94 (m, 2H), 2.93-2.79 (m, 1H), 1.61 (s, 1H), 1.51-1.43 (m, 3H), 1.38 (t, J=7.1 Hz, 3H).

Intermediate 73b (0.32 g, 1.42 mmol, yield 87%) $^1$H NMR (300 MHz, $CDCl_3$) δ 7.96 (s, 1H), 4.32 (q, J=7.1 Hz, 2H), 4.10 (t, J=1.8 Hz, 2H), 3.15 (ddt, J=17.1, 4.3, 1.3 Hz, 1H), 3.06-2.92 (m, 1H), 2.47 (ddt, J=17.0, 10.1, 2.2 Hz, 1H), 1.57 (s, 1H), 1.38 (t, J=7.1 Hz, 3H), 1.30 (d, J=6.4 Hz, 4H).

Step 4: ethyl (R)-6-(imidazo[1,2-a]pyridine-3-carbonyl)-7-methyl-4,5,6,7-tetrahydrothieno[2,3-c]pyridine-3-carboxylate (Intermediate 74)

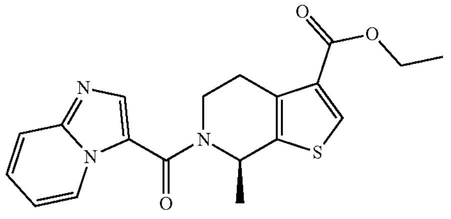 [SMILES: CCOC(=O)c1csc2c1CCN(C(=O)c1cnc3ccccn13)[C@@H]2C]

Intermediate 73a (0.48 g, 2.130 mmol) and imidazo[1,2-a]pyridine-3-carboxylic acid (0.415 g, 2.56 mmol) were dissolved in DMF (5.33 ml) and DCM (15.98 ml) then DIPEA (1.488 ml, 8.52 mmol) and HATU (2.025 g, 5.33 mmol) were added. The reaction mixture was stirred at RT overnight, diluted with DCM, water was added and this mixture was stirred for 10 min. Then the phases were separated, aqueous phases washed with DCM (3×50 mL), combined organic phases washed with brine, dried over $MgSO_4$, filtrated and concentrated under reduced pressure. The crude product was purified via FCC with DCM:MeOH (from 0% to 10% MeOH) to afford the title compound (0.66 g, 1.786 mmol, 84% yield).

$^1$H NMR (300 MHz, $CDCl_3$) δ 9.01 (dt, J=7.1, 1.2 Hz, 1H), 8.03 (s, 1H), 7.97 (s, 1H), 7.70 (dt, J=9.1, 1.2 Hz, 1H), 7.36 (ddd, J=9.1, 6.8, 1.3 Hz, 1H), 6.95 (td, J=6.9, 1.2 Hz, 1H), 5.76 (q, J=6.7 Hz, 1H), 4.67 (dd, J=13.8, 5.4 Hz, 1H), 4.32 (q, J=7.1 Hz, 2H), 3.45 (t, J=12.6 Hz, 1H), 3.28 (dd, J=17.1, 3.7 Hz, 1H), 3.07 (ddd, J=17.1, 12.1, 4.6 Hz, 1H), 1.70 (d, J=6.7 Hz, 3H), 1.37 (t, J=7.1 Hz, 3H).

Step 5: lithium (R)-6-(imidazo[1,2-a]pyridine-3-carbonyl)-7-methyl-4,5,6,7-tetrahydrothieno[2,3-c]pyridine-3-carboxylate (Intermediate 75)

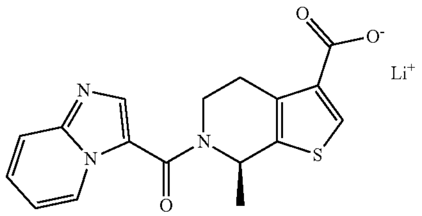 [SMILES: C[C@@H]1c2scc(C(=O)[O-])c2CCN1C(=O)c1cnc2ccccn12 ; [Li+]]

To a solution of Intermediate 74 (0.66 g, 1.786 mmol) in MeOH (8.93 ml), 1M LiOH (3.57 ml, 3.57 mmol) was added and the reaction mixture was stirred at RT overnight. The solution was concentrated under vacuum to afford the title compound in quantitative yield.

$^1$H NMR (300 MHz, DMSO-$d_6$) δ 8.85 (d, J=7.0 Hz, 1H), 8.00 (s, 1H), 7.69 (d, J=9.0 Hz, 1H), 7.57 (s, 1H), 7.45 (ddd, J=8.6, 6.8, 1.3 Hz, 1H), 7.08 (dd, J=7.6, 6.3 Hz, 1H), 5.55 (d, J=6.8 Hz, 1H), 4.41 (dd, J=14.0, 5.0 Hz, 1H), 3.38 (s, 1H), 3.24 (d, J=17.4 Hz, 1H), 2.92-2.75 (m, 1H), 2.67 (s, 6H), 1.57 (d, J=6.6 Hz, 3H).

Step 6: (R)-6-(imidazo[1,2-a]pyridine-3-carbonyl)-7-methyl-N-(3-(trifluoromethyl)phenyl)-4,5,6,7-tetrahydrothieno[2,3-c]pyridine-3-carboxamide (Example 100)

Intermediate 75 (0.10 g, 0.288 mmol) and 3-(trifluoromethyl)aniline (0.072 ml, 0.576 mmol) were dissolved in DMF (0.720 ml) and DCM (2.159 ml) then DIPEA (0.302 ml, 1.728 mmol) and HATU (0.274 g, 0.720 mmol) were added. The reaction mixture was stirred at RT overnight, diluted with DCM and water was added. This mixture was stirred 15 min and phases separated, organic phases were washed with water, 5% wt solution of citric acid and twice with water, dryed over $Na_2SO_4$, filtered and concentrated under reduced pressure. The crude material was purified by FC (DCM/MeOH from 0% to 10% MeOH) to afford the title compound (54.03 mg, 0.112 mmol, 38.7% yield). Absolute configuration was assigned by inference, performing non-racemizing chemical reactions on reagents whose absolute configuration is known.

$^1$H NMR (300 MHz, DMSO-$d_6$) δ 10.41 (s, 1H), 8.97-8.89 (m, 1H), 8.21 (d, J=5.7 Hz, 2H), 8.09 (s, 1H), 7.98 (d, J=8.2 Hz, 1H), 7.73 (dt, J=9.1, 1.2 Hz, 1H), 7.59 (t, J=8.0 Hz, 1H), 7.50-7.40 (m, 2H), 7.09 (td, J=6.9, 1.3 Hz, 1H), 5.71 (q, J=6.6 Hz, 1H), 4.57-4.47 (m, 1H), 3.53-3.39 (m, 1H), 3.17-2.94 (m, 2H), 1.64 (d, J=6.7 Hz, 3H).

LC-MS (ESI) method 11: $t_R$=2.14 min; m/z (M+1)=485.1

The compound reported in the following table was prepared via amido coupling as described for Example 100, steps 1-6, applying the corresponding, commercially available aryl amine in step 6.

| Example No | Structure | Amount Intermediate 75 | Amount product (yield) | Purification method | Data |
|---|---|---|---|---|---|
| 101 | 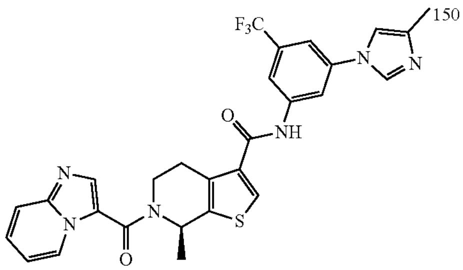 | 150 mg | 59.7 mg (25%) | FCC | $^1$H NMR (300 MHz, DMSO-$d_6$) δ 10.58 (s, 1H), 8.93 (dd, J = 6.9, 1.2 Hz, 1H), 8.25 (s, 1H), 8.22-8.17 (m, 2H), 8.09 (d, J = 2.0 Hz, 2H), 7.78-7.66 (m, 2H), 7.52 - 7.40 (m, 2H), 7.10 (td, J = 6.9, 1.3 Hz, 1H), 5.71 (q, J = 6.6 Hz, 1H), 4.52 (dd, J = 13.5, 4.9 Hz, 1H), 3.53-3.43 (m, 1H), 3.20-2.95 (m, 2H), 2.18 (d, J = 1.0 Hz, 3H), 1.64 (d, J = 6.6 Hz, 3H). LC-MS (ESI): method 3 $t_R$ = 1.56 min; m/z (M + 1) = 565.1 |

Example 102: 6-(imidazo[1,2-a]pyridine-3-carbonyl)-7,7-dimethyl-N-(3-(trifluoromethyl)phenyl)-4,5,6,7-tetrahydrothieno[2,3-c]pyridine-3-carboxamide Example 102

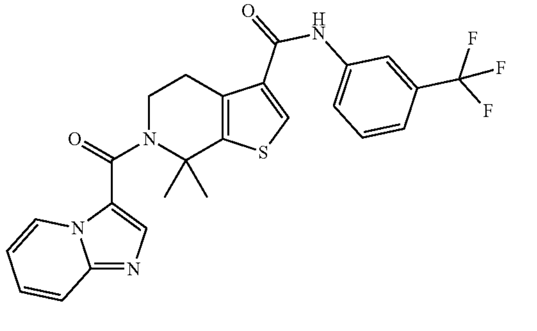

Step 1: 6-(tert-butyl) 3-ethyl 2-amino-7,7-dimethyl-4,7-dihydrothieno[2,3-c]pyridine-3,6(5H)-dicarboxylate (Intermediate 76a) & 6-(tert-butyl) 3-ethyl 2-amino-5,5-dimethyl-4,7-dihydrothieno[2,3-c]pyridine-3,6(5H)-dicarboxylate (Intermediate 76b)

76a

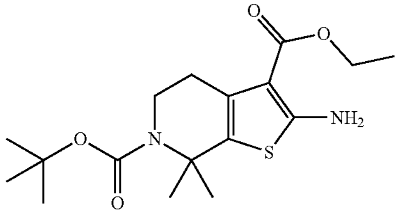

76b

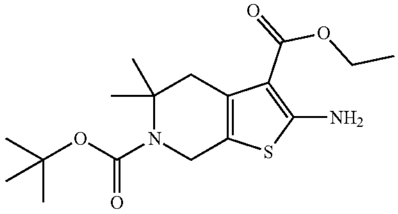

To a mixture of tert-butyl 2,2-dimethyl-4-oxopiperidine-1-carboxylate (5 g, 22.00 mmol) and sulfur (0.705 g, 22.00 mmol) in Ethanol (44.0 ml), ethyl 2-cyanoacetate (2.341 ml, 22.00 mmol) and TEA (4.38 ml, 31.5 mmol) were added and refluxed for 6 hr. The solvent was evaporated and crude material purified by FCC (Hexane:AcOEt from 95:5 to 85:15) to afford the pure regioisomers as follows:

Intermediate 76a (0.67 g, 1.890 mmol, 8.59% yield). $^1H$ NMR (300 MHz, $CDCl_3$) δ 5.98 (s, 2H), 4.26 (q, J=7.1 Hz, 3H), 3.64 (dd, J=5.9, 5.1 Hz, 2H), 2.78 (t, J=5.5 Hz, 2H), 1.68 (s, 6H), 1.50 (s, 9H), 1.34 (t, J=7.1 Hz, 3H).

Intermediate 76b (4.27 g, 12.05 mmol, 54.8% yield). $^1H$ NMR (300 MHz, $CDCl_3$) δ 5.96 (s, 2H), 4.35 (d, J=1.5 Hz, 2H), 4.28 (q, J=7.1 Hz, 2H), 2.85 (s, 2H), 1.47 (s, 9H), 1.44 (s, 6H), 1.35 (t, J=7.1 Hz, 3H). The exact regioisomeric structure were assigned by $^1H$-NMR spectra.

Step 2: 6-(tert-butyl) 3-ethyl 7,7-dimethyl-4,7-dihydrothieno[2,3-c]pyridine-3,6(5H)-dicarboxylate (Intermediate 77)

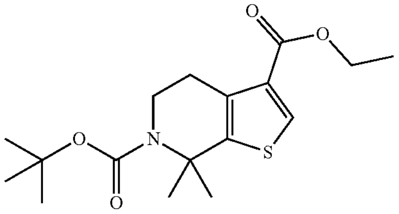 [SMILES: CCOC(=O)c1csc2c1CCN(C(=O)OC(C)(C)C)C2(C)C]

To a solution of Intermediate 76a (0.67 g, 1.890 mmol) in THF (9.45 ml) at 0° C., isoamyl nitrite (0.382 ml, 2.84 mmol) was added dropwise, reaction mixture was heated to RT and stirred for 30 minutes. The reaction mixture was heated to reflux for 6 hours, concentrated under vacuum and the crude product was purified by FCC with Hexane:AcOEt (from 95:5 to 90:10) to afford the title compound (160 mg, 0.471 mmol, 24.94% yield)$^1H$ NMR (300 MHz, $CDCl_3$) δ 7.97 (s, 1H), 4.30 (q, J=7.1 Hz, 2H), 3.69 (t, J=5.5 Hz, 2H), 2.96 (t, J=5.5 Hz, 2H), 1.79 (s, 6H), 1.51 (s, 9H), 1.36 (t, J=7.1 Hz, 3H).

Step 3: ethyl 7,7-dimethyl-4,5,6,7-tetrahydrothieno[2,3-c]pyridine-3-carboxylate hydrochloride (Intermediate 78)

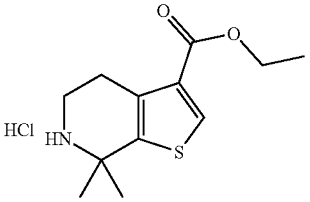 [SMILES: Cl ; CCOC(=O)c1csc2c1CCNC2(C)C]

To a solution of Intermediate 77 (0.16 g, 0.471 mmol) in DCM (3.93 ml), 4N HCl in Dioxane (1.768 ml, 7.07 mmol) was added and the reaction mixture was stirred at RT overnight-Solid was filtered off and residual solvent evaporated under vacuum to obtained the title compound (0.10 g, 0.363 mmol, 77% yield).

$^1H$ NMR (300 MHz, DMSO-$d_6$) δ 9.73 (s, 2H), 8.35 (s, 1H), 4.26 (q, J=7.1 Hz, 2H), 3.45 (t, J=6.1 Hz, 2H), 3.07 (t, J=6.1 Hz, 2H), 1.69 (s, 6H), 1.29 (t, J=7.1 Hz, 3H).

Step 4: ethyl 6-(imidazo[1,2-a]pyridine-3-carbonyl)-7,7-dimethyl-4,5,6,7-tetrahydrothieno[2,3-c]pyridine-3-carboxylate (Intermediate 79)

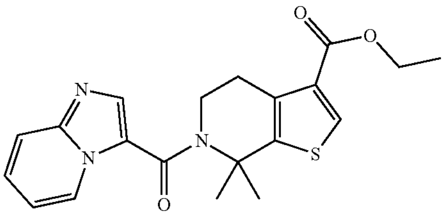 [SMILES: CCOC(=O)c1csc2c1CCN(C(=O)c1cnc3ccccn13)C2(C)C]

Intermediate 78 (0.10 g, 0.363 mmol) and imidazo[1,2-a]pyridine-3-carboxylic acid (0.071 g, 0.435 mmol) was dissolved in DMF (0.906 ml) and DCM (2.72 ml) then DIPEA (0.317 ml, 1.813 mmol) and HATU (0.345 g, 0.906 mmol) were added. the reaction mixture was stirred at RT overnight. In order to obtain full conversion the temperature was increased until 80° C. and further addiction of HATU and imidazo[1,2-a]pyridine-3-carboxylic acid were necessary. The reaction mixture was cooled down diluted with DCM and water was added, then it was stirred 15 min and phases separated. Organic phases were washed with 5% citric acid, water, brine, dried over $Na_2SO_4$, filtered and concentrated under reduced pressure. The crude material was purified by FC (DCM/MeOH from 0% to 10%) to afford the title compound (74 mg, 0.193 mmol, 53.2% yield).

$^1$H NMR (300 MHz, $CDCl_3$) δ 9.05 (d, J=7.0 Hz, 1H), 8.05 (s, 1H), 7.96 (s, 1H), 7.70 (d, J=9.0 Hz, 1H), 7.36 (dd, J=9.0, 6.8 Hz, 1H), 6.97 (t, J=6.9 Hz, 1H), 4.34 (q, J=7.1 Hz, 2H), 3.98 (t, J=5.4 Hz, 2H), 3.21 (t, J=5.5 Hz, 2H), 1.98 (s, 6H), 1.38 (t, J=7.1 Hz, 3H).

Step 5: lithium 6-(imidazo[1,2-a]pyridine-3-carbonyl)-7,7-dimethyl-4,5,6,7-tetrahydrothieno[2,3-c]pyridine-3-carboxylate (Intermediate 80)

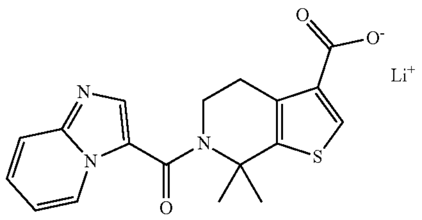 [SMILES: CC1(C)c2scc(C(=O)[O-])c2CCN1C(=O)c1cnc2ccccn12 ; [Li+]]

To a solution of Intermediate 79 (74 mg, 0.193 mmol) in MeOH (965 μl), 1M LiOH (772 μl, 0.772 mmol) was added, reaction mixture was stirred at RT overnight. Then the crude was concentrated under vacuum to afford the title compound (68 mg, 0.188 mmol, 98% yield).

$^1$H NMR (300 MHz, DMSO-$d_6$) δ 8.90 (dt, J=7.0, 1.3 Hz, 1H), 7.99 (s, 1H), 7.71 (dt, J=9.0, 1.2 Hz, 1H), 7.51 (s, 1H), 7.48-7.38 (m, 1H), 7.09 (td, J=6.9, 1.2 Hz, 1H), 3.81 (t, J=5.3 Hz, 2H), 3.20-3.11 (m, 3H), 1.87 (s, 6H).

Step 6: 6-(imidazo[1,2-a]pyridine-3-carbonyl)-7,7-dimethyl-N-(3-(trifluoromethyl)phenyl)-4,5,6,7-tetrahydrothieno[2,3-c]pyridine-3-carboxamide (Example 102)

Intermediate 80 (0.065 g, 0.180 mmol) was dissolved in DMF (0.84 ml) and DCM (2 ml) then DIPEA (0.189 ml, 1.079 mmol) and HATU (0.171 g, 0.450 mmol) were added. The reaction mixture was stirred for 15 minutes and then 3-(trifluoromethyl)aniline (0.058 g, 0.360 mmol) was added and stirred at RT overnight. Further addiction of amine and HATU were necessary to obtain complete conversion. The reaction mixture was cooled down diluted with DCM and water was added, it was stirred 15 min and phases separated. Organic phases was washed with 5% citric acid, water, brine, dryed over $Na_2SO_4$, filtered and concentrated under reduced pressure. The crude material was purified through FC (DCM/MeOH from 0% to 10%) to afford the title compound (29 mg, 0.058 mmol, 32.3% yield).

$^1$H NMR (300 MHz, DMSO-$d_6$) δ 10.43 (s, 1H), 8.93 (dt, J=7.0, 1.2 Hz, 1H), 8.24 (s, 1H), 8.22 (s, 1H), 8.05 (s, 1H), 7.98 (d, J=8.3 Hz, 1H), 7.73 (dt, J=9.1, 1.2 Hz, 1H), 7.60 (t, J=8.0 Hz, 1H), 7.46 (ddd, J=9.0, 6.8, 1.4 Hz, 2H), 7.11 (td, J=6.9, 1.3 Hz, 1H), 3.88 (t, J=5.3 Hz, 2H), 3.13 (t, J=5.2 Hz, 2H), 1.93 (s, 6H).

LC-MS (ESI) method 2: $t_R$=2.93 min; m/z (M+1)=499.1

Example 103: 6-(imidazo[1,2-a]pyrazin-3-ylmethyl)-7-methyl-N-(3-(trifluoromethyl)phenyl)-4,5,6,7-tetrahydrothieno[2,3-c]pyridine-3-carboxamide Example 103

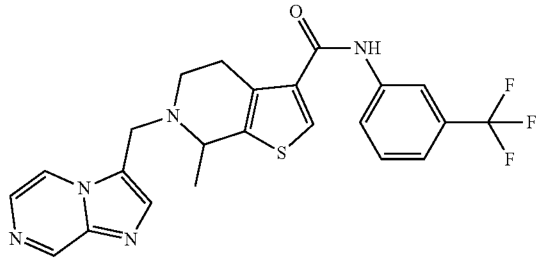

Example 104: 6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide—first eluting Example 104

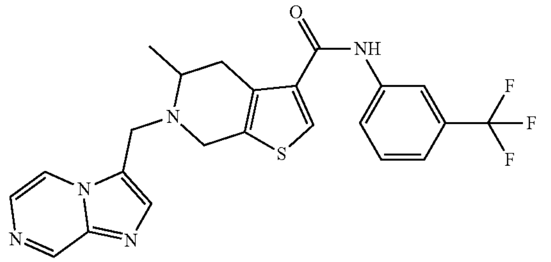

Example 105: 6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide—second eluting Example 105

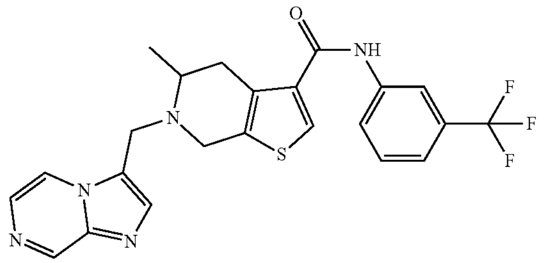

Step 1: lithium 6-(tert-butoxycarbonyl)-7-methyl-4,5,6,7-tetrahydrothieno[2,3-c]pyridine-3-carboxylate (Intermediate 81a), lithium 6-(tert-butoxycarbonyl)-5-methyl-4,5,6,7-tetrahydrothieno[2,3-c]pyridine-3-carboxylate (Intermediate 81b)

81a

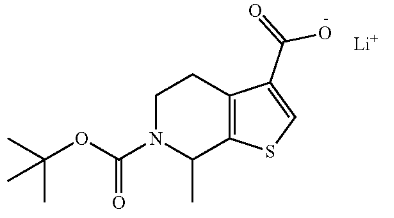

81b

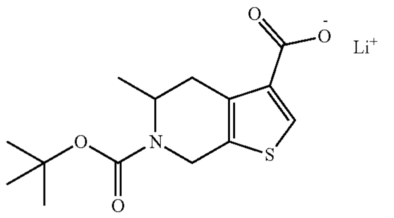

Intermediate 67a (0.430 g, 1.32 mmol) was dissolved in MeOH (26.4 ml), then 1M LiOH (5.29 ml, 5.29 mmol) was added. The reaction mixture was stirred overnight at 40° C. The crude was concentrated under vacuum to afford a mixture of title compounds.

Step 2: tert-butyl 7-methyl-3-((3-(trifluoromethyl)phenyl)carbamoyl)-4,7-dihydrothieno[2,3-c]pyridine-6(5H)-carboxylate (Intermediate 82a) & tert-butyl 5-methyl-3-((3-(trifluoromethyl)phenyl)carbamoyl)-4,7-dihydrothieno[2,3-c]pyridine-6(5H)-carboxylate (Intermediate 82b)

82a

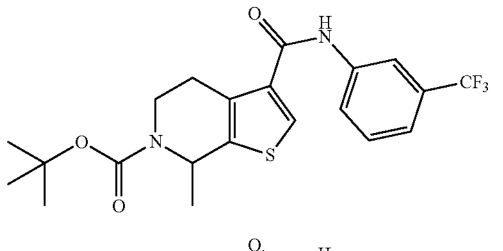

82b

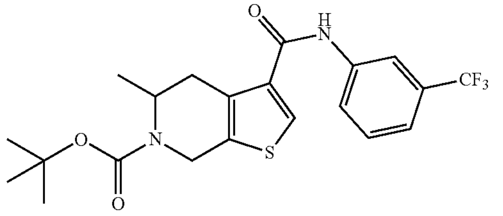

A mixture of Intermediate 81a and Intermediate 81b (0.90 g, 2.96 mmol) were dissolved in DMF (7.42 ml) and DCM (22.26 ml) then DIPEA (2.073 ml, 11.87 mmol) and HATU (2.82 g, 7.42 mmol) were added. The reaction mixture was stirred at RT for 15 min, 3-(trifluoromethyl)aniline (0.741 ml, 5.93 mmol) was added and the mixture stirred at 40° C. overnight. Then it was diluted with DCM and water was added. This mixture was stirred 15 min and phases separated, organic phases was washed with water, 5% wt solution of citric acid, twice with water and brine, dryed over $Na_2SO_4$, filtered and concentrated under reduced pressure. The crude material was purified by FC (DCM/MeOH from 0% to 10% MeOH). The product obtained was triturated with pentane to afford 750 mg of a mixture of title compounds.

Step 3: 7-methyl-N-(3-(trifluoromethyl)phenyl)-4,5,6,7-tetrahydrothieno[2,3-c]pyridine-3-carboxamide hydrochloride (Intermediate 83a) & 5-methyl-N-(3-(trifluoromethyl)phenyl)-4,5,6,7-tetrahydrothieno[2,3-c]pyridine-3-carboxamide hydrochloride (Intermediate 83b)

83a

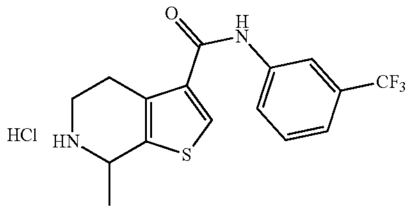

83b

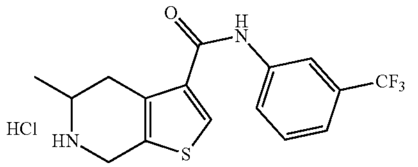

A mixture of Intermediate 82a and Intermediate 82b (750 mg, 1.70 mmol) was dissolved in mi DCM (20 ml) and MeOH (4 ml). then 4N HCl in Dioxane (4.26 ml, 17.03 mmol) was added and the mixture stirred at RT overnight. $Et_2O$ was added till no more precipitation was observed, then solid was filtered off and residual solvent evaporated under vacuum to obtain 650 mg of a mixture of title compounds Step 4: 6-(imidazo[1,2-a]pyrazin-3-ylmethyl)-7-methyl-N-(3-(trifluoromethyl)phenyl)-4,5,6,7-tetrahydrothieno[2,3-c]pyridine-3-carboxamide (Example 103), 6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide (Example 104), 6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide (Example 105)

A mixture of Intermediate 83a and 83b (0.140 g, 0.372 mmol), imidazo[1,2-a]pyrazine-3-carbaldehyde (0.066 g, 0.446 mmol) and magnesium sulfate (0.045 g, 0.372 mmol) were placed in roundbottom flask under argon. Anhydrous DCM (3.72 ml) was added followed by TEA (0.052 ml, 0.372 mmol) and the reaction mixture was stirred 30 min at rt. Then STAB (0.236 g, 1.115 mmol) was added and reaction mixture stirred until LC-MS showed complete consumption of starting material. Then the reaction mixture was diluted with DCM and washed with a mixture of $Na_2CO_{3(sat)}$ and water 1:1. Aqueous phase was extracted with DCM twice. Combined organic phases were washed with brine, dried over $Na_2SO_4$ and evaporated under reduced pressure. The crude was prepurified via FCC (DCM/MeOH from 0% to 5% MeOH) to afford 60 mg of regioisomeric mixture. The mixture was dissolved to 11 mg/mL in MeOH and was then purified by Preparative HPLC (method prep1) to afford Example 105 (3.3 mg, 0.007 mmol, yield 2%) and a mixture of Example 103 and Example 104 that was furtherly separated through SFC (method prep2) to afford Example 103 (12.9 mg, 0.027 mmol, yield 7%) and Example 104 (2.8 mg, 0.006 mmol, yield 1%).

Example 105: $^1H$ NMR (400 MHz, DMSO-$d_6$) δ 10.35 (s, 1H), 9.06 (d, J=1.5 Hz, 1H), 8.49 (dd, J=4.6, 1.5 Hz, 1H), 8.20 (s, 1H), 8.11 (s, 1H), 7.98-7.93 (m, 1H), 7.92 (d, J=4.6 Hz, 1H), 7.78 (s, 1H), 7.58 (t, J=8.0 Hz, 1H), 7.43 (d, J=7.7 Hz, 1H), 4.11 (s, 2H), 3.68 (s, 2H), 3.17 (q, J=5.6 Hz, 1H), 3.06-2.97 (m, 1H), 2.75-2.68 (m, 1H), 1.15 (d, J=6.6 Hz, 3H). LC-MS (ESI) method 12: $t_R$=4.23 min; m/z (M+1) =472.2; e.e. 99.3%

Example 103: $^1H$ NMR (300 MHz, DMSO-$d_6$) δ 10.34 (s, 1H), 9.07 (d, J=1.4 Hz, 1H), 8.51 (dd, J=4.7, 1.5 Hz, 1H), 8.18 (s, 1H), 8.14 (s, 1H), 8.01-7.88 (m, 2H), 7.82 (s, 1H), 7.57 (t, J=8.0 Hz, 1H), 7.42 (d, J=7.8 Hz, 1H), 4.26 (d, J=14.4 Hz, 1H), 4.04 (d, J=14.4 Hz, 1H), 3.95 (q, J=6.6 Hz, 1H), 2.99-2.78 (m, 2H), 2.76-2.62 (m, 2H), 1.44 (d, J=6.6 Hz, 3H).

LC-MS (ESI) method 12: $t_R$=4.99 min; m/z (M+1)=472.2; e.e. 100%

Example 104: $^1H$ NMR (400 MHz, DMSO-$d_6$) δ 10.35 (s, 1H), 9.06 (d, J=1.5 Hz, 1H), 8.49 (dd, J=4.6, 1.5 Hz, 1H), 8.20 (s, 1H), 8.11 (s, 1H), 7.98-7.93 (m, 1H), 7.92 (d, J=4.6 Hz, 1H), 7.78 (s, 1H), 7.58 (t, J=8.0 Hz, 1H), 7.43 (d, J=7.7 Hz, 1H), 4.11 (s, 2H), 3.68 (s, 2H), 3.17 (q, J=5.6 Hz, 1H), 3.06-2.97 (m, 1H), 2.74-2.68 (m, 1H), 1.15 (d, J=6.6 Hz, 3H).

LC-MS (ESI) method 12: $t_R$=3.57 min; m/z (M+1)=472.2; e.e. 98.3%.

Example 106: 6-((1H-pyrrolo[2,3-b]pyridin-5-yl)methyl)-7-methyl-N-(3-(trifluoromethyl)phenyl)-4,5,6,7-tetrahydrothieno[2,3-c]pyridine-3-carboxamide—first eluting enantiomer Example 106

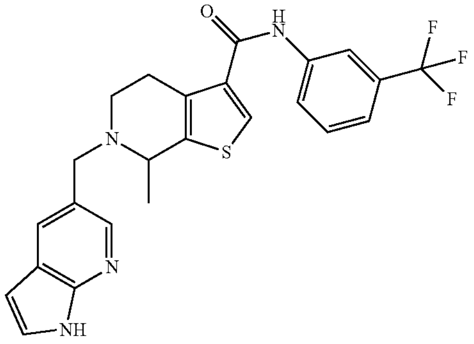

Example 107: 6-((1H-pyrrolo[2,3-b]pyridin-5-yl)methyl)-7-methyl-N-(3-(trifluoromethyl)phenyl)-4,5,6,7-tetrahydrothieno[2,3-c]pyridine-3-carboxamide—second eluting enantiomer)

Example 107

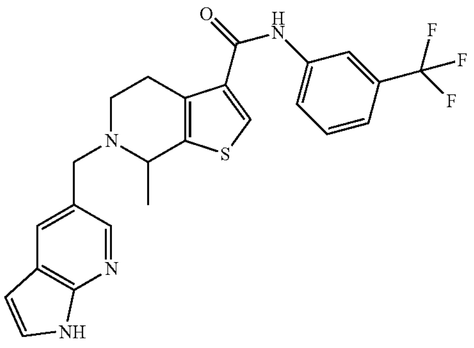

Step 1: 6-((1H-pyrrolo[2,3-b]pyridin-5-yl)methyl)-7-methyl-N-(3-(trifluoromethyl)phenyl)-4,5,6,7-tetrahydrothieno[2,3-c]pyridine-3-carboxamide—first eluting enantiomer (Example 106) and 6-((1H-pyrrolo[2,3-b]pyridin-5-yl)methyl)-7-methyl-N-(3-(trifluoromethyl)phenyl)-4,5,6,7-tetrahydrothieno[2,3-c]pyridine-3-carboxamide—second eluting enantiomer (Example 107)

A mixture of Intermediate 83a and 83b, (0.20 g, 0.531 mmol), 1H-pyrrolo[2,3-b]pyridine-5-carbaldehyde (0.078 g, 0.531 mmol) and magnesium sulfate (0.064 g, 0.531 mmol) were placed in roundbottom flask under argon. Anhydrous DCM (5.31 ml) was added followed by TEA (0.074 ml, 0.531 mmol). Reaction mixture was stirred 30 min at rt. and STAB (0.337 g, 1.592 mmol) was added and reaction mixture stirred at RT. Further addition of STAB and aldehyde were necessary to obtain full conversion of SM. The reaction mixture was diluted with DCM, $NaHCO_{3(sat)}$ was added and this mixture was stirred for 15 min. The phases were separated and aqueous phases extracted twice with DCM, organic phases were combined, washed with brine dryed over $Na_2SO_4$ and evaporated under reduced pressure. The crude was prepurified via FCC (DCM/MeOH from 0% to 5%) to afford 190 mg of an enantiomer mixture that was then purified via chiral SFC (Method prep3) to afford:

Example 106: (39 mg, 0.082 mmol, 31% yield)

$^1H$ NMR (300 MHz, DMSO-$d_6$) δ 11.57 (s, 1H), 10.34 (s, 1H), 8.19 (d, J=2.2 Hz, 2H), 8.12 (s, 1H), 7.96 (d, J=8.2 Hz, 1H), 7.91 (d, J=2.0 Hz, 1H), 7.57 (t, J=8.0 Hz, 1H), 7.48-7.38 (m, 2H), 6.42 (dd, J=3.5, 1.2 Hz, 1H), 3.95 (d, J=13.5 Hz, 1H), 3.89 (d, J=6.7 Hz, 1H), 3.68 (d, J=13.4 Hz, 1H), 3.05-2.93 (m, 1H), 2.93-2.78 (m, 1H), 2.77-2.58 (m, 2H), 1.45 (d, J=6.5 Hz, 3H).

SFC-MS (ESI) method 13: $t_R$=6.92 min; m/z (M+1)=471.2;

Example 107: (36 mg, 0.077 mmol, 29% yield).

$^1H$ NMR (300 MHz, DMSO-$d_6$) δ 11.57 (s, 1H), 10.34 (s, 1H), 8.19 (d, J=2.2 Hz, 2H), 8.12 (s, 1H), 7.96 (d, J=8.2 Hz, 1H), 7.91 (d, J=2.0 Hz, 1H), 7.57 (t, J=8.0 Hz, 1H), 7.48-7.38 (m, 2H), 6.42 (dd, J=3.5, 1.2 Hz, 1H), 3.95 (d, J=13.5 Hz, 1H), 3.89 (d, J=6.7 Hz, 1H), 3.68 (d, J=13.4 Hz, 1H), 3.05-2.93 (m, 1H), 2.93-2.78 (m, 1H), 2.77-2.58 (m, 2H), 1.45 (d, J=6.5 Hz, 3H).

SFC-MS (ESI) method 13: $t_R$=9.73 min; m/z (M+1) =471.2

Example 109; Preparation of compound 6-(pyrazolo[1,5-a]pyrimidine-3-carbonyl)-N-(5-(trifluoromethyl)pyridin-3-yl)-4,5,6,7-tetrahydrothieno[2,3-c]pyridine-3-carboxamide Example 109

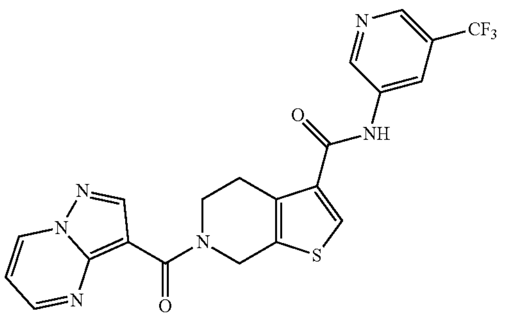

Step 1: tert-butyl 3-((5-(trifluoromethyl)pyridin-3-yl)carbamoyl)-4,7-dihydro thieno[2,3-c]pyridine-6(5H)-carboxylate (Intermediate 89)

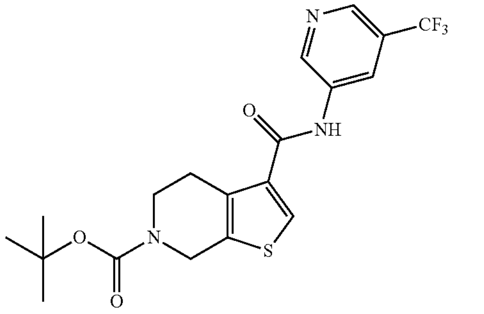 [SMILES: CC(C)(C)OC(=O)N1CCc2c(C(=O)Nc3cncc(C(F)(F)F)c3)csc2C1]

To a suspension of 6-(tert-butoxycarbonyl)-4,5,6,7-tetrahydrothieno[2,3-c]pyridine-3-carboxylic acid (250 mg, 0.882 mmol) in anhydrous acetonitrile (4.4 mL) was added 5-(trifluoromethyl)pyridin-3-amine (157 mg, 0.971 mmol) and 1-methylimidazole (0.25 mL, 3.09 mmol), resulting in complete solution. TCFH (371 mg, 1.32 mmol) was then added and the reaction mixture was stirred at room temperature, under an atmosphere of argon, for 22 h. The reaction mixture was partitioned between saturated $NaHCO_{3(aq)}$ and EtOAc, and the aqueous phase extracted with EtOAc. The combined organic phases were passed through a hydrophobic frit and concentrated in vacuo. Purification by column chromatography on silica gel (0-25% EtOAc in cyclohexane+0.1% $NEt_3$) provided desired compound (265 mg, 0.62 mmol, 70%).

$^1$H NMR (400 MHz, DMSO-$d_6$) δ 10.63 (s, 1H), 9.12 (d, J=2.3 Hz, 1H), 8.68 (d, J=1.0 Hz, 1H), 8.58 (t, J=1.9 Hz, 1H), 8.22 (s, 1H), 4.60 (s, 2H), 3.61-3.56 (m, 2H), 2.89-2.84 (m, 2H), 1.43 (s, 9H).

Step 2: N-(5-(trifluoromethyl)pyridin-3-yl)-4,5,6,7-tetrahydrothieno[2,3-c]pyridine-3-carboxamide (Intermediate 90)

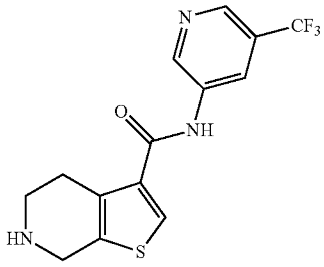 [SMILES: O=C(Nc1cncc(C(F)(F)F)c1)c1csc2c1CCNC2]

To a stirred solution of Intermediate 89 (290 mg, 0.678 mmol) in anhydrous DCM (6.78 ml), cooled over an ice/water bath under an atmosphere of argon, was added TFA (0.52 mL, 6.78 mmol), dropwise over 5 min. The reaction mixture was stirred for 3 h. Further TFA (0.17 ml, 2.26 mmol) was added, the reaction mixture was allowed to warm to room temperature and stirred for 1 h. The reaction mixture was concentrated in vacuo, the residue was dissolved in 1:1 DCM:MeOH and applied to a pre-conditioned 5 g Isolute SCX-II cartridge, washed with MeOH, then released with 2 M $NH_3$/MeOH. The 2 M $NH_3$/MeOH eluent was concentrated in vacuo to give desired product (193 mg, 0.59 mmol, 87%).

$^1$H NMR (400 MHz, DMSO-$d_6$) δ 10.58 (s, 1H), 9.12 (d, J=2.3 Hz, 1H), 8.67 (d, J=1.0 Hz, 1H), 8.59-8.57 (m, 1H), 8.12 (s, 1H), 3.88 (s, 2H), 3.17 (d, J=5.0 Hz, 1H), 2.90 (t, J=5.7 Hz, 2H), 2.78-2.73 (m, 2H).

Step 3: 6-(pyrazolo[1,5-a]pyrimidine-3-carbonyl)-N-(5-(trifluoromethyl) pyridin-3-yl)-4,5,6,7-tetrahydrothieno[2,3-c]pyridine-3-carboxamide (Example 109)

Prepared from Intermediate 90 (40 mg, 0.122 mmol) and pyrazolo[1,5-a]pyrimidine-3-carboxylic acid (17 mg, 0.104 mmol) according to general procedure G. Purification by reverse phase preparative HPLC (Sunfire C18 19×150 mm, 10 μm 20-80% acetonitrile/water-10 mM $NH_4HCO_3$), 20 mL/min) gave the title compound (6 mg, 0.013 mmol, 12%).

LCMS (ESI): Method 6 $t_R$=3.79 min, m/z [M+1]+=473.3.

$^1$H NMR (400 MHz, DMSO-$d_6$) δ 10.66 (s, 1H), 9.26 (dd, J=1.8, 7.0 Hz, 1H), 9.13 (d, J=2.3 Hz, 1H), 8.75 (dd, J=1.6, 4.0 Hz, 1H), 8.69 (d, J=1.0 Hz, 1H), 8.62-8.59 (m, 1H), 8.49 (s, 1H), 8.25 (brs, 1H), 7.23 (dd, J=4.0, 7.0 Hz, 1H), 4.89 (s, 2H), 3.91-3.75 (m, 2H), 3.11-3.02 (m, 2H).

The compounds reported in the following table were prepared via amido coupling as described for Example 109, step 1-3, applying the corresponding, commercially available or previously synthesized carboxylic acid in step 3. Modifications of coupling agents, salt free-basing or chromatographic purification conditions (e.g. Prep HPLC or flash chromatography) were reported in the table.

| Example No | Structure | General procedure - Amount reagents | Amount product (yield) | Purification method | Data |
|---|---|---|---|---|---|
| 108 | 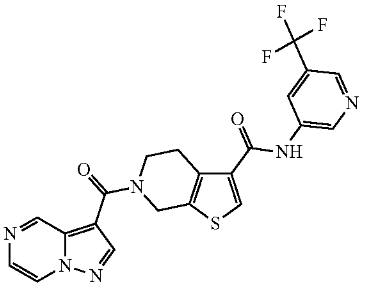 [SMILES: O=C(Nc1cncc(C(F)(F)F)c1)c1csc2c1CCN(C(=O)c1cnn3ccncc13)C2] | General procedure G<br>Carboxylic acid (15 mg, 0.0889 mmol):<br>Intermediate 90: 30 mg (1.1 eq)<br>DCM/DMF mixture replaced by DMF | 3 mg (7%) | Prep HPLC | $^1H$ NMR (400 MHz, DMSO-$d_6$) δ 10.66 (s, 1H), 9.37 (d, J = 1.4 Hz, 1H), 9.14 (d, J = 2.3 Hz, 1H), 8.94 (dd, J = 1.4, 4.7 Hz, 1H), 8.70 (d, J = 1.0 Hz, 1H), 8.62-8.59 (m, 1H), 8.57 (s, 1H), 8.26 (s, 1H), 8.11 (d, J = 4.6 Hz, 1H), 5.01 (s, 2H), 3.98-3.93 (m, 2H), 3.11-3.05 (m, 2H).<br>LCMS (ESI): Method 7 $t_R$ = 3.92 min; m/z [M + H]+ = 473.4 |
| 110 | 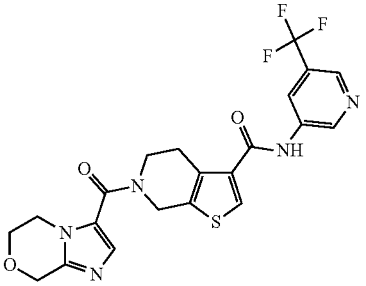 [SMILES: O=C(Nc1cncc(C(F)(F)F)c1)c1csc2c1CCN(C(=O)c1cnc3n1CCOC3)C2] | General procedure G<br>Carboxylic acid (17 mg, 0.0831 mmol):<br>Intermediate 90: 30 mg (1.1 eq) | 20 mg (50%) | Prep HPLC | $^1H$ NMR (400 MHz, DMSO-$d_6$) δ 10.65 (s, 1H), 9.14 (d, J = 2.4 Hz, 1H), 8.71-8.69 (m, 1H), 8.62-8.59 (m, 1H), 8.26 (s, 1H), 7.41 (s, 1H), 4.93 (s, 2H), 4.80 (s, 2H), 4.14 (t, J = 5.2 Hz, 2H), 4.00 (t, J = 5.2 Hz, 2H), 3.95-3.91 (m, 2H), 3.07-3.01 (m, 2H)<br>LCMS (ESI): Method 7 $t_R$ = 3.28 min; m/z [M + H]+ = 478.5 |
| 111 | 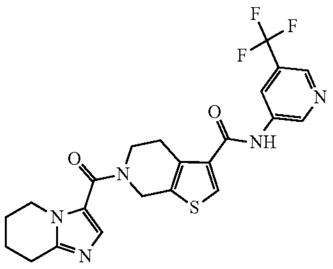 [SMILES: O=C(Nc1cncc(C(F)(F)F)c1)c1csc2c1CCN(C(=O)c1cnc3n1CCCC3)C2] | General procedure G<br>Carboxylic acid (17 mg, 0.0839 mmol):<br>Intermediate 90: 30 mg (1.1 eq) | 25 mg (61%) | Prep HPLC | $^1H$ NMR (400 MHz, DMSO-$d_6$) δ 10.65 (s, 1H), 9.13 (d, J = 2.3 Hz, 1H), 8.71-8.69 (m, 1H), 8.61-8.59 (m, 1H), 8.25 (s, 1H), 7.29 (s, 1H), 4.91 (s, 2H), 4.05 (t, J = 5.7 Hz, 2H), 3.90 (t, J = 5.7 Hz, 2H), 3.04-2.99 (m, 2H), 2.82-2.77 (m, 2H), 1.91-1.81 (m, 4H)<br>LCMS (ESI): Method 7 $t_R$ = 3.16 min; m/z [M + H]+ = 476.5 |
| 120 | 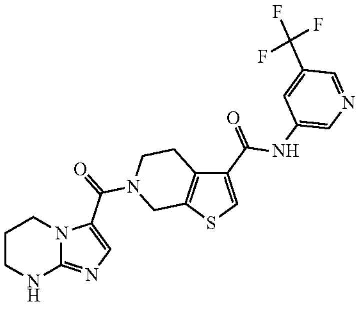 [SMILES: O=C(Nc1cncc(C(F)(F)F)c1)c1csc2c1CCN(C(=O)c1cnc3n1CCCN3)C2] | General procedure G<br>Carboxylic acid (100 mg, 0.598 mmol):<br>Intermediate 90: 196 mg (1.0 eq) | 69 mg (24%) | Prep HPLC; Further purification (Xbridge Phenyl 19 × 150 mm, 10 um 20-80% MeOH/$H_2O$ (10 mM $NH_4CO_3$), 20 ml/min, RT) | $^1H$ NMR (400 MHz, DMSO-$d_6$) δ 10.64 (s, 1H), 9.14 (d, J = 2.4 Hz, 1H), 8.70 (d, J = 1.1 Hz, 1H), 8.60 (t, J = 2.2 Hz, 1H), 8.24 (s, 1H), 7.05 (s, 1H), 6.79 (t, J = 2.2 Hz, 1H), 4.89 (s, 2H), 4.00 (t, J = 5.9 Hz, 2H), 3.88 (t, J = 5.9 Hz, 2H), 3.25-3.21 (m, 2H), 2.99 (t, J = 5.5 Hz, 2H), 1.93-1.87 (m, 2H).<br>LCMS (ESI): Method 7 $t_R$ = 3.13; m/z [M + H]+ = 477.2 |
| 124 | 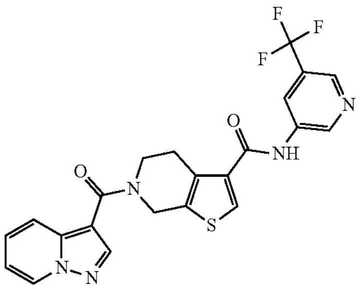 [SMILES: O=C(Nc1cncc(C(F)(F)F)c1)c1csc2c1CCN(C(=O)c1cnn3ccccc13)C2] | General procedure G<br>Carboxylic acid (66 mg, 0.40 mmol):<br>Intermediate 90: 133 mg (1.0 eq) | 8 mg (4%) | Prep HPLC | $^1H$ NMR (400 MHz, DMSO-$d_6$) δ 10.68 (s, 1H), 9.19 (d, J = 2.2 Hz, 1H), 8.87 (td, J = 0.9, 7.0 Hz, 1H), 8.75 (d, J = 1.1 Hz, 1H), 8.65 (t, J = 2.0 Hz, 1H), 8.44 (s, 1H), 8.30 (s, 1H), 7.99 (td, J = 1.0, 9.1 Hz, 1H), 7.52 (ddd, J = 1.0, 6.8, 8.9 Hz, 1H), 7.14 (dt, J = 1.3, 6.8 Hz, 1H), 5.00 (s, 2H), 3.97 (t, J = 5.7 Hz, 2H), 3.10 (t, J = 5.6 Hz, 2H).<br>LCMS (ESI): Method 7 $t_R$ = 4.22 min; m/z [M + H]+ = 472.5 |

-continued

| Example No | Structure | General procedure - Amount reagents | Amount product (yield) | Purification method | Data |
|---|---|---|---|---|---|
| 140 | 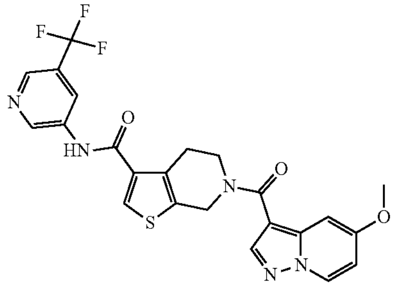 [SMILES: COc1ccn2ncc(C(=O)N3CCc4c(C(=O)Nc5cncc(C(F)(F)F)c5)csc4C3)c2c1] | General procedure G Carboxylic acid (50 mg, 0.26 mmol): Intermediate 90: 85 mg (1.0 eq) | 15 mg (12%) | Prep HPLC | $^1$H NMR (400 MHz, DMSO-$d_6$) δ 10.66 (s, 1H), 9.15 (d, J = 1.9 Hz, 1H), 8.71 (d, J = 1.0 Hz, 1H), 8.68 (dd, J = 0.5, 7.6 Hz, 1H), 8.60 (t, J = 2.0 Hz, 1H), 8.30 (s, 1H), 8.25 (s, 1H), 7.25 (d, J = 2.6 Hz, 1H), 6.77 (dd, J = 2.9, 7.5 Hz, 1H), 4.96 (s, 2H), 3.92 (t, J = 5.7 Hz, 2H), 3.88 (s, 3H), 3.05 (t, J = 5.2 Hz, 2H). LC-MS (ESI) method 7: $t_R$ = 4.39 min; m/z [M + H]+ = 502.2. |
| 141 | 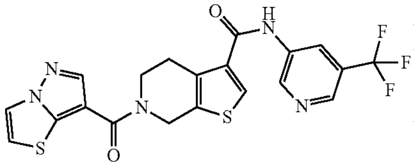 [SMILES: O=C(Nc1cncc(C(F)(F)F)c1)c1csc2c1CCN(C(=O)c1cnn3ccsc13)C2] | General procedure N (ACN replaced with DMF) Carboxylic acid (50 mg, 0.260 mmol) Intermediate 90: 95 mg (1.05 eq) | 57 mg (40%) | Precipitation from water | $^1$H NMR (400 MHz, DMSO-$d_6$) δ 10.68 (1H, s), 9.18 (1H, d, J = 2.3 Hz), 8.74 (1H, d, J = 1.0 Hz), 8.64 (1H, t, J = 2.3 Hz), 8.44 (1H, d, J = 1.3 Hz), 8.38 (1H, d, J = 4.2 Hz), 8.30 (1H, s), 7.59 (1H, dd, J = 1.4, 4.2 Hz), 5.04 (2H, s), 4.02 (2H, t, J = 5.3 Hz), 3.10 (2H, t, J = 5.3 Hz); LC-MS (ESI) method 6: $t_R$ = 4.13 min; m/z [M + H]+ = 478.2 |
| 142 | 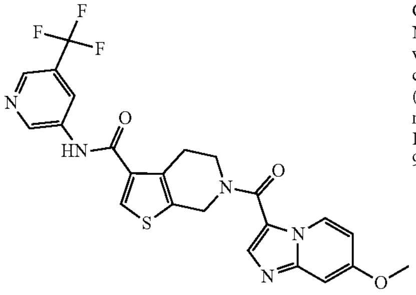 | General procedure N (ACN replaced with DMF) carboxylic acid (50 mg, 0.260 mmol) Intermediate 90: 95 mg (1.05 eq) | 71 mg (53%) | Precipitation from water | $^1$H NMR (400 MHz, DMSO-$d_6$) δ 10.69 (1H, s), 9.19 (1H, d, J = 2.3 Hz), 8.89 (1H, d, J = 7.6 Hz), 8.75 (1H, d, J = 1.0 Hz), 8.65 (1H, t, J = 2.2 Hz), 8.31 (1H, s), 8.07 (1H, s), 7.17 (1H, d, J = 2.5 Hz), 6.86 (1H, dd, J = 2.5, 7.6 Hz), 5.07 (2H, s), 4.03 (2H, t, J = 5.5 Hz), 3.94 (3H, s), 3.13 (2H, t, J = 5.5 Hz). LC-MS (ESI) method 6: $t_R$ = 4.2 min; m/z [M $^+$ H]$^+$ = 502.2 |
| 143 | 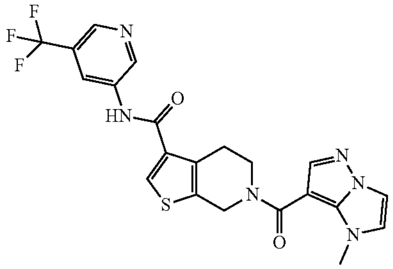 [SMILES: Cn1ccn2ncc(C(=O)N3CCc4c(C(=O)Nc5cncc(C(F)(F)F)c5)csc4C3)c12] | General procedure N (ACN replaced with DMF) carboxylic acid (43 mg, 0.260 mmol) Intermediate 90: 95 mg (1.0 eq) | 7.4 mg (6%) | Prep HPLC | $^1$H NMR (400 MHz, DMSO-$d_6$) δ 10.65 (s, 1H), 9.14 (d, J = 2.4 Hz, 1H), 8.69 (s, 1H), 8.61-8.60 (m, 1H), 8.25-8.24 (m, 1H), 7.90 (d, J = 1.1 Hz, 1H), 7.70 (d, J = 2.3 Hz, 1H), 7.30 (dd, J = 1.2, 2.2 Hz, 1H), 4.94 (s, 2H), 3.95-3.90 (m, 2H), 3.84 (s, 3H), 3.06-3.03 (m, 2H). LC-MS (ESI) method 6: $t_R$ = 3.85 min; m/z [M $^+$ H]$^+$ = 475.5 |
| 144 | 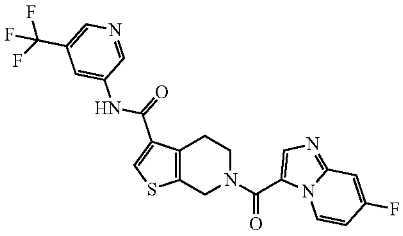 [SMILES: O=C(Nc1cncc(C(F)(F)F)c1)c1csc2c1CCN(C(=O)c1cnc3cc(F)ccn13)C2] | General procedure N (ACN replaced with DMF) carboxylic acid (47 mg, 0.260 mmol): Intermediate 90: 95 mg (1.0 eq) | 47 mg (36%) | Precipitation from water | $^1$H NMR (400 MHz, DMSO-$d_6$) δ 10.66 (s, 1H), 9.15 (d, J = 2.3 Hz, 1H), 9.02 (dd, J = 5.8, 7.5 Hz, 1H), 8.71 (d, J = 1.1 Hz, 1H), 8.61 (t, J = 1.9 Hz, 1H), 8.27 (s, 1H), 8.15 (s, 1H), 7.65 (dd, J = 2.2, 9.7 Hz, 1H), 7.20-7.15 (m, 1H), 5.04 (s, 2H), 4.02-3.98 (m, 2H), 3.12-3.09 (m, 2H). LC-MS (ESI) method 6: $t_R$ = 4.24 min; m/z [M $^+$ H]$^+$ = 490.2 |

Example 112; Preparation of compound N-(3-(tert-butyl)isoxazol-5-yl)-6-(5,6-dihydro-8H-imidazo[2,1-c][1,4]oxazine-3-carbonyl)-4,5,6,7-tetrahydrothieno[2,3-c]pyridine-3-carboxamide Example 112

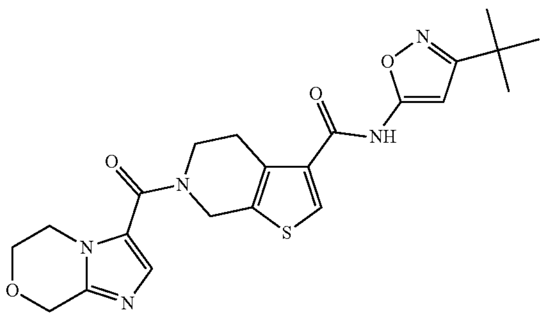

Step 1; ethyl 6-(6,8-dihydro-5H-imidazo[2,1-c][1,4]oxazine-3-carbonyl)-5,7-dihydro-4H-thieno[2,3-c]pyridine-3-carboxylate (Intermediate 91)

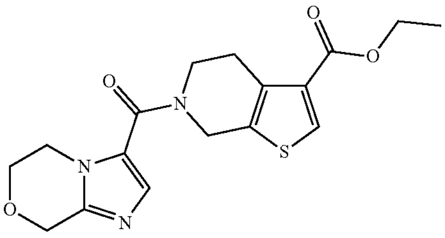 [SMILES: CCOC(=O)c1csc2c1CCN(C(=O)c1cnc3n1CCOC3)C2]

To a suspension of Intermediate 38 (125 mg, 0.505 mmol), 6,8-dihydro-5H-imidazo[2,1-c][1,4]oxazine-3-carboxylic acid hydrochloride (124 mg, 0.605 mmol) and O-(Benzotriazol-1-yl)-N,N,N',N'-tetramethyluronium tetrafluoroborate (232 mg, 0.722 mmol) in anhydrous DCM (2.00 ml) and DMF (2.00 ml) was added N,N-diisopropylethylamine (0.35 mL, 2.02 mmol). The reaction mixture was stirred at room temperature, under an atmosphere of nitrogen, for 2 h, and left to stand for 16 h. The reaction mixture was diluted with and the organic phase was washed with saturated $NaHCO_{3(aq)}$, then saturated $NaCl_{(aq)}$ dried over $Na_2SO_4$ and concentrated in vacuo. The residue was purified by FCC eluting with DCM-methanolic ammonia (2M; 20:1)/0-100% to afford desired product (196 mg, 0.477 mmol, 95%).

$^1H$ NMR (400 MHz, $CDCl_3$) δ 8.02 (s, 1H), 7.33 (s, 1H), 4.94 (s, 2H), 4.88 (s, 2H), 4.32 (q, J=7.2 Hz, 2H), 4.28 (t, J=5.4 Hz, 2H), 4.05 (t, J=5.2 Hz, 2H), 4.01 (t, J=5.5 Hz, 2H), 3.17-3.12 (m, 2H), 1.37 (t, J=7.1 Hz, 3H).

Step 2; 6-(6,8-dihydro-5H-imidazo[2,1-c][1,4]oxazine-3-carbonyl)-5,7-dihydro-4H-thieno[2,3-c]pyridine-3-carboxylic acid (Intermediate 92)

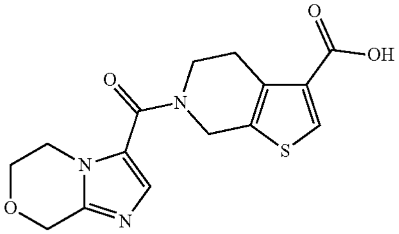 [SMILES: O=C(O)c1csc2c1CCN(C(=O)c1cnc3n1CCOC3)C2]

Sodium hydroxide (68 mg, 1.71 mmol) was added to a solution of Intermediate 91 (191 mg, 0.528 mmol) in methyl alcohol (10) and water (0.50) and the mixture stirred at 50° C. for 3 days.

The mixture was cooled in an ice bath and 1 M Hydrogen chloride (1.7 mL, 1.71 mmol) added dropwise. The solution was concentrated in vacuo resulting in the precipitation of a colourless solid which was filtered off, washed with acetone (2) to give desired product (76 mg, 0.228 mmol, 43%) and used as it is in the next step.

Step 3; N-(3-(tert-butyl)isoxazol-5-yl)-6-(5,6-dihydro-8H-imidazo[2,1-c][1,4]oxazine-3-carbonyl)-4,5,6,7-tetrahydrothieno[2,3-c]pyridine-3-carboxamide (Example 112)

Thionyl chloride (0.13 mL, 1.80 mmol) was added to Intermediate 92 (30 mg, 0.0900 mmol) and the mixture stirred at room temperature overnight. The mixture was taken to dryness in vacuo and the residue suspended in dry pyridine (1.0 ml), 3-tert-butylisoxazol-5-amine (19 mg, 0.135 mmol) was added and the mixture stirred for 1 h. The mixture was taken to dryness in vacuo and the residue dissolved in 9:1 DMSO:water (1.0 mL) and submitted for purification by Sunfire C18 19×150 mm, 10 um 5-60% ACN/$H_2O$ (0.1% FA), 20 ml/min to give desired product (17 mg, 0.0381 mmol, 42%).

LCMS (ESI): Method 15 $t_R$=3.48 min, $[M+H]^+$=456.2

$^1H$ NMR (400 MHz, DMSO-$d_6$) δ 11.77 (s, 1H), 8.34 (s, 1H), 7.40 (s, 1H), 6.37 (s, 1H), 4.95-4.89 (s, 2H), 4.80-4.79 (m, 2H), 4.14 (t, J=5.1 Hz, 2H), 4.00 (t, J=5.1 Hz, 2H), 3.91 (t, J=5.4 Hz, 2H), 3.02 (s, 2H), 1.29 (s, 9H)

Example 113; Preparation of compound N-(3-(tert-butyl)isoxazol-5-yl)-6-(pyrazolo[1,5-a]pyrazine-3-carbonyl)-4,5,6,7-tetrahydrothieno[2,3-c]pyridine-3-carboxamide Example 113

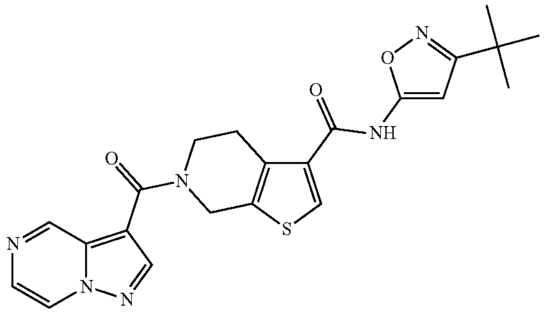

Step 1: Ethyl 6-(pyrazolo[1,5-a]pyrazine-3-carbonyl)-4,5,6,7-tetrahydrothieno[2,3-c]pyridine-3-carboxylate (Intermediate 93)

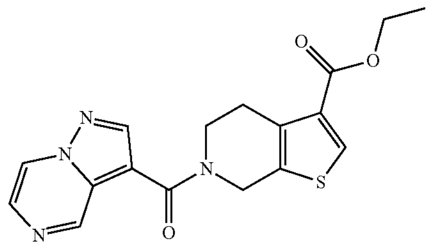 [SMILES: CCOC(=O)c1csc2c1CCN(C(=O)c1cnn3ccncc13)C2]

To a suspension of Intermediate 38 (125 mg, 0.505 mmol), pyrazolo[1,5-a]pyrazine-3-carboxylic acid (99 mg, 0.605 mmol) and TBTU (232 mg, 0.722 mmol) in DCM (2 ml) and DMF (2 ml), N,N-Diisopropylethylamine (0.35 mL, 2.02 mmol) was added. The reaction mixture was stirred at room temperature for 18 h. The reaction mixture was diluted with and the organic phase was washed with saturated $NaHCO_{3(aq)}$ then saturated $NaCl_{(aq)}$ and concentrated in vacuo. The residue was purified chromatography on silica by elution with DCM-methanolic ammonia (2M; 20:1)/0-100% to give title compound (149 mg, 82%).

$^1$H NMR (400 MHz, $CDCl_3$) δ 9.48 (d, J=1.5 Hz, 1H), 8.43 (dd, J=1.5, 4.8 Hz, 1H), 8.20 (s, 1H), 8.05 (d, J=4.8 Hz, 1H), 8.04 (s, 1H), 4.98 (s, 2H), 4.32 (q, J=7.0 Hz, 2H), 4.02 (t, J=5.9 Hz, 2H), 3.23-3.18 (m, 2H), 1.38 (t, J=7.0 Hz, 3H)

Step 2: 6-(pyrazolo[1,5-a]pyrazine-3-carbonyl)-4,5,6,7-tetrahydrothieno[2,3-c]pyridine-3-carboxylic acid (Intermediate 94)

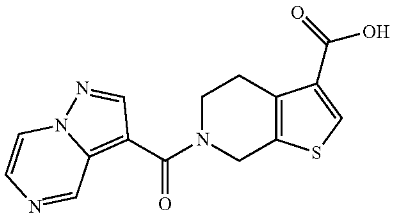 [SMILES: O=C(O)c1csc2c1CCN(C(=O)c1cnn3ccncc13)C2]

Sodium hydroxide (49 mg, 1.23 mmol) was added to a solution of Intermediate 93 (142 mg, 0.398 mmol) in methyl alcohol (10 ml) and water (0.5 ml) and the mixture stirred at 50° C. for 64 h. The mixture was cooled in an ice bath and 1 M aqueous hydrogen chloride (1.2 ml, 1.23 mmol) added dropwise. The solution was concentrated in vacuo resulting in the precipitation of a colourless solid which was filtered off, washed with acetone (2 mL) to give title compound (86 mg, 66%).

LCMS (ESI): Method 15 $t_R$=0.47 min; m/z $[M+H]^+$=329.2

Step 3: N-(3-tert-butyl)isoxazol-5-yl)-6-(pyrazolo[1,5-a]pyrazine-3-carbonyl)-4,5,6,7-tetrahydrothieno[2,3-c]pyridine-3-carboxamide (Example 113)

Prepared from Previous Intermediate 94 (30 mg, 0.0914 mmol) and 3-tert-butylisoxazol-5-amine (19 mg, 0.137 mmol) according to general procedure I. Purification by reverse phase preparative HPLC (Sunfire C18 19×150 mm, 10 um 20-80% ACN/H2O (0.1% FA), 20 ml/min, RT) gave the title compound (4 mg, 9%).

LCMS (ESI): Method 7 $t_R$=3.92 min; m/z [M+H]+=451.2

$^1$H NMR (400 MHz, DMSO-$d_6$) δ 11.78 (s, 1H), 9.36 (d, J=1.5 Hz, 1H), 8.93 (dd, J=1.4, 4.7 Hz, 1H), 8.55 (s, 1H), 8.34 (s, 1H), 8.11 (d, J=4.6 Hz, 1H), 6.37 (s, 1H), 4.99 (s, 2H), 3.95 (t, J=5.8 Hz, 2H), 3.07 (t, J=6.0 Hz, 2H), 1.29 (s, 9H)

Example 116; Preparation of compound N-(5-(tert-butyl)-1-methyl-1H-pyrazol-3-yl)-6-(pyrazolo[1,5-a]pyrazine-3-carbonyl)-4,5,6,7-tetrahydrothieno[2,3-c]pyridine-3-carboxamide Example 116

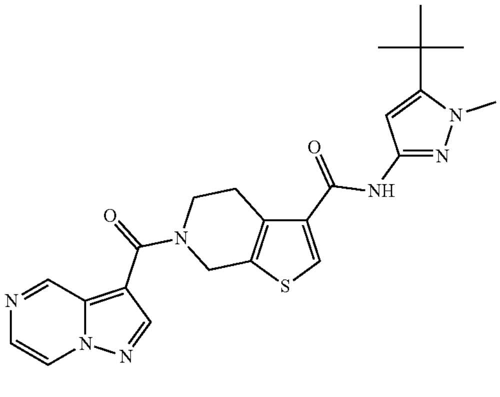

Step 1; tert-butyl 3-((5-(tert-butyl)-1-methyl-1H-pyrazol-3-yl)carbamoyl)-4,7-dihydrothieno[2,3-c]pyridine-6(5H)-carboxylate (Intermediate 95)

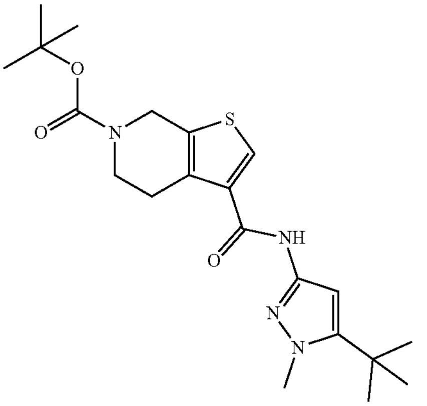 [SMILES: Cn1nc(NC(=O)c2csc3c2CCN(C(=O)OC(C)(C)C)C3)cc1C(C)(C)C]

To a solution of 6-(tert-butoxycarbonyl)-4,5,6,7-tetrahydrothieno[2,3-c]pyridine-3-carboxylic acid (142 mg, 0.500 mmol) and DMF (0.0019 mL, 0.0250 mmol) in CPME (1 ml) at 20° C. Oxalyl chloride (0.050 mL, 0.600 mmol) was added dropwise. The reaction mixture was stirred at room temperature for 2 hours. The reaction mixture was concentrated in vacuo and the residue azeotroped with CPME, the residue was suspended in ACN (1 ml) and cooled to 0° C. in an ice bath, to the mixture was added 5-tert-butyl-2-methyl-pyrazol-3-amine (77 mg, 0.500 mmol) and Pyridine (0.081 mL, 1.00 mmol) in ACN (1 ml). The reaction mixture was allowed to warm to room temperature and stirred for 1 h. The reaction mixture was concentrated in vacuo and the residue was partitioned between water and DCM. The combined organic phases were filtered through a hydrophobic frit and the solvent was concentrated in vacuo. The residue was purified by FCC on silica gel (0-50% EtOAc in cyclohexane) to give desired (186 mg, 0.444 mmol, 89%).

$^1$H NMR (400 MHz, $CDCl_3$) δ 7.75 (s, 1H), 6.08 (s, 1H), 4.57 (s, 2H), 3.65 (s, 3H), 3.62 (m, 2H), 2.95 (t, J=5.4 Hz, 2H), 1.47 (s, 9H), 1.26 (s, 9H).

Step 2; N-(5-tert-butyl-1-methyl-pyrazol-3-yl)-4,5,6,7-tetrahydrothieno[2,3-c]pyridine-3-carboxamide (Intermediate 96)

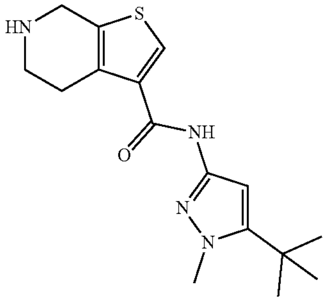 [SMILES: Cn1nc(NC(=O)c2csc3c2CCNC3)cc1C(C)(C)C]

To a solution of Intermediate 95 (186 mg, 0.444 mmol) in 1,4-dioxane (3 ml) was added 4N HCl Dioxane (3 ml). The reaction mixture was stirred at room temperature for 3 hrs then it was diluted with ether and filtered to yield a white solid, that was washed with ether and dried in vacuo overnight to give desired product as Di-hydrochloride salt (144 mg, 0.368 mmol, 83%).

$^1$H NMR (400 MHz, DMSO-$d_6$) δ 10.34 (s, 1H), 9.73-9.69 (m, 2H), 8.44 (s, 1H), 6.16 (s, 1H), 4.42 (s, 2H), 3.70 (s, 3H), 3.40-3.40 (m, 2H), 3.13 (t, J=5.6 Hz, 2H), 1.29 (s, 9H).

Step 3; N-(5-(tert-butyl)-1-methyl-1H-pyrazol-3-yl)-6-(pyrazolo[1,5-a]pyrazine-3-carbonyl)-4,5,6,7-tetrahydrothieno[2,3-c]pyridine-3-carboxamide (Example 116)

Prepared from pyrazolo[1,5-a]pyrazine-3-carboxylic acid (10 mg, 0.068 mmol) and Intermediate 96 (20 mg, 0.068 mmol) according to general procedure I. Purification by reverse phase preparative HPLC (Xbridge Phenyl 19×150 mm, 10 um 40-100% MeOH/$H_2O$ (10 mM $NH_4CO_3$), 20 ml/min) gave the title compound (7 mg, 0.015 mmol 26%).

LCMS (ESI): Method 7 $t_R$=3.91 min, m/z [M+H]+=464.2.

$^1$H NMR (400 MHz, DMSO-$d_6$) δ 10.54 (s, 1H), 9.40 (d, J=1.3 Hz, 1H), 8.97 (dd, J=1.4, 4.7 Hz, 1H), 8.59 (s, 1H), 8.24 (s, 1H), 8.14 (d, J=4.5 Hz, 1H), 6.47 (s, 1H), 5.04-4.97 (m, 2H), 3.97 (t, J=5.8 Hz, 2H), 3.88 (s, 3H), 3.12-3.09 (m, 2H), 1.40 (s, 9H).

The compound reported in the following table was prepared via Amido coupling as described for Example 116, step 1-3, applying the corresponding, commercially available or previously synthesized aldehyde in step 3. Such procedure may involve minor variations. Where the modification involved coupling agent are reported in the following table.

| Ex. No | Structure | Reagents Amount | Product Amount (yield) | Purification method | Data |
|---|---|---|---|---|---|
| 145 | 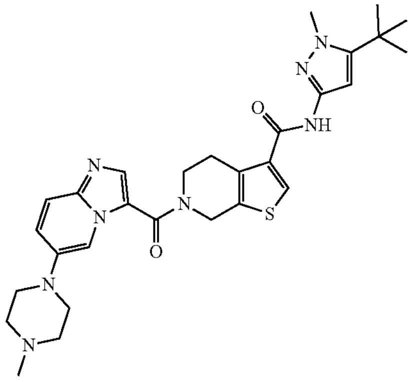 [SMILES: CN1CCN(c2ccc3ncc(C(=O)N4CCc5c(C(=O)Nc6cc(C(C)(C)C)n(C)n6)csc5C4)n3c2)CC1] | General procedure N Intermediate 95: 69 mg, 0.175 mmol Intermediate 113: 117 mg, 0.175 mmol | 41 mg (38%) | Prep HPLC | $^1$H NMR (400 MHz, DMSO-$d_6$) δ 10.51 (s, 1H), 8.40 (d, J = 1.9 Hz, 1H), 8.21 (s, 1H), 8.02 (s, 1H), 7.61 (d, J = 9.8 Hz, 1H), 7.48 (dd, J = 2.3, 9.8 Hz, 1H), 6.43 (s, 1H), 4.99 (s, 2H), 3.96 (t, J = 5.6 Hz, 2H), 3.84 (s, 3H), 3.07-3.07 (m, 6H), 2.50 (m, 4H), 2.24 (s, 3H), 1.36 (s, 9H). LCMS (ESI): Method 7 $t_R$ = 2.74 min, m/z $[M + H]^+$ = 561.5 |

Example 119; Preparation of compound 6-(imidazo[1,2-a]pyridine-3-carbonyl)-N-(3-(tert-pentyl)isoxazol-5-yl)-4,5,6,7-tetrahydrothieno[2,3-c]pyridine-3-carboxamide Example 119

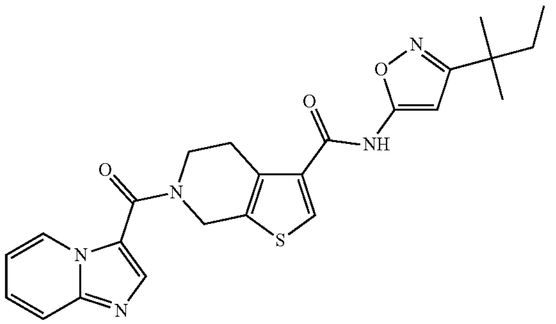

Step 1; tert-butyl 3-((3-(tert-pentyl)isoxazol-5-yl)carbamoyl)-4,7-dihydrothieno[2,3-c]pyridine-6(5H)-carboxylate (Intermediate 97)

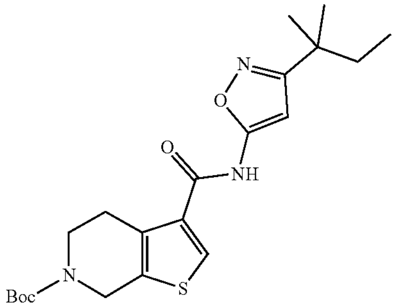 [SMILES: CCC(C)(C)c1cc(NC(=O)c2csc3c2CCN(C(=O)OC(C)(C)C)C3)on1]

To a solution of 6-(tert-butoxycarbonyl)-4,5,6,7-tetrahydrothieno[2,3-c]pyridine-3-carboxylic acid (150 mg, 0.529 mmol) and DMF (2 μl, 0.0265 mmol) in CPME (1 ml) oxalyl chloride (55 μl, 0.635 mmol) was added dropwise. The reaction mixture was stirred at room temperature for 1 hr. The reaction mixture was concentrated in vacuo and the residue azeotroped with CPME. The residue was suspended in ACN (2 ml) and cooled to 0° C. in an ice bath, to the mixture was added 3-(1,1-dimethylpropyl)isoxazol-5-amine (82 mg, 0.529 mmol) and pyridine (86 μl, 1.06 mmol). The reaction mixture was allowed to warm to room temperature and stirred for 3 hours. The reaction mixture was concentrated in vacuo. The residue was partitioned between DCM and water. The combined organic phases were filtered through a hydrophobic frit and the solvent was concentrated in vacuo. The residue was purified by reverse phase chromatography to afford desired product (14 mg, 0.033 mmol; 6%).

$^1$H NMR (400 MHz, $CDCl_3$) δ 8.61-8.61 (m, 1H), 7.67 (s, 1H), 6.23 (s, 1H), 4.51 (s, 2H), 3.55 (t, J=5.6 Hz, 2H), 2.88 (t, J=5.6 Hz, 2H), 1.52 (q, J=7.5 Hz, 2H) 1.36 (s, 9H), 1.17 (s, 6H), 0.69 (t, J=7.5 Hz, 3H)

Step 2; N-(3-(tert-pentyl)isoxazol-5-yl)-4,5,6,7-tetrahydrothieno[2,3-c]pyridine-3-carboxamide hydrochloride (Intermediate 98)

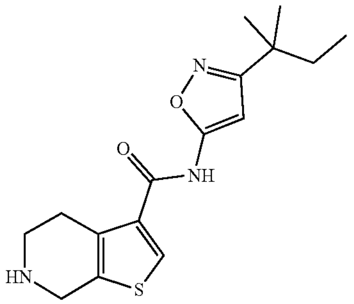 [SMILES: CCC(C)(C)c1cc(NC(=O)c2csc3c2CCNC3)on1]

To a solution of Intermediate 97 (14 mg, 0.0334 mmol) in 1,4-dioxane (1 ml) hydrogen chloride 4N in dioxane (1.0 ml, 0.033 mmol) was added. The reaction mixture was stirred at room temperature for 2 hrs. The reaction mixture was diluted with ether and filtered to yield a white solid, washed with ether and dried in vacuo to afford the title compound as hydrochloride in quantitative yield.

LCMS (ESI): Method 16 $t_R$=1.04 min; m/z [M+H]=320.1

Step 3; 6-(imidazo[1,2-a]pyridine-3-carbonyl)-N-(3-(tert-pentyl)isoxazol-5-yl)-4,5,6,7-tetrahydrothieno [2,3-c]pyridine-3-carboxamide (Example 119)

Prepared from imidazo[1,2-a]pyridine-3-carboxylic acid (7 mg, 0.04 mmol) and Intermediate 98 (assumed 0.0334 mmol) according to general procedure N. The reaction was quenched with water and filtered, solid washed with water and dried in vacuo overnight to afford the title compound (17 mg, 0.027 mmol; 81%).

LCMS (ESI): Method 7 $t_R$=4.52 min; m/z $[M+H]^+$=464.8.

$^1$H NMR (400 MHz, DMSO-$d_6$) δ 11.80 (s, 1H), 9.01 (d, J=7.1 Hz, 1H), 8.39 (s, 1H), 8.18 (s, 1H), 7.78 (d, J=8.8 Hz, 1H), 7.54-7.49 (m, 1H), 7.17-7.12 (m, 1H), 6.37 (s, 1H), 5.07 (s, 2H), 4.03 (t, J=5.6 Hz, 2H), 3.12 (t, J=5.9 Hz, 2H), 1.66 (q, J=7.4 Hz, 2H), 1.29 (s, 6H), 0.81 (t, J=7.5 Hz, 3H).

Example 121; Preparation of compound N-(6-methoxy-5-(trifluoromethyl)pyridin-3-yl)-6-(pyrazolo[1,5-a]pyrazine-3-carbonyl)-4,5,6,7-tetrahydrothieno[2,3-c]pyridine-3-carboxamide Example 121

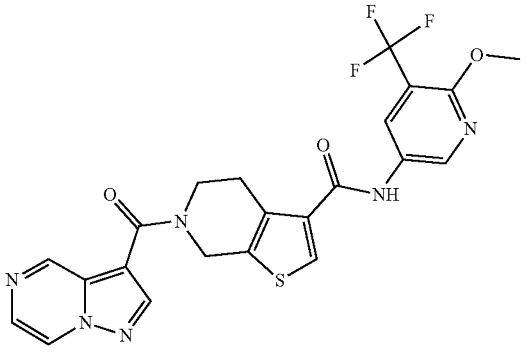

Step 1; tert-butyl 3-[[6-methoxy-5-(trifluoromethyl)-3-pyridyl]carbamoyl]-5,7-dihydro-4H-thieno [2,3-c]pyridine-6-carboxylate (Intermediate 99)

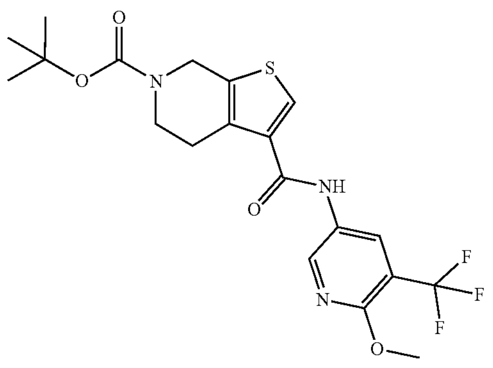 [SMILES: COc1ncc(NC(=O)c2csc3c2CCN(C(=O)OC(C)(C)C)C3)cc1C(F)(F)F]

Intermediate 99 was prepared starting from 6-(tert-butoxycarbonyl)-4,5,6,7-tetrahydrothieno[2,3-c]pyridine-3-carboxylic acid (167 mg, 0.589 mmol) following the procedure described in Example 109 step 1. The reaction mixture was concentrated in vacuo, quenched with water and filtered to yield a solid, which was washed with water and dried in vacuo to afford title compound (220 mg, 0.481 mmol, 82%).

$^1$H NMR (400 MHz, $CDCl_3$) δ 8.46 (m, 1H), 8.29 (m, 1H), 7.71-7.64 (m, 1H), 4.60 (s, 2H), 4.03 (s, 3H), 3.67 (t, J=5.4 Hz, 2H), 2.99 (t, J=5.7 Hz, 2H), 2.80 (s, 2H), 1.50 (s, 9H).

Step 2; N-[6-methoxy-5-(trifluoromethyl)-3-pyridyl]-4,5,6,7-tetrahydro thieno[2,3-c]pyridine-3-carboxamide (Intermediate 100)

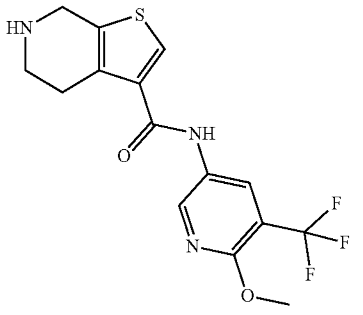 [SMILES: COc1ncc(NC(=O)c2csc3c2CCNC3)cc1C(F)(F)F]

To a solution of Intermediate 99 (220 mg, 0.481 mmol) in 1,4-dioxane (5 ml) was added 4N Hydrogen chloride in dioxane (5.0 ml, 0.481 mmol) at 0° C. The reaction mixture was stirred at room temperature for 18 hours. The reaction mixture was diluted with ether and filtered, and the resultant solid washed with ether and dried in vacuo to afford title compound as dihydrochloride (240 mg, 0.558 mmol, 116%).

$^1$H NMR (400 MHz, DMSO-$d_6$) δ 10.70 (s, 1H), 9.68 (s, 2H), 8.81 (d, J=2.1 Hz, 1H), 8.54 (d, J=2.4 Hz, 1H), 8.48 (s, 1H), 4.38 (m, 2H), 3.99 (s, 3H), 3.35 (m, 2H), 3.13 (t, J=5.7 Hz, 2H).

Step 3; N-[6-methoxy-5-(trifluoromethyl)-3-pyridyl]-6-(pyrazolo[1,5-a]pyrazine-3-carbonyl)-5,7-dihydro-4H-thieno[2,3-c]pyridine-3-carboxamide (Example 121)

To a solution of Intermediate 100 (50 mg, 0.116 mmol), pyrazolo[1,5-a]pyrazine-3-carboxylic acid (19 mg, 0.116 mmol) and 1-methylimidazole (0.074 mL, 0.930 mmol) in ACN (5.00 ml) was added Chloro-N,N,N',N'-tetramethylformamidinium hexafluorophosphate (49 mg, 0.174 mmol). The reaction mixture was stirred at room temperature for 18 hours. The reaction was quenched with water and extracted with DCM. The combined organic phases were filtered through a hydrophobic frit and the solvent was concentrated in vacuo. The residue was submitted for purification by preparative HPLC (Sunfire C18 19×150 mm, 10 um 5-60% ACN/$H_2O$ (10 mM $NH_4CO_3$), 20 ml/min) to afford the title compound, (4.02 mg, 97%).

LCMS (ESI): Method 7 $t_R$=4.36 min; m/z [M+H]+=503.2

$^1$H NMR (400 MHz, DMSO-$d_6$) δ 10.40 (s, 1H), 9.37 (d, J=1.5 Hz, 1H), 8.94 (dd, J=1.4, 4.7 Hz, 1H), 8.74 (d, J=2.1 Hz, 1H), 8.56 (s, 1H), 8.48 (d, J=2.5 Hz, 1H), 8.19 (s, 1H), 8.11 (d, J=4.6 Hz, 1H), 5.00-5.00 (m, 2H), 3.99 (s, 3H), 3.95 (t, J=5.8 Hz, 2H), 3.07-3.07 (m, 2H).

Example 122; Preparation of compound N-(5-(1,1-difluoroethyl)pyridin-3-yl)-6-(pyrazolo[1,5-a]pyrazine-3-carbonyl)-4,5,6,7-tetrahydrothieno[2,3-c]pyridine-3-carboxamide Example 122

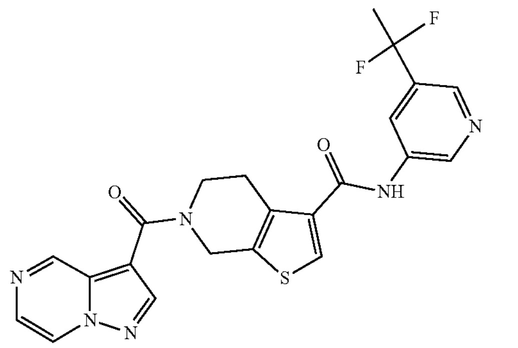

Step 1; tert-butyl 3-[[5-(1,1-difluoroethyl)-3-pyridyl]carbamoyl]-5,7-dihydro-4H-thieno[2,3-c]pyridine-6-carboxylate (Intermediate 101)

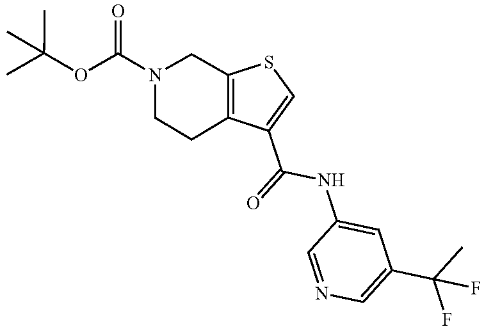 [SMILES: CC(C)(C)OC(=O)N1CCc2c(C(=O)Nc3cncc(C(C)(F)F)c3)csc2C1]

Intermediate 101 was prepared starting from 6-(tert-butoxycarbonyl)-4,5,6,7-tetrahydrothieno[2,3-c]pyridine-3-carboxylic acid (167 mg, 0.589 mmol) following the procedure described in Example 109 step 1. The obtained residue was triturated with water and left to stand overnight. Solid was filtered, washed with water and dried in vacuo to afford title compound (182 mg, 0.430 mmol, 73%).

$^1$H NMR (400 MHz, $CDCl_3$) δ 8.74 (m, 1H), 8.53 (s, 1H), 8.40 (s, 1H), 7.71 (s, 1H), 4.61 (s, 2H), 3.71-3.65 (m, 2H), 3.00 (t J=5.4 Hz, 2H), 1.97 (t, J=18.2 Hz, 3H), 1.50 (s, 9H).

Step 2; N-[5-(1,1-difluoroethyl)-3-pyridyl]-4,5,6,7-tetrahydrothieno[2,3-c]pyridine-3-carboxamide (Intermediate 102)

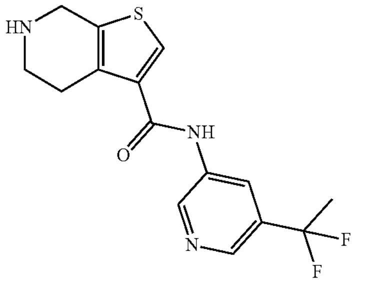 [SMILES: CC(F)(F)c1cncc(NC(=O)c2csc3c2CCNC3)c1]

Intermediate 102 was prepared starting from Intermediate 101 (182 mg, 0.430 mmol), following the procedure described in Example 121 step 2. The title compound was afforded as dihydrochloride (151 mg, 0.381 mmol, 89%).

$^1$H NMR (400 MHz, DMSO-$d_6$) δ 10.91 (s, 1H), 9.65 (s, 2H), 9.15 (d, J=1.9 Hz, 1H), 8.61 (s, 1H), 8.56 (s, 2H), 4.40 (t, J=4.9 Hz, 2H), 3.48-3.34 (m, 2H), 3.17-3.10 (m, 2H), 2.06 (t, J=19.1 Hz, 3H).

Step 3; N-(5-(1,1-difluoroethyl)pyridin-3-yl)-6-(pyrazolo[1,5-a]pyrazine-3-carbonyl)-4,5,6,7-tetrahydrothieno[2,3-c]pyridine-3-carboxamide (Example 122)

To a solution of Intermediate 102 (50 mg, 0.126 mmol), pyrazolo[1,5-a]pyrazine-3-carboxylic acid (21 mg, 0.126 mmol) and 1-Methylimidazole (0.080 mL, 1.01 mmol) in ACN (5 ml) was added Chloro-N,N,N',N'-tetramethylformamidinium hexafluorophosphate (53 mg, 0.189 mmol). The reaction mixture was stirred at room temperature for 30 minutes then left to stand overnight. Reaction quenched with water and washed with DCM, the combined organic phases were filtered through a hydrophobic frit and the solvent was concentrated in vacuo. The residue was submitted for purification by preparative HPLC (Xbridge Phenyl 19×150 mm, 10 μm 20-80% MeOH/$H_2O$ (10 mM $NH_4CO_3$), 20 ml/min, RT) to afford the title compound (7.5 mg, 0.0160 mmol, 13%).

LCMS (ESI): Method 7 $t_R$=3.94 min; m/z [M+H]+=516.5

$^1$H NMR (400 MHz, DMSO-$d_6$) δ 10.18 (s, 1H), 9.36 (d, J=1.4 Hz, 1H), 8.93 (dd, J=1.4, 4.7 Hz, 1H), 8.56 (s, 1H), 8.20 (s, 1H), 8.11 (d, J=4.6 Hz, 1H), 6.31 (s, 1H), 4.99-4.99 (m, 2H), 3.95 (dd, J=5.8, 5.8 Hz, 2H), 3.67 (s, 3H), 3.08-3.03 (m, 2H), 1.33-1.21 (m, 4H).

Example 123; Preparation of compound N-(5-(tert-butyl)pyridin-3-yl)-6-(pyrazolo[1,5-a]pyrazine-3-carbonyl)-4,5,6,7-tetrahydrothieno[2,3-c]pyridine-3-carboxamide Example 123

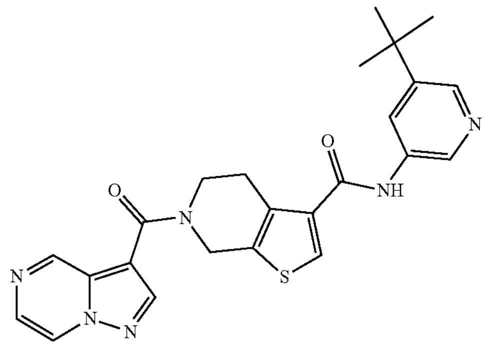

Step 1; tert-butyl 3-[(5-tert-butyl-3-pyridyl)carbamoyl]-5,7-dihydro-4H-thieno[2,3-c]pyridine-6-carboxylate (Intermediate 103)

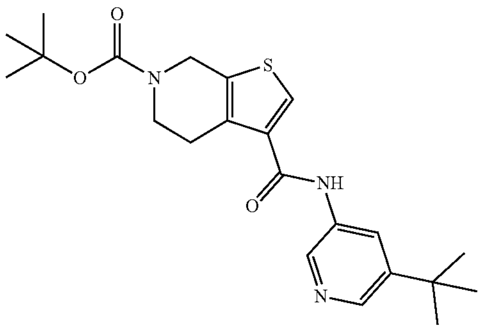 [SMILES: CC(C)(C)OC(=O)N1CCc2c(C(=O)Nc3cncc(C(C)(C)C)c3)csc2C1]

Intermediate 103 was prepared starting from 6-(tert-butoxycarbonyl)-4,5,6,7-tetrahydrothieno[2,3-c]pyridine-3-carboxylic acid (83 mg, 0.293 mmol), following the procedure described in Example 109 step 1. The title compound was obtained (56 mg, 0.135 mmol, 46%).

$^1$H NMR (400 MHz, $CDCl_3$) δ 9.07-8.64 (m, 1H), 8.54 (s, 1H), 8.33 (d, J=1.5 Hz, 1H), 8.24 (t, J=2.0 Hz, 1H), 7.72 (s, 1H), 4.58 (s, 2H), 3.66 (t, J=5.6 Hz, 2H), 3.00 (t, J=5.4 Hz, 2H), 1.49 (s, 9H), 1.33 (s, 9H).

Step 2; N-(5-tert-butyl-3-pyridyl)-4,5,6,7-tetrahydrothieno[2,3-c]pyridine-3-carboxamide (Intermediate 104)

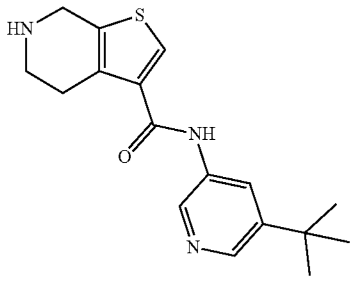 [SMILES: CC(C)(C)c1cncc(NC(=O)c2csc3c2CCNC3)c1]

Intermediate 104 was prepared starting from Intermediate 103 (56 mg, 0.135 mmol), following the procedure described in Example 121 step 2. Desired product was obtained as di-hydrochloride salt (41 mg, 0.106 mmol, 78%).

$^1$H NMR (400 MHz, DMSO-$d_6$) δ 11.20 (s, 1H), 9.58-9.58 (m, 2H), 9.21 (d, J=1.8 Hz, 1H), 8.78 (s, 1H), 8.67 (s, 1H), 8.65 (d, J=1.8 Hz, 1H), 4.41 (t, J=4.8 Hz, 2H), 3.4 (m, 2H) (Under water peak), 3.14 (t, J=5.7 Hz, 2H), 1.38 (s, 9H).

Step 3—N-(5-tert-butyl-3-pyridyl)-6-(pyrazolo[1,5-a]pyrazine-3-carbonyl)-5,7-dihydro-4H-thieno[2,3-c]pyridine-3-carboxamide (Example 123)

To a solution of Intermediate 104 (41 mg, 0.106 mmol), pyrazolo[1,5-a]pyrazine-3-carboxylic acid (17 mg, 0.106 mmol) and 1-Methylimidazole (0.067 ml, 0.845 mmol, 8.00 eq) in ACN (4.1 ml) chloro-N,N,N',N'-tetramethylformamidinium hexafluorophosphate (44 mg, 0.158 mmol) was added. The reaction mixture was stirred at room temperature for 30 minutes and left to stand overnight. The reaction was quenched with water and washed with DCM. The combined organic phases were filtered through a hydrophobic frit and the solvent was concentrated in vacuo to yield a light brown gum. The residue was submitted for purification by preparative HPLC (Xbridge Phenyl 19×150 mm, 10 um 20-80% MeOH/H2O (10 mM NH4CO3), 20 ml/min,) to afford the title compound (48 mg, 0.0677 mmol, 64%).

LCMS (ESI): Method 7 $t_R$=3.94 min; m/z [M+H]+=516.5

$^1$H NMR (400 MHz, DMSO-$d_6$) δ 10.18 (s, 1H), 9.36 (d, J=1.4 Hz, 1H), 8.93 (dd, J=1.4, 4.7 Hz, 1H), 8.56 (s, 1H), 8.20 (s, 1H), 8.11 (d, J=4.6 Hz, 1H), 6.31 (s, 1H), 4.99-4.99 (m, 2H), 3.95 (dd, J=5.8, 5.8 Hz, 2H), 3.67 (s, 3H), 3.08-3.03 (m, 2H), 1.33-1.21 (m, 4H).

Example 125; Preparation of compound N-(5-(difluoromethoxy)pyridin-3-yl)-6-(pyrazolo[1,5-a]pyrazine-3-carbonyl)-4,5,6,7-tetrahydrothieno[2,3-c]pyridine-3-carboxamide Example 125

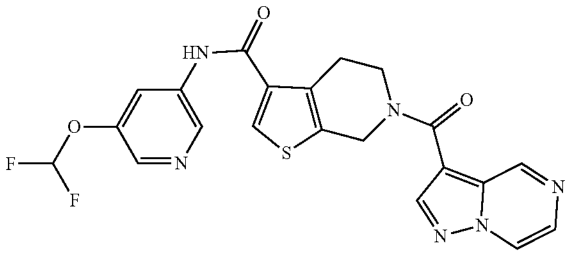

Step 1; tert-butyl 3-[[5-(difluoromethoxy)-3-pyridyl]carbamoyl]-5,7-dihydro-4H-thieno[2,3-c]pyridine-6-carboxylate (Intermediate 105)

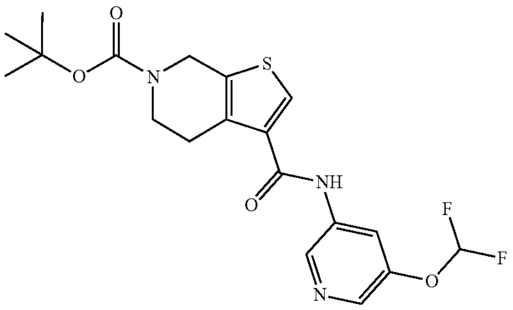 [SMILES: CC(C)(C)OC(=O)N1CCc2c(C(=O)Nc3cncc(OC(F)F)c3)csc2C1]

Intermediate 105 was prepared starting from 6-(tert-butoxycarbonyl)-4,5,6,7-tetrahydrothieno[2,3-c]pyridine-3-carboxylic acid (167 mg, 0.589 mmol), following the procedure described in Example 109 step 1. Desired product was obtained (179 mg, 0.421 mmol, 71%).

$^{1}$H NMR (400 MHz, $CDCl_3$) δ 8.50-8.49 (m, 1H), 8.24 (m, 3H), 7.69 (s, 1H), 6.79-6.39 (t, J=73.6 Hz, 1H), 4.61 (s, 2H), 3.72-3.65 (m, 2H), 2.99 (t, J=5.6 Hz, 2H), 1.50 (s, 9H).

Step 2; N-[5-(difluoromethoxy)-3-pyridyl]-4,5,6,7-tetrahydrothieno[2,3-c]pyridine-3-carboxamide; dihydrochloride (Intermediate 106)

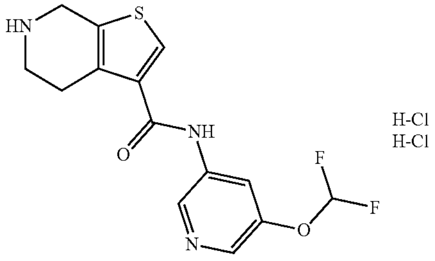 [SMILES: O=C(Nc1cncc(OC(F)F)c1)c1csc2c1CCNC2]

Intermediate 106 was prepared starting from Intermediate 105 (179 mg, 0.421 mmol), following the procedure described in Example 121 step 2. Desired product was obtained as di-hydrochloride salt (146 mg, 0.367 mmol, 87%).

$^{1}$H NMR (400 MHz, DMSO-$d_6$) δ 10.90 (s, 1H), 9.70 (s, 2H), 8.93 (s, 1H), 8.56 (s, 1H), 8.31 (s, 1H), 8.27 (t, J=26.8 Hz, 1H), 7.36 (s, 1H), 4.38 (s, 2H), 3.43-3.36 (m, 2H), 3.16-3.08 (m, 2H).

Step 3; N-(5-(difluoromethoxy)pyridin-3-yl)-6-(pyrazolo[1,5-a]pyrazine-3-carbonyl)-4,5,6,7-tetrahydrothieno[2,3-c]pyridine-3-carboxamide (Example 125)

To a solution of Intermediate 106 (50 mg, 0.126 mmol), pyrazolo[1,5-a]pyrazine-3-carboxylic acid (20 mg, 0.126 mmol) and 1-Methylimidazole (0.080 ml, 1.00 mmol) in ACN (5 ml), TCFH (53 mg, 0.188 mmol) was added. The reaction mixture was stirred at room temperature for 30 min, left to stand overnight. The reaction was quenched with water and washed with DCM. The combined organic phases were filtered through a hydrophobic frit and the solvent was concentrated in vacuo. The residue was submitted for purification by preparative HPLC (Xbridge Phenyl 19×150 mm, 10 um 20-80% $MeOH/H_2O$ (10 mM $NH_4CO_3$), 20 ml/min) to afford title compound (59 mg, 0.0238 mmol, 19%).

LCMS (ESI): Method 7 $t_R$=3.94 min; m/z [M+H]+=516.5

$^{1}$H NMR (400 MHz, DMSO-$d_6$) δ 10.18 (s, 1H), 9.36 (d, J=1.4 Hz, 1H), 8.93 (dd, J=1.4, 4.7 Hz, 1H), 8.56 (s, 1H), 8.20 (s, 1H), 8.11 (d, J=4.6 Hz, 1H), 6.31 (s, 1H), 4.99-4.99 (m, 2H), 3.95 (dd, J=5.8, 5.8 Hz, 2H), 3.67 (s, 3H), 3.08-3.03 (m, 2H), 1.33-1.21 (m, 4H)

Example 126; Preparation of compound 6-(pyrazolo[1,5-a]pyrazine-3-carbonyl)-N-(5-(1,1,1-trifluoro-2-methylpropan-2-yl)isoxazol-3-yl)-4,5,6,7-tetrahydrothieno[2,3-c]pyridine-3-carboxamide Example 126

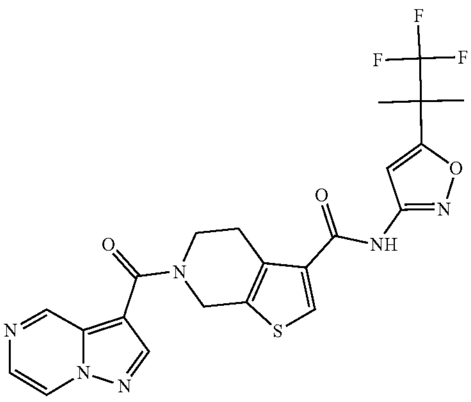

Step 1; tert-butyl 3-((5-(1,1,1-trifluoro-2-methylpropan-2-yl)isoxazol-3-yl)carbamoyl)-4,7-dihydrothieno[2,3-c]pyridine-6(5H)-carboxylate (Intermediate 107)

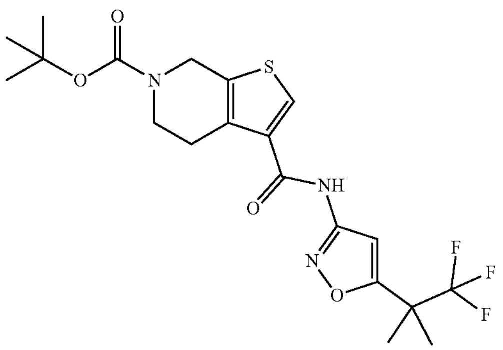 [SMILES: CC(C)(C)OC(=O)N1CCc2c(C(=O)Nc3cc(C(C)(C)C(F)(F)F)on3)csc2C1]

To a solution of 6-(tert-butoxycarbonyl)-4,5,6,7-tetrahydrothieno[2,3-c]pyridine-3-carboxylic acid (250 mg, 0.882 mmol) and DMF (0.0034 mL, 0.0441 mmol) in CPME (2 ml) at 20° C. Oxalyl chloride (0.088 mL, 1.06 mmol) was added dropwise. The reaction mixture was stirred at room temperature for 2 hours. The reaction mixture was concentrated in vacuo. and the residue azeotroped with CPME, the residue was suspended in ACN (1 ml) and cooled to 0° C. in an ice bath. To the mixture was added 5-(2,2,2-trifluoro-1,1-dimethyl-ethyl)isoxazol-3-amine (171 mg, 0.882 mmol) and Pyridine (0.14 ml, 1.76 mmol) in ACN (1 ml). The reaction mixture was allowed to warm to room temperature and stirred for 1 h. The reaction mixture was concentrated in vacuo and the residue partitioned between DCM and water. The combined organic phases were filtered through a hydrophobic frit and the solvent was concentrated in vacuo. The residue was purified by column chromatography on silica gel, (0-100% EtOAc in Cyclohexane) to afford title compound (255 mg, 0.555 mmol, 63%).

$^1$H NMR (400 MHz, $CDCl_3$) δ 9.65 (s, 1H), 7.91 (s, 1H), 7.13 (s, 1H), 4.64 (s, 2H), 3.68 (t, J=5.4 Hz, 2H), 3.01 (t, J=5.8 Hz, 2H), 1.60 (s, 6H), 1.49 (s, 9H).

Step 2; N-(5-(1,1,1-trifluoro-2-methylpropan-2-yl)isoxazol-3-yl)-4,5,6,7-tetrahydrothieno[2,3-c]pyridine-3-carboxamide (Intermediate 108)

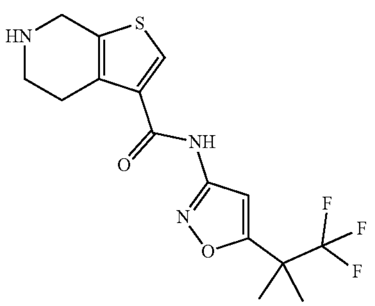 [SMILES: CC(C)(c1cc(NC(=O)c2csc3c2CCNC3)no1)C(F)(F)F]

To a solution of Intermediate 107 (255 mg, 0.555 mmol) in 1,4-dioxane (3 ml) 4N HCl in dioxane (3.0 m, 0.555 mmol) was added at 0° C. The reaction mixture was allowed to warm to RT and stirred at room temperature over the weekend. The reaction mixture was then diluted with diethyl ether and filtered, the resultant solid was washed with ether and dried in vacuo to afford title compound as HCl salt (190 mg, 0.480 mmol, 86%).

$^1$H NMR (400 MHz, DMSO-$d_6$) δ 11.49 (s, 1H), 9.64-9.55 (m, 2H), 8.52 (s, 1H), 7.11 (s, 1H), 4.42 (s, 2H), 3.15 (t, J=5.6 Hz, 2H), 1.63 (s, 6H).

Step 3; 6-(pyrazolo[1,5-a]pyrazine-3-carbonyl)-N-[5-(2,2,2-trifluoro-1,1-dimethyl-ethyl)isoxazol-3-yl]-5,7-dihydro-4H-thieno[2,3-c]pyridine-3-carboxamide (Example 126)

To a solution of Intermediate 108 (50 mg, 0.126 mmol), pyrazolo[1,5-a]pyrazine-3-carboxylic acid (21 mg, 0.126 mmol) and 1-methylimidazole (0.081 mL, 1.01 mmol) in ACN (2 ml) chloro-N,N,N',N'-tetramethylformamidinium hexafluorophosphate (53 mg, 0.189 mmol) was added. The reaction mixture was stirred at room temperature for 18 hrs. The reaction was then quenched with aqueous $NH_4Cl$ and filtered to yield a solid, washed with water and dried in vacuo, solid washed with ether, filtered and dried in vacuo and purified by preparative HPLC (Xbridge Phenyl 19×150 mm, 10 um 40-100% MeOH/$H_2O$ (10 mM $NH_4CO_3$), 20 ml/min, RT) to afford the title compound (14 mg, 0.0282 mmol, 22%).

LCMS (ESI): Method 7 $t_R$=4.42 min, m/z [M+H]+=505.4

$^1$H NMR (400 MHz, DMSO-$d_6$) δ 11.40-11.36 (s, 1H), 9.40 (s, 1H), 8.96 (d, J=3.8 Hz, 1H), 8.59 (s, 1H), 8.41 (s, 1H), 8.14 (d, J=4.5 Hz, 1H), 7.12 (s, 1H), 5.03-4.98 (s, 2H), 3.98 (t, J=4.9 Hz, 2H), 3.10 (s, 2H), 1.63 (s, 6H).

Example 127; Preparation of compound 6-(imidazo[1,2-a]pyrazine-3-carbonyl)-N-(5-(trifluoromethyl)pyridin-3-yl)-4,5,6,7-tetrahydrothieno[2,3-c]pyridine-3-carboxamide Example 127

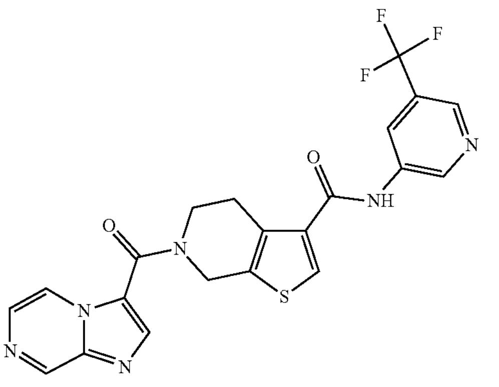

Step 1; tert-butyl 3-[[5-(trifluoromethyl)-3-pyridyl]carbamoyl]-5,7-dihydro-4H-thieno[2,3-c]pyridine-6-carboxylate (Intermediate 109)

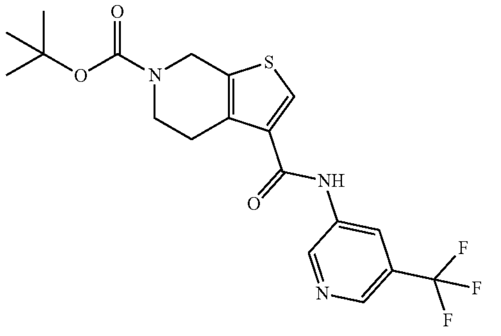 [SMILES: CC(C)(C)OC(=O)N1CCc2c(C(=O)Nc3cncc(C(F)(F)F)c3)csc2C1]

To a solution of 6-tert-butoxycarbonyl-5,7-dihydro-4H-thieno[2,3-c]pyridine-3-carboxylic acid (1500 mg, 5.29 mmol), chloro-N,N,N',N'-tetramethylformamidinium hexafluorophosphate (3713 mg, 13.2 mmol) and 1-methylimidazole (1.3 mL, 15.9 mmol) in ACN (150 ml) 5-(trifluoromethyl)pyridin-3-amine (858 mg, 5.29 mmol) was added and the mixture was stirred overnight. The reaction mixture was diluted in ethyl acetate and washed with water, brine, dried over MgSO4, filtered and concentrated.

The residue was purified by FCC (80 g, 0-100% EtOAc in c-Hex, 10 CV) to afford title compound (1866 mg, 4.37 mmol, 82%).

$^1$H NMR (400 MHz, $CDCl_3$) δ 8.92 (m, 1H), 8.65 (s, 1H), 8.60 (s, 1H), 7.67-7.63 (m, 1H), 4.62-4.57 (m, 2H), 3.69 (t, J=5.4 Hz, 2H), 3.02 (t, J=5.4 Hz, 2H), 1.52 (s, 9H).

Step 2; N-[5-(trifluoromethyl)-3-pyridyl]-4,5,6,7-tetrahydrothieno[2,3-c]pyridine-3-carboxamide; hydrochloride (Intermediate 110)

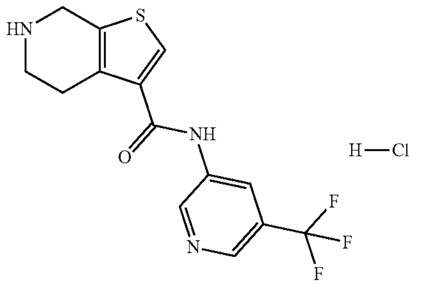

To a solution of Intermediate 109 (2612 mg, 6.11 mmol) in 1,4-dioxane (16.80 ml) 4 M HCl (38 ml, 0.153 mol) was added and the mixture was stirred at room temperature overnight. The mixture was concentrated and then diluted in MeOH. The obtained solid was filtered off and dried to afford title compound as hydrochloride (1819 mg; 5.00 mmol, 82%)

$^1$H NMR (400 MHz, DMSO-$d_6$) δ 10.85 (s, 1H), 9.38 (s, 2H), 9.22 (d, J=2.3 Hz, 1H), 8.76 (d, J=1.3 Hz, 1H), 8.66 (t, J=1.9 Hz, 1H), 8.49 (s, 1H), 4.45 (s, 2H), 3.45-3.41 (m, 2H), 3.17 (t, J=6.1 Hz, 2H).

Step 3; 6-(imidazo[1,2-a]pyrazine-3-carbonyl)-N-(5-(trifluoromethyl)pyridin-3-yl)-4,5,6,7-tetrahydrothieno[2,3-c]pyridine-3-carboxamide (Example 127)

Imidazo[1,2-a]pyrazine-3-carboxylic acid (100 mg, 0.613 mmol, 1.00 eq) in Thionyl chloride (0.89 mL, 12.3 mmol, 20.0 eq) was heated to reflux overnight. The reaction mixture was allowed to cool to room temperature and concentrated in vacuo. The residue was suspended in toluene and re-concentrated to give the intermediate acyl chloride.

Imidazo[1,2-a]pyrazine-3-carbonyl chloride (111 mg, 0.611 mmol) and Intermediate 110 (222 mg, 0.611 mmol) were dissolved in THE (10 ml) followed by addition of DIPEA (0.23 ml, 1.34 mmol) and 4-(Dimethylamino)pyridine (3.7 mg, 0.0306 mmol). The reaction was stirred at room temperature for two hours before concentrating under reduced pressure and the resultant residue purified by preparative HPLC (Sunfire C18 19×150 mm, 10 um 20-80% ACN/H2O (0.1% FA), 20 ml/min, RT) to afford the title compound (3.03 mg, 1.04%).

LCMS (ESI): Method 6 $t_R$=3.79 min; m/z [M+H]+=473.2.

$^1$H NMR (400 MHz, DMSO-$d_6$) δ 10.68 (s, 1H), 9.25 (d, J=1.6 Hz, 1H), 9.15 (d, J=2.0 Hz, 1H), 8.89 (dd, J=1.4, 4.8 Hz, 1H), 8.71 (d, J=0.9 Hz, 1H), 8.61 (t, J=1.8 Hz, 1H), 8.35 (s, 1H), 8.28 (s, 1H), 8.10 (d, J=4.6 Hz, 1H).

Example 128; Preparation of compound 6-(pyrazolo[1,5-a]pyrazine-3-carbonyl)-N-(5-(trifluoromethoxy)pyridin-3-yl)-4,5,6,7-tetrahydrothieno[2,3-c]pyridine-3-carboxamide Example 128

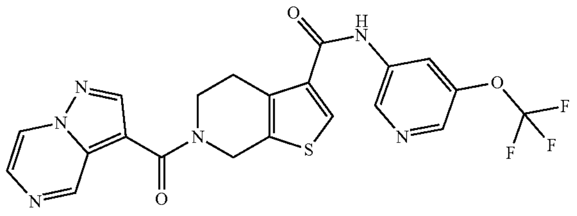

Step 1; 6-(pyrazolo[1,5-a]pyrazine-3-carbonyl)-N-(5-(trifluoromethoxy)pyridin-3-yl)-4,5,6,7-tetrahydrothieno[2,3-c]pyridine-3-carboxamide (Example 128)

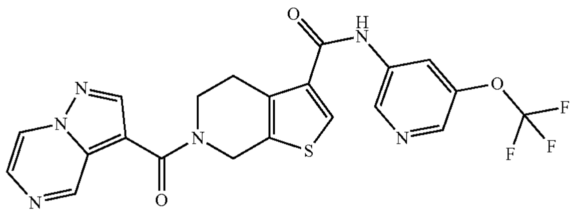 [SMILES: O=C(Nc1cncc(OC(F)(F)F)c1)c1csc2c1CCN(C(=O)c1cnn3ccncc13)C2]

A mixture of Intermediate 93 (40 mg, 0.117 mmol) and Intermediate 86 (30 mg, 0.140 mmol) in THE (2 ml) was cooled to −30° C., then n-Butyl lithium solution (1.7 M pentanes, 0.247 mL, 0.420 mmol.) was added and the reaction stirred while allowing to warm to room temperature. The reaction was quenched with $NH_4Cl$ (sat. aq), and organics extracted with DCM. The combined organic phases were filtered through a hydrophobic frit and the solvent was concentrated in vacuo. Purification by washing resultant crude residue with DCM gave the title compound (5.1 mg, 0.010 mmol, 8.9%).

LCMS (ESI): Method 7 $t_R$=4.04 min; m/z [M+H]+=489.3

$^1$H NMR (400 MHz, DMSO-$d_6$) δ 10.66 (s, 1H), 9.41 (d, J=1.3 Hz, 1H), 8.99-8.94 (m, 2H), 8.60 (s, 1H), 8.45 (d, J=2.0 Hz, 1H), 8.38 (s, 1H), 8.29 (s, 1H), 8.15 (d, J=4.8 Hz, 1H), 5.04 (s, 2H), 3.99 (t, J=5.6 Hz, 2H), 3.11 (s, 2H).

Example 146; Preparation of N-(3-cyclopropyl-1-methyl-1H-pyrazol-5-yl)-6-((3-methyl-1H-pyrazolo[3,4-b]pyridin-5-yl)methyl)-4,5,6,7-tetrahydrothieno[2,3-c]pyridine-3-carboxamide Example 146

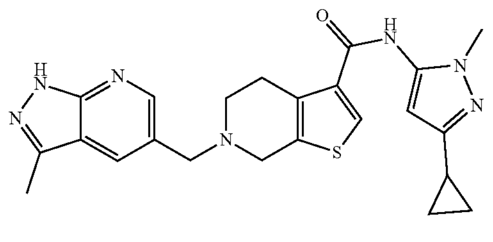

Step 1: ethyl 6-((3-methyl-1H-pyrazolo[3,4-b]pyridin-5-yl)methyl)-4,5,6,7-tetrahydrothieno[2,3-c]pyridine-3-carboxylate (Intermediate 133)

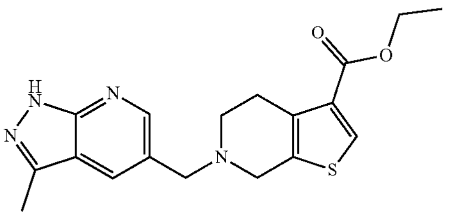 [SMILES: CCOC(=O)c1csc2c1CCN(Cc1cnc3[nH]nc(C)c3c1)C2]

Following general procedure C, starting from 3-methyl-1H-pyrazolo[3,4-b]pyridine-5-carbaldehyde (450 mg, 2.79 mmol) and Intermediate 38 (692 mg, 2.79 mmol) the obtained crude product was purified by column chromatography on silica gel (0-100% EtOAc in cyclohexane) to give the title compound (529 mg, 1.48 mmol, 53%).

$^1$H NMR (400 MHz, DMSO-d6) δ 13.15 (s, 1H), 8.46 (d, J=1.7 Hz, 1H), 8.13-8.10 (m, 2H), 4.22 (q, J=7.1 Hz, 2H), 3.80 (s, 2H), 3.63 (s, 2H), 2.89-2.85 (m, 2H), 2.78-2.74 (m, 2H), 2.49 (s, 3H), 1.27 (t, J=7.1 Hz, 3H).

Step 2: 6-((3-methyl-1H-pyrazolo[3,4-b]pyridin-5-yl)methyl)-4,5,6,7-tetrahydrothieno[2,3-c]pyridine-3-carboxylic acid (Intermediate 134)

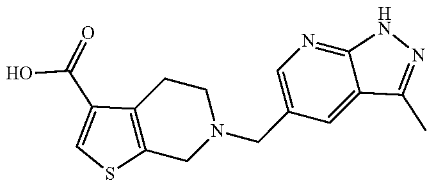 [SMILES: Cc1n[nH]c2ncc(CN3CCc4c(C(=O)O)csc4C3)cc12]

To a suspension of Intermediate 133 (529 mg, 1.48 mmol) in MeOH (12 mL), 5M $NaOH_{(aq)}$ (0.89 mL, 4.45 mmol) was added. The reaction mixture was stirred at 60° C., under an atmosphere of nitrogen, for 2.5 h, then at RT for 16 h. The reaction mixture was acidified to pH 5-6 by dropwise addition of 1 M $HCl_{(aq)}$ and concentrated in vacuo. The residue was suspended in water, filtered and the solid was washed with water and dried in vacuo to give the title compound (416 mg, 85%).

$^1$H NMR (400 MHz, DMSO-d6) δ 13.15 (brs, 1H), 12.52 (brs, 1H), 8.46 (d, J=1.7 Hz, 1H), 8.12 (d, J=1.5 Hz, 1H), 8.07 (s, 1H), 3.81 (s, 2H), 3.62 (s, 2H), 2.89-2.85 (m, 2H), 2.79-2.74 (m, 2H), 2.49 (s, 3H).

Step 3: N-(3-cyclopropyl-1-methyl-1H-pyrazol-5-yl)-6-((3-methyl-1H-pyrazolo[3,4-b]pyridin-5-yl)methyl)-4,5,6,7-tetrahydrothieno[2,3-c]pyridine-3-carboxamide (Example 146)

Prepared from 5-cyclopropyl-2-methyl-pyrazol-3-amine (14 mg, 0.100 mmol) and Intermediate 134 (22 mg, 0.0670 mmol) according to general procedure I but without addition of DMAP or DIPEA. The crude product was purified by prep HPLC (Sunfire C18 19×150 mm, 10 um 20-80% acetonitrile/water (10 mM $NH_4HCO_3$), 20 ml/min) followed by lyophilization to give the title compound (9.5 mg, 32%).

LC-MS (ESI) method 7: $t_R$=2.58 min; m/z [M+H]+=448.3.

$^1$H NMR (400 MHz, DMSO) δ 13.17 (s, 1H), 9.98 (s, 1H), 8.48 (d, J=2.0 Hz, 1H), 8.13 (d, J=1.6 Hz, 1H), 8.09 (s, 1H), 5.91 (s, 1H), 3.83 (s, 2H), 3.65 (s, 2H), 3.58 (s, 3H), 2.85 (d, J=5.1 Hz, 2H), 2.79-2.68 (m, 2H), 2.52 (s, 3H), 1.84-1.77 (m, 1H), 0.85-0.80 (m, 2H), 0.64-0.59 (m, 2H).

The compounds reported in the following table were prepared via amido coupling as described for Example 146, steps 1-3, applying the corresponding, commercially available amine in step 3.

| Example No | Structure | Intermediate 134 Amount | Product Amount (yield) | Purification method | Data |
|---|---|---|---|---|---|
| 147 | 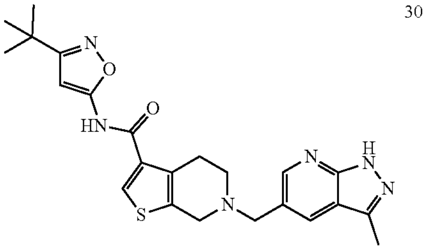 | 30 mg | 12 mg (27%) | Prep HPLC | $^1$H NMR (400 MHz, DMSO) δ 13.17 (s, 1H), 11.69 (s, 1H), 8.48 (s, 1H), 8.26 (s, 1H), 8.14 (s, 1H), 6.36 (s, 1H), 3.83 (s, 2H), 3.65 (s, 2H), 2.90 (t, J = 5.5 Hz, 2H), 2.80-2.75 (m, 2H), 2.52 (s, 3H), 1.29-1.28 (m, 9H). LC-MS (ESI) method 7: $t_R$ = 3.08 min; m/z [M + H]+ = 451.4 |

-continued

| Example No | Structure | Intermediate 134 Amount | Product Amount (yield) | Purification method | Data |
|---|---|---|---|---|---|
| 148 | 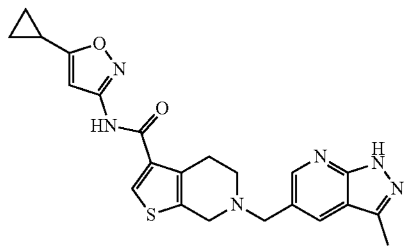 [SMILES: Cc1n[nH]c2ncc(CN3CCc4c(C(=O)Nc5cc(C6CC6)on5)csc4C3)cc12] | 30 mg | 8 mg (19%) | Prep HPLC | $^1$H NMR (400 MHz, DMSO) δ 13.17 (s, 1H), 11.05 (s, 1H), 8.48 (d, J = 1.9 Hz, 1H), 8.25 (s, 1H), 8.13 (d, J = 1.9 Hz, 1H), 6.66-6.66 (m, 1H), 3.83-3.81 (m, 2H), 3.66-3.63 (m, 2H), 2.90-2.85 (m, 2H), 2.79-2.73 (m, 2H), 2.52 (s, 3H), 2.18-2.10 (m, 1H), 1.10-1.04 (m, 2H), 0.94-0.89 (m, 2H). LC-MS (ESI) method 7: $t_R$ = 2.75 min; m/z [M + H]+ = 435.5 |

Example 149; Preparation of 6-((3-(4-methylpiperazin-1-yl)-1H-pyrazolo[3,4-b]pyridin-5-yl)methyl)-N-(5-(trifluoromethyl)pyridin-3-yl)-4,5,6,7-tetrahydrothieno[2,3-c]pyridine-3-carboxamide Example 149

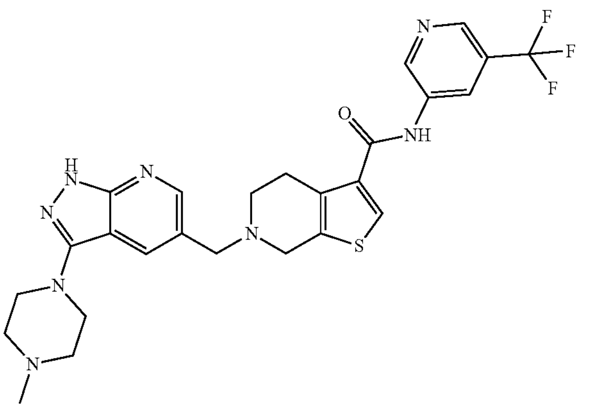

Step 1; 6-[[3-(4-methylpiperazin-1-yl)-1-(2-trimethylsilylethoxymethyl) pyrazolo[3,4-b]pyridin-5-yl] methyl]-N-[5-(trifluoromethyl)-3-pyridyl]-5,7-dihydro-4H-thieno[2,3-c]pyridine-3-carboxamide (Intermediate 135)

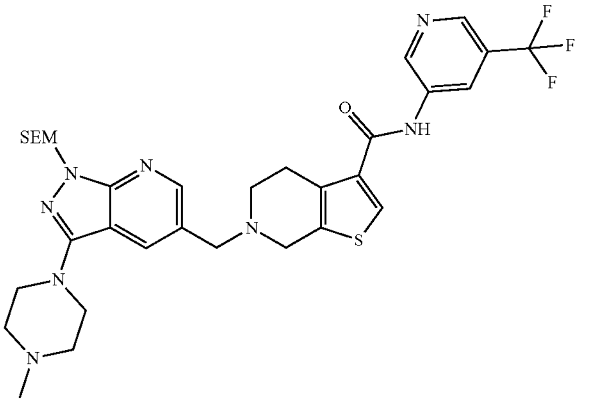 [SMILES: CN1CCN(c2nn(COCC[Si](C)(C)C)c3ncc(CN4CCc5c(C(=O)Nc6cncc(C(F)(F)F)c6)csc5C4)cc23)CC1]

Prepared from Intermediate 126 (35 mg, 0.09 mmol) and Intermediate 90 (30 mg, 0.09 mmol) according to general procedure K. The residue was purified by FCC (0-50% [75:15:10 EtOAc:EtOH:7M $NH_3$/MeOH] in cyclohexane) to give title compound.

LC-MS (ESI) method 16 $t_R$=1.86 min; m/z $[M-H]^-$ 685

Step 2; 6-[[3-(4-methylpiperazin-1-yl)-1H-pyrazolo [3,4-b]pyridin-5-yl]methyl]-N-[5-(trifluoromethyl)-3-pyridyl]-5,7-dihydro-4H-thieno[2,3-c]pyridine-3-carboxamide (Example 149)

To a mixture of Intermediate 135 (59 mg, 0.0859 mmol) in DCM (2 mL) was added TFA (0.020 mL, 0.258 mmol). The mixture was stirred overnight at RT. Another portion of TFA (0.020 mL, 0.258 mmol, 3.00 eq) was added and the mixture stirred for a further 2 h. The mixture was then diluted with water, basified with saturated $Na_2CO_3$ and extracted with EtOAc 2×. The combined organic phases dried with $MgSO_4$, filtered and concentrated. Purification by prep HPLC (Xbridge Phenyl 19×150 mm, 10 um 40-100% MeOH/$H_2O$ (10 mM $NH_4CO_3$), 20 ml/min) gave the title compound (3 mg, 6%).

LC-MS (ESI) method 7: $t_R$=2.36 min; m/z $[M^+H]^+$=557.4.

$^1$H NMR (400 MHz, DMSO-d6) δ 12.53 (s, 1H), 10.59 (s, 1H), 9.12 (d, J=2.1 Hz, 1H), 8.68 (s, 1H), 8.59 (t, J=2.1 Hz, 1H), 8.42 (d, J=1.9 Hz, 1H), 8.20 (d, J=1.8 Hz, 1H), 8.16 (s, 1H), 3.80 (s, 2H), 3.65 (s, 2H), 2.90 (t, J=5.5 Hz, 2H), 2.77 (t, J=5.6 Hz, 2H), 2.25 (s, 3H).

The compounds reported in the following table were prepared via reductive amination as described for Example 149, step 1, applying the corresponding, commercially available or previously synthesized aldehyde.

| Example No | Structure | Reagents Amount | Product Amount (yield) | Purification method | Data |
|---|---|---|---|---|---|
| 150 | 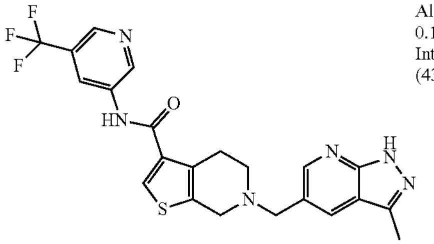 | Aldehyde (20 mg, 0.124 mmol): Intermediate 90 (43 mg, 1.05 eq) | 32 mg (55%) | Prep HPLC | $^1$H NMR (400 MHz, DMSO-d6) δ 13.18 (s, 1H), 10.59 (s, 1H), 9.13 (d, J = 2.3 Hz, 1H), 8.69 (d, J = 1.0 Hz, 1H), 8.61-8.58 (m, 1H), 8.49 (d, J = 1.9 Hz, 1H), 8.17 (s, 1H), 8.14 (d, J = 1.9 Hz, 1H), 3.84 (s, 2H), 3.67 (s, 2H), 2.94-2.88 (m, 2H), 2.81-2.76 (m, 2H). LCMS (ESI): Method 7 $t_R$ = 2.89 min; m/z [M + H]+ = 473.4 |
| 151 | 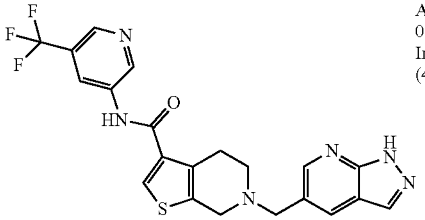 | Aldehyde (18 mg, 0.122 mmol): Intermediate 90 (42 mg, 1.05 eq) | 34 mg (60%) | Prep HPLC | $^1$H NMR (400 MHz, DMSO-d6) δ 13.62 (s, 1H), 10.59 (s, 1H), 9.13 (d, J = 2.4 Hz, 1H), 8.69 (d, J = 1.0 Hz, 1H), 8.61-8.58 (m, 1H), 8.54 (d, J = 2.0 Hz, 1H), 8.19 (d, J = 2.0 Hz, 1H), 8.17 (s, 1H), 8.14 (s, 1H), 3.85 (s, 2H), 3.67 (s, 2H), 2.93-2.88 (m, 2H), 2.81- 2.76 (m, 2H) LCMS (ESI): Method 6 $t_R$ = 4.01 min; m/z [M + H]+ = 459.4 |
| 152 | 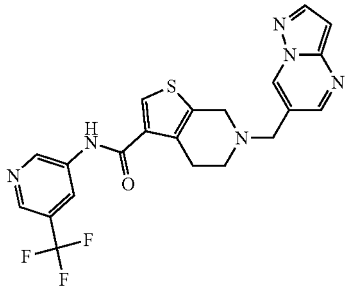 [SMILES: O=C(Nc1cncc(C(F)(F)F)c1)c1csc2c1CCN(Cc1cnc3ccnn3c1)C2] | Aldehyde (18 mg, 0.122 mmol): Intermediate 90 (42 mg, 1.05 eq) | 38mg (66%) | Prep HPLC | $^1$H NMR (400 MHz, DMSO-d6) δ 10.61 (s, 1H), 9.13 (d, J = 2.3 Hz, 1H), 9.08 (dd, J = 0.7, 1.9 Hz, 1H), 8.70-8.68 (m, 1H), 8.61-8.58 (m, 2H), 8.22 (d, J = 2.4 Hz, 1H), 8.17 (s, 1H), 6.73 (dd, J = 0.9, 2.4 Hz, 1H), 3.81 (s, 2H), 3.74 (s, 2H), 2.95-2.91 (m, 2H), 2.85-2.79 (m, 2H) LCMS (ESI): Method 7 $t_R$ = 2.94 min; m/z [M + H]+ = 459.4 |
| 153 | 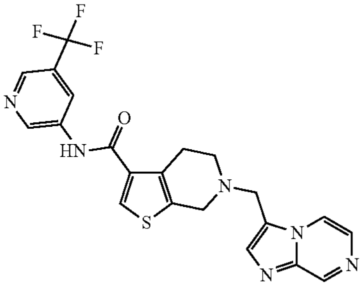 [SMILES: O=C(Nc1cncc(C(F)(F)F)c1)c1csc2c1CCN(Cc1cnc3cnccn13)C2] | Aldehyde (18 mg, 0.122 mmol): Intermediate 90 (42 mg, 1.05 eq) | 34 mg (59%) | Prep HPLC | $^1$H NMR (400 MHz, DMSO-d6) δ 10.59 (s, 1H), 9.12 (d, J = 2.3 Hz, 1H), 9.08 (d, J = 1.5 Hz, 1H), 8.70-8.68 (m, 1H), 8.59-8.57 (m, 2H), 8.17 (s, 1H), 7.93 (d, J = 4.6 Hz, 1H), 7.84 (s, 1H), 4.14 (s, 2H), 3.70 (s, 2H), 2.90-2.86 (m, 2H), 2.82-2.76 (m, 2H) LCMS (ESI): Method 6 $t_R$ = 3.91 min; m/z [M + H]+ = 459.5 |
| 154 | 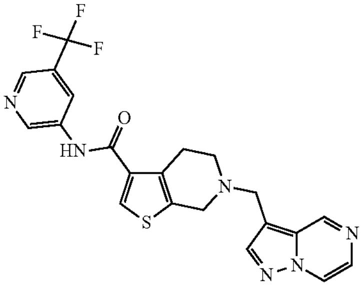 [SMILES: O=C(Nc1cncc(C(F)(F)F)c1)c1csc2c1CCN(Cc1cnn3ccncc13)C2] | General procedure K ($NaBH_3CN$ as reductive agent) Intermediate 124 (30 mg, 0.2 mmol): Intermediate 90 (66 mg, 1.0 eq) | 8 mg (8%) | Prep HPLC | $^1$H NMR (400 MHz, DMSO-d6) δ 10.59 (s, 1H), 9.30 (d, J = 1.4 Hz, 1H), 9.13 (d, J = 2.3 Hz, 1H), 8.76 (dd, J = 1.5, 4.7 Hz, 1H), 8 .69 (d, J = 1.2 Hz, 1H), 8.59 (t, J = 1.9 Hz, 1H), 8.16 (d, J = 1.8 Hz, 2H), 7.90 (d, J = 4.9 Hz, 1H), 4.03 (s, 2H), 3.69 (s, 2H), 2.90 (t, J = 5.7 Hz, 2H), 2.79 (t, J = 5.7 Hz, 2H). LCMS (ESI): Method 7 $t_R$ = 2.86 min; m/z [M + H]+ = 459.5 |

-continued

| Example No | Structure | Reagents Amount | Product Amount (yield) | Purification method | Data |
|---|---|---|---|---|---|
| 155 | 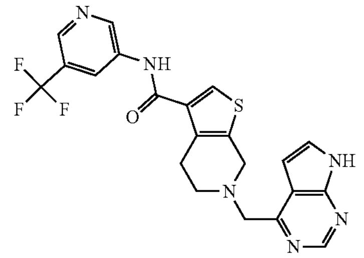 [SMILES: O=C(Nc1cncc(C(F)(F)F)c1)c1csc2c1CCN(Cc1ncnc3[nH]ccc13)C2] | Aldehyde (30 mg, 0.204 mmol: Intermediate 90 (67 mg, 1.0 eq) | 24mg (26%) | Prep HPLC | $^1$H NMR (400 MHz, DMSO-d6) δ 12.09 (s, 1H), 10.61 (s, 1H), 9.13 (d, J = 2.5 Hz, 1H), 8.70-8.68 (m, 2H), 8.59 (t, J = 2.0 Hz, 1H), 8.18 (s, 1H), 7.51 (dd, J = 2.4, 3.4 Hz, 1H), 6.80 (dd, J = 1.7, 3.3 Hz, 1H), 4.10 (s, 2H), 3.78 (s, 2H), 2.92 (t, J = 5.5 Hz, 2H), 2.85 (t, J = 5.6 Hz, 2H). LC-MS (ESI) method 7: $t_R$ = 2.95 min; m/z [M + H]$^+$ = 495.2 |

Example 156; Preparation of compound N-(3-(tert-butyl)isoxazol-5-yl)-6-(pyrazolo[1,5-a]pyrimidin-6-ylmethyl)-4,5,6,7-tetrahydrothieno[2,3-c]pyridine-3-carboxamide Example 156

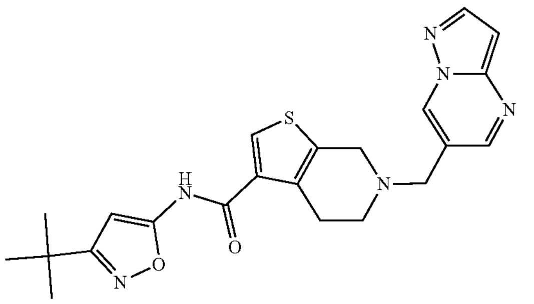

Step 1; Ethyl 6-(pyrazolo[1,5-a]pyrimidin-6-yl)methyl)-4,5,6,7-tetrahydrothieno[2,3-c]pyridine-3-carboxylate (Intermediate 136)

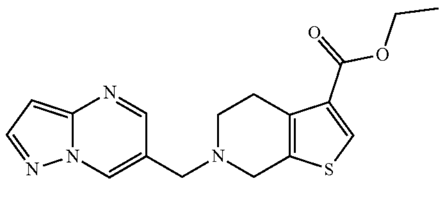 [SMILES: CCOC(=O)c1csc2c1CCN(Cc1cnc3ccnn3c1)C2]

Prepared from pyrazolo[1,5-a]pyrimidine-6-carbaldehyde (82 mg, 0.555 mmol) and Intermediate 38 (125 mg, 0.505 mmol) according to general procedure L. Purification by FCC (0 to 100% DCM/2M methanolic ammonia in DCM 20:1) gave desired product (123 mg, 71%).

$^1$H NMR (400 MHz, $CDCl_3$) δ 8.66-8.65 (m, 1H), 8.55 (d, J=2.4 Hz, 1H), 8.12 (d, J=2.5 Hz, 1H), 7.96 (s, 1H), 6.71 (dd, J=0.9, 2.3 Hz, 1H), 4.30 (q, J=7.1 Hz, 2H), 3.78-3.73 (m, 4H), 3.06-3.01 (m, 2H), 2.88 (t, J=5.8 Hz, 2H), 1.35 (t, J=7.0 Hz, 3H).

Step 2; 6-(Pyrazolo[1,5-a]pyrimidin-6-yl)methyl)-4,5,6,7-tetrahydrothieno [2,3-c]pyridine-3-carboxylic acid (Intermediate 137)

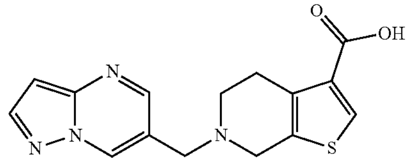 [SMILES: O=C(O)c1csc2c1CCN(Cc1cnc3ccnn3c1)C2]

Following the procedure as per Intermediate 94, starting from Intermediate 136 (120 mg, 0.350 mmol) desired product was obtained (102 mg, 93%)

LCMS (ESI) Method 15: $t_R$=0.71 min; m/z [M+H]+=315.2

Step 3; N-(3-tert-butyl)isoxazol-5-yl) 6-(pyrazolo[1,5-a]pyrimidin-6-yl)methyl)-4,5,6,7-tetrahydrothieno[2,3-c]pyridine-3-carboxamide (Example 156)

Prepared from Intermediate 137 (30 mg, 0.095 mmol) and 3-tert-butylisoxazol-5-amine (20 mg, 0.143 mmol) according to general procedure I. Purification by prep HPLC (Sunfire C18 19×150 mm, 10 um 20-80% ACN/$H_2O$ (10 mM $NH_4CO_3$), 20 ml/min) gave the title compound (4 mg, 10%)

LCMS (ESI): Method 7 $t_R$=3.15 min, m/z [M+H]+=437.2

$^1$H NMR (400 MHz, DMSO-d6) δ 11.71 (s, 1H), 9.08 (d, J=1.1 Hz, 1H), 8.59 (d, J=2.1 Hz, 1H), 8.24 (s, 1H), 8.22 (d, J=2.3 Hz, 1H), 6.73 (dd, J=0.8, 2.3 Hz, 1H), 6.35 (s, 1H), 3.79 (s, 2H), 3.72 (s, 2H), 2.92 (t, J=6.3 Hz, 2H), 2.81 (t, J=5.8 Hz, 2H), 1.28 (s, 9H).

Example 157; Preparation of compound (R)—N-(3-((3-(dimethylamino) pyrrolidin-1-yl)methyl)-5-(trifluoromethyl)phenyl)-6-((3-methyl-1H-pyrazolo[3,4-b]pyridin-5-yl)methyl)-4,5,6,7-tetrahydrothieno[2,3-c]pyridine-3-carboxamide Example 157

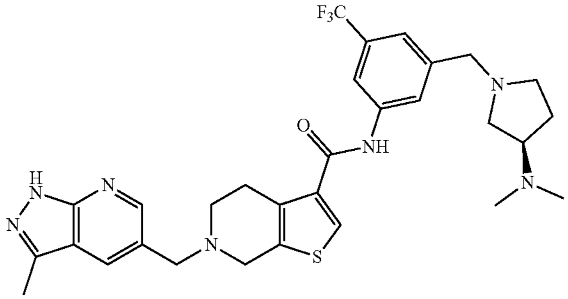

Step 1; tert-butyl (R)-3-((3-((3-(dimethylamino) pyrrolidin-1-yl)methyl)-5-(trifluoromethyl)phenyl) carbamoyl)-4,7-dihydrothieno[2,3-c]pyridine-6(5H)-carboxylate (Intermediate 138)

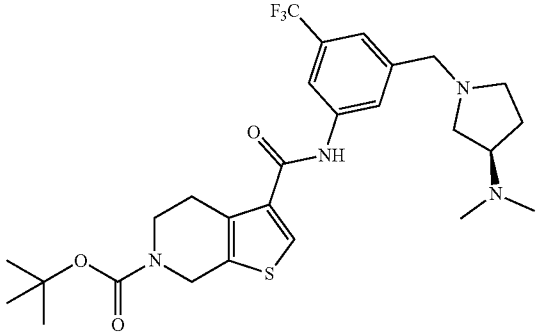 [SMILES: CN(C)[C@@H]1CCN(Cc2cc(NC(=O)c3csc4c3CCN(C(=O)OC(C)(C)C)C4)cc(C(F)(F)F)c2)C1]

Prepared starting from 6-(tert-butoxycarbonyl)-4,5,6,7-tetrahydrothieno[2,3-c]pyridine-3-carboxylic acid (350 mg, 1.24 mmol) and Intermediate 14 (355 mg, 1.24 mmol) following preparation of Example 47, step 1. Purification by FCC (0-10% 2M $NH_3$/MeOH in DCM) gave title compound (580 mg, 84%).

$^1$H NMR (300 MHz, CDC13) δ 8.29-8.22 (m, 2H), 7.86 (s, 1H), 7.67 (s, 1H), 7.19 (s, 1H), 4.61 (s, 2H), 3.70-3.55 (m, 5H), 3.05-2.96 (m, 4H), 2.82 (s, 6H), 2.57 (dd, J=6.4, 11.5 Hz, 1H), 2.46-2.23 (m, 2H), 2.07-1.99 (m, 1H), 1.48 (s, 9H)

Step 2; (R)—N-(3-((3-(dimethylamino)pyrrolidin-1-yl)methyl)-5-(trifluoro methyl)phenyl)-4,5,6,7-tetrahydrothieno[2,3-c]pyridine-3-carboxamide (Intermediate 139)

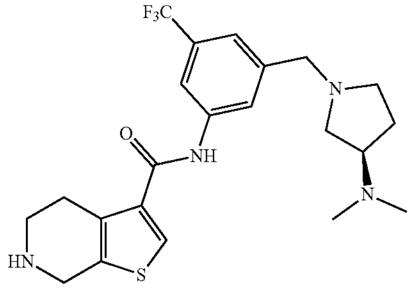 [SMILES: CN(C)[C@@H]1CCN(Cc2cc(NC(=O)c3csc4c3CCNC4)cc(C(F)(F)F)c2)C1]

To a solution of Intermediate 138 (576 mg, 1.04 mmol) in anhydrous DCM (10.4 mL), stirred over an ice/water bath under an atmosphere of argon, TFA (1.6 mL, 20.8 mmol) was added dropwise over 5 min. The reaction mixture was stirred for 1.5 h, concentrated in vacuo and the residue was dissolved in MeOH, applied to a MeOH pre-conditioned 20 g Isolute SCX-II cartridge, washed with MeOH, then released with 2M $NH_3$/MeOH. The 2M $NH_3$/MeOH eluent was concentrated in vacuo to give title compound was obtained (356 mg, 75%).

$^1$H NMR (300 MHz, $CDCl_3$) δ 8.00-7.92 (m, 2H), 7.69 (d, J=5.3 Hz, 2H), 7.34 (s, 1H), 4.06 (s, 2H), 3.71 (d, J=13.5 Hz, 1H), 3.59 (d, J=13.3 Hz, 1H), 3.17-3.11 (m, 2H), 2.99-2.92 (m, 2H), 2.87-2.54 (m, 5H), 2.45 (dd, J=6.3, 8.5 Hz, 1H), 2.24 (s, 6H), 2.09-1.95 (m, 1H), 1.84-1.72 (m, 1H)

Step 3; (R)—N-(3-((3-(dimethylamino)pyrrolidin-1-yl)methyl)-5-(trifluoro methyl)phenyl)-6-((3-methyl-1H-pyrazolo[3,4-b]pyridin-5-yl)methyl)-4,5,6,7-tetrahydrothieno[2,3-c]pyridine-3-carboxamide (Example 157)

Prepared from Intermediate 139 (59 mg, 0.130 mmol) and 3-methyl-1H-pyrazolo[3,4-b]pyridine-5-carbaldehyde (20 mg, 0.124 mmol) according to general procedure J. Purification by prep HPLC (Xbridge Phenyl 19×150 mm, 10 μm 40-100%, methanol/water (10 mM $NH_4HCO_3$), 20 mL/min, RT) gave the title compound (34 mg, 45%).

LCMS (ESI): Method 7 $t_R$=2.18 min; m/z [M+H]+=598.4

$^1$H NMR (400 MHz, DMSO) δ 13.17 (s, 1H), 10.32 (s, 1H), 8.49 (d, J=2.0 Hz, 1H), 8.15-8.10 (m, 3H), 7.94 (s, 1H), 7.33 (s, 1H), 3.84 (s, 2H), 3.70 (d, J=13.6 Hz, 1H), 3.66 (s, 2H), 3.57 (d, J=13.7 Hz, 1H), 2.93-2.87 (m, 2H), 2.81-2.65 (m, 4H), 2.63-2.55 (m, 1H), 2.49-2.43 (m, 1H), 2.31 (dd, J=5.7, 7.8 Hz, 1H), 2.09 (s, 6H), 1.93-1.82 (m, 1H), 1.68-1.59 (m, 1H).

The compounds reported in the following table were prepared via reductive amination as described for Example 157, step 1-3, applying the corresponding, commercially available or previously synthesized aldehyde in step 3.

| Example No | Structure | Reagents Amount | Product Amount (yield) | Purification method | Data |
|---|---|---|---|---|---|
| 158 | 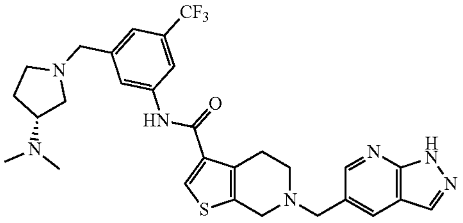 [SMILES: CN(C)[C@@H]1CCN(Cc2cc(NC(=O)c3csc4c3CCN(Cc3cnc5[nH]ncc5c3)C4)cc(C(F)(F)F)c2)C1] | Aldehyde (18 mg, 0.122 mmol): Intermediate 139: 58 mg (1.05 eq) | 37 mg (51%) | Prep HPLC | $^1H$ NMR (400 MHz, DMSO) δ 13.62 (s, 1H), 10.32 (s, 1H), 8.53 (d, J = 2.0 Hz, 1H), 8.19 (d, J = 2.0 Hz, 1H), 8.14-8.10 (m, 3H), 7.94 (s, 1H), 7.33 (s, 1H), 3.85 (s, 2H), 3.70 (d, J = 13.6 Hz, 1H), 3.66 (s, 2H), 3.57 (d, J = 13.7 Hz, 1H), 2.93-2.89 (m, 2H), 2.81-2.66 (m, 4H), 2.64-2.57 (m, 1H), 2.49-2.43 (m, 1H), 2.31 (dd, J = 5.7, 7.8 Hz, 1H), 2.09 (s, 6H), 1.92-1.82 (m, 1H), 1.68-1.58 (m, 1H). LCMS (ESI): Method 7 $t_R$ = 2.09 min; m/z [M + H]+ = 584.3 |
| 159 | 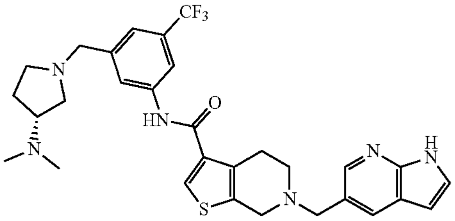 [SMILES: CN(C)[C@@H]1CCN(Cc2cc(NC(=O)c3csc4c3CCN(Cc3cnc5[nH]ccc5c3)C4)cc(C(F)(F)F)c2)C1] | Aldehyde (19 mg, 0.123 mmol): Intermediate 139: 59 mg (1.05 eq) | 33 mg (45%) | Prep HPLC | $^1H$ NMR (400 MHz, DMSO) δ 11.61 (s, 1H), 10.32 (s, 1H), 8.21 (d, J = 2.0 Hz, 1H), 8.12-8.10 (m, 2H), 7.95-7.92 (m, 2H), 7.47 (dd, J = 2.6, 3.2 Hz, 1H), 7.33 (s, 1H), 6.44 (dd, J = 1.8, 3.4 Hz, 1H), 3.80 (s, 2H), 3.70 (d, J = 13.6 Hz, 1H), 3.63 (s, 2H), 3.57 (d, J = 13.6 Hz, 1H), 2.92-2.86 (m, 2H), 2.79-2.66 (m, 4H), 2.64-2.57 (m, 1H), 2.50-2.43 (m, 1H), 2.31 (dd, J = 5.6, 7.7 Hz, 1H), 2.09 (s, 6H), 1.92-1.82 (m, 1H), 1.68-1.58 (m, 1H) LCMS (ESI): Method 7 $t_R$ = 2.25 min; m/z $[M + H]^+$ = 583.3 |
| 160 | 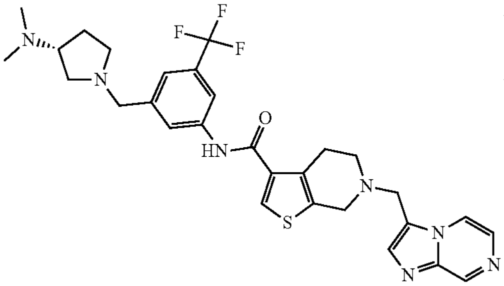 [SMILES: CN(C)[C@@H]1CCN(Cc2cc(NC(=O)c3csc4c3CCN(Cc3cnc5cnccn35)C4)cc(C(F)(F)F)c2)C1] | Aldehyde (18 mg, 0.122 mmol): Intermediate 139: 58 mg (1.05 eq) | 38 mg (53%) | Prep HPLC | $^1H$ NMR (400 MHz, DMSO) δ 10.31 (s, 1H), 9.08 (d, J = 1.5 Hz, 1H), 8.58 (dd, J = 1.6, 4.7 Hz, 1H), 8.13 (s, 1H), 8.12-8.09 (m, 1H), 7.94-7.92 (m, 2H), 7.83 (s, 1H), 7.33 (s, 1H), 4.13 (s, 2H), 3.73-3.67 (m, 3H), 3.56 (d, J = 13.7 Hz, 1H), 2.89-2.85 (m, 2H), 2.82-2.77 (m, 2H), 2.75-2.66 (m, 2H), 2.64-2.57 (m, 1H), 2.49-2.43 (m, 1H), 2.31 (dd, J = 5.7, 7.8 Hz, 1H), 2.09 (s, 6H), 1.92- 1.82 (m, 1H), 1.67-1.58 (m, 1H). LCMS (ESI): Method 7 $t_R$ = 2.16 min; m/z $[M + H]^+$ = 584.4 |
| 161 | 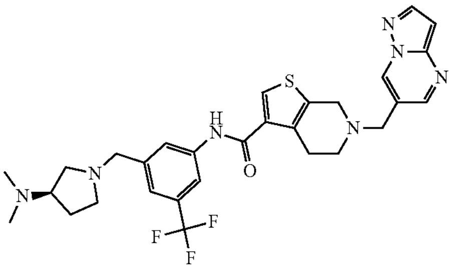 [SMILES: CN(C)[C@@H]1CCN(Cc2cc(NC(=O)c3csc4c3CCN(Cc3cnc5ccnn5c3)C4)cc(C(F)(F)F)c2)C1] | Aldehyde (18 mg, 0.122 mmol): Intermediate 139: 58 mg (1.05 eq) | 34 mg (47%) | Prep HPLC | $^1H$ NMR (400 MHz, DMSO) δ 10.33 (s, 1H), 9.08 (d, J = 1.1 Hz, 1H), 8.60 (d, J = 2.0 Hz, 1H), 8.22 (d, J = 2.4 Hz, 1H), 8.14 (s, 1H), 8.12 (s, 1H), 7.94 (s, 1H), 7.33 (s, 1H), 6.73 (dd, J = 0.9, 2.4 Hz, 1H), 3.80 (s, 2H), 3.74-3.68 (m, 3H), 3.57 (d, J = 13.6 Hz, 1H), 2.93-2.88 (m, 2H), 2.85-2.80 (m, 2H), 2.75-2.66 (m, 2H), 2.64-2.57 (m, 1H), 2.49-2.44 (m, 1H), 2.31 (dd, J = 5.6, 7.7 Hz, 1H), 2.09 (s, 6H), 1.93-1.82 (m, 1H), 1.69-1.59 (m, 1H) LCMS (ESI): Method 7 $t_R$ = 2.19 min; m/z $[M + H]^+$ = 584.4 |

Example 162; Preparation of (R)—N-(3-((3-(dimethylamino)pyrrolidin-1-yl)methyl)-5-(trifluoromethyl)phenyl)-6-(5-methylimidazo[1,2-a]pyridine-3-carbonyl)-4,5,6,7-tetrahydrothieno[2,3-c]pyridine-3-carboxamide Example 162

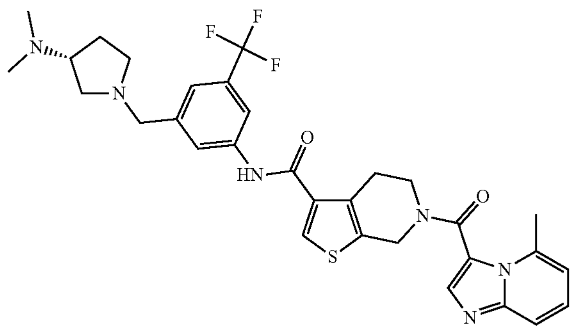

Step 1; (R)—N-(3-((3-(dimethylamino)pyrrolidin-1-yl)methyl)-5-(trifluoro methyl)phenyl)-6-(5-methylimidazo[1,2-a]pyridine-3-carbonyl)-4,5,6,7-tetrahydrothieno[2,3-c]pyridine-3-carboxamide (Example 162)

Prepared from Intermediate 139 (40 mg, 0.0884 mmol) and lithium 5-methylimidazo[1,2-a]pyridine-3-carboxylate (16 mg, 0.0884 mmol) according to general procedure H. Purification by reverse phase preparative HPLC (Xbridge Phenyl 19×150 mm, 10 μm 40-100%, MeOH/water (10 mM $NH_4HCO_3$), 20 mL/min, RT) gave the title compound (22 mg, 39%). LC-MS (ESI) method 7: $t_R$=2.55 min; m/z $[M+H]^+$=611.3.

$^1$H NMR (400 MHz, DMSO-d6) δ 10.40 (s, 1H), 8.7-8.21 (m, 1H), 8.12 (s, 1H), 7.6-7.93 (m, 2H), 7.4-7.60 (m, 1H), 7.39 (dd, J=6.9, 8.9 Hz, 1H), 7.35 (s, 1H), 6.91 (s, 1H), 4.98 (s, 2H), 3.89 (s, 2H), 3.71 (d, J=13.6 Hz, 1H), 3.58 (d, J=13.6 Hz, 1H), 3.04 (s, 2H), 2.4-2.69 (m, 2H), 2.5-2.58 (m, 1H), 2.9-2.43 (m, 1H), 2.32 (dd, J=5.6, 7.5 Hz, 1H), 2.09 (s, 6H), 1.0-1.83 (m, 1H), 1.8-1.59 (m, 1H).

Example 163; Preparation of compound 6-[(3-methyl-1H-pyrazolo[3,4-b]pyridin-5-yl)methyl]-N-[3-(2-pyrrolidin-1-ylethoxy)-5-(trifluoromethyl)phenyl]-5,7-dihydro-4H-thieno[2,3-c]pyridine-3-carboxamide Example 163

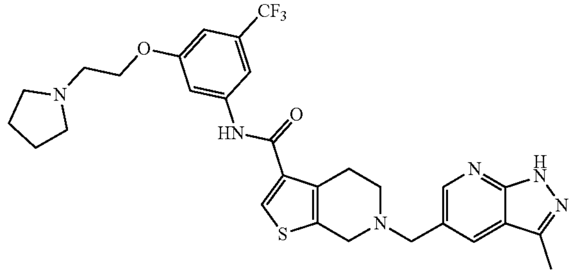

Step 1; tert-butyl 3-[[3-(2-pyrrolidin-1-ylethoxy)-5-(trifluoromethyl) phenyl]carbamoyl]-5,7-dihydro-4H-thieno[2,3-c]pyridine-6-carboxylate (Intermediate 140)

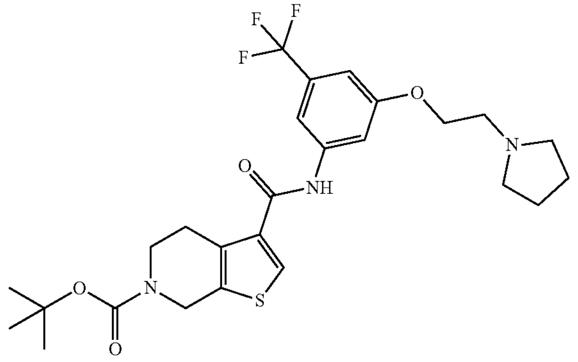 [SMILES: CC(C)(C)OC(=O)N1CCc2c(C(=O)Nc3cc(OCCN4CCCC4)cc(C(F)(F)F)c3)csc2C1]

Prepared from 6-tert-butoxycarbonyl-5,7-dihydro-4H-thieno[2,3-c]pyridine-3-carboxylic acid (190 mg, 0.671 mmol) and Intermediate 18 (193 mg, 0.704 mmol) according to general procedure M. The residue was purified by FCC (0-100% EtOAc in cyclohexane followed by 0-20% 7N $NH_3$ in EtOAc). The residue was dissolved in MeOH and loaded onto an SCX cartridge, which was washed with MeOH. The compound was released using 7N $NH_3$ in MeOH. The solution was concentrated under reduced pressure.

$^1$H NMR (400 MHz, $CDCl_3$) δ 7.69 (s, 1H), 7.58 (s, 1H), 7.37 (s, 1H), 6.93 (s, 1H), 4.62 (s, 2H), 4.16 (dd, J=5.8, 5.8 Hz, 2H), 3.71-3.64 (m, 2H), 3.02-2.96 (m, 2H), 2.95-2.88 (m, 2H), 2.80 (s, 9H), 2.66-2.61 (m, 4H), 1.84-1.78 (m, 4H)

Step 2; N-[3-(2-pyrrolidin-1-ylethoxy)-5-(trifluoromethyl)phenyl]-4,5,6,7-tetrahydrothieno[2,3-c]pyridine-3-carboxamide Intermediate 141)

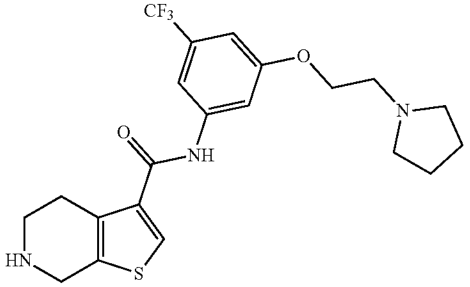 [SMILES: O=C(Nc1cc(OCCN2CCCC2)cc(C(F)(F)F)c1)c1csc2c1CCNC2]

Following the procedure as per Intermediate 139, starting from Intermediate 140 (60 mg, 0.111 mmol) desired product was obtained (44 mg, 90% yield).

$^1$H NMR (400 MHz, $CDCl_3$) δ 7.74 (s, 1H), 7.63 (s, 1H), 7.55 (s, 1H), 7.34 (s, 1H), 6.93 (s, 1H), 4.16 (t, J=5.8 Hz, 2H), 4.06 (s, 2H), 3.13 (t, J=5.9 Hz, 2H), 2.94-2.90 (m, 4H), 2.66-2.61 (m, 4H), 1.84-1.80 (m, 4H)

Step 3; 6-[(3-methyl-1H-pyrazolo[3,4-b]pyridin-5-yl)methyl]-N-[3-(2-pyrrolidin-1-ylethoxy)-5-(trifluoromethyl)phenyl]-5,7-dihydro-4H-thieno[2,3-c]pyridine-3-carboxamide (Example 163)

Prepared from Intermediate 141 (40 mg, 0.0910 mmol) and 3-methyl-1H-pyrazolo[3,4-b]pyridine-5-carbaldehyde (15 mg, 0.0910 mmol) according to general procedure J. Purification by reverse phase preparative HPLC (Xbridge Phenyl 19×150 mm, 10 um 40-100% MeOH/$H_2O$ (10 mM $NH_4CO_3$), 20 ml/min, RT) gave the title compound (15 mg, 28%).

LCMS (ESI): Method 7 $t_R$=2.64 min, m/z $[M+H]^+$=585.2 $^1H$ NMR (400 MHz, DMSO) δ 13.17 (s, 1H), 10.28 (s, 1H), 8.49 (d, J=2.0 Hz, 1H), 8.14 (d, J=1.9 Hz, 1H), 8.10 (s, 1H), 7.76 (s, 1H), 7.65 (s, 1H), 6.98 (s, 1H), 4.14 (t, J=5.8 Hz, 2H), 3.84 (s, 2H), 3.66 (s, 2H), 2.91-2.87 (2H, m), 2.84-2.77 (4H, m) 1.72-1.68 (m, 4H).

The compound reported in the following table was prepared via reductive amination as described for Example 163, step 1-3, applying the corresponding, commercially available or previously synthesized aldehyde in step 3.

| Example No | Structure | Reagents Amount | Product Amount (yield) | Purification method | Data |
|---|---|---|---|---|---|
| 164 | 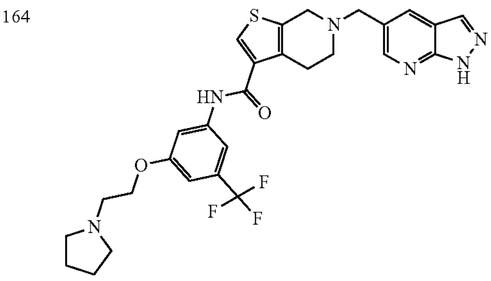 | Aldehyde, Intermediate 18 (16 mg, 0.108 mmol): Intermediate 141 45 mg (1.0 eq) | 21 mg (34%) | Prep HPLC | $^1H$ NMR (400 MHz, DMSO) δ 10.30 (br s, 1H), 8.52 (d, J = 1.9 Hz, 1H), 8.17 (d, J = 2.0 Hz, 1H), 8.11 (d, J = 7.5 Hz, 2H), 7.76 (s, 1H), 7.66 (t, J = 2.2 Hz, 1H), 6.97 (s, 1H), 4.16-4.10 (m, 2H), 3.85 (s, 2H), 3.66 (s, 2H), 2.90-2.75 (m, 6H), 1.72-1.67 (m, 4H). LCMS (ESI): Method 7 $t_R$ = 2.65 min, m/z $[M + H]^+$ = 571.2 |

Example 165; Preparation of 6-(6-(4-methylpiperazin-1-yl)imidazo[1,2-a]pyridine-3-carbonyl)-N-(5-(trifluoromethyl)pyridin-3-yl)-4,5,6,7-tetrahydrothieno[2,3-c]pyridine-3-carboxamide Example 165

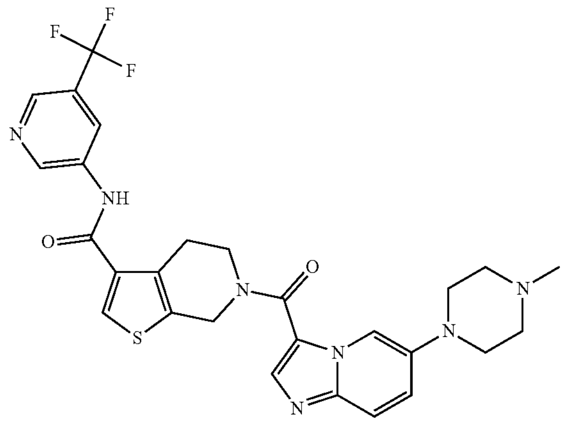

Step 1; ethyl 6-[6-(4-methylpiperazin-1-yl)imidazo[1,2-a]pyridine-3-carbonyl]-5,7-dihydro-4H-thieno[2,3-c]pyridine-3-carboxylate (Intermediate 142)

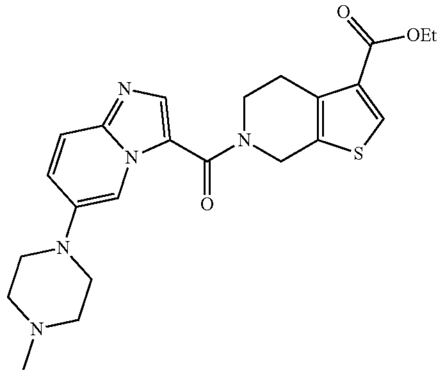 [SMILES: CCOC(=O)c1csc2c1CCN(C(=O)c1cnc3ccc(N4CCN(C)CC4)cn13)C2]

Prepared from Intermediate 38 (405 mg, 1.6 mmol) and Intermediate 113 (851 mg, 1.6 mmol) according to general procedure M. The residue was purified by FCC (0-100% EtOAc in cyclohexane followed by 0-100% MeOH in EtOAc) to give desired product (330 mg, 45%).

$^1$H NMR (400 MHz, $CDCl_3$) δ 8.52 (d, J=1.8 Hz, 1H), 8.03 (s, 1H), 7.89 (s, 1H), 7.57 (d, J=9.6 Hz, 1H), 7.25 (m, 1H), 5.01 (s, 2H), 4.32 (q, J=7.1 Hz, 2H), 4.09 (m, 2H), 3.24-3.14 (m, 6H), 2.61 (t, J=4.7 Hz, 4H), 2.37 (s, 3H), 1.38 (t, J=7.1 Hz, 3H).

Step 2; 6-[6-(4-methylpiperazin-1-yl)imidazo[1,2-a]pyridine-3-carbonyl]-5,7-dihydro-4H-thieno[2,3-c]pyridine-3-carboxylic acid (Intermediate 143)

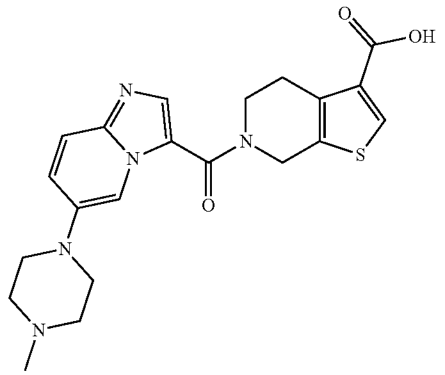 [SMILES: CN1CCN(c2ccc3ncc(C(=O)N4CCc5c(C(=O)O)csc5C4)n3c2)CC1]

Following the procedure as per Example 140, step 2, starting from Intermediate 142 (330 mg, 0.728 mmol), the obtained crude was washed with MeOH, the combined organic phases were evaporated to give the title compound (310 mg, 100%).

$^1$H NMR (400 MHz, MeOH-d4) δ 8.46 (d, J=1.8 Hz, 1H), 8.00 (s, 1H), 7.93 (s, 1H), 7.60 (d, J=9.6 Hz, 1H), 7.52 (dd, J=2.3, 9.6 Hz, 1H), 5.03 (s, 2H), 4.07 (t, J=5.7 Hz, 2H), 3.19 (t, 5.4 Hz, 2H), 3.07 (t, J=4.7 Hz, 4H), 2.68 (s, 3H).

Step 3; 6-[6-(4-methylpiperazin-1-yl)imidazo[1,2-a]pyridine-3-carbonyl]-N-[5-(trifluoromethyl)-3-pyridyl]-5,7-dihydro-4H-thieno[2,3-c]pyridine-3-carboxamide (Example 165)

Prepared from 5-(trifluoromethyl)pyridin-3-amine (19 mg, 0.118 mmol) and Intermediate 143 (assumed 50% purity, 100 mg, 0.118 mmol) according to general procedure N. The residue, purified by preparative HPLC (Xbridge Phenyl 19×150 mm, 10 um 40-100% MeOH/$H_2O$ (10 mM $NH_4CO_3$), 20 ml/min, RT), gave the title compound (13 mg, 19% yield).

LC-MS (ESI) method 7: $t_R$=2.70 min; m/z $[M^+H]^+$=570.4.

$^1$H NMR (400 MHz, DMSO) δ 10.66 (s, 1H), 9.15 (d, J=2.1 Hz, 1H), 8.70 (s, 1H), 8.61 (t, J=2.1 Hz, 1H), 8.41 (d, J=1.9 Hz, 1H), 8.27 (s, 1H), 8.03 (s, 1H), 7.61 (d, J=9.8 Hz, 1H), 7.49 (dd, J=2.3, 9.8 Hz, 1H), 5.03 (s, 2H), 3.99 (t, J=5.7 Hz, 2H), 3.08 (m, 6H), 2.51 (m, 4H-under DMSO peak), 2.24 (s, 3H).

Example 166; Preparation of 6-(6-(6-methyl-2,6-diazaspiro[3.3]heptan-2-yl)imidazo[1,2-a]pyridine-3-carbonyl)-N-(3-(trifluoromethyl)phenyl)-4,5,6,7-tetrahydrothieno[2,3-c]pyridine-3-carboxamide Example 166

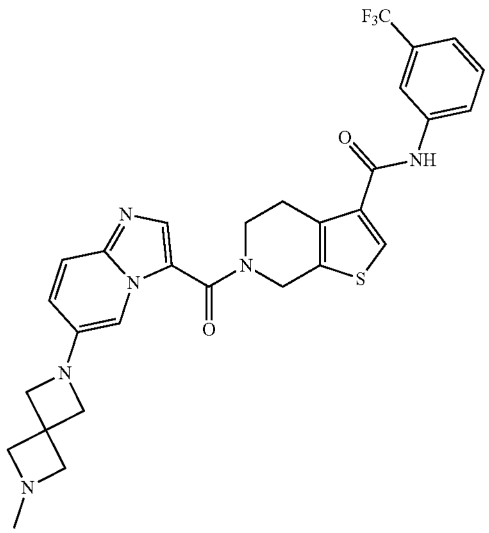

Step 1; 6-[(2-aminopyrimidin-5-yl)methyl]-N-(5-isobutyl-2-methyl-pyrazol-3-yl)-5,7-dihydro-4H-thieno[2,3-c]pyridine-3-carboxamide (Intermediate 144)

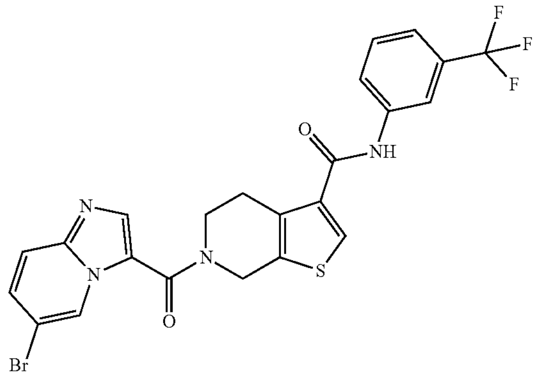 [SMILES: O=C(Nc1cccc(C(F)(F)F)c1)c1csc2c1CCN(C(=O)c1cnc3ccc(Br)cn13)C2]

Prepared from 6-bromoimidazo[1,2-a]pyridine-3-carboxylic acid (406 mg, 1.68 mmol) and Intermediate 64 (550 mg, 0.40 mmol) according to general procedure H. The reaction was diluted with aqueous $NH_4Cl$ and filtered to yield a solid which was dried in vacuo. The solid was washed with MeOH to yield title compound (533 mg, 57%).

$^1$H NMR (400 MHz, DMSO-d6) δ 10.46 (s, 1H), 9.17 (s, 1H), 8.27 (s, 2H), 8.22 (s, 1H), 8.04 (d, J=8.1 Hz, 1H), 7.79 (d, J=9.6 Hz, 1H), 7.68-7.61 (m, 2H), 7.49 (d, J=7.8 Hz, 1H), 5.09 (s, 2H), 4.06-3.99 (m, 2H), 3.16-3.10 (m, 2H)

Step 2; 6-(6-(6-methyl-2,6-diazaspiro[3.3]heptan-2-yl)imidazo[1,2-a]pyridine-3-carbonyl)-N-(3-(trifluoromethyl)phenyl)-4,5,6,7-tetrahydrothieno[2,3-c]pyridine-3-carboxamide (Example 166)

Intermediate 144 (35 mg, 0.0637 mmol) and Pd-PEPPSI™-IPent catalyst (5.1 mg, 6.37 mol) were charged into a nitrogen flushed microwave vial. THF (2.0 mL) was added and the solution degassed while 2M sodium tert-butoxide (0.37 mL, 0.733 mmol) and 2-methyl-2,6-diazaspiro[3.3]heptane dihydrochloride (117 mg, 0.63 mmol) were added, the reaction was then heated in the microwave at 120° C. for 2 hours. The reaction mixture was concentrated and the residue purified by preparative HPLC (Luna Phenyl-Hexyl 21.2×150 mm, 10 um 20-80% MeOH/$H_2O$ (0.1% FA), 20 ml/min). The isolated material was dissolved in EtOAc and washed with sat. aq. $NaHCO_3$ and the organics were concentrated and freeze dried to give the title compound (2.3 mg, 6%).

LC-MS (ESI) method 7: $t_R$=3.12 min; m/z $[M^+H]^+$=581.2.

$^1$H NMR (300 MHz, DMSO-d6) δ 10.42 (s, 1H), 8.22 (s, 2H), 8.07 (d, J=1.8 Hz, 1H), 8.01-7.98 (m, 2H), 7.63-7.58 (m, 2H), 7.46 (d, J=7.4 Hz, 1H), 6.98 (dd, J=2.3, 9.5 Hz, 1H), 5.01 (s, 2H), 3.98 (dd, J=5.5, 5.5 Hz, 2H), 3.89 (s, 4H), 3.28 (s, 4H), 3.08-3.06 (m, 2H), 2.20 (s, 3H).

Example 167; Preparation of 6-(6-(1-methyl-1,2,3,6-tetrahydropyridin-4-yl)imidazo[1,2-a]pyridine-3-carbonyl)-N-(3-(trifluoromethyl)phenyl)-4,5,6,7-tetrahydrothieno[2,3-c]pyridine-3-carboxamide Example 167

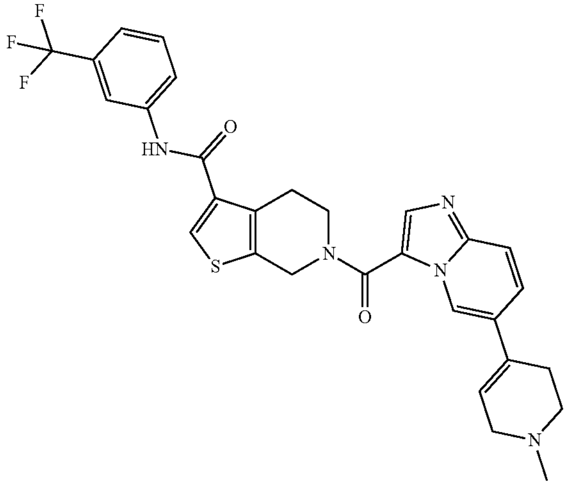

Step 1; 6-[6-(1-methyl-3,6-dihydro-2H-pyridin-4-yl)imidazo[1,2-a]pyridine-3-carbonyl]-N-[3-(trifluoromethyl)phenyl]-5,7-dihydro-4H-thieno[2,3-c]pyridine-3-carboxamide (Example 167)

To a solution of Intermediate 144 (150 mg, 0.273 mmol) in DMF (1.5 mL) and water (0.5 mL) was added 1-methyl-1,2,3,6-tetrahydropyridine-4-boronic acid pinacol ester (79 mg, 0.355 mmol), $K_2CO_3$ (45 mg, 0.328 mmol), Pd(dppf)$Cl_2$·DCM (3.4 mg, 4.10 mol). The reaction was heated at 100° C. under a flow of nitrogen for 4 h. Water was added to the mixture followed by extraction with DCM. The organic phase was separated, passed through a hydrophobic frit and concentrated in vacuo. The residue was purified by FCC (0-20% MeOH in DCM) to yield title compound (75 mg, 49%).

LC-MS (ESI) method 7: $t_R$=3.29 min; m/z $[M^+H]^+$=566.3.

$^1$H NMR (400 MHz, DMSO-d6) δ 10.42 (s, 1H), 8.91 (s, 1H), 8.22 (s, 2H), 8.12 (s, 1H), 8.00 (d, J=8.9 Hz, 1H), 7.72-7.70 (m, 2H), 7.60 (t, J=8.0 Hz, 1H), 7.45 (d, J=7.7 Hz, 1H), 6.34 (t, J=3.6 Hz, 1H), 5.05 (s, 2H), 4.00 (t, J=5.6 Hz, 2H), 3.10-3.04 (m, 4H), 2.60 (t, J=5.6 Hz, 2H), 2.30 (s, 3H).

Example 168; N-(3-(tert-butyl)isoxazol-5-yl)-6-(6-(4-methylpiperazin-1-yl)imidazo[1,2-a]pyridine-3-carbonyl)-4,5,6,7-tetrahydrothieno[2,3-c]pyridine-3-carboxamide Example 168

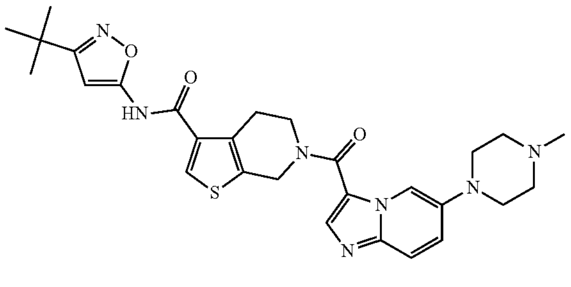

Step 1; tert-butyl 3-[(5-tert-butylisoxazol-3-yl)carbamoyl]-5,7-dihydro-4H-thieno[2,3-c]pyridine-6-carboxylate (Intermediate 145)

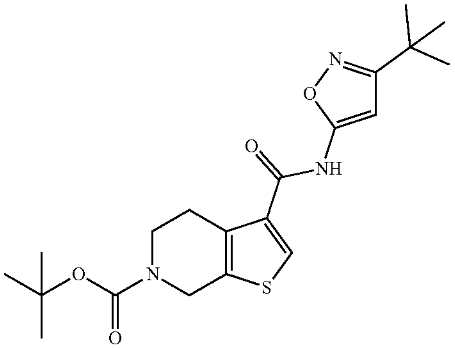 [SMILES: CC(C)(C)OC(=O)N1CCc2c(C(=O)Nc3cc(C(C)(C)C)no3)csc2C1]

Following the procedure as per Intermediate 95, starting from 6-tert-butoxycarbonyl-5,7-dihydro-4H-thieno[2,3-c]pyridine-3-carboxylic acid (142 mg, 0.500 mmol) and 3-Amino-5-tert-butylisoxazole (70 mg, 0.500 mmol), the title compound was obtained (164 mg, 0.404 mmol, 81%).

$^1$H NMR (400 MHz, $CDCl_3$) δ 10.84 (s, 1H), 8.10 (s, 1H), 6.88 (s, 1H), 4.67-4.62 (m, 2H), 3.68 (t, J=4.9 Hz, 2H), 3.03 (t, J=5.8 Hz, 2H), 1.42 (s, 9H), 1.37 (s, 9H).

Step 2; N-(3-tert-butylisoxazol-5-yl)-4,5,6,7-tetrahydrothieno[2,3-c]pyridine-3-carboxamide hydrochloride (Intermediate 146)

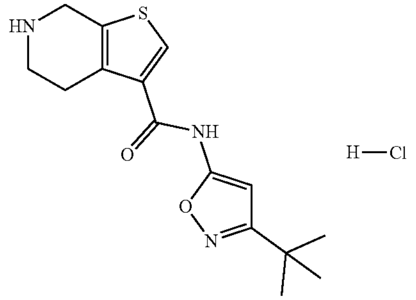 [SMILES: CC(C)(C)c1cc(NC(=O)c2csc3c2CCNC3)on1 ; Cl]

Following the procedure as per Intermediate 86, starting from Intermediate 145 (100 mg, 0.247 mmol) the title compound was obtained (56 mg, 0.162 mmol, 66%)

$^1$H NMR (400 MHz, DMSO-d6) δ 11.93 (s, 1H), 9.65-9.60 (m, 2H), 8.52 (s, 1H), 6.41 (s, 1H), 4.47-4.38 (m, 2H), 3.40 (m, 2H), 3.20-3.12 (m, 2H), 1.33 (s, 9H).

Step 3: N-(3-(tert-butyl)isoxazol-5-yl)-6-(6-(4-methylpiperazin-1-yl)imidazo[1,2-a]pyridine-3-carbonyl)-4,5,6,7-tetrahydrothieno[2,3-c]pyridine-3-carboxamide Example 168

Prepared from Intermediate 113 (107 mg, 0.161 mmol) and Intermediate 146 (55 mg, 0.161 mmol) according to procedure of Example 122, step 3. The residue was purified by preparative HPLC (Sunfire C18 19×150 mm, 10 um 5-60% ACN/$H_2O$ (0.1% FA), 20 ml/min, RT) and on SCX cartridge eluting with 1N $NH_3$ in methanol to give the title compound (9 mg, 10%).

LC-MS (ESI) method 7: $t_R$=2.88 min; m/z $[M^+H]^+$=548.5.

$^1$H NMR (400 MHz, DMSO-d6) δ 11.78 (s, 1H), 8.41 (d, J=1.8 Hz, 1H), 8.36 (s, 1H), 8.03 (s, 1H), 7.62 (d, J=9.8 Hz, 1H), 7.49 (dd, J=2.3, 9.8 Hz, 1H), 6.39 (s, 1H), 5.02 (s, 2H), 3.98 (t, J=5.6 Hz, 2H), 3.09-3.08 (m, 6H), 2.57-2.55 (m, 2H), 2.29 (s, 3H), 1.30 (s, 9H).

Example 169; Preparation of 6-((1H-pyrrolo[2,3-b]pyridin-5-yl)methyl)-N-(1-methyl-5-(trifluoromethyl)-1H-pyrazol-3-yl)-4,5,6,7-tetrahydrothieno[2,3-c]pyridine-3-carboxamide Example 169

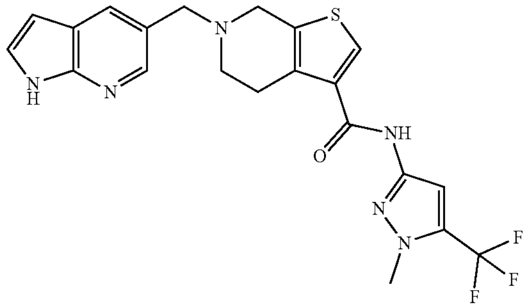

Step 1: 6-((1H-pyrrolo[2,3-b]pyridin-5-yl)methyl)-N-(1-methyl-5-(trifluoromethyl)-1H-pyrazol-3-yl)-4,5,6,7-tetrahydrothieno[2,3-c]pyridine-3-carboxamide (Example 169)

Following the procedure as per Example 1, step 3, starting from 1-methyl-5-(trifluoromethyl)-1H-pyrazol-3-amine (145 mg, 0.879 mmol) and Intermediate 54 (100 mg, 0.293 mmol) the desired product was obtained (44 mg, 0.095 mmol, 11%). LC-MS (ESI) method 1: $t_R$=0.88 min; m/z $[M^+H]^+$=461.1.

$^1$H NMR (ACN-d3, 400 MHz) δ 9.60 (br s, 1H), 8.97 (br s, 1H), 8.23 (s, 1H), 7.92 (s, 1H), 7.83 (s, 1H), 7.36 (br s, 1H), 7.09 (s, 1H), 6.46 (br s, 1H), 3.88 (s, 3H), 3.80 (s, 2H), 3.66 (s, 2H), 2.91 (br t, 2H, J=5.6 Hz), 2.79 (t, 2H, J=5.8 Hz)

Example 170; Preparation of 6-(6-(2-morpholino-ethoxy)imidazo[1,2-a]pyridine-3-carbonyl)-N-(3-(trifluoromethyl)phenyl)-4,5,6,7-tetrahydro thieno[2,3-c]pyridine-3-carboxamide Example 170

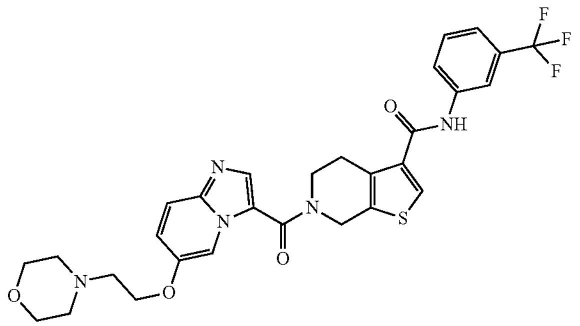

Step 1; 6-(6-hydroxyimidazo[1,2-a]pyridine-3-carbonyl)-N-[3-(trifluoromethyl)phenyl]-5,7-dihydro-4H-thieno[2,3-c]pyridine-3-carboxamide (Intermediate 147)

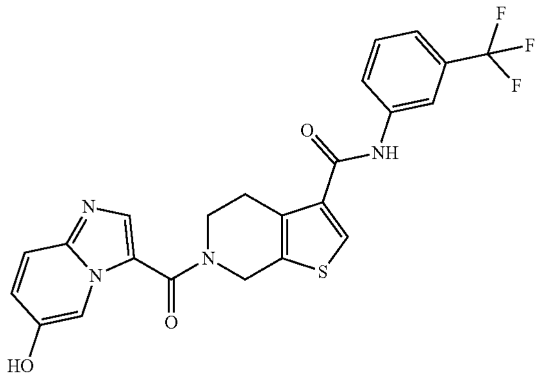 [SMILES: O=C(Nc1cccc(C(F)(F)F)c1)c1csc2c1CCN(C(=O)c1cnc3ccc(O)cn13)C2]

Following the procedure as per Example 90 from 6-hydroxyimidazo[1,2-a]pyridine-3-carboxylic acid (110 mg, 0.617 mmol) and Intermediate 64 (202 mg, 0.617 mmol) the title compound was obtained (169 mg, 0.347 mmol, 56%).

$^1$H NMR (400 MHz, DMSO-d6) δ 10.41 (s, 1H), 9.79 (s, 1H), 8.59 (d, J=2.0 Hz, 1H), 8.22 (d, J=4.4 Hz, 2H), 8.00-7.96 (m, 2H), 7.63-7.58 (m, 2H), 7.45 (d, J=7.9 Hz, 1H), 7.17 (dd, J=2.4, 9.5 Hz, 1H), 5.02 (s, 2H), 4.01-3.96 (m, 2H), 3.09-3.06 (m, 2H).

Step 2; 6-(6-(2-morpholinoethoxy)imidazo[1,2-a]pyridine-3-carbonyl)-N-(3-(trifluoromethyl)phenyl)-4,5,6,7-tetrahydrothieno[2,3-c]pyridine-3-carboxamide (Example 170)

To a solution of Intermediate 147 (109 mg, 0.224 mmol) in DMF (2.0 mL) were added $K_2CO_3$ (77 mg, 0.560 mmol) and 4-(2-chloroethyl)morpholine hydrochloride (46 mg, 0.246 mmol) and the mixture was heated to 85° C. and stirred for 6 hours. The reaction mixture was diluted in EtOAc and washed with water, water:brine 1:1, brine, dried over $MgSO_4$, filtered and concentrated. The residue was purified by prep HPLC (Xbridge Phenyl 19×150 mm, 10 um 40-100% MeOH/$H_2O$ (10 mM $NH_4CO_3$), 20 ml/min) to give the title compound (20 mg, 14%).

LC-MS (ESI) method 7: $t_R$=3.22 min; m/z $[M^+H]^+$=600.5.

$^1$H NMR (400 MHz, DMSO-d6) δ 10.42 (s, 1H), 8.63 (d, J=2.1 Hz, 1H), 8.22 (s, 2H), 8.09 (s, 1H), 7.99 (d, J=8.5 Hz, 1H), 7.67 (d, J=9.7 Hz, 1H), 7.60 (dd, J=8.0, 8.0 Hz, 1H), 7.45 (d, J=7.7 Hz, 1H), 7.30 (dd, J=2.4, 9.7 Hz, 1H), 5.04 (s, 2H), 4.12 (t, J=5.6 Hz, 2H), 3.99 (t, J=5.6 Hz, 2H), 3.59 (t, J=4.6 Hz, 3H), 3.08 (s, 2H), 2.74 (t, J=5.6 Hz, 2H).

Example 171; Preparation of N-(4-((dimethyl-amino)methyl)-3-(trifluoro methyl)phenyl)-6-(pyrazolo[1,5-a]pyrazine-3-carbonyl)-4,5,6,7-tetrahydro thieno[2,3-c]pyridine-3-carboxamide Example 171

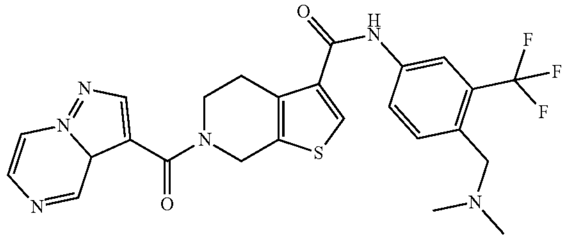

Step 1; tert-butyl 3-[[4-[(dimethylamino)methyl]-3-(trifluoromethyl) phenyl]carbamoyl]-5,7-dihydro-4H-thieno[2,3-c]pyridine-6-carboxylate (Intermediate 148)

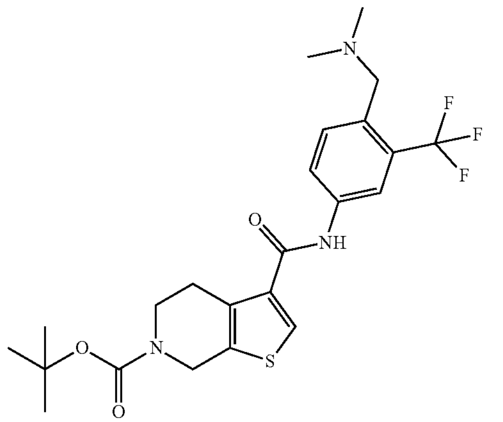 [SMILES: CN(C)Cc1ccc(NC(=O)c2csc3c2CCN(C(=O)OC(C)(C)C)C3)cc1C(F)(F)F]

Prepared from 6-tert-butoxycarbonyl-5,7-dihydro-4H-thieno[2,3-c]pyridine-3-carboxylic acid (96 mg, 0.339 mmol) and Intermediate 27 (74 mg, 0.339 mmol) according to general procedure N. The crude residue was purified by FCC (0-6% 2M NH3/MeOH in DCM) to afford the title compound (121 mg, 0.250 mmol 73%).

$^1$H NMR (400 MHz, DMSO-d6) δ 10.33 (s, 1H), 8.15-8.13 (m, 2H), 7.97 (d, J=8.5 Hz, 1H), 7.68 (d, J=8.5 Hz, 1H), 4.59 (s, 2H), 3.60-3.55 (m, 2H), 3.50 (s, 2H), 2.88-2.82 (m, 2H), 2.19 (s, 6H), 1.43 (s, 9H)

Step 2; N-[4-[(dimethylamino)methyl]-3-(trifluoromethyl)phenyl]-4,5,6,7-tetrahydrothieno[2,3-c]pyridine-3-carboxamide (Intermediate 149)

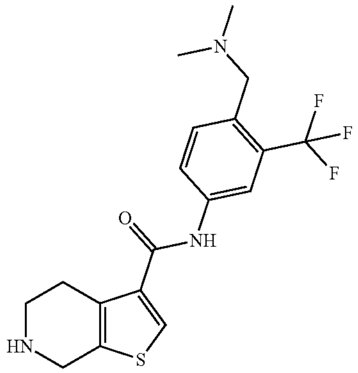 [SMILES: CN(C)Cc1ccc(NC(=O)c2csc3c2CCNC3)cc1C(F)(F)F]

Following the procedure as per Intermediate 139, starting from Intermediate 148 (121 mg, 0.250 mmol) the title compound was obtained (78 mg, 81%).

$^1$H NMR (400 MHz, DMSO) δ 10.28 (s, 1H), 8.14 (d, J=2.1 Hz, 1H), 8.04 (s, 1H), 7.97 (dd, J=1.8, 8.5 Hz, 1H), 7.67 (d, J=8.5 Hz, 1H), 3.87 (s, 2H), 3.48 (s, 2H), 2.92-2.87 (m, 2H), 2.77-2.71 (m, 2H), 2.17 (s, 6H)

Step 3; N-(4-((dimethylamino)methyl)-3-(trifluoro methyl)phenyl)-6-(pyrazolo[1,5-a]pyrazine-3-carbonyl)-4,5,6,7-tetrahydro thieno[2,3-c]pyridine-3-carboxamide (Example 171)

Following the procedure as per Example 125, step 3, from pyrazolo[1,5-a]pyrazine-3-carboxylic acid (12 mg, 0.0756 mmol) and Intermediate 149 (29 mg, 0.0756 mmol) the title compound was obtained (11 mg, 27%).

LC-MS (ESI) method 7: $t_R$=4.41 min; m/z $[M^+H]^+$=529.2

$^1$H NMR (400 MHz, DMSO-d6) δ 10.38-10.36 (m, 1H), 9.37 (d, J=1.5 Hz, 1H), 8.93 (dd, J=1.4, 4.7 Hz, 1H), 8.56 (s, 1H), 8.20-8.10 (m, 3H), 7.99 (dd, J=1.9, 8.5 Hz, 1H), 7.72-7.68 (m, 1H), 4.99 (s, 2H), 3.95 (t, J=5.7 Hz, 2H), 3.06 (s, 2H), 2.19 (s, 6H).

Example 172; Preparation of N-(3-(morpholinomethyl)-5-(trifluoromethyl) phenyl)-6-(pyrazolo[1,5-a]pyrazine-3-carbonyl)-4,5,6,7-tetrahydrothieno[2,3-c]pyridine-3-carboxamide Example 172

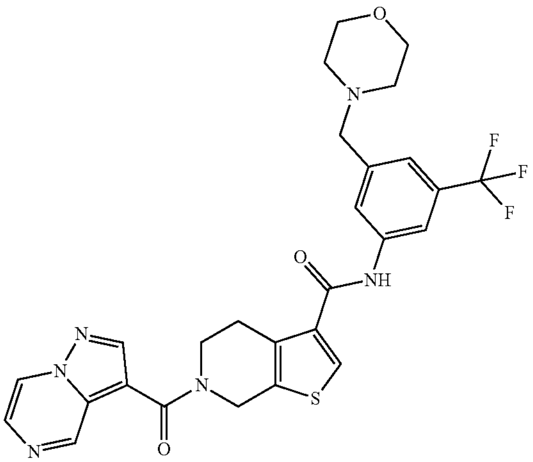

Step 1; tert-butyl 3-[[3-(morpholinomethyl)-5-(trifluoromethyl)phenyl]carbamoyl]-5,7-dihydro-4H-thieno[2,3-c]pyridine-6-carboxylate (Intermediate 150)

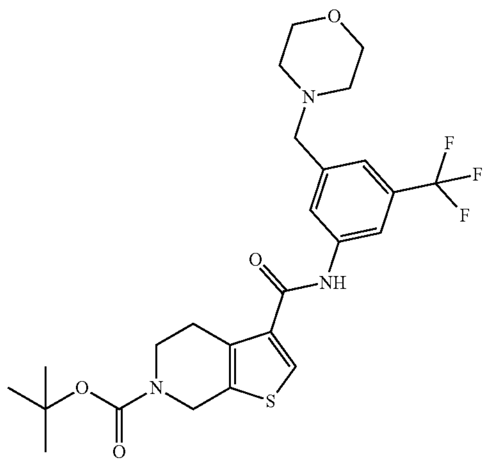 [SMILES: CC(C)(C)OC(=O)N1CCc2c(C(=O)Nc3cc(CN4CCOCC4)cc(C(F)(F)F)c3)csc2C1]

Following the procedure as per Intermediate 89, starting from 6-tert-butoxycarbonyl-5,7-dihydro-4H-thieno[2,3-c]pyridine-3-carboxylic acid (327 mg, 1.15 mmol) and Intermediate 12 (300 mg, 1.15 mmol), the desired product was obtained (370 mg, 58%).

$^1$H NMR (400 MHz, $CDCl_3$) δ 7.85 (s, 1H), 7.79 (s, 1H), 7.65 (s, 1H), 7.37 (s, 1H), 5.30 (s, 2H), 4.61 (s, 2H), 3.74-3.64 (m, 6H), 3.53 (s, 2H), 3.00 (t, J=5.7 Hz, 2H), 2.46 (t, J=4.4 Hz, 4H), 1.51 (s, 9H).

Step 2; N-[3-(morpholinomethyl)-5-(trifluoromethyl)phenyl]-4,5,6,7-tetra hydrothieno[2,3-c]pyridine-3-carboxamide dihydrochloride (Intermediate 151)

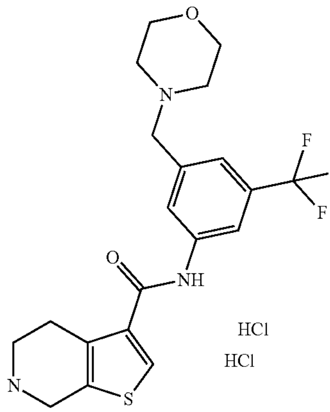

Following the procedure as per Intermediate 90, starting from Intermediate 150 (350 mg, 0.666 mmol) the title compound was obtained (314 mg, 94.6%).

$^1$H NMR (400 MHz, DMSO-d6) δ 11.51 (s, 1H), 10.87 (s, 1H), 9.81-9.73 (m, 2H), 8.57 (s, 1H), 8.35 (s, 1H), 8.26 (s, 1H), 7.92 (s, 1H), 4.52-4.40 (m, 4H), 4.00 (d, J=11.9 Hz, 2H), 3.86 (t, J=11.6 Hz, 2H), 3.45-3.37 (m, 2H), 3.31 (d, J=12.1 Hz, 2H), 3.18 (t, J=5.4 Hz, 4H).

Step 3; N-[3-(morpholinomethyl)-5-(trifluoromethyl)phenyl]-6-(pyrazolo[1,5-a]pyrazine-3-carbonyl)-5,7-dihydro-4H-thieno[2,3-c]pyridine-3-carboxamide (Example 172)

Prepared from pyrazolo[1,5-a]pyrazine-3-carboxylic acid (49 mg, 0.301 mmol) and Intermediate 151 (150 mg, 0.301 mmol) following procedure M. The title compound was obtained by trituration with $Et_2O$ (90 mg, 49%).

LC-MS (ESI) method 7: $t_R$=3.05 min; m/z $[M^+H]^+$=571.2

$^1$H NMR (400 MHz, DMSO-d6) δ 10.44 (s, 1H), 9.41 (d, J=1.5 Hz, 1H), 8.97 (dd, J=1.4, 4.7 Hz, 1H), 8.60 (s, 1H), 8.27 (s, 1H), 8.19 (s, 1H), 8.15 (d, J=4.8 Hz, 1H), 8.01 (s, 1H), 7.41 (s, 1H), 5.04-5.01 (m, 2H), 3.99 (dd, J=5.7, 5.7 Hz, 2H), 3.62 (d, J=20.2 Hz, 6H), 3.11 (s, 2H), 2.46 (s, 4H).

Example 173; Preparation of 6-(imidazo[1,2-a]pyridine-3-carbonyl)-N-(5-(trifluoromethyl)pyridazin-3-yl)-4,5,6,7-tetrahydrothieno[2,3-c]pyridine-3-carboxamide Example 173

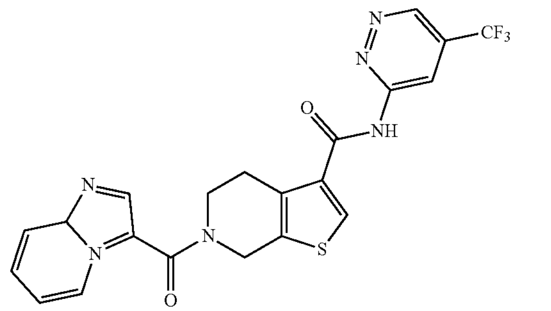

Step 1; 6-(imidazo[1,2-a]pyridine-3-carbonyl)-N-(5-(trifluoromethyl) pyridazin-3-yl)-4,5,6,7-tetrahydrothieno[2,3-c]pyridine-3-carboxamide (Example 173)

To a stirred suspension of 5-(trifluoromethyl)pyridazin-3-amine (33 mg, 0.202 mmol) in THE (0.5 mL) at −78° C., lithium bis(trimethylsilyl)amide (1M solution in THF, 0.32 mL, 0.318 mmol) was added dropwise over 2 min. The reaction mixture was stirred for 1.5 h, then a suspension of 6-(imidazo[1,2-a]pyridine-3-carbonyl)-5,7-dihydro-4H-thieno[2,3-c]pyridine-3-carbonyl chloride, obtained starting from Intermediate 40 (acid form) following procedure H, (50 mg, 0.145 mmol) in DCM (1.2 mL) was added dropwise. The reaction mixture was stirred at room temperature for 2 h. The reaction mixture was quenched with saturated $NH_4Cl_{(aq)}$ and the aqueous phase was extracted with DCM. The organic phases were passed through a hydrophobic frit and concentrated in vacuo. Purification by prep HPLC (Luna Phenyl-Hexyl 21.2×150 mm, 10 μm 40-100% MeOH/water (0.1% FA) 20 mL/min, RT) gave the title compound (6 mg, 8%)

LC-MS (ESI) method 7: $t_R$=3.37 min; m/z $[M^+H]^+$=473.2

$^1$H NMR (400 MHz, DMSO-d6) δ 11.72 (s, 1H), 9.39 (d, J=1.6 Hz, 1H), 8.89 (td, J=1.1, 7.0 Hz, 1H), 8.62 (dd, J=0.8, 2.0 Hz, 1H), 8.47 (s, 1H), 8.07 (s, 1H), 7.66 (td, J=1.1, 9.0 Hz, 1H), 7.40 (ddd, J=1.3, 6.8, 9.0 Hz, 1H), 7.03 (dt, J=1.2, 6.9 Hz, 1H), 4.97 (s, 2H), 3.94-3.89 (m, 2H), 3.07-3.02 (m, 2H)

Example 174; Preparation of 6-((1H-pyrazolo[3,4-b]pyridin-5-yl)methyl)-N-(3-fluoro-5-(trifluoromethoxy)phenyl)-4,5,6,7-tetrahydrothieno[2,3-c]pyridine-3-carboxamide Example 174

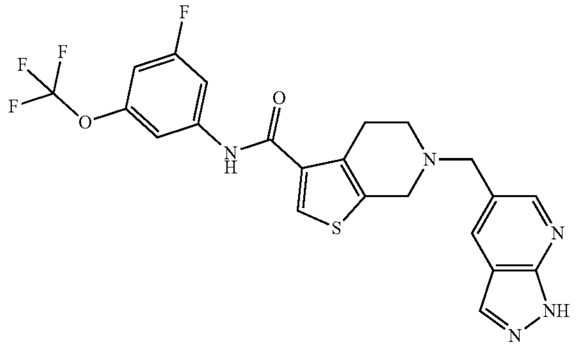

Step 1; tert-butyl 3-((3-fluoro-5-(trifluoromethoxy)phenyl)carbamoyl)-4,7-dihydrothieno[2,3-c]pyridine-6(5H)-carboxylate (Intermediate 152)

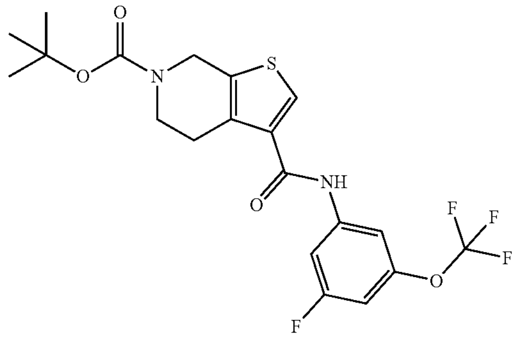 [SMILES: CC(C)(C)OC(=O)N1CCc2c(C(=O)Nc3cc(F)cc(OC(F)(F)F)c3)csc2C1]

Following the procedure as per Example 1, step 4, starting from 6-(tert-butyl) 3-ethyl 4,7-dihydrothieno[2,3-c]pyridine-3,6(5H)-dicarboxylate (271 mg, 0,871 mmol) and N-3-fluoro-5-(trifluoromethoxy)aniline (600 mg, 2.61 mmol) the title compound was obtained (153 mg, 0.332 mmol, 38%).

Step 2; N-(3-fluoro-5-(trifluoromethoxy)phenyl)-4,5,6,7-tetrahydrothieno[2,3-c]pyridine-3-carboxamide (Intermediate 153)

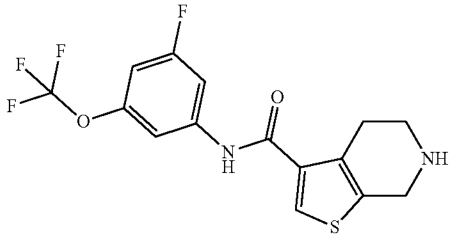 [SMILES: O=C(Nc1cc(F)cc(OC(F)(F)F)c1)c1csc2c1CCNC2]

Following the procedure as per Intermediate 139, starting from Intermediate 152 (303 mg, 0.658 mmol) the title compound was obtained (80 mg, 0.222 mmol, 34%).

Step 3; 6-((1H-pyrazolo[3,4-b]pyridin-5-yl)methyl)-N-(3-fluoro-5-(trifluoro methoxy)phenyl)-4,5,6,7-tetrahydrothieno[2,3-c]pyridine-3-carboxamide (Example 174)

Following procedure K, starting from 1H-pyrazolo[3,4-b]pyridine-5-carbaldehyde (36 mg, 0,244 mmol) and Intermediate 153 (80 mg, 0,222 mmol) the title compound was obtained (15 mg, 0,031 mmol, 14%).

LC-MS (ESI) method 7: $t_R$=5.16 min; m/z (M+1)=492.3

$^1$H NMR (ACN-d3, 400 MHz) δ 11.47 (bs, 1H), 8.79 (br s, 1H), 8.54 (d, 1H, J=2.0 Hz), 8.12 (d, 1H, J=2.0 Hz), 8.04 (s, 1H), 7.86 (s, 1H), 7.5-7.6 (m, 2H), 6.84 (br d, 1H, J=8.6 Hz), 3.84 (s, 2H), 3.69 (s, 2H), 2.93 (br t, 2H, J=5.8 Hz), 2.81 (t, 2H, J=5.8 Hz)

Example 175; Preparation of N-(5-(tert-butyl)isoxazol-3-yl)-6-(pyrazolo[1,5-a]pyrazine-3-carbonyl)-4,5,6,7-tetrahydrothieno[2,3-c]pyridine-3-carboxamide Example 175

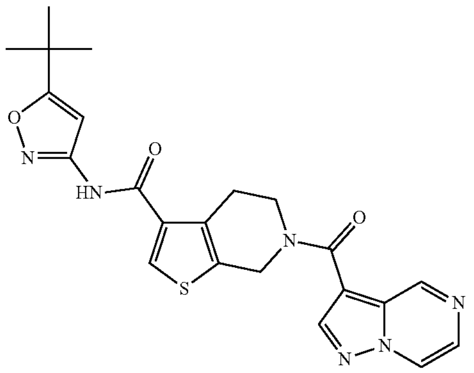

Step 1; tert-butyl 3-((5-(tert-butyl)isoxazol-3-yl)carbamoyl)-4,7-dihydro thieno[2,3-c]pyridine-6(5H)-carboxylate (Intermediate 154)

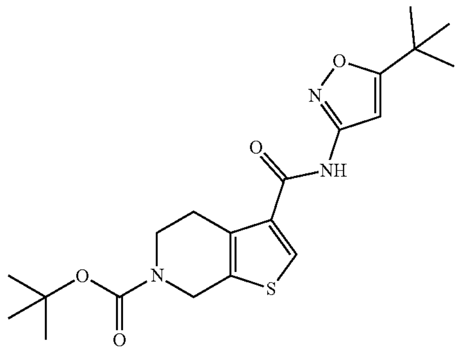 [SMILES: CC(C)(C)OC(=O)N1CCc2c(C(=O)Nc3cc(C(C)(C)C)on3)csc2C1]

Following the procedure as per Intermediate 95 starting from 6-tert-butoxycarbonyl-5,7-dihydro-4H-thieno[2,3-c]pyridine-3-carboxylic acid (142 mg, 0.500 mmol) and 3-Amino-5-tert-butylisoxazole (70 mg, 0.500 mmol) the title compound was obtained (164 mg, 0.404 mmol, 81%).

$^1$H NMR (400 MHz, $CDCl_3$) δ 10.84 (s, 1H), 8.10 (s, 1H), 6.88 (s, 1H), 4.67-4.62 (m, 2H), 3.68 (t, J=4.9 Hz, 2H), 3.03 (t, J=5.8 Hz, 2H), 1.42 (s, 9H), 1.37 (s, 9H).

Step 2; N-(5-tert-butylisoxazol-3-yl)-4,5,6,7-tetrahydrothieno[2,3-c]pyridine-3-carboxamide hydrochloride (Intermediate 155)

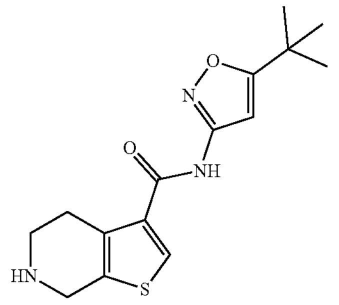 [SMILES: CC(C)(C)c1cc(NC(=O)c2csc3c2CCNC3)no1]

Following the procedure as per Intermediate 86 starting from Intermediate 154 (164 mg, 0.404 mmol, 1.00 eq) the title product was obtained.

$^1$H NMR (400 MHz, DMSO-d6) δ 11.32 (s, 1H), 9.65-9.56 (m, 2H), 8.49 (s, 1H), 6.74 (s, 1H), 4.42 (s, 2H), 3.39 (m, 2H-under water peak), 3.15 (t, J=5.8 Hz, 2H), 1.37 (s, 9H).

Step 3; N-(5-(tert-butyl)isoxazol-3-yl)-6-(pyrazolo[1,5-a]pyrazine-3-carbonyl)-4,5,6,7-tetrahydrothieno[2,3-c]pyridine-3-carboxamide (Example 175)

Prepared from Intermediate 155 (52 mg, 0.152 mmol) and pyrazolo[1,5-a]pyrazine-3-carboxylic acid (25 mg, 0.152 mmol) according to procedure N. Purification, achieved by washing with DMSO followed by water and drying before further washing with DCM, gave the title compound (28.39 mg, 40.26%).

LC-MS (ESI) method 6: $t_R$=4.20 min; m/z $[M^+H]^+$=451.4

$^1$H NMR (400 MHz, DMSO-d6) δ 11.22-11.19 (s, 1H), 9.41-9.39 (d, J=1.46 Hz, 1H), 8.97 (dd, J=1.4, 4.7 Hz, 1H), 8.59 (s, 1H), 8.38 (s, 1H), 8.14 (d, J=4.5 Hz, 1H), 6.75 (s, 1H), 5.02-5.00 (s, 2H), 4.01-3.95 (t, J=5.7 Hz, 2H), 3.10 (s, 2H), 1.37 (s, 9H).

Example 176; Preparation of compound N-(4-chloro-3-(trifluoromethyl)phenyl)-6-(pyrazolo[1,5-a]pyrazine-3-carbonyl)-4,5,6,7-tetrahydrothieno[2,3-c]pyridine-3-carboxamide Example 176

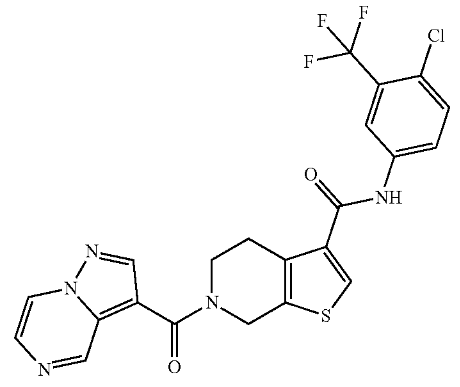

Step 1: tert-butyl 3-((4-chloro-3-(trifluoromethyl)phenyl)carbamoyl)-4,7-dihydrothieno[2,3-c]pyridine-6(5H)-carboxylate (Intermediate 156)

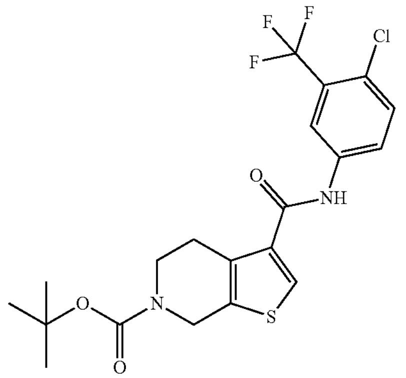 [SMILES: CC(C)(C)OC(=O)N1CCc2c(C(=O)Nc3ccc(Cl)c(C(F)(F)F)c3)csc2C1]

Following the procedure as per Example 47, step 1, starting from 6-(tert-butoxycarbonyl)-4,5,6,7-tetrahydrothieno[2,3-c]pyridine-3-carboxylic acid (200 mg, 0.706 mmol) and 4-Chloro-3-(trifluoromethyl)aniline (138 mg, 0.706 mmol) the obtained crude residue was purified by FCC (0-50% EtOAc in cyclohexane) to afford title compound (231 mg, 0.501 mmol, 71%).

$^1$H NMR (400 MHz, DMSO-d6) δ 10.49 (s, 1H), 8.32 (d, J=2.4 Hz, 1H), 8.18 (s, 1H), 8.04 (dd, J=2.3, 8.8 Hz, 1H), 7.71 (d, J=8.8 Hz, 1H), 4.60 (s, 2H), 3.59 (t, J=5.6 Hz, 2H), 2.86 (t, J=5.6 Hz, 2H), 1.44 (s, 9H).

Step 2: N-[4-chloro-3-(trifluoromethyl)phenyl]-4,5,6,7-tetrahydrothieno[2,3-c]pyridine-3-carboxamide (Intermediate 157)

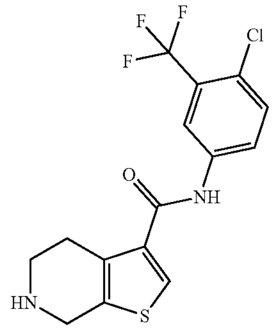 [SMILES: O=C(Nc1ccc(Cl)c(C(F)(F)F)c1)c1csc2c1CCNC2]

Following the procedure as per Intermediate 96, starting from Intermediate 156 (230 mg, 0.499 mmol), title compound was afforded (180 mg, 0.454 mmol, 91%).

$^1$H NMR (400 MHz, DMSO-d6) δ 10.48 (s, 1H), 8.33 (d, J=2.5 Hz, 1H), 8.13 (s, 1H), 8.05 (dd, J=2.4, 8.8 Hz, 1H), 7.71 (d, J=8.8 Hz, 1H), 4.11 (s, 1H), 3.97 (s, 2H), 2.98 (t, J=5.8 Hz, 2H), 2.81 (t, J=5.6 Hz, 2H).

Step 3: N-(4-chloro-3-(trifluoromethyl)phenyl)-6-(pyrazolo[1,5-a]pyrazine-3-carbonyl)-4,5,6,7-tetrahydrothieno[2,3-c]pyridine-3-carboxamide (Example 176)

Following the procedure as per Example 121, step 3, from pyrazolo[1,5-a]pyrazine-3-carboxylic acid (81 mg, 0.499 mmol) and Intermediate 157 (180 mg, 0.499 mmol) the title compound was obtained (4.39 mg, 1.64%).

LC-MS (ESI) method 6: $t_R$=4.78 min; m/z $[M^+H]^+$=506.2

$^1$H NMR (400 MHz, DMSO-d6) δ 10.51 (s, 1H), 9.37 (d, J=1.5 Hz, 1H), 8.94 (dd, J=1.4, 4.7 Hz, 1H), 8.56 (s, 1H), 8.33 (d, J=2.4 Hz, 1H), 8.22 (s, 1H), 8.11 (d, J=4.8 Hz, 1H), 8.05 (dd, J=2.5, 8.8 Hz, 1H), 7.72 (d, J=8.9 Hz, 1H), 5.00 (s, 2H), 3.95 (t, J=5.6 Hz, 2H), 3.06 (s, 2H).

Example 177; Preparation of 6-(imidazo[1,2-a]pyridine-3-carbonyl)-N-(3-(4-methylpiperazin-1-yl)-5-(trifluoromethyl)phenyl)-4,5,6,7-tetrahydrothieno[2,3-c]pyridine-3-carboxamide Example 177

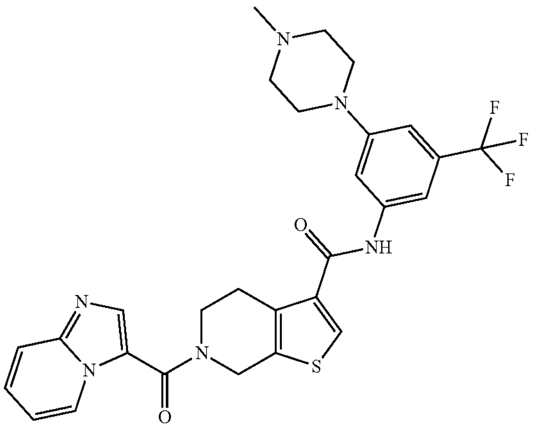

Step 1: tert-butyl 3-[[3-(4-methylpiperazin-1-yl)-5-(trifluoromethyl) phenyl]carbamoyl]-5,7-dihydro-4H-thieno[2,3-c]pyridine-6-carboxylate (Intermediate 158)

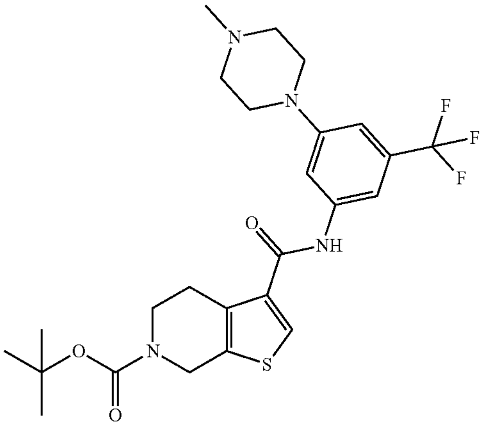 [SMILES: CN1CCN(c2cc(NC(=O)c3csc4c3CCN(C(=O)OC(C)(C)C)C4)cc(C(F)(F)F)c2)CC1]

Following the procedure as per Example 109, step 1, from 6-tert-butoxycarbonyl-5,7-dihydro-4H-thieno[2,3-c]pyridine-3-carboxylic acid (300 mg, 1.06 mmol) and 3-(4-methylpiperazin-1-yl)-5-(trifluoromethyl)aniline (275 mg, 1.06 mmol) the title compound was obtained (516 mg, 0.984 mmol, 93%).

$^1$H NMR (400 MHz, DMSO-d6) δ 10.18 (s, 1H), 8.14 (s, 1H), 7.61-7.56 (m, 2H), 6.94 (s, 1H), 4.60 (s, 2H), 3.66-3.57 (t, 2H), 3.21 (t, J=4.9 Hz, 4H), 2.86 (t, J=5.7 Hz, 2H), 2.47 (t, J=5.0 Hz, 4H), 2.24 (s, 3H), 1.44 (s, 9H).

Step 2: N-(3-(4-methylpiperazin-1-yl)-5-(trifluoromethyl)phenyl)-4,5,6,7-tetrahydrothieno[2,3-c]pyridine-3-carboxamide (Intermediate 159)

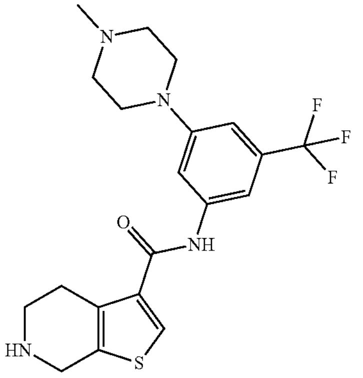 [SMILES: CN1CCN(c2cc(NC(=O)c3csc4c3CCNC4)cc(C(F)(F)F)c2)CC1]

Following the procedure as per Intermediate 86, starting from Intermediate 158 (515 mg, 0.982 mmol) the obtained residue was diluted in MeOH, flushed through an SCX cartridge (5 g, eluted with 1N $NH_3$/MeOH) and concentrated to afford title compound (430 mg, 1.01 mmol, 103%)

$^1$H NMR (400 MHz, DMSO-d6) δ 10.22 (s, 1H), 8.18 (s, 1H), 7.62 (s, 1H), 7.58 (s, 1H), 6.94 (s, 1H), 4.14 (s, 3H), 3.22 (t, J=5.71 Hz, 4H), 3.15 (t, J=6.43 Hz, 2H), 2.93 (t, J=5.3 Hz, 2H), 2.25 (s, 3H).

Step 3: 6-(imidazo[1,2-a]pyridine-3-carbonyl)-N-(3-(4-methylpiperazin-1-yl)-5-(trifluoromethyl)phenyl)-4,5,6,7-tetrahydrothieno[2,3-c]pyridine-3-carboxamide (Example 177)

Following general procedure M, starting from imidazo[1,2-a]pyridine-3-carboxylic acid (79 mg, 0.490 mmol) and Intermediate 159 (208 mg, 0.490 mmol) the resultant crude was purified by prep HPLC (Sunfire C18 19×150 mm, 10 um 20-80% ACN/$H_2O$ (10 mM $NH_4CO_3$), 20 m/min, RT) to give the title compound (49 mg, 17.59%).

LC-MS (ESI) method 7: $t_R$=2.84 min; m/z $[M^+H]^+$=569.2

$^1$H NMR (400 MHz, DMSO-d6) δ 10.20 (s, 1H), 8.98 (d, J=7.0 Hz, 1H), 8.19 (s, 1H), 8.15 (s, 1H), 7.75 (d, J=8.9 Hz, 1H), 7.62 (s, 1H), 7.59 (s, 1H), 7.51-7.45 (m, 1H), 7.13-7.09 (m, 1H), 6.95 (s, 1H), 5.06-5.02 (i, 2H), 4.00 (t, J=5.6 Hz, 2H), 3.22 (t, J=4.9 Hz, 4H), 3.09 (t, J=6.5 Hz, 2H), 2.50-2.45 (m, 4H), 2.25 (s, 3H).

The compound reported in the following table was prepared via amide coupling as described for Example 177, steps 1-3, applying the corresponding, commercially available carboxylic acid in step 3.

| Ex. No | Structure | Reagents Amount | Product Amount (yield) | Purification method | Data |
|---|---|---|---|---|---|
| 178 | 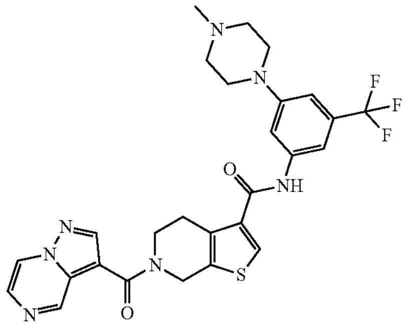 [SMILES: CN1CCN(c2cc(NC(=O)c3csc4c3CCN(C(=O)c3cnn5ccncc35)C4)cc(C(F)(F)F)c2)CC1] | carboxylic acid (80 mg, 0.49 mmol, 1.00 eq) Intermediate 159 208 mg | 153 mg (53%) | FCC | $^1$H NMR (400 MHz, DMSO-d6) δ 10.20 (s, 1H), 9.37 (d, J = 1.4 Hz, 1H), 8.93 (dd, J = 1.5, 4.8 Hz, 1H), 8.56 (s, 1H), 8.18 (s, 1H), 8.11 (d, J = 4.8 Hz, 1H), 7.61 (s, 1H), 7.59 (s, 1H), 6.94 (s, 1H), 4.99-4.99 (m, 2H), 3.95 (t, J = 5.6 Hz, 2H), 3.22 (dt, J = 4.6 Hz, 6H), 3.06 (s, 4H), 2.25 (s, 3H). LC-MS (ESI) method 7: $t_R$ = 3.14 min; m/z $[M + H]^+$ = 570.2 |

Example 179; Preparation of N-(3-(tert-pentyl)isoxazol-5-yl)-6-(pyrazolo[1,5-a]pyrazine-3-carbonyl)-4,5,6,7-tetrahydrothieno[2,3-c]pyridine-3-carboxamide Example 179

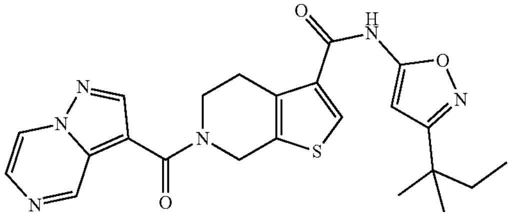

Step 1: tert-butyl 3-((3-(tert-pentyl)isoxazol-5-yl)carbamoyl)-4,7-dihydro thieno[2,3-c]pyridine-6(5H)-carboxylate (Intermediate 160)

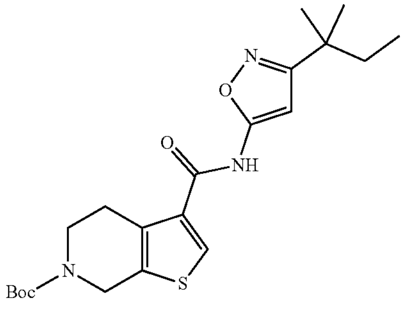 [SMILES: CCC(C)(C)c1cc(NC(=O)c2csc3c2CCN(C(=O)OC(C)(C)C)C3)on1]

Following the procedure as per Intermediate 95 from 6-tert-butoxycarbonyl-5,7-dihydro-4H-thieno[2,3-c]pyridine-3-carboxylic acid (150 mg, 0.529 mmol) and 3-(1,1-dimethylpropyl)isoxazol-5-amine (82 mg, 0.529 mmol) the title compound was obtained (14 mg, 6%)

$^1$H NMR (400 MHz, $CDCl_3$) δ 8.61-8.61 (m, 1H), 7.67 (s, 1H), 6.23 (s, 1H), 4.51 (s, 2H), 3.55 (t, J=5.6 Hz, 2H), 2.88 (t, J=5.6 Hz, 2H), 1.52 (q, J=7.5 Hz, 2H) 1.36 (s, 9H), 1.17 (s, 6H), 0.69 (t, J=7.5 Hz, 3H)

Step 2: N-(3-(tert-pentyl)isoxazol-5-yl)-4,5,6,7-tetrahydrothieno[2,3-c]pyridine-3-carboxamide hydrochloride (Intermediate 161)

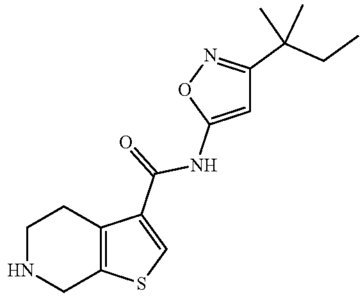 [SMILES: CCC(C)(C)c1cc(NC(=O)c2csc3c2CCNC3)on1]

Following the procedure as per Intermediate 86 from Intermediate 160 (14 mg, 0.0334 mmol) the title compound was obtained by precipitation from $Et_2O$ (17 mg, assumed quantitative).

LC-MS (ESI) Method 16: $t_R$=1.04 min; m/z $[M^+H]^+$ =320.1

Step 3: N-(3-(tert-pentyl)isoxazol-5-yl)-6-(pyrazolo[1,5-a]pyrazine-3-carbonyl)-4,5,6,7-tetrahydrothieno[2,3-c]pyridine-3-carboxamide (Example 179)

Following the procedure as per Example 121, step 3, from Intermediate 161 (52 mg, 0.146 mmol) and pyrazolo[1,5-a]pyrazine-3-carboxylic acid (24 mg, 0.146 mmol) a crude was obtained which was purified by SFC (TORUS-2PIC 20×250 mm, 5 um 5-15% MeOH (0.1% DEA)/$CO_2$, 100 ml/min, 120 bar, 40 C, DAD 260 nm) to afford the title compound (15 mg, 23%).

LC-MS (ESI) method 7: $t_R$=4.45 min; m/z $[M^+H]^+$=465.6

$^1$H NMR (400 MHz, DMSO-d6) δ 11.76-11.76 (s, 1H), 9.36 (d, J=1.4 Hz, 1H), 8.93 (dd, J=1.4, 4.7 Hz, 1H), 8.55 (s, 1H), 8.34 (s, 1H), 8.11 (d, J=4.8 Hz, 1H), 6.32 (s, 1H), 4.99-4.99 (s, 2H), 3.95 (t, J=5.8 Hz, 2H), 3.07-3.07 (m, 2H), 1.62 (q, J=7.4 Hz, 2H), 1.25 (s, 6H), 0.77 (t, J=7.5 Hz, 3H).

Example 180; Preparation of compound N-(4-(hydroxymethyl)-3-(trifluoromethyl)phenyl)-6-(pyrazolo[1,5-a]pyrazine-3-carbonyl)-4,5,6,7-tetrahydrothieno[2,3-c]pyridine-3-carboxamide Example 180

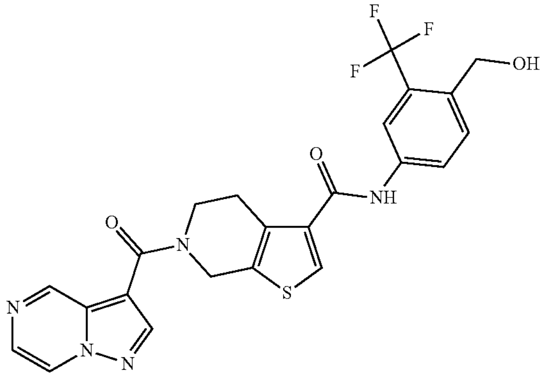

Step 1: methyl 6-(pyrazolo[1,5-a]pyrazine-3-carbonyl)-4,5,6,7-tetrahydrothieno[2,3-c]pyridine-3-carboxylate (Intermediate 162)

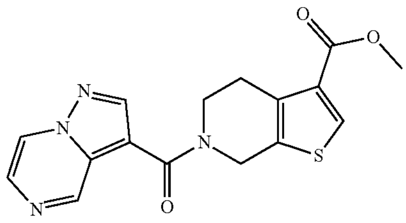 [SMILES: COC(=O)c1csc2c1CCN(C(=O)c1cnn3ccncc13)C2]

A pyrazolo[1,5-a]pyrazine-3-carboxylic acid (0.083 g, 0.507 mmol) was placed in to the flask, then DMF (1.491 ml) was added. Next DIPEA (0.195 ml, 1.115 mmol) was added. After 5 min HATU (0.212 g, 0.558 mmol) was added and the solution was stirred at RT for 30 min. Next Intermediate 36 (0.1 g, 0.507 mmol) was added and the reaction mixture was stirred at RT for 1 h. The RM was poured into ice and the solid was filtered on Schoot's funnel to afford the title compound (0.153 g, 0.447 mmol, 88%)

$^1$H NMR (300 MHz, DMSO-d6) δ 9.33 (d, J=1.4 Hz, 1H), 8.91 (dd, J=4.7, 1.5 Hz, 1H), 8.54 (s, 1H), 8.25 (s, 1H), 8.08 (d, J=4.7 Hz, 1H), 4.95 (s, 2H), 3.93 (t, J=5.8 Hz, 2H), 3.78 (s, 3H), 3.03 (s, 2H).

Step; N-(4-(hydroxymethyl)-3-(trifluoromethyl)phenyl)-6-(pyrazolo[1,5-a]pyrazine-3-carbonyl)-4,5,6,7-tetrahydrothieno[2,3-c]pyridine-3-carboxamide (Example 180)

Following the procedure as per Example 128, step 1, from Intermediate 162 (50 mg, 0.146 mmol) and Intermediate 112 (33 mg, 0.175 mmol) the obtained crude was purified by SFC (YMC Amylose-C MeOH TORUS-2PIC 20×250 mm, 5um 15-25% MeOH (0.1% DEA)/$CO_2$, 100 ml/min, 120 bar, 40 C, DAD 260 nm) to give the title compound (15 mg, 21%).

LC-MS (ESI) method 7: $t_R$=3.74 min; m/z $[M^{+}H]^{+}$=502.5

$^1$H NMR (400 MHz, DMSO-d6) δ 10.37 (s, 1H), 9.37 (d, J=1.5 Hz, 1H), 8.94 (dd, J=1.4, 4.7 Hz, 1H), 8.56 (s, 1H), 8.20 (s, 1H), 8.16 (d, J=2.0 Hz, 1H), 8.11 (d, J=4.6 Hz, 1H), 8.01 (dd, J=1.7, 8.6 Hz, 1H), 7.74 (d, J=8.5 Hz, 1H), 5.00-5.00 (m, 2H), 4.65 (s, 2H), 3.95 (dd, J=5.8, 5.8 Hz, 2H), 3.07-3.05 (m, 2H), 2.58-2.55 (m, 1H).

Example 181; Preparation of compound 6-(imidazo[1,2-a]pyridine-3-carbonyl)-N-(3-morpholino-5-(trifluoromethyl)phenyl)-4,5,6,7-tetrahydrothieno[2,3-c]pyridine-3-carboxamide Example 181

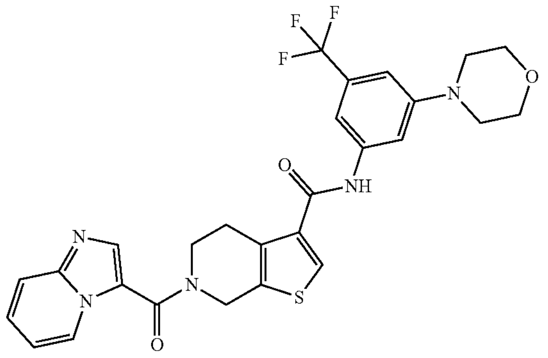

Step 1; tert-butyl 3-[[3-morpholino-5-(trifluoromethyl)phenyl]carbamoyl]-5,7-dihydro-4H-thieno[2,3-c]pyridine-6-carboxylate (Intermediate 163)

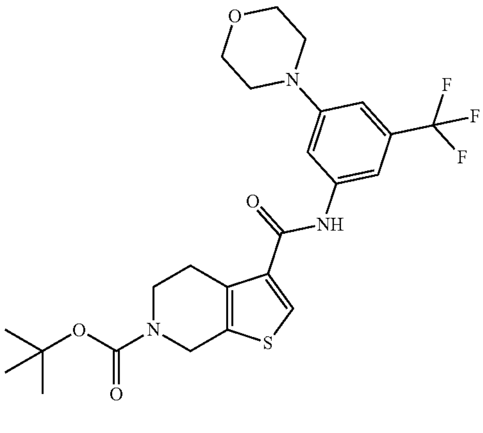 [SMILES: CC(C)(C)OC(=O)N1CCc2c(C(=O)Nc3cc(N4CCOCC4)cc(C(F)(F)F)c3)csc2C1]

Following the procedure as per Intermediate 89 starting from 6-tert-butoxycarbonyl-5,7-dihydro-4H-thieno[2,3-c]pyridine-3-carboxylic acid (300 mg, 1.06 mmol) and 3-morpholino-5-(trifluoromethyl)aniline (261 mg, 1.06 mmol) the title compound was obtained (489 mg, 0.956 mmol, 90%)

$^1$H NMR (400 MHz, DMSO-d6) δ 10.21 (s, 1H), 8.14 (s, 1H), 7.63 (s, 1H), 7.59 (s, 1H), 6.96 (s, 1H), 4.60 (s, 2H), 3.77 (t, J=4.8 Hz, 4H), 3.59 (t, J=5.8 Hz, 2H), 3.19 (t, J=4.8 Hz, 4H), 2.85 (t, J=5.6 Hz, 2H), 1.44 (s, 9H).

Step 2; N-[3-morpholino-5-(trifluoromethyl)phenyl]-4,5,6,7-tetrahydro thieno[2,3-c]pyridine-3-carboxamide (Intermediate 164)

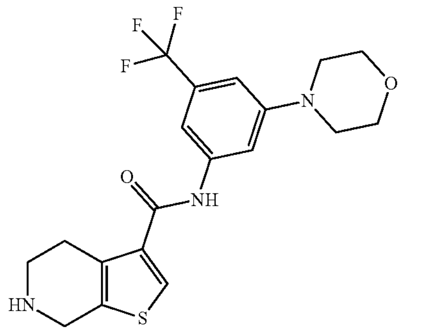 [SMILES: O=C(Nc1cc(N2CCOCC2)cc(C(F)(F)F)c1)c1csc2c1CCNC2]

Following the procedure as per Intermediate 86, starting from Intermediate 163 (489 mg, 0.956 mmol) the title compound was obtained (404 mg, 0.982 mmol, quantitative yield).

$^1$H NMR (400 MHz, DMSO-d6) δ 10.16 (s, 1H), 8.05 (s, 1H), 7.64 (s, 1H), 7.59 (s, 1H), 6.95 (s, 1H), 3.90 (s, 2H), 3.77 (t, J=4.8 Hz, 4H), 3.20-3.16 (m, 4H), 2.92 (t, J=5.6 Hz, 2H), 2.76 (t, J=5.5 Hz, 2H).

Step 3; 6-(imidazo[1,2-a]pyridine-3-carbonyl)-N-(3-morpholino-5-(trifluoro methyl)phenyl)-4,5,6,7-tetrahydrothieno[2,3-c]pyridine-3-carboxamide (Example 181)

Following general procedure M, from Intermediate 164 (196 mg, 0.476 mmol) and imidazo[1,2-a]pyridine-3-carboxylic acid (77 mg, 0.476 mmol), the crude product was purified by FCC (25 g, 0-50% 3:1 EtOAc:EtOH in cyclohexane) to afford title compound (162 mg, 60%).

LC-MS (ESI) method 7: $t_R$=3.97 min; m/z $[M^+H]^+$=556.2

$^1$H NMR (400 MHz, DMSO-d6) δ 10.23 (s, 1H), 8.97 (d, J=6.9 Hz, 1H), 8.19 (s, 1H), 8.15 (s, 1H), 7.75 (d, J=9.0 Hz, 1H), 7.64 (s, 1H), 7.60 (s, 1H), 7.51-7.45 (m, 1H), 7.13-7.10 (m, 1H), 6.97 (s, 1H), 5.04 (s, 2H), 3.99 (t, J=5.6 Hz, 2H), 3.77 (t, J=4.8 Hz, 4H), 3.22-3.16 (m, 4H), 3.09 (t, J=5.8 Hz, 3H).

The compound reported in the following table was prepared via amide coupling as described for Example 181, step 1-3, applying the corresponding, commercially available or previously synthesized carboxylic acid in step 3.

| Example No | Structure | Reagents Amount | Product Amount (yield) | Purification method | Data |
|---|---|---|---|---|---|
| 182 | 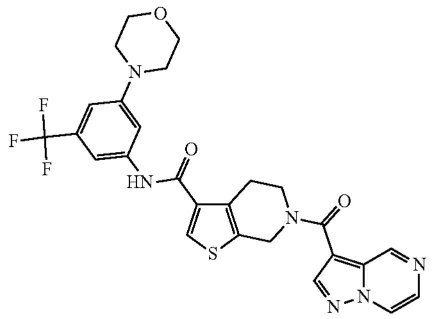 [SMILES: O=C(Nc1cc(N2CCOCC2)cc(C(F)(F)F)c1)c1csc2c1CCN(C(=O)c1cnn3ccncc13)C2] | Carboxylic acid (78 mg, 0.476 mmol): Intermediate 164: 196 mg (1.0 eq) | 16 mg (6%) | FCC | $^1$H NMR (400 MHz, DMSO-d6) d 10.24 (s, 1H), 9.36 (d, J = 1.5 Hz, 1H), 8.93 (dd, J = 1.4, 4.8 Hz, 1H), 8.56 (s, 1H), 8.18 (s, 1H), 8.11 (d, J = 4.8 Hz, 1H), 7.64 (s, 1H), 7.59 (s, 1H), 6.96 (s, 1H), 5.00-4.99 (s, 2H), 3.95 (t, J = 5.8 Hz, 2H), 3.77 (t, J = 4.8 Hz, 4H), 3.19 (t, J = 4.8 Hz, 4H), 3.06-3.06 (s, 3H). LC-MS (ESI) method 6: $t_R$ = 4.40 min; m/z $[M + H]^+$ = 557.3 |

Example 183; Preparation of compound N-(3-isobutylisoxazol-5-yl)-6-(pyrazolo[1,5-a]pyrazine-3-carbonyl)-4,5,6,7-tetrahydrothieno[2,3-c]pyridine-3-carboxamide Example 183

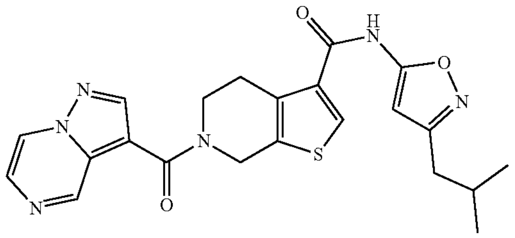

Step 1; tert-butyl 3-[(3-isobutylisoxazol-5-yl)carbamoyl]-5,7-dihydro-4H-thieno[2,3-c]pyridine-6-carboxylate (Intermediate 165)

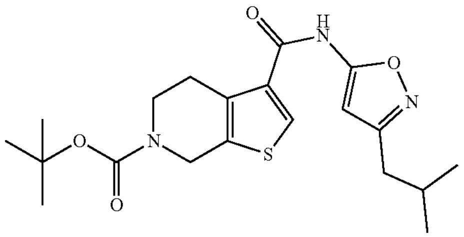 [SMILES: CC(C)Cc1cc(NC(=O)c2csc3c2CCN(C(=O)OC(C)(C)C)C3)on1]

Following the procedure as per Intermediate 95 from 6-tert-butoxycarbonyl-5,7-dihydro-4H-thieno[2,3-c]pyridine-3-carboxylic acid (250 mg, 0.882 mmol) and 3-isobutylisoxazol-5-amine title compound was obtained (226 mg, 0.557 mmol, 63%).

$^1$H NMR (400 MHz, $CDCl_3$) δ 8.63-8.62 (s, 1H), 7.76 (s, 1H), 6.31 (s, 1H), 4.64 (s, 2H), 3.68 (t, J=5.6 Hz, 2H), 3.01 (t, J=5.4 Hz, 2H), 2.51 (d, J=7.1 Hz, 2H), 2.05-1.96 (m, 1H), 1.61 (s, 4H), 1.49 (s, 9H), 0.99-0.96 (d, J=6.7 Hz, 6H).

Step 2; N-(3-isobutylisoxazol-5-yl)-4,5,6,7-tetrahydrothieno[2,3-c]pyridine-3-carboxamide (Intermediate 166)

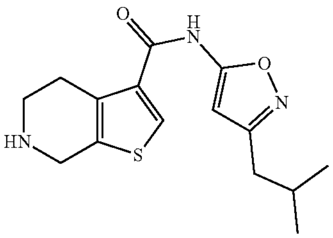 [SMILES: CC(C)Cc1cc(NC(=O)c2csc3c2CCNC3)on1]

Following procedure of Intermediate 96, starting from Intermediate 165 (226 mg, 0.557 mmol) title compound was obtained (143 mg, 0.418 mmol, 75%).

$^1$H NMR (400 MHz, DMSO-d6) δ 8.52 (s, 1H), 6.31 (s, 1H), 4.41 (s, 2H), 3.15 (t, J=5.2 Hz, 2H), 2.51 (d, J=7.0 Hz, 2H), 2.05-1.96 (m, 1H), 0.97 (d, J=6.6 Hz, 6H).

Step 3; N-(3-isobutylisoxazol-5-yl)-6-(pyrazolo[1,5-a]pyrazine-3-carbonyl)-4,5,6,7-tetrahydrothieno[2,3-c]pyridine-3-carboxamide (Example 183)

Following the procedure as per Example 121, step 3, starting from Intermediate 166 (52 mg, 0.152 mmol) and pyrazolo[1,5-a]pyrazine-3-carboxylic acid (25 mg, 0.152 mmol) obtained residue was submitted for purification by prep HPLC (Sunfire C18 3×50 mm, 3 um 5-95% ACN/$H_2O$ (10 mM $NH_4CO_3$), 1.7 ml/min, RT) gave the title compound (13.16 mg, 19.21%).

LC-MS (ESI) method 17: $t_R$=4.26 min; m/z $[M^+H]^+$=451.4

$^1$H NMR (400 MHz, DMSO-d6) δ 11.77-11.77 (m, 1H), 9.36 (d, J=1.4 Hz, 1H), 8.93 (dd, J=1.4, 4.7 Hz, 1H), 8.56 (s, 1H), 8.34 (s, 1H), 8.11 (d, J=4.8 Hz, 1H), 6.27 (s, 1H), 4.99-4.99 (m, 2H), 3.94 (t, J=5.8 Hz, 2H), 3.10-3.05 (m, 2H), 2.47 (d, J=7.2 Hz, 2H), 2.01-1.93 (m, 1H), 0.94 (d, J=6.5 Hz, 6H).

Example 184; Preparation of compound N-(3-cyano-5-(trifluoromethyl) phenyl)-6-(pyrazolo[1,5-a]pyrazine-3-carbonyl)-4,5,6,7-tetrahydrothieno[2,3-c]pyridine-3-carboxamide Example 184

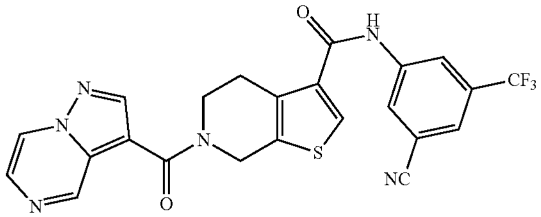

Step 1; tert-butyl 3-((3-cyano-5-(trifluoromethyl) phenyl)carbamoyl)-4,7-dihydrothieno[2,3-c]pyridine-6(5H)-carboxylate (Intermediate 167)

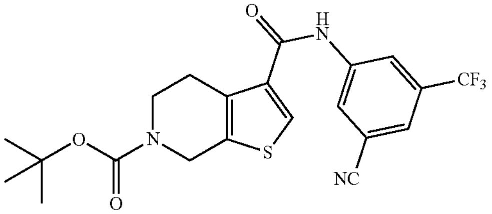 [SMILES: CC(C)(C)OC(=O)N1CCc2c(C(=O)Nc3cc(C#N)cc(C(F)(F)F)c3)csc2C1]

Following the procedure as per Example 47, step 1, starting from 6-tert-butoxycarbonyl-5,7-dihydro-4H-thieno[2,3-c]pyridine-3-carboxylic acid (500 mg, 1.76 mmol) and 3-amino-5-(trifluoromethyl)benzonitrile (345 mg, 1.85 mmol) the title compound was obtained by precipitation in water (704 mg, 1.56 mmol, 88%).

$^1$H NMR (400 MHz, $CDCl_3$) δ 8.68 (s, 1H), 8.33-8.32 (s, 1H), 8.17-8.15 (s, 1H), 7.64 (s, 2H), 4.58-4.56 (m, 2H), 3.69 (t, J=5.6 Hz, 2H), 3.01 (t, J=5.4 Hz, 3H), 1.57 (s, 9H).

Step 2; N-(3-cyano-5-(trifluoromethyl)phenyl)-4,5,6,7-tetrahydrothieno[2,3-c]pyridine-3-carboxamide (Intermediate 168)

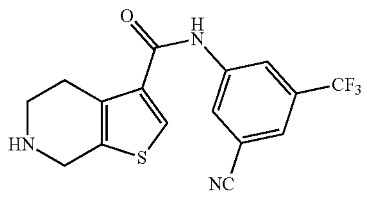 [SMILES: N#Cc1cc(NC(=O)c2csc3c2CCNC3)cc(C(F)(F)F)c1]

Following the procedure as per Intermediate 86, starting from Intermediate 167 (704 mg, 1.56 mmol) the title product was obtained by precipitation with $Et_2O$ as the HCl salt (596 mg, 1.54 mmol, 99%).

$^1$H NMR (400 MHz, DMSO-d6) δ 11.00 (s, 1H), 9.60-9.52 (m, 2H), 8.55 (d, J=9.1 Hz, 3H), 8.10 (s, 1H), 4.44 (s, 2H), 3.43 (t, J=5.8 Hz, 2H), (t, J=5.8 Hz, 2H).

Step 3; N-(3-cyano-5-(trifluoromethyl)phenyl)-6-(pyrazolo[1,5-a]pyrazine-3-carbonyl)-4,5,6,7-tetrahydrothieno[2,3-c]pyridine-3-carboxamide (Example 184)

Following the procedure as per Example 121, step 3, starting from Intermediate 168 (75 mg, 0.213 mmol) and pyrazolo[1,5-a]pyrazine-3-carboxylic acid (35 mg, 0.213 mmol) the title compound was obtained by precipitation from water (63 mg, 0.126 mmol, 59%).

LC-MS (ESI) method 6: $t_R$=4.44 min; m/z $[M^+H]^+$=497.5

$^1$H NMR (400 MHz, DMSO-d6) δ 10.72 (s, 1H), 9.41 (s, 1H), 8.97 (d, J=3.5 Hz, 1H), 8.61 (s, 1H), 8.52-8.47 (m, 2H), 8.30 (s, 1H), 8.15 (d, J=4.0 Hz, 1H), 8.09 (s, 1H), 5.04-5.00 (m, 2H), 4.00 (s, 2H), 3.11 (s, 2H).

Example 185; Preparation of 6-(imidazo[1,2-a]pyridine-3-carbonyl)-4-methyl-N-(3-(trifluoromethyl)phenyl)-4,5,6,7-tetrahydrothieno[2,3-c]pyridine-3-carboxamide Example 185

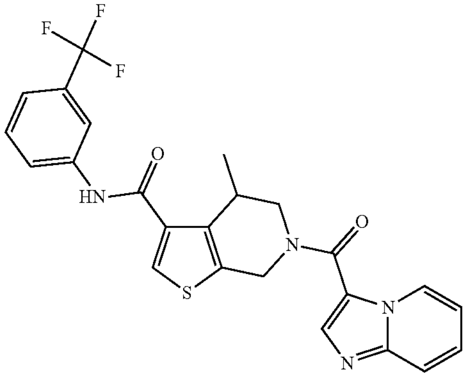

Step 1: 6-(tert-butyl) 3-ethyl 2-amino-4-methyl-4,7-dihydrothieno[2,3-c]pyridine-3,6(5H)-dicarboxylate (Intermediate 169)

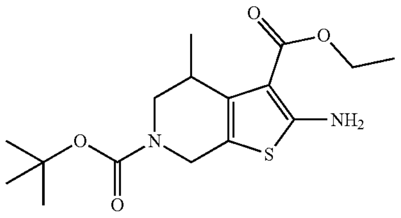 [SMILES: CCOC(=O)c1c(N)sc2c1C(C)CN(C(=O)OC(C)(C)C)C2]

To a solution of tert-butyl 3-methyl-4-oxo-piperidine-1-carboxylate (5000 mg, 23.4 mmol) in EtOH (50 mL), ethyl cyanoacetate (2.5 mL, 23.4 mmol), sulfur (750 mg, 23.4 mmol) and TEA (4.7 mL, 33.5 mmol) were added. The reaction mixture was heated at reflux for 90 min. After cooling to RT and filtering, the residue was purified by FCC (0-50% EtOAc in cyclohexane) and triturated with cyclohexane to afford the title compound (2540 mg, 7.46 mmol, 32%).

$^1$H NMR (400 MHz, $CDCl_3$) δ 6.08-6.01 (s, 2H), 4.89-4.59 (m, 1H), 4.36-4.22 (m, 2H), 4.14-3.91 (m, 2H), 3.34-2.96 (m, 2H), 1.49 (s, 9H), 1.36 (t, J=7.1 Hz, 3H), 1.17 (d, J=6.8 Hz, 3H).

Step 2: 6-(tert-butyl) 3-ethyl 4-methyl-4,7-dihydrothieno[2,3-c]pyridine-3,6(5H)-dicarboxylate (Intermediate 170)

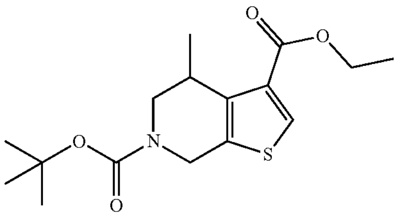 [SMILES: CCOC(=O)c1csc2c1C(C)CN(C(=O)OC(C)(C)C)C2]

To a suspension of Intermediate 169 (200 mg, 0.587 mmol) in 1,4-dioxane (2 mL) at −5° C. conc HCl (0.50 mL, 0.587 mmol) was added, followed by dropwise addition of sodium nitrite (45 mg, 0.646 mmol) in 0.2 mL of water. The reaction mixture was stirred at −5° C. for 1 hr and was then added to 50% phosphoric acid solution (1.0 mL, 17.2 mmol) and $Et_2O$ (1 mL). The reaction mixture was allowed to warm to RT and was stirred for 45 min. The reaction was poured on to ice and extracted with DCM. The organic phases were filtered through a hydrophobic frit and the solvent was concentrated in vacuo and the residue was purified by FCC (0-50% EtOAc in Cyclohexane) to afford title compound (90 mg, 0.277 mmol, 47%).

$^1$H NMR (400 MHz, $CDCl_3$) δ 7.99 (s, 1H), 5.13-4.86 (m, 1H), 4.35-4.27 (m, 2H), 4.23-4.02 (m, 2H), 3.53-3.47 (m, 1H), 3.18-3.06 (m, 1H), 1.42 (s, 9H), 1.36 (t, J=7.1 Hz, 3H), 1.22 (d, J=6.8 Hz, 3H).

Step 3: ethyl 4-methyl-4,5,6,7-tetrahydrothieno[2,3-c]pyridine-3-carboxylate (Intermediate 171)

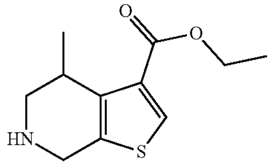

Following the procedure as per Intermediate 86 starting from Intermediate 170 (90 mg, 0.277 mmol) the title compound was obtained (60 mg, 0.229 mmol, 83%).

$^1$H NMR (400 MHz, DMSO-d6) δ 9.45-9.45 (m, 2H), 8.37 (s, 1H), 4.44 (d, J=15.9 Hz, 1H), 4.37-4.28 (m, 3H), 3.61-3.54 (m, 1H), 1.35 (dd, J=7.1, 7.1 Hz, 6H).

Step 4: ethyl 6-(imidazo[1,2-a]pyridine-3-carbonyl)-4-methyl-4,5,6,7-tetrahydrothieno[2,3-c]pyridine-3-carboxylate (Intermediate 172)

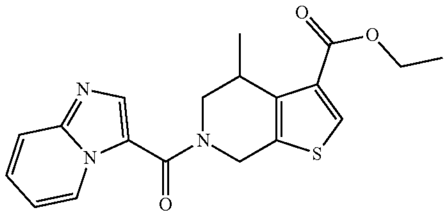 [SMILES: CCOC(=O)c1csc2c1C(C)CN(C(=O)c1cnc3ccccn13)C2]

Following the procedure as per Example 121, step 3, starting from Intermediate 171 (60 mg, 0.229 mmol) and imidazo[1,2-a]pyridine-3-carboxylic acid (37 mg, 0.229 mmol) the title compound was obtained (73 mg, 0.178 mmol, 78%).

$^1$H NMR (400 MHz, $CDCl_3$) δ 8.94 (d, J=6.8 Hz, 1H), 7.96 (s, 1H), 7.92 (s, 1H), 7.61 (d, J=9.1 Hz, 1H), 7.31-7.25 (t, J=7.2 Hz, 1H), 5.36 (d, J=16.4 Hz, 1H), 4.63-4.48 (m, 2H), 4.28-4.21 (m, 2H), 3.55 (d, J=3.5 Hz, 1H), 3.42 (d, J=11.1 Hz, 1H), 1.32-1.26 (d, J=7.1 Hz, 1H), 1.26-1.21 (d, J=6.7 Hz, 3H).

Step 4: 6-(imidazo[1,2-a]pyridine-3-carbonyl)-4-methyl-N-(3-(trifluoromethyl)phenyl)-4,5,6,7-tetrahydrothieno[2,3-c]pyridine-3-carboxamide (Example 185)

To a solution of Intermediate 172 (73 mg, 0.198 mmol) and 3-(Trifluoromethyl)aniline (0.030 mL, 0.237 mmol) in THE (3 mL) at −40° C., tert-butyl-lithium solution 1.7M in pentane (0.35 mL, 3.77 mmol) was added dropwise. The reaction mixture was allowed to warm to RT and left to stir overnight. Reaction carefully quenched with aqueous $NH_4Cl$ and extracted with DCM. The organic phase was filtered through a hydrophobic frit and the solvent was concentrated in vacuo. The residue was submitted for purification by prep HPLC (Sunfire C18 19×150 mm, 10 um 20-80% ACN/$H_2O$ (10 mM $NH_4CO_3$), 20 ml/min, RT) to afford title (19 mg, 0.0386 mmol, 20%).

LC-MS (ESI) method 6: $t_R$=4.79 min; m/z $[M^+H]^+$=485.5

$^1$H NMR (400 MHz, DMSO-d6) δ 10.48 (s, 1H), 8.96 (d, J=7.0 Hz, 1H), 8.21 (s, 1H), 8.16 (d, J=9.3 Hz, 2H), 8.00 (d, J=8.2 Hz, 1H), 7.75 (m, 1H), 7.60 (t, J=8.0 Hz, 1H), 7.51-7.45 (m, 2H), 7.13-7.09 (m, 1H), 5.32 (d, J=16.7 Hz, 1H), 4.33 (d, J=12.3 Hz, 1H), 3.58-3.56 (m, 3H), 1.18 (d, J=6.8 Hz, 3H).

Example 186; Preparation of 6-(imidazo[1,2-a]pyridine-3-carbonyl)-N-(5-(trifluoromethoxy)pyridin-3-yl)-4,5,6,7-tetrahydrothieno[2,3-c]pyridine-3-carboxamide Example 186

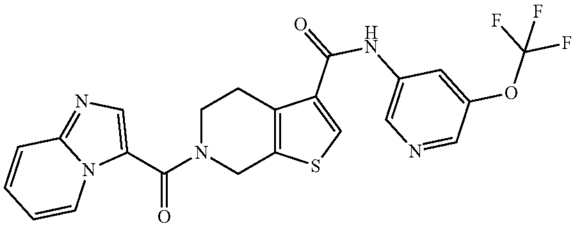

Step 1: tert-butyl 3-((5-(trifluoromethoxy)pyridin-3-yl)carbamoyl)-4,7-dihydrothieno[2,3-c]pyridine-6(5H)-carboxylate (Intermediate 173)

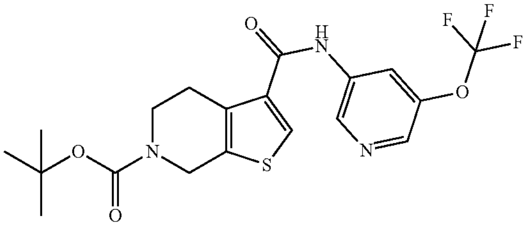 [SMILES: CC(C)(C)OC(=O)N1CCc2c(C(=O)Nc3cncc(OC(F)(F)F)c3)csc2C1]

Following the procedure as per Intermediate 89, starting from 6-tert-butoxycarbonyl-5,7-dihydro-4H-thieno[2,3-c]pyridine-3-carboxylic acid (85 mg, 0.298 mmol) and Intermediate 86 (64 mg, 0.298 mmol), the title compound was obtained by precipitation from water (100 mg, 0.226 mmol, 76%).

$^1$H NMR (400 MHz, $CDCl_3$) δ 8.55 (s, 1H), 8.33 (s, 2H), 8.04 (m, 1H), 7.68 (s, 1H), 4.62 (s, 2H), 3.68 (t, J=5.3 Hz, 2H), 3.00 (t, J=5.7 Hz, 2H), 1.50 (s, 9H).

Step 2: N-(5-(trifluoromethoxy)pyridin-3-yl)-4,5,6,7-tetrahydrothieno[2,3-c]pyridine-3-carboxamide (Intermediate 174)

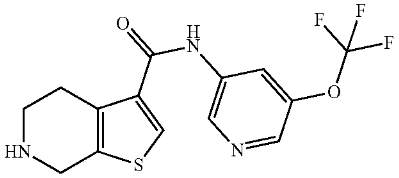 [SMILES: O=C(Nc1cncc(OC(F)(F)F)c1)c1csc2c1CCNC2]

Following the procedure as per Intermediate 86, starting from Intermediate 173 (100 mg, 0.226 mmol) the title compound was obtained (78 mg, 0.205 mmol, 91%).

$^1$H NMR (400 MHz, DMSO-d6) δ 10.92 (s, 1H), 9.64 (s, 2H), 9.04 (d, J=2.0 Hz, 1H), 8.56 (s, 1H), 8.44 (m, 2H), 4.43 (t, J=4.8 Hz, 2H), 3.41 (m, 2H), 3.17 (t, J=5.8 Hz, 2H).

Step 3: 6-(imidazo[1,2-a]pyridine-3-carbonyl)-N-(5-(trifluoromethoxy) pyridin-3-yl)-4,5,6,7-tetrahydrothieno[2,3-c]pyridine-3-carboxamide (Example 186)

Following the procedure as per Example 121, step 3, starting from Intermediate 174 (38 mg, 0.100 mmol) and imidazo[1,2-a]pyridine-3-carboxylic acid (16 mg, 0.100 mmol) the title compound was obtained by preparative HPLC (22 mg, 0.0445 mmol, 44%).

LC-MS (ESI) method 7: $t_R$=3.54 min; m/z $[M^+H]^+$=488.5

$^1$H NMR (400 MHz, DMSO-d6) δ 10.63 (s, 1H), 8.98 (d, J=7.0 Hz, 1H), 8.92 (d, J=2.0 Hz, 1H), 8.41 (d, J=2.3 Hz, 1H), 8.35 (s, 1H), 8.26 (s, 1H), 8.15 (s, 1H), 7.75 (d, J=9.0 Hz, 1H), 7.50-7.45 (m, 1H), 7.12 (m, 1H), 5.04 (s, 2H), 4.00 (t, J=5.6 Hz, 2H), 3.10 (m, 2H).

Example 187; Preparation of N-(3-(hydroxymethyl)-5-(trifluoromethyl) phenyl)-6-(pyrazolo[1,5-a] pyrazine-3-carbonyl)-4,5,6,7-tetrahydrothieno[2,3-c] pyridine-3-carboxamide Example 187

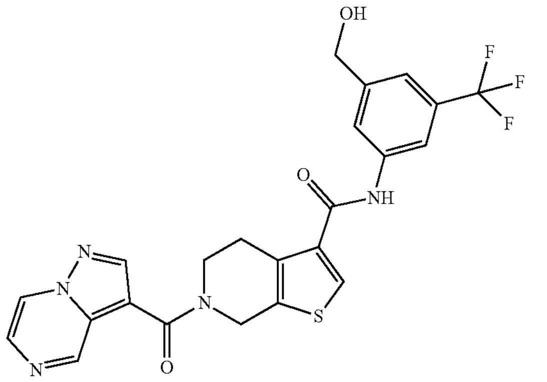

Step 1: tert-butyl 3-[[3-(hydroxymethyl)-5-(trifluoromethyl)phenyl]carbamoyl]-5,7-dihydro-4H-thieno [2,3-c]pyridine-6-carboxylate (Intermediate 175)

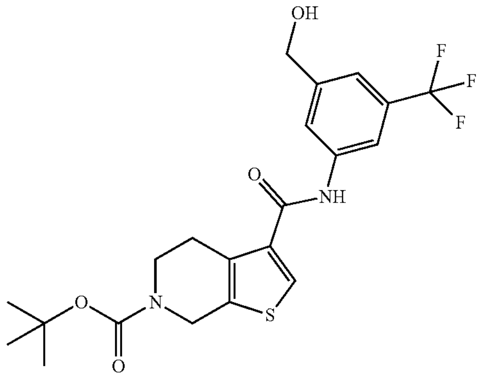 [SMILES: CC(C)(C)OC(=O)N1CCc2c(C(=O)Nc3cc(CO)cc(C(F)(F)F)c3)csc2C1]

Following the procedure as per Intermediate 89, starting from 6-tert-butoxycarbonyl-5,7-dihydro-4H-thieno[2,3-c] pyridine-3-carboxylic acid (300 mg, 1.06 mmol) and [3-amino-5-(trifluoromethyl)phenyl]methanol (241 mg, 1.06 mmol) the title compound was obtained (414 mg, 0.907 mmol, 86%).

$^1$H NMR (400 MHz, DMSO-d6) δ 10.37 (s, 1H), 8.19 (s, 1H), 8.07 (s, 1H), 7.98 (s, 1H), 7.37 (s, 1H), 5.46 (t, J=5.7 Hz, 1H), 4.64-4.57 (m, 4H), 3.59 (t, J=5.8 Hz, 2H), 2.87 (t, J=5.6 Hz, 2H), 1.45 (s, 9H).

Step 2: N-[3-(hydroxymethyl)-5-(trifluoromethyl) phenyl]-4,5,6,7-tetrahydro thieno[2,3-c]pyridine-3-carboxamide; hydrochloride (Intermediate 176)

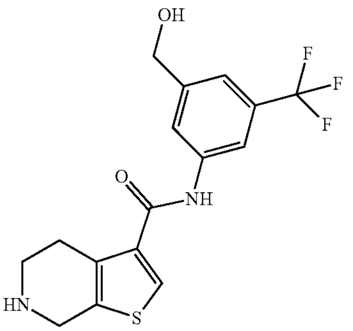 [SMILES: O=C(Nc1cc(CO)cc(C(F)(F)F)c1)c1csc2c1CCNC2]

Following the procedure as per Intermediate 86, starting from Intermediate 175 (414 mg, 0.907 mmol) the title compound was obtained (344 mg, 0.876 mmol, 97%).

$^1$H NMR (400 MHz, DMSO-d6) δ 10.49 (s, 1H), 8.41 (s, 1H), 8.20 (s, 1H), 8.02 (d, J=6.1 Hz, 1H), 7.63-7.59 (m, 2H), 4.06 (s, 2H), 3.19 (s, 2H), 3.07 (t, J=5.8 Hz, 2H), 2.88 (t, J=5.6 Hz, 2H).

Step 3: N-[3-(hydroxymethyl)-5-(trifluoromethyl) phenyl]-6-(pyrazolo[1,5-a]pyrazine-3-carbonyl)-5,7-dihydro-4H-thieno[2,3-c]pyridine-3-carboxamide (Example 187)

Following the procedure as per Example 121, step 3, starting from Intermediate 176 (169 mg, 0.429 mmol) and pyrazolo[1,5-a]pyrazine-3-carboxylic acid (70 mg, 0.429 mmol) title compound was obtained (13 mg, 0.0259 mmol, 6.0%).

LC-MS (ESI) method 6: $t_R$=3.84 min; m/z $[M^+H]^+$=502.4

$^1$H NMR (400 MHz, DMSO-d6) δ 10.39 (s, 1H), 9.37 (d, J=1.4 Hz, 1H), 8.94 (dd, J=1.4, 4.7 Hz, 1H), 8.56 (s, 1H), 8.22 (s, 1H), 8.12-8.08 (m, 2H), 7.99 (s, 1H), 7.38 (s, 1H), 5.46 (t, J=5.7 Hz, 1H), 5.09-4.89 (m, 2H), 4.60 (d, J=5.5 Hz, 2H), 3.96 (t, J=5.8 Hz, 2H), 3.10-3.02 (m, 2H).

Comparative newly synthesised compounds characterized by:

- the amido group substituting the thienyl ring linked at the α position with respect to the sulphur (Example C1)
- simultaneously the amido group substituting the thienyl ring linked at the a position with respect to the sulphur and the Hy group substituting the tetrahydropyridyl ring linked through a spacer to the nitrogen at the 5 position (Example C2)

Example C1: 6-(imidazo[1,2-a]pyridine-3-carbonyl)-N-(3-((4-methylpiperazin-1-yl)methyl)-5-(trifluoromethyl)phenyl)-4,5,6,7-tetrahydrothieno[2,3-c]pyridine-2-carboxamide Example C1

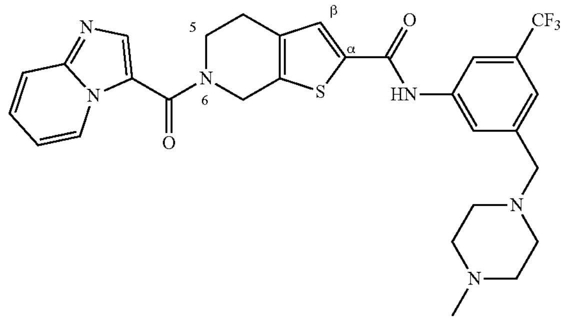

Step 1: methyl 6-(imidazo[1,2-a]pyridine-3-carbonyl)-4,5,6,7-tetrahydrothieno[2,3-c]pyridine-2-carboxylate (intermediate 84)

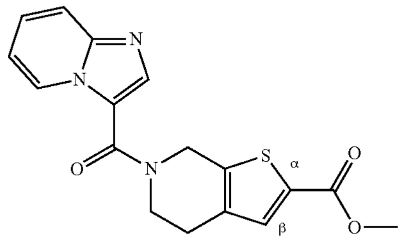 [SMILES: COC(=O)c1cc2c(s1)CN(C(=O)c1cnc3ccccn13)CC2]

Imidazo[1,2-a]pyridine-3-carboxylic acid (153 mg, 0.941 mmol), methyl 4,5,6,7-tetrahydrothieno[2,3-c]pyridine-2-carboxylate hydrochloride (200 mg, 0.856 mmol) and TBTU (412 mg, 1.284 mmol) were dissolved in 6 mL DCM/DMF 1:1, then N-ethyl-N-isopropylpropan-2-amine (598 μl, 3.42 mmol) was added in one portion. The solution was stirred at rt for 1 hr. The crude was diluted with DCM (10 mL) then was washed with satured sol. $NH_4Cl$ (2×15 mL) and satured solution $NaHCO_3$ (2×15). The organic phase was dried over $Na_2SO_4$, filtered and concentrated to dryness. The crude product was purified by FCC (28 g column KP-NH gradient A:B from 30:70 to 0:100 with 10 CV, eluent A:n-Heptane eluent B:acetone). Appropriate fractions were combined and evaporated to afford the title compound (187.2 mg, 0.548 mmol, 64.1% yield).

$^1$H NMR (ACN-$d_3$, 400 MHz) δ 8.96 (td, 1H, J=1.1, 7.0 Hz), 8.8-8.9 (m, 1H), 8.0-8.0 (m, 2H), 7.88 (s, 1H), 7.63 (d, 1H, J=9.1 Hz), 7.60 (s, 1H), 7.4-7.4 (m, 2H), 7.00 (dt, 1H, J=1.1, 6.9 Hz), 5.04 (s, 2H), 4.05 (t, 2H, J=5.8 Hz), 3.59 (s, 2H), 2.92 (br t, 3H, J=5.8 Hz), 2.5-2.8 (m, 8H), 2.39 (s, 3H)

Step 2: 6-(imidazo[1,2-a]pyridine-3-carbonyl)-N-(3-((4-methylpiperazin-1-yl)methyl)-5-(trifluoromethyl)phenyl)-4,5,6,7-tetrahydrothieno[2,3-c]pyridine-2-carboxamide (Example C1)

3-((4-methylpiperazin-1-yl)methyl)-5-(trifluoromethyl)aniline (80 mg, 0.293 mmol) was dissolved in dry THE (Volume: 8 ml) under Nitrogen and the mixture was stirred at −78° C. for 15 min, then n-BuLi 2.5M in hexanes (0.094 ml, 0.234 mmol) was added dropwise in 5 min and the reaction was stirred for 1 hr at −78° C. A solution of Intermediate Y (40 mg, 0.117 mmol) in THE (Volume: 6.00 ml) was added dropwise for 10 min, then the temperature was increased at rt and the reaction was stirred for 1 hr. 5 mL of water was added to quench the reaction and the solvent was evaporated by reduce pressure. The solid was dissolved in DCM (20 mL) and the organic layer was washed with water (2×20 mL) and Brine (1×20 mL). The organic layer was dried with $Na_2SO_4$, filtrated and concentrated until dryness. The crude product was purified by FCC in reverse Phase (C18 column gradient A:B from 100:0 to 0:100, eluent A:$H_2O$:ACN:HCOOH 95:5:0.1 eluent B:$H_2O$:ACN:HCOOH 5:95:0.1). Fractions were combined and evaporated to afford the title compound (31.20 mg, 0.054 mmol, 45.7% yield).

$^1$H NMR (400 MHz, ACN-$d_3$) δ ppm 8.96 (dt, J=7.02, 1.10 Hz, 1H), 8.87 (bs, 1H), 7.97-8.01 (m, 2H), 7.88 (s, 1H), 7.60-7.65 (m, 2H), 7.36-7.43 (m, 2H), 7.00 (td, J=6.91, 1.10 Hz, 1H), 5.04 (s, 2H), 4.05 (t, J=5.81 Hz, 2H), 3.59 (s, 2H), 2.92 (br t, J=5.81 Hz, 3H), 2.49-2.76 (m, 7H), 2.39 (s, 5H), 2.11 (s, 2H).

LC-MS (ESI): m/z (M+1)=583.1; rt=0.98 min; (method 1)

Example C2: 5-(imidazo[1,2-a]pyridine-3-carbonyl)-N-(3-((4-methylpiperazin-1-yl)methyl)-5-(trifluoromethyl)phenyl)-4,5,6,7-tetrahydrothieno[3,2-c]pyridine-2-carboxamide Example C2

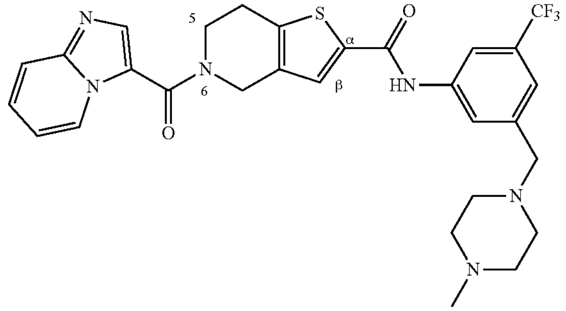

Step 1: methyl 5-(imidazo[1,2-a]pyridine-3-carbonyl)-4,5,6,7-tetrahydrothieno[3,2-c]pyridine-2-carboxylate (Intermediate 85)

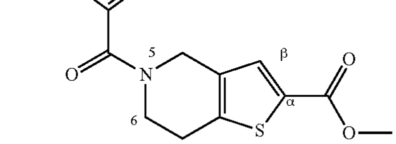

Imidazo[1,2-a]pyridine-3-carboxylic acid (46.1 mg, 0.284 mmol), methyl 4,5,6,7-tetrahydrothieno[3,2-c]pyridine-2-carboxylate hydrochloride (44.3 mg, 0.190 mmol) and TBTU (91 mg, 0.284 mmol) were dissolved in DMF (Volume: 2 ml) then DIPEA (0.132 ml, 0.758 mmol) was added in one portion. The solution was stirred at 50° C. on. The crude was diluted with DCM (10 mL) then was extracted with HCl 0.5M (2×15 mL). the aqueous layers were combined and basified with $NaHCO_3$ sat. until pH 7-8, then was extracted with DCM (3×20 mL) and washed with brine (1×10 mL). The organic phase was dried over $Na_2SO_4$, filtered and concentrated to dryness. The crude product was purified by FCC (KP-NH column gradient A:B from 100:0 to 0:100, eluent A:n-Heptane eluent B:acetone). Appropriate fractions were combined and evaporated to afford the title compound (48.2 mg, 0.141 mmol, 74.5% yield).

$^1$H NMR (400 MHz, $CDCl_3$) δ ppm 9.15 (br d, J=6.80 Hz, 1H) 8.12 (s, 1H) 8.06 (br d, J=7.89 Hz, 1H) 7.67 (br s, 1H) 7.49-7.55 (m, 1H) 7.23 (br s, 1H) 4.93 (s, 2H) 4.14 (t, J=5.70 Hz, 2H) 3.89 (s, 3H) 3.10 (br t, J=5.48 Hz, 2H).

Step 2: 5-(imidazo[1,2-a]pyridine-3-carbonyl)-N-(3-((4-methylpiperazin-1-yl)methyl)-5-(trifluoromethyl)phenyl)-4,5,6,7-tetrahydrothieno[3,2-c]pyridine-2-carboxamide (Example C2)

3-((4-methylpiperazin-1-yl)methyl)-5-(trifluoromethyl)aniline (72.1 mg, 0.264 mmol) was dissolved in dry THE (Volume: 8 ml) under Nitrogen and the mixture was stirred at −78° C. for 15 min, then n-BuLi 2.5M in hexanes (0.105 ml, 0.264 mmol) was added dropwise in 5 min and the reaction was stirred for 1 hr at −78° C. A solution of Intermediate 85 (45 mg, 0.132 mmol) in THE (Volume: 6.00 mL) was added dropwise for 10 min then the temperature was increased at rt and the reaction was stirred for 1 hr. 10 mL of water was added to quench the reaction and the solvent was evaporated by reduce pressure. The solid was dissolved in DCM (20 mL) and the organic layer was washed with $H_2O$ (2×20 mL) and Brine (1×20 mL). The organic layer was dried with $Na_2SO_4$, filtrated and concentrated until dryness. The crude product was purified by FCC in reverse Phase (C18 column gradient A:B from 100:0 to 0:100, eluent A:$H_2O$:ACN:HCOOH 95:5:0.1 eluent B:$H_2O$:ACN:HCOOH 5:95:0.1). Fractions were combined and evaporated to afford the title compound (25.3 mg, 0.043 mmol, 32.9% yield).

$^1$H NMR (400 MHz, ACN-$d_3$) 6 ppm 8.96 (d, J=7.02 Hz, 1H), 8.82 (s, 1H), 7.96-8.02 (m, 2H), 7.85 (s, 1H), 7.64 (d, J=8.99 Hz, 1H), 7.56 (s, 1H), 7.35-7.43 (m, 2H), 7.00 (t, J=6.70 Hz, 1H), 4.91 (s, 2H), 4.10 (t, J=5.70 Hz, 2H), 3.55 (s, 2H), 3.07 (br t, J=5.59 Hz, 2H), 2.14-2.58 (m, 11H). LC-MS (ESI): m/z (M+1)=583.2; rt=0.95 min; (method 1)

Pharmacological Activity of the Compounds of the Invention

In Vitro Assays

Binding Assays

DDR1 and DDR2 binding assays were performed using Life Technologies LanthaScreen™ Europium Kinase Binding assay. The compounds were incubated with 5 nM DDR1 (Carna Biosciences) or 5 nM DDR2 (Life Technologies) for 1 hour at room temperature in white 384-well OptiPlate (PerkinElmer), containing 20 nM or 10 nM Kinase Tracer 178 respectively and 2 nM Europium labelled anti-GST antibody (Life Technologies) in assay buffer (50 mM HEPES pH 7.5, 10 mM MgCl2, 1 mM EGTA and 0.01% BRIJ35).

The ratio of fluorescence emission 665 nm/615 nm after excitation at 340 nm was obtained using the Tecan Spark 20M plate reader. IC50 values were determined in GraphPad Prism 7.0 software, using 4 parameter model: log(inhibitor) vs. response. IC50 values were converted in Ki using the Cheng-Prusoff equation $$(Ki = IC50/(1 + [\text{Tracer}]/Kd).$$

DDR1 Cell Based Assay

The inhibition of DDR1 receptor activation by compounds was evaluated by PathHunter® U2OS DDR1 assay (Eurofins DiscoverX), according to the manufacturer's instructions. Briefly, U2OS-DDR1 cells were seeded in white 384-well plates at a density of 5000 cells/well and incubated for 2 hours at 37° C. and 5% CO2. Cells were then treated with compounds at different concentrations and incubated for 30 minutes, before stimulation with bovine Type II Collagen 20 μg/ml and incubation overnight at 37° C. and 5% CO2. PathHunter Detection Reagents were prepared according to the protocol provided by DiscoverX and 20 μl/well of this mix were added to each well. After incubating the plates for 1 hour at room temperature in the dark, luminescence signal was acquired with a plate reader. Raw data were normalized to vehicle control (0% for normalization) and positive control (100% for normalization; cells treated with 20 μg/ml collagen II) and IC50 parameters were calculated in GraphPad Prism 8.0 software, using sigmoidal dose-response curve fitting with variable slope.

DDR2 Cell Based Assay

The inhibition of DDR2 phosphorylation by compounds was evaluated in HEK293T-DDR2 recombinant cells by phospho-ELISA assay. Briefly, HEK293T-DDR2 cells were seeded in poly-D-lysine-coated 24-well plates at a density of 250.000 cells/well and incubated for 1.5 hours at 37° C. and 5% $CO_2$ in DMEM+10% FBS. After that, the medium was changed to serum-free DMEM and cells were incubated for 3 hours. Then. test compounds were added at different concentrations 30 minutes before stimulation with bovine Type II Collagen at 50 μg/ml for further 3 hours. For DDR2 phospho-ELISA assay (DuoSet IC Human Phospho-DDR2; R&D Systems), protein extracts were obtained by adding 60 μl/well of lysis buffer prepared according to the manufacturer's instructions. Protein concentration in the samples was determined by BCA assay and the levels of phospho-DDR2 were determined following R&D Systems indications. Raw data were normalized to maximal inhibition control (0% for normalization) and positive control (100% for normalization; cells treated with 20 μg/ml collagen II) and IC50 parameters were calculated in GraphPad Prism 8.0 software, using sigmoidal dose-response curve fitting with variable slope.

The results for individual compounds are provided below in Table 6, wherein the compounds are classified in terms of potency (nM) in binding and cell based assay with respect to their inhibitory activity on DDR1 and DDR2:

TABLE 6

| Example No. | Ki DDR1 | Ki DDR2 | IC50 DDR1 | IC50 DDR2 |
|---|---|---|---|---|
| 1 | +++ | +++ | ++ | +++ |
| 2 | +++ | +++ | ++ | − |

TABLE 6-continued

| Example No. | Ki DDR1 | Ki DDR2 | IC50 DDR1 | IC50 DDR2 |
|---|---|---|---|---|
| 3 | +++ | +++ | +++ | +++ |
| 4 | +++ | +++ | +++ | +++ |
| 5 | +++ | +++ | ++ | − |
| 6 | +++ | +++ | ++ | − |
| 7 | +++ | +++ | +++ | +++ |
| 8 | +++ | +++ | +++ | +++ |
| 9 | +++ | +++ | +++ | +++ |
| 10 | +++ | +++ | +++ | − |
| 11 | +++ | +++ | +++ | − |
| 12 | +++ | +++ | +++ | +++ |
| 13 | +++ | +++ | +++ | − |
| 14 | +++ | +++ | +++ | − |
| 15 | +++ | +++ | ++ | − |
| 16 | +++ | +++ | +++ | − |
| 17 | +++ | +++ | ++ | − |
| 18 | +++ | +++ | + | − |
| 19 | +++ | +++ | +++ | − |
| 20 | +++ | +++ | +++ | +++ |
| 21 | +++ | +++ | ++ | − |
| 22 | +++ | +++ | + | − |
| 23 | +++ | +++ | +++ | ++ |
| 24 | +++ | +++ | +++ | ++ |
| 25 | +++ | +++ | ++ | − |
| 26 | +++ | +++ | ++ | − |
| 27 | +++ | +++ | ++ | − |
| 28 | +++ | +++ | +++ | − |
| 29 | +++ | +++ | + | − |
| 30 | +++ | +++ | + | − |
| 31 | +++ | +++ | + | − |
| 32 | +++ | +++ | ++ | − |
| 33 | +++ | +++ | ++ | − |
| 34 | +++ | +++ | +++ | − |
| 35 | +++ | +++ | ++ | − |
| 36 | +++ | +++ | + | − |
| 37 | +++ | +++ | ++ | − |
| 38 | +++ | +++ | ++ | − |
| 39 | +++ | +++ | ++ | − |
| 40 | +++ | +++ | ++ | − |
| 41 | +++ | +++ | ++ | − |
| 42 | +++ | +++ | + | − |
| 43 | +++ | +++ | ++ | − |
| 44 | +++ | +++ | ++ | − |
| 45 | +++ | +++ | ++ | − |
| 46 | +++ | +++ | +++ | +++ |
| 47 | +++ | +++ | ++ | − |
| 48 | +++ | ++ | + | − |
| 49 | +++ | +++ | +++ | − |
| 50 | +++ | +++ | ++ | − |
| 51 | +++ | +++ | ++ | − |
| 52 | +++ | +++ | +++ | − |
| 53 | +++ | +++ | + | − |
| 54 | +++ | +++ | + | − |
| 55 | +++ | +++ | + | − |
| 56 | +++ | +++ | +++ | − |
| 57 | +++ | +++ | +++ | − |
| 58 | +++ | +++ | ++ | − |
| 59 | ++ | ++ | ++ | − |
| 60 | +++ | +++ | + | − |
| 61 | +++ | +++ | ++ | − |
| 62 | +++ | +++ | ++ | − |
| 63 | +++ | +++ | + | − |
| 64 | +++ | +++ | ++ | − |
| 65 | +++ | +++ | + | − |
| 66 | +++ | +++ | +++ | +++ |
| 67 | +++ | +++ | +++ | ++ |
| 68 | +++ | +++ | ++ | − |
| 69 | +++ | +++ | +++ | ++ |
| 70 | +++ | +++ | +++ | ++ |
| 71 | +++ | +++ | +++ | +++ |
| 72 | +++ | +++ | +++ | +++ |
| 73 | +++ | ++ | +++ | +++ |
| 74 | +++ | +++ | +++ | +++ |
| 75 | +++ | +++ | +++ | +++ |
| 76 | +++ | ++ | + | − |
| 77 | +++ | +++ | +++ | − |
| 78 | +++ | +++ | +++ | +++ |
| 79 | +++ | +++ | ++ | − |

TABLE 6-continued

| Example No. | Ki DDR1 | Ki DDR2 | IC50 DDR1 | IC50 DDR2 |
|---|---|---|---|---|
| 80 | +++ | +++ | ++ | − |
| 81 | +++ | +++ | + | − |
| 82 | +++ | +++ | ++ | − |
| 83 | +++ | +++ | ++ | − |
| 84 | +++ | +++ | +++ | +++ |
| 85 | +++ | +++ | +++ | +++ |
| 86 | +++ | +++ | +++ | +++ |
| 87 | +++ | +++ | + | − |
| 88 | +++ | +++ | +++ | − |
| 89 | +++ | +++ | +++ | − |
| 90 | +++ | +++ | +++ | +++ |
| 91 | +++ | +++ | +++ | − |
| 92 | +++ | +++ | +++ | − |
| 93 | +++ | +++ | +++ | +++ |
| 94 | +++ | +++ | + | − |
| 95 | +++ | +++ | +++ | − |
| 96 | +++ | +++ | +++ | − |
| 97 | +++ | +++ | +++ | − |
| 98 | +++ | +++ | +++ | +++ |
| 99 | +++ | + | ++ | − |
| 100 | +++ | +++ | +++ | +++ |
| 101 | +++ | +++ | +++ | +++ |
| 102 | +++ | +++ | +++ | ++ |
| 103 | +++ | +++ | +++ | ++ |
| 104 | +++ | +++ | +++ | + |
| 105 | +++ | +++ | + | − |
| 106 | +++ | +++ | +++ | ++ |
| 107 | +++ | +++ | +++ | − |
| 108 | +++ | +++ | +++ | ++ |
| 109 | +++ | +++ | ++ | − |
| 110 | +++ | +++ | ++ | − |
| 111 | +++ | +++ | + | − |
| 112 | +++ | +++ | ++ | − |
| 113 | +++ | +++ | ++ | − |
| 114 | +++ | +++ | + | − |
| 115 | +++ | +++ | + | − |
| 116 | +++ | +++ | ++ | − |
| 117 | +++ | +++ | +++ | − |
| 118 | +++ | +++ | ++ | − |
| 119 | +++ | +++ | ++ | − |
| 120 | +++ | +++ | + | − |
| 121 | +++ | +++ | + | − |
| 122 | +++ | +++ | + | − |
| 123 | +++ | +++ | + | − |
| 124 | +++ | +++ | +++ | − |
| 125 | +++ | +++ | ++ | − |
| 126 | +++ | +++ | ++ | − |
| 127 | +++ | +++ | ++ | − |
| 128 | +++ | +++ | +++ | − |
| 129 | +++ | ++ | ++ | − |
| 130 | +++ | +++ | + | − |
| 131 | +++ | +++ | ++ | − |
| 132 | +++ | +++ | +++ | − |
| 133 | +++ | +++ | +++ | +++ |
| 134 | +++ | +++ | +++ | +++ |
| 135 | +++ | ++ | ++ | − |
| 136 | +++ | +++ | +++ | +++ |
| 137 | +++ | +++ | +++ | − |
| 138 | +++ | +++ | +++ | − |
| 139 | +++ | +++ | ++ | − |
| 140 | +++ | +++ | +++ | − |
| 141 | +++ | +++ | +++ | − |
| 142 | +++ | +++ | + | − |
| 143 | +++ | +++ | +++ | − |
| 144 | +++ | +++ | +++ | − |
| 145 | +++ | ++ | ++ | − |
| 146 | +++ | +++ | ++ | − |
| 147 | +++ | +++ | +++ | − |
| 148 | +++ | +++ | +++ | − |
| 149 | +++ | +++ | ++ | − |
| 150 | +++ | +++ | +++ | +++ |
| 151 | +++ | +++ | +++ | +++ |
| 152 | +++ | +++ | +++ | +++ |
| 153 | +++ | +++ | +++ | +++ |
| 154 | +++ | +++ | + | − |
| 155 | +++ | +++ | ++ | − |
| 156 | +++ | +++ | +++ | − |

TABLE 6-continued

| Example No. | Ki DDR1 | Ki DDR2 | IC50 DDR1 | IC50 DDR2 |
|---|---|---|---|---|
| 157 | +++ | ++ | ++ | − |
| 158 | +++ | +++ | +++ | ++ |
| 159 | +++ | +++ | ++ | − |
| 160 | +++ | +++ | + | − |
| 161 | +++ | +++ | ++ | − |
| 162 | +++ | ++ | ++ | − |
| 163 | +++ | +++ | +++ | − |
| 164 | +++ | +++ | +++ | − |
| 165 | +++ | +++ | +++ | ++ |
| 166 | +++ | +++ | + | − |
| 167 | +++ | +++ | ++ | − |
| 168 | +++ | +++ | ++ | − |
| 169 | +++ | +++ | +++ | − |
| 170 | +++ | +++ | ++ | − |
| 171 | +++ | +++ | + | − |
| 172 | +++ | +++ | ++ | − |
| 173 | +++ | +++ | ++ | − |
| 174 | +++ | +++ | +++ | + |
| 175 | +++ | +++ | + | − |
| 176 | +++ | +++ | + | − |
| 177 | +++ | +++ | + | − |
| 178 | +++ | +++ | + | − |
| 179 | +++ | +++ | + | − |
| 180 | +++ | +++ | ++ | − |
| 181 | +++ | +++ | ++ | − |
| 182 | +++ | +++ | +++ | − |
| 183 | +++ | +++ | + | − |
| 184 | +++ | +++ | +++ | ++ |
| 185 | +++ | +++ | +++ | − |
| 186 | +++ | +++ | +++ | − |
| 187 | +++ | +++ | +++ | − |

+: Ki between 50 and 80 nM
++: Ki between 25 and 50 nM
+++: Ki lower than 25 nM
+: IC50 between 50 and 80 nM
++: IC50 between 25 and 50 nM
+++: IC50 lower than 25 nM
−: not available As it can be appreciated, the compounds of Table 6, i.e. the compounds of the invention, show a good activity as antagonist of DDR1 and DDR2. Accordingly, the compounds of the invention can be effectively used for treating disease, disorder or condition associated with DDR receptors, such as fibrosis, e.g. pulmonary fibrosis, idiopathic pulmonary fibrosis (IPF), hepatic fibrosis, renal fibrosis, ocular fibrosis, cardiac fibrosis, arterial fibrosis and systemic sclerosis.

COMPARATIVE EXAMPLES

Compounds of the examples C1 and C2 were tested in the same in vitro binding assay described above.

TABLE 7

| Example No | DDR1 Ki (nM) | DDR2 Ki (nM) |
|---|---|---|
| C1 | 312 | 531 |
| C2 | 195 | 160 |

The compounds of the present invention, as shown in Table 6, have both a binding affinity for DDR1 and DDR2 receptors expressed as Ki and an inhibitory potency expressed as IC50 against DDR1 and DDR2 receptors lower than 80 nM, and for most of the compounds lower than 50 nM or even lower than 25 nM. Conversely, the comparative examples C1 and C2, as shown in Table 7, have a binding affinity of 312 and of 195 nM on DDR1 receptor, and of 531 and of 160 nM on DDR2 receptor, respectively.

These data demonstrate that, conversely to the compound C1, characterized by the —C(O)NH— group substitution at the α position with respect to the sulphur, instead of the β position as in Example 1 of the present invention, the presence of the above mentioned substitution at the β position in the present invention compounds unexpectedly and remarkably determines a relevant increase in the inhibitory activity on the DDR1 and DDR2 receptors. As a further evidence, conversely to the compound C2, characterized by simultaneously the —C(O)NH— group substituting the thienyl ring linked at the α position with respect to the sulphur and the Hy group substituting the tetrahydropyridyl ring linked through a spacer to the nitrogen at the 5 position, in Example 1 of the present invention, the presence of —C(O)NH— group substituting the thienyl ring linked at the β position with respect to the sulphur and the Hy group substituting the tetrahydropyridyl ring linked through a spacer to the nitrogen at the 6 position in the present invention compounds unexpectedly and noteworthy determines a relevant increase in the inhibitory activity against the DDR1 and DDR2 receptors.

The invention claimed is:

1. A compound of formula (I)

(I)

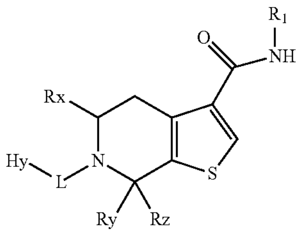

wherein

Rx, Ry and Rz are independently H or —$(C_1-C_4)$alkyl;

L is selected from the group consisting of —C(O)— and —$CH_2$—;

Hy is a bicyclic heteroaryl optionally substituted with at least one substituent selected from the group consisting of —$(C_1-C_4)$alkyl, a halogen atom, cyano, —O—$(C_1-C_4)$alkyl, —O—$(C_1-C_4)$alkylene-OH, —O—$(C_1-C_4)$alkylene-O—$(C_1-C_4)$alkyl, —O—$(C_1-C_4)$alkylene-heterocycloalkyl, —$(C_1-C_4)$alkylene-$NR_4R_5$, —$(C_1-C_6)$haloalkyl and heterocycloalkyl optionally substituted by one or more —$(C_1-C_4)$alkyl, or Hy is a bicyclic semisaturated heteroaryl;

$R_1$ is selected from the group consisting of Het and X:

Het is a heteroaryl optionally substituted with one or more substituents selected from the group consisting of —$(C_1-C_4)$alkyl, —$(C_1-C_4)$haloalkyl, cycloalkyl optionally substituted by one or more —$(C_1-C_6)$haloalkyl, —O—$(C_1-C_4)$haloalkyl, —O—$(C_1-C_4)$alkyl, —$(C_1-C_4)$alkylene-OH, —$(C_1-C_4)$alkylene-$NR_4R_5$, heterocycloalkyl, —$(C_1-C_4)$alkylene-aryl and aryl, wherein said aryl is optionally substituted with one or more groups selected from —$(C_1-C_4)$alkyl and a halogen atom, and

X (X)

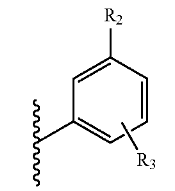

wherein $R_2$ is H or is selected from the group consisting of —$O(C_1$-$C_4)$haloalkyl, a halogen atom, —O-cycloalkyl and —$(C_1$-$C_4)$haloalkyl;

$R_3$ is H or is selected from the group consisting of a halogen atom, cyano, heterocycloalkyl optionally substituted by one or more —$(C_1$-$C_4)$alkyl, —$(C_1$-$C_4)$alkylene-heterocycloalkyl, —$(C_1$-$C_4)$alkylene-heterocycloalkyl-$(CH_2)_n$—$NR_4R_5$, —$(C_1$-$C_4)$alkylene-$NR_4R_5$, —$(C_1$-$C_4)$alkylene-$NR_4R_6$, —$O(C_1$-$C_4)$alkyl, —$O(C_1$-$C_4)$haloalkyl, —O—$(C_1$-$C_4)$alkylene-OH, heteroaryl optionally substituted with —$(C_1$-$C_4)$alkyl, —O—$(C_1$-$C_4)$alkylene-$NR_4R_5$, —O—$(C_1$-$C_4)$alkylene-O—$(C_1$-$C_4)$alkyl, —O—$(C_1$-$C_4)$alkylene-heterocycloalkyl and —O-heterocycloalkyl, wherein each of said heterocycloalkyl is optionally substituted with one or more groups selected from —$(C_1$-$C_4)$alkyl, oxo, a halogen atom, —C(O)—$(C_1$-$C_4)$ alkyl and heterocycloalkyl;

n is 0, 1 or 2;

$R_4$ is H or —$(C_1$-$C_4)$alkyl;

$R^5$ is H or —$(C_1$-$C_4)$alkyl;

$R_6$ is selected from the group consisting of -heterocycloalkyl,

—$(C_1$-$C_4)$alkylene-O—$(C_1$-$C_4)$alkyl and —$(C_1$-$C_4)$alkylene-OH;

or a pharmaceutically acceptable salt thereof.

2. The compound of formula (I) or pharmaceutically acceptable salt thereof according to claim 1, wherein $R_1$ is X'

(X')

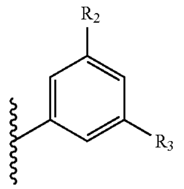

wherein the compound is represented by formula (Ia)

(Ia)

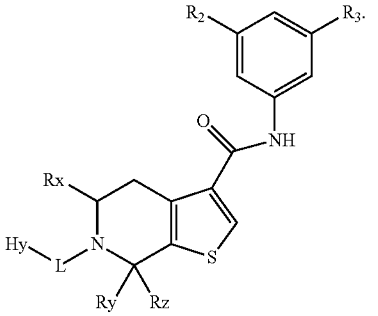

3. The compound of formula (Ia) or pharmaceutically acceptable salt thereof according to claim 2, wherein L is —$CH_2$—, wherein the compound is represented by formula (Iaa)

(Iaa)

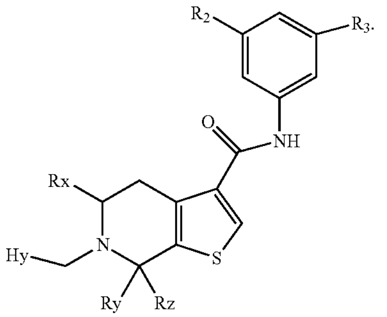

4. The compound of formula (Iaa) or pharmaceutically acceptable salt thereof according to claim 3, wherein the compound is selected from the group consisting of:

6-(imidazo[1,2-a]pyridine-3-carbonyl)-N-(3-((4-methylpiperazin-1-yl)methyl)-5-(trifluoromethyl)phenyl)-4,5,6,7-tetrahydrothieno[2,3-c]pyridine-3-carboxamide;

6-(imidazo[1,2-a]pyridin-3-ylmethyl)-N-(3-(4-methyl-1H-imidazol-1-yl)-5-(trifluoromethyl)phenyl)-4,5,6,7-tetrahydrothieno[2,3-c]pyridine-3-carboxamide;

6-((1H-pyrazolo[3,4-b]pyridin-5-yl)methyl)-N-(3-(trifluoromethoxy)phenyl)-4,5,6,7-tetrahydrothieno[2,3-c]pyridine-3-carboxamide;

6-((1H-pyrazolo[3,4-b]pyridin-5-yl)methyl)-N-(3-fluoro-5-(trifluoromethyl)phenyl)-4,5,6,7-tetrahydrothieno[2,3-c]pyridine-3-carboxamide;

6-((1H-pyrrolo[2,3-b]pyridin-5-yl)methyl)-N-(3-(trifluoromethyl)phenyl)-4,5,6,7-tetrahydrothieno[2,3-c]pyridine-3-carboxamide;

6-((1H-pyrrolo[2,3-b]pyridin-5-yl)methyl)-N-(3-(trifluoromethoxy)phenyl)-4,5,6,7-tetrahydrothieno[2,3-c]pyridine-3-carboxamide;

6-((1H-pyrrolo[2,3-b]pyridin-5-yl)methyl)-N-(3-fluoro-5-(trifluoromethyl)phenyl)-4,5,6,7-tetrahydrothieno[2,3-c]pyridine-3-carboxamide 6-(imidazo[1,2-a]pyrazin-3-ylmethyl)-N-(3-(trifluoromethyl)phenyl)-4,5,6,7-tetrahydrothieno[2,3-c]pyridine-3-carboxamide;

6-((1H-pyrazolo[3,4-b]pyridin-5-yl)methyl)-N-(3-(trifluoromethyl)phenyl)-4,5,6,7-tetrahydrothieno[2,3-c]pyridine-3-carboxamide;

6-((1H-pyrrolo[2,3-b]pyridin-4-yl)methyl)-N-(3-(trifluoromethyl)phenyl)-4,5,6,7-tetrahydrothieno[2,3-c]pyridine-3-carboxamide;

6-(imidazo[1,2-b]pyridazin-3-ylmethyl)-N-(3-(trifluoromethyl)phenyl)-4,5,6,7-tetrahydrothieno[2,3-c]pyridine-3-carboxamide;

6-(pyrazolo[1,5-a]pyrimidin-6-ylmethyl)-N-(3-(trifluoromethyl)phenyl)-4,5,6,7-tetrahydrothieno[2,3-c]pyridine-3-carboxamide;

6-(pyrazolo[1,5-a]pyrimidin-3-ylmethyl)-N-(3-(trifluoromethyl)phenyl)-4,5,6,7-tetrahydrothieno[2,3-c]pyridine-3-carboxamide;

6-(imidazo[1,2-a]pyrazin-3-ylmethyl)-7-methyl-N-(3-(trifluoromethyl)phenyl)-4,5,6,7-tetrahydrothieno[2,3-c]pyridine-3-carboxamide;

6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide;

6-(imidazo[1,2-a]pyrazin-3-ylmethyl)-5-methyl-N-(3-(trifluoromethyl)phenyl)-4,5,6,7-tetrahydrothieno[2,3-c]pyridine-3-carboxamide;

6-((1H-pyrrolo[2,3-b]pyridin-5-yl)methyl)-7-methyl-N-(3-(trifluoromethyl)phenyl)-4,5,6,7-tetrahydrothieno [2,3-c]pyridine-3-carboxamide;

6-((1H-pyrrolo[2,3-b]pyridin-5-yl)methyl)-7-methyl-N-(3-(trifluoromethyl)phenyl)-4,5,6,7-tetrahydrothieno [2,3-c]pyridine-3-carboxamide;

(R)-N-(3-((3-(dimethylamino)pyrrolidin-1-yl)methyl)-5-(trifluoromethyl)phenyl)-6-((3-methyl-1H-pyrazolo[3,4-b]pyridin-5-yl)methyl)-4,5,6,7-tetrahydrothieno[2,3-c]pyridine-3-carboxamide;

(R)-6-((1H-pyrazolo[3,4-b]pyridin-5-yl)methyl)-N-(3-((3-(dimethylamino)pyrrolidin-1-yl)methyl)-5-(trifluoromethyl)phenyl)-4,5,6,7-tetrahydrothieno[2,3-c]pyridine-3-carboxamide;

(R)-6-((1H-pyrrolo[2,3-b]pyridin-5-yl)methyl)-N-(3-((3-(dimethylamino)pyrrolidin-1-yl)methyl)-5-(trifluoromethyl)phenyl)-4,5,6,7-tetrahydrothieno[2,3-c]pyridine-3-carboxamide;

(R)-N-(3-((3-(dimethylamino)pyrrolidin-1-yl)methyl)-5-(trifluoromethyl)phenyl)-6-(imidazo[1,2-a]pyrazin-3-ylmethyl)-4,5,6,7-tetrahydrothieno[2,3-c]pyridine-3-carboxamide;

(R)-N-(3-((3-(dimethylamino)pyrrolidin-1-yl)methyl)-5-(trifluoromethyl)phenyl)-6-(pyrazolo[1,5-a]pyrimidin-6-ylmethyl)-4,5,6,7-tetrahydrothieno[2,3-c]pyridine-3-carboxamide;

6-((3-methyl-1H-pyrazolo[3,4-b]pyridin-5-yl)methyl)-N-(3-(2-(pyrrolidin-i-yl)ethoxy)-5-(trifluoromethyl)phenyl)-4,5,6,7-tetrahydrothieno[2,3-c]pyridine-3-carboxamide;

6-((1H-pyrazolo[3,4-b]pyridin-5-yl)methyl)-N-(3-(2-(pyrrolidin-1-yl)ethoxy)-5-(trifluoromethyl)phenyl)-4,5,6,7-tetrahydrothieno[2,3-c]pyridine-3-carboxamide; and 6-((1H-pyrazolo[3,4-b]pyridin-5-yl)methyl)-N-(3-fluoro-5-(trifluoromethoxy)phenyl)-4,5,6,7-tetrahydrothieno [2,3-c]pyridine-3-carboxamide.

5. The compound of formula (Ia) or pharmaceutically acceptable salt thereof according to claim 2, wherein L is —C(O)—, wherein the compound is represented by formula (Iab)

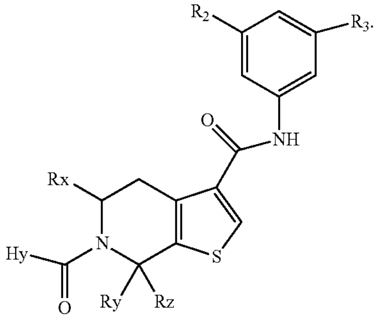

(Iab)

6. The compound of formula (Iab) or pharmaceutically acceptable salt thereof according to claim 5, wherein the compound is selected from the group consisting of:

6-(imidazo[1,2-a]pyridine-3-carbonyl)-N-(3-((4-methylpiperazin-1-yl)methyl)-5-(trifluoromethyl)phenyl)-4,5,6,7-tetrahydrothieno[2,3-c]pyridine-3-carboxamide;

6-(imidazo[1,2-a]pyridine-3-carbonyl)-N-(3-(trifluoromethyl)phenyl)-4, 5, 6,7-tetrahydrothieno[2,3-c]pyridine-3-carboxamide;

6-(imidazo[1,2-a]pyridine-3-carbonyl)-N-(3-(trifluoromethoxy)phenyl)-4, 5,6,7-tetrahydrothieno[2,3-c] pyridine-3-carboxamide;

N-(3-fluoro-5-(trifluoromethoxy)phenyl)-6-(imidazo[1, 2-a]pyridine-3-carbonyl)-4,5,6,7-tetrahydrothieno[2,3-c]pyridine-3-carboxamide;

6-(imidazo[1,2-a]pyridine-3-carbonyl)-N-(3-(pyrrolidin-1l-ylmethyl)-5-(trifluoromethyl)phenyl)-4,5,6,7-tetrahydrothieno[2,3-c]pyridine-3-carboxamide;

N-(3-((dimethylamino)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(3-(morpholinomethyl)-5-(trifluoromethyl)phenyl)-4,5,6,7-tetrahydrothieno[2,3-c]pyridine-3-carboxamide;

6-(imidazo[1,2-a]pyridine-3-carbonyl)-N-(3-(2-morpholinoethoxy)-5-(trifluoromethyl)phenyl)-4,5,6,7-tetrahydrothieno[2,3-c]pyridine-3-carboxamide;

N-(3-(2-(dimethylamino)ethoxy)-5-(trifluoromethyl)phenyl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(3-(2-(pyrrolidin-1-yl)ethoxy)-5-(trifluoromethyl)phenyl)-4,5,6,7-tetrahydrothieno[2,3-c]pyridine-3-carboxamide;

(S)-N-(3-((3-(dimethylamino)pyrrolidin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

(R)-N-(3-((3-(dimethylamino)pyrrolidin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-fluoro-5-(trifluoromethyl)phenyl)-6-(imidazo[1,2-a]pyridine-3-carbonyl)-4,5,6,7-tetrahydrothieno[2,3-c] pyridine-3-carboxamide;

N-(3-((4-(dimethylamino)piperidin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-((6-oxa-1-azaspiro[3.3]heptan-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-((2-oxa-5-azabicyclo[2.2.1]heptan-5-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-((3-fluoropyrrolidin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-(azetidin-1-ylmethyl)-5-(trifluoromethyl)phenyl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(3-((methyl(oxetan-3-yl)amino)methyl)-5-(trifluoromethyl)phenyl)-4,5,6,7-tetrahydrothieno[2,3-c]pyridine-3-carboxamide;

6-(imidazo[1,2-a]pyridine-3-carbonyl)-N-(3-((4-(oxetan-3-yl)piperazin-1-yl)methyl)-5-(trifluoromethyl)phenyl)-4,5,6,7-tetrahydrothieno[2,3-c]pyridine-3-carboxamide;

N-(3-((3-((dimethylamino)methyl)pyrrolidin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-((3-(dimethylamino)pyrrolidin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-(((2-hydroxyethyl)(methyl)amino)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-((4-acetylpiperazin-1-yl)methyl)-5-(trifluoromethyl)phenyl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(3-((4-methyl-3-oxopiperazin-1-yl)methyl)-5-(trifluoromethyl)phenyl)-4,5,6,7-tetrahydrothieno[2,3-c]pyridine-3-carboxamide;

6-(imidazo[1,2-a]pyridine-3-carbonyl)-N-(3-(piperidin-1-ylmethyl)-5-(trifluoromethyl)phenyl)-4,5,6,7-tetrahydrothieno[2,3-c]pyridine-3-carboxamide;

6-(imidazo[1,2-a]pyridine-3-carbonyl)-N-(3-(((2-methoxyethyl)(methyl)amino)methyl)-5-(trifluoromethyl)phenyl)-4,5,6,7-tetrahydrothieno[2,3-c]pyridine-3-carboxamide;

6-(imidazo[1,2-a]pyridine-3-carbonyl)-N-(3-(2-(4-methylpiperazin-1-yl)ethoxy)-5-(trifluoromethyl)phenyl)-4,5,6,7-tetrahydrothieno[2,3-c]pyridine-3-carboxamide;

6-(imidazo[1,2-a]pyridine-3-carbonyl)-N-(3-((1-methylpyrrolidin-3-yl)oxy)-5-(trifluoromethyl)phenyl)-4,5,6,7-tetrahydrothieno[2,3-c]pyridine-3-carboxamide;

6-(1H-pyrrolo[2,3-b]pyridine-5-carbonyl)-N-(3-(trifluoromethyl)phenyl)-4,5,6,7-tetrahydrothieno[2,3-c]pyridine-3-carboxamide;

6-(imidazo[1,2-a]pyridine-3-carbonyl)-N-(3-(4-methyl-1H-imidazol-1-yl)-5-(trifluoromethyl)phenyl)-4,5,6,7-tetrahydrothieno[2,3-c]pyridine-3-carboxamide;

6-(imidazo[1,2-a]pyrazine-3-carbonyl)-N-(3-(trifluoromethyl)phenyl)-4,5,6,7-tetrahydrothieno[2,3-c]pyridine-3-carboxamide;

6-(1H-pyrazolo[3,4-b]pyridine-5-carbonyl)-N-(3-(trifluoromethyl)phenyl)-4,5,6,7-tetrahydrothieno[2,3-c]pyridine-3-carboxamide;

6-(imidazo[1,2-b]pyridazine-3-carbonyl)-N-(3-(trifluoromethyl)phenyl)-4,5,6,7-tetrahydrothieno[2,3-c]pyridine-3-carboxamide;

6-(pyrazolo[1,5-a]pyrazine-3-carbonyl)-N-(3-(trifluoromethyl)phenyl)-4,5,6,7-tetrahydrothieno[2,3-c]pyridine-3-carboxamide;

6-(pyrazolo[1,5-a]pyrimidine-3-carbonyl)-N-(3-(trifluoromethyl)phenyl)-4,5,6,7-tetrahydrothieno[2,3-c]pyridine-3-carboxamide;

6-(5,6,7,8-tetrahydroimidazo[1,2-a]pyridine-3-carbonyl)-N-(3-(trifluoromethyl)phenyl)-4,5,6,7-tetrahydrothieno[2,3-c]pyridine-3-carboxamide;

6-(5,6-dihydro-8H-imidazo[2,1-c][1,4]oxazine-3-carbonyl)-N-(3-(trifluoromethyl)phenyl)-4,5,6,7-tetrahydrothieno[2,3-c]pyridine-3-carboxamide;

N-(3-fluoro-5-(trifluoromethyl)phenyl)-6-(pyrazolo[1,5-a]pyrimidine-3-carbonyl)-4,5,6,7-tetrahydrothieno[2,3-c]pyridine-3-carboxamide;

6-(imidazo[1,2-a]pyridine-3-carbonyl)-7-methyl-N-(3-(4-methyl-1H-imidazol-1-yl)-5-(trifluoromethyl)phenyl)-4,5,6,7-tetrahydrothieno[2,3-c]pyridine-3-carboxamide;

(R)-6-(imidazo[1,2-a]pyridine-3-carbonyl)-7-methyl-N-(3-(trifluoromethyl)phenyl)-4,5,6,7-tetrahydrothieno[2,3-c]pyridine-3-carboxamide;

(R)-6-(imidazo[1,2-a]pyridine-3-carbonyl)-7-methyl-N-(3-(4-methyl-1H-imidazol-1-yl)-5-(trifluoromethyl)phenyl)-4,5,6,7-tetrahydrothieno[2,3-c]pyridine-3-carboxamide;

6-(imidazo[1,2-a]pyridine-3-carbonyl)-7,7-dimethyl-N-(3-(trifluoromethyl)phenyl)-4,5,6,7-tetrahydrothieno[2,3-c]pyridine-3-carboxamide;

(R)-N-(3-(3-(dimethylamino)pyrrolidine-1-carbonyl)-5-(trifluoromethyl)phenyl)-6-(imidazo[1,2-a]pyridine-3-carbonyl)-4,5,6,7-tetrahydrothieno[2,3-c]pyridine-3-carboxamide;

N-(3-cyano-5-(trifluoromethyl)phenyl)-6-(imidazo[1,2-a]pyridine-3-carbonyl)-4,5,6,7-tetrahydrothieno[2,3-c]pyridine-3-carboxamide;

6-(6-((dimethylamino)methyl)imidazo[1,2-a]pyridine-3-carbonyl)-N-(3-(trifluoromethyl)phenyl)-4,5,6,7-tetrahydrothieno[2,3-c]pyridine-3-carboxamide;

6-(6-(4-methylpiperazin-1-yl)imidazo[1,2-a]pyridine-3-carbonyl)-N-(3-(trifluoromethyl)phenyl)-4,5,6,7-tetrahydrothieno[2,3-c]pyridine-3-carboxamide;

6-(6-(2-hydroxyethoxy)imidazo[1,2-a]pyridine-3-carbonyl)-N-(3-(trifluoromethyl)phenyl)-4,5,6,7-tetrahydrothieno[2,3-c]pyridine-3-carboxamide;

6-(7-(2-methoxyethoxy)imidazo[1,2-a]pyridine-3-carbonyl)-N-(3-(trifluoromethyl)phenyl)-4,5,6,7-tetrahydrothieno[2,3-c]pyridine-3-carboxamide;

6-(7-(2-morpholinoethoxy)imidazo[1,2-a]pyridine-3-carbonyl)-N-(3-(trifluoromethyl)phenyl)-4,5,6,7-tetrahydrothieno[2,3-c]pyridine-3-carboxamide;

(R)-N-(3-((3-(dimethylamino)pyrrolidin-1-yl)methyl)-5-(trifluoromethyl)phenyl)-6-(5-methylimidazo[1,2-a]pyridine-3-carbonyl)-4,5,6,7-tetrahydrothieno[2,3-c]pyridine-3-carboxamide;

6-(6-(6-methyl-2,6-diazaspiro[3.3]heptan-2-yl)imidazo[1,2-a]pyridine-3-carbonyl)-N-(3-(trifluoromethyl)phenyl)-4,5,6,7-tetrahydrothieno[2,3-c]pyridine-3-carboxamide;

6-(6-(1-methyl-1,2,3,6-tetrahydropyridin-4-yl)imidazo[1,2-a]pyridine-3-carbonyl)-N-(3-(trifluoromethyl)phenyl)-4,5,6,7-tetrahydrothieno[2,3-c]pyridine-3-carboxamide;

6-(6-(2-morpholinoethoxy)imidazo[1,2-a]pyridine-3-carbonyl)-N-(3-(trifluoromethyl)phenyl)-4,5,6,7-tetrahydrothieno[2,3-c]pyridine-3-carboxamide;

N-(3-(morpholinomethyl)-5-(trifluoromethyl)phenyl)-6-(pyrazolo[1,5-a]pyrazine-3-carbonyl)-4,5,6,7-tetrahydrothieno[2,3-c]pyridine-3-carboxamide;

6-(imidazo[1,2-a]pyridine-3-carbonyl)-N-(3-(4-methylpiperazin-1-yl)-5-(trifluoromethyl)phenyl)-4,5,6,7-tetrahydrothieno[2,3-c]pyridine-3-carboxamide;

N-(3-(4-methylpiperazin-1-yl)-5-(trifluoromethyl)phenyl)-6-(pyrazolo[1,5-a]pyrazine-3-carbonyl)-4,5,6,7-tetrahydrothieno[2,3-c]pyridine-3-carboxamide;

6-(imidazo[1,2-a]pyridine-3-carbonyl)-N-(3-morpholino-5-(trifluoromethyl)phenyl)-4,5,6,7-tetrahydrothieno[2,3-c]pyridine-3-carboxamide;

N-(3-morpholino-5-(trifluoromethyl)phenyl)-6-(pyrazolo[1,5-a]pyrazine-3-carbonyl)-4,5,6,7-tetrahydrothieno[2,3-c]pyridine-3-carboxamide;

N-(3-cyano-5-(trifluoromethyl)phenyl)-6-(pyrazolo[1,5-a]pyrazine-3-carbonyl)-4,5,6,7-tetrahydrothieno[2,3-c]pyridine-3-carboxamide;

6-(imidazo[1,2-a]pyridine-3-carbonyl)-4-methyl-N-(3-(trifluoromethyl)phenyl)-4,5,6,7-tetrahydrothieno[2,3-c]pyridine-3-carboxamide; and N-(3-(hydroxymethyl)-5-(trifluoromethyl)phenyl)-6-(pyrazolo[1,5-a]pyrazine-3-carbonyl)-4,5,6,7-tetrahydrothieno[2,3-c]pyridine-3-carboxamide.

7. The compound of formula (I) or pharmaceutically acceptable salt thereof according to claim 1, wherein Ri is Het, wherein the compound is represented by formula (Ib)

(Ib)

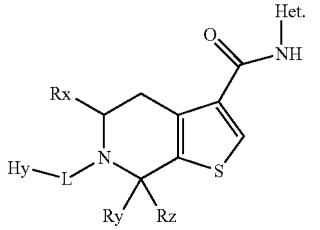

8. The compound of formula (Ib) or pharmaceutically acceptable salt thereof according to claim 7, wherein L is-C(O)-, wherein the compound is represented by formula (Ibb)

(Ibb)

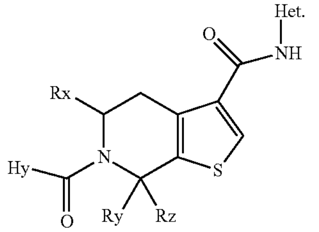

9. The compound of formula (Ibb) or pharmaceutically acceptable salt thereof according to claim 8, wherein the compound is selected from the group consisting of:

N-(3-(tert-butyl)-1-(p-tolyl)-1H-pyrazol-5-yl)-6-(imidazo[1,2-a]pyridine-3-carbonyl)-4,5,6,7-tetrahydrothieno[2,3-c]pyridine-3-carboxamide;

N-(3-(tert-butyl)-1-methyl-1H-pyrazol-5-yl)-6-(imidazo[1,2-a]pyridine-3-carbonyl)-4,5,6,7-tetrahydrothieno[2,3-c]pyridine-3-carboxamide;

N-(3-(tert-butyl)-1-(4-fluorophenyl)-1H-pyrazol-5-yl)-6-(imidazo[1,2-a]pyridine-3-carbonyl)-4,5,6,7-tetrahydrothieno[2,3-c]pyridine-3-carboxamide;

N-(3-(tert-butyl)-1-phenyl-1H-pyrazol-5-yl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(5-(1,1,1-trifluoro-2-methylpropan-2-yl)isoxazol-3-yl)-4,5,6,7-tetrahydrothieno[2,3-c]pyridine-3-carboxamide;

6-(imidazo[1,2-a]pyridine-3-carbonyl)-N-(2-(trifluoromethyl)pyridin-4-yl)-4,5,6,7-tetrahydrothieno[2,3-c]pyridine-3-carboxamide;

6-(imidazo[1,2-a]pyridine-3-carbonyl)-N-(6-(trifluoromethyl)pyrimidin-4-yl)-4,5,6,7-tetrahydrothieno[2,3-c]pyridine-3-carboxamide;

6-(imidazo[1,2-a]pyridine-3-carbonyl)-N-(5-(trifluoromethyl)pyridin-3-yl)-4,5,6,7-tetrahydrothieno[2,3-c]pyridine-3-carboxamide;

6-(imidazo[1,2-a]pyridine-3-carbonyl)-N-(4-(trifluoromethyl)pyridin-2-yl)-4,5,6,7-tetrahydrothieno[2,3-c]pyridine-3-carboxamide;

6-(imidazo[1,2-a]pyridine-3-carbonyl)-N-(4-(trifluoromethyl)pyrimidin-2-yl)-4,5,6,7-tetrahydrothieno[2,3-c]pyridine-3-carboxamide;

N-(5-(tert-butyl)isoxazol-3-yl)-6-(imidazo[1,2-a]pyridine-3-carbonyl)-4,5,6,7-tetrahydrothieno[2,3-c]pyridine-3-carboxamide;

N-(3-(tert-butyl)isoxazol-5-yl)-6-(imidazo[1,2-a]pyridine-3-carbonyl)-4,5,6,7-tetrahydrothieno[2,3-c]pyridine-3-carboxamide;

N-(3-cyclobutyl-1-methyl-1H-pyrazol-5-yl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(3-isopropyl-1-methyl-1H-pyrazol-5-yl)-4,5,6,7-tetrahydrothieno[2,3-c]pyridine-3-carboxamide;

N-(2-(tert-butyl)pyridin-4-yl)-6-(imidazo[1,2-a]pyridine-3-carbonyl)-4,5,6,7-tetrahydrothieno[2,3-c]pyridine-3-carboxamide;

N-(3-(tert-butyl)-1-isopropyl-1H-pyrazol-5-yl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(1-methyl-3-propyl-1H-pyrazol-5-yl)-4,5,6,7-tetrahydrothieno[2,3-c]pyridine-3-carboxamide;

N-(3-(tert-butyl)-1-(2,2,2-trifluoroethyl)-1H-pyrazol-5-yl)-6-(imidazo[1,2-a]pyridine-3-carbonyl)-4,5,6,7-tetrahydrothieno[2,3-c]pyridine-3-carboxamide;

N-(1-benzyl-3-(tert-butyl)-1H-pyrazol-5-yl)-6-(imidazo[1,2-a]pyridine-3-carbonyl)-4,5,6,7-tetrahydrothieno[2,3-c]pyridine-3-carboxamide;

N-(3-(tert-butyl)-1-ethyl-1H-pyrazol-5-yl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(3-isobutyl-1-methyl-1H-pyrazol-5-yl)-4,5,6,7-tetrahydrothieno[2,3-c]pyridine-3-carboxamide;

N-(4-(tert-butyl)oxazol-2-yl)-6-(imidazo[1,2-a]pyridine-3-carbonyl)-4,5,6,7-tetrahydrothieno[2,3-c]pyridine-3-carboxamide;

N-(3-(tert-butyl)-1-(2-hydroxyethyl)-1H-pyrazol-5-yl)-6-(imidazo[1,2-a]pyridine-3-carbonyl)-4,5,6,7-tetrahydrothieno[2,3-c]pyridine-3-carboxamide;

N-(3-(tert-butyl)-1-methyl-1H-pyrazol-5-yl)-6-(7-methylimidazo[1,2-a]pyridine-3-carbonyl)-4,5,6,7-tetrahydrothieno[2,3-c]pyridine-3-carboxamide;

N-(3-(tert-butyl)-1-methyl-1H-pyrazol-5-yl)-6-(6-methylimidazo[1,2-a]pyridine-3-carbonyl)-4,5,6,7-tetrahydrothieno[2,3-c]pyridine-3-carboxamide;

N-(3-(tert-butyl)-1-methyl-1H-pyrazol-5-yl)-6-(6-fluoroimidazo[1,2-a]pyridine-3-carbonyl)-4,5,6,7-tetrahydrothieno[2,3-c]pyridine-3-carboxamide;

N-(3-(tert-butyl)-1-methyl-1H-pyrazol-5-yl)-6-(6-(trifluoromethyl)imidazo[1,2-a]pyridine-3-carbonyl)-4,5,6,7-tetrahydrothieno[2,3-c]pyridine-3-carboxamide;

N-(3-(tert-butyl)-1-methyl-1H-pyrazol-5-yl)-6-(6-chloroimidazo[1,2-a]pyridine-3-carbonyl)-4,5,6,7-tetrahydrothieno[2,3-c]pyridine-3-carboxamide;

N-(3-(tert-butyl)-1-methyl-1H-pyrazol-5-yl)-6-(imidazo[1,2-a]pyridine-3-carbonyl)-7-methyl-4,5,6,7-tetrahydrothieno[2,3-c]pyridine-3-carboxamide;

6-(pyrazolo[1,5-a]pyrazine-3-carbonyl)-N-(5-(trifluoromethyl)pyridin-3-yl)-4,5,6,7-tetrahydrothieno[2,3-c]pyridine-3-carboxamide;

6-(pyrazolo[1,5-a]pyrimidine-3-carbonyl)-N-(5-(trifluoromethyl)pyridin-3-yl)-4,5,6,7-tetrahydrothieno[2,3-c]pyridine-3-carboxamide;

6-(5,6-dihydro-8H-imidazo [2,1-c][1,4]oxazine-3-carbonyl)-N-(5-(trifluoro methyl)pyridin-3-yl)-4,5,6,7-tetrahydrothieno[2,3-c]pyridine-3-carboxamide;

6-(5,6,7,8-tetrahydroimidazo[1,2-a]pyridine-3-carbonyl)-N-(5-(trifluoromethyl)pyridin-3-yl)-4,5,6,7-tetrahydrothieno[2,3-c]pyridine-3-carboxamide;

N-(3-(tert-butyl)isoxazol-5-yl)-6-(5, 6-dihydro-8H-imidazo[2,1-c][1,4]oxazine-3-carbonyl)-4,5,6,7-tetrahydrothieno[2,3-c]pyridine-3-carboxamide;

N-(3-(tert-butyl)isoxazol-5-yl)-6-(pyrazolo[1,5-a]pyrazine-3-carbonyl)-4,5,6,7-tetrahydrothieno[2,3-c]pyridine-3-carboxamide;

6-(imidazo[1,2-a]pyridine-3-carbonyl)-N-(1-methyl-3-(1-(trifluoromethyl)cyclopropyl)-1H-pyrazol-5-yl)-4,5,6,7-tetrahydrothieno[2,3-c]pyridine-3-carboxamide;

N-(5-(1,1-difluoroethyl)pyridin-3-yl)-6-(imidazo[1,2-a]pyridine-3-carbonyl)-4,5,6,7-tetrahydrothieno[2,3-c]pyridine-3-carboxamide;

N-(5-(tert-butyl)-1-methyl-1H-pyrazol-3-yl)-6-(pyrazolo[1,5-a]pyrazine-3-carbonyl)-4,5,6,7-tetrahydrothieno[2,3-c]pyridine-3-carboxamide;

N-(5-(tert-butyl)pyridin-3-yl)-6-(imidazo[1,2-a]pyridine-3-carbonyl)-4,5,6,7-tetrahydrothieno[2,3-c]pyridine-3-carboxamide;

N-(5-(difluoromethoxy) pyridin-3-yl)-6-(imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(3-(tert-pentyl)isoxazol-5-yl)-4,5,6,7-tetrahydrothieno[2,3-c]pyridine-3-carboxamide;

6-(5,6,7,8-tetrahydroimidazo[1,2-a]pyrimidine-3-carbonyl)-N-(5-(trifluoromethyl)pyridin-3-yl)-4,5,6,7-tetrahydrothieno[2,3-c]pyridine-3-carboxamide;

N-(6-methoxy-5-(trifluoromethyl)pyridin-3-yl)-6-(pyrazolo[1,5-a]pyrazine-3-carbonyl)-4,5,6,7-tetrahydrothieno[2,3-c]pyridine-3-carboxamide;

N-(5-(1,1-difluoroethyl)pyridin-3-yl)-6-(pyrazolo[1,5-a]pyrazine-3-carbonyl)-4,5,6,7-tetrahydrothieno[2,3-c]pyridine-3-carboxamide;

N-(5-(tert-butyl)pyridin-3-yl)-6-(pyrazolo[1,5-a]pyrazine-3-carbonyl)-4,5,6,7-tetrahydrothieno[2,3-c]pyridine-3-carboxamide;

6-(pyrazolo[1,5-a]pyridine-3-carbonyl)-N-(5-(trifluoromethyl)pyridin-3-yl)-4,5,6,7-tetrahydrothieno[2,3-c]pyridine-3-carboxamide;

N-(5-(difluoromethoxy)pyridin-3-yl)-6-(pyrazolo[1,5-a]pyrazine-3-carbonyl)-4,5,6,7-tetrahydrothieno[2,3-c]pyridine-3-carboxamide;

6-(pyrazolo[1,5-a]pyrazine-3-carbonyl)-N-(5-(1,1,1-trifluoro-2-methylpropan-2-yl)isoxazol-3-yl)-4,5,6,7-tetrahydrothieno[2,3-c]pyridine-3-carboxamide;

6-(imidazo[1,2-a]pyrazine-3-carbonyl)-N-(5-(trifluoromethyl)pyridin-3-yl)-4,5,6,7-tetrahydrothieno[2,3-c]pyridine-3-carboxamide;

6-(pyrazolo[1,5-a]pyrazine-3-carbonyl)-N-(5-(trifluoromethoxy)pyridin-3-yl)-4,5,6,7-tetrahydrothieno[2,3-c]pyridine-3-carboxamide;

N-(2-((dimethylamino)methyl)-6-(trifluoromethyl)pyridin-4-yl)-6-(imidazo[1,2-a]pyridine-3-carbonyl)-4,5,6,7-tetrahydrothieno[2,3-c]pyridine-3-carboxamide;

6-(5-methoxypyrazolo[1,5-a]pyridine-3-carbonyl)-N-(5-(trifluoromethyl)pyridin-3-yl)-4,5,6,7-tetrahydrothieno[2,3-c]pyridine-3-carboxamide;

6-(pyrazolo[5,1-b]thiazole-7-carbonyl)-N-(5-(trifluoromethyl)pyridin-3-yl)-4,5,6,7-tetrahydrothieno[2,3-c]pyridine-3-carboxamide;

6-(7-methoxyimidazo[1,2-a]pyridine-3-carbonyl)-N-(5-(trifluoromethyl)pyridin-3-yl)-4,5,6,7-tetrahydrothieno[2,3-c]pyridine-3-carboxamide;

6-(1-methyl-1H-imidazo[1,2-b]pyrazole-7-carbonyl)-N-(5-(trifluoromethyl)pyridin-3-yl)-4,5,6,7-tetrahydrothieno[2,3-c]pyridine-3-carboxamide;

6-(7-fluoroimidazo[1,2-a]pyridine-3-carbonyl)-N-(5-(trifluoromethyl)pyridin-3-yl)-4,5,6,7-tetrahydrothieno[2,3-c]pyridine-3-carboxamide;

N-(5-(tert-butyl)-1-methyl-1H-pyrazol-3-yl)-6-(6-(4-methylpiperazin-1-yl)imidazo[1,2-a]pyridine-3-carbonyl)-4,5,6,7-tetrahydrothieno[2,3-c]pyridine-3-carboxamide;

6-(6-(4-methylpiperazin-1-yl)imidazo[1,2-a]pyridine-3-carbonyl)-N-(5-(trifluoromethyl)pyridin-3-yl)-4,5,6,7-tetrahydrothieno[2,3-c]pyridine-3-carboxamide;

N-(3-(tert-butyl)isoxazol-5-yl)-6-(6-(4-methylpiperazin-1-yl)imidazo[1,2-a]pyridine-3-carbonyl)-4,5,6,7-tetrahydrothieno[2,3-c]pyridine-3-carboxamide;

6-(imidazo[1,2-a]pyridine-3-carbonyl)-N-(5-(trifluoromethyl)pyridazin-3-yl)-4,5,6,7-tetrahydrothieno[2,3-c]pyridine-3-carboxamide;

N-(5-(tert-butyl)isoxazol-3-yl)-6-(pyrazolo[1,5-a]pyrazine-3-carbonyl)-4,5,6,7-tetrahydrothieno[2,3-c]pyridine-3-carboxamide;

N-(3-(tert-pentyl)isoxazol-5-yl)-6-(pyrazolo[1,5-a]pyrazine-3-carbonyl)-4,5,6,7-tetrahydrothieno[2,3-c]pyridine-3-carboxamide;

N-(3-isobutylisoxazol-5-yl)-6-(pyrazolo[1,5-a]pyrazine-3-carbonyl)-4,5,6,7-tetrahydrothieno[2,3-c]pyridine-3-carboxamide; and 6-(imidazo[1,2-a]pyridine-3-carbonyl)-N-(5-(trifluoromethoxy)pyridin-3-yl)-4,5,6,7-tetrahydrothieno[2,3-c]pyridine-3-carboxamide.

10. A pharmaceutical composition comprising the compound of formula (I) or pharmaceutically acceptable salt thereof according to claim 1, in admixture with one or more pharmaceutically acceptable carrier or excipient.

11. The pharmaceutical composition according to claim 10, formulated for administration by inhalation.

12. A method of treating fibrosis and/or diseases, disorders or conditions that involve fibrosis, the method comprising administering to a subject in need thereof the compound of formula (I) or pharmaceutically acceptable salt thereof according to claim 1, wherein the fibrosis is at least one selected from the group consisting of pulmonary fibrosis, idiopathic pulmonary fibrosis (IPF), hepatic fibrosis, renal fibrosis, ocular fibrosis, cardiac fibrosis, arterial fibrosis and systemic sclerosis.

13. The method according to claim 12, wherein the fibrosis comprises idiopathic pulmonary fibrosis (IPF).

* * * * *